(12) United States Patent
Black et al.

(10) Patent No.: US 7,115,591 B2
(45) Date of Patent: *Oct. 3, 2006

(54) PROSTAGLANDIN ENDOPEROXIDE H SYNTHASE BIOSYNTHESIS INHIBITORS

(75) Inventors: Lawrence A. Black, Libertyville, IL (US); Anwer Basha, Lake Forest, IL (US); Teodozyj Kolasa, Lake Villa, IL (US); Michael E. Kort, Lake Bluff, IL (US); Huaqing Liu, Buffalo Grove, IL (US); Catherine M. McCarty, Brookline, MA (US); Meena Patel, Chicago, IL (US); Jeffrey J. Rohde, Evanston, IL (US); Michael J. Coghlan, Grayslake, IL (US); Andrew O. Stewart, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/464,928

(22) Filed: Jun. 19, 2003

(65) Prior Publication Data

US 2004/0158064 A1 Aug. 12, 2004

Related U.S. Application Data

(60) Division of application No. 09/871,195, filed on May 31, 2001, now abandoned, which is a division of application No. 09/427,768, filed on Oct. 27, 1999, now Pat. No. 6,307,047, which is a continuation-in-part of application No. 09/261,872, filed on Mar. 3, 1999, now abandoned, which is a continuation-in-part of application No. 09/179,605, filed on Oct. 27, 1998, now abandoned, which is a continuation-in-part of application No. 09/129,570, filed on Aug. 5, 1998, now abandoned.

(60) Provisional application No. 60/056,733, filed on Aug. 22, 1997.

(51) Int. Cl.
*A61K 31/50* (2006.01)
*A61K 31/675* (2006.01)
*C07D 237/16* (2006.01)
*C07F 9/6509* (2006.01)

(52) U.S. Cl. ................ 514/85; 514/247; 544/232; 544/238; 544/239; 544/240; 544/241

(58) Field of Classification Search ............ 544/232, 544/238–241; 514/85, 247
See application file for complete search history.

(56) References Cited

U.S. PATENT DOCUMENTS

| | | | |
|---|---|---|---|
| 3,004,027 A | 10/1961 | Gordon et al. | |
| 4,238,490 A | 12/1980 | Powers et al. | |
| 5,474,995 A | 12/1995 | Ducharme et al. | |
| 5,521,207 A | 5/1996 | Graneto | |
| 5,580,985 A | 12/1996 | Lee et al. | |
| 5,622,948 A | 4/1997 | Dunn et al. | |
| 5,763,440 A | 6/1998 | Ross et al. | |
| 6,307,047 B1 * | 10/2001 | Black et al. | |

FOREIGN PATENT DOCUMENTS

| | | |
|---|---|---|
| EP | 0711759 | 5/1996 |
| EP | 0714895 | 6/1996 |
| WO | 88/09675 | 12/1988 |
| WO | 95/00501 | 1/1995 |
| WO | 96/10012 | 4/1996 |
| WO | 96/16934 | 6/1996 |
| WO | 96/21662 | 7/1996 |
| WO | 96/24584 | 8/1996 |
| WO | 96/24585 | 8/1996 |
| WO | 96/25405 | 8/1996 |
| WO | 96/31509 | 10/1996 |
| WO | 96/36617 | 11/1996 |
| WO | 96/36623 | 11/1996 |
| WO | 96/37476 | 11/1996 |
| WO | 97/14691 | 4/1997 |
| WO | 98/41511 | 9/1998 |
| WO | 99/10331 | 3/1999 |
| WO | 99/10332 | 3/1999 |

OTHER PUBLICATIONS

Vane, Nature, vol. 367, p. 215-216 (1994).*
Griswold et al. Medicinal Research Reviews 16, p. 181-206 (1986).*
Kashfi et al. Biochemical Pharmacology, vol. 70, p. 969-986 (2005).*

(Continued)

*Primary Examiner*—Emily Bernhardt
(74) *Attorney, Agent, or Firm*—Portia Chen

(57) ABSTRACT

The present invention describes pyridazinone compounds of formula I

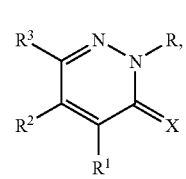

which are cyclooxygenase (COX) inhibitors, and in particular, are selective inhibitors of cyclooxygenase-2 (COX-2), COX-2 is the inducible isoform associated with inflammation, as opposed to the constitutive isoform, cyclooxygenase-1 (COX-1) which is an important "housekeeping" enzyme in many tissues, including the gastrointestinal (GI) tract and the kidneys. The selectivity of these compounds for COX-2 minimizes the unwanted GI and renal side-effects seen with currently markered non-steroidal anti-inflammatory drugs (NSAIDs).

10 Claims, No Drawings

OTHER PUBLICATIONS

Rigas et al. Medline Abstract for J. Pharmacol. Exp. Ther. vol. 314, p. 1-8 (2005).*
Anzinger, H., et al., "Stabilizing Acid-labile Protecting Groups", Angew. Chem., Int. Ed. Engl. 18(9) 686 (1979).
Eichholzer; J., et al., "Synthesis of (S)-N-(2,3-Dihydroxy-3-methylbutyl)acetamide", Australian Journal of Chemistry 39(11) 1907-1909 (1986).
Browner, M., "X-ray crystal structure of human COX-2", Roche Bioscience.
Battistini, B., et al., "COX-1 and COX-2: Toward the Development of More Selective NSAIDs", DN&P, 7(8):501-512 (1994).
Bertenshaw, S.R., et al., Conformationally Restricted 1,5-Diarylpyrazoles are Selective COX-2 Inhibitors:, Bioorganic &Medicinal Chemistry Letters, 23:2827-2830 (1996).
Carruthers, N.I., et al., "Selective Cyclooxygenase Inhibitors", Chemtracts-Organic Chemistry, 8:273-276 (1995).
Cashman, J.N., "The Mechanisms of Action of NSAIDs in Analgesia",Drugs, 52(5):13-23 (1996).
Cho, S-D., "Concurrent Alkylation-Methoxylation of 4,5-Dihalopyridazin-6-ones and Synthesis of 5-Halo-4-hydroxypyridazin-6-ones", J. Heterocyclic Chem., 33:1579-1582 (1996).
DeWitt, D.L., "The Differential Susceptibility of Prostaglandin Endoperoxide H Synthases-1 and -2 to Nonsteroidal Anti-inflammatory Drugs: Aspirin Derivatives as Selective Inhibitors", Med. Chem. Res., 5:325-343 (1995).
Fieser & Fieser, Reagents for Organic Synthesis, 1: 172-173 (1967) John Wiley & Sons, NY, NY.
Ford-Hutchinson, A.W., "COX-2 inhibitors", Merck Frosst Center for Therapeutic Research.
Freisen, R.W., "Novel 1,2-Diarylcyclobutenes: Selective and Orally Active Cox-2 Inhibitors", Bioorganic & Medicinal Chemistry Letters, 6(22):2677-2682 (1996).
Frenette, R., et al., "Novel 1,2Diarylcyclobutenes: Selective and Orally Active COX-2 Inhibitors", Merck Frosst Center for Therapeutic Research.
Gierse, et al, Expression and Selective Inhibition of the Constituitive and Inducible Forms of Cyclooxygenase, Biochem J., 305:479 (1995).
Gierse, J.K. et al, A Single Amino Acid Difference Between COX-1 and 2 Reverses the Selectivity of COX-2 Specific Inhibitors, Monsanto/Searle Research, p. 40.
Gauthier, J.Y., Synthesis and Biological Evaluation of 2,3-Diarylthiopenes as Selective COX-2 Inhibitors. Part II: Reolacing the Heterocycle, Bioorganic & Medicinal Chemistry Letters, 6(1):87-92 (1996).
Huang, H-C, Diaryl Indenes and Benzofurans: Novel Classes of Potent and Selective and Cyclooxygenase2 Inhibitors, Bioorganic & Medicinal Chemistry Letters, 5(20):2377-2380 (1995).
Schmid, G., et al., "Reaction of Areneselenyl Chlorides and Akenes. An Example of neucleophilic Displacement at Bivalent Selenium", J.Org. Chem, 48:4169-4172 (1983).
Krief, A., et al., "Synthesis of Selenones: A Comparative Study", J. Org. Chem Soc., Chem. Comm.. 569570 (1985).
Hoffman, R., et al, "2-[[(p-Nitrophenyl)sulfonyl]oxy] 3-Keto Esters as Intermediates for Regiospecific Preparation of 2-[[(p-Nitrophenyl)sulfonyl]oxy] Ketones", J. Org. Chem, 59(7): 1933-1936 (1994).
Aberhart, J., "(S)-(+)-2,3-Dihydroxy-3-methylbutanoic Acid by Syn Dihydroxyation of 3-Methylcrotonic Acid", J. Org. Chem, 45(25): 2518-5220 (1980).
Ramsey, B.G., et al., "Anisyl Neighboring Group Participation in Carbonium Ion Formation in Antimony Pentafluoride and Sulfur Dioxide", J. Org. Chem, 37(21): 3310-3322 (1972).
Kita, Y., et al., "A Convenient Synthesis of Dicarboxylic Monoesters Using Isopropenyl Esters: Synthesis of Oxaunomycin Derivatives", J. Chem Soc., Chem. Commun., 410-412 (1993).
Liesen, G., et a., "Activated Anhydrides of Tartaric and Malic Acid", J. Organic Chemistry, 52(3):455-457 (1987).
Kurumbail, R.G. et al, Structural Basis for selective inhibition of cyclooxygenase-2 by anti-inflammatory agents, Nature, 384(19/26): 644-648 (1996).
Li, J.J. et al, 1,2-Diarylcyclopentenes as Selective Cyclooxygenase-2 Inhibitors and Orally Active Anti-inflammatory Agents, J. Med. Chem., 38(22):4570-4578 (1995).
Li, J.J. et al, Novel Terphenyls as Selective Cyclooxygenase-2 Inhibitors and Orally Active Anti-inflammatory Agents, J. Med. Chem., 39:1846-1856 (1996).
Magolds, R.L., Structure-Activity-Relationship (SAR) with a Novel Series of Selective Cyclooxygenase-2 Inhibitors, Dupont Merck Pharmaceutical Company, 1-4.
Mitchell, J.A., Cyclooxygenase-2: Regulation and Relevance in Inflammation, Biochemical Pharmacology, 50(10):53-60 (1995).
Nannini, G. et al, Synthesis and pharmacological activity of some 5, 6-diphenylpyridazines, Eur. J. Med. Chem., 14(1):53-60 (1979).
Tsuijii, M., et al., "Cyclooxygenase-2-in Human Colon Cancer Cells Increases Metastatic Potential", Proc. Natl. Acad. Sci., 94: 3336-3340 (1997).
Penning, T.D. et al, Synthesis and Biological Evaluation of the 1,5-Diarylpyrazole Class of Cyclooxygenase-2 Inhibitors: Identification of 4-[5-(4-Methylphenyl)-3-(trifluoromethyl)-1$H$-pyrazol-1-yl]benzenesulfonamide (SC-58635, Celecoxib), J. Med. Chem., 40:1347-1365 (1997).
Pinto, D.J.P. et al, Chemistry and Pharmacokinetics of Diarylthiophenes and Terphenyls as Selective Cox-2 Inhibitors[1], Bioorganic & Medicinal Chemistry Letters, 6(24):2907-2912 (1996).
Reitz, D.B. et al., Novel 1,2-Diarylcyclopentenes are Selective, Potent, and Orally Active Cyclooxygenase Inhibitors, Med. Chem. Res., 5:351-363 (1995).
Reitz, D.B. et al., Selective Cyclooxygenase Inhibitors: Novel 4-Spiro 1,2- Diarylcyclopentenes are Potent and Orally Active COX-2 Inhibitors, Bioorganic & Medicinal Chemistry Letters, 5(8):867-872 (1995).
Bitan, G., et al., Building Units for N-Backbone Cyclic Peptides. 2. Synthesis of Protected N-(∞-thioalkylene)Amino Acids and Their Incorporation into Dipeptide Units, Tetrahedron, 1995, 51(38), 10513-10522.
Thérien, M., Synthesis and Biological Evaluation of 5,6-Diarylimidazo[2.1-b]Thiazole as Selective COX-2 Inhibitors, Bioorganic & Medicinal Chemistry Letters, 7(1):47-52 (1997).
Wilkerson, W.W. et al, Antiinflammatory 4,5-Diarylpyrooles. 2. Activity as a Function of Cyclooxygenase-2 Inhibition, J. Med. Chem., 38:3895-3901 (1995).
Wilkerson, W.W. et al, Antiinflammatory 4,5-Diarylpyrooles: Synthesis and QSAR, J. Med. Chem., 37:988-998 (1995).
Wong, E et al, Conversion of Prostaglandin G/H Synthase—1 into an Enzyme Sensitive to PGHS-2-selective Inhibitors by a Double His$^{513}$ΨArg and Iie$^{523}$ΨVal Mutation*, Journ. of Biol. Chem., 272(14):9280-9285 (1997).

* cited by examiner

PROSTAGLANDIN ENDOPEROXIDE H SYNTHASE BIOSYNTHESIS INHIBITORS

This application is a divisional application of U.S. Ser. No. 09/871,195, filed May 31, 2001, now abandoned; which is a divisional application of U.S. Ser. No. 09/427,768, filed Oct. 27, 1999, issued as U.S. Pat. No. 6,307,047; which is a continuation-in-part of U.S. Ser. No. 09/261,872, filed Mar. 3, 1999, now abandoned; which is a continuation-in-part of U.S. Ser. No. 09/179,605, filed Oct. 27, 1998, now abandoned; which is a continuation-in-part of U.S. Ser. No. 09/129,570, filed Aug. 5, 1998, now abandoned; which is based in-part on provisional application 60/056,733, filed Aug. 22, 1997.

TECHNICAL FIELD

The present invention encompasses novel pyridazinone compounds useful in the treatment of cyclooxygenase-2 mediated diseases. More particularly, this invention concerns a method of inhibiting prostaglandin biosynthesis, particularly the induced prostaglandin endoperoxide H synthase (PGHS-2, cyclooxygenase-2, COX-2) protein.

BACKGROUND OF THE INVENTION

The prostaglandins are extremely potent substances which produce a wide variety of biological effects, often in the nanomolar to picomolar concentration range. The discovery of two forms of prostaglandin endoperoxide H synthase, isoenzymes PGHS-1 and PGHS-2, that catalyze the oxidation of arachidonic acid leading to prostaglandin biosynthesis has resulted in renewed research to delineate the role of these two isozymes in physiology and pathophysiology. These isozymes have been shown to have different gene regulation and represent distinctly different prostaglandin biosynthesis pathways. The PGHS-1 pathway is expressed constitutively in most cell types. It responds to produce prostaglandins that regulate acute events in vascular homeostasis and also has a role in maintaining normal stomach and renal function. The PGHS-2 pathway involves an induction mechanism which has been linked to inflammation, mitogenesis and ovulation phenomena.

Prostaglandin inhibitors provide therapy for pain, fever, and inflammation, and are useful therapies, for example in the treatment of rheumatoid arthritis and osteoarthritis. The non-steroidal anti-inflammatory drugs (NSAIDs) such as ibuprofen, naproxen and fenamates inhibit both isozymes. Inhibition of the constitutive enzyme PGHS-1 results in gastrointestinal side effects including ulcers and bleeding and incidence of renal problems with chronic therapy. Inhibitors of the induced isozyme PGHS-2 may provide anti-inflammatory activity without the side effects of PGHS-1 inhibitors.

The problem of side-effects associated with NSAID administration has never completely been solved in the past. Enteric coated tablets and co-administration with misoprostol, a prostaglandin derivative, have been tried in an attempt to minimize stomach toxicity. It would be advantageous to provide compounds which are selective inhibitors of the induced isozyme PGHS-2.

The present invention discloses novel compounds which are selective inhibitors of PGHS-2.

SUMMARY OF THE INVENTION

The present invention discloses pyridazinone compounds which are selective inhibitors of cyclooxygenase-2 (COX-2). The compounds of the present invention have the formula I:

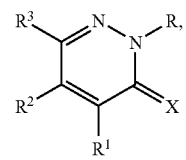

or a pharmaceutically acceptable salt, ester, or prodrug thereof, wherein

X is selected from the group consisting of O, S, —$NR^4$, —$NOR^a$, and —$NNR^bR^c$;

$R^4$ is selected from the group consisting of alkenyl, alkyl, aryl, arylalkyl, cycloalkenyl, cycloalkenylalkyl, cycloalkyl, cycloalkylalkyl, heterocyclic, and heterocyclic alkyl;

$R^a$, $R^b$, and $R^c$ are independently selected from the group consisting of alkyl, aryl, arylalkyl, cycloalkyl, and cycloalkylalkyl;

R is selected from the group consisting of alkenyl, alkoxy, alkoxyalkyl, alkoxyiminoalkoxy, alkyl, alkylcarbonylalkyl, alkylsulfonylalkyl, alkynyl, aryl, arylalkenyl, arylalkoxy, arylalkyl, arylalkynyl, arylhaloalkyl, arylhydroxyalkyl, aryloxy, aryloxyhaloalkyl, aryloxyhydroxyalkyl, arylcarbonylalkyl, carboxyalkyl, cyanoalkyl, cycloalkenyl, cycloalkenylalkyl, cycloalkyl, cycloalkylalkyl, cycloalkylidenealkyl, haloalkenyl, haloalkoxyhydroxyalkyl, haloalkyl, haloalkynyl, heterocyclic, heterocyclic alkoxy, heterocyclic alkyl, heterocyclic oxy, hydroxyalkyl, hydroxyiminoalkoxy, —$(CH_2)_nC(O)R^5$, —$(CH_2)_nCH(OH)R^5$, —$(CH_2)_nC(NOR^d)R^5$, —$(CH_2)_nCH(NOR^d)R^5$, —$(CH_2)_nCH(NR^dR^e)R^5$, —$R^6R^7$, —$(CH_2)_nC\equiv CR^7$, —$(CH_2)_n[CH(CX'_3)]_m(CH_2)_pR^7$, —$(CH_2)_n(CX'_2)_m(CH_2)_pR^7$, and —$(CH_2)_n(CHX')_m(CH_2)_pR^7$;

$R^5$ is selected from the group consisting of hydrogen, alkenyl, alkyl, alkynyl, aryl, arylalkyl, cycloalkenyl, cycloalkyl, haloalkenyl, haloalkyl, haloalkynyl, heterocyclic, and heterocyclic alkyl;

$R^6$ is selected from the group consisting of alkenylene, alkylene, halo-substituted alkenylene, and halo-substituted alkylene;

$R^7$ is selected from the group consisting of hydrogen, alkenyl, alkyl, alkynyl, aryl, arylalkyl, cycloalkyl, cycloalkenyl, haloalkyl, heterocyclic, and heterocyclic alkyl;

$R^d$ and $R^e$ are independently selected from the group consisting of hydrogen, alkenyl, alkyl, alkynyl, aryl, arylalkyl, cycloalkenyl, cycloalkyl, haloalkyl, heterocyclic, and heterocyclic alkyl;

X' is halogen;

m is an integer from 0–5;

n is an integer from 0–10; and p is an integer from 0–10; and $R^1$, $R^2$, and $R^3$ are independently selected from the group consisting of hydrogen, alkenyl, alkoxyalkyl, alkoxyiminoalkoxy, alkoxyiminoalkyl, alkyl, alkynyl, alkylcarbonylalkoxy, alkylcarbonylamino, alkylcarbonylaminoalkyl, aminoalkoxy, aminoalkylcarbonyloxyalkoxy aminocarbonylalkyl, aryl, arylalkenyl, arylalkyl, arylalkynyl, carboxyalkylcarbonyloxyalkoxy, cyano, cycloalkenyl, cycloalkyl, cycloalkylidenealkyl, haloalkenyloxy, haloalkoxy, haloalkyl, halogen, heterocyclic, hydroxyalkoxy, hydroxyiminoalkoxy, hydroxyiminoalkyl, mercaptoalkoxy, nitro, phosphonatoalkoxy, Y, and W; provided that one of $R^1$, $R^2$, or $R^3$ must be W, and further provided that only one of $R^1$, $R^2$, or $R^3$ is W;

W is selected from the group consisting of

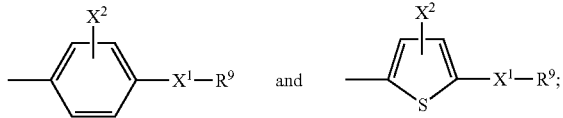

$X^1$ is selected from the group consisting of $S(O)_2$, $S(O)(NR^{10})$, $S(O)$, $Se(O)_2$, $P(O)(OR^{11})$, and $P(O)(NR^{12}R^{13})$;

$X^2$ is selected from the group consisting of hydrogen, alkenyl, alkyl, alkynyl and halogen;

$R^9$ is selected from the group consisting of alkenyl, alkoxy, alkyl, alkylamino, alkylcarbonylamino, alkynyl, amino, cycloalkenyl, cycloalkyl, dialkylamino, —NHNH$_2$, and —NCHN($R^{10}$)$R^{11}$;

$R^{10}$, $R^{11}$, $R^{12}$, and $R^{13}$ are independently selected from the group consisting of hydrogen, alkyl, and cycloalkyl, or $R^{12}$ and $R^{13}$ can be taken together, with the nitrogen to which they are attached, to form a 3–6 membered ring containing 1 or 2 heteroatoms selected from the group consisting of O, S, and $NR^7$;

Y is selected from the group consisting of —$OR^{14}$, —$SR^{14}$, —$C(R^{16})(R^{17})R^{14}$, —$C(O)R^{14}$, —$C(O)OR^{14}$, —$N(R^{16})C(O)R^{14}$, —$NC(R^{16})R^{14}$, and —$N(R^{16})R^{14}$;

$R^{14}$ is selected from the group consisting of hydrogen, alkenyl, alkoxyalkyl, alkyl, alkylthioalkyl, alkynyl, cycloalkenyl, cycloalkenylalkyl, cycloalkyl, cycloalkylalkyl, aryl, arylalkyl, heterocyclic, heterocyclic alkyl, hydroxyalkyl, and $NR^{18}R^{19}$; and $R^{16}$, $R^{17}$, $R^{18}$, and $R^{19}$ are independently selected from the group consisting of hydrogen, alkenyl, alkoxy, alkyl, cycloalkenyl, cycloalkyl, aryl, arylalkyl, heterocyclic, and heterocyclic alkyl.

DETAILED DESCRIPTION OF THE INVENTION

All patents, patent applications, and literature references cited in the specification are hereby incorporated by reference in their entirety. In the case of inconsistencies, the present disclosure, including definitions, will prevail.

In one embodiment, compounds of the present invention have formula I wherein, $R^2$ is W;

$X^1$ is selected from $S(O)_2$, $S(O)$, $Se(O)_2$, and $S(O)(NR^{10})$;

$R^9$ is selected from alkenyl, alkoxy, alkyl, alkylamino, alkylcarbonylamino, alkynyl, amino, cycloalkenyl, cycloalkyl, and dialkylamino; and X, $X^2$, R, $R^1$, $R^3$, and $R^{10}$ are as defined in formula I.

In another embodiment, compounds of the present invention have formula I wherein, $R^2$ is W;

W is

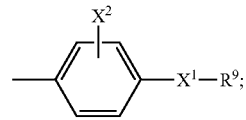

$X^1$ is selected from $S(O)_2$, $S(O)$, $Se(O)_2$, and $S(O)(NR^{10})$;

$R^9$ is selected from alkenyl, alkoxy, alkyl, alkylamino, alkylcarbonylamino, alkynyl, amino, cycloalkenyl, cycloalkyl, and dialkylamino; and X, $X^2$, R, $R^1$, $R^3$, and $R^{10}$ are as defined in formula I.

In another embodiment, compounds of the present invention have formula I wherein, $R^2$ is W;

W is

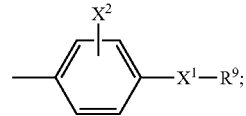

$X^2$ is selected from hydrogen and halogen;

R is selected from hydrogen, alkenyl, alkyl, alkynyl, alkylcarbonylalkyl, alkylsulfonylalkyl, carboxyalkyl, cyanoalkyl, haloalkyl, hydroxyalkyl, cycloalkyl, cycloalkylalkyl, aryl, arylalkenyl, arylalkynyl, heterocyclic, heterocyclic alkyl, arylalkyl, —$(CH_2)_nC(O)R^5$, —$(CH_2)_nC\equiv CR^7$, and —$(CH_2)_n[CH(CX'_3)]_m(CH_2)_pR^7$;

$R^1$ and $R^3$ are independently selected from hydrogen, alkenyl, alkoxyalkyl, alkyl, alkynyl, alkylcarbonylamino, alkylcarbonylaminoalkyl, aminocarbonylalkyl, aryl, cyano, cycloalkenyl, cycloalkenylalkyl, cycloalkyl, cycloalkylalkyl, haloalkyl, halogen, nitro, and Y; and X, $X^1$, X', $R^5$, $R^7$, $R^9$, n, m, p, and Y are as defined in formula I.

In another embodiment, compounds of the present invention have formula I wherein, $R^2$ is W;

W is

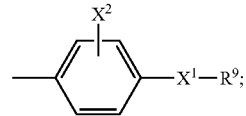

$X^2$ is selected from hydrogen and halogen;

R is selected from hydrogen, alkenyl, alkyl, alkynyl, alkylcarbonylalkyl, alkylsulfonylalkyl, carboxyalkyl, cyanoalkyl, haloalkyl, hydroxyalkyl, cycloalkyl, cycloalkylalkyl, aryl, arylalkenyl, arylalkynyl, heterocyclic, heterocyclic alkyl, arylalkyl, and —$(CH_2)_nC(O)R^5$;

$R^1$ and $R^3$ are independently selected from hydrogen, alkenyl, alkoxyalkyl, alkyl, alkynyl, alkylcarbonylamino, alkylcarbonylaminoalkyl, aminocarbonylalkyl, aryl, cyano, cycloalkenyl, cycloalkenylalkyl, cycloalkyl, cycloalkylalkyl, haloalkyl, halogen, heterocyclic, heterocyclic alkyl, nitro, and Y; and X, $X^1$, $R^5$, $R^9$, n, and Y are as defined in formula I.

In another embodiment, compounds of the present invention have formula I wherein, $R^2$ is W;

W is

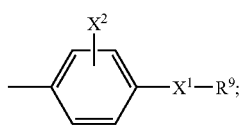

$X^2$ is selected from hydrogen and halogen;
R is selected from hydrogen, alkyl aryl, haloalkyl, heterocyclic, heterocyclic alkyl, and —$(CH_2)_nC(O)R^5$;
$R^1$ and $R^3$ are independently selected from hydrogen, alkenyl, alkoxyalkyl, alkyl, alkynyl, alkylcarbonylamino, alkylcarbonylamninoalkyl, aminocarbonylalkyl, aryl, cyano, cycloalkenyl, cycloalkenylalkyl, cycloalkyl, cycloalkylalkyl, haloalkyl, halogen, heterocyclic, heterocyclic alkyl, nitro, and Y; and
X, $X^1$, $R^5$, $R^9$, n, and Y are as defined in formula I.

In another embodiment, compounds of the present invention have formula I wherein,
$R^2$ is W;
W is

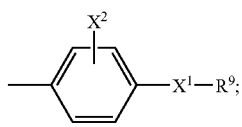

$X^2$ is selected from hydrogen and halogen;
R is selected from alkyl, aryl, haloalkyl, heterocyclic, heterocyclic alkyl, and arylalkyl wherein the aryl portion is optionally substituted with 1, 2, 3, 4, or 5 substituents selected from halogen; and
$R^1$ is selected from aryl, arylalkyl, heterocyclic, heterocyclic alkyl, hydroxyalkoxy, and Y; and
X, $X^1$, $R^3$, $R^9$, and Y are as defined in formula I.

In another embodiment, compounds of the present invention have formula I wherein,
$R^2$ is W;
W is

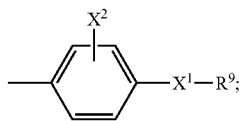

$X^2$ is selected hydrogen and halogen;
R is selected from the group consisting of alkyl, aryl, haloalkyl, heterocyclic, heterocyclic alkyl and arylalkyl wherein the aryl portion is optionally substituted with 1, 2, 3, 4, or 5 substituents selected from halogen;
$R^1$ is selected from the group consisting of aryl, arylalkyl, heterocyclic, heterocyclic alkyl, hydroxyalkoxy, and Y;
Y is —$OR^{14}$;
$R^{14}$ is selected from the group consisting of alkenyl, alkyl, and aryl;
$R^3$ is hydrogen; and
X, $X^1$, and $R^9$ are as defined in formula I.

In another embodiment, compounds of the present invention have formula I wherein,
$R^2$ is W;
W is

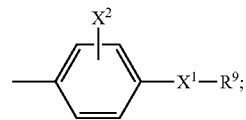

$X^1$ is $S(O)_2$;
$X^2$ is selected from hydrogen and halogen;
R is selected from aryl, haloalkyl, heterocyclic, heterocyclic alkyl and arylalkyl wherein the aryl portion is optionally substituted with 1, 2, 3, 4, or 5 substituents selected from halogen;
$R^1$ is aryl optionally substituted with 1, 2, or 3 substituents independently selected from chlorine and fluorine;
$R^3$ is hydrogen; and
X and $R^9$ are as defined in formula I.

In another embodiment, compounds of the present invention have formula I wherein,
$R^2$ is W;
W is

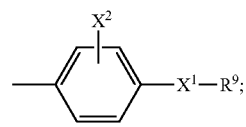

X is O;
$X^1$ is $S(O)_2$;
$R^9$ is selected from the group consisting of alkyl and amino;
$X^2$ is selected from hydrogen and halogen;
R is selected from alkenyl, alkyl, alkynyl, aryl, arylalkyl, and haloalkyl;
$R^1$ is selected from alkyl, aryl, arylalkyl, haloalkoxy, hydroxyalkoxy, and Y;
Y is —$OR^{14}$;
$R^{14}$ is selected from alkenyl, alkyl, and aryl; and
$R^3$ is hydrogen.

In another embodiment, compounds of the present invention have formula I wherein,
$R^2$ is W;
W is

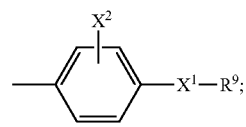

$X^1$ is $S(O)_2$;
$R^9$ is selected from alkyl and amino;
$X^2$ is selected from hydrogen and fluorine;
R is selected from haloalkyl, aryl, and alkyl;
$R^1$ is selected from isobutyloxy, isopentyloxy, 1-(3-methyl-3-butenyl)oxy, 2-hydroxy-2-methyl-propyloxy, 3-hydroxy-3-methylbutoxy, neopentyloxy, isopentyl, aryloxy, 4-fluorophenoxy, and aryl optionally substituted with 1, 2, or 3 substituents independently selected from the group consisting of chlorine and fluorine;
$R^3$ is hydrogen; and
X is as defined in formula I.

In another embodiment, compounds of the present invention have formula I wherein,
$R^2$ is W;
W is

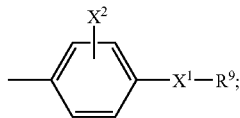

X is O;
$X^1$ is selected from $S(O)_2$ and $S(O)(NR^{10})$;
$R^9$ is alkyl;
$X^2$ is selected from hydrogen and fluorine;
R is selected from alkenyl, alkyl, alkynyl, aryl, arylalkyl and haloalkyl;
$R^1$ is selected from alkyl, aryl, hydroxyalkoxy and Y;
Y is —$OR^{14}$;
$R^{14}$ is selected from alkenyl, alkyl, and aryl;
$R^3$ is hydrogen; and
$R^{10}$ is as defined in formula I.

In another embodiment, compounds of the present invention have formula I wherein,
$R^2$ is W;
W is

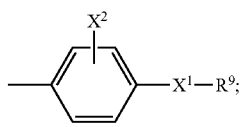

X is O;
$X^1$ is $S(O)_2$;
$R^9$ is amino;
$X^2$ is selected from hydrogen and fluorine;
R is selected from alkenyl, alkyl, alkynyl, aryl, arylalkyl, and haloalkyl;
$R^1$ is selected from alkyl, aryl, hydroxyalkoxy and Y;
Y is —$OR^4$;
$R^{14}$ is selected from alkenyl, alkyl, and aryl; and
$R^3$ is hydrogen.

In another embodiment, compounds of the present invention have formula I wherein,
$R^2$ is W;
W is

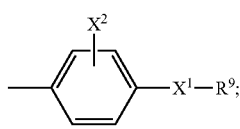

X is O;
$X^1$ is $SO_2$;
$R^9$ is methyl;
$X^2$ is hydrogen;
R is selected from t-butyl, 3-chlorophenyl, 3,4-difluorophenyl, 4-fluorophenyl, 4-chloro-3-fluorophenyl, 3-chloro-4-fluorophenyl, and 2,2,2-trifluoroethyl;
$R^1$ is selected from isobutoxy, isopentyloxy, (3-methyl-3-butenyl)oxy, 2-hydroxy-2-methyl-propoxy, 3-hydroxy-3-methylbutoxy, neopentyloxy, isopentyl, 4-fluorophenyl, 4-chlorophenyl, 4-chloro-3-fluoro-phenyl, 4-fluorophenoxy and Y;
Y is —$OR^{14}$;
$R^{14}$ is aryl; and
$R^3$ is hydrogen.

In another embodiment, compounds of the present invention have formula I wherein,
$R^2$ is W;
W is

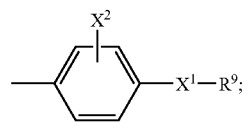

X is O;
$X^1$ $S(O)_2$;
$R^9$ is amino;
$X^2$ is hydrogen;
R is selected from t-butyl, 3-chlorophenyl, 3,4-difluorophenyl, 4-fluorophenyl, 4-chloro-3-fluorophenyl, 3-chloro-4-fluorophenyl, and 2,2,2-trifluoroethyl;
$R^1$ is selected consisting of isobutoxy, isopentyloxy, (3-methyl-3-butenyl)oxy, 2-hydroxy-2-methyl-propoxy, 3-hydroxy-3-methylbutoxy, neopentyloxy, isopentyl, 4-fluorophenyl, 4-chlorophenyl, 4-chloro-3-fluoro-phenyl, 4-fluorophenoxy, and Y;
Y is —$OR^{14}$;
$R^{14}$ is aryl; and
$R^3$ is hydrogen.

Another embodiment of the present invention relates to pharmaceutical compositions comprising a therapeutically effective amount of a compound of formula I or a pharmaceutically acceptable salt, ester, amide, or prodrug thereof in combination with a pharmaceutically acceptable carrier for inhibiting prostaglandin biosynthesis.

Another embodiment of the invention relates to a method of inhibiting prostaglandin biosynthesis comprising administering a therapeutically effective amount of a compound of formula I or a pharmaceutically acceptable salt, ester, amide, or prodrug thereof.

Another embodiment of the invention relates to a method of treating pain, fever, inflamation, rheumatoid arthritis, osteoartbritis, adhesions, and cancer comprising administering a therapeutically effective amount of a compound of formula I or a pharmaceutically acceptable salt, ester, amide, or prodrug thereof.

Another embodiment of the present invention relates to a method of preparing a compound of formula I wherein,
$R^2$ is W;
W is

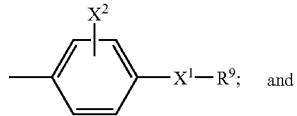

and

X, $X^1$, $X^2$, R, $R^1$, and $R^3$ are as defined in formula I; comprising the step of treating a compound of formula I wherein R is hydrogen with an alkylating agent.

Another embodiment of the present invention relates to a method of preparing a compound of formula I wherein, R² is W;
W is

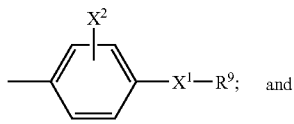

X, X¹, X², R, R¹, R², and R³ are as defined in formula I;

comprising the step of treating a compound of formula I wherein R is hydrogen with an alkylating agent, wherein the alkylating agent has the formula $R^{99}$-Q wherein Q is a leaving group and $R^{99}$ is selected from the group consisting of methyl, ethyl, 1,1,1-trifluoroethyl, cyclopropylmethyl, 3-(2-methyl)propenyl, 4-(2-methyl)but-2-enyl, 1,1-dichloropropen-3-yl, 2,2-dimethyl-3-oxo-4-butyl, 2,3,3,4,4,4-hexafluorobuten-1-yl, propargyl, phenylpropargyl, phenyl, phenethyl, 1-phenylpropen-3-yl, benzyl, α-methyl-4-fluorobenzyl, 2,3,4,5,6-pentafluorobenzyl, 4-trifluomethoxyphenacyl, 4-fluorobenzyl, 4-fluorophenyl, 2-trifluoromethylbenzyl, 2,4-difluorobenzyl, 2,4-difluorophenacyl, 4-trifluomethylphenacyl, phenacyl, 4-carboxyphenacyl, 4-chlorophenacyl, 4-cyanophenacyl, 4-diethylaminophenacyl, 3-thienylmethyl, 5-methylthien-2-ylmethyl, 5-chlorothien-2-ylmethyl, 2-benzo[b]thienylmethyl, 3-benzothienacyl, 5-chlorothiazol-2-ylmethyl, 5-methylthiazol-2-ylmethyl, 2-pyridylmethyl, 3-pyridylmethyl, 4-pyridylmethyl, quinolin-2-ylmethyl, and fluoroquinolin-2-ylmethyl.

Another embodiment of the present invention relates to a method of preparing a compound of formula I wherein,
R² is W;
W is

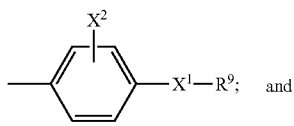

X, X¹, X², R, R¹, R², and R³ are as defined in formula I;

comprising the step of treating a compound of formula I wherein R is hydrogen with an alkylating agent, wherein the alkylating agent has the formula $R^{99}$-Q wherein Q is a leaving group and $R^{99}$ is selected from the group consisting of methyl, ethyl, 1,1,1-trifluoroethyl, cyclopropylmethyl, 3-(2-methyl)propenyl, 4-(2-methyl)but-2-enyl, 1,1-dichloropropen-3-yl, 2,3,3,4,4,4-hexafluorobuten-1-yl, propargyl, phenylpropargyl, phenyl, phenethyl, 1-phenylpropen-3-yl, benzyl, α-methyl-4-fluorobenzyl, 2,3,4,5,6-pentafluorobenzyl, 4-trifluomethoxyphenacyl, 4-fluorobenzyl, 4-fluorophenyl, 2,4-difluorobenzyl, 2,4-difluorophenacyl, 4-trifluomethylphenacyl, phenacyl, 4-carboxyphenacyl, 4-chlorophenacyl, 4-cyanophenacyl, 4-diethylamindphenacyl, 3-thienylmethyl, 5-methylthien-2-ylmethyl, 5-chlorothien-2-ylmethyl, 2-benzo[b]thienylmethyl, and 3-benzothienacyl.

Another embodiment of the present invention relates to a method of preparing a compound of formula I wherein,
R² is W;
W is

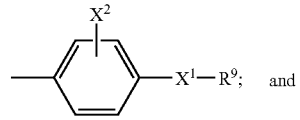

X, X¹, X², R, R¹, R², and R³ are as defined in formula I;

comprising the step of treating a compound of formula I wherein R is hydrogen with an alkylating agent, wherein the alkylating agent has the formula $R^{99}$-Q wherein Q is a leaving group and $R^{99}$ is selected from the group consisting of 1,1,1-trifluoroethyl, 3-(2-methyl)propenyl, 4-(2-methyl)but-2-enyl, 1,1-dichloropropen-3-yl, 2,3,3,4,4,4-hexafluorobuten-1-yl, propargyl, phenylpropargyl, phenyl, benzyl, α-methyl-4-fluorobenzyl, 2,3,4,5,6-pentafluorobenzyl, 4-fluorobenzyl, 4-fluorophenyl, 2,4-difluorobenzyl, 3-thienylmethyl, 5-methylthien-2-ylmethyl, 5-chlorothien-2-ylmethyl, and 2-benzo[b]thienylmethyl.

Another embodiment of the present invention relates to a method of preparing a compound of formula I wherein,
R² is W;
W is

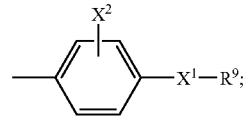

X, X¹, X², R, R¹, R², and R³ are as defined in formula I;

comprising the step of treating a compound of formula I wherein R is hydrogen with an alkylating agent, wherein the alkylating agent has the formula $R^{99}$-Q wherein Q is a leaving group and $R^{99}$ is selected from the group consisting of 1,1,1-trifluoroethyl, phenyl, benzyl, α-methyl 4-fluorobenzyl, 4-fluorobenzyl, 4-fluorophenyl, and 2,4-difluorobenzyl.

Another embodiment of the present invention relates to a method of preparing a compound of formula I wherein,
R² is W;
W is

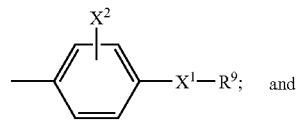

X, X¹, X², R, R¹, R², and R³ are as defined in formula I;

comprising the step of treating a compound of formula I wherein R is hydrogen with an alkylating agent, wherein the alkylating agent has the formula $R^{99}$-Q wherein Q is a leaving group and $R^{99}$ is selected from the group consisting of 1,1,1-trifluoroethyl, benzyl, and 4-fluorophenyl.

Another embodiment of the present invention relates to a method for regioselectively preparing a 4,5-disubstituted pyridazinone comprising the steps of a) treating a compound of formula IV

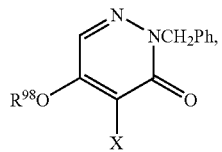

wherein $R^{98}$ is an alkyl or aryl group; and X is a leaving group;

with a nucleophilic agent to displace the X group;

b) converting the —$OR^{98}$ to a leaving group; and c) treating the compound with a second nucleophilic agent to provide the 4,5-disubstituted pyridazinone.

Another embodiment of the present invention relates to a method for regioselectively preparing a 4,5-disubstituted pyridazinone comprising the steps of a) treating a compound of formula IV

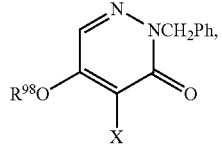

wherein $R^{98}$ is an alkyl or aryl group; and X is a leaving group;

with a nucleophilic agent to displace the X group;

b) converting the —$OR^{98}$ to a leaving group; and c) treating the compound with a second nucleophilic agent to provide the 4,5-disubstituted pyridazinone wherein the benzyl group is removed using a Lewis acid.

Another embodiment of the present invention relates to a method for regioselectively preparing a 4,5-disubstituted pyridazinone comprising the steps of treating a compound of formula V

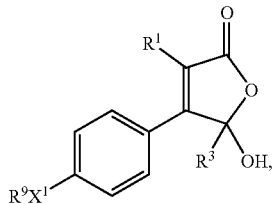

wherein $R^1$ and $R^3$ are independently selected from the group consisting of hydrogen, alkenyl, alkoxyalkyl, alkyl, alkynyl, alkylcarbonylamino, alkylcarbonylaminoalkyl, aminoalkoxy, alkylcarbonylalkoxy, aminocarbonylalkyl, aryl, arylalkenyl, arylalkyl, arylalkynyl, cyano, cycloalkenyl, cycloalkenylalkyl, cycloalkyl, cycloalkylalkyl, cycloalkylidenealkyl, haloalkenyloxy, haloalkoxy, haloalkyl, halogen, heterocyclic, heterocyclic alkyl, hydroxyalkoxy, hydroxyalkylamino, hydroxyalkylthio, mercaptoalkoxy, nitro, and Y;

Y is selected from the group consisting of —$OR^{14}$, —$SR^{14}$, —$C(R^{16})(R^{17})R^{14}$, —$C(O)R^{14}$, —$C(O)OR^{14}$, —$N(R^{16})C(O)R^{14}$, —$NC(R^{16})R^{14}$, and —$N(R^{16})R^{14}$;

$R^{14}$ is selected from the group consisting of hydrogen, alkenyl, alkoxyalkyl, alkyl, alkylthioalkyl, alkynyl, cycloalkenyl, cycloalkenylalkyl, cycloalkyl, cycloalkylalkyl, aryl, arylalkyl, heterocyclic, heterocyclic alkyl and $NR^{18}R^{19}$; and $R^{16}$, $R^{17}$, $R^{18}$, and $R^{19}$ are independently selected from the group consisting of hydrogen, alkenyl, alkoxy, alkyl, cycloalkenyl, cycloalkyl, aryl, arylalkyl, heterocyclic, and heterocyclic alkyl;

$X^1$ is selected from the group consisting of $S(O)_2$, $S(O)(NR^{10})$, $S(O)$, $Se(O)_2$, $P(O)(OR^{11})$, and $P(O)(NR^{12}R^{13})$;

$R^9$ is selected from the group consisting of alkenyl, alkoxy, alkyl, alkynyl, amino, cycloalkenyl, cycloalkyl, dialkylamino, —$NHNH_2$, and —$NCHN(R^{10})R^{11}$; and $R^{10}$, $R^{11}$, $R^{12}$, and $R^{13}$ are independently selected from the group consisting of hydrogen, alkyl, and cycloalkyl, or $R^{12}$ and $R^{13}$ can be taken together, with the nitrogen to which they are attached, to form a 3–6 membered ring containing 1 or 2 heteroatoms selected from the group consisting of O, S, and $NR^7$;

$R^7$ is selected from the group consisting of hydrogen, alkenyl, alkyl, alkynyl, aryl, arylalkyl, cycloalkyl, cycloalkenyl, haloalkyl, heterocyclic, and heterocyclic alkyl;

with a hydrazine having the formula $RNHNH_2$ wherein R is selected from the group consisting of alkenyl, alkoxy, alkoxyalkyl, alkyl, alkylcarbonylalkyl, alkylsulfonylalkyl, alkynyl, aryl, arylalkenyl, arylalkoxy, arylalkyl, arylalkynyl, arylhaloalkyl, arylhydroxyalkyl, aryloxy, aryloxyhaloalkyl, aryloxyhydroxyalkyl, arylcarbonylalkyl, carboxyalkyl, cyanoalkyl, cycloalkenyl, cycloalkenylalkyl, cycloalkyl, cycloalkylalkyl, haloalkenyl, haloalkoxyhydroxyalkyl, haloalkyl, haloalkynyl, heterocyclic, heterocyelic alkoxy, heterocyclic alkyl, heterocyclic oxy, hydroxyalkyl, —$(CH_2)_n$ $C(O)R^5$, —$(CH_2)_n CH(OH)R^5$, —$(CH_2)_n C(NOR^d)R^5$, —$(CH_2)_n CH(NOR^d)R^5$, —$(CH_2)_n CH(NR^d R^e) R^5$, —$R^6 R^7$, —$(CH_2)_n C\equiv CR^7$, —$(CH_2)_n [CH(CX'_3)]_m (CH_2)_n R^7$, —$(CH_2)_n (CX'_2)_m (CH_2)_n R^7$, and —$(CH_2)_n (CHX')_m (CH_2)_n$ $R^7$;

$R^5$ is selected from the group consisting of alkenyl, alkyl, alkynyl, aryl, arylalkyl, cycloalkenyl, cycloalkyl, haloalkenyl, haloalkyl, haloalkynyl, heterocyclic, and heterocyclic alkyl;

$R^6$ is selected from the group consisting of alkenylene, alkylene, halo-substituted alkenylene, and halo-substituted alkylene;

$R^7$ is selected from the group consisting of hydrogen, alkenyl, alkyl, alkynyl, aryl, arylalkyl, cycloalkyl, cycloalkenyl, haloalkyl, heterocyclic, and heterocyclic alkyl;

$R^d$ and $R^e$ are independently selected from the group consisting of hydrogen, alkenyl, alkyl, alkynyl, aryl, arylalkyl, cycloalkenyl, cycloalkyl, haloalkyl, heterocyclic, and heterocyclic alkyl;

X' is halogen;

n is an integer from 0–10;

m is an integer from 0–5;

to furnish the pyridazinone of formula III

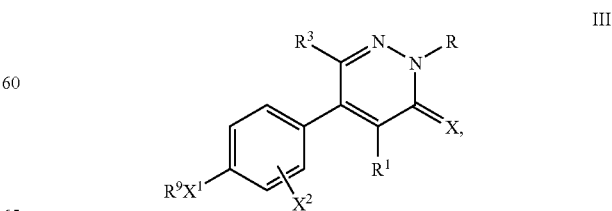

wherein $X^1$, R, $R^1$, $R^3$, and $R^9$ are as previously defined;

X is selected from the group consisting of O, S, —NR⁴, —NOR$^a$, and —NNR$^b$R$^c$;

R⁴ is selected from the group consisting of alkenyl, alkyl, aryl, arylalkyl, cycloalkenyl, cycloalkenylalkyl, cycloalkyl, cycloalkylalkyl, heterocyclic, and heterocyclic alkyl;

R$^a$, R$^b$, and R$^c$ are independently selected from the group consisting of alkyl, aryl, arylalkyl, cycloalkyl, and cycloalkylalkyl; and X² is selected from the group consisting of hydrogen, alkenyl, alkyl, alkynyl and halogen.

A preferred embodiment of the present invention relates to a compound of formula VI

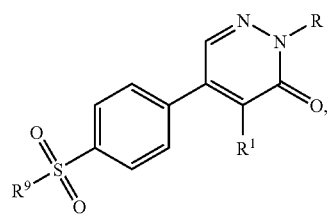

VI or a pharmaceutically acceptable salt, ester, or prodrug thereof, wherein

R is selected from alkyl aryl, arylalkyl, haloalkyl, and haloalkenyl;

R¹ is selected from alkoxy, aminoalkylcarbonyloxyalkoxy, carboxyalkylcarbonyloxyalkoxy, hydroxyalkyl, hydroxyalkoxy, and phosphonatoalkoxy, R⁹ is selected from alkyl, alkylcarbonylamino, and amino.

Another preferred embodiment of the present invention relates to a compound of formula VI wherein, R is aryl;
R¹ is hydroxyalkoxy; and
R⁹ is selected from alkyl and amino.

Another preferred embodiment of the present invention relates to a compound of formula VI wherein, R is aryl;
R¹ is hydroxyalkoxy; and
R⁹ is methyl.

Another preferred embodiment of the present invention relates to a compound of formula VI wherein, R is phenyl optionally substituted with 1, 2, 3, 4, or 5 substituents independently selected from halogen and haloalkyl;
R¹ is hydroxyalkoxy; and
R⁹ is selected from alkyl and amino.

Another preferred embodiment of the present invention relates to a compound of formula VI wherein, R is phenyl optionally substituted with 1 or 2 substituents independently selected from chlorine and fluorine;
R¹ is hydroxyalkoxy; and
R⁹ is selected from alkyl and amino.

Another preferred embodiment of the present invention relates to a compound of formula VI wherein, R is haloalkyl; and
R¹ is hydroxyalkoxy; and
R⁹ is selected from alkyl and amino.

Another preferred embodiment of the present invention relates to a compound of formula VI wherein, R is phenyl optionally substituted with 1, 2, 3, 4, or 5 substituents independently selected from halogen and haloalkyl;
R¹ is aminoalkylcarbonyloxyalkoxy; and R⁹ is selected from alkyl and amino.

Another preferred embodiment of the present invention relates to a compound of formula VI wherein, R is phenyl optionally substituted with 1, 2, 3, 4, or 5 substituents each independently selected from halogen and haloalkyl;
R¹ is carboxyalkylcarbonyloxyalkoxy; and
R⁹ is selected from alkyl and amino.

Another preferred embodiment of the present invention relates to a compound of formula VI wherein, R is phenyl optionally substituted with 1, 2, 3, 4, or 5 substituents each independently selected from halogen and haloalkyl;
R¹ is phosphonatoalkoxy; and
R⁹ is selected from alkyl and amino.

Another preferred embodiment of the present invention relates to a compound of formula VI wherein, R is phenyl optionally substituted with 1, 2, 3, 4, or 5 substituents each independently selected from halogen and haloalkyl;
R¹ is hydroxyalkoxy; and
R⁹ is alkylcarbonylamino.

Another preferred embodiment of the present invention relates to a compound of formula VI wherein, R is selected from haloalky and phenyl optionally substituted with 1, 2, 3, 4, or 5 substituents independently selected from halogen and haloalkyl;
R¹ is alkoxy; and
R⁹ is selected from the group consisting of alkyl, alkylcarbonylamino, and amino.

Another preferred embodiment of the present invention relates to a compound of formula VI wherein, R is tert-butyl;
R¹ is selected from the group consisting of aminoalkylcarbonyloxyalkoxy, carboxyalkylcarbonyloxyalkoxy, hydroxyalkoxy, and phosphonatoalkoxy; and
R⁹ is selected from the group consisting of alkyl, alkylcarbonylamino, and amino.

Another preferred embodiment of the present invention relates to 2-(3,4-difluorophenyl)-4-(3-hydroxy-3-methyl-1-butoxy)-5-[4-(methylsulfonyl)phenyl]-3(2H)-pyridazinone or a pharmaceutically acceptable salt, ester, or prodrug thereof.

Definitions of Terms

As used throughout this specification and the appended claims; the following terms have the following meanings:

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

The term "alkenylene," denotes a divalent group derived from a straight or branched chain hydrocarbon of from 2 to 10 carbon atoms containing at least one double bond. Representative examples of alkenylene include, but are not limited to, —CH=CH—, —CH=CH₂CH₂—, —CH=C(CH₃)CH₂—, and the like.

The term "alkoxy," as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, pentyloxy, hexyloxy and the like.

The term "alkoxyalkoxy," as used herein, refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, methoxymethoxy, and the like.

The term "alkoxyalkoxyalkyl," as used herein, refers to an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, 2-(2-methoxyethoxy)ethyl, and the like.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, methoxymethyl, and the like.

The term "alkoxyalkylcarbonyl," as used herein, refers to an alkoxyalkyl group, as defined herein, appended to the parent molecular moiety through a carbonyl group, as defined herein. Representative examples of alkoxyalkylcarbonyl include, but are not limited to, tert-butoxymethylcarbonyl, 2-ethoxyethylcarbonyl, 2-methoxyethylcarbonyl, methoxyethylcarbonyl, and the like.

The term "alkoxycarbonyl," as used herein, refers to an alkoxy group, as defined, herein, appended to the parent molecular moiety through a carbonyl group, as defined herein. Representative examples of alkoxycarbonyl include, but are not limited to, methoxycarbonyl, ethoxycarbonyl, tert-butoxycarbonyl, and the like.

The term "alkoxycarbonylalkenyl," as used herein, refers to an alkoxycarbonyl group, as defined herein, appended to the parent molecular moiety through an alkenyl group, as defined herein. Representative examples of alkoxycarbonylalkenyl include, but are not limited to, 3-methoxycarbonyl-1-propenyl, 4-ethoxycarbonyl-2-butenyl, and the like.

The term "alkoxycarbonylalkyl," as used herein, refers to an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, 2-tert-butoxycarbonylethyl, and the like.

The term "alkoxycarbonylalkylthio," as used herein, refers to an alkoxycarbonylalkyl group, as defined herein, appended to the parent molecular moiety through a thio moiety, as defined herein. Representative examples of alkoxycarbonylalkylthio include, but are not limited to, 3-methoxycarbonylpropylsulfanyl, 4-ethoxycarbonylbutylsulfanyl, and the like.

The term "alkoxyimino," refers to a $R_{85}ON=$ group wherein $R_{85}$ is alkyl, as defined herein.

The term "alkoxyiminoalkoxy," as used herein, refers to an alkoxyimino group, as defined herein, appended to the parent molecular moiety through an alkoxy group, as defined herein. Representative examples of alkoxyiminoalkoxy include, but are not limited to, 2-(methoxyimino)ethoxy, 2-(ethoxyimino)-1-propoxy, 3-(isopropoxyimino)-1-butoxy, and the like.

The term "alkoxyiminoalkyl," as used herein, refers to an alkoxyimino group, as defined herein, appended to the parent molecular moiety through an alkyl group, as defined herein. Representative examples of alkoxyiminoalkyl include, but are not limited to, 2-(methoxyimino)ethyl, 2-(ethoxyimino)-1-propyl, 3-(isopropoxyimino)-1-butyl, and the like.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like.

The term "alkylamino," as used herein, refers to an alkyl group, as defined herein, appended to the parent molecular moiety through an amino group, as defined herein. Representative examples of alkylamino include, but are not limited to, methylamino, ethylamino, propylamino, and the like.

The term "alkylaminosulfonyl," as used herein, refers to an alkylamino group, as defined herein, appended to the parent molecular moiety through a sulfonyl group, as defined herein. Representative examples of alkylaminosulfonyl include, but are not limited to, methylaminosulfonyl, ethylaminosulfonyl, propylaminosulfonyl, and the like.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, 1-oxopentyl, and the like.

The term "alkylcarbonylalkoxy," as used herein, refers to an alkylcarbonyl group, as defined herein, appended to the parent molecular moiety through an alkoxy group, as defined herein. Representative examples of alkylcarbonylalkoxy include, but are not limited to, 2-oxopropoxy, 3,3-dimethyl-2-oxopropoxy, 3-oxobutoxy, 3-oxobutoxy, 3-oxopentyloxy, and the like.

The term "alkylcarbonylalkyl," as used herein, refers to an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, 3-oxopentyl, and the like.

The term "alkylcarbonylamino," as used herein, refers to an alkylcarbonyl group, as defined herein, appended to the parent molecular moiety through an amino group, as defined herein. Representative examples of alkylcarbonylamino include, but are not limited to, acetylamino, 1-oxopropylamino, 2,2-dimethyl-1-oxopropylamino, and the like.

The term "alkylcarbonylamninoalkyl," as used herein, refers to an alkylcarbonylamino group, as defined herein, appended to the parent molecular moiety through an alkyl group, as defined herein. Representative examples of alkylcarbonylaminoalkyl include, but are not limited to, acetylaminomethyl, 2-(1-oxopropylamino)ethyl, and the like.

The term "alkylcarbonyloxy," as used herein, refers to an alkylcarbonyl group, as defined herein, appended to the parent molecular moiety through an oxy moiety, as defined herein. Representative examples of alkylcarbonyloxy include, but are not limited to, acetyloxy, ethylcarbonyloxy, tert-butylcarbonyloxy, and the like.

The term "alkylene," denotes a divalent group derived from a straight or branched chain hydrocarbon of from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, —$CH_2CH(CH_3)CH_2$—, and the like.

The term "alkylimino," as used herein, refers to $R_{81}N=$ group, wherein $R_{81}$ is alkyl, as defined herein.

The term "alkylsulfinyl," as used herein, refers to an alkyl group, as defined herein, appended to the parent molecular moiety through a sulfinyl group, as defined herein. Representative examples of alkylsulfinyl include, but are not limited, methylsulfinyl, ethylsulfinyl, and the like.

The term "alkylsulfinylalkyl," as used herein, refers to an alkylsulfinyl group, as defined herein, appended to the parent molecular moiety through an alkyl group, as defined herein. Representative examples of alkylsulfinylalkyl include, but are not limited, methylsulfinylmethyl, ethylsulfinylmethyl, and the like The term "alkylsulfonyl," as used herein, refers to an alkyl group, as defined herein, appended to the parent molecular moiety through a sulfonyl group, as defined herein. Representative examples of alkylsulfonyl include, but are not limited, methylsulfonyl, ethylsulfonyl, and the like.

The term "alkylsulfonylalkyl," as used herein, refers to an alkylsulfonyl group, as defined herein, appended to the parent molecular moiety through an alkyl group, as defined herein. Representative examples of alkylsulfonylalkyl include, but are not limited, methylsulfonylmethyl, 2-(ethylsulfonyl)ethyl, and the like.

The term "alkylsulfonylamino," as used herein, refers to an alkylsulfonyl group, as defined herein, appended to the parent molecular moiety through an amino group, as defined herein. Representative examples of alkylsulfonylamino include, but are not limited, methylsulfonylamino, ethylsulfonylamino, and the like.

The term "alkylthio," as used herein, refers to an alkyl group, as defined herein, appended to the parent molecular moiety through a thio moiety, as defined herein. Representative examples of alkylthio include, but are not limited, methylsulfanyl, ethylsulfanyl, tert-butylsulfanyl, hexylsulfanyl, and the like.

The term "alkylthioalkyl," as used herein, refers to an alkylthio group, as defined herein, appended to the parent molecular moiety through an alkyl group, as defined herein. Representative examples of alkylthioalkyl include, but are not limited, methylsulfanylmethyl, 2-(ethylsulfanyl)ethyl, and the like.

The term "alkylthioalkylcarbonyl," as used herein, refers to an alkylthioalkyl group, as defined herein, appended to the parent molecular moiety through a carbonyl group, as defined herein. Representative examples of alkylthioalkylcarbonyl include, but are not limited to, methylsulfanylmethylcarbonyl, 2-(ethylsulfanyl)ethylcarbonyl, and the like.

The term "alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, 1-butynyl and the like.

The term "alkynylene," denotes a divalent group derived from a straight or branched chain hydrocarbon of from 2 to 10 carbon atoms containing at least one triple bond. Representative examples of alkynylene include, but are not limited to, —C≡C—, —CH$_2$C≡C—, —CH(CH$_3$)CH$_2$C≡C—, —C≡CCH$_2$—, —C≡CCH(CH$_3$)CH$_2$—, and the like.

The term "amino," as used herein, refers to a —NH$_2$ group.

The term "aminoalkoxy," as used herein, refers to an amino group, as defined herein, appended to the parent molecular moiety through an alkoxy group, as defined herein. Representative examples of aminoalkoxy include, but are not limited to, 2-aminomethoxy, 3-aminopropoxy, 4-amino-1-methylhexyloxy, and the like.

The term "aminoalkyl," as used herein, refers to an amino group, as defined herein, appended to the parent molecular moiety through an alkyl group, as defined herein. Representative examples of aminoalkyl include, but are not limited to, aminomethyl, 2-aminoethyl, 3-aminopropyl, 4-amino-1-methylhexyl, and the like.

The term "aminoalkylcarbonyl," as used herein, refers to an aminoalkyl group, as defined herein, appended to the parent molecular moiety through an carbonyl group, as defined herein. Representative examples of aminoalkylcarbonyl include, but are not limited to, 2-amino-1-oxoethyl (2-aminoacetyl), 3-amino-1-oxopropyl, and the like.

The term "aminoalkylcarbonyloxy," as used herein, refers to an aminoalkylcarbonyl group, as defined herein, appended to the parent molecular moiety through an oxy moiety, as defined herein. Representative examples of aminoalkylcarbonyloxy include, but are not limited to, 2-amino-1-oxoethyloxy (2-aminoacetoxy), 3-amino-1-oxopropyloxy, and the like.

The term "aminoalkylcarbonyloxyalkoxy," as used herein, refers to an aminoalkylcarbonyloxy group, as defined herein, appended to the parent molecular moiety through an alkoxy group, as defined herein. Representative examples of aminoalkylcarbonyloxyalkoxy include, but are not limited to, 2-(2-amino-1-oxoethyloxy)ethoxy, 4-(3-amino-1-oxopropyloxy)butoxy, 3-(3-amino-1-oxopropyloxy)-3-methyl-1-butoxy, 3-(2-amino-1-oxoethyloxy)-3-methyl-1-butoxy and the like.

The term "aminocarbonyl," as used herein, refers to a H$_2$NC(O)— group.

The term "aminocarbonylalkoxy," as used herein, refers to an aminocarbonyl group, as defined herein, appended to the parent molecular moiety through an alkoxy group, as defined herein. Representative examples of aminocarbonylalkoxy include, but are not limited to, 2-(aminocarbonyl)ethoxy, 3-(aminocarbonyl)propoxy, and the like.

The term "aminocarbonylalkyl," as used herein, refers to an aminocarbonyl group, as defined herein, appended to the parent molecular moiety through an alkyl group, as defined herein. Representative examples of aminocarbonylalkyl include, but are not limited to, 2-(aminocarbonyl)ethyl, 3-(aminocarbonyl)propyl, and the like.

The term "aminosulfonyl," as used herein, refers to H$_2$NS(O)$_2$— group.

The term "aryl," as used herein, refers to a monocyclic-ring system, or a bicyclic- or a tricyclic-fused ring system wherein one or more of the fused rings are aromatic. Representative examples of aryl include, but are not limited to, azulenyl, indanyl, indenyl, naphthyl, phenyl, tetrahydronaphthyl, and the like.

The aryl groups of this invention can be substituted with 1, 2, or 3 substituents independently selected from alkenyl, alkenyloxy, alkoxy, alkoxyalkoxy, alkoxyalkoxyalkyl, alkoxyalkyl, alkoxyalkylcarbonyl, alkoxycarbonyl, alkoxycarbonylalkenyl, alkoxycarbonylalkyl, alkoxycarbonylalkylthio, alkyl, alkylamino, alkylaminosulfonyl, alkylcarbonyl, alkylcarbonylalkyl, alkylcarbonylamino, alkylcarbonyloxy, alkylimino, alkylsulfinyl, alkylsulfinylalkyl, alkylsulfonyl, alkylsulfonylalkyl, alkylsulfonylamino, alkylthio, alkylthioalkyl, alkylthioalkylcarbonyl, alkynyl, amino, aminocarbonyl, aminocarbonylalkoxy, aminosulfonyl, aryl, arylalkoxy, arylalkyl, aryloxy, arylcarbonyl, carboxy, carboxyalkenyl, carboxyalkoxy, carboxyalkyl, cyano, cyanoalkoxy, cyanoalkyl, cycloalkyl, dialkylamino, dialkylaminosulfonyl, ethylenedioxy, formyl, formylalkyl, halogen, haloalkoxy, haloalkyl, heterocyclic, heterocyclic alkoxy, heterocyclic alkyl, heterocyclic carbonyl, hydroxy, hydroxyalkoxy, hydroxyalkyl, methylenedioxy, mercapto, nitro, and sulfo. Representative examples of substituted aryl include, but are not limited to, 3-chlorophenyl, 3-fluorophenyl, 4-chlorophenyl, 4-fluorophenyl, 3,4-dichlorophenyl, 3-chloro-4-fluorophenyl, 3,4,-difluoorophenyl, 4-methylsulfonylphenyl, 4-aminosulfonylphenyl, pentaflurophenyl, and the like.

The term "arylalkenyl," as used herein, refers to an aryl group, as defined herein, appended to the parent molecular moiety through an alkenyl group, as defined herein. Representative examples of arylalkenyl include, but are not limited to, 3-phenylpropen-2-yl, 3-phenylpropen-3-yl, 2-naphth-2-ylbuten-4-yl, and the like.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy, 5-phenylpentyloxy, and the like.

The term "arylalkoxycarbonyl," as used herein, refers to an arylalkoxy group, as defined herein, appended to the parent molecular moiety through a carbonyl group, as defined herein. Representative examples of arylalkoxycarbonyl include, but are not limited to, benzyloxycarbonyl, naphth-2-ylmethoxycarbonyl, and the like.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

The term "arylalkylthio," as used herein, refers to an arylalkyl group, as defined herein, appended to the parent molecular moiety through a thio moiety, as defined herein. Representative examples of arylalkylthio include, but are not limited to, 2-phenylethylsulfanyl, 3-naphth-2-ylpropylsulfanyl, 5-phenylpentylsulfanyl and the like.

The term "arylalkynyl," as used herein, refers to an aryl group, as defined herein, appended to the parent molecular moiety through an alkynyl group, as defined herein. Representative examples of arylalkynyl include, but are not limited to, 3-phenylpropyn-2-yl, 3-phenylpropyn-3-yl, 2-naphth-2-ylbutyn-4-yl, and the like.

The term "arylcarbonyl," as used herein, refers to an aryl group, as defined herein, appended to the parent molecular moiety through a carbonyl group, as defined herein. Representative examples of arylcarbonyl include, but are not limited to, benzoyl, naphthoyl, and the like.

The term "arylcarbonylalkyl," as used herein, refers to an arylcarbonyl group, as defined herein, appended to the parent molecular moiety through an alkyl group, as defined herein. Representative examples of arylcarbonylalkyl include, but are not limited to, 3-benzoylpropyl, 3-naphthoylpropyl, and the like.

The term "arylhaloalkyl," as used herein, refers to an aryl group, as defined herein, appended to the parent molecular moiety through a haloalkyl group, as defined herein. Representative examples of arylhaloalkyl include, but are not limited to, 1,1-difluoro-3-phenylpropyl, 1,1-dibromo-3-phenylpropyl, 1,1-difluoro-2-naphth-2-ylethyl, and the like.

The term, "arylhydroxyalkyl," as used herein, refers to an aryl group, as defined herein, appended to the parent molecular moiety through a hydroxyalkyl group, as defined herein. Representative examples of arylhydroxyalkyl include, but are not limited to, 1-hydroxy-3-phenylpropyl, 2-hydroxy-3-phenylpropyl, 1-hydroxy-2-naphth-2-ylethyl, and the like.

The term "aryloxy," as used herein, refers to an aryl group, as defined herein, appended to the parent molecular moiety through an oxy moiety, as defined herein. Representative examples of aryloxy include, but are not limited to, phenoxy, naphthyloxy, 3-bromophenoxy, 4-chlorophenoxy, 4-methylphenoxy, 3,5-dimethoxyphenoxy, and the like.

The term "aryloxyalkyl," as used herein, refers to an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl, 3-bromophenoxymethyl, and the like.

The term "aryloxyhaloalkyl," as used herein, refers to an aryloxy group, as defined herein, appended to the parent molecular moiety through a haloalkyl group, as defined herein. Representative examples of aryloxyhaloalkyl include, but are not limited to, 1,1-difluoro-3-(naphth-2-yloxy)propyl, 1,1-difluoro-3-(4-bromophenoxy)butyl, and the like.

The term "aryloxyhydroxyalkyl," as used herein, refers to an aryloxy group, as defined herein, appended to the parent molecular moiety through a hydroxyalkyl group, as defined herein. Representative examples of aryloxyhydroxyalkyl include, but are not limited to, 1-hydroxy-3-(naphth-2-yloxy)propyl, 1-hydroxy-3-(4-bromophenoxy)butyl, and the like.

The term "arylthio," as used herein, refers to an aryl group, as defined herein, appended to the parent molecular moiety through a thio moiety, as defined herein. Representative examples of arylthio include, but are not limited to, phenylsulfanyl, naphth-2-ylsulfanyl, 5-phenylhexylsulfanyl, and the like.

The term "arylthioalkyl," as used herein, refers to an arylthio group, as defined herein, appended to the parent molecular moiety through an alkyl group, as defined herein. Representative examples of arylthioalkyl include, but are not limited to, phenylsulfanylmethyl, 2-naphth-2-ylsulfanylethyl, 5-phenylhexylsulfanylmethyl, and the like.

The term "azido," as used herein, refers to a —$N_3$ group.

The term "carbonyl," as used herein, refers to a —C(O)— group.

The term "carboxy," as used herein, refers to a —$CO_2H$ group.

The term "carboxyalkenyl," as used herein, refers to a carboxy group, as defined herein, appended to the parent molecular moiety through an alkenyl group, as defined herein. Representative examples of carboxyalkenyl include, but are not limited to, 3-carboxy-1-propenyl, 4-carboxy-1-butenyl, and the like.

The term "carboxyalkoxy," as used herein, refers to a carboxy group, as defined herein, appended to the parent molecular moiety through an alkoxy group, as defined herein. Representative examples of carboxyalkoxy include, but are not limited to, 3-carboxypropoxy, 4-carboxybutoxy, and the like.

The term "carboxyalkyl," as used herein, refers to a carboxy group, as defined herein, appended to the parent molecular moiety through an alkyl group, as defined herein. The alkyl portion of carboxyalkyl may contain 1 or 2 hydroxy groups, as defined herein. Representative examples of carboxyalkyl include, but are not limited to, carboxymethyl, 2-carboxyethyl, 1-hydroxy-3-carboxypropyl, 1,2-dihydroxy-3-carboxypropyl and the like.

The term "carboxyalkylcarbonyl," as used herein, refers to a carboxyalkyl group, as defined herein, appended to the parent molecular moiety through a carbonyl group, as defined herein. Representative examples of carboxyalkylcarbonyl include, but are not limited to, 2-carboxy-1-oxoethyl, 3-carboxy-2,3-dihydroxy-1-oxopropyl, 3-carboxy-1-oxopropyl, and the like.

The term "carboxyalkylcarbonyloxy," as used herein, refers to a carboxyalkylcarbonyl group, as defined herein, appended to the parent molecular moiety through an oxy moiety, as defined herein. Representative examples of carboxyalkylcarbonyloxy include, but are not limited to, 2-carboxy-1-oxoethoxy, 3-carboxy-2,3-dihydroxy-1-oxopropoxy, 3-carboxy-1-oxopropoxy, and the like.

The term "carboxyalkylcarbonyloxyalkoxy," as used herein, refers to a carboxyalkylcarbonyloxy group, as defined herein, appended to the parent molecular moiety through an alkoxy group, as defined herein. Representative examples of carboxyalkylcarbonyloxyalkoxy include, but are not limited to, 2-(2-carboxy-1-oxoethoxy)ethoxy, 3-(3-carboxy-2,3-dihydroxy-1-oxopropoxy)-3-methylbutoxy, 3-(3-carboxy-1-oxopropoxy)-2-methyl-1-propoxy, and the like.

The term "cyano," as used herein, refers to a —CN group.

The term "cyanoalkoxy," as used herein, refers to a cyano group, as defined herein, appended to the parent molecular moiety through an alkoxy group, as defined herein. Representative examples of cyanoalkoxy include, but are not limited to, 2-cyanoethoxy, 3-cyanopropoxy, and the like.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, 3-cyanopropyl, and the like.

The term "cycloalkenyl," as used herein, refers to a cyclalkyl group, as defined herein, containing one double bond. Representative examples of cycloalkenyl include, but are not limited to, cyclopentenyl, cyclohexenyl, cycloheptenyl, and the like.

The cycloalkenyl groups of this invention can be substituted with 1, 2, or 3 substituents selected from alkoxy, alkoxyalkoxy, alkoxycarbonyl, alkyl, alkylamino, alkylimino, alkylthio, amino, aminocarbonyl, aryl, arylalkyl, carboxy, cyano, cycloalkyl, dialkylamino, formyl, halogen, haloalkyl, hydroxy, oxo, mercapto, and nitro.

The term "cycloalkenylalkyl," as used herein, refers to cycloalkenyl group, as defined herein, appended to the parent molecular moiety through an alkyl group, as defined herein. Representative examples of cycloalkenylalkyl include, but are not limited to, cyclopentenylmethyl, cyclohexenylmethyl, and the like.

The term "cycloalkyl," as used herein, refers to a saturated cyclic hydrocarbon group containing from 3 to 8 carbons. Representative examples of cycloalkyl include, cyclopropyl, cyclobutyl, cyclopentyl, cyclohexyl, cycloheptyl, and cyclooctyl.

The cycloalkyl groups of this invention can be substituted with 1, 2, or 3 substituents selected from alkoxy, alkoxyalkoxy, alkoxycarbonyl, alkyl, alkylamino, alkylimino, alkylthio, amino, aminocarbonyl, aryl, arylalkyl, carboxy, cyano, cycloalkyl, dialkylamino, formyl, halogen, haloalkyl, hydroxy, oxo, mercapto, and nitro.

The term "cycloalkylalkyl," as used herein, refers to cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, 4-cycloheptylbutyl, and the like.

The term "cycloalkylcarbonyl," as used herein, refers to cycloalkyl group, as defined herein, appended to the parent molecular moiety through a carbonyl group, as defined herein. Representative examples of cycloalkylcarbonyl include, but are not limited to, cyclopropylcarbonyl, 2-cyclobutylcarbonyl, cyclohexylcarbonyl, and the like.

The term "cycloalkylidene," as used herein, refers to cycloalkyl group, as defined herein, appended to the parent molecular moiety through a double bond. Representative examples of cycloalkylidene include, but are not limited to, cyclopropylidene, cyclohexylidene, and the like.

The term "cycloalkylidenealkyl," as used herein, refers to cycloalkylidene group, as defined herein, appended to the parent molecular moiety through an alkyl group, as defined herein. Representative examples of cycloalkylidenealkyl include, but are not limited to, 2-cyclopropylideneethyl, 3-cyclohexylidenepropyl, and the like.

The term "dialkylamino," as used herein, refers to two independent alkyl groups, as defined herein, appended to the parent molecular moiety through an amino group. Representative examples of dialkylamino include, but are not limited to, diethylamino, dimethylamino, ethylmethylamino, and the like.

The term "dialkylaminosulfonyl," as used herein, refers to a dialkylamino group, as defined herein, appended to the parent molecular moiety through a sulfonyl group. Representative examples of dialkylaminosulfonyl include, but are not limited to, diethylaminosulfonyl, dimethylaminosulfonyl, ethylmethylaminosulfonyl, and the like.

The term "ethylenedioxy," as used herein, refers to a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl," as used herein, refers to a —C(O)H group.

The term "formylalkyl," as used herein, refers to a formyl group, as defined herein, appended to the parent molecular moiety through an alkyl group, as defined herein. Representative examples of formylalkyl include, but are not limited to, formylmethyl, 2-formylethyl, and the like.

The term "halo" or "halogen," as used herein, refers to —Cl, —Br, —I or —F.

The term "haloalkenyl," as used herein, refers to at least one halogen, as defined herein, appended to the parent molecular moiety through an alkenyl group, as defined herein. Representative examples of haloalkenyl include, but are not limited to, 2,3,3-trifluoropropen-3-yl, 2,2-difluoroethenyl, and the like.

The term "haloalkenyloxy," as used herein, refers to a haloalkenyl group, as defined herein, appended to the parent molecular moiety through an oxy group, as defined herein. Representative examples of haloalkenyloxy include, but are not limited to, 2,3,3-trifluoropropen-3-yloxy, 2,2-difluoroethenyloxy, and the like.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, pentafluoroethoxy, and the like.

The term "haloalkoxyhydroxyalkyl," as used herein, refers to a haloalkoxy group, as defined herein, appended to the parent molecular moiety through a hydroxyalkyl group, as defined herein. Representative examples of haloalkoxyhydroxyalkyl include, but are not limited to, 4-(trifluoromethoxy)-1-hydroxybutyl, 4-(difluoromethoxy)-1-hydroxybutyl, and the like.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

The term "haloalkynyl," as used herein, refers to at least one halogen, as defined herein, appended to the parent molecular moiety through an alkynyl group, as defined herein. Representative examples of haloalkynyl include, but are not limited to, 4,4,4-trifluorobutyn-2-yl, 3,3-difluoropropy-1-nyl, and the like.

The term "heterocycle" or "heterocyclic," as used herein, refers to a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepinyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, pyrrolyl, pyrrolinyl, pyrrolidinyl, tetrahydrofuranyl, tetrahydrothiophenyl, tetrazinyl, tetrazolyl, thiadiazolyl, thiadiazolinyl, thiadiazolidinyl, thiazolyl, thiazolinyl, thiazolidinyl, thiophenyl, thiomorpholinyl, 1,1-dioxidothiomorpholinyl, thiopyranyl, triazinyl, triazolyl, trithianyl, and the like. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzothiazolyl, benzothiophenyl, benzoxazolyl, benzofuranyl, benzopyranyl, benzothiopyranyl, benzodioxinyl, 1,3-benzodioxolyl, cinnolinyl, indazolyl, indolyl, indolinyl, indolizinyl, naphthyridinyl, isobenzofuranyl, isobenzothiophenyl, isoindolyl, isoindolinyl, isoquinolyl, phthalazinyl, pyranopyridyl, quinolyl, quinolizinyl, quinoxalinyl, quinazolinyl, tetrahydroisoquinolyl, tetrahydroquinolyl, thiopyranopyridyl, and the like. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzofuranyl, dibenzothiophenyl, naphthofuranyl, naphthothiophenyl, oxanthrenyl, phenazinyl, phenoxathiinyl, phenoxazinyl, phenothiazinyl, thianthrenyl, thioxanthenyl, xanthenyl, and the like.

The heterocyclic groups of this invention can be substituted with 1, 2,or 3 substituents independently selected from alkenyl, alkenyloxy, alkoxy, alkoxyalkoxy, alkoxyalkoxyalkyl, alkoxyalkyl, alkoxyalkylcarbonyl, alkoxycarbonyl, alkoxycarbonylalkenyl, alkoxycarbonylalkyl, alkoxycarbonylalkylthio, alkyl, alkylamino, alkylaminosulfonyl, alkylcarbonyl, alkylcarbonylalkyl, alkylcarbonylamino, alkylcarbonyloxy, alkylimino, alkylsulfinyl, alkylsulfinylalkyl, alkylsulfonyl, alkylsulfonylalkyl, alkylsulfonylamino, alkylthio, alkylthioalkyl, alkylthioalkylcarbonyl, alkynyl, amino, aminocarbonyl, aminocarbonylalkoxy, aminosulfonyl, aryl, arylalkoxy, arylalkyl, aryloxy, arylcarbonyl, carboxy, carboxyalkenyl, carboxyalkoxy, carboxyalkyl, cyano, cyanoalkoxy, cyanoalkyl, cycloalkyl, dialkylamino, dialkylaminosulfonyl, ethylenedioxy, formyl, formylalkyl, halogen, haloalkoxy, haloalkyl, heterocyclic, heterocyclic alkoxy, heterocyclic alkyl, heterocyclic carbonyl, hydroxy, hydroxyalkoxy, hydroxyalkyl, methylenedioxy, mercapto, nitro, and sulfo.

The term "heterocyclic alkoxy," as used herein, refers to a heterocyclic group, as defined herein, appended to the parent molecular moiety through an alkoxy group, as defined herein. Representative examples of heterocyclic alkoxy include, but are not limited to, 2-pyrid-3-ylethoxy, 3-quinolin-3-ylpropoxy, 5-pyrid-4-ylpentyloxy, and the like.

The term "heterocyclic alkyl," as used herein, refers to a heterocyclic, as defined herein, appended to the parent molecular moiety through an alkyl group, as defined herein. Representative examples of heterocyclic alkyl include, but are not limited to, pyrid-3-ylmethyl, 2-pyrimidin-2-ylpropyl, and the like.

The term "heterocyclic alkylthio," as used herein, refers to a heterocyclic alkyl group, as defined herein, appended to the parent molecular moiety through a thio moiety, as defined herein. Representative examples of heterocyclic alkylthio include, but are not limited to, 2-pyrid-3-ylethysulfanyl, 3-quinolin-3-ylpropysulfanyl, 5-pyrid-4-ylpentylsulfanyl, and the like.

The term "heterocyclic carbonyl," as used herein, refers to a heterocyclic, as defined herein, appended to the parent molecular moiety through a carbonyl group, as defined herein. Representative examples of heterocyclic carbonyl include, but are not limited to, pyrid-3-ylcarbonyl, quinolin-3-ylcarbonyl, sulfanylphen-2-ylcarbonyl, and the like.

The term "heterocyclic oxy," as used herein, refers to a heterocyclic group, as defined herein, appended to the parent molecular moiety through an oxy moiety, as defined herein. Representative examples of heterocyclic oxy include, but are not limited to, pyrid-3-yloxy, quinolin-3-yloxy, and the like.

The term "heterocyclic oxyalkyl," as used herein, refers to a heterocyclic oxy group, as defined herein, appended to the parent molecular moiety through an alkyl group, as defined herein. Representative examples of heterocyclic oxyalkyl include, but are not limited to, pyrid-3-yloxymethyl, 2-quinolin-3-yloxyethyl, and the like.

The term "heterocyclic thio," as used herein, refers to a heterocyclic group, as defined herein, appended to the parent molecular moiety through a thio moiety, as defined herein. Representative examples of heterocyclic thio include, but are not limited to, pyrid-3-ylsulfanyl, quinolin-3-ylsulfanyl, and the like.

The term "heterocyclic thioalkyl," as used herein, refers to a heterocyclic thio group, as defined herein, appended to the parent molecular moiety through an alkyl group, as defined herein. Representative examples of heterocyclic thioalkyl include, but are not limited to, pyrid-3-ylsulfanylmethyl, 2-quinolin-3-ylsulfanylethyl, and the like.

The term "hydroxy," as used herein, refers to an —OH group.

The term "hydroxyalkoxy," as used herein, refers to 1 or 2 hydroxy groups, as defined herein, appended to the parent molecular moiety through an alkoxy group, as defined herein. Representative examples of hydroxyalkoxy include, but are not limited to, hydroxymethoxy, 2-hydroxyethoxy, 2-hydroxy-2-methylethoxy, 3-hydroxy-1-propoxy, 4-hydroxy-1-butoxy, 3-hydroxy-3-methyl-1-butoxy, 2,3-dihydroxy-1-propoxy, and the like.

The term "hydroxyalkyl," as used herein, refers to 1 or 2 hydroxy groups, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2-ethyl-4-hydroxyheptyl, 2,3-dihydroxypropyl, and the like.

The term "hydroxyimino," refers to a HON= group.

The term "hydroxylminoalkoxy," as used herein, refers to a hydroxyimino group, as defined herein, appended to the parent molecular moiety through an alkoxy group, as defined herein. Representative examples of hydroxyiminoalkoxy include, but are not limited to, hydroxyiminomethoxy, 2-hydroxyiminoethoxy, 2-hydroxyiminopropoxy, and the like.

The term "hydroxyiminoalkyl," as used herein, refers to a hydroxyimino group, as defined herein, appended to the parent molecular moiety through an alkyl group, as defined herein. Representative examples of hydroxyiminoalkyl include, but are not limited to, hydroxyiminomethyl, 2-hydroxyiminoethyl, 2-hydroxyiminopropyl, and the like.

The term "imino," as used herein, refers to a HN= group.

The term "iminoalkoxy," as used herein, refers to an imino group, as defined herein, appended to the parent molecular moiety through an alkoxy group, as defined herein. Representative examples of iminoalkoxy include, but are not limited to, 2-iminoethoxy, 2-imino-1-propoxy, 3-imino-1-butoxy, and the like.

The term "iminoalkyl," as used herein, refers to an imino group, as defined herein, appended to the parent molecular moiety through an alkyl group, as defined herein. Representative examples of iminoalkyl include, but are not limited to, 2-iminoethyl, 2-imino-1-propyl, 3-imino-1-butyl, and the like.

The term "mercapto," as used herein, refers to a —SH group.

The term "mercaptoalkoxy," as used herein, refers to a mercapto group, as defined herein, appended to the parent molecular moiety through an alkoxy group, as defined herein. Representative examples of mercaptoalkoxy include, but are not limited to, 2-mercaptoethoxy, 3-mercaptopropoxy, and the like.

The term "mercaptoalkyl," as used herein, refers to a mercapto group, as defined herein, appended to the parent molecular moiety through an alkyl group, as defined herein. Representative examples of mercaptoalkyl include, but are not limited to, 2-mercaptoethyl, 3-mercaptopropyl, and the like.

The term "methylenedioxy," as used herein, refers to a —OCH$_2$O— group wherein the oxygen atoms of the methylenedioxy are attached to the parent molecular moiety through two adjacent carbon atoms.

The term "nitro," as used herein, refers to a —NO$_2$ group.

The term "oxo," as used herein, refers to a =O moiety.

The term "oxy," as used herein, refers to a —O— moiety.

The term "phosphonato," as used herein, refers to a (R$_{84}$O)$_2$P(O)O— group wherein R$_{84}$ is selected from hydrogen and alkyl, as defined herein.

The term "phosphonatoalkoxy," refers to a phosphonato group, as defined herein, appended to the parent molecular moiety through an alkoxy group, as defined herein. Representative example of phosphonatoalkoxy include, but are not limited to, 3-hydroxypropyl dihydrogen phosphate, 3-hydroxy-1,1-dimethylpropyl dihydrogen phosphate, and the like.

The term "sulfinyl," as used herein, refers to a —S(O)— group.

The term "sulfo," as used herein, refers to a —SO$_3$H group.

The term "sulfonyl," as used herein, refers to a —S(O)$_2$— group.

The term "thio," as used herein, refers to a —S— moiety.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quatemized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid.

Basic addition salts can be prepared in situ during the final isolation and purification of the compounds of formula I, or separately by reacting a carboxylic acid function with a suitable base such as the hydroxide, carbonate or bicarbonate of a pharmaceutically acceptable metal cation or with ammonia, or an organic primary, secondary or tertiary amine. Such pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary arumonium, and amine cations, including, but not limited to ammonium, tetramethylammonium, tetraethylammonium, methylamine, dimethylamine, trimethylaamine, triethylamine, ethylamine, and the like. Other representative organic amines useful for the formation of base addition salts include diethylamine, ethylenediamine, ethanolamine, diethanolamine, piperazine and the like.

The term "pharmaceutically acceptable ester" as used herein refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyates, acrylates and ethylsuccinates.

The term "pharmaceutically acceptable prodrug" as used herein refers to those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to provide the parent compound having the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

As used throughout this specification and the appended claims, the term metabolically cleavable group denotes a moiety which is readily cleaved in vivo from the compound bearing it, wherein said compound, after cleavage remains or becomes pharmacologically active. Metabolically cleavable groups form a class of groups reactive with the carboxyl group of the compounds of this invention are well known to practitioners of the art. They include, but are not limited to groups such as, for example, alkylcarbonyl, such as acetyl, propionyl, butyryl, and the like; unsubstituted and substituted arylcarbonyl, such as benzoyl and substituted benzoyl; alkoxycarbonyl, such as ethoxycarbonyl; trialkylsilyl, such as trimethyl- and triethysilyl; monoesters formed with dicarboxylic acids, such as succinyl, and the like. Because of the ease with which the metabolically cleavable groups of the compounds of this invention are cleaved in vivo, the compounds bearing such groups act as pro-drugs of other prostaglandin biosynthesis inhibitors. The compounds bearing the metabolically cleavable groups have the advantage that they may exhibit improved bioavailability as a result of enhanced solubility and/or rate of absorption conferred upon the parent compound by virtue of the presence of the metabolically cleavable group.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

The present invention discloses pyridazinone compounds which are cyclooxygenase (COX) inhibitors and are selective inhibitors of cyclooxygenase-2 (COX-2). COX-2 is the inducible isoform associated with inflammation, as opposed to the constitutive isoform, cyclooxygenase-1 (COX-1) which is an important "housekeeping" enzyme in many tissues, including the gastrointestinal (GI) tract and the kidneys.

Preferred compounds of the present invention include, but are not limited to,

2-Benzyl-4-(4-fluorophenyl)-5-[4-(methylthio)phenyl]-3(2H)-pyridazinone;

2-Benzyl-4-(4-fluorophenyl)-5-[4-(methylsulfonyl)phenyl]-3(2H)-pyridazinone;

2-Benzyl-4-(4-fluorophenyl)-5-methoxy-3(2H)-pyridazinone;

2-Benzyl-4-(4-fluorophenyl)-5-hydroxy-3(2H)-pyridazinone;

2-Benzyl-4-(4-fluorophenyl)-5-(trifluoromethylsulfonyloxy)-3(2H)-pyridazinone;

2-Benzyl-4-(4-fluorophenyl)-5-[4-(methylthio)phenyl]-3(2H)-pyridazinone;

2-Benzyl-4-(4-fluorophenyl)-5-[4-(methylsulfonyl)phenyl]-3(2H)-pyridazinone;

2-Phenyl-4-(4-fluorophenyl)-5-[4-(methylsulfonyl)phenyl]-3(2H)-pyridazinone;

2-(4-Fluorobenzyl)-4-(4-fluorophenyl)-5-[4-(methylsulfonyl)phenyl]-3(2H)-pyridazinone;

2-(Phenylpropargyl)-4-(4-fluorophenyl)-5-[4-(methylsulfonyl)phenyl]-3(2H)-pyridazinone;

2-(2,4-Difluorobenzyl)-4-(4-fluorophenyl)-5-[4-(methylsulfonyl)phenyl]-3(2H)-pyridazinone;

2-(Methyl-2-propenyl)-4-(4-fluorophenyl)-5-[4-(methylsulfonyl)phenyl]-3(2H)-pyridazinone;

2-(3-Methyl-2-butenyl)-4-(4-fluorophenyl)-5-[4-(methylsulfonyl)phenyl]-3(2H)-pyridazinone;

2-(2-Trifluoromethylbenzyl)-4-(4-fluorophenyl)-5-[4-(methylsulfonyl)phenyl]-3(2H)-pyridazinone;

2-(Cyclopropylmethyl)-4-(4-fluorophenyl)-5-[4-(methylsulfonyl)phenyl]-3(2H)-pyridazinone;

2-(2-Pyridylmethyl)-4-(4-fluorophenyl)-5-[4-(methylsulfonyl)phenyl]-3(2H)-pyridazinone;

2-(4-Pyridylmethyl)-4-(4-fluorophenyl)-5-[4-(methylsulfonyl)phenyl]-3(2H)-pyridazinone;

2-(3-Pyridylmethyl)-4-(4-fluorophenyl)-5-[4-(methylsulfonyl)phenyl]-3(2H)-pyridazinone;

2-(6-Fluoroquinolin-2-ylmethyl)-4-(4-fluorophenyl)-5-[4-(methylsulfonyl)phenyl]-3(2H)-pyridazinone;

2-(Quinolin-2-ylmethyl)-4-(4-fluorophenyl)-5-[4-(methylsulfonyl)phenyl]-3(2H)-pyridazinone;

2-Benzyl-4-(4-fluorophenyl)-5-[4-(methylsulfonyl)phenyl]-3(2H)-pyridazinethione

2-Benzyl-4-(4-fluorophenyl)-5-[4-(aminosulfonyl)phenyl]-3(2H)-pyridazinone;

2-(2,2,2-Trifluoroethyl)-4-(4-fluorophenyl)-5-[4-(methylsulfonyl)phenyl]-3(2H)-pyridazinone;

2-(3,3-Dichloro-2-propenyl)-4-(4-fluorophenyl)-5-[4-(methylsulfonyl)phenyl]-3(2H)-pyridazinone;

2-(3-Phenyl-2-propenyl)-4-(4-fluorophenyl)-5-[4-(methylsulfonyl)phenyl]-3(2H)-pyridazinone;

2-(4-Carboxyphenacyl)-4-(4-fluorophenyl)-5-[4-(methylsulfonyl)phenyl]-3(2H)-pyridazinone;

2-(5-Methylthiazol-2-ylmethyl)-4-(4-fluorophenyl)-5-[4-(methylsulfonyl)phenyl]-3(2H)-pyridazinone;

2-(5-Chlorothiazol-2-ylmethyl)-4-(4-fluorophenyl)-5-[4-(methylsulfonyl)phenyl]-3(2H)-pyridazinone;

2-(2,3,3,4,4,4-Hexafluorobuten-1-yl)-4-(4-fluorophenyl)-5-[4-(methylsulfonyl)phenyl]-3(2H)-pyridazinone;

2-(2,4-Difluorophenacyl)-4-(4-fluorophenyl)-5-[4-(methylsulfonyl)phenyl]-3(2H)-pyridazinone;

2-(5-Chlorothien-2-ylmethyl)-4-(4-fluorophenyl)-5-[4-(methylsulfonyl)phenyl]-3(2H)-pyridazinone;

2-(5-Methylthien-2-ylmethyl)-4-(4-fluorophenyl)-5-[4-(methylsulfonyl)phenyl]-3(2H)-pyridazinone;

2-(4-Diethylaminophenacyl)-4-(4-fluorophenyl)-5-[4-(methylsulfonyl)phenyl]-3(2H)pyridazinone;
2-(2,3,4,5,6-Pentafluorobenzyl)-4-(4-fluorophenyl)-5-[4-(methylsulfonyl)phenyl]-3(2H)-pyridazinone;
2-(Phenacyl)-4-(4-fluorophenyl)-5-[4-(methylsulfonyl)phenyl]-3(2H)-pyridazinone;
2-(4-Chlorophenacyl)-4-(4-fluorophenyl)-5-[4-(methylsulfonyl)phenyl]-3(2H)-pyridazinone;
2-(Propargyl)-4-(4-fluorophenyl)-5-[4-(methylsulfonyl)phenyl]-3(2H)-pyridazinone;
2-(4-Cyanophenacyl)-4-(4-fluorophenyl)-5-[4-(methylsulfonyl)phenyl]-3(2H)-pyridaznoee;
2-(α-Methyl-4-fluorobenzyl)-4-(4-fluorophenyl)-5-[4-(methylsulfonyl)phenyl]-3(2H)-pyridazinone;
2-Phenethyl-4-(4-fluorophenyl)-5-[4-(methylsulfonyl)phenyl]-3(2H)-pyridazinone;
2-Benzyl-4-(3-chloro-4-fluorophenyl)-5-[4-(methylsulfonyl)phenyl]-3(2H)-pyridazinone;
2-Benzyl-4-(4-chlorophenyl)-5-[4-(methylsulfonyl)phenyl]-3(2H)-pyridazinone;
2-(2,2,2-Trifluoroethyl)-4-(3-chloro-4-fluorophenyl)-5-[4-(methylsulfonyl)phenyl]-3(2H)-pyridazinone;
2-(4-Trifluoromethoxyphenacyl)-4-(4-fluorophenyl)-5-[4-(methylsulfonyl)phenyl]-3(2H)-pyridazinone;
2-(4-Trifluoromethylphenacyl)-4-(4-fluorophenyl)-5-[4-(methylsulfonyl)phenyl]-3(2H)-pyridazinone;
2-[2-(Benzo[b]thien-3-yl)-2-oxoethyl]-4-(4-fluorophenyl)-5-[4-(methylsulfonyl)phenyl]-3(2H)-pyridazinone;
2-(2,2,2-Trifluoroethyl)-4-(4-chlorophenyl)-5-[4-(methylsulfonyl)phenyl]-3(2H)-pyridazinone;
2-(3,3-Dimethyl-2-oxobutyl)-4-(4-fluorophenyl)-5-[4-(methylsulfonyl)phenyl]-3(2H)-pyridazinone;
2-(3-Thienylmethyl)-4-(4-fluorophenyl)-5-[4-(methylsulfonyl)phenyl]-3(2H)-pyridazinone;
2-(2-Benzo[b]thienylmethyl)-4-(4-fluorophenyl)-5-[4-(methylsulfonyl)phenyl]-3(2H)-pyridazinone;
2,4-Bis(4-fluorophenyl)-5-[4-(methylsulfonyl)phenyl]-3(2H)-pyridazinone;
4-(4-Fluorophenyl)-5-[4-(methylsulfonyl)phenyl]-6-methyl-3(2H)-pyridazinone;
2-(2,2,2-Trifluoroethyl)-4-(4-fluorophenyl)-5-[4-(methylsulfonyl)phenyl]-6-methyl-3(2H)-pyridazinone;
2-Benzyl-4-(3,4-dichlorophenyl)-5-[4-(methylsulfonyl)phenyl]-3(2H)-pyridazinone;
2-(2,2,2-Trifluoroethyl)-4-(4-n-propylphenyl)-5-[4-(methylsulfonyl)phenyl]-3(2H)-pyridazinone;
2-(2,2,2-Trifluoroethyl)-4-(4-chloro-3-fluorophenyl)-5-[4-(methylsulfonyl)phenyl]-3(2H)-pyridazinone;
2-(2,2,2-Trifluoroethyl)-4-(4-fluorophenyl)-5-[4-(aminosulfonyl)phenyl]-3(2H)-pyridazinone;
2-(2,2,2-Trifluoroethyl)-4-(4-chlorophenyl)-5-[4-(aminosulfonyl)phenyl]-3(2H)-pyridazinone;
2-(2,2,2-Trifluoroethyl)-4-(2-propoxy)-5-[4-(aminosulfonyl)phenyl]-3(2H)-pyridazinone;
2-(2,2,2-Trifluoroethyl)-4-(4-fluorophenoxy)-5-[4-(aminosulfonyl)phenyl]-3(2H)-pyridazinone;
2,4-Bis-(4-fluorophenyl)-5-[3-fluoro-4-(aminosulfonyl)phenyl]-3(2H)-pyridazinone;
2-(2,2,2-Trifluoroethyl)-4-(4-chloro-3-fluorophenyl)-5-[4-(aminosulfonyl)phenyl]-3(2H)-pyridazinone;
2-Benzyl-4-(2-propoxy)-5-[4-(methylsulfonyl)phenyl]-3(2H)-pyridazinone;
2-Benzyl-4-(4-fluorophenoxy)-5-[4-(methylsulfonyl)phenyl]-3(2H)-pyridazinone;
2-(2,2,2-Trifluoroethyl)-4-(4-fluorophenoxy)-5-[4-(methylsulfonyl)phenyl]-3(2H)-pyridazinone;
2-(2,2,2-Trifluoroethyl)-4-(4-chlorophenyl)-5-[4-(methylsulfinyl)phenyl]-3(2H)-pyridazinone;
2-Benzyl-4-chloro-5-[4-(methylsulfonyl)phenyl]-3(2H)-pyridazinone;
2-(2,2,2-Trifluoroethyl)-4-(4-methylphenyl)-5-[4-(methylsulfonyl)phenyl]-3(2H)-pyridazinone;
2-(2,2,2-Trifluoroethyl)-4-(4-chloro-3-fluorophenyl)-5-[4-(aminosulfonyl)phenyl]-3(2H)-pyridazinone;
2-(2,2,2-Trifluoroethyl)-4-(3,4-dichlorophenyl)-5-[4-(methylsulfonyl)phenyl]-3(2H)-pyridazinone;
2-Benzyl-4-(2-propylamino)-5-[4-(methylsulfonyl)phenyl]-3(2H)-pyridazinone;
2-(2,2,2-Trifluoroethyl)-4-(2-propoxy)-5-[4-(methylsulfonyl)phenyl]-3(2H)-pyridazinone;
2-(2,2,2-Trifluoroethyl)-4-cyclohexyloxy-5-[4-(methylsulfonyl)phenyl]-3(2H)-pyridazinone;
2-(2,2,2-Trifluoroethyl)-4-cyclopentyloxy-5-[4-(methylsulfonyl)phenyl]-3(2H)-pyridazinone;
2-(2,2,2-Trifluoroethyl)-4-(2propylamino)-5-[4-(methylsulfonyl)phenyl]-3(2H)-pyridazinone;
2-Benzyl-4-(4-morpholino)-5-[4-(methylsulfonyl)phenyl]-3(2H)-pyridazinone;
2-(2,3,3-Trifluoro-2-propen-1-yl)]-4-(4-fluorophenyl)-5-[4-(methylsulfonyl)phenyl]-3(2H)-pyridazinone;
2,4-Bis(4-fluorophenyl)-5-[4-(aminosulfonyl)phenyl]-3(2H)-pyridazinone;
2-(2,2,2-Trifluoroethyl)-4-cyclopropylmethoxy-5-[4-(methylsulfonyl)phenyl]-3(2H)-pyridazinone;
2-(2,2,2-Trifluoroethyl)-4-(3-propen-1-oxy)-5-[4-(methylsulfonyl)phenyl]-3(2H)-pyridazinone;
2-(2,2,2-Trifluoroethyl)-4-(4-fluoro-α-methylbenzyloxy)-5-[4-(methylsulfonyl)phenyl]-3(2H)-pyridazinone;
2-[4-(Methylthio)phenyl]-4-(4-fluorophenyl)-5-[4-(methylsulfonyl)phenyl]-3(2H)-pyridazinone;
2,5-Bis[4-(methylsulfonyl)phenyl]-4-(4-fluorophenyl)-3(2H)-pyridazinone;
2-(3-Methyl-2-thienyl)-4-(4-fluorophenyl)-5-[4-(methylsulfonyl)phenyl]-3(2H)-pyridazinone;
2-(2-Trifluoromethyl-4-nitrophenyl)-4-(4-fluorophenyl)-5-[4-(methylsulfonyl)phenyl]-3(2H)-pyridazinone;
2-[3-(Methylthio)phenyl]-4-(4-fluorophenyl)-5-[4-(methylsulfonyl)phenyl]-3(2H)-pyridazinone;
2-[3-(Methylsulfonyl)phenyl]-4-(4-fluorophenyl)-5-[4-(methylsulfonyl)phenyl]-3(2H)-pyridazinone;
2-(4-Fluorophenyl)-4-(4-chlorophenyl)-5-[4-(methylsulfonyl)phenyl]-3(2H)-pyridazinone;
2-(5-Chloro-2-thienyl)-4-(4-chlorophenyl)-5-[4-(methylsulfonyl)phenyl]-3(2H)-pyridazinone;
2-(3-Trifluoromethylphenyl)-4-(4-chlorophenyl)-5-[4-(methylsulfonyl)phenyl]-3(2H)-pyridazinone;
2-(3-Chloro-4-fluorophenyl)-4-(4-chlorophenyl)-5-[4-(methylsulfonyl)phenyl]-3(2H)-pyridazinone;
2-(3-Fluorophenyl)-4-(4-fluorophenyl)-5-[4-(methylsulfonyl)phenyl]-3(2H)-pyridazinone;
2-[2-(Methylthio)phenyl]-4-(4-fluorophenyl)-5-[4-(methylsulfonyl)phenyl]-3(2H)-pyridazinone;
2-(5-Nitro-2-thienyl)-4-(4-fluorophenyl)-5-[4-(methylsulfonyl)phenyl]-3(2H)-pyridazinone;
2-(3,4-Difluorophenyl)-4-(4-chlorophenyl)-5-[4-(methylsulfonyl)phenyl]-3(2H)-pyridazinone;
2-(3-Benzothienyl)-4-(4-fluorophenyl)-5-[4-(methylsulfonyl)phenyl]-3(2H)-pyridazinone;
2-(4-Fluorophenyl)-4-(4-fluorophenoxy)-5-[4-(methylsulfonyl)phenyl]-3(2H)-pyridazinone;
2-(3,4-Difluorophenyl)-4-(4-fluorophenoxy)-5-[4-(methylsulfonyl)phenyl]-3(2H)-pyridazinone;

2-(3-Bromophenyl)-4-(4-fluorophenoxy)-5-[4-(methylsulfonyl)phenyl]-3(2H)-pyridazinone;
2-(3,5-Difluorophenyl)-4-(4-fluorophenoxy)-5-[4-(methylsulfonyl)phenyl]-3(2H)-pyridazinone;
2-(3-Chlorophenyl)-4-(4-fluorophenoxy)-5-[4-(methylsulfonyl)phenyl]-3(2H)-pyridazinone;
2-(4-Nitrobenzyl)-4-(4-fluorophenyl)-5-[4-(methylsulfonyl)phenyl]-3(2H)-pyridazinone;
2-(4-Acetoxybenzyl)-4-(4-fluorophenyl)-5-[4-(methylsulfonyl)phenyl]-3(2H)-pyridazinone;
2-(4-Hydroxybenzyl)-4-(4-fluorophenyl)-5-[4-(methylsulfonyl)phenyl]-3(2H)-pyridazinone;
2-(3-Nitrobenzyl)-4-(4-fluorophenyl)-5-[4-(methylsulfonyl)phenyl]-3(2H)-pyridazinone;
2-(3,4,4-Trifluoro-3-butenyl)-4-(4-fluorophenyl)-5-[4-(methylsulfonyl)phenyl]-3(2H)-pyridazinone;
2-(2-Hexynyl)-4-(4-fluorophenyl)-5-[4-(methylsulfonyl)phenyl]-3(2H)-pyridazinone;
2-(3,3-Dichloro-2-propenyl)-4-(4-fluorophenyl)-5-[4-(aminosulfonyl)phenyl]-3(2H)-pyridazinone;
2-Cyclohexyl-4-(4-fluorophenyl)-5-[4-(methylsulfonyl)phenyl]-3(2H)-pyridazinone;
2-Cyclopentyl-4-(4-fluorophenyl)-5-[4-(methylsulfonyl)phenyl]-3(2H)-pyridazinone;
2-Cyclobutyl-4-(4-fluorophenyl)-5-[4-(Methylsulfonyl)phenyl]-3(2H)-pyridazinone;
2-(3-Methyl-2-butenyl)-4-(4-fluorophenyl)-5-[3-fluoro-4-(aminosulfonyl)phenyl]-3(2H)-pyridazinone;
2-(2,4-Difluorobenzyl)-4-(4-fluorophenyl)-5-[4-(aminosulfonyl)phenyl]-3(2H)-pyridazinone;
2-(Pentafluorobenzyl)-4-(4-fluorophenyl)-5-[4-(aminosulfonyl)phenyl]-3(2H)-pyridazinone;
2-(3-Cyclohexenyl)-4-(4-fluorophenyl)-5-[4-(aminosulfonyl)phenyl]-3(2H)-pyridazinone;
2-(3,4-Difluorobenzyl)-4-(4-fluorophenyl)-5-[4-(aminosulfonyl)phenyl]-3(2H)-pyridazinone;
2-(2,3-Dihydro-1H-inden-2-yl)-4-(4-fluorophenyl)-5-[4-(methylsulfonyl)phenyl]-3(2H)-pyridazinone;
2-(2,3-Dihydro-1H-inden-1-yl)-4-(4-fluorophenyl)-5-[4-(methylsulfonyl)phenyl]-3(2H)-pyridazinone;
2-(4-Tetrahydro-2H-pyran-4-yl)-4-(4-fluorophenyl)-5-[4-(methylsulfonyl)phenyl]-3(2H)-pyridazinone;
2-(2-Methylcyclopentyl)-4-(4-fluorophenyl)-5-[4-(methylsulfonyl)phenyl]-3(2H)-pyridazinone;
2-(2-Adarmantyl)-4-(4-fluorophenyl)-5-[4-(methylsulfonyl)phenyl]-3(2H)-pyridazinone;
2-(3-Methylcyclopentyl)-4-(4-fluorophenyl)-5-[4-(methylsulfonyl)phenyl]-3(2H)-pyridazinone;
2-(1-Methylcyclopentyl)-4-(4-fluorophenyl)-5-[4-(methylsulfonyl)phenyl]-3(2H)-pyridazinone;
2-(3,4-Difluorophenyl)-4-(4-fluoro-3-vinylphenyl)-5-[4-(methylsulfonyl)phenyl]-3(2H)-pyridazinone;
2-(3,4-Difluorophenyl)-4-(6-methyl-3-heptenyl)-5-[4-(methylsulfonyl)phenyl]-3(2H)-pyridazinone;
2-(3,4-Difluorophenyl)-4-(3-cyclopropylidenepropyl)-5-[4-(methylsulfonyl)phenyl]-3(2H)-pyridazinone;
2-(3,4-Difluorophenyl)-4-(5-methyl-3-hexenyl)-5-[4-(methylsulfonyl)phenyl]-3(2H)-pyridazinone;
2-(3,4-Difluorophenyl)-4-(5-methylhexyl)-5-[4-(methylsulfonyl)phenyl]-3(2H)-pyridazinone;
2-(3-Chloro-1-methyl-2E-propenyl)-4-(4-fluorophenyl)-5-[4-(aminosulfonyl)phenyl]-3(2H)-pyridazinone;
2-(2,3,3-Trifluoro-2-propen-1-yl)-4-(4-fluorophenyl)-5-[4-(aminosulfonyl)phenyl]-3(2H)-pyridazinone;
2-(1,1,2-Trifluoro-2-propenyl)-4-(4-fluorophenyl)-5-[4-(aminosulfonyl)phenyl]-3(2H)-pyridazinone;
2-(3,3-Difluoro-2-propenyl)-4-(4-fluorophenyl)-5-[4-(aminosulfonyl)phenyl]-3(2H)-pyridazinone;
2-(α-Methyl-3-fluorobenzyl)-4-(4-fluorophenyl)-5-[4-(aminosulfonyl)phenyl]-3(2H)-pyridazinone;
2-(1-Cyclohexenylmethyl)-4-(4-fluorophenyl)-5-[4-(aminosulfonyl)phenyl]-3(2H)-pyridazinone;
2-(α-Methyl-2,3,4-trifluorobenzyl)-4-(4-fluorophenyl)-5-[4-(aminosulfonyl)phenyl]-3(2H)-pyridazinone;
2-(α-Methyl-3,5-difluorobenzyl)-4-(4-fluorophenyl)-5-[4-(aminosulfonyl)phenyl]-3(2H)-pyridazinone;
2-(α-Methyl-3,4-difluorobenzyl)-4-(4-fluorophenyl)-5-[4-(aminosulfonyl)phenyl]-3(2H)-pyridazinone;
2-(3-Fluorobenzyl)-4-(4-fluorophenyl)-5-[4-(aminosulfonyl)phenyl]-3(2H)-pyridazinone;
2-(4-Fluorobenzyl)-4-(4-fluorophenyl)-5-[4-(aminosulfonyl)phenyl]-3(2H)-pyridazinone;
2-(2,4,6-Trifluorobenzyl)-4-(4-fluorophenyl)-5-[4-(aminosulfonyl)phenyl]-3(2H)-pyridazinone;
2-(2,4,5-Trifluorobenzyl)-4-(4-fluorophenyl)-5-[4-(aminosulfonyl)phenyl]-3(2H)-pyridazinone;
2-(2,3,4-Trifluorobenzyl)-4-(4-fluorophenyl)-5-[4-(aminosulfonyl)phenyl]-3(2H)-pyridazinone;
2-(4,4,4-Trifluoro-3-methyl-2E-butenyl)-4-(4-fluorophenyl)-5-[4-(aminosulfonyl)phenyl]-3(2H)-pyridazinone;
2-(4-Biphenyl)-4-(4-fluorophenyl)-5-[4-(methylsulfonyl)phenyl]-3(2H)-pyridazinone;
2-(4-Bromophenyl)-4-(4-fluorophenyl)-5-[4-(methylsulfonyl)phenyl]-3(2H)-pyridazinone;
2-(4-Nitrophenyl)-4-(4-fluorophenyl)-5-[4-(methylsulfonyl)phenyl]-3(2H)-pyridazinone;
2-(4-Phenoxyphenyl)-4-(4-fluorophenyl)-5-[4-(methylsulfonyl)phenyl]-3(2H)-pyridazinone;
2-(4-t-Butylphenyl)-4-(4-fluorophenyl)-5-[4-(methylsulfonyl)phenyl]-3(2H)-pyridazinone;
2-(4-Chlorophenyl)-4-(4-fluorophenyl)-5-[4-(methylsulfonyl)phenyl]-3(2H)-pyridazinone;
2-(3-Methylphenyl)-4-(4-fluorophenyl)-5-[4-(methylsulfonyl)phenyl]-3(2H)-pyridazinone;
2-(3-Vinylphenyl)-4-(4-fluorophenyl)-5-[4-(methylsulfonyl)phenyl]-3(2H)-pyridazinone;
2-(2-Formylphenyl)-4-(4-fluorophenyl)-5-[4-(methylsulfonyl)phenyl]-3(2H)-pyridazinone;
2-(2-Nitrophenyl)-4-(4-fluorophenyl)-5-[4-(methylsulfonyl)phenyl]-3(2H)-pyridazinone;
2-(3-Chlorophenyl)-4-(4-fluorophenyl)-5-[4-(methylsulfonyl)phenyl]-3(2H)-pyridazinone;
2-(3-Bromophenyl)-4-(4-fluorophenyl)-5-[4-(methylsulfonyl)phenyl]-3(2H)-pyridazinone;
2-(4-Cyanophenyl)-4-(4-fluorophenyl)-5-[4-(methylsulfonyl)phenyl]-3(2H)-pyridazinone;
2-(5-Methyl-2-thienyl))-4-(4-fluorophenyl)-5-[4-(methylsulfonyl)phenyl]-3(2H)-pyridazinone;
2-(3-Biphenyl)-4-(4-fluorophenyl)-5-[4-(methylsulfonyl)phenyl]-3(2H)-pyridazinone;
2-(3,5-Dimethylphenyl)-4-(4-fluorophenyl)-5-[4-(methylsulfonyl)phenyl]-3(2H)-pyridazinone;
2-(3,4-Difluorophenyl)-4-(4-fluorobenzyl)-5-[4-(methylsulfonyl)phenyl]-3(2H)-pyridazinone;
2-(3-Chloro-4-fluorophenyl)-4-(4-fluorobenzyl)-5-[4-(methylsulfonyl)phenyl]-3(2H)-pyridazinone;
2-(2-Thienyl)-4-(4-fluorophenyl)-5-[4-(methylsulfonyl)phenyl]-3(2H)-pyridazinone;
2-(4-Trifluoromethylphenyl)-4-(4-fluorophenyl)-5-[4-(methylsulfonyl)phenyl]-3(2H)-pyridazinone;
2-[4-(1-Pyrroyl)phenyl]-4-(4-fluorophenyl)-5-[4-(methylsulfonyl)phenyl]-3(2H)-pyridazinone;

2-(5-Chloro-2-thienyl)-4-(4-fluorophenyl)-5-[4-(methylsulfonyl)phenyl]-3(2H)-pyridazinone;

2-(4-Methylphenyl)-4-(4-fluorophenyl)-5-[4-(methylsulfonyl)phenyl]-3(2H)-pyridazinone;

2-(4-Fluorophenyl)-4-(2-ethyl-1-hexyloxy)-5-[4-(methylsulfonyl)phenyl]-3(2H)-pyridazinone;

2-(3-Thienyl)-4-(4-fluorophenyl)-5-[4-(methylsulfonyl)phenyl]-3(2H)-pyridazinone;

2-(3,5-Difluorophenyl)-4-(4-fluorophenyl)-5-[4-(methylsulfonyl)phenyl]-3(2H)-pyridazinone;

2-(2,4-Difluorophenyl)-4-(4-fluorophenyl)-5-[4-(methylsulfonyl)phenyl]-3(2H)-pyridazinone;

2-(3,4-Difluorophenyl)-4-(4-fluorophenyl)-5-[4-(methylsulfonyl)phenyl]-3(2H)-pyridazinone;

2-(3-Furyl)-4-(4-fluorophenyl)-5-[4-(methylsulfonyl)phenyl]-3(2H)-pyridazinone;

2-(3-Fluoro-4-methoxyphenyl)-4-(4-fluorophenyl)-5-[4-(methylsulfonyl)phenyl]-3(2H)-pyridazinone;

2-(2-Fluorophenyl)-4-(4-fluorophenyl)-5-[4-(methylsulfonyl)phenyl]-3(2H)-pyridazinone;

2-[4-(Aminosulfonyl)phenyl]-4-(4-fluorophenyl)-5-[4-(methylsulfonyl)phenyl]-3(2H)-pyridazinone;

2-(3-Chloro-4-fluorophenyl)-4-(4-fluorophenyl)-5-[4-(methylsulfonyl)phenyl]-3(2H)-pyridazinone;

2-(3,5-Dichlorophenyl)-4-(4-fluorophenyl)-5-[4-(methylsulfonyl)phenyl]-3(2H)-pyridazinone;

2-(4-Fluoro-3-methylphenyl)-4-(4-fluorophenyl)-5-[4-(methylsulfonyl)phenyl]-3(2H)-pyridazinone;

2-(4-Chloro-3-fluorophenyl)-4-(4-fluorophenyl)-5-[4-(methylsulfonyl)phenyl]-3(2H)-pyridazinone;:

2-(4-Chloro-2-fluorophenyl)-4-(4-fluorophenyl)-5-[4-(methylsufonyl)phenyl]-3(2H)-pyridazinone;:

2-(1-Adamantyloxycarbonyl)-4-(4-fluorophenyl)-5-[4-(methylsulfonyl)phenyl]-3(2H)-pyridazinone;

2-(2,2,2-Trifluoroethyl)-4-(4-fluorobenzyl)-5-[4-(methylsulfonyl)phenyl]-3(2H)-pyridazinone;

2-(4-Fluorophenyl)-4-(4-fluorophenoxymethyl)-5-[4-(methylsulfonyl)phenyl]-3(2H)-pyridazinone;

2-(4-Fluorophenyl)-4-(3-fluorophenoxymethyl)-5-[4-(methylsulfonyl)phenyl]-3(2H)-pyridazinone;

2-(4-Fluorophenyl)-4-phenoxymethyl-5-[4-(methylsulfonyl)phenyl]-3(2H)-pyridazinone;

2-(4-Fluorophenyl)-4-(t-butylthiomethyl)-5-[4-(methylsulfonyl)phenyl]-3(2H)-pyridazinone;

2-(4-Fluorophenyl)-4-(2-methylpropylthiomethyl)-5-[4-(methylsulfonyl)phenyl]-3(2H)-pyridazinone;

2-(4-Fluorophenyl)-4-(2-propoxy)-5-[4-(methylthio)phenyl]-3(2H)-pyridazinone;

2-(4-Fluorophenyl)-4-(2-propoxy)-5-[4-(methylsulfonyl)phenyl]-3(2H)-pyridazinone;

2-(3-Chlorophenyl)-4-(2-propoxy)-5-[4-(methylsulfonyl)phenyl]-3(2H)-pyridazinone;

2-(3-Fluorophenyl)-4-(2-propoxy)-5-[4-(methylsulfonyl)phenyl]-3(2H)-pyridazinone;

2-(3-Bromophenyl)-4-(2-propoxy)-5-[4-(methylsulfonyl)phenyl]-3(2H)-pyridazinone;

2-(2,5-Difluorophenyl)-4-(2-propoxy)-5-[4-(methylsulfonyl)phenyl]-3(2H)-pyridazinone;

2-(3-Chloro-4-fluorophenyl)-4-(2-methylpropoxy)-5-[3-fluoro-4-(methylsulfonyl)phenyl]-3(2H)-pyridazinone;

2-(3,4-Difluorophenyl)-4-(4-fluorophenyl)-5-[3-methyl-4-(methylsulfonyl)phenyl]-3(2H)-pyridazinone;

2-(3-Chlorophenyl)-4-(4-fluorophenoxymethyl)-5-[4-(methylsulfonyl)phenyl]-3(2H)-pyridazinone;

2-(3-Chlorophenyl)-4-(benzoyloxymethyl)-5-[4-(methylsulfonyl)phenyl]-3(2H)-pyridazinone;

2-(2,2,2-Trifluoroethyl)-4-(3-methylbutyl)-5-[4-(methylsulfonyl)phenyl]-3(2H)-pyridazinone;

2-(2,2,2-Trifluoroethyl)-4-(4-fluoro-3-methylphenyl)-5-[4-(methylsulfonyl)phenyl]-3(2H)-pyridazinone;

2-(2,2,2-Trifluoroethyl)-4-(3,5-dichlorophenyl)-5-[4-(methylsulfonyl)phenyl]-3(2H)-pyridazinone;

2-(2,2,2-Trifluoroethyl)-4-(3-ethoxyphenyl)-5-[4-(methylsulfonyl)phenyl]-3(2H)-pyridazinone;

2-(2,2,2-Trifluoroethyl)-4-(4-trifluoromethylphenyl)-5-[4-(methylsulfonyl)phenyl]-3(2H)-pyridazinone;

2-(2,2,2-Trifluoroethyl)-4-(3-nitrophenyl)-5-[4-(methylsulfonyl)phenyl]-3(2H)-pyridazinone;

2-(2,2,2-Trifluoroethyl)-4-(2-methylphenyl)-5-[4-(Methylsulfonyl)phenyl]-3(2H)-pyridazinone;

2-(2,2,2-Trifluoroethyl)-4-(4-vinylphenyl)-5-[4-(methylsulfonyl)phenyl]-3(2H)-pyridazinone;

2-(2,2,2-Trifluoroethyl)-4-[3-(trifluoromethyl)phenyl]-5-[4-(methylsulfonyl)phenyl]-3(2H)-pyridazinone;

2-(2,2,2-Trifluoroethyl)-4-(3-fluoro-4-methoxyphenyl)-5-[4-(methylsulfonyl)phenyl]-3(2H)-pyridazinone;

2-(2,2,2-Trifluoroethyl)-4-(3-fluoro-4-methylphenyl)-5-[4-(methylsulfonyl)phenyl]-3(2H)-pyridazinone;

2-(2,2,2-Trifluoroethyl)-4-(3,5-difluoro-4-methoxyphenyl)-5-[4-(methylsulfonyl)phenyl]-3(2H)-pyridazinone;

2-(2,2,2-Trifluoroethyl)-4-(1-oxo-1,3-dihydro-2-benzofuran-5-yl)-5-[4-(methylsulfonyl)phenyl]-3(2H)-pyridazinone;

2-(2,2,2-Trifluoroethyl)-4-(2-propenyl)-5-[4-(methylsulfonyl)phenyl]-3(2H)-pyridazinone;

2-(2,2,2-Trifluoroethyl)-4-(2-buten-2-yl)-5-[4-(methylsulfonyl)phenyl]-3(2H)-pyridazinone;

2-(2,2,2-Trifluoroethyl)-4-(3-fluorobenzyl)-5-[4-(methylsulfonyl)phenyl]-3(2H)-pyridazinone;

2-(2,2,2-Trifluoroethyl)-4-(1-cyclohexenyl)-5-[4-(methylsulfonyl)phenyl]-3(2H)-pyridazinone;

2-(2,2,2-Trifluoroethyl)-4-(3-methylbutyl)-5-[3-fluoro-4-(aminosulfonyl)phenyl]-3(2H)-pyridazinone;

2-(2,2,2-Trifluoroethyl)-4-benzyl-5-[4-(methylsulfonyl)phenyl]-3(2H)-pyridazinone;

2-(4-Fluorophenyl)-4-cyclohexyl-5-[4-(methylsulfonyl)phenyl]-3(2H)-pyridazinone;

2-(4-Fluorophenyl)-4-(4-methylphenyl)-5-[4-(methylsulfonyl)phenyl]-3(2H)-pyridazinone;

2-(4-Fluorophenyl)-4-benzyl-5-[4-(methylsulfonyl)phenyl]-3(2H)-pyridazinone;

2-(4-Fluorophenyl)-4-(phenylethynyl)-5-[4-(methylsulfonyl)phenyl]-3(2H)-pyridazinone;

2-(3,4-Difluorophenyl)-4-cyclohexyl-5-[4-(methylsulfonyl)phenyl]-3(2H)-pyridazinone;

2-(3,4-Difluorophenyl)-4-benzyl-5-[4-(methylsulfonyl)phenyl]-3(2H)-pyridazinone;

2-(3,4-Difluorophenyl)-4-(4-methylphenyl)-5-[4-(methylsulfonyl)phenyl]-3(2H)-pyridazinone;

2-(3,4-Difluorophenyl)-4-(4-fluoro-3-methylphenyl)-5-[4-(methylsulfonyl)phenyl]-3(2H)-pyridazinone;

2-(3,4-Difluorophenyl)-5-[4-(methylsulfonyl)phenyl]-4-vinyl-3(2H)-pyridazinone;

2-(3,4-Difluorophenyl)-4-(2-thienyl)-5-[4-(methylsulfonyl)phenyl]-3(2H)-pyridazinone;

2-(3,4-Difluorophenyl)-4-(1-propynyl)-5-[4-(methylsulfonyl)phenyl]-3(2H)-pyridazinone;

2-(3,4-Difluorophenyl)-4-t-butyl-5-[4-(methylsulfonyl)phenyl]-3(2H)-pyridazinone;

2-(2,2,2-Trifluoroethyl)-4-cyclohexyl-5-[4-(methylsulfonyl)phenyl]-3(2H)-pyridazinone;

2-(3-Chlorophenyl)-4-(3-fluorobenzyl)-5-[4-(methylsulfonyl)phenyl]-3(2H)-pyridazinone;

2-(4-Fluorophenyl)-4-(3-fluorobenzyl)-5-[4-(methylsulfonyl)phenyl]-3(2H)-pyridazinone;

2-(3,4-Difluorophenyl)-4-(3-fluorobenzyl)-5-[4-(methylsulfonyl)phenyl]-3(2H)-pyridazinone;

2-(3-Chlorophenyl)-4-(4-fluoro-3-methylphenyl)-5-[4-(methylsulfonyl)phenyl]-3(2H)-pyridazinone;

2-(4-Fluorophenyl)-4-(4-fluoro-3-methylphenyl)-5-[4-(Methylsulfonyl)phenyl]-3(2H)-pyridazinone;

2-(3-Chloro-4-fluorophenyl)-4-cyclohexyl-5-[4-(methylsulfonyl)phenyl]-3(2H)-pyridazinone;

2-(3-Chloro-4-fluorophenyl)-4-(4-fluoro-3-methylphenyl)-5-[4-(methylsulfonyl)phenyl]-3(2H)-pyridazinone;

2-(3-Chloro-4-fluorophenyl)-4-benzyl-5-[4-(methylsulfonyl)phenyl]-3(2H)-pyridazinone;

2-(3-Chloro-4-fluorophenyl)-4-(3-fluorobenzyl)-5-[4-(methylsulfonyl)phenyl]-3(2H)-pyridazinone;

2-(4-Fluorophenyl)-4-(3-fluoro-4-methylphenyl)-5-[4-(methylsulfonyl)phenyl]-3(2H)-pyridazinone;

2-(3-Chloro-4-fluorophenyl)-4-(3,5-difluoro-4-methoxyphenyl)-5-[4-(methylsulfonyl)phenyl]-3(2H)-pyridazinone;

2-(3-Chloro-4-fluorophenyl)-4-(3-methylbutyl)-5-[3-fluoro-4-(methylsulfonyl)phenyl]-3(2H)-pyridazinone;

2-(4-Fluorophenyl)-4-(3-fluorobenzyl)-5-[4-(aminosulfonyl)phenyl]-3(2H)-pyridazinone;

2-(3,4-Difluorophenyl)-4-(phenylethynyl)-5-[4-(methylsulfonyl)phenyl]-3(2H)-pyridazinone;

2-(3,4-Difluorophenyl)-4-(3,4-difluorobenzyl)-5-[4-(methylsulfonyl)phenyl]-3(2H)-pyridazinone;

2-(3,4-Difluorophenyl)-4-(3-methylbutyl)-5-[4-(methylsulfonyl)phenyl]-3(2H)-pyridazinone;

2-(3-Chloro-4-fluorophenyl)-4-(3-methylbutyl)-5-[4-(methylsulfonyl)phenyl]-3(2H)-pyridazinone;

2-(3,4-Difluorophenyl)-4-(3-methylbutyl)-5-[3-fluoro-4-(methylsulfonyl)phenyl]-3(2H)-pyridazinone;

2-[4-Fluoro-3-(methylthio)phenyl]-4-(4-fluorophenyl)-5-[4-(methylsulfonyl)phenyl]-3(2H)-pyridazinone;

2-Benzyl-4-(4-fluorophenyl)-5-[4-(trifluoromethylsulfonyl)phenyl]-3(2H)-pyridazinone;

2-(2,2,2-Trifluoroethyl)-4-(2,2-dimethylpropoxy)-5-[4-(methylsulfonyl)phenyl]-3(2H)-pyridazinone;

2-(2,2,2-Trifluoroethyl)-4-(4-methoxyphenoxy)-5-[4-(methylsulfonyl)phenyl]-3(2H)-pyridazinone;

2-(2,2,2-Trifluoroethyl)-4-(2-fluoro-5-trifluoromethylphenoxy)-5-[4-(methylsulfonyl)phenyl]-3(2H)-pyridazinone;

2-(2,2,2-Trifluoroethyl)-4-(4-cyanophenoxy)-5-[4-(methylsulfonyl)phenyl]-3(2H)-pyridazinone;

2-(2,2,2-Trifluoroethyl)-4-(3-pyridyloxy)-5-[4-(methylsulfonyl)phenyl]-3(2H)-pyridazinone;

2-(2,2,2-Trifluoroethyl)-4-(4-n-propylphenoxy)-5-[4-(methylsulfonyl)phenyl]-3(2H)-pyridazinone;

2-(2,2,2-Trifluoroethyl)-4-[(methylsulfonyl)phenoxy]-5-[4-(methylsulfonyl)phenyl]-3(2H)-pyridazinone;

2-(2,2,2-Trifluoroethyl)-4-(4-phenylphenoxy)-5-[4-(methylsulfonyl)phenyl]-3(2H)-pyridazinone;

2-(2,2,2-Trifluoroethyl)-4-[2-(methylthio)ethoxy]-5-[4-(methylsulfonyl)phenyl]-3(2H)-pyridazinone;

2-(2,2,2-Trifluoroethyl)-4-(phenylmethoxy)-5-[4-(methylsulfonyl)phenyl]-3(2H)-pyridazinone;

2-(2,2,2-Trifluoroethyl)-4-(2-furylmethoxy)-5-[4-(methylsulfonyl)phenyl]-3(2H)-pyridazinone;

2-(2,2,2-Trifluoroethyl)-4-[2-(3,4-dimethoxyphenyl)ethoxy)]-5-[4-(methylsulfonyl)phenyl]-3(2H)-pyridazinone;

2-(2,2,2-Trifluoroethyl)-4-[2-(4-morpholino)ethoxy)]-5-[4-(methylsulfonyl)phenyl]-3(2H)-pyridazinone;

2-(2,2,2-Trifluoroethyl)-4-[2-(1-piperidinyl)ethoxy)]-5-[4-(methylsulfonyl)phenyl]-3(2H)-pyridazinone;

2-(2,2,2-Trifluoroethyl)-4-[4-(carboxamido)phenoxy)]-5-[4-(methylsulfonyl)phenyl]-3(2H)-pyridazinone;

2-(2,2,2-Trifluoroethyl)-4-(1-indanyloxy)-5-[4-(methylsulfonyl)phenyl]-3(2H)-pyridazinone;

2-(2,2,2-Trifluoroethyl)-4-[4-(acetamido)phenoxy)]-5-[4-(methylsulfonyl)phenyl]-3(2H)-pyridazinone;

2-(2,2,2-Trifluoroethyl)-4-(2-methylpropoxy)-5-[4-(methylsulfonyl)phenyl]-3(2H)-pyridazinone;

2-(2,2,2-Trifluoroethyl)-4-(1-methylcyclopropylmethoxy)-5-[4-(methylsulfonyl)phenyl]-3(2H)-pyridazinone;

2-(2,2,2-Trifluoroethyl)-4-(3,3-dimethylbutoxy)-5-[4-(methylsulfonyl)phenyl]-3(2H)-pyridazinone;

2-(3,4-Difluorophenyl)-4-(4-chlorophenoxy)-5-[4-(methylsulfonyl)phenyl]-3(2H)-pyridazinone;

2-(3,4-Difluorophenyl)-4-(4-bromophenoxy)-5-[4-(methylsulfonyl)phenyl]-3(2H)-pyridazinone;

2-(2,2,2-Trifluoroethyl)-4-(cyclopentylthio)-5-[4-(methylsulfonyl)phenyl]-3(2H)-pyridazinone;

2-(2,2,2-Trifluoroethyl)-4-(1H-1,2,4-triazole-3-ylthio)-5-[4-(methylsulfonyl)phenyl]-3(2H)-pyridazinone;

2-(2,2,2-Trifluoroethyl)-4-phenylmethylthio-5-[4-(methylsulfonyl)phenyl]-3(2H)-pyridazinone;

2-(2,2,2-Trifluoroethyl)-4-(4-fluorophenylthio)-5-[4-(methylsulfonyl)phenyl]-3(2H)-pyridazinone;

2-(2,2,2-Trifluoroethyl)-4-(cyclohexylthio)-5-[4-(methylsulfonyl)phenyl]-3(2H)-pyridazinone;

2-(2,2,2-Trifluoroethyl)-4-(3-chloro-4-fluorophenylthio)-5-[4-(methylsulfonyl)phenyl]-3(2H)-pyridazinone;

2-(2,2,2-Trifluoroethyl)-4-(2,2,2-trifluoroethylthio)-5-[4-(methylsulfonyl)phenyl]-3(2H)-pyridazinone;

2-(2,2,2-Trifluoroethyl)-4-(tert-butylthio)-5-[4-(methylsulfonyl)phenyl]-3(2H)-pyridazinone;

2-(2,2,2-Trifluoroethyl)-4-(4-acetamidophenylthio)-5-[4-(methylsulfonyl)phenyl]-3(2H)-pyridazinone;

2-(2,2,2-Trifluoroethyl)-4-(2-propylthio)-5-[4-(methylsulfonyl)phenyl]-3(2H)-pyridazinone;

2-(2,2,2-Trifluoroethyl)-4-(2-methylprop-1-ylthio)-5-[4-(methylsulfonyl)phenyl]-3(2H)-pyridazinone;

2-(2,2,2-Trifluoroethyl)-4-amino-5-[4-(methylsulfonyl)phenyl]-3(2H)-pyridazinone;

2-(2,2,2-Trifluoroethyl)-4-(methoxypropylamino)-5-[4-(methylsulfonyl)phenyl]-3(2H)-pyridazinone;

2-(2,2,2-Trifluoroethyl)-4-(cyclopentylamino)-5-[4-(methylsulfonyl)phenyl]-3(2H)-pyridazinone;

2-(2,2,2-Trifluoroethyl)-4-(cyclobutylamino)-5-[4-(methylsulfonyl)phenyl]-3(2H)-pyridazinone;

2-(2,2,2-Trifluoroethyl)-4-(3,4-dimethoxyphenethylamino)-5-[4-(methylsulfonyl)phenyl]-3(2H)-pyridazinone;

2-(2,2,2-Trifluoroethyl)-4-(cyclohexylamino)-5-[4-(methylsulfonyl)phenyl]-3(2H)-pyridazinone;

2-(2,2,2-Trifluoroethyl)-4-[2-(1-piperidinyl)ethylamino]-5-[4-(methylsulfonyl)phenyl]-3(2H)-pyridazinone;

2-(2,2,2-Trifluoroethyl)-4-(2-tetrahydrofurfurylamino)-5-[4-(methylsulfonyl)phenyl]-3(2H)-pyridazinone;

2-(2,2,2-Trifluoroethyl)-4-(cyclopropylmethylamino)-5-[4-(methylsulfonyl)phenyl]-3(2H)-pyridazinone;

2-(2,2,2-Trifluoroethyl)-4-(2,3-dihydro-1H-inden-1-ylamino)-5-[4-(methylsulfonyl)phenyl]-3(2H)-pyridazinone;

2-(2,2,2-Trifluoroethyl)-4-(1-piperidinyl)-5-[4-(methylsulfonyl)phenyl]-3(2H)-pyridazinone;

2-(2,2,2-Trifluoroethyl)-4-(3-hydroxypropylamino)-5-[4-(methylsulfonyl)phenyl]-3(2H)-pyridazinone;

2-(2,2,2-Trifluoroethyl)-4-[3-(1H-imidazol-1-yl)propylamino]-5-[4-(methylsulfonyl)phenyl]-3(2H)-pyridazinone;

2-(2,2,2-Trifluoroethyl)-4-(2R-hydroxylpropylamino)-5-[4-(methylsulfonyl)phenyl]-3(2H)-pyridazinone;

2-(2,2,2-Trifluoroethyl)-4-(2-cyanoethylamino)-5-[4-(methylsulfonyl)phenyl]-3(2H)-pyridazinone;

2-(2,2,2-Trifluoroethyl)-4-(4-cyanoanilino)-5-[4-(methylsulfonyl)phenyl]-3(2H)-pyridazinone;

2-(2,2,2-Trifluoroethyl)-4-[3-methoxy-5-(trifluoromethyl)anilino]-5-[4-(methylsulfonyl)phenyl]-3(2H)-pyridazinone;

2-(2,2,2-Trifluoroethyl)-4-anilino-5-[4-(methylsulfonyl)phenyl]-3(2H)-pyridazinone;

2-(2,2,2-Trifluoroethyl)-4-(2,5-dimethoxyphenylamino)-5-[4-(methylsulfonyl)phenyl]-3(2H)-pyridazinone;

2-(2,2,2-Trifluoroethyl)-4-(3-fluoroanilino)-5-[4-(methylsulfonyl)phenyl]-3(2H)-pyridazinone;

2-(2,2,2-Trifluoroethyl)-4-(2,4-difluoroanilino)-5-[4-(methylsulfonyl)phenyl]-3(2H)-pyridazinone;

2-(2,2,2-Trifluoroethyl)-4-(2,3,5-trifluoroanilino)-5-[4-(methylsulfonyl)phenyl]-3(2H)-pyridazinone;

2-(2,2,2-Trifluoroethyl)-4-(4-fluoroanilino)-5-[4-(methylsulfonyl)phenyl]-3(2H)-pyridazinone;

2-Benzyl-4-(3-thienyl)-5-[4-(methylsulfonyl)phenyl]-3(2H)-pyridazinone;

2-Benzyl-4-(2-benzofuranyl)-5-[4-(methylsulfonyl)phenyl]-3(2H)-pyridazinone;

2-Benzyl-4-(1-oxo-1,3-dihydro-2-benzoffuran-5-yl)-5-[4-(methylsulfonyl)phenyl]-3(2H)-pyridazinone;

2-Benzyl-4-(5-chloro-2-thienyl)-5-[4-(methylsulfonyl)phenyl]-3(2H)-pyridazinone;

2-Benzyl-4-(3-nitrophenyl)-5-[4-(methylsulfonyl)phenyl]-3(2H)-pyridazinone;

2-Benzyl-4-(4-vinylphenyl)-5-[4-(methylsulfonyl)phenyl]-3(2H)-pyridazinone;

2-Benzyl-4-(4-trifluormethylphenyl)-5-[4-(methylsulfonyl)phenyl]-3(2H)-pyridazinone;

2-Benzyl-4-(2-methoxyphenyl)-5-[4-(methylsulfonyl)phenyl]-3(2H)-pyridazinone;

2-Benzyl-4-(3,4-dimethylphenyl)-5-[4-(methylsulfonyl)phenyl]-3(2H)-pyridazinone;

2-Benzyl-4-(3-fluoro-4-methoxyphenyl)-5-[4-(methylsulfonyl)phenyl]-3(2H)-pyridazinone;

2-Benzyl-4-(2-methoxypyrid-3-yl)-5-[4-(methylsulfonyl)phenyl]-3(2H)-pyridazinone;

2-Benzyl-4-(3-ethoxyphenyl)-5-[4-(methylsulfonyl)phenyl]-3(2H)-pyridazinone;

2-Benzyl-4-(4-fluorobenzyl)-5-[4-(methylsulfonyl)phenyl]-(2H)-pyridazinone;

2-(tert-Butyl)-4-(3-methylbutoxy)-5-[4-(methylsulfonyl)phenyl]-3(2H)-pyridazinone;

2-(3-Chlorophenyl)-4-methoxy-5-[4-(methylsulfonyl)phenyl]-3(2H)-pyridazinone;

2-(3-Chlorophenyl)-4-hydroxy-5-[4-(methylsulfonyl)phenyl]-3(2H)-pyridazinone;

2-(3-Chlorophenyl)-4-chloro-5-[4-(methylsulfonyl)phenyl]-3(2H)-pyridazinone;

2-(3-Chlorophenyl)-4-(2-methylpropoxy)-5-[4-(methylsulfonyl)phenyl]-3(2H)-pyridazinone;

2-(3-Chlorophenyl)-4-(t-butoxy)-5-[4-(methylsulfonyl)phenyl]-3(2H)-pyridazinone;

2-(3-Chlorophenyl)-4-(cyclohexyloxy)-5-[4-(methylsulfonyl)phenyl]3(2H)-pyridazinone;

2-(3-Chlorophenyl)-4-(2,2-dimethylpropoxy)-5-[4-(methylsulfonyl)phenyl]-3(2H)-pyridazinone;

2-(3-Chlorophenyl)-4-(3-methylbutoxy)-5-[4-(methylsulfonyl)phenyl]-3(2H)-pyridazinone;

2-(3-Chlorophenyl)-4-(3-octyn-1-yloxy)-5-[4-(methylsulfonyl)phenyl]-3(2H)-pyridazinone;

2-(3-Chlorophenyl)-4-[2-(dimethylamino)ethoxy]-5-[4-(methylsulfonyl)phenyl]-3(2M)-pyridazinone;

2-(3-Chlorophenyl)-4-[2-methyl-1-(1-methylethyl)propoxy]-5-[4-(methylsulfonyl)phenyl]-3(2H)-pyridazinone;

2-(3-Chlorophenyl)-4-(phenoxy)-5-[4-(methylsulfonyl)phenyl]-3(2H)-pyridazinone;

2-(3-Chlorophenyl)-4-[3-(dimethylamino)phenoxy]-5-[4-(methylsulfonyl)phenyl]-3(2H)-pyridazinone;

2-(3-Chlorophenyl)-4-(4-methoxyphenoxy)-5-[4-(methylsulfonyl)phenyl]-3(2H)-pyriazinone;

2-(3,4-Difluorophenyl)-4-(2-methylpropoxy)-5-[4-(methylsulfonyl)phenyl]-3(2H)-pyridazinone;

2-(3,4-Difluorophenyl)-4-(3-methyl-1-butoxy)-5-[4-(methylsulfonyl)phenyl]-3(2H)-pyridazinone;

2-(3,4-Difluorophenyl)-4-(4-fluorophenoxy)-5-[3-fluoro-4-(methylsulfonyl)phenyl]-3(2H)-pyridazinone;

2-(3,4-Difluorophenyl)-4-(2,2-dimethylpropoxy)-5-[4-(methylsulfonyl)phenyl]-3(2H)-pyridazinone;

2-(3,4-Difluorophenyl)-4-[2-(isopropoxy)ethoxy]-5-[4-(methylsulfonyl)phenyl]-3(2H)-pyridazinone;

2-(3,4-Difluorophenyl)-4-(3-methylpentyloxy)-5-[4-(methylsulfonyl)phenyl]-3(2H)-pyridazinone;

2-(3,4-Difluorophenyl)-4-(4-methyl-3-penten-1-yloxy)-5-[4-(methylsulfonyl)phenyl]-5-3(2H)-pyridazinone;

2-(3,4-Difluorophenyl)-4-[3-(methoxy)butoxy]-5-[4-(methylsulfonyl)phenyl]-3(2H)-pyridazinone;

2-(3-Chlorophenyl)-4-(N-methylbenzylamino)-5-[4-(methylsulfonyl)phenyl]-3(2H)-pyridazinone;:

2-(4-Fluorophenyl)-4-(1-piperidinyl)-5-[4-(methylsulfonyl)phenyl]-3(2H)-pyridazinone;

2-(4-Fluorophenyl)-4-(1-pyrrolidinyl)-5-[4-(methylsulfonyl)phenyl]-3(2H)-pyridazinone;

2-(3-Chlorophenyl)-4-(4-methylphenylthio)-5-[4-(methylsulfonyl)phenyl]-3(2H)-pyridazinone;

2-(3-Chlorophenyl)-4-(2-pyridylthio)-5-[4-(methylsulfonyl)phenyl]-3(2H)-pyridazinone;

2-(3-Chlorophenyl)-4-(phenylmethylthio)-5-[4-(methylsulfonyl)phenyl]-3(2H)-pyridazinone;

2-(3-Chlorophenyl)-4-(2-furylmethylthio)-5-[4-(methylsulfonyl)phenyl]-3(2H)-pyridazinone;

2-(3-Chlorophenyl)-4-]2-(methylpropyl)thio]-5-[4-(methylsulfonyl)phenyl]-3(2H)-pyridazinone;

2-(3-Chlorophenyl)-4-(cyclopentyl)-5-[4-(methylsulfonyl)phenyl]-3(2H)-pyridazinone;

2-(3-Chlorophenyl)-4-(2-methylpropyl)-5-[4-(methylsulfonyl)phenyl]-3(2H)-pyridazinone;

2-(3-Chlorophenyl)-4-(cyclopentylmethyl)-5-[4-(methylsulfonyl)phenyl]-3(2H)-pyridazinone;

2-(3-Chlorophenyl)-4-(2-cyclopentylethyl)-5-[4-(methylsulfonyl)phenyl]-3(2H)-pyridazinone;

2-(3-Chlorophenyl)-4-(3-methylbutyl)-5-[4-(methylsulfonyl)phenyl]-3(2H)-pyridazinone;

2-(3-Chlorophenyl)-4-benzyl-5-[4-(methylsulfonyl)phenyl]-3(2H)-pyridazinone;

2-(3-Chlorophenyl)-4-cyclohexyl-5-[4-(methylsulfonyl)phenyl]-3(2H)-pyridazinone;

2-(3-Chlorophenyl)-4-(4-fluorobenzyl)-5-[4-(methylsulfonyl)phenyl]-3(2H)-pyridazinone;

2-(3-Chlorophenyl)-4-(4-methylphenyl)-5-[4-(methylsulfonyl)phenyl]-3(2H)-pyridazinone;

2-(3,4-Difluorophenyl)-4-(3-fluoro-4-methylphenyl)-5-[4-(methylsulfonyl)phenyl]-3(2H)-pyridazinone;

2-(3-Chlorophenyl)-4-(phenethyl)-5-[4-(methylsulfonyl)phenyl]-3(2H)-pyridazinone;

2-(3-Chlorophenyl)-4-(2-methylpropoxy)-5-[3-fluoro-4-(methylsulfonyl)phenyl]-3(2H)-pyridazinone;

2-(3-Chlorophenyl)-4-(benzyloxy)-5-[4-(methylsulfonyl)phenyl]-3(2H)-pyridazinone;

2-(4-Fluorophenyl)-4-(3-methylbutoxy)-5-[4-(methylsulfonyl)phenyl]-3(2H)-pyridazinone;

2-(4-Fluorophenyl)-4-(2-methylpropoxy)-5-[4-(methylsulfonyl)phenyl]-3(2H)-pyridazinone;

2-(4-Fluorophenyl)-4-(4-fluorobenzyl)-5-[4-(methylsulfonyl)phenyl]-3(2H)-pyridazinone;

2-(4-Fluorophenyl)-4-(3-methylbutyl)-5-[4-(methylsulfonyl)phenyl]-3(2H)-pyridazinone;

2-(Tetrahydro-2H-pyrano-2-yl)-4-(4-fluorophenyl)-5-[4-(methylsulfonyl)phenyl]-3(2H)-pyridazinone;

2-(3-(4-Fluorophenyl)phenyl)-4-(4-fluorophenyl)-5-[4-(methylsulfonyl)phenyl]-3(2H)-pyridazinone;

2-(2,2,2-Trifluoroethyl)-4-(2,2-dimethylpropoxy)-5-[3-fluoro-4-(aminosulfonyl)phenyl]-3(2H)-pyridazinone;

2-(2,2,2-Trifluoroethyl)-4-(2-methylpropoxy)-5-[3-fluoro-4-(aminosulfonyl)phenyl]-3(2H)-pyridazinone;

2-Benzyl-4-(4-fluorobenzyl)-5-[4-(aminosulfonyl)phenyl]-3(2H)-pyridazinone;

2-Benzyl-4-(4-fluorophenyl)-5-[4-(aminosulfonyl)phenyl]-3(2H)-pyridazinone;

2-(4-Fluorophenyl)-4-(4-fluorophenoxy)-5-[4-(aminosulfonyl)phenyl]-3(2H)-pyridazinone;

2-(3,4-Difluorophenyl)-4-(3-fluoro-4-methylphenyl)-5-[4-(aminosulfonyl)phenyl]-3(2H)-pyridazinone;

2-(4-Fluorophenyl)-4-(3-fluoro-4-methylphenyl)-5-[4-(aminosulfonyl)phenyl]-3(2H)-pyridazinone;

2-(3,4-Difluorophenyl)-4-(4-fluorophenoxy)-5-[4-(aminosulfonyl)phenyl]-3(2H)-pyridazinone;

2-(3-Chloro-4-fluorophenyl)-4-(4-fluoro-3-methylphenyl)-5-[4-(aminosulfonyl)phenyl]-3(2H)-pyridazinone;

2-(4-Fluorophenyl)-4-(4-fluoro-3-methylphenyl)-5-[4-(aminosulfonyl)phenyl]-3(2H)-pyridazinone;

2-(3-Chlorophenyl)-4-(4-fluoro-3-methylphenyl)-5-[4-(aminosulfonyl)phenyl]-3(2h)-pyridazinone;

2-(3-Chlorophenyl)-4-(3-methylbutyl)-5-[4-(aminosulfonyl)phenyl]-3(2H)-pyridazinone;

2-(3-Chlorophenyl)-4-(phenethyl)-5-[4-(aminosulfonyl)phenyl]-3(2H)-pyridazinone;

2-(3-Chlorophenyl)-4-(3-methylbutoxy)-5-[4-(aminosulfonyl)phenyl]-3(2H)-pyridazinone;

2-(3-Chlorophenyl)-4-(2-methylpropoxy)-5-[4-(aminosulfonyl)phenyl]-3(2H)-pyridazinone;

2-(4-Fluorophenyl)-4-(3-methylbutyl)-5-[4-(aminosulfonyl)phenyl]-3(2H)-pyridazinone;

2-(4-Fluorophenyl)-4-(2-methylpropoxy)-5-[4-(aminosulfonyl)phenyl]-3(2H)-pyridazinone;

2-(4-Fluorophenyl)-4-(3-methylbutoxy)-5-[4-(aminosulfonyl)phenyl]-3(2H)-pyridazinone;

2-(t-Butyl)-4-(3-methyl-1-butoxy)-5-[4-(aminosulfonyl)phenyl]-3(2H)-pyridazinone;

2-(3,4-Difluorophenyl)-4-(4-fluorophenyl)-5-[4-(aminosulfonyl)phenyl]-3(2H)-pyridazinone;

2-(3-Chloro-4-fluorophenyl)-4-(4-fluorophenyl)-5-[4-(aminosulfonyl)phenyl]-3(2H)-pyridazinone;

2-(3,4-Difluorophenyl)-4-(4-fluoro-3-methylphenyl)-5-[4-(aminosulfonyl)phenyl]-3(2H)-pyridazinone;

2-(3,4-Difluorophenyl)-4-(2-methylpropoxy)-5-[4-(aminosulfonyl)phenyl]-3(2H)-pyridazinone;

2-(3,4-Difluorophenyl)-4-(3-methylbutyl)-5-[4-(aminosulfonyl)phenyl]-3(2H)-pyridazinone;

2-(3-Chloro-4-fluorophenyl)-4-(3-methylbutyl)-5-[4-(aminosulfonyl)phenyl]-3(2H)-pyridazinone;

2-(3,4-Difluorophenyl)-4-(2,2-dimethylpropoxy)-5-[4-(aminosulfonyl)phenyl]-3(2H)-pyridazinone;

2-(3,4-Difluorophenyl)-4-(4-fluorophenoxy)-5-[3-fluoro-4-(aminosulfonyl)phenyl]-3(2H)-pyridazinone;

2-(3,3-Difluoro-2-propenyl)]-4-(4-fluorophenyl)-5-[3-fluoro-4-(aminosulfonyl)phenyl]-3(2H)-pyridazinone;

2-(3,4-Difluorophenyl)-4-[2-(2-propoxy)ethoxy]-5-[4-(aminosulfonyl)phenyl]-3(2H)-pyridazinone;

2-(3,4-Difluorophenyl)-4-(4-methyl-3-pentenyloxy)-5-[4-(aminosulfonyl)phenyl]-3(2H)-pyridazinone;

2-(3-Chlorophenyl)-4-(3-fluorophenoxy)-5-[4-(methylsulfonyl)phenyl]-3(2H)-pyridazinone;

2-(3-Chlorophenyl)-4-(2-methylpropoxy)-5-[3-fluoro-4-(aminosulfonyl)phenyl]-3(2H)-pyridazinone;

2-(3-Chlorophenyl)-4-(4-methylpentyloxy)-5-[4-(methylsulfonyl)phenyl]-3(2H)-pyridazinone;

2-(4-Fluorophenyl)-4-(4-methylpentyloxy)-5-[4-(methylsulfonyl)phenyl]-3(2H)-pyridazinone;

2-(4-Fluorophenyl)-4-hydroxy-5-[4-(methylsulfonyl)phenyl]-3(2H)-pyridazinone;

2-(4-Fluorophenyl)-4-cyclopropylmethoxy-5-[4-(methylsulfonyl)phenyl]-3(2H)-pyridazinone;

2-(4-Fluorophenyl)-4-(2-cyclopropyl-1-ethoxy)-5-[4-(methylsulfonyl)phenyl]-3(2H)-pyridazinone;

2-(3-Chlorophenyl)-4-cyclopropanemethoxy-5-[4-(methylsulfonyl)phenyl]-3(2H)-pyridazinone;

2-(3-Chlorophenyl)-4-(2-cyclopropane-1-ethoxy)-5-[4-(methylsulfonyl)phenyl]-3(2H)-pyridazinone;

2-(4-Fluorophenyl)-4-(4-methylpentyl)-5-[4-(methylsulfonyl)phenyl]-3(2H)-pyridazinone;

2-(3-Chlorophenyl)-4-(4-methylpentyl)-5-[4-(methylsulfonyl)phenyl]-3(2H)-pyridazinone;

2-(4-Fluorophenyl)-4-(3-methyl-2-butenoxy)-5-[4-(methylsulfonyl)phenyl]-3(2H)-pyriazinone;

2-(3-Chlorophenyl)-4-(3-methyl-2-butenoxy)-5-[4-(mdthylsulfonyl)phenyl]-3(2H)-pyridazinone;

2-(4-Fluorophenyl)-4-(4-methyl-3-pentenyloxy)-5-[4-(methylsulfonyl)phenyl]-3(2H)-pyridazinone;

2-(4-Fluorophenyl)-4-(3-methyl-3-butenoxy)-5-[4-(methylsulfonyl)phenyl]-3(2H)-pyridazinone;

2-(3-Chlorophenyl)-4-(4-methyl-3-pentenyloxy)-5-[4-(methylsulfonyl)phenyl]-3(2H)-pyridazinone;

2-(3-Chlorophenyl)-4-(3-methyl-3-butenoxy)-5-[4-(methylsulfonylphenyl]-3(2H)-pyridazinone;

2-(4-Fluorophenyl)-4-(1,5-hexadienyl-3-oxy)-5-[4-(methylsulfonyl)phenyl]-3(2H)-pyridazinone;

2-(4-Fluorophenyl)-4-(5-methyl-2-hexyloxy)-5-[4-(methylsulfonyl)phenyl]-3(2H)-pyridazinone;

2-(4-Fluorophenyl)-4-(2-ethyl-1-butoxy)-5-[4-(methylsulfonyl)phenyl]-3(2H)-pyridazinone;

2-(4-Fluorophenyl)-4-(2-thioisopropyl-1-ethoxy)-5-[4-(methylsulfonyl)phenyl]-3(2H)-pyridazinone;

2-(4-Fluorophenyl)-4-(3-methylthio-1-hexyloxy)-5-[4-(methylsulfonyl)phenyl]-3(2H)-pyridazinone;

2-(4-Fluorophenyl)-4-(2-methyl-4-pentenyl-1-oxy)-5-[4-(methylsulfonyl)phenyl]-3(2H)-pyridazinone;

2-(3,4-Difluorophenyl)-4-(3-trifluoromethyl-1-butoxy)-5-[4-(methylsulfonyl)phenyl]-3(2H)-pyridazinone;

2-(3,4-Difluorophenyl)-4-ethoxy-5-[4-(methylsulfonyl)phenyl]-3(2H)-pyridazinone;

2-(3,4-Difluorophenyl)-4-(4-methyl-1-pentyloxy)-5-[4-(methylsulfonyl)phenyl]-3(2H)-pyridazinone;

2-(3,4-Difluorophenyl)-4-(4-methyl-2-pentyloxy)-5-[4-(methylsulfonyl)phenyl]-3(2H)-pyridazinone;

2-(3,4-Difluorophenyl)-4-(2-cyclopentyl-1-ethoxy)-5-[4-(methylsulfonyl)phenyl]-3(2H)-pyridazinone;

2-(3,4-Difluorophenyl)-4-(2-cyclopent-2-enyl-1-ethoxy)-5-[4-(methylsulfonyl)phenyl]-3(2H)-pyridazinone;

2-(2-Hydroxy-2-phenylethyl)-4-(4-fluorophenyl)-5-[4-(methylsulfonyl)phenyl]-3(2H)-pyridazinone;

2-(2-Methoxy-2-phenylethyl)-4-(4-fuorophenyl)-5-[4-(methylsulfonyl)phenyl]-3(2H)-pyridazinone;

2-(2-Methoxyimino-2-phenylethyl)-4-(4-fluorophenyl)-5-[4-(methylsulfonyl)phenyl]-3(2H)-pyridazinone;

2-(3,4-Difluorophenyl)-4-(4-methylpentyl)-5-[4-(methylsulfonyl)phenyl]-3(2H)-pyridazinone;

2-(3,4-Difluorophenyl)-4-(3-methyl-1-butoxy)-5-[4-(aminosulfonyl)phenyl]-3(2H)-pyridazinone;

2-(2,2,2-Trifluoroethyl)-4-(2,2-dimethylpropoxy)-5-[4-(aminosulfonyl)phenyl]-3(2H)-pyridazinone;

2-(2,2,2-Trifluoroethyl)-4-(3-methylbutoxy)-5-[4-(methylsulfonyl)phenyl]-3(2H)-pyridazinone;

2-(2,2,2-Trifluoroethyl)-4-(3-methylbutoxy)-5-[4-(aminosulfonyl)phenyl]-3(2H)-pyridazinone;

2-(2,2,2-Trifluoroethyl)-4-(2-methylpropoxy)-5-[4-(aminosulfonyl)phenyl]-3(2H)-pyridazinone;

2-(2,3,3-Trifluoropropenyl)-4-(4-fluorophenyl)-5-[4-(aminosulfonyl)phenyl]-3(2H)-pyridazinone;

2-(4-fluorophenyl)-4-(3-hydroxy-3-methyl-1-butoxy)-5-[4-(methylsulfonyl)phenyl]-3(2H)-pyridazinone;

2-(3,4-Difluorophenyl)-4-(2-hydroxy-2-methyl-1-propoxy)-5-[4-(methylsulfonyl)phenyl]-3(2H)-pyridazinone;

2-(3,4-Difluorophenyl)-4-methoxy-5-[4-(methylsulfonyl)phenyl]-3(2H)-pyridazinone;

2-(2,3,4,5,6-Pentafluorobenzyl)-4-(4-fluorophenyl)-5-[4-(dimethylamino)methylaminosulfonylphenyl]-3(2H)-pyridazinone;

2-(2,4-Difluorobenzyl)-4-(4-fluorophenyl)-5-[4-(dimethylamino)methylaminosulfonylphenyl]-3(2H)-pyridazinone;

(4-Fluorophenyl)-5-[4-(methylselenonyl)phenyl]-3(2H)-pyridazinone;

2-(3,4-Difluorophenyl)-4-(3-fluorophenyl)-5-[4-(methylsulfonyl)phenyl]-3(2H)-pyridazinone;

2-(4-Fluorophenyl)-4-(3-fluorophenyl)-5-[4-(methylsulfonyl)phenyl]-3(2H)-pyridazinone;

2-(3,4-Difluorophenyl)-4-(2-hydroxy-2-methyl-1-propoxy)-5-[4-(aminosulfonyl)phenyl]-3(2H)-pyridazinone;

2-(3,4-Difluorophenyl)-4-(2-oxo-1-propoxy)-5-[4-(methylsulfonyl)phenyl]-3(2H)-pyridazinone;

2-(3,4-Difluorophenyl)-4-[2-(methoxyimino)-1-propoxy]-5-[4-(methylsulfonyl)phenyl]-3(2H)-pyridazinone;

(S)-2-(3,4-Difluorophenyl)-4-(3-hydroxy-2-methyl-1-propoxy)-5-[4-(methylsulfonyl)phenyl]-3(2H)-pyridazinone;

(R)-2-(3,4-Difluorophenyl)-4-(3-hydroxy-2-methyl-1-propoxy)-5-[4-(methylsulfonyl)phenyl]-3(2H)-pyridazinone;

(S)-2-(3,4-Difluorophenyl)-4-(3-hydroxy-2-methyl-1-propoxy)-5-[4-(aminosulfonyl)phenyl]-3(2H)-pyridazinone;

(R)-2-(3,4-Difluorophenyl)-4-(3-hydroxy-2-methyl-1-propoxy)-5-[4-(aminosulfonyl)phenyl]-3(2H)-pyridazinone;

2-(4-Fluorophenyl)-4-(4-hydroxy-3-methyl-1-butoxy)-5-[4-(methylsulfonyl)phenyl]-3(2H)-pyridazinone;

2-(3,4-Difluorophenyl)-4-(3-oxo-1-butoxy)-5-[4-(methylsulfonyl)phenyl]-3(2H)-pyridazinone;

2-(4-Fluorophenyl)-4-(3-oxo-1-butoxy)-5-[4-(methylsulfonyl)phenyl]-3(2H)-pyridazinone;

2-(4-Fluorophenyl)-4-(4-hydroxy-2-methyl-1-butoxy)-5-[4-(methylsulfonyl)phenyl]-3(2H)-pyridazinone;

2-(4-Fluorophenyl)-4-(3-hydroxy-3-methyl-1-butoxy)-5-[4-(aminosulfonyl)phenyl]-3(2H)-pyridazinone;

2-(3,4-Difluorophenyl)-4-(3-hydroxy-3-methyl-1-butoxy)-5-[4-(methylsulfonyl)phenyl]-3(2H)-pyridazinone;

2-(3,4-Difluorophenyl)-4-(3-hydroxy-3-methyl-1-butoxy)-5-[4-(aminosulfonyl)phenyl]-3(2H)-pyridazinone;

2-(3-Chloro-4-fluorophenyl)-4-(3-hydroxy-3-methyl-1-butoxy)-5-[4-(methylsulfonyl)phenyl]-3(2H)-pyridazinone;

2-(3-Chloro-4-fluorophenyl)-4-(3-hydroxy-3-methyl-1-butoxy)-5-[4-(aminosulfonyl)phenyl]-3(2H)-pyridazinone;

2-(3-Chlorophenyl)-4-(3-hydroxy-3-methyl-1-butoxy)-5-[4-(methylsulfonyl)phenyl]-3(2H)-pyridazinone;

2-(3-Chlorophenyl)-4-(3-hydroxy-3-methyl-1-butoxy)-5-[4-(aminosulfonyl)phenyl]-3(2H)-pyridazinone;

2-(4-Fluorophenyl)-4-(2-hydroxy-2-methyl-1-propoxy)-5-[4-(methylsulfonyl)phenyl]-3(2H)-pyridazinone;

2-(4-Fluorophenyl)-4-(2-hydroxy-2-methyl-1-propoxy)-5-[4-(aminosulfonyl)phenyl]-3(2H)-pyridazinone;

2-(3-Chloro-4-fluorophenyl)-4-(2-hydroxy-2-methyl-1-propoxy)-5-[4-(methylsulfonyl)phenyl]-3(2H)-pyridazinone;

2-(3-Chloro-4-fluorophenyl)-4-(2-hydroxy-2-methyl-1-propoxy)-5-[4-(aminosulfonyl)phenyl]-3(2H)-pyridazinone;

2-(3-Chlorophenyl)-4-(2-hydroxy-2-methyl-1-propoxy)-5-[4-(methylsulfonyl)phenyl]-3(2H)-pyridazinone;

2-(3-Chlorophenyl)-4-(2-hydroxy-2-methyl-1-propoxy)-5-[4-(aminosulfonyl)phenyl]-3(2H)-pyridazinone;

2-(2,2,2-Trifluoroethyl)-4-(2-hydroxy-2-methyl-1-propoxy)-5-[4-(methylsulfonyl)phenyl]-3(2H)-pyridazinone;

2-(2,2,2-Trifluoroethyl)-4-(2-hydroxy-2-methyl-1-propoxy)-5-[4-(aminosulfonyl)phenyl]-3(2H)-pyridazinone;

2-(2,2,2-Trifluoroethyl)-4-(3-hydroxy-2,2-dimethyl-1-propoxy)-5-[4-(methylsulfonyl)phenyl]-3(2H)-pyridazinone;

2-(2,2,2-Trifluoroethyl)-4-(3-hydroxy-2,2-dimethyl-1-propoxy)-5-[4-(aminosulfonyl)phenyl]-3(2H)-pyridazinone;

2-(4-Fluorophenyl)-4-(4-hydroxy-3-methyl-1-butoxy)-5-[4-(aminosulfonyl)phenyl]-3(2H)-pyridazinone;

2-(3,4-Difluorophenyl)-4-(4-hydroxy-3-methyl-1-butoxy)-5-[4-(methylsulfonyl)phenyl]-3(2H)-pyridazinone;

2-(3-Chloro-4-fluorophenyl)-4-(4-hydroxy-3-methyl-1-butoxy)-5-[4-(methylsulfonyl)phenyl]-3(2H)-pyridazinone;

2-(3-Chlorophenyl)-4-(4-hydroxy-3-methyl-1-butoxy)-5-[4-(methylsulfonyl)phenyl]-3(2H)-pyridazinone;

2-(3,4-Difluorophenyl)-4-(4-hydroxy-3-methyl-1-butoxy)-5-[4-(aminosulfonyl)phenyl]-3(2H)-pyridazinone;

2-(3-Chloro-4-fluorophenyl)-4-(4-hydroxy-3-methyl-1-butoxy)-5-[4-(aminosulfonyl)phenyl]-3(2H)-pyridazinone;

2-(3-Chlorophenyl)-4-(4-hydroxy-3-methyl-1-butoxy)-5-[4-(aminosulfonyl)phenyl]-3(2H)-pyridazinone;

(S)-2-(4-Fluorophenyl)-4-(3-hydroxy-2-methyl-1-propoxy)-5-[4-(aminosulfonyl)phenyl]-3(2H)-pyridazinone;

(R)-2-(4-Fluorophenyl)-4-(3-hydroxy-2-methyl-1-propoxy)-5-[4-(aminosulfonyl)phenyl]-3(2H)-pyridazinone;

(S)-2-(3-Chloro-4-fluorophenyl)-4-(3-hydroxy-2-methyl-1-propoxy)-5-[4-(methylsulfonyl)phenyl]-3(2H)-pyridazinone;

(S)-2-(3-Chloro-4-fluorophenyl)-4-(3-hydroxy-2-methyl-1-propoxy)-5-[4-(aminosulfonyl)phenyl]-3(2H)-pyridazinone;

(R)-2-(3-Chloro-4-fluorophenyl)-4-(3-hydroxy-2-methyl-1-propoxy)-5-[4-(methylsulfonyl)phenyl]-3(2H)-pyridazinone;

(R)-2-(3-Chloro-4-fluorophenyl)-4-(3-hydroxy-2-methyl-1-propoxy)-5-[4-(aminosulfonyl)phenyl]-3(2H)-pyridazinone;

(S)-2-(3-Chlorophenyl)-4-(3-hydroxy-2-methyl-1-propoxy)-5-[4-(methylsulfonyl)phenyl]-3(2H)-pyridazinone;

(S)-2-(3-Chlorophenyl)-4-(3-hydroxy-2-methyl-1-propoxy)-5-[4-(aminosulfonyl)phenyl]-3(2H)-pyridazinone;

(R)-2-(3-Chlorophenyl)-4-(3-hydroxy-2-methyl-1-propoxy)-5-[4-(methylsulfonyl)phenyl]-3(2H)-pyridazinone;

(R)-2-(3-Chlorophenyl)-4-(3-hydroxy-2-methyl-1-propoxy)-5-[4-(aminosulfonyl)phenyl]-3(2H)-pyridazinone;

(S)-2-(2,2,2-Trifluoroethyl)-4-(3-hydroxy-2-methyl-1-propoxy)-5-[4-(methylsulfonyl)phenyl]-3(2H)-pyridazinone;

(S)-2-(2,2,2-Trifluoroethyl)-4-(3-hydroxy-2-methyl-1-propoxy)-5-[4-(aminosulfonyl)phenyl]-3(2H)-pyridazinone;

(R)-2-(2,2,2-Trifluoroethyl)-4-(3-hydroxy-2-methyl-1-propoxy)-5-[4-(methylsulfonyl)phenyl]-3(2H)-pyridazinone;

(R)-2-(2,2,2-Trifluoroethyl)-4-(3-hydroxy-2-methyl-1-propoxy)-5-[4-(aminosulfonyl)phenyl]-3(2H)-pyridazinone;

2-(4-Fluorophenyl)-4-(3-hydroxy-2,2-dimethyl-1-propoxy)-5-[4-(methylsulfonyl)phenyl]-3(2H)-pyridazinone;

2-(4-Fluorophenyl)-4-(3-hydroxy-2,2-dimethyl-1-propoxy)-5-[4-(aminosulfonyl)phenyl]-3(2H)-pyridazinone;

2-(3,4-Difluorophenyl)-4-(3-hydroxy-2,2-dimethyl-1-propoxy)-5-[4-(methylsulfonyl)phenyl]-3(2H)-pyridazinone;

2-(3,4-Difluorophenyl)-4-(3-hydroxy-2,2-dimethyl-1-propoxy)-5-[4-(aminosulfonyl)-phenyl]-3(2H)-pyridazinone;

2-(3-Chloro-4-fluorophenyl)-4-(3-hydroxy-2,2-dimethyl-1-propoxy)-5-[4-(methylsulfonyl)phenyl]-3(2H)-pyridazinone;

2-(3-Chloro-4-fluorophenyl)-4-(3-hydroxy-2,2-dimethyl-1-propoxy)-5-[4-(aminosulfonyl)phenyl]-3(2H)-pyridazinone;

2-(3-Chlorophenyl)-4-(3-hydroxy-2,2-dimethyl-1-propoxy)-5-[4-(methylsulfonyl)phenyl]-3(2H)-pyridazinone;

2-(3-Chlorophenyl)-4-(3-hydroxy-2,2-dimethyl-1-propoxy)-5-[4-(aminosulfonyl)phenyl]-3(2H)-pyridazinone;

N-[[4-[2-(3,4-Difluorophenyl)-4-(2-methyl-1-propoxy)-2H-pyridazin-3-on-5-yl]phenyl]sulfonyl]acetamide;

N-[[4-[2-(3,4-Difluorophenyl)-4-(2-methyl-1-propoxy)-2H-pyridazin-3-on-5-yl]phenyl-sulfonyl]acetamide, sodium salt;

N-[[4-[2-(4-Fluorophenyl)-4-(3-hydroxy-3-methyl-1-butoxy)-2H-pyridazin-3-on-5-yl]phenyl]sulfonyl]acetamide;

N-[[4-[2-(4-Fluorophenyl)-4-(3-hydroxy-3-methyl-1-butoxy)-2H-pyridazin-3-on-5-yl]phenyl]sulfonyl]acetamide, sodium salt;

N-[[4-[2-(3,4-Difluorophenyl)-4-(2-hydroxy-2-methyl-1-propoxy)-2H-pyridazin-3-on-5-yl]phenyl]sulfonyl]acetamide;

N-[[4-[2-(3,4-Difluorophenyl)-4-(2-hydroxy-2-methyl-1-propoxy)-2H-pyridazin-3on-5-yl]phenyl]sulfonyl]acetamide, sodium salt;

N-[[4-[2-(3-Chloro-4-fluorophenyl)-4-(2-hydroxy-2-methyl-1-propoxy)-2H-pyridazin-3-on-5-yl]phenyl]sulfonyl] acetamide;

N-[[4-[2-(3-Chloro-4-fluorophenyl)-4-(2-hydroxy-2-methyl-1-propoxy)-2H-pyridazin-3-on-5-yl]phenyl]sulfonyl] acetamide, sodium salt;

N-[[4-[2-(3-Chlorophenyl)-4-(2-hydroxy-2-methyl-1-propoxy)-2H-pyridazin-3-on-5-yl]phenyl]sulfonyl]acetamide;

N-[[4-[2-(3-Chlorophenyl)-4-(2-hydroxy-2-methyl-1-propoxy)-2H-pyridazin-3-on-5-yl]phenyl]sulfonyl]acetamide, sodium salt;

N-[[4-[2-(2,2,2-Trifluoroethyl)-4-(2-hydroxy-2-methyl-1-propoxy)-2H-pyridazin-3-on-5-yl]phenyl]sulfonyl]acetamide;

N-[[4-[2-(2,2,2-Trifluoroethyl)-4-(2-hydroxy-2-methyl-1-propoxy)-2H-pyridazin-3-on-5-yl]phenyl]sulfonyl]acetamide, sodium salt;

N-[[4-[2-(2,2,2-Trifluoroethyl)-4-(3-hydroxy-2,2-dimethyl-1-propoxy)-2H-pyridazin-3-on-5-yl]phenyl]sulfonyl] acetamide;

N-[[4-[2-(2,2,2-Trifluoroethyl)-4-(3-hydroxy-2,2-dimethyl-1-propoxy)-2H-pyridazin-3-on-5-yl]phenyl]sulfonyl] acetamide, sodium salt;

2-(2,2,2-Trifluoroethyl)-4-(3-hydroxy-3-methyl-1-butoxy)-5-[4-(methylsulfonyl)phenyl]-3(2H)-pyridazinone;

2-(2,2,2-Trifluoroethyl)-4-(3-hydroxy-3-methyl-1-butoxy)-5-[4-(aminosulfonyl)phenyl]-3(2H)-pyridazinone;

2-(3,4-Dichlorophenyl)-4-(3-hydroxy-3-methyl-1-butoxy)-5-[4-(methylsulfonyl)phenyl]-3(2H)-pyridazinone;

2-[(3-Trifluoromethyl)phenyl]-4-(2-hydroxy-2-methyl-1-propoxy)-5-[4-(methylsulfonyl)phenyl]-3(2H)-pyridazinone;

2-(3,4-Dichlorophenyl)-4-(2-hydroxy-2-methyl-1-propoxy)-5-[4-(methylsulfonyl)phenyl]-3(2H)-pyridazinone;

(R,S)-2-(4-Fluorophenyl)-4-(3-hydroxy-1-butoxy)-5-[4-(methylsulfonyl)phenyl]-3(2H)-pyridazinone;

2-(3,4-Difluorophenyl)-4-(1-butoxy)-5-[4-(methylsulfonyl)phenyl]-3(2H)-pyridazinone;

2-(3-Chloro-4-fluorophenyl)-4-(2-methyl-1-propoxy)-5-[4-(methylsulfonyl)phenyl]-3(2H)-pyridazinone;

2-(3-Chloro-4-fluorophenyl)-4-(3-methyl-1-butoxy)-5-[4-(methylsulfonyl)phenyl]-3(2H)-pyridazinone;

2-(3,4-Dichlorophenyl)-4-(2-methyl-1-propoxy)-5-[4-(methylsulfonyl)phenyl]-3(2H)-pyridazinone;

2-(3,4-Dichlorophenyl)-4-(3-methyl-1-butoxy)-5-[4-(methylsulfonyl)phenyl]-3(2H)-pyridazinone;

2-(3,4-Difluorophenyl)-4-(4-hydroxy-1-butoxy)-5-[4-(methylsulfonyl)phenyl]-3(2H)-pyridazinone;

2-[3-(Trifluoromethyl)phenyl]-4-(2-methyl-1-propoxy)-5-[4-(methylsulfonyl)phenyl]-3(2H)-pyridazinone;

2-[3-(Trifluoromethyl)phenyl]-4-(3-methyl-1-butoxy)-5-[4-(methylsulfonyl)phenyl]-3(2H)-pyridazinone;

2-[3-(Trifluoromethyl)phenyl]-4-(3-hydroxy-3-methyl-1-butoxy)-5-[4-(methylsulfonyl)phenyl]-3(2H)-pyridazinone;

(R)-2-(3,4-Difluorophenyl)-4-(3-hydroxy-1-butoxy)-5-[4-(methylsulfonyl)phenyl]-3(2H)-pyridazinone;

(S)-2-(3,4-Difluorophenyl)-4-(3-hydroxy-1-butoxy)-5-[4-(methylsulfonyl)phenyl]-3(2H)-pyridazinone;

(S)-2-(3,4-Difluorophenyl)-4-(2-hydroxy-3-methyl-1-butoxy)-5-[4-(methylsulfonyl)phenyl]-3(2H)-pyridazinone;

(S)-2-(4-fluorophenyl)-4-(2-hydroxy-3-methyl-1-butoxy)-5-[4-(methylsulfonyl)phenyl]-3(2H)-pyridazinone;

(S)-2-(4-chlorophenyl)-4-(2-hydroxy-3-methyl-1-butoxy)-5-[4-(methylsulfonyl)phenyl]-3(2H)-pyridazinone;

(S)-2-(3-fluorophenyl)-4-(2-hydroxy-3-methyl-1-butoxy)-5-[4-(methylsulfonyl)phenyl]-3(2H)-pyridazinone;

(S)-2-(3-chlorophenyl)-4-(2-hydroxy-3-methyl-1-butoxy)-5-[4-(methylsulfonyl)phenyl]-3(2H)-pyridazinone;

(S)-2-(3-bromophenyl)-4-(2-hydroxy-3-methyl-1-butoxy)-5-[4-(methylsulfonyl)phenyl]-3(2H)-pyridazinone;

(S)-2-(3-trifluoromethylphenyl)-4-(2-hydroxy-3-methyl-1-butoxy)-5-[4-(methylsulfonyl)phenyl]-3(2H)-pyridazinone;

(S)-2-(3-chloro-4-fluorophenyl)-4-(2-hydroxy-3-methyl-1-butoxy)-5-[4-(methylsulfonyl)phenyl]-3(2H)-pyridazinone;

(S)-2-(3-fluoro-4-chlorophenyl)-4-(2-hydroxy-3-methyl-1-butoxy)-5-[4-(methylsulfonyl)phenyl]-3(2H)-pyridazinone;

(S)-2-(3,4-dichlorophenyl)-4-(2-hydroxy-3-methyl-1-butoxy)-5-[4-(methylsulfonyl)phenyl]-3(2H)-pyridazinone;

(S)-2-(3-trifluoromethyl-4-fluorophenyl)-4-(2-hydroxy-3-methyl-1-butoxy)-5-[4-(methylsulfonyl)phenyl]-3(2H)-pyridazinone;

(S)-2-(3-bromo-4-fluorophenyl)-4-(2-hydroxy-3-methyl-1-butoxy)-5-[4-(methylsulfonyl)phenyl]-3(2H)-pyridazinone;

(R)-2-(3,4-Difluorophenyl)-4-(2-hydroxy-3-methyl-1-butoxy)-5-[4-(methylsulfonyl)phenyl]-3(2H)-pyridazinone;

(R)-2-(4-fluorophenyl)-4-(2-hydroxy-3-methyl-1-butoxy)-5-[4-(methylsulfonyl)phenyl]-3(2H)-pyridazinone;

(R)-2-(4-chlorophenyl)-4-(2-hydroxy-3-methyl-1-butoxy)-5-[4-(methylsulfonyl)phenyl]-3(2H)-pyridazinone;

(R)-2-(3-fluorophenyl)-4-(2-hydroxy-3-methyl-1-butoxy)-5-[4-(methylsulfonyl)phenyl]-3(2H)-pyridazinone;

(R)-2-(3-chlorophenyl)-4-(2-hydroxy-3-methyl-1-butoxy)-5-[4-(methylsulfonyl)phenyl]-3(2H)-pyridazinone;

(R)-2-(3-bromophenyl)-4-(2-hydroxy-3-methyl-1-butoxy)-5-[4-(methylsulfonyl)phenyl]-3(2H)-pyridazinone;

(R)-2-(3-trifluoromethylphenyl)-4-(2-hydroxy-3-methyl-1-butoxy)-5-[4-(methylsulfonyl)phenyl]-3(2H)-pyridazinone;

(R)-2-(3-chloro-4-fluorophenyl)-4-(2-hydroxy-3-methyl-1-butoxy)-5-[4-(methylsulfonyl)phenyl]-3(2H)-pyridazinone;

(R)-2-(3-fluoro-4-chlorophenyl)-4-(2-hydroxy-3-methyl-1-butoxy)-5-[4-(methylsulfonyl)phenyl]-3(2H)-pyridazinone;

(R)-2-(3,4-dichlorophenyl)-4-(2-hydroxy-3-methyl-1-butoxy)-5-[4-(methylsulfonyl)phenyl]-3(2H)-pyridazinone;

(R)-2-(3-trifluoromethyl-4-fluorophenyl)-4-(2-hydroxy-3-methyl-1-butoxy)-5-[4-(methylsulfonyl)phenyl]-3(2H)-pyridazinone;

(R)-2-(3-bromo-4-fluorophenyl)-4-(2-hydroxy-3-methyl-1-butoxy)-5-[4-(methylsulfonyl)phenyl]-3(2H)-pyridazinone;

2-(3,4-Difluorophenyl)-4-[(S)-2,3-dihydroxy-3-methyl-1-butoxy]-5-[4-(methylsulfonyl)phenyl]-3(2H)-pyridazinone;

2-(4-fluorophenyl)-4-[(S)-2,3-dihydroxy-3-methyl-1-butoxy]-5-[4-(methylsulfonyl)phenyl]-3(2H)-pyridazinone;

2-(4-chlorophenyl)-4-[(S)-2,3-dihydroxy-3-methyl-1-butoxy]-5-[4-(methylsulfonyl)phenyl]-3(2H)-pyridazinone;

2-(3-fluorophenyl)-4-[(S)-2,3-dihydroxy-3-methyl-1-butoxy]-5-[4-(methylsulfonyl)phenyl]-3(2H)-pyridazinone;

2-(3-chlorophenyl)-4-[(S)-2,3-dihydroxy-3-methyl-1-butoxy]-5-[4-(methylsulfonyl)phenyl]-3(2H)-pyridazinone;

2-(3-bromophenyl)-4-[(S)-2,3-dihydroxy-3-methyl-1-butoxy]-5-[4-(methylsulfonyl)phenyl]-3(2H)-pyridazinone;

2-(3-trifluoromethylphenyl)-4-[(S)-2,3-dihydroxy-3-methyl-1-butoxy]-5-[4-(methylsulfonyl)phenyl]-3(2H)-pyridazinone;

2-(3-chloro-4-fluorophenyl)-4-[(S)-2,3-dihydroxy-3-methyl-1-butoxy]-5-[4-(methylsulfonyl)phenyl]-3(2H)-pyridazinone;

2-(3-fluoro-4-chlorophenyl)-4-[(S)-2,3-dihydroxy-3-methyl-1-butoxy]-5-[4-(methylsulfonyl)phenyl]-3(2H)-pyridazinone;

2-(3,4-dichlorophenyl)-4-[(S)-2,3-dihydroxy-3-methyl-1-butoxy]-5-[4-(methylsulfonyl)phenyl]-3(2H)-pyridazinone;

2-(3-trifluoromethyl-4-fluorophenyl)-4-[(S)-2,3-dihydroxy-3-methyl-1-butoxy]-5-[4-(methylsulfonyl)phenyl]-3(2H)-pyridazinone;

2-(3-bromo-4-fluorophenyl)-4-[(S)-2,3-dihydroxy-3-methyl-1-butoxy]-5-[4-(methylsulfonyl)phenyl]-3(2H)-pyridazinone;

2-(3,4-Difluorophenyl)-4-[(R)-2,3-dihydroxy-3-methyl-1-butoxy]-5-[4-(methylsulfonyl)phenyl]-3(2H)-pyridazinone;

2-(4-fluorophenyl)-4-[(R)-2,3-dihydroxy-3-methyl-1-butoxy]-5-[4-(methylsulfonyl)phenyl]-3(2H)-pyridazinone;

2-(4-chlorophenyl)-4-[(R)-2,3-dihydroxy-3-methyl-1-butoxy]-5-[4-(methylsulfonyl)phenyl]-3(2H)-pyridazinone;

2-(3-fluorophenyl)-4-[(R)-2,3-dihydroxy-3-methyl-1-butoxy]-5-[4-(methylsulfonyl)phenyl]-3(2H)-pyridazinone;

2-(3-chlorophenyl)-4-[(R)-2,3-dihydroxy-3-methyl-1-butoxy]-5-[4-(methylsulfonyl)phenyl]-3(2H)-pyridazinone;

2-(3-bromophenyl)-4-[(R)-2,3-dihydroxy-3-methyl-1-butoxy]-5-[4-(methylsulfonyl)phenyl]-3(2H)-pyridazinone;

2-(3-trifluoromethylphenyl)-4-[(R)-2,3-dihydroxy-3-methyl-1-butoxy]-5-[4-(methylsulfonyl)phenyl]-3(2H)-pyridazinone;

2-(3-chloro-4-fluorophenyl)-4-[(R)-2,3-dihydroxy-3-methyl-1-butoxy]-5-[4-(methylsulfonyl)phenyl]-3(2H)-pyridazinone;

2-(3-fluoro-4-chlorophenyl)-4-[(R)-2,3-dihydroxy-3-methyl-1-butoxy]-5-[4-(methylsulfonyl)phenyl]-3(2H)-pyridazinone;

2-(3,4-dichlorophenyl)-4-[(R)-2,3-dihydroxy-3-methyl-1-butoxy]-5-[4-(methylsulfonyl)phenyl]-3(2H)-pyridazinone;

2-(4-fluoro-3-trifluoromethylphenyl)-4-[(R)-2,3-dihydroxy-3-methyl-1-butoxy]-5-[4-(methylsulfonyl)phenyl]-3(2H)-pyridazinone;

2-(3-bromo-4-fluorophenyl)-4-[(R)-2,3-dihydroxy-3-methyl-1-butoxy]-5-[4-(methylsulfonyl)phenyl]-3(2H)-pyridazinone;

2-(3,4-dichlorophenyl)-4-[(S)-2,3-dihydroxy-3-methyl-1-butoxy]-5-[4-(methylsulfonyl)phenyl]-3(2H)-pyridazinone;

2-(3-trifluoromethyl-4-fluorophenyl)-4-[(S)-2,3-dihydroxy-3-methyl-1-butoxy]-5-[4-(methylsulfonyl)phenyl]-3(2H)-pyridazinone;

2-(3-bromo-4-fluorophenyl)-4-[(S)-2,3-dihydroxy-3-methyl-1-butoxy]-5-[4-(methylsulfonyl)phenyl]-3(2H)-pyridazinone;

2-(3,4-Difluorophenyl)-4-[(R)-2,3-dihydroxy-3-methyl-1-butoxy]-5-[4-(methylsulfonyl)phenyl]-3(2H)-pyridazinone;

2-(4-fluorophenyl)-4-[(R)-2,3-dihydroxy-3-methyl-1-butoxy]-5-[4-(methylsulfonyl)phenyl]-3(2H)-pyridazinone;

2-(4-chlorophenyl)-4-[(R)-2,3-dihydroxy-3-methyl-1-butoxy]-5-[4-(methylsulfonyl)phenyl]-3(2H)-pyridazinone;

2-(3-fluorophenyl)-4-[(R)-2,3-dihydroxy-3-methyl-1-butoxy]-5-[4-(methylsulfonyl)phenyl]-3(2H)-pyridazinone;

2-(3-chlorophenyl)-4-[(R)-2,3-dihydroxy-3-methyl-1-butoxy]-5-[4-(methylsulfonyl)phenyl]-3(2H)-pyridazinone;

2-(3-bromophenyl)-4-[(R)-2,3-dihydroxy-3-methyl-1-butoxy]-5-[4-(methylsulfonyl)phenyl]-3(2H)-pyridazinone;

2-(3-trifluoromethylphenyl)-4-[(R)-2,3-dihydroxy-3-methyl-1-butoxy]-5-[4-(methylsulfonyl)phenyl]-3(2H)-pyridazinone;

2-(3-chloro-4-fluorophenyl)-4-[(R)-2,3-dihydroxy-3-methyl-1-butoxy]-5-[4-(methylsulfonyl)phenyl]-3(2H)-pyridazinone;

2-(3-fluoro-4-chlorophenyl)-4-[(R)-2,3-dihydroxy-3-methyl-1-butoxy]-5-[4-(methylsulfonyl)phenyl]-3(2H)-pyridazinone;

2-(3,4-dichlorophenyl)-4-[(R)-2,3-dihydroxy-3-methyl-1-butoxy]-5-[4-(methylsulfonyl)phenyl]-3(2H)-pyridazinone;

2-(4-fluoro-3-trifluoromethylphenyl)-4-[(R)-2,3-dihydroxy-3-methyl-1-butoxy]-5-[4-(methylsulfonyl)phenyl]-3(2H)-pyridazinone;

2-(3-bromo-4-fluorophenyl)-4-[(R)-2,3-dihydroxy-3-methyl-1-butoxy]-5-[4-(methylsulfonyl)phenyl]-3(2H)-pyridazinone;

2-(3,4-Difluorophenyl)-4-(4-hydroxy-4-methyl-1-pentyloxy)-5-[4-(methylsulfonyl)phenyl]-3(2H)-pyridazinone;

2-(4-fluorophenyl)-4-(4-hydroxy-4-methyl-1-pentyloxy)-5-[4-(methylsulfonyl)phenyl]-3(2H)-pyridazinone;

2-(4-chlorophenyl)-4-(4-hydroxy-4-methyl-1-pentyloxy)-5-[4-(methylsulfonyl)phenyl]-3(2H)-pyridazinone;

2-(3-fluorophenyl)-4-(4-hydroxy-4-methyl-1-pentyloxy)-5-[4-(methylsulfonyl)phenyl]-3(2H)-pyridazinone;

2-(3-chlorophenyl)-4-(4-hydroxy-4-methyl-1-pentyloxy)-5-[4-(methylsulfonyl)phenyl]-3(2H)-pyridazinone;

2-(3-bromophenyl)-4-(4-hydroxy-4-methyl-1-pentyloxy)-5-[4-(methylsulfonyl)phenyl]-3(2H)-pyridazinone;

2-(3-trifluoromethylphenyl)-4-(4-hydroxy-4-methyl-1-pentyloxy)-5-[4-(methylsulfonyl)phenyl]-3(2H)-pyridazinone;

2-(3-chloro-4-fluorophenyl)-4-(4-hydroxy-4-methyl-1-pentyloxy)-5-[4-(methylsulfonyl)phenyl]-3(2H)-pyridazinone;

2-(3-fluoro-4-chlorophenyl)-4-(4-hydroxy-4-methyl-1-pentyloxy)-5-[4-(methylsulfonyl)phenyl]-3(2H)-pyridazinone;

2-(3,4-dichlorophenyl)-4-(4-hydroxy-4-methyl-1-pentyloxy)-5-[4-(methylsulfonyl)phenyl]-3(2H)-pyridazinone;

2-(4-fluoro-3-trifluoromethylphenyl)-4-(4-hydroxy-4-methyl-1-pentyloxy)-5-[4-(methylsulfonyl)phenyl]-3(2H)-pyridazinone;

2-(3-bromo-4-fluorophenyl)-4-(4-hydroxy-4-methyl-1-pentyloxy)-5-[4-(methylsulfonyl)phenyl]-3(2H)-pyridazinone;

2-(3,4-Difluorophenyl)-4-[3-(2-aminoacetyloxy)-3-methyl-1-butoxy]-5-[4-(methylsulfonyl)phenyl]-3(2H)-pyridazinone;

2-(4-fluorophenyl)-4-[3-(2-aminoacetyloxy)-3-methyl-1-butoxy]-5-[4-(methylsulfonyl)phenyl]-3(2H)-pyridazinone;

2-(4-chlorophenyl)-4-[3-(2-aminoacetyloxy)-3-methyl-1-butoxy]-5-[4-(methylsulfonyl)phenyl]-3(2H)-pyridazinone;

2-(3-fluorophenyl)-4-[3-(2-aminoacetyloxy)-3-methyl-1-butoxy]-5-[4-(methylsulfonyl)phenyl]-3(2H)-pyridazinone;

2-(3-chlorophenyl)-4-[3-(2-aminoacetyloxy)-3-methyl-1-butoxy]-5-[4-(methylsulfonyl)phenyl]-3(2H)-pyridazinone;

2-(3-bromophenyl)-4-[3-(2-aminoacetyloxy)-3-methyl-1-butoxy]-5-[4-(methylsulfonyl)phenyl]-3(2H)-pyridazinone;

2-(3-trifluoromethylphenyl)-4-[3-(2-aminoacetyloxy)-3-methyl-1-butoxy]-5-[4-(methylsulfonyl)phenyl]-3(2H)-pyridazinone;

2-(3-chloro-4-fluorophenyl)-4-[3-(2-aminoacetyloxy)-3-methyl-1-butoxy]-5-[4-(methylsulfonyl)phenyl]-3(2H)-pyridazinone;

2-(3-fluoro-4-chlorophenyl)-4-[3-(2-aminoacetyloxy)-3-methyl-1-butoxy]-5-[4-(methylsulfonyl)phenyl]-3(2H)-pyridazinone;

2-(3,4-dichlorophenyl)-4-[3-(2-aminoacetyloxy)-3-methyl-1-butoxy]-5-[4-(methylsulfonyl)phenyl]-3(2H)-pyridazinone;

2-(4-fluoro-3-trifluoromethylphenyl)-4-[3-(2-aminoacetyloxy)-3-methyl-1-butoxy]-5-[4-(methylsulfonyl)phenyl]-3(2H)-pyridazinone;

2-(3-bromo-4-fluorophenyl)-4-[3-(2-aminoacetyloxy)-3-methyl-1-butoxy]-5-[4-(methylsulfonyl)phenyl]-3(2H)-pyridazinone;

2-(3,4-Difluorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(4-fluorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(4-chlorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-fluorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-chlorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-bromophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-trifluoromethylphenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-chloro-4-fluorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-fluoro-4-chlorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3,4-dichlorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-trifluoromethyl-4-fluorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-bromo-4-fluorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

3-({2-(3,4-difluorophenyl)-5-[4-(methylsulfonyl)phenyl]-3-oxo-2,3-dihydro-4-pyridazinyl}oxy)-1,1-dimethylpropyl dihydrogen phosphate;

3-({2-(4-fluorophenyl)-5-[4-(methylsulfonyl)phenyl]-3-oxo-2,3-dihydro-4-pyridazinyl}oxy)-1,1-dimethylpropyl dihydrogen phosphate;

3-({2-(4-chlorophenyl)-5-[4-(methylsulfonyl)phenyl]-3-oxo-2,3-dihydro-4 pyridazinyl}oxy)-1,1-dimethylpropyl dihydrogen phosphate;

3-({2-(3-fluorophenyl)-5-[4-(methylsulfonyl)phenyl]-3-oxo-2,3-dihydro-4-pyridazinyl}oxy)-1,1-dimethylpropyl dihydrogen phosphate;

3-({2-(3-chlorophenyl)-5-[4-(methylsulfonyl)phenyl]-3-oxo-2,3-dihydro-4-pyridazinyl}oxy)-1,1-dimethylpropyl dihydrogen phosphate;

3-({2-(3-bromophenyl)-5-[4-(methylsulfonyl)phenyl]-3-oxo-2,3-dihydro-4-pyridazinyl}oxy)-1,1-dimethylpropyl dihydrogen phosphate;

3-({2-(3-tifluoromethylphenyl)-5-[4-(methylsulfonyl)phenyl]-3-oxo-2,3-dihydro-4-pyridazinyl}oxy)-1,1-dimethylpropyl dihydrogen phosphate;

3-({2-(3-chloro-4-fluorophenyl)-5-[4-(methylsulfonyl)phenyl]-3-oxo-2,3-dihydro-4-pyridazinyl}oxy)-1,1-dimethylpropyl dihydrogen phosphate;

3-({2-(3-fluoro-4-chlorophenyl)-5-[4-(methylsulfonyl)phenyl]-3-oxo-2,3-dihydro-4-pyridazinyl}oxy)-1,1-dimethylpropyl dihydrogen phosphate;

3-({2-(3,4-dichlorophenyl)-5-[4-(methylsulfonyl)phenyl]-3-oxo-2,3-dihydro-4-pyridazinyl}oxy)-1,1-dimethylpropyl dihydrogen phosphate;

3-({2-(3-trifluoromethyl-4-fluorophenyl)-5-[4-(methylsulfonyl)phenyl]-3-oxo-2,3-dihydro-4-pyridazinyl}oxy)-1,1-dimethylpropyl dihydrogen phosphate;

3-({2-(3-bromo-4-fluorophenyl)-5-[4-(methylsulfonyl)phenyl]-3-oxo-2,3-dihydro-4-pyridazinyl}oxy)-1,1-dimethylpropyl dihydrogen phosphate;

2-(tert-Butyl)-4-(3-hydroxy-3-methyl-1-butoxy)-5-[4-(methylsulfonyl)phenyl]-3(2H)-pyridazinone;

2-(tert-Butyl)-4-[3-(2-aminoacetyloxy)-3-methyl-1-butoxy]-5-[4-(methylsulfonyl)phenyl]-3(2H)-pyridazinone;

2-(tert-butyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone; and 3-({2-(tert-butyl)-5-[4-(methylsulfonyl)phenyl]-3-oxo-2,3-dihydro-4-pyridazinyl}oxy)-1,1-dimethylpropyl dihydrogen phosphate; or pharmaceutically acceptable salts or prodrugs thereof.

Preparation of Compounds of the Invention
Abbreviations

As used throughout this specification and the appended claims, the following abbreviations have been used:

ACD for acid citrate dextrose, CAP for carrageenan induced air pouch prostaglandin, CIP for rat carrageenan pleural inflammation model, COX-2 for cyclooxygenase-2, CPE for carrageenan induced paw edema in rats, DBAD for di-t-butylazodicarboxylate, DEAD for diethyl azodicarboxylate, DIAD for disopropylazodicarboxylate, DMAP for 4-(dimethylamino)pyridine, DME for 1,2-dimethoxyethane, DMF for N,N-dimethylformamide, DMSO for dimethyl sulfoxide, DMSO for dimethyl sulfoxide, EDTA for ethylenediaminetetraacetic acid, EIA for enzyme immunoassay, FAB for fast atom bombardment, GI for gastrointestinal, HMDS, lithium or Li HMDS for lithium 1,1,1,3,3,3-hexamethyldisilazide, HWPX for Human Whole Platelet Cyclooxygenase-1, MCPBA for meta-chloroperoxybenzoic acid, NSAIDs for non-steroidal anti-inflammatory drugs, PEG 400 for polyethyleneglycol, $PGE_2$ for prostaglandin $E_2$, PGHS for prostaglandin endoperoxide H synthase, RHUCX1 for recombinant human cyclooxygenase-1, RHUCX2 for recombinant human cyclooxygenase-2, r-hu Cox 1 for recombinant human Cox-1, TEA for triethylamine, TFA for trifluoroacetic acid, and THF for tetrahydrofuran and WISH for human amnionic whole cell cyclooxygenase-2. The following examples illustrate the process of the invention, without limitation.

The compounds of the invention may be prepared by a variety of synthetic routes. Representative procedures are outlined in Schemes 1–10, below.

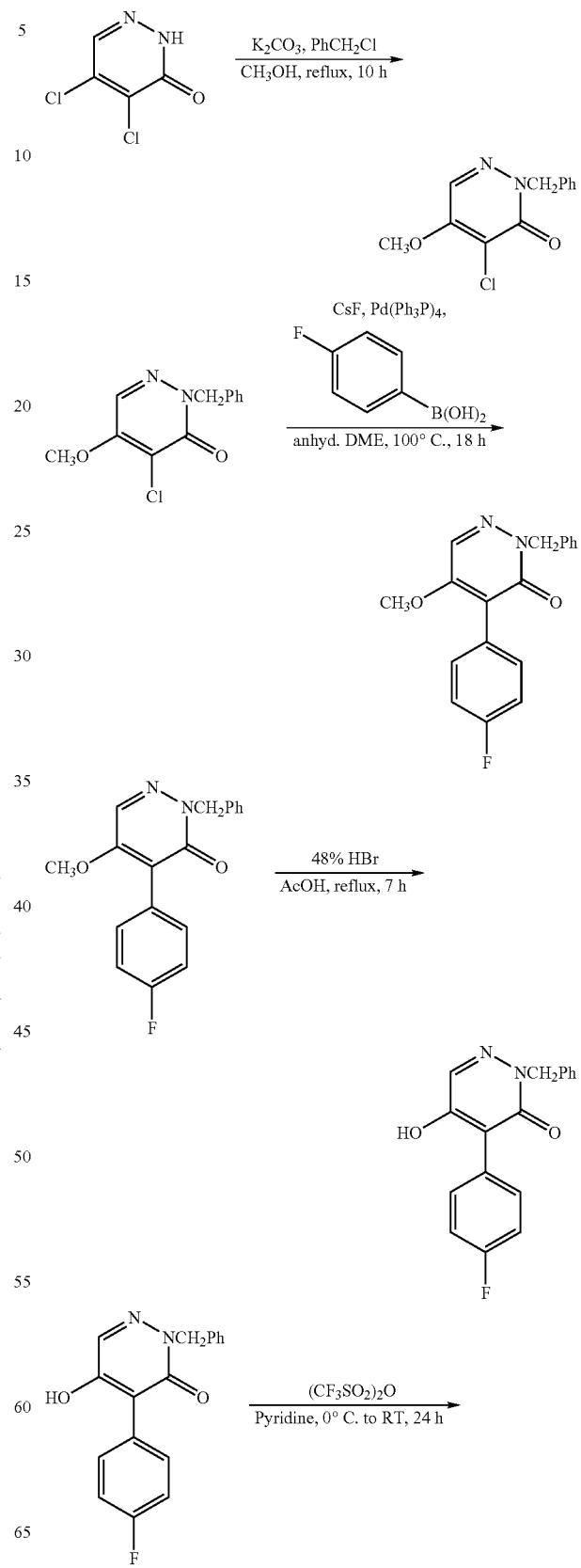

Scheme 1

-continued

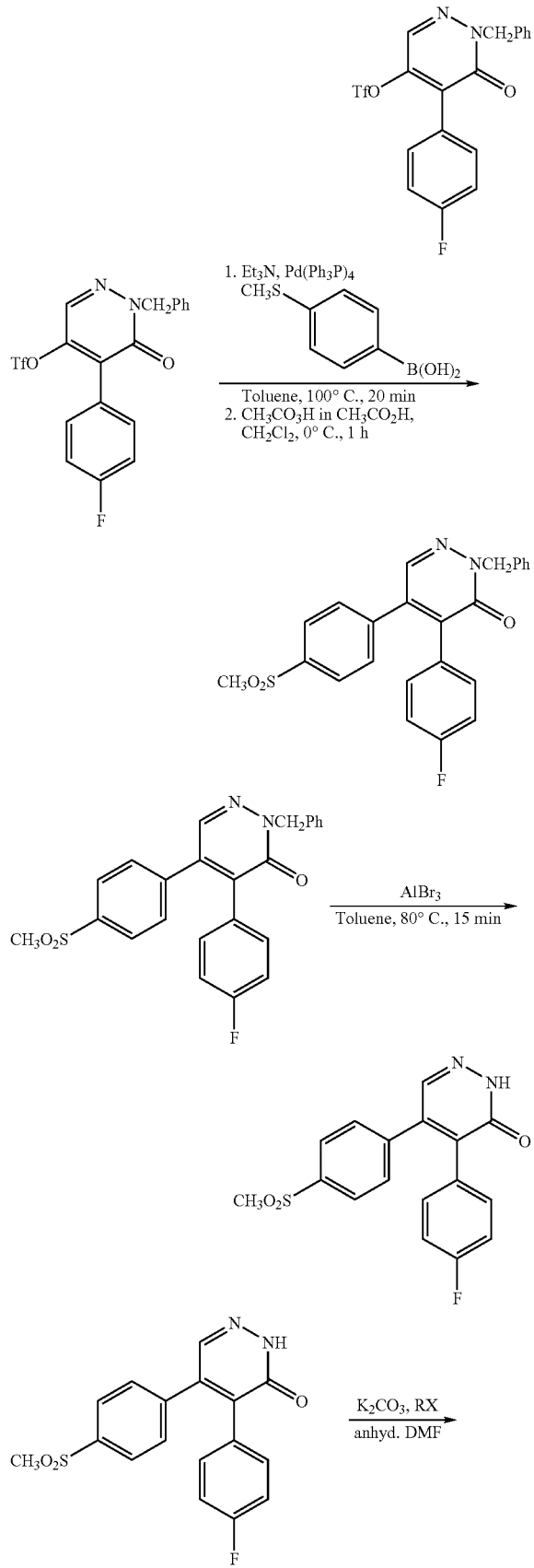

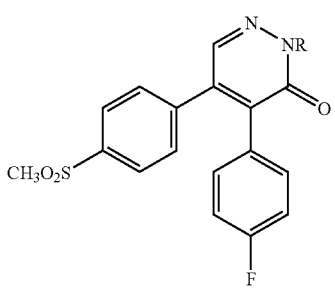

-continued

A general route to the compounds of the invention having Formula III, where the aryl group at the 5-position on the pyridazinone ring is substituted with a sulfonyl group is described in Scheme 1. Dichloro-3(2H)-pyridazinone can be treated with benzyl chloride and potassium carbonate in methanol to provide 2-benzyl-4-chloro-5-methoxy-3(2H)-pyridazinone. 2-Benzyl-4-chloro-5-methoxy-3(2H)-pyridazinone can be treated with a boronic acid such as 4-fluorobenzeneboronic acid (shown) and a palladium catalyst and the methoxy group can be hydrolyzed with 48% hydrobromic acid to provide the 5-hydroxypyridazinone compound. The 5-hydroxypyridazinone product can be treated with triflic anhydride followed by substitution on the pyridazinone ring using 4-methylthiobenzeneboronic acid to provide the methyl thioether compound. The methyl thioether compound which can be treated with peracetic acid in acetic acid and methylene chloride to provide the methyl sulfone. The benzyl group can be removed using aluminum bromide or another suitable Lewis acid. The R group can be added using an appropriate alkylating agent and base.

Scheme 2

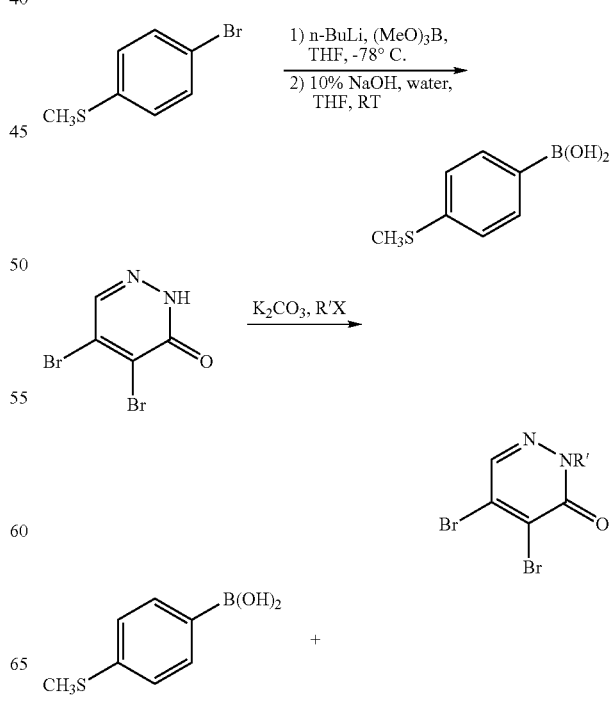

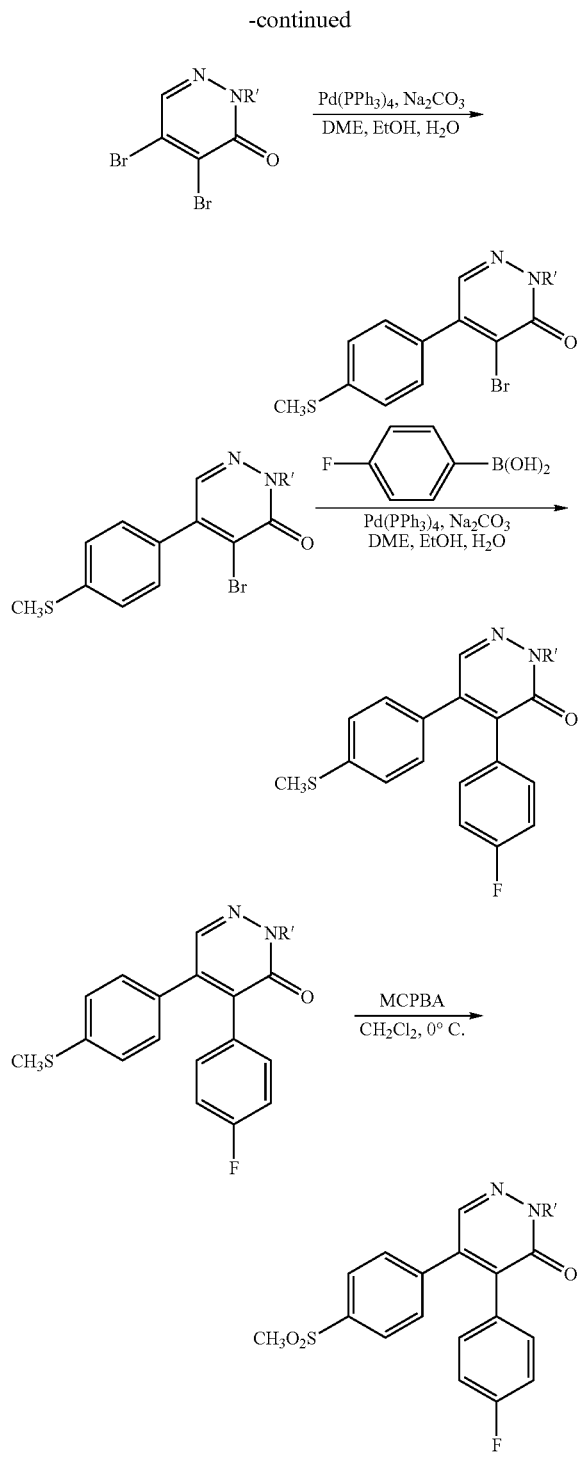

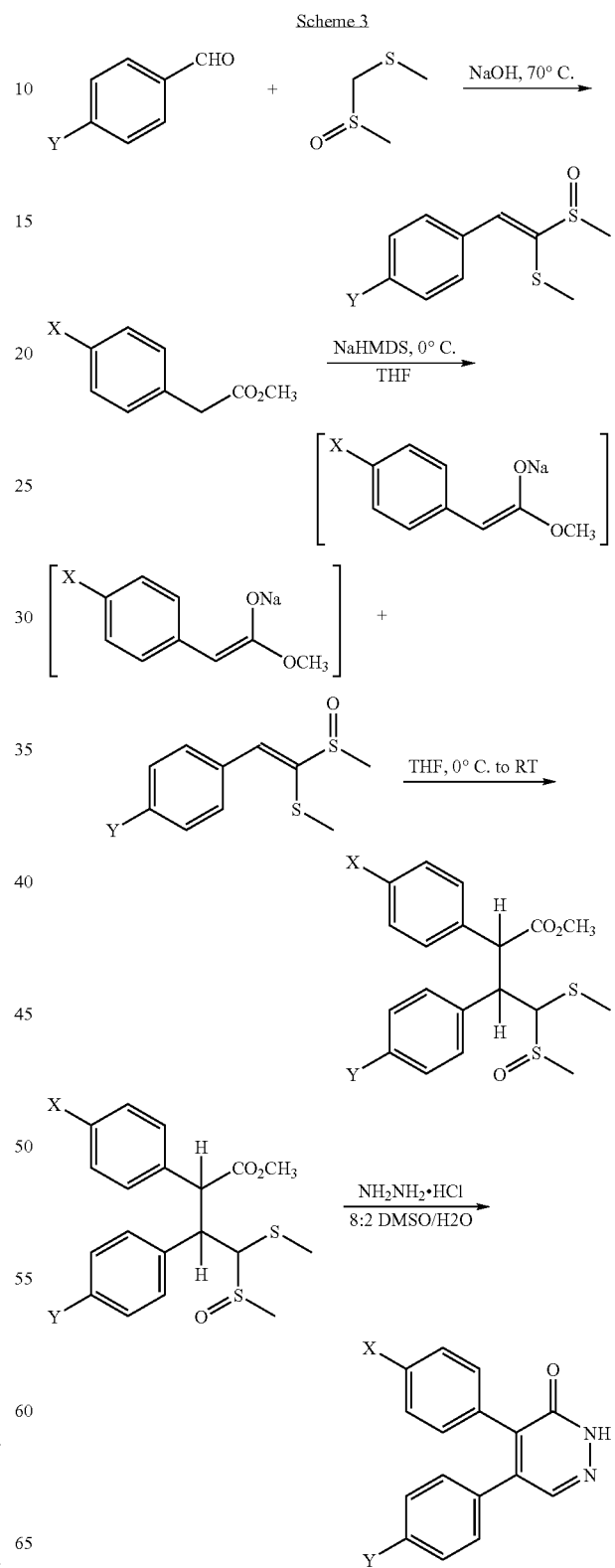

acid (shown) in the presence of a palladium catalyst to provide the thioether. The methyl thioether compound can be treated with meta-chloroperoxybenzoic acid (MCPBA) in methylene chloride to provide the methyl sulfone.

An alternative route to the compounds of the present invention having Formula III is described in Scheme 2. 4-Bromothioanisole or another suitable thioether can be treated with a trialkoxyborate, such as trimethoxyborate or triisopropylborate to provide 4-(methylthio)benzeneboronic acid. The boronic acid can be treated with 2-benzyl-4,5-dibromo-3(2H)-pyridazinone using tetrakis(triphenylphosphine)palladium (0)in dimethoxyethane and then coupled with a second boronic acid such as 4-fluorobenzeneboronic

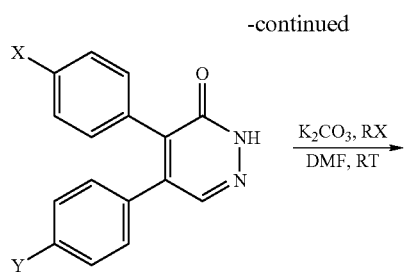
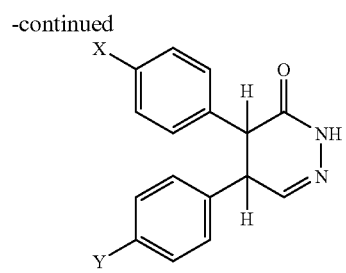
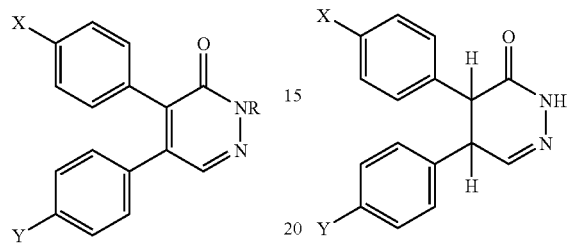

An alternative route to the compounds of the present invention having Formula III is described in Scheme 3. (4-Thiomethylphenyl)dimethylthioketene acetal, mono-S-oxide can be prepared by reaction of 4-thiomethylbenzaldehyde (Y is CH₃S) with methyl(methylsulfinylmethyl) sulfide and sodium hydroxide. The thioketene acetal and methyl 4-fluorophenylacetate or suitable ester (X is fluorine) can be treated with a strong base such as sodium hexamethyldisilazide in THF to provide the butyrate ester. The dithioacetal ketene can be directly cyclized to the N-unsubstituted pyridazinone using hydrazine and a salt. The pyridazinone can be then be alkylated using an appropriate alkylating agent and a base.

Scheme 4

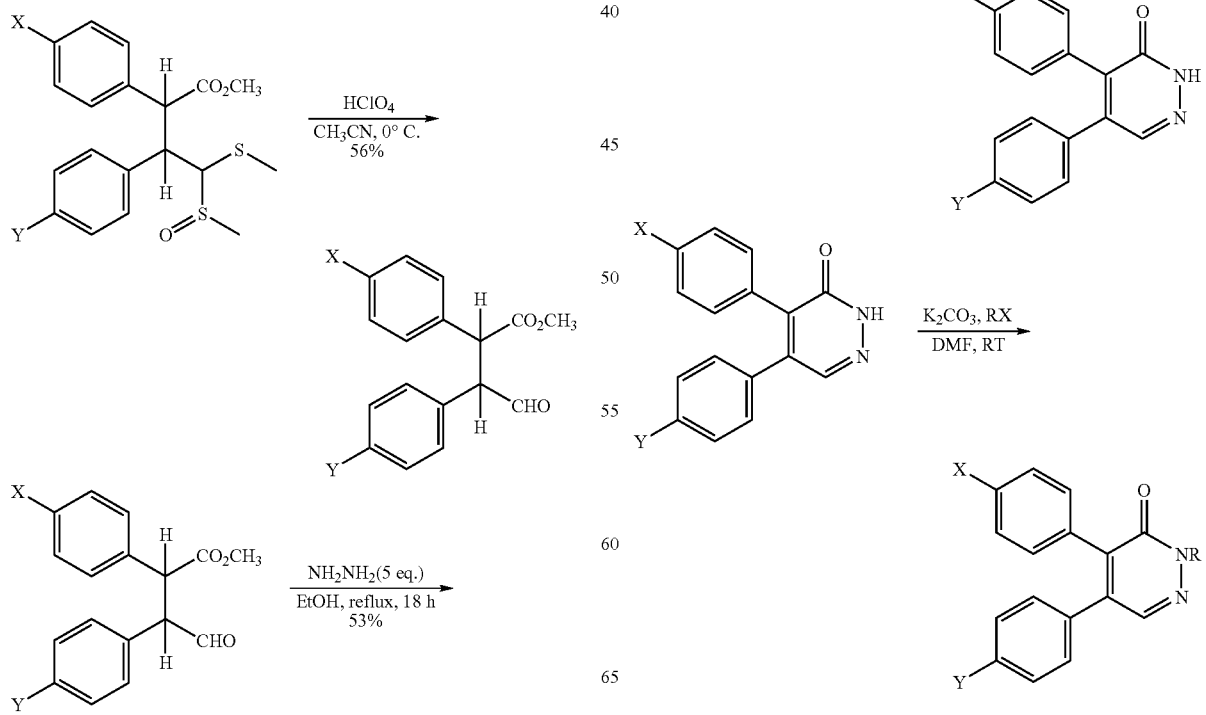
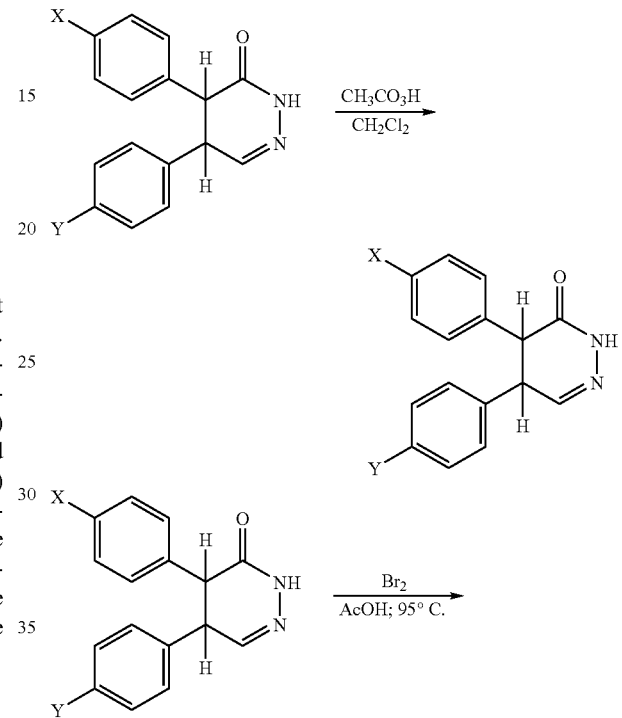

In an alternate route, shown in Scheme 4, the thioacetal ketene (X=F and Y=CH₃S) can be treated with perchloric acid to provide an ester-aldehyde as a mixture of diastereomers. The oxidation products can be treated with hydrazine and then oxidized with peroxyacetic acid to provide the sulfonyl dihydropyridazinone (Y=CH₃SO₂). The dihydropyridazinone can be dehydrogenated to form the pyridazinone by treatment with reagents such as bromine in acetic acid. The R group may be added via substitution using an appropriate alkylating agent and base.

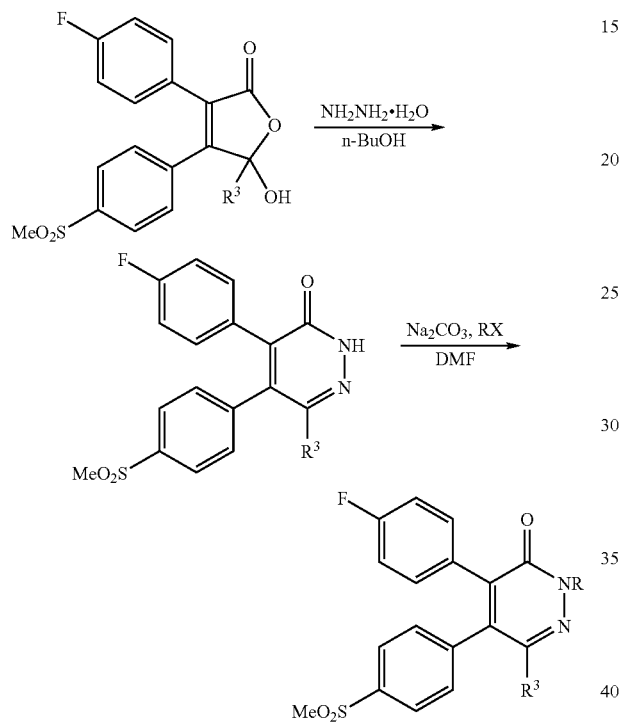

The preparation of the 5-hydroxy-2(5H)-furanones can be accomplished by the application of methodologies published in a variety of sources, including: J. Med. Chem., 1987, 30, 239–249 and WO 96/36623, hereby completely incorporated by reference. These 5-hydroxy-2(5H)-furanones can be converted to 6-substituted-4,5-diaryl-3(2H)pyridazinones as described in Scheme 5.

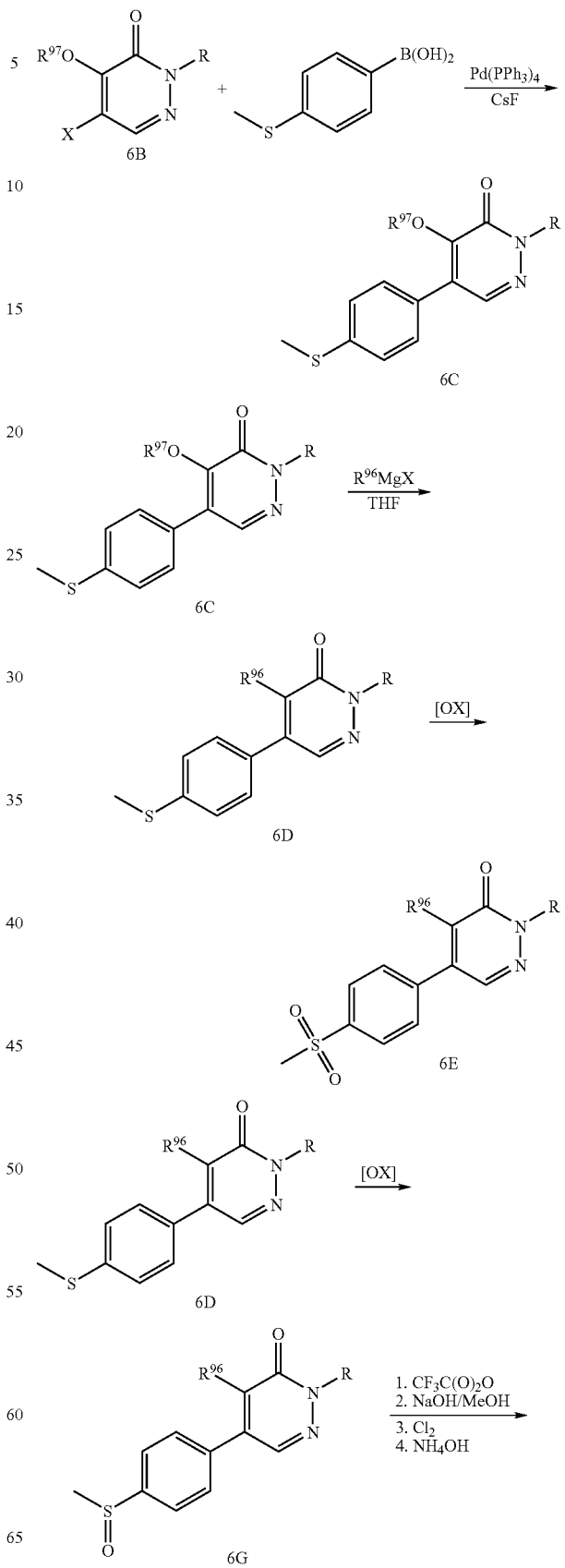

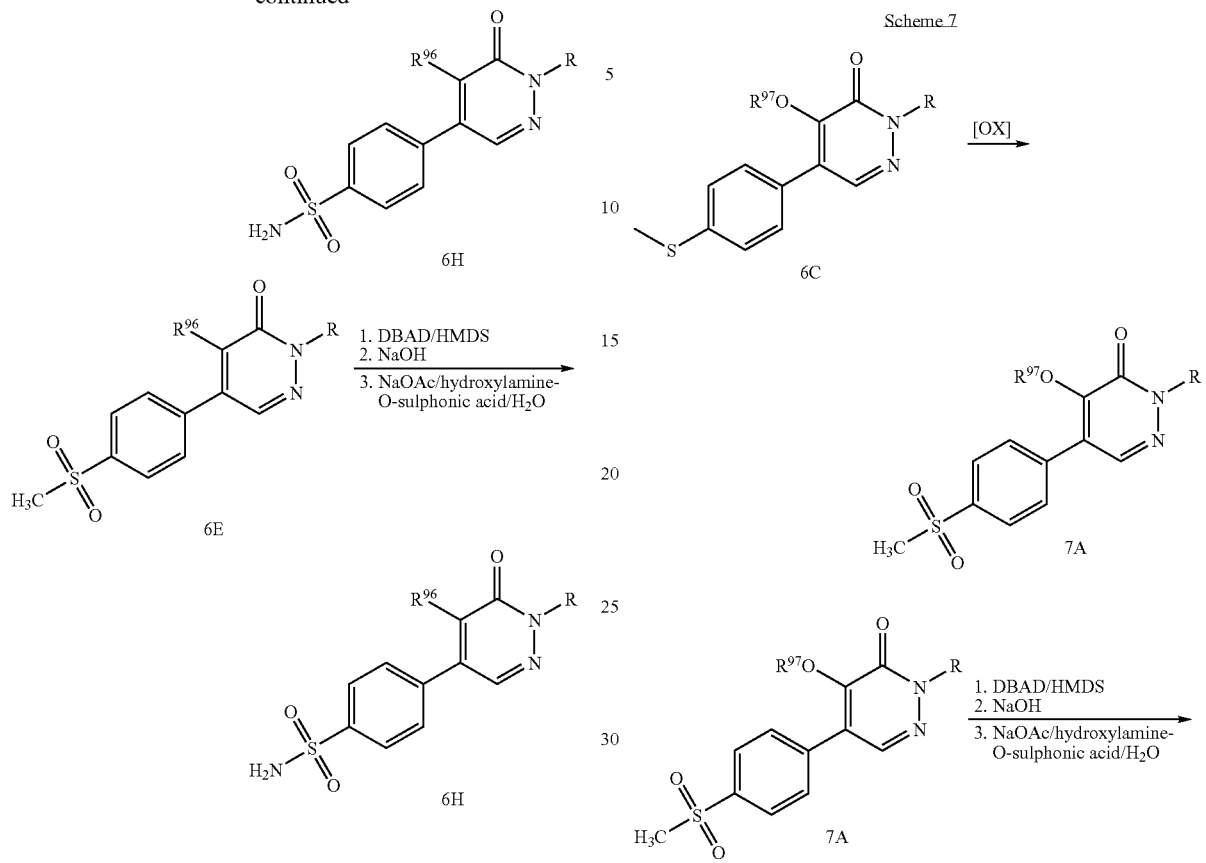

A general route to the compounds of the invention having Formula III, where the aryl group at the 5-position on the pyridazinone ring is substituted with a para-sulfonyl group is described in Scheme 6. A mucohalo acid, such as mucobromic or mucochloric acid, can be treated with an hydrazine having the desired R group to provide the dihalopyridazinone compound, 6A. The dihalo-compound can be treated with an alcohol in the presence of a base, such as sodium or potassium hydride, to provide an alkoxide 6B where $R^{97}$ is selected from alkyl, aryl, arylalkyl, heterocyclic, and heterocyclic alkyl. (If the alkoxy group is to be removed at a later time then methanol is the preferred alcohol.) The alkoxy-halide can be treated with methylthiophenylboronic acid to provide the alkoxy-pyridazinone 6C. The alkoxy group can be converted to a hydrocarbyl group by treatment with a Grignard reagent to provide thioether 6D where $R^{96}$ is alkyl. The thioether 6D can be oxidized with an oxidizing agent, such as peracetic acid, meta-chloroperoxybenzoic acid and the like, to form the sulfinyl compound 6G, or the methylsulfone compound 6E. The methylsulfinyl compound, 6G, can be treated with trifluoroacetic anhydride and NaOH/MeOH followed by addition of chlorine gas and then ammonia hydroxide to provide the aminosulfonyl compound, 6H. Alternatively, the methylsulfonyl compound, 6E, can be treated with a diazodicarboxylate, such as DBAD, DIAD, DEAD and the like, and a disilazane anion, such as lithium HMDS and the like, followed by treatment with sodium acetate and hydroxylamine-O-sulphonic acid in water to provide the aminosulfonyl compound, 6H.

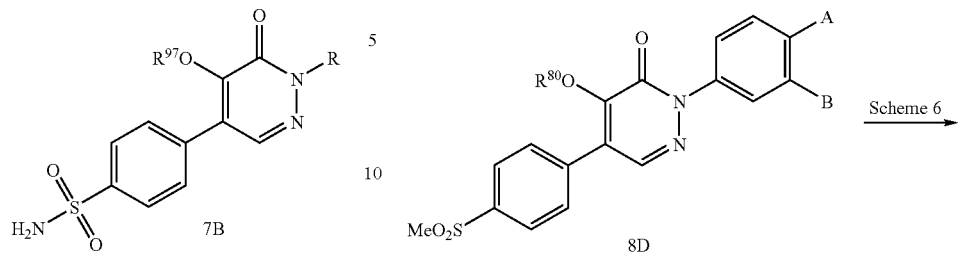

Methylsulfonyl alkoxy pyridazinones and aminosulfonyl alkoxy pyridazinones can be prepared as described in Scheme 7. Alkoxy-pyridazinone, 6C, from Scheme 6, can be oxidized using peracetic acid to provide methyl sulfone, 7A. Methyl sulfone alkoxy pyridazinone, 7A, can be treated as described in Scheme 6 to provide aminosulfonyl alkoxy pyridazinone, 7B. Alternatively, alkoxy-pyridazinone 6C, from Scheme 6, can be oxidized with one equivalent of meta-chloroperoxybenzoic acid or one equivalent of hydroxy(tosyloxy)iodobenzene to provide the methylsulfinyl alkoxy pyridazinone, 7C. Methylsulfinyl alkoxy pyridazinone, 7C, can be treated as described in Scheme 6 to provide aminosulfonyl alkoxy pyridazinone, 7B.

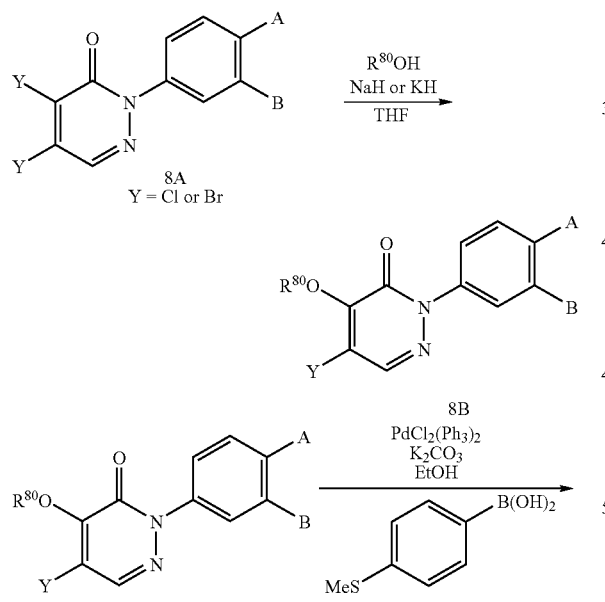

Pyridazinones of general formula 8D and 8E, wherein $R^{80}$ is hydroxyalkyl, and A and B are selected from alkenyl, alkyl, haloalkyl, and halogen, can be prepared as described in Scheme 8. Pyridazinones of general formula 8A can be treated with diols and a base such as sodium hydride or potassium hydride in THF to selectively provide 4-substituted pyridazinones of general formula 8B. 4-Substituted pyridazinones of general formula 8B can be treated with 4-(methylthio)phenylboronic acid, a base such as potassium carbonate, and a palladium catalyst such as dichlorobis(triphenylphosphine)palladium(II) in ethanol to provide methylthio compounds of general formula 8C. Methylthio compounds of general formula 8C can be oxidized with meta-chloroperoxybenzoic acid or peracetic acid to provide methylsulfones of general formula 8D. Methylsulfones of general formula 8D can be processed as described in Scheme 6 to provide aminosulfonyl compounds of general formula 8E. Alternatively, methylthio compounds of general formula 8C can be oxidized to the sulfoxide and then processed as described in Scheme 6 to provide aminosulfonyl compounds of general formula 8E.

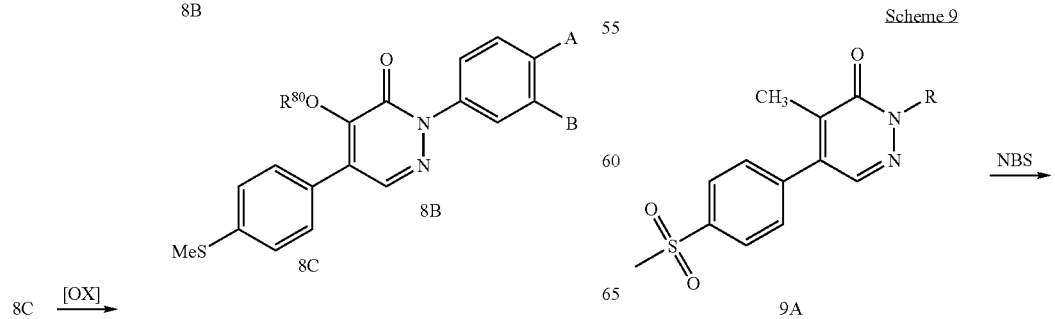

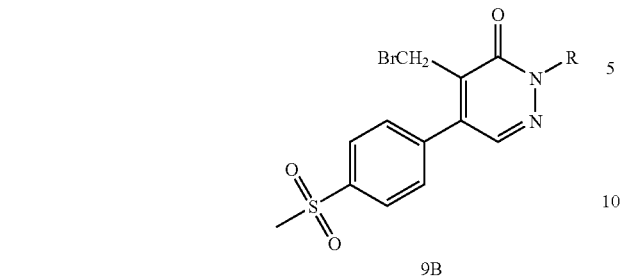

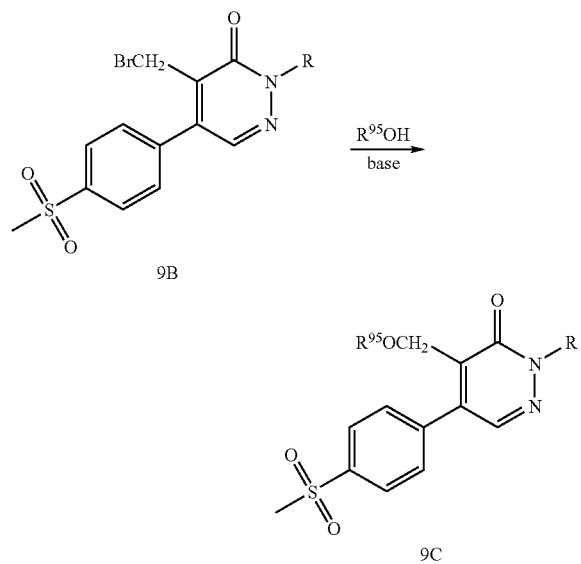

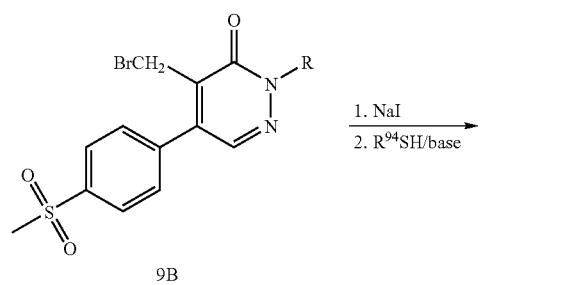

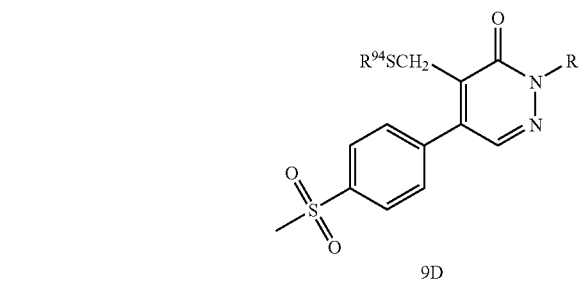

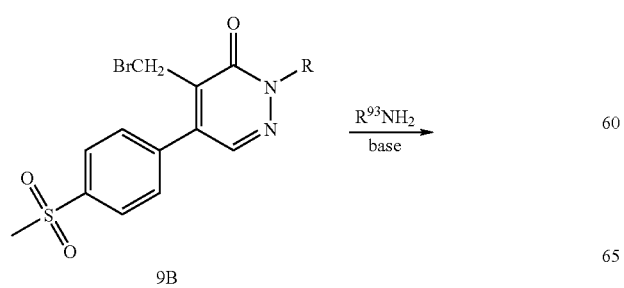

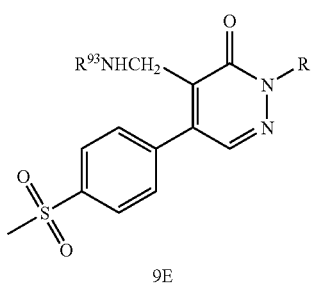

Preparation of compounds of the invention having Formula III, where the group at the 4-position on the pyridazinone ring is a substituted alkyl or alkenyl group is described in Scheme 9. Pyridazinone 9A can be treated with a halogenating reagent, such as NBS and peroxide, to provide bromo compound 9B. The bromo compound can be reacted with an alcohol and a weak base, such as sodium or potassium carbonate, to provide 4-alkyl-ether, 9C where $R^{95}$ is alkyl. Alternatively, bromo compound 9B can be treated with a thio compound in the presence of a base, such as silver carbonate, to provide 4-alkyl-thioether, 9D where $R^{94}$ is alkyl. Alternatively, bromo compound 9B can be treated with an amine and a weak base, such as sodium or potassium carbonate to provide 4-alkylaminoalkyl compound 9E where $R^{93}$ is alkyl.

Scheme 10

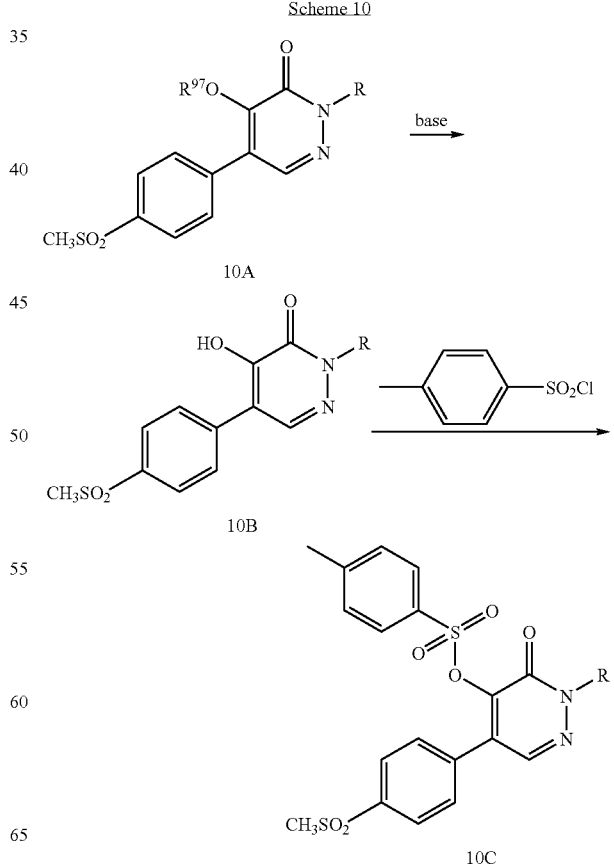

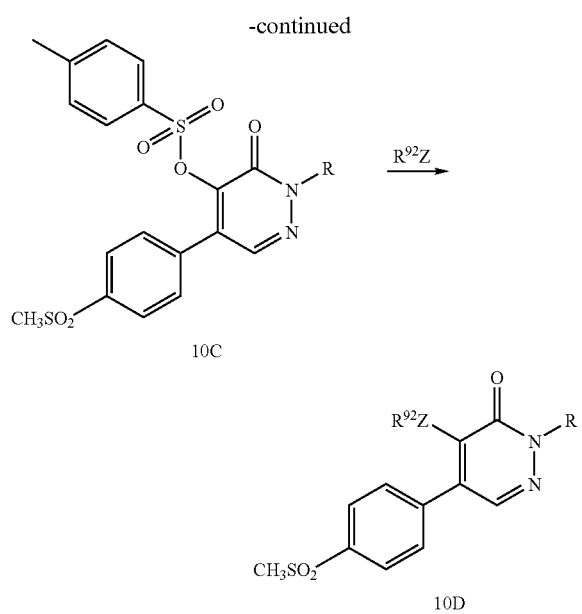

A general route to the compounds of the present invention having Formula III, where the group at the 4-position on the pyridazinone ring can be readily substituted is illustrated in Scheme 10. Alkoxide, 10A, where $R^{97}$ is methyl, can be treated with a base, such as sodium or potassium hydroxide, to provide 4-hydroxy-pyridazinone, 10B. The alcohol can be treated with p-toluenesulfonyl chloride to provide tosyloxy compound, 10C. The tosyloxy compound can be readily substituted with a compound $R^{92}Z$ that can undergo a $S_NAr$ reaction. Examples of these compounds are alcohols, thiols, amines or hydrocarbyl anions.

Compounds of the present invention include, but are not intended to be limited to, the following Examples:

EXAMPLE 1

4-(Methylthio)benzeneboronic acid

A stirred solution of 4-bromothioanisole (5.0 g, 0.0246 mol) in anhydrous tetrahydrofuran (THF) was chilled to −78° C. under a nitrogen atmosphere. A 2.5 M solution of n-butyl lithium (12 mL, 0.030 mol) in hexanes was added dropwise to the chilled solution. When the addition was complete, the reaction mixture was stirred at −78° C. for about 45 minutes. Trimethylborate (8.5 mL, 0.0748) was introduced via syringe. The reaction mixture was then allowed to warm to room temperature overnight. The room temperature solution was treated successively with 10% aqueous sodium hydroxide solution (50 mL) and water (33.5 mL) and stirred at room temperature for 1 hour. The reaction mixture was lowered to about pH=4–5 using 10% aqueous citric acid and the THF was removed under reduced pressure. The aqueous residue was saturated with sodium chloride and extracted with ethyl acetate. The organic extract was dried over MgSO$_4$ and filtered. The filtrate was concentrated under reduced pressure to provide a white solid which was washed with hexanes to provide the product as a white solid (yield: 1.5 g; 36%). mp 170° C. $^1$H NMR (300 MHz, DMSO-d$_6$) δ 2.47 (s, 3H), 7.20 (d, J=8 Hz, 2H), 7.71 (d, J=8 Hz, 2H), 7.96 (br s, 2H).

EXAMPLE 2

2-Benzyl-4,5-dibromo-3(2H)-pyridazinone

Benzyl bromide (0.59 mL, 0.005 mol) was added to a stirred solution of 4,5-dibromo-3(2H)-pyridazinone (1.27 g, 0.005 mol) and potassium carbonate (0.76 g, 0.0055 mol) in 20 mL of anhydrous dimethylformamide (DMF). The solution was stirred overnight at room temperature, and partitioned between aqueous citric acid and ethyl acetate. The aqueous layer was extracted twice with ethyl acetate. The combined organic extracts were washed with brine, dried over MgSO$_4$ and filtered. The filtrate was concentrated under reduced pressure to provide a beige solid, which was purified by column chromatography (silica gel, 9:1 hexanes/ethyl acetate). The product was obtained as a white solid (yield: 1.32 g, 76.7%). mp 95–96° C. $^1$H NMR (300 MHz, CDCl$_3$) δ 5.31 (s, 2H), 7.29–7.37 (m, 3H), 7.41–7.47 (m, 2H), 7.79 (s, 1H). MS (DCI/NH$_3$) m/z 345 (M+H)$^+$. IR (KBr) 1645 cm$^{-1}$.

EXAMPLE 3

2-Benzyl-4-bromo-5-[4-(methylthio)phenyl]-3(2H)-pyridazinone

A solution of the boronic acid (0.318 g, 0. mol), from Example 1, the dibromopyridazinone (0.975 g, 0. mol), prepared according to the method of Example 2, and tetrakis (triphenylphosphine)palladium (0) (0.16 g, 0.0142 mol), in dimethoxyethane (30 mL) was prepared. A 2 M aqueous solution of sodium carbonate (2.83 mL, 0. mol) was added to the dimethoxyethane solution and the mixture was heated at reflux. After 16 hours, a chromatographic (TLC) check (9:1 hexanes/ethyl acetate) indicated that both starting materials were still present and a fresh aliquot of palladium catalyst was added. The reaction mixture was stirred at reflux for an additional 5 hours, allowed to cool to room temperature and stand over the weekend. The volatile materials were removed under reduced pressure and the residue was partitioned between water and ethyl acetate. The aqueous layer was extracted with ethyl acetate. The combined organic extracts were washed with brine, dried over MgSO$_4$, and filtered. The filtrate was concentrated under reduced pressure to provide an oil which was purified by column chromatography (silica gel, 95:5 hexanes/ethyl acetate). Fractions containing the desired product were combined and concentrated under reduced pressure. This material was rechromatographed (95:5 hexanes/ethyl acetate) to furnish 0.200 g of a beige solid. The solid was crystallized from ether/hexanes to provide white crystals (yield: 110 mg, 15%) mp 115–118° C. $^1$H NMR (300 MHz, CDCl$_3$) δ 2.53 (s, 3H), 5.40 (s, 2H), 7.30–7.42 (m, 7 H), 7.49–7.54 (m, 2H), 7.65 (s, 1H). MS (DCI/NH$_3$) m/z 387 (M+H)$^+$.

EXAMPLE 4

2-Benzyl-4-(4-fluorophenyl)-5-[4-(methylthio)phenyl]-3(2H)-pyridazinone

A solution of the product from Example 3, (0.100 g, 0. mol), 4-fluorobenzeneboronic acid (0.072 g, 0. mol), tetrakis (triphenylphosphine)palladium (0) (0.015 g, 0. mol), and a 2 M aqueous solution of sodium carbonate (0.64 mL, 0. mol) in 30 mL of dimethoxyethane (DME) was stirred at reflux for 16 hours. A fresh aliquot of palladium catalyst was added with an additional equivalent of the boronic acid. The reaction was maintained at reflux for 24 hours. The volatile materials were removed under reduced pressure and the residue was partitioned between water and ethyl acetate. The aqueous layer was extracted with ethyl acetate. The combined organic layers were washed with brine, dried over $MgSO_4$, and filtered. The filtrate was adsorbed onto silica gel. The silica gel/product was placed at the top of a column of silica gel and the product eluted with 93:7 hexanes/ethyl acetate. Fractions containing product were combined and concentrated under reduced pressure. The residue was purified further by a second column chromatography (silica gel, 95:5 hexanes/ethyl acetate). Fractions containing product were concentrated under reduced pressure to provide a viscous oil (yield: 0.028 g, 27%). $^1$H NMR (300 MHz, $CDCl_3$) δ 2.46 (s, 3H), 5.39 (s, 2H), 6.95 (t, J=9 Hz, 2H), 6.99 (d, J=9 Hz, 2H), 7.11 (d, J=9 Hz, 2H), 7.16–7.23 (m, 2H), 7.30–7.40 (m, 3H), 7.52–7.57 (m, 2H), 7.86 (s, 1H). MS ($DCI/NH_3$) m/z 403 $(M+H)^+$.

EXAMPLE 5

2-Benzyl-4-(4-fluorophenyl)-5-[4-(methylsulfonyl) phenyl]-3(2H)-pyridazinone

A solution of meta-chloroperoxybenzoic acid (MPCBA) (0.039 g, 0.00013 mol) in dichloromethane (5 mL) was added dropwise to a stirred solution of the sulfide (0.027 g, 0. mol), from Example 4, in chilled (0° C.) dichloromethane (10 mL). After 5 minutes, TLC (1:1 hexanes/ethyl acetate) indicated that the starting sulfide had been consumed. The reaction was quenched with aqueous sodium sulfite. The organic layer was washed twice with aqueous sodium hydroxide and once with brine. The dichloromethane solution was dried over $MgSO_4$, and filtered. The filtrate was concentrated under reduced pressure. The residue was purified by column chromatography (silica gel, 7:3 hexanes/ethyl acetate) to provide the desired sulfone product. Further elution with 100% ethyl acetate removed the sulfoxide from the column. The sulfoxide product was re-subjected to the MCA oxidant (0.04 g, 1 hour, 0° C.) and worked-up as described above. The residue obtained was combined with the sulfone from the first column and the mixture was purified by column chromatography (silica gel, 7:3 hexanes/ethyl acetate). Fractions containing product were combined and concentrated under reduced pressure. The residue was crystallized from ether/hexanes to provide the product as white crystals (yield: 13 mg, 44.6%). mp 101–103° C. $^1$H NMR (300 MHz, $CDCl_3$) δ 3.05 (s, 3H), 5.40 (s, 2H), 6.95 (t, J=9 Hz, 2H), 7.12–7.20 (m, 2H), 7.28–7.41 (m, 3H), 7.31 (d, J=9 Hz, 2H), 7.58–7.53 (m, 2H), 7.84 (s, 1H), 7.87 (d, J=9 Hz, 2H). MS ($DCI/NH_3$) m/z 435 $(M+H)^+$. MS (F, high res.) calculated: m/z 435.1179 $(M+H)^+$. found: m/z 435.1184 $(M+H)^+$.

EXAMPLE 6

2-Benzyl-4-(4-fluorophenyl)-5-methoxy-3(2H)-pyridazinone

To a mixture of 2-benzyl-5-methoxy-4-bromo-3(2H)-pyridazinone, prepared according to the method of (S. Cho et al. described in J. Het. Chem., (1996), 33, 1579–1582), (2.94 g; 10 mmol), 4-fluorobenzeneboronic acid (1.54 g; 11 mmol), and CsF (3.04 g; 22 mmol) in 25 mL of anhydrous DME, under $N_2$, was added $Pd(Ph_3P)_4$ (347 mg 0.3 mmol). After addition, the mixture was heated at reflux for at 100° C., for 18 hours. The mixture was concentrated in vacuo and the residue partitioned between ethyl acetate and water. The acetate layer was washed with brine, dried over $MgSO_4$ and concentrated in vacuo. The solid residue was suspended in ethyl ether-hexanes and filtered to provide a solid product (yield: 3.1 g; about 100%; >95% purity). $^1$H NMR (300 MHz, $CDCl_3$) δ 3.90 (s, 3H), 5.36 (s, 2H), 7.09 (t, J=9 Hz, 2H), 7.31 (m, 3H), 7.50 (m, 4H), 7.91 (s, 1H). MS ($DCI/NH_3$) m/z 311 $(M+H)^+$, 328 $(M+NH_4)^+$.

EXAMPLE 7

2-Benzyl-4-(4-fluorophenyl)-5-hydroxy-3(2H)-pyridazinone

The product from Example 6 (1.24 g; 4 mmol) in 20 mL of acetic acid was treated with aqueous 48% HBr (25 mL). The mixture was heated at reflux for about 5 to about 8 hours (TLC analysis). The mixture was concentrated in vacuo. The product was dissolved in ethyl acetate, washed with 10% bicarbonate, brine and concentrated in vacuo. The residue was treated with diethyl ether-hexanes (2:1) and the solid was filtered to provide an almost pure product (yield: 1.16 g; 98%). $^1$H NMR (300 MHz, DMSO-$d_6$) δ 5.24 (2H), 7.21 (m, 2H), 7.30 (m, 5H), 7.55 (m, 2H), 7.85 (s, 1H), 11.31 (br s, 1H). MS ($DCI/NH_3$) m/z 296 $(M+H)^+$, 314 $(M+NH_4)^+$.

EXAMPLE 8

2-Benzyl-4-(4-fluorophenyl)-5-(trifluoromethylsulfonyloxy)-3(2H)-pyridazinone

A solution of the product from Example 7, (89 mg, 0.3 mmol) in 2.5 mL of anhydrous pyridine under a $N_2$ atmosphere and maintained at 0° C. was treated with triflic anhydride ($Tf_2O$; 0.06 mL; 0.32 mmol) dropwise. The resulting mixture was stirred at 0° C. for 5 minutes and at room temperature for 16 hours. (The pyridine and $Tf_2O$ should be pure for good results. Occasionally an additional amount of $Tf_2O$ is necessary to force the reaction to completion.) The mixture was then poured to a cold solution of citric acid and extracted with ethyl acetate to obtain an almost pure product (yield: 127 mg, about 99%). $^1$H NMR (300 MHz, DMSO-$d_6$) δ 5.34 (s, 2H), 7.35 (m, 7H), 7.60 (m, 2H), 8.48 (s, 1H). MS ($DCI/NH_3$) m/z 429 $(M+H)^+$, 446 $(M+NH_4)^+$.

EXAMPLE 9

2-Benzyl-4-(4-fluorophenyl)-5-[4-(methylthio)phenyl]-3(2H)-pyridazinone

A mixture of the product from Example 8 (154 mg, 0.36 mmol), 4-(methylthio)benzeneboronic acid (67 mg, 0.4 mmol), $Et_3N$ (0.11 mmol; 0.8 mmol) and $Pd(Ph_3P)_4$ (30 mg, 0.025 mmol) in 15 mL of toluene was heated at reflux, about 100° C. for about 45 minutes. The mixture was concentrated in vacuo and the residue purified by column chromatography (hexanes-ethyl acetate 3:1) to provide the title compound (yield: 98 mg, 68%). $^1$H NMR (300 MHz, $CDCl_3$) δ 2.47 (s, 3H), 5.38 (s, 2H), 6.98 (m, 4H), 7.12 (m, 2H), 7.20 (m, 2H), 7.35 (m, 3H), 7.54 (m, 2H), 7.86 (s, 1H). MS ($DCI/NH_3$) m/z 403 $(M+H)^+$, 420 $(M+NH_4)^+$.

EXAMPLE 10

2-Benzyl-4-(4-fluorophenyl)-5-[4-(methylsulfonyl) phenyl]-3(2H)-pyridazinone

To a solution of the product from Example 9 (140 mg, 0.348 mmol), in 10 mL of $CH_2Cl_2$, at 0° C. was added peracetic acid ($CH_3COOOH$; 0.5 mL; 30%). The mixture was stirred at 0° C. for 90 minutes. The dichloromethane was then removed in vacuo. The residue was dissolved in ethyl acetate, washed with 10% $NaHCO_3$, and brine. The ethyl acetate was removed under reduced pressure. The residue was chromatographed (silica gel, $CH_2Cl_2$-diethyl ether 19:1) to provide the title compound (yield: 130 mg, 86%). $^1$H NMR (300 MHz, $CDCl_3$) δ 3.04 (s, 3H), 5.40 (s, 2H), 6.95 (m, 2H), 7.16 (m, 2H), 7.33 (m, 5H), 7.55 (m, 2H), 7.86 (m, 3H). MS ($DCI/NH_3$) m/z 434 (M+H)$^+$, 452 (M+NH$_4$)$^+$.

EXAMPLE 11

4-(4-Fluorophenyl)-5-[4-(methylsulfonyl)phenyl]-3 (2H)-pyridazinone

A mixture of the product from Example 10 (37 mg, 0.085 mmol) and $AlBr_3$ (70 mg, 0.26 mmol) in 10 mL of toluene was heated at reflux, about 80° C. for about 15 minutes and cooled to 0° C. The cooled mixture was treated with 1N HCl and extracted with ethyl acetate. The acetate layer was washed with water, brine and concentrated in vacuo. Purification of the residue on silica gel column (ethyl acetate as an eluent) provided the title compound (yield: 22 mg, 76%). $^1$H NMR (300 MHz, $CDCl_3$) δ 3.07 (s, 3H), 7.00 (t, J=9 Hz, 2H), 7.20 (m, 2H), 7.56 (d, J=9 Hz, 2H), 7.86 (s, 1H), 7.91 (d, J=9 Hz, 2H), 10.94 (br s, 1H). MS ($DCI/NH_3$) m/z 345 (M+H)$^+$, 362 (M+NH$_4$)$^+$.

EXAMPLE 12

2-Phenyl-4-(4-fluorophenyl)-5-[4-(methylsulfonyl) phenyl]-3(2H)-pyridazinone

Example 12A

2-Phenyl-4-chloro-5-methoxy-3(2H)-pyridazinone

The title compound was prepared according to the method of (S. Cho et al. described in J. Het. Chem., (1996), 33, 1579–1582), starting with the N-phenyl-dichloropyridazinone. A mixture of 2-phenyl-4,5-dichloro-3(2H)-pyridazinone (1 g, 4.1 mmol) and finely powdered, anhydrous $K_2CO_3$ (580 mg, 4.2 mmol) in 50 mL of methanol was heated at reflux for 5 hours and concentrated in vacuo. The residue was partitioned between water and ethyl acetate. The acetate layer was washed with water, and brine to provide 2-phenyl-4-chloro-5-methoxy-3(2H)-pyridazinone (yield: 920 mg, 95%). $^1$H NMR (300 MHz, DMSO-$d_6$) δ 4.15 (s, 3H), 7.50 (m, 5H), 8.43 (s, 1H). MS ($DCI/NH_3$) m/z 237 (M+H)$^+$, 254 (M+NH$_4$)$^+$.

Example 12B

2-Phenyl-4-(4-fluorophenyl)-5-methoxy-3(2H)-pyridazinone

The 2-phenyl-4-chloro-5-methoxy-3(2H)-pyridazinone product was coupled with 4-fluorophenylboronic acid according to the method of Example 6 to provide 2-phenyl-4-(4-fluorophenyl)-5-methoxy-3(2H)-pyridazinone (yield: 1.1 g; 96%). $^1$H NMR (300 MHz, $CDCl_3$) δ 4.00 (s, 3H), 7.10 (t, J=9 Hz, 2H), 7.45 (m, 3H), 7.60 (m, 4H), 8.06 (s, 1H). MS ($DCI/NH_3$) m/z 297 (M+H)$^+$.

Example 12C

2-Phenyl-4-(4-fluorophenyl)-5-hydroxy-3(2H)-pyridazinone

The 2-phenyl-4-(4-fluorophenyl)-5-methoxy-3(2H)-pyridazinone product was treated with 48% HBr according to the method of Example 7 to furnish 2-phenyl-4-(4-fluorophenyl)-5-hydroxy-3(2H)-pyridazinone (yield: 957 mg, 92%). MS ($DCI/NH_3$) m/z 283 (M+H)$^+$, 300 (M+NH$_4$)$^+$.

Example 12D

2-Phenyl-4-(4-fluorophenyl)-5-trifluoromethanesulfonyloxy-3(2H)-pyridazinone

The 2-phenyl-4-(4-fluorophenyl)-5-hydroxy-3(2H)-pyridazinone product was sulfonylated according to the method of Example 8 to furnish 2-phenyl-4-(4-fluorophenyl)-5-trifluoromethanesulfonyloxy-3(2H)-pyridazinone (yield: 1.35 g; 96%) MS ($DCI/NH_3$) m/z 415 (M+H)$^+$, 432 (M+NH$_4$)$^+$.

Example 12E

2-Phenyl-4-(4-fluorophenyl)-5-[4-(methylsulfonyl) phenyl]-3(2H)-pyridazinone

The 2-phenyl-4-(4-fluorophenyl)-5-trifluoromethanesulfonyloxy-3(2H)-pyridazinone was coupled with 4-(methylthio)phenylboronic acid as in Example 9 to provide 2-phenyl-4-(4-fluorophenyl)-5-[4-(methylthio)phenyl]-3 (2H)-pyridazinone (yield: 915 mg, 92%) which was immediately oxidized with peracetic acid as in Example 9 to provide the title compound after column chromatography (silica gel, 1:1 hexanes-ethyl acetate) and crystallization from diethyl ether-hexanes (yield: 288 mg, 69%). mp 219–220° C. $^1$H NMR (300 MHz, DMSO-$d_6$) δ 3.25 (s, 3H), 7.15 (t, J=9 Hz, 2H), 7.30 (m, 2H), 7.46 (m, 1H), 7.56 (m, 4H), 7.64 (m, 2H), 7.90 (d, J=9 Hz, 2H), 8.24 (s, 1H). MS ($DCI/NH_3$) m/z 421 (M+H)$^+$, 438 (M+NH$_4$)$^+$.

EXAMPLE 13

4-Fluorophenylacetic acid, methyl ester

A catalytic amount (0.5 mL) of concentrated sulfuric acid was added to a solution of 4-fluorophenylacetic acid (30.8 g, 0.20 mol) in 500 mL of methanol. The solution was stirred at reflux for 4 hours. The volatile materials were removed under reduced pressure to furnish a colorless oil which was dissolved in ether/ethyl acetate and washed with 2 N aqueous $Na_2CO_3$, brine, dried over $MgSO_4$, and filtered. The filtrate was concentrated under reduced pressure to provide an oil which was dried overnight under high vacuum (yield: 33.6 g; 95%). $^1$H NMR (300 MHz, $CDCl_3$) δ 3.59 (s, 2H), 3.65 (s, 3H), 7.01 (t, J=9 Hz, 2H), 7.20–7.28 (m, 2H). MS ($DCI/NH_3$) m/z 186 (M+NH$_4$)$^+$.

EXAMPLE 14

[4-(Methylthio)phenyl]dimethylthioketene acetal, mono-S-oxide

A mixture of methyl(methylsulfinylmethyl)sulfide (50 g, 0.40 mol), and finely powdered sodium hydroxide (3.12 g, 0.078 mol) was stirred at 70° C. for 4 hours. 4-(Methylthio) benzaldehyde (27.4 mL, 0.195 mol) was then added in one lot and the reaction mixture was stirred at 70° C. for an additional 4 hours. The mixture was cooled to room temperature and partitioned between 10% aqueous citric acid and dichloromethane. The organic layer was dried over $MgSO_4$ and filtered. The filtrate was concentrated under reduced pressure to provide a brown oil. The oil was purified by column chromatography (7:3 hexanes/ethyl acetate) to provide a solid. The solid was crystallized from ether/hexanes (yield: 24.7 g; 72%). mp 52–53° C. $^1$H NMR (300 MHz, CDCl$_3$) δ 2.33 (s, 3H), 2.53 (s, 3H), 2.77 (s, 3H), 7.17 (d, J=9 Hz, 2H), 7.57 (s, 1H), 7.86 (d, J=9 Hz, 2H). MS (DCI/NH$_3$) m/z 259 (M+H)$^+$ and m/z 276 (M+NH$_4$)$^+$.

EXAMPLE 15

2-(4-Fluorophenyl)-3-[4-(methylthio)phenyl]-4-methylthio-4-methylsulfinyl-n-butyric acid, methyl ester A solution of the ester product from Example 13, (16.24 g, 0.0966 mol) in 50 mL of THF was added dropwise to a stirred solution of 1.0 M sodium hexamethyldisilazide in THF (96.6 mL, 0.0966 mol), maintained at 0° C., under an atmosphere of dry nitrogen. After 30 minutes, a solution of the ketene thioacetal, prepared according to the method of Example 14 (20.8 g, 0.0805 mol), in 50 mL of THF, was added dropwise to the reaction mixture maintained at 0° C. After 4 hours, the reaction mixture was acidified with 10% aqueous citric acid. The aqueous layer was washed twice with ethyl acetate. The organic extracts were combined, washed with brine, dried over MgSO$_4$ and filtered. The filtrate was concentrated under reduced pressure to provide a brown oil which was purified by column chromatography (85:15 to 1:1 dichloromethane/ethyl acetate gradient). Several products having different Rf values and NMR spectra were isolated. These compounds had identical mass spectra. The mixture of compounds was carried on in the following reactions (yield: 22.4 g; 65%). MS (DCI/NH$_3$) m/z 444 (M+NH$_4$)$^+$.

EXAMPLE 16

2-(4-Fluorophenyl)-3-[4-(methylthio)phenyl]-3-formyl-n-propanoic acid, methyl ester The mixture of compounds from Example 17, (9.0 g, 0.021 mol) were dissolved in acetonitrile (80 mL) and cooled to 0° C. Perchloric acid (60%; 1.06 g, 0.006 mol) was added to the stirred solution. The reaction mixture was stirred at 0° C. for 8 hours, and quenched with 2 N aqueous Na$_2$CO$_3$. The acetonitrile was removed under reduced pressure and the resulting aqueous mixture was extracted with ethyl acetate. The organic solution was dried over MgSO$_4$ and filtered. The filtrate was concentrated under reduced pressure to give a yellow oil which was purified by column chromatography (silica gel, 7:3 hexanes/ethyl acetate). Fractions containing the highest Rf diastereomers from the product mixture were concentrated in vacuo and the residue was crystallized from methanol to furnish the title aldehyde-ester compound as white crystals (yield: 0.27 g, 4.0%). mp=112–113° C. $^1$H NMR (300 MHz, CDCl$_3$) δ 2.49 (s, 3H), 2.46 (s, 3H), 4.39 (s, 2H), 7.03 (t, J=9 Hz, 1H), 7.21 (d, J=9 Hz, 1H), 7.25 (d, J=9 Hz, 2H), 7.40–7.47 (m, 2H). MS (DCI/NH$_3$) m/z 333 (M+H)$^+$ and m/z 350 (M+NH$_4$)$^{30}$. Fractions containing lower Rf compounds from the product mixture were concentrated in vacuo and the residue was identified as the hydrate of the aldehyde-ester (yield: 2.6 g, 35.2%). $^1$H NMR (300 MHz, CDCl$_3$) δ 2.44 & 2.46 (2 s, 3H), 3.56 & 3.48 (2 s, 3H), 3.55 & 3.76 (2 dd, J=6 Hz, J=6 Hz, 1H), 3.98 & 4.26 (2 d, J=12 Hz, 1H), 5.41 & 5.47 (2 d, J=6 Hz, 1H), 6.96 & 7.00 (t, J=9 Hz, 2H), 7.11–7.26 (m, 6H). MS (DCI/NH$_3$) m/z 333 (M+H)$^+$ and m/z 350 (M+NH$_4$)$^+$.

The lowest Rf compound was identified as the hydroxy lactone formed when a hydroxy group from the hydrate displaces the methoxy group from the ester (yield: 1.1 g, 16.4%). $^1$H NMR (300 MHz, CDCl$_3$) δ 2.45 (s, 3H), 3.54–3.71 (m, 1H), 3.98–4.21 (m, 1H), 4.61 (br s, 1H), 5.85–6.01 (m, 1H), 6.98 (t, J=9 Hz, 2H), 7.12–7.27 (m, 6H). MS (DCI/NH$_3$) m/z 336 (M+NH$_4$)$^+$.

EXAMPLE 17

4-(4-Fluorophenyl)-5-[4-(methylthio)phenyl]-4,5-dihydro-3(2H)-pyridazinone

The aldehyde-ester, hydrate, and hydroxy lactone from Example 16 (0.10 g, 3 mmol), were dissolved in 100 mL of ethanol. This solution was treated with hydrazine monohydrate (0.15 mL, 30 mmol) and the resulting solution was stirred at reflux in a Soxhelet apparatus containing molcular sieves. After 18 hours, the reaction mixture was cooled and the volatile materials removed under reduced pressure. The residue was partitioned between ethyl acetate and aqueous HCl. The aqueous layer was washed twice with ethyl acetate. The combined organic extracts were washed twice with brine, dried over MgSO$_4$, and filtered. The filtrate was concentrated under reduced pressure and the residue was purified by column chromatography (4:1 hexanes/ethyl acetate) to obtain the title compound (yield: 50 mg, 53%). $^1$H NMR (300 MHz, CDCl$_3$) δ 2.46 (s, 3H), 3.75 (d, J=12 Hz, 1H), 3.87 (d, J=12 Hz, 1H), 6.93–7.08 (m, 6H), 7.16 (d, J=9 Hz, 2H), 8.71 (s(br), 1H). MS (DCI/NH$_3$) m/z 315 (M+H)$^+$ and m/z 332 (M+NH$_4$)$^+$.

EXAMPLE 18

4-(4-Fluorophenyl)-5-[4-(methylsulfonyl)phenyl]-4,5-dihydro-3(2H)-pyridazinone

A solution of peracetic acid, 32% in acetic acid, (0.4 mL, 1.6 mmol) was added to a stirred solution of the sulfide from Example 17 (0.050 g, 0.16 mmol) in dichloromethane, and maintained at 0° C. The reaction mixture was stirred for 5 hours at 0° C. then diluted with water. The organic layer was dried over MgSO$_4$ and filtered. The filtrate was concentrated under reduced pressure to provide an oil which solidified on trituration with ether (yield: 47 mg, 85%). $^1$H NMR (300 MHz, CDCl$_3$) δ 3.05 (s, 3H), 3.77 (d, J=12 Hz, 1H), 4.05 (d, J=12 Hz, 1H), 6.95–7.08 (m, 4H), 7.28 (d, J=9 Hz, 2H), 7.90 (d, J=9 Hz, 2H), 8.75 (s, broad, 1H). MS (DCI/NH$_3$) m/z 364 (M+NH$_4$)$^+$.

EXAMPLE 19

4-(4-Fluorophenyl)-5-[4-(methylsulfonyl)phenyl]-3(2H)-pyridazinone

The dihydropyridazinone product from Example 18 (47 mg, 0.136 mmol) was dissolved in acetic acid (25 mL). Bromine (0.025 mL, 0.16 mmol) was added to the solution and the reaction mixture was stirred at 95° C. for 20 minutes. The reaction mixture was concentrated under reduced pressure. The residue was partitioned between ethyl acetate and water. The organic layer was washed with brine, dried over MgSO$_4$ and filtered. The filtrate was concentrated under reduced pressure to provide a solid which was eluted through a short pad of silica gel with ethyl acetate. The title compound was crystallized from ethyl acetate/hexanes (yield: 35 mg, 75%). mp 255–256° C. $^1$H NMR (300 MHz, CDCl$_3$) δ 3.07 (s, 3H), 6.98 (t, J=9 Hz, 2H), 7.16–7.23 (m, 2H), 7.35 (d, J=9 Hz, 2H), 7.86 (s, 1H), 7.91 (d, J=9 Hz, 2H). MS (DCI/NH$_3$) m/z 345 (M+H)$^+$ and m/z 362 (M+NH$_4$)$^+$.

EXAMPLE 20

2-(4-Fluorobenzyl)-4-(4-fluorophenyl)-5-[4-(methylsulfonyl)phenyl]-3(2H)-pyridazinone A solution of the nitrogen-unsubstituted pyridazinone product from Example 19 (160 mg, 0.465 mmol), K$_2$CO$_3$ (193 mg, 1.4 mmol), 4-fluorobenzylbromide (0.09 mL, 0.7 mmol) and NaI (catalytic) in 10 mL of anhydrous N,N-dimethylformamide (DMF) was stirred at room temperature for 18 hours. The reaction mixture was quenched with 2N HCl, extracted with ethyl acetate (2×20 mL), washed with brine and water, dried over MgSO$_4$, filtered and concentrated in vacuo. The residue was purified by column chromatography (2:2:6 ethyl acetate/dichloromethane/pentanes). Crystallization from ether/pentanes provided white crystals (yield: 110 mg, 52%). mp 153–154° C. $^1$H NMR (CDCl$_3$, 300 MHz) δ 3.06 (s, 3H), 5.36 (s, 2H), 6.96 (t, J=8.4 Hz, 2H), 7.04 (t, J=8.7 Hz, 2H), 7.16 (dd, J=9.1 Hz, J=5.4 Hz, 2H), 7.31 (d, J=8.5 Hz, 2H), 7.54 (dd, J=8.8 Hz, 5.5 Hz, 2H), 7.84 (s, 1H), 7.87 (d, J=8.8 Hz, 2H). MS (DCI/NH$_3$) m/z 453 (M+H)$^+$.

EXAMPLE 21

2-(Phenylpropgyl)-4-(4-fluorophenyl)-5-[4-(methylsulfonyl)phenyl]-3(2H)-pyridazinone The title compound was prepared according to the method of Example 20, substituting phenylpropargyl bromide for 4-fluorobenzyl bromide. mp 100–103° C. $^1$H NMR (CDCl$_3$, 300 MHz) δ 3.06 (s, 3H), 5.26 (s, 2H), 6.97 (t, J=9 Hz, 2H), 7.20 (dd, J=9 Hz, J=6 Hz, 2H), 7.31 (m, 3H), 7.34 (d, J=9 Hz, 2H), 7.48 (m, 2H), 7.89 (d, J=9 Hz, 2H), 7.9 (s, 1H). MS (DCI/NH$_3$) m/z 459 (M+H)$^+$.

EXAMPLE 22

2-(2,4-Difluorobenzyl)-4-(4-fluorophenyl)-5-[4-(methylsulfonyl)phenyl]-3(2H)-pyridazinone The title compound was prepared according to the method of Example 20, substituting 2,4-difluorobenzyl bromide for 4-fluorobenzyl bromide. mp 179–182° C. $^1$H NMR (CDCl$_3$, 300 MHz) δ 3.06 (s, 3H), 5.45 (s, 2H), 6.87 (m, 2H), 6.96 (t, J=9 Hz, 2H), 7.17 (dd, J=9 Hz, J=6 Hz, 2H), 7.32 (d, J=9 Hz, 2H), 7.54 (m, 1H), 7.86 (s, 1H), 7.88 (d, J=9 Hz, 2H). MS (DCI/NH$_3$) m/z 471 (M+H)$^+$.

EXAMPLE 23

2-(Methyl-2-propenyl)-4-(4-fluorophenyl)-5-[4-(methylsulfonyl)phenyl]-3(2H)-pyridazinone The title compound was prepared according to the method of Example 20, substituting 3-chloro-2-methylpropene for 4-fluorobenzyl bromide. mp 140–142° C. $^1$H NMR (CDCl$_3$, 300 MHz) δ 1.86 (s, 3H), 3.08 (s, 3H), 4.83 (s, 2H), 4.94 (t, J=1 Hz, 1H), 5.05 (t, J=1 Hz, 1H), 6.98 (t, J=9 Hz, 2H), 7.21 (dd, J=9 Hz, J=6 Hz, 2H), 7.37 (d, J=9 Hz, 2H), 7.89 (s, 1H), 7.91 (d, J=9 Hz, 2H). MS (DCI/NH$_3$) m/z 399 (M+H)$^+$.

EXAMPLE 24

2-(3-Methyl-2-butenyl)-4-(4-fluorophenyl)-5-[4-(methylsulfonyl)phenyl]-3(2H)-pyridazinone The desired compound was prepared according to the method of Example 20 substituting 4-bromo-2-methyl-2-butene for 4-fluorobenzyl bromide. mp 169–172° C. $^1$H NMR (CDCl$_3$, 300 MHz) δ 1.78 (s, 3H), 1.85 (s, 3H), 3.06 (s, 3H), 4.86 (d, J=7.5 Hz, 2H), 5.47 (t, J=7.5 Hz, 1H), 6.96 (t, J=9 Hz, 2H), 7.18 (dd, J=9 Hz, J=6 Hz, 2H), 7.33 (d, J=9 Hz, 2H), 7.84 (s, 1H), 7.88 (d, J=9 Hz, 2H). MS (DCI/NH$_3$) m/z 413 (M+H)$^+$.

EXAMPLE 25

2-(2-Trifluoromethylbenzyl)-4-(4-fluorophenyl)-5-[4-(methylsulfonyl)phenyl]-3(2H)-pyridazinone The title compound was prepared according to the method of Example 20, substituting 2-(trifluoromethyl)benzyl bromide for 4-fluorobenzyl bromide. mp 87–90° C. $^1$H NMR (CDCl$_3$, 300 MHz) δ 3.07 (s, 3H), 5.66 (s, 2H), 6.97 (t, J=9 Hz, 2H), 7.21 (dd, J=9 Hz, J=6 Hz, 2H), 7.26 (d, J=7.7 Hz 1H), 7.37 (d, J=9 Hz, 2H), 7.42 (t J=7.7 Hz, 1H), 7.53 (t, J=7.7 Hz, 1H), 7.73 (d J=7.7 Hz, 1H), 7.9 (s, 1H), 7.91 (d, J=9 Hz, 2H). MS (DCI/NH$_3$) m/z 503 (M+H)$^+$.

EXAMPLE 26

2-(Cyclopropylmethyl)-4-(4-fluorophenyl)-5-[4-(methylsulfonyl)phenyl]-3(2H)-pyridazinone The title compound was prepared according to the method of Example 20, substituting 2-(bromomethyl)cyclopropane for 4-fluorobenzyl bromide. mp 118–121° C. $^1$H NMR (CDCl$_3$, 300 MHz) δ 0.45–0.52 (m, 2H), 0.54–0.63 (m, 2H), 1.40–1.52 (m, 1H), 3.07 (s, 3H), 4.07 (d, J=7 Hz, 2H), 6.97 (t, J=9 Hz, 2H), 7.19 (dd, J=9 Hz, J=6 Hz, 2H), 7.35 (d, J=9 Hz, 2H), 7.83 (s, 1H), 7.88 (d, J=9 Hz, 2H). MS (DCI/NH$_3$) m/z 399 (M+H)$^+$ and m/z 416 (M+NH$_4$)$^+$.

EXAMPLE 27

2-(2-Pyridylmethyl)-4-(4-fluorophenyl)-5-[4-(methylsulfonyl)phenyl]-3(2H)-pyridazinone The title compound was prepared according to the method of Example 20, substituting 2-(bromomethyl)pyridine for 4-fluorobenzyl bromide. mp 182–184° C. $^1$H NMR (CDCl$_3$, 300 MHz) δ 3.07 (s, 3H), 5.56 (s, 2H), 6.95 (m, 2H), 7.17

(m, 2H), 7.26 (m, 1H), 7.35 (m, 2H), 7.46 (m, 1H), 7.71 (m, 1H), 7.90 (m, 3H), 8.63 (m, 1H). MS (DCI/NH$_3$) m/z 436 (M+H)$^+$.

EXAMPLE 28

2-(4-Pyridylmethyl)-4-(4-fluorophenyl)-5-[4-(methylsulfonyl)phenyl]-3(2H)-pyridazinone The title compound was prepared according to the method of Example 20, substituting 4-(bromomethyl)pyridine for 4-fluorobenzyl bromide. mp 153–156° C. $^1$H NMR (CDCl$_3$, 300 MHz) δ 3.07 (s, 3H), 5.40 (s, 2H), 6.97 (m, 2H), 7.17 (m, 2H), 7.34 (m, 2H), 7.42 (m, 2H), 7.90 (m, 3H), 8.63 (m, 2H). MS (DCI/NH$_3$) m/z 436 (M+H)$^+$.

EXAMPLE 29

2-(3-Pyridylmethyl)-4-(4-fluorophenyl)-5-[4-(methylsulfonyl)phenyl]-3(2H)-pyridazinone The title compound was prepared according to the method of Example 20, substituting 3-(bromomethyl)pyridine for 4-fluorobenzyl bromide. mp 160–161° C. $^1$H NMR (CDCl$_3$, 300 MHz) δ 3.07 (s, 3H), 5.43 (s, 2H), 6.97 (m, 2H), 7.15 (m, 2H), 7.34 (m, 4H), 7.35 (m, 2H), 7.87 (m, 2H), 7.97 (s, 1H), 8.60 (m, 1H), 8.81 (m, 1H). MS (DCI/NH$_3$) m/z 436 (M+H)$^+$.

EXAMPLE 30

2-(6-Fluoroquinolin-2-ylmethyl)-4-(4-fluorophenyl)-5-[4-(methylsulfonyl)phenyl]-3(2H)-pyridazinone The title compound was prepared according to the method of Example 20, substituting 2-(chloromethyl)-6-fluoroquinoline for 4-fluorobenzyl bromide. mp 116–119° C. $^1$H NMR (CDCl$_3$, 300 MHz) δ 3.07 (s, 3H), 5.73 (s, 2H), 6.96 (m, 2H), 7.18 (m, 2H), 7.34 (m, 4H), 7.35 (m, 2H), 7.46 (m, 2H), 7.58 (m, 3H), 7.90 (m, 3H), 8.12 (m, 2H). MS (DCI/NH$_3$) m/z 504 (M+H)$^+$.

EXAMPLE 31

2-(Quinolin-2-ylmethyl)-4-(4-fluorophenyl)-5-[4-(methylsulfonyl)phenyl]-3(2H)-pyridazinone The title compound was prepared according to the method of Example 20, substituting 2-(chloromethyl)-quinoline for 4-fluorobenzyl bromide. mp 97–100° C. $^1$H NMR (CDCl$_3$, 300 MHz) δ 3.06 (s, 3H), 5.75 (s, 2H), 6.95 (m, 2H), 7.19 (m, 2H), 7.35 (m, 2H), 7.55 (m, 2H), 7.73 (m, 1H), 7.82 (m, 1H), 7.90 (m, 3H), 8.15 (m, 2H). MS (DCI/NH$_3$) m/z 386 (M+H)$^+$.

EXAMPLE 32

2-Benzyl-4-(4-fluorophenyl)-5-[4-(methylsulfonyl)phenyl]-3(2H)-pyridazinethione

A mixture of 2-benzyl-4-(4-fluorophenyl)-5-[4-(methylsulfonyl)phenyl]-3(2H)-pyridazinone, prepared according to the method of Example 5, (109 mg, 0.25 mmol) and Lawesson's reagent (202 mg, 0.5 mmol) in 15 mL of toluene was stirred at reflux for 48 hours. The mixture was concentrated in vacuo and the residue was chromatographed (silica gel, ethyl acetate) to provide the title compound (yield: 100 mg, 88%). mp 88–90° C. $^1$H NMR (300 MHz, CDCl$_3$) δ 3.04 (s, 3H), 6.05 (s, 2H), 6.96 (m, 2H), 7.08 (m, 2H), 7.26 (m, 2H), 7.37 (m, 3H), 7.61 (m, 2H), 7.84 (d, J=9 Hz, 2H), 8.13 (s, 1H). MS (DCI/NH$_3$) m/z 451 (M+H)$^+$.

EXAMPLE 33

2-Benzyl-4-(4-fluorophenyl)-5-[4-(aminosulfonyl)phenyl]-3(2H)-pyridazinone

Example 33 was prepared using a similar procedure as that described in (M. De Vleeschauwer and J. V. Gauthier, Syn. Lett., (1997) 375).

Example 33A

2-Benzyl-4-(4-fluorophenyl)-5-[4-(methylsulfinyl)phenyl]-3(2H)-pyridazinone

A solution of 2-benzyl-4-(4-fluorophenyl)-5-[4-(methylthio)phenyl]-3(2H)-pyridazinone, prepared according to the method of Example 4, (450 mg, 1.12 mmol) in CH$_2$Cl$_2$ (10 mL) was added dropwise to a suspension of hydroxy (tosyloxy)iodobenzene (439 mg, 1.12 mmol) in CH$_2$Cl$_2$ (15 mL) and the mixture was stirred until a clear solution was obtained (about 1 hour). The reaction mixture was then washed with water and dried with MgSO$_4$. Removal of solvent in vacuo provided the corresponding sulfoxide (yield: 485 mg, about 100%). $^1$H NMR (300 MHz, CDCl$_3$) δ 2.72 (s, 3H), 5.40 (s, 2H), 6.90 (m, 2H), 7.15 (m, 3H), 7.33 (m, 3H), 7.57 (m, 3H), 7.71 (m, 1H), 7.86 (s, 1H). MS (DCI/NH$_3$) m/z 419 (M+H)$^+$, 436 (M+NH$_4$)$^+$.

Example 33B 2-benzyl-4-(4-fluorophenyl)-5-(acetoxymethylsulfonylphenyl)-3(2H)-pyridazinone A suspension of the sulfoxide from Example 33A, (485 mg, 1.12 mmol) and AcONa (1.4 g) in 15 mL of Ac$_2$O was stirred at reflux for 2 hours and concentrated in vacuo. The residue was distilled twice with toluene, dissolved in 25 mL of CH$_2$Cl$_2$, cooled to 0° C., and treated with CH$_3$CO$_3$H (1 mL). After 1 hour, the mixture was washed, successively, with saturated NaHCO$_3$ and brine. The solvent was removed in vacuo. The residue was chromatographed (silica gel, 1:1 hexanes-ethyl acetate) to provide the desired product, 2-benzyl-4-(4-fluorophenyl)-5-(acetoxymethylsulfonylphenyl)-3 (2H)-pyridazinone (yield: 150 mg, 27%). MS (DCI/NH$_3$) m/z 493 (M+H)$^+$.

Example 33C

2-Benzyl-4-(4-fluorophenyl)-5-[4-(sodiumsulfinate)phenyl]-3(2H)-pyridazinone

To a solution of the acetoxymethylsulfone from Example 33B (150 mg, 0.305 mmol), in 10 mL of THF and 5 mL of methanol at 0° C., was added 1 N NaOH (0.305 mL, 0.305 mmol). The mixture was stirred at 0° C. for 1 hour. The mixture was concentrated in vacuo, the residual water was removed via an EtOH/toluene azeotrope followed by a toluene azeotrope. The residue was dried under high vacuum for 48 hours to provide the sodium sulfinate (yield: 140 mg, 96%). MS (DCI/NH$_3$) m/z 443 (M+H)$^+$

Example 33D

2-Benzyl-4-(4-fluorophenyl)-5-[4-(chlorosulfonyl) phenyl]-3(2H)-pyridazinone

The sodium sulfinate (about 0.31 mmol) in $CH_2Cl_2$ (10 mL) was treated at 0° C. with $SOCl_2$ (0.033 mL, 0.4 mmol) for 2 hours. The mixture was washed with brine, dried with $MgSO_4$ and concentrated in vacuo to provide the crude sulfonyl chloride (yield: 145 mg, about 100%). MS (DCI/$NH_3$) m/z 455 $(M+H)^+$.

Example 33E

2-Benzyl-4-(4-fluorophenyl)-5-[4-(aminosulfonyl) phenyl]-3(2H)-pyridazinone

The crude chloride prepared according to the method of Example 33D, in 10 mL of THF, was added to a solution of 50% $NH_4OH$, in 10 mL of THF, maintained at 0° C. The mixture was allowed to warm to room temperature over 3.5 hours. The THF was removed in vacuo and the product was extracted with ethyl acetate. The ethyl acetate was removed in vacuo and the residue was treated with diethyl ether-hexanes 2:1 to provide the sulfonamide (yield: 113 mg, 84%). mp 188–191° C. $^1H$ NMR (300 MHz, DMSO-$d_6$) δ 2.70 (dd, J=15 Hz, 2H), 5.36 (s, 2H), 7.13 (t, J=9 Hz, 2H), 7.22 (m, 2H), 7.40 (m, 7H), 7.73 (d, J=9 Hz, 2H), 8.11 (s, 1H). MS (DCI/$NH_3$) m/z 436 $(M+H)^+$.

EXAMPLE 34

2-(2,2,2-Trifluoroethyl)-4-(4-fluorophenyl)-5-[4-(methylsulfonyl)phenyl]-3(2H)-pyridazinone The title compound was prepared according to the method of Example 20, substituting 2-iodo-1,1,1-trifluoroethane for 4-fluorobenzyl bromide. mp 177–179° C. $^1H$ NMR (CDCl$_3$, 300 MHz) δ 3.06 (s, 3H), 4.88 (q, J=9 Hz, 2H), 6.98 (t, J=9 Hz, 2H), 7.18 (dd, J=9 Hz, J=6 Hz, 2H), 7.35 (d, J=9 Hz, 2H), 7.89 (s, 1H), 7.91 (d, J=9 Hz, 2H). MS (DCI/$NH_3$) m/z 427 $(M+H)^+$ and m/z 444 $(M+NH_4)^+$.

EXAMPLE 35

2-(3,3-Dichloro-2-propenyl)-4-(4-fluorophenyl)-5-[4-(methylsulfonyl)phenyl]-3(2H)-pyridazinone The title compound was prepared according to the method of Example 20, substituting 1,1,3-trichloropropene for 4-fluorobenzyl bromide. mp 150–152° C. $^1H$ NMR (CDCl$_3$, 300 MHz) δ 3.06 (s, 3H), 4.98 (d, J=7 Hz, 2H), 6.25 (t, J=7 Hz, 1H), 6.98 (t, J=9 Hz, 2H), 7.18 (dd, J=9 Hz, J=6 Hz, 2H), 7.33 (d, J=9 Hz, 2H), 7.85 (s, 1H), 7.89 (d, J=9 Hz, 2H). MS (DCI/$NH_3$) m/z 453 $(M+H)^+$ and m/z 470 $(M+NH_4)^+$.

EXAMPLE 36

2-(3-Phenyl-2propenyl)-4-(4-fluorophenyl)-5-[4-(methylsulfonyl)phenyl]-3(2H)-pyridazinone The title compound was prepared according to the method of Example 20, substituting cinnamyl bromide for 4-fluorobenzyl bromide. mp 165–167° C. $^1H$ NMR (CDCl$_3$, 300 MHz) δ 3.06 (s, 3H), 5.01 (d, J=7 Hz, 2H), 6.48 (dt, J=15 Hz, 7 Hz, 1H), 6.79 (d, J=15 Hz, 1H), 6.97 (t, J=9 Hz, 2H), 7.19 (dd, J=9 Hz, J=6 Hz, 2H), 7.25–7.44 (m, 5H), 7.37 (d, J=9 Hz, 2H), 7.86 (s, 1H), 7.89 (d, J=9 Hz, 2H). MS (DCI/$NH_3$) m/z 461 $(M+H)^+$ and m/z 478 $(M+NH_4)^+$.

EXAMPLE 37

2-(4-Carboxyphenacyl)-4-(4-fluorophenyl)-5-[4-(methylsulfonyl)phenyl]-3(2H)-pyridazinone The title compound was prepared according to the method of Example 20, substituting methyl 4-(bromomethyl)benzoate for 4-fluorobenzyl bromide and hydrolysis of the resulting ester. mp 239–241° C. $^1H$ NMR (CDCl$_3$, 300 MHz) δ 3.06 (s, 3H), 5.46 (s, 2H), 6.96 (t, J=9 Hz, 2H), 7.17 (dd, J=9 Hz, 6 Hz, 2H), 7.33 (d, J=9 Hz, 2H), 7.63 (d, J=9 Hz, 2H), 7.87 (s, 1H), 7.89 (d, J=9 Hz, 2H), 8.08 (d, J=9 Hz, 2H). MS (DCI/$NH_3$) m/z 479 $(M+H)^+$ and m/z 496 $(M+NH_4)^+$.

EXAMPLE 38

2-(5-Methylthiazol-2-ylmethyl)-4-(4-fluorophenyl)-5-[4-(methylsulfonyl)phenyl]-3(2H)-pyridazinone The title compound was prepared according to the method of Example 20, substituting 2-(bromomethyl)-5-methylthiazole for 4-fluorobenzyl bromide. mp 114–116° C. $^1H$ NMR (d$_6$-DMSO, 300 MHz) δ 2.64 (s, 3H), 3.23 (s, 2H), 5.37 (s, 2H), 7.13 (m, 2H), 7.23 (m, 2H), 7.40 (s, 1H), 7.47 (d, J=8 Hz, 2H), 7.87 (d, J=8 Hz, 2H), 8.10 (s, 1H). MS (DCI/$NH_3$) m/z 356 $(M+H)^+$.

EXAMPLE 39

2-(5-Chlorothiazol-2-ylmethyl)-4-(4-fluorophenyl)-4-(methylsulfonyl)phenyl]-3(2H)-pyridazinone The title compound was prepared according to the method of Example 20, substituting 2-(bromomethyl)-5-chlorothiazole for 4-fluorobenzyl bromide. mp 185–186° C. $^1H$ NMR (d$_6$-DMSO, 300 MHz) δ 2.32 (s, 3H), 5.50 (s, 2H), 7.15 (m, 2H), 7.24 (m, 2H), 7.47 (m, 2H), 7.87 (m, 3H), 8.14 (s, 1H). MS (DCI/$NH_3$) m/z 476 $(M+H)^+$ and m/z 493 $(M+NH_4)^+$.

EXAMPLE 40

2-(2,3,3,4,4,4-Hexafluorobuten-1-yl)-4-(4-fluorophenyl)-5-[4-(methylsulfonyl)phenyl]-3(2H)-pyridazinone The title compound was prepared according to the method of Example 20, substituting 2,2,3,3,4,4,4-heptafluoro-1-iododobutane for 4-fluorobenzyl bromide. Under the alkylation conditions, elimination of HF provided the unsaturated product. mp 167–169° C. $^1H$ NMR (CDCl$_3$, 300 MHz) δ 3.07 (s, 3H), 7.00 (t, J=9 Hz, 2H), 7.17 (dd, J=9 Hz, 6 Hz, 2H), 7.33 (d, J=9 Hz, 2H), 7.68 (d, J=24 Hz, 1H), 7.93 (d, J=9 Hz, 2H), 8.01 (s, 1H). MS (DCI/$NH_3$) m/z 507 $(M+H)^+$ and m/z 524 $(M+NH_4)^+$.

EXAMPLE 41

2-(2,4-Difluorophenacyl)-4-(4-fluorophenyl)-5-[4-(methylsulfonyl)phenyl]-3(2H)-pyridazinone The title compound was prepared according to the method of Example 20, substituting 2-chloro-2',4'-difluoroacetophenone for 4-fluorobenzyl bromide. mp 191–192° C. $^1H$ NMR (CDCl$_3$, 300 MHz) δ 3.08 (s, 3H), 5.57 (d, J=3 Hz, 2H), 6.94–7.07 (m, 2H), 6.96 (t, J=9 Hz, 2H), 7.39 (dd, J=9 Hz, 6 Hz, 2H), 7.91 (s, 1H), 7.91 (d, J=9 Hz, 2H), 8.03–8.12 (m, 1H). MS (DCI/NH$_3$) m/z 499 (M+H)$^+$ and m/z 516 (M+NH$_4$)$^+$.

EXAMPLE 42

2-(5-Chlorothien-2-ylmethyl)-4-(4-fluorophenyl)-5-[4-(methylsulfonyl)phenyl]-3(2H)-pyridazinone The title compound was prepared according to the method of Example 20, substituting 2-(bromomethyl)-5-chlorothiophene for 4-fluorobenzyl bromide. mp 139–141° C. $^1$H NMR (d$_6$-DMSO, 300 MHz) δ 3.23 (s, 3H), 5.43 (s, 2H), 7.03 (d, J=4 Hz, 1H). 7.09–7.29 (m, 5H), 7.47 (d, J=8 Hz, 2H), 7.87 (d, J=8 Hz, 3H), 8.13 (s, 1H). MS (DCI/NH$_3$) m/z 474 (M+H)$^+$ and m/z 492 (M+NH$_4$)$^+$.

EXAMPLE 43

2-(5-Methylthien-2-ylmethyl)-4-(4-fluorophenyl)-5-[4-(methylsulfonyl)phenyl]-3(2H)-pyridazinone The title compound was prepared according to the method of Example 20, substituting 2-(bromomethyl)-5-methylthiophene for 4-fluorobenzyl bromide. mp 172–175° C. $^1$H NMR (d$_6$-DMSO, 300 MHz) δ 3.22 (s, 3H), 5.49 (s, 2H), 7.03 (m, 1H), 7.14 (m, 2H), 7.23 (m, 3H), 7.48 (m, 3H), 7.86 (m, 2H), 8.11 (s, 1H). MS (DCI/NH$_3$) m/z 441 (M+H)$^+$ and m/z 458 (M+NH$_4$)$^+$.

EXAMPLE 44

2-(4-Diethylaminophenacyl)-4-(4-fluorophenyl)-5-[4-(methylsulfonyl)phenyl]-3(2H)-pyridazinone The title compound was prepared according to the method of Example 20, substituting 2-chloro-4'-diethylaminoacetophenone for 4-fluorobenzyl bromide. mp 105–108° C. $^1$H NMR (CDCl$_3$, 300 MHz) δ 1.23 (t, J=7 Hz, 3H), 3.07 (s, 3H), 3.44 (q, J=7 Hz, 2H), 5.61 (s, 2H), 6.66 (d, J=9 Hz, 2H), 6.94 (t, J=9 Hz, 2H), 7.21 (dd, J=9 Hz, 6 Hz, 2H), 7.38 (d, J=9 Hz, 2H), 7.87–7.94 (m, 4H), 7.90 (s, 1H). MS (DCI/NH$_3$) m/z 534 (M+H)$^+$.

EXAMPLE 45

2-(2,3,4,5,6-Pentafluorobenzyl)-4-(4-fluorophenyl)-5-[4-(methylsulfonyl)phenyl]-3(2H)-pyridazinone The title compound was prepared according to the method of Example 20, substituting 2,3,4,5,6-pentafluorobenzyl bromide for 4-fluorobenzyl bromide. mp 115–116° C. $^1$H NMR (CDCl$_3$, 300 MHz) 3.06 (s, 3H), 5.50 (s, 2H), 6.96 (t, J=9 Hz, 2H), 7.17 (dd, J=9 Hz, 6 Hz, 2H), 7.33 (d, J=9 Hz, 2H), 7.82 (s, 1H), 7.89 (d, J=9 Hz, 2H). MS (DCI/NH$_3$) m/z 525 (M+H)$^+$ and m/z 542 (M+NH$_4$)$^+$.

EXAMPLE 46

2-(Phenacyl)-4-(4-fluorolphenyl)-5-[4-(methylsulfonyl)phenyl]-3(2H)-pyridazinone The title compound was prepared according to the method of Example 20, substituting 2-bromoacetophenone for 4-fluorobenzyl bromide. mp 228–230° C. $^1$H NMR (CDCl$_3$, 300 MHz) 3.07 (s, 3H), 5.68 (s, 2H), 6.95 (t, J=9 Hz, 2H), 7.20 (dd, J=9 Hz, 6 Hz, 2H), 7.38 (d, J=9 Hz, 2H), 7.53 (t, J=7 Hz, 2H), 7.65 (t, J=7 Hz, 1H), 7.90 (d, J=9 Hz, 2H), 7.91 (s, 1H), 8.04 (d, J=7 Hz, 2H). MS (DCI/NH$_3$) m/z 463 (M+H)$^+$ and m/z 480 (M+NH$_4$)$^+$.

EXAMPLE 47

2-(4-Chlorophenacyl)-4(4-fluorophenyl)-5-[4-(methylsulfonyl)phenyl]-3(2H)-pyridazinone The title compound was prepared according to the method of Example 20, substituting 2-bromo-4'-chloroacetophenone for 4-fluorobenzyl bromide. mp 186–188° C. $^1$HNMR (CDCl$_3$, 300 MHz) 3.07 (s, 3H), 5.63 (s, 2H), 6.95 (t, J=9 Hz, 2H), 7.19 (dd, J=9 Hz, 6 Hz, 2H), 7.38 (d, J=9 Hz, 2H), 7.51 (d, J=9 Hz, 2H), 7.65 (t, J=7 Hz, 1H), 7.90 (d, J=9 Hz, 2H), 7.91 (s, 1H), 7.98 (d, J=9 Hz, 2H). MS (DCI/NH$_3$) m/z 497 (M+H)$^+$ and m/z 514 (M+NH$_4$)$^+$.

EXAMPLE 48

2-(Propargyl)-4-(4-fluorophenyl)-5-[4-(methylsulfonyl)phenyl]-3(2H)-pyridazinone The title compound was prepared according to the method of Example 20, substituting propargyl bromide for 4-fluorobenzyl bromide. mp 196–198° C. $^1$H NMR (CDCl$_3$, 300 MHz) 2.42 (t, J=3 Hz, 1H), 3.06 (s, 3H), 5.04 (d, J=3 Hz, 2H), 6.97 (t, J=9 Hz, 2H), 7.19 (dd, J=9 Hz, 6 Hz, 2H), 7.34 (d, J=9 Hz, 2H), 7.90 (s, 1H), 7.91 (d, J=9 Hz, 2H). MS (DCI/NH$_3$) m/z 383 (M+H)$^+$ and m/z 400 (M+NH$_4$)$^+$.

EXAMPLE 49

2-(4-Cyanophenacyl)-4-(4-fluorophenyl)-5-[4-(methylsulfonyl)phenyl]-3(2H)-pyridazinone The title compound was prepared according to the method of Example 20, substituting 2-bromo-4'-cyanoacetophenone for 4-fluorobenzyl bromide. mp 188–189° C. $^1$H NMR (CDCl$_3$, 300 MHz) 3.08 (s, 3H), 5.64 (s, 2H), 6.96 (t, J=9 Hz, 2H), 7.19 (dd, J=9 Hz, 6 Hz, 2H), 7.38 (d, J=9 Hz, 2H), 7.84 (d, J=9 Hz, 2H), 7.91 (d, J=9 Hz, 2H), 7.93 (s, 1H), 8.14 (d, J=9 Hz, 2H). MS (DCI/NH$_3$) m/z 488 (M+H)$^+$.

EXAMPLE 50

2-(α-Methyl-4-fluorobenzyl)-4-(4-fluorophenyl)-5-[4-(methylsulfonyl)phenyl]-3(2H-pyridazinone The title compound was prepared according to the method of Example 20, substituting α-methyl-4-fluorobenzyl bromide for 4-fluorobenzyl bromide. mp 162–164° C. $^1$H NMR (CDCl$_3$, 300 MHz) 3.06 (s, 3H), 6.40 (t, J=9 Hz, 2H), 6.95 (t, J=9 Hz, 2H), 7.05 (t, J=9 Hz, 2H), 7.15 (dd, J=9 Hz and 6 Hz, 2H), 7.31 (d, J=9 Hz, 2H), 7.53 (dd, J=9 Hz and 6 Hz, 2H), 7.87 (d, J=9 Hz, 2H), 7.88 (s, 1H). MS (DCI/NH$_3$) m/z 467 (M+H)$^+$ and m/z 484 (M+NH$_4$)$^+$.

EXAMPLE 51

2-Phenethyl-4-(4-fluorophenyl)-5-[4-(methylsulfonyl)phenyl]-3(2H)-pyridazinone

The title compound was prepared according to the method of Example 20, substituting (2-bromoethyl)benzene for 4-fluorobenzyl bromide. mp 170–171° C. $^1$H NMR (CDCl$_3$, 300 MHz) 3.07 (s, 3H), 3.20 (t, J=9 Hz, 2H), 4.28 (t, J=9 Hz, 2H), 6.98 (t, J=9 Hz, 2H), 7.18 (dd, J=9 Hz and 6 Hz, 2H), 7.22–37 (m, 5 H), 7.34 (d, J=9 Hz, 2H), 7.83 (s, 1H), 7.89 (d, J=9 Hz, 2H). MS (DCI/NH$_3$) m/z 449 (M+H)$^+$ and m/z 466 (M+NH$_4$)$^+$.

EXAMPLE 52

2-Benzyl-4-(3-chloro-4-fluorophenyl)-5-[4-(methylsulfonyl)phenyl]-3(2H)-pyridazinone The title compound was prepared according to the method described in Examples 6–10 substituting 3-chloro-4-fluorobenzeneboronic acid for 4-fluorobenzeneboronic acid in Example 6. mp 134–136° C. $^1$H NMR (CDCl$_3$, 300 MHz) 3.06 (s, 3H), 5.41 (s, 2H), 6.96–7.02 (m, 2H), 7.29–7.41 (m, 3H), 7.33 (d, J=9 Hz, 2H), 7.51–7.56 (m, 2H), 7.85 (s, 1H), 7.91 (d, J=9 Hz, 2H). MS (DCI/NH$_3$) m/z 469 (M+H)$^+$ and m/z 486 (M+NH$_4$)$^+$.

EXAMPLE 53

2-Benzyl-4-(4-chlorophenyl)-5-[4-(methylsulfonyl)phenyl]-3(2H)-pyridazinone

The title compound was prepared according to the method described in Examples 6–10 except substituting 4-chlorobenzeneboronic acid for 4-fluorobenzeneboronic acid in Example 6. mp 157–159° C. $^1$H NMR (CDCl$_3$, 300 MHz) 3.05 (s, 3H), 5.40 (s, 2H), 7.11 (d, J=9 Hz, 2H), 7.24 (d, J=9 Hz, 2H), 7.28–7.40 (m, 2H), 7.31 (d, J=9 Hz, 2H), 7.51–7.57 (m, 2H), 7.84 (s, 1H), 7.88 (d, J=9 Hz, 2H). MS (DCI/NH$_3$) m/z 451 (M+H)$^+$ and m/z 468 (M+NH$_4$)$^+$.

EXAMPLE 54

2-(2,2,2-Trifluoroethyl)-4-(3-chloro-4-fluorophenyl)-5-[4-(methylsulfonyl)phenyl]-3(2H)-pyridazinone The title compound was prepared by N-debenzylation of the product, prepared in Example 52 according to the method of Example 11, followed by alkylation with 2-iodo-1,1,1-trifluoroethane according to the method of Example 20. mp 165–166° C. $^1$H NMR (CDCl$_3$, 300 MHz) 3.07 (s, 3H), 4.89 (q, J=9 Hz, 2H), 7.00–7.06 (m, 2H), 7.31–7.35 (m, 1H), 7.37 (d, J=9 Hz, 2H), 7.90 (s, 1H), 7.94 (d, J=9 Hz, 2H). MS (DCI/NH$_3$) m/z 461 (M+H)$^+$ and m/z 478 (M+NH$_4$)$^+$.

EXAMPLE 55

2-(4-Trifluoromethoxyphenacyl)-4-(4-fluorophenyl)-5-[4-(methylsulfonyl)phenyl]-3(2H)-pyridazinone The title compound was prepared according to the method of Example 20, substituting 2-bromo-4'-trifluoromethoxyacetophenone for 4-fluorobenzyl bromide. mp 160–161° C. $^1$H NMR (CDCl$_3$, 300 MHz) 3.08 (s, 3H), 5.65 (s, 2H), 6.96 (t, J=9 Hz, 2H), 7.20 (dd, J=9 Hz, 6 Hz, 2H), 7.37 (d, J=9 Hz, 2H), 7.91 (d, J=9 Hz, 2H), 7.93 (s, 1H), 8.11 (d, J=9 Hz, 2H). MS (DCI/NH$_3$) m/z 547 (M+H)$^+$ and m/z 564 (M+NH$_4$)$^+$.

EXAMPLE 56

2-(4-Trifluoromethylphenacyl)-4-(4-fluorophenyl)-5-4-(methylsulfonyl)phenyl]-3(2H)-pyridazinone The title compound was prepared according to the method of Example 20, substituting 2-bromo-4'-trifluoromethylacetophenone for 4-fluorobenzyl bromide. mp 205–206° C. $^1$H NMR (CDCl$_3$, 300 MHz) 3.07 (s, 3H), 5.66 (s, 2H), 6.96 (t, J=9 Hz, 2H), 7.20 (dd, J=9 Hz, 6 Hz, 2H), 7.38 (d, J=9 Hz, 2H), 7.80 (d, J=9 Hz, 2H), 7.91 (d, J=9 Hz, 2H), 7.92 (s, 1H), 8.15 (d, J=9 Hz, 2H). MS (DCI/NH$_3$) m/z 531 (M+H)$^+$ and m/z 548 (M+NH$_4$)$^+$.

EXAMPLE 57

2-[2-(Benzo[b]thien-3-yl)-2-oxoethyl]-4-(4-fluorophenyl)-5-[4-(methylsulfonyl)phenyl]-3(2H)-pyridazinone The title compound was prepared according to the method of Example 20, substituting 3-chloroacetylbenzo[b]thiophene for 4-fluorobenzyl bromide. mp 183–184° C. $^1$H NMR (CDCl$_3$, 300 MHz) 3.08 (s, 3H), 5.68 (s, 2H), 6.96 (t, J=9 Hz, 2H), 7.21 (dd, J=9 Hz, 6 Hz, 2H), 7.39 (d, J=9 Hz, 2H), 7.42–7.54 (m, 2H), 7.91 (d, J=9 Hz, 2H), 7.91 (d, J=7 Hz, 1H), 7.94 (s, 1H), 8.53 (s, 1H), 8.72 (d, J=7 Hz, 1H). MS (DCI/NH$_3$) m/z 519 M+H)$^+$.

EXAMPLE 58

2-(2,2,2-Trifluoroethyl)-4-(4-chlorophenyl)-5-[4-(methylsulfonyl)phenyl]-3(2H)-pyridazinone The title compound was prepared by N-debenzylation of the product, prepared in Example 53 according to the method of Example 12, followed by alkylation with 2-iodo-1,1,1-trifluoroethane according to the method of Example 20. mp 55–57° C. $^1$H NMR (CDCl$_3$, 300 MHz) 3.07 (s, 3H), 4.88 (q, J=9 Hz, 2H), 7.13 (d, J=9 Hz, 2H), 7.26 (d, J=9 Hz, 2H), 7.36 (d, J=9 Hz, 2H), 7.89 (s, 1H), 7.92 (d, J=9 Hz, 2H). MS (DCI/NH$_3$) m/z 443 (M+H)$^+$ and m/z 460 (M+NH$_4$)$^+$.

EXAMPLE 59

2-(3,3-Dimethyl-2-oxobutyl)-4-(4-fluorophenyl)-5-[4-(methylsulfonyl)phenyl]-3(2H)-pyridazinone The title compound was prepared according to the method of Example 20, substituting 1-bromopinacolone for 4-fluorobenzyl bromide. mp 168–170° C. $^1$H NMR (CDCl$_3$, 300 MHz) 1.31 (s, 9H), 3.06 (s, 3H), 5.21 (s, 2H), 6.95 (t, J=9 Hz, 2H), 7.17 (dd, J=9 Hz, 6 Hz, 2H), 7.35 (d, J=7 Hz, 2H), 7.86 (s, 1H) 7.89 (d, J=9 Hz, 2H). MS (DCI/NH$_3$) m/z 443 (M+H)$^+$ and m/z 460 (M+NH$_4$)$^+$.

EXAMPLE 60

2-(3-Thienylmethyl)-4-(4-fluorophenyl)-5-[4-(methylsulfonyl)phenyl]-3(2H)-pyridazinone The title compound was prepared according to the method of Example 20, substituting 3-(chloromethyl)thiophene for 4-fluorobenzyl bromide. mp 169–172° C. $^1$H NMR (300 MHz, DMSO d$_6$) δ 3.22 (s, 3H), 5.36 (s, 2H), 7.18 (m, 5H), 7.51 (m, 4H), 7.88 (m, 2H); 8.08 (s, 1H). MS (DCI/NH$_3$) m/z 441 (M+H)$^+$ and m/z 458 (M+NH$_4$)$^+$.

EXAMPLE 61

2-(2-Benzo[b]thienylmethyl)-4-(4-fluorophenyl)-5-[4-(methylsulfonyl)phenyl]-3(2H)-pyridazinone The title compound was prepared according to the method of Example 20 substituting 2-(chloromethyl)benzo[b]thiophene for 4-fluorobenzyl bromide. mp 93–96° C. $^1$H NMR (300 MHz, CDCl$_3$) δ 3.05 (s, 3H), 5.64 (s, 2H), 6.97 (m, 2H), 7.18 (m, 2H), 7.33 (m, 5H), 7.78 (m, 2H), 7.86 (m, 3H). MS (DCI/NH$_3$) m/z 491 (M+H)$^+$ and m/z 508 (M+NH$_4$)$^+$.

EXAMPLE 62

2,4-Bis(4-fluorophenyl)-5-[4-(methylsulfonyl)phenyl]-3(2H)-pyridazinone

A mixture of 4-(4-fluorophenyl)-5-[4-(methylsulfonyl)phenyl]-3(2H)-pyridazinone (172 mg, 0.5 mmol), prepared according to the method of Example 10, Cu powder (32 mg), anhydrous K$_2$CO$_3$ (207 mg, 1.5 mmol) and 4-fluoroiodobenzene (0.12 mL, 1 mmol) was prepared in 20 mL of pyridine. The solution was stirred at reflux for 14 hours. The mixture was then cooled to room temperature and partitioned between water and ethyl acetate. The ethyl acetate layer was washed with 10% citric acid, water, brine and concentrated in vacuo. Separation by column chromatography (silica gel, CH$_2$Cl$_2$-diethyl ether 15:1) provided 190 mg of crude product. Crystallization from CH$_2$Cl$_2$-diethyl ether-hexanes furnished the title compound (yield: 175 mg, 79.9%). mp 168–169° C. $^1$H NMR (300 MHz, CDCl$_3$) δ 3.07 (s, 3H), 6.98 (t, J=9 Hz, 2H), 7.20 (m, 4H), 7.40 (d, J=9 Hz, 2H), 7.69 (m, 2H), 7.92 (d, J=9 Hz, 2H), 7.98 (s, 1H). MS (DCI/NH$_3$) m/z 439 (M+H)$^+$, 456 (M+NH4)$^+$. Anal. calc. for C$_{23}$H$_{16}$F$_2$N$_2$O$_3$S.0.25 H$_2$O: C, 62.36; H, 3.75; N, 6.32. Found: C, 62.23; H, 3.55; N, 6.26.

EXAMPLE 63

4-(4-Fluorophenyl)-5-[4-(methylsulfonyl)phenyl]-6-methyl-3(2H)-pyridazinone

The 5-hydroxy-5-methyl-2(5H)-furanone prepared via above cited methods (454 mg, 1.25 mmol) was dissolved in n-butanol (10 mL) and treated with hydrazine hydrate (0.3 mL, 6.2 mmol) and stirred at reflux for 18 hours. On cooling, white crystals (224 mg, 50%) were obtained. mp 290° C. (dec.) 1HNMR (300 MHz, d$_6$-DMSO) δ 1.99 (s, 3H), 3.10 (s, 3H), 7.05 (t, J=9 Hz, 2H), 7.15 (dd, J=6 Hz, J=9 Hz, 2H), 7.48 (d, J=9 Hz, 2H), 7.85 (d, J=9 Hz, 2H), 13.10 (br s, 1H). MS (DCI/NH$_3$) 376 (M+NH$_4$)$^+$. Anal. calc. for C$_{18}$H$_{15}$N$_2$FSO$_3$ 0.25 H$_2$O: C, 59.57; H, 4.30; N, 7.71. Found: C, 59.28; H, 4.39; N, 8.39.

EXAMPLE 64

2-(2,2,2-Trifluoroethyl)-4-(4-fluorophenyl)-5-[4-(methylsulfonyl)phenyl]-6-methyl-3(2H)-pyridazinone The product of Example 63 (100 mg, 0.28 mmol) was dissolved in anhydrous DMF (3 mL) and treated with 1,1,1-trifluoro-2-iodoethane (27.5 mL, 280 mmol) in presence of anhydrous sodium carbonate (130 mg, 1.2 mmol) at 50–60° C. for 2 hours. The reaction mixture was partitioned between water and ethyl acetate to provide the desired compound as an amorphous solid (60 mg, 48%). 1HNMR (300 MHz, CDCl$_3$) δ 2.10 (s, 3H), 3.10 (s, 3H), 4.85 (q, J=9 Hz, 2H), 6.90 (m, 2H), 7.10 (dd, J=6 Hz, J=9 Hz, 2H), 7.25 (m, 2H), 7.95 (d, J=9 Hz, 2H). MS (DCI/NH$_3$) 458 (M+NH$_4$)$^+$ Anal. calc. for C$_{20}$H$_{16}$N$_2$F$_4$SO$_3$: C, 54.54; H, 3.66; N, 6.36. Found: C, 54.41; H, 3.56; N, 6.35.

EXAMPLE 65

2-Benzyl-4-(3,4-dichlorophepyl)-5-[4-(methylsulfonyl)phenyl]-3(2H)-pyridazinone

The title compound was prepared by coupling 3,4-dichlorophenylboronic acid with 2-benzyl-4-bromo-5-methoxy-3 (2H)-pyridazinone (J. Het. Chem., (1996) 33, 1579–1582) according to the method of Example 6. This product was converted to the 5-hydroxy-derivative according to the method of Example 7. The 5-hydroxy compound was converted to the 5-trifluoromethylsufonyloxy-derivative according to the method of Example 8. Coupling of 4-(methylthio)phenylboronic acid to the triflate according to the method of Example 9 provided the 5-[4-(methylthio)phenyl]-intermediate which was oxidized according to the method of Example 10 to provide the final product (yield: 780 mg, 84%). mp 161–163° C. $^1$H NMR (300 MHz, DMSO-d$_6$) δ 3.22 (s, 3H), 5.35 (s, 2H), 7.08 (dd, J=9 Hz, 3 Hz, 1H), 7.32–7.44 (m, 5H), 7.47 (dd, J=9 Hz, 3 Hz, 3H), 7.48 (d, J=3 Hz, 1H), 7.90 (d, J=9 Hz, 2H), 8.13 (s, 1H). MS (DCI/NH$_3$) m/z 485 (M+H)$^+$. Anal. calc. for C$_{24}$H$_{18}$Cl$_2$N$_2$O$_3$S: C, 59.38; H, 3.73; N, 5.77. Found: C, 59.28; H, 3.92; N, 5.42.

EXAMPLE 66

2-(2,2,2-Trifluoroethyl)-4-(4-n-propylphenyl)-5-[4-(methylsulfonyl)phenyl]-3(2H)-pyridazinone The title compound was prepared by coupling 4-(n-propyl)phenylboronic acid with 2-benzyl-4-bromo-5-methoxy-3(2H)-pyridazinone (J. Het. Chem., 1996, 33, 1579–1582) according to the method of Example 6. This product was converted to the 5-hydroxy derivative according to the method of Example 7. This product was converted to the 5-trifluoromethylsufonyloxy-derivative according to the method of Example 8. Coupling of 4-(methylthio)phenylboronic acid to the triflate according to the method of Example 9 provided the 5-[4-(methylthio)phenyl]-intermediate which was oxidized according to the method of Example 10 to provide the final product (yield: 220 mg, 70%). mp 64–66° C. $^1$H NMR (300 MHz, CDCl$_3$) δ 0.91 (t, J=7.5 Hz, 3H), 1.6 (h, J=7.5 Hz, 2H), 2.55 (q, J=7.5 Hz, 2H), 3.05 (s, 3H), 4.88 (q, J=9 Hz, 2H), 7.08 (s, 4H), 7.35 (d, J=9 Hz, 2H), 7.86 (d, J=9 Hz, 2H), 7.87 (s, 1H). MS (DCI/NH$_3$) m/z 451 (M+H)$^+$. Anal. calc. for C$_{22}$H$_{21}$F$_3$N$_2$O$_3$S: C, 58.65; H, 4.69; N, 6.21. Found: C, 58.71; H, 4.72; N, 6.20.

EXAMPLE 67

2-(2,2,2-Trifluoroethyl)-4-(4-chloro-3-fluorophenyl)-5-[4-(methylsulfonyl)phenyl]-3(2H)-pyridazinone The title compound was prepared by first coupling 3-fluoro-4-chlorophenylboronic acid with 2-benzyl-4-chloro-5-methoxy-3(2H)-pyridazinone according to the method of Example 6. The product was converted to the 5-hydroxy compound according to the method of Example 7. This 5-hydroxy compound was converted to the 5-trifluoromethylsufonyloxy-derivative according to the method of Example 8. Coupling of 4-(methylthio)phenylboronic acid to the triflate according to the method of Example 9 provided the 5-[4-(methylthio)phenyl]-intermediate which was oxidized according to the method of Example 10 to provide the final product (yield: 170 mg, 84%). mp 174–175° C. $^1$H NMR (300 MHz, CDCl$_3$) δ 3.09 (s, 3H), 4.89 (q, J=9 Hz, 2H), 6.87 (dm, J=9 Hz, 1H), 7.09 (dd, J=9 Hz, 3 Hz, 1H), 7.30 (t, J=9 Hz, 1H), 7.39 (d, J=9 Hz, 2H), 7.91 (s, 1H), 7.95 (d, J=9 Hz, 2H). MS (DCI/NH$_3$) m/z 461 (M+H)$^+$. Anal. calc. for C$_{19}$H$_{13}$ClF$_4$N$_2$O$_3$S: C, 49.52; H, 2.84; N, 6.07. Found: C, 49.66; H, 2.70; N, 5.96.

EXAMPLE 68

2-(2,2,2-Trifluoroethyl)-4-(4-fluorophenyl)-5-[4-(aminosulfonyl)phenyl-3(2H)-pyridazinone A solution of 2-(2,2,2-trifluoroethyl)-4-(4-fluorophenyl)-5-[4-(methylsulfinyl)phenyl]-3(2H)-pyridazinone (680 mg, 1.53 mmol) in trifluoroacetic anhydride (30 mL) was stirred at room temperature for 1 hour. The excess solvent was evaporated in vacuo and the residue was treated with a deoxygenated 1N solution of methanol-NaOH (50 mL, 4:1) at 0° C. The solution was stirred at room temperature for 2 hours and quenched with dilute HCl solution until acidic. The white suspension formed was concentrated in vacuo to evaporate the methanol. THF was added to the resulting suspension until a clear solution was obtained. Chlorine gas was slowly bubbled into the solution, maintained at 0° C. After 10 minutes, nitrogen gas was bubbled into the solution for a few minutes to displace residual chlorine. Ammonium hydroxide solution (30%, 5 to 10 mL), at 0° C., was slowly added to the solution (to consume all starting sulfonyl chloride) and stirred at room temperature for 5 minutes The solution was partitioned between water and ethyl acetate. The organic layer was washed first with water, then brine, and dried over MgSO$_4$, and filtered. The filtrate was concentrated in vacuo. The residue was purified by chromatography on silica gel (40:60 ethyl acetate/hexanes) to provide the title compound (yield: 500 mg, 75%). mp 193–195° C. $^1$H NMR (300 MHz, CDCl$_3$) δ 4.82 (s, 2H), 4.88 (q, J=9 Hz, 2H), 6.98 (t, J=9 Hz, 2H), 7.19 (dd, J=9 Hz, 6 Hz, 2H), 7.30 (d, J=9 Hz, 2H), 7.88 (d, J=9 Hz, 2H), 7.90 (s, 1H). MS (DCI/NH$_3$) m/z 428 (M+H)$^+$. Anal. calc. for C$_{18}$H$_{13}$F$_4$N$_3$O$_3$S: C, 50.58; H, 3.06; N, 9.83. Found: C, 51.04; H, 3.26; N, 9.63.

EXAMPLE 69

2-(2,2,2-Trifluoroethyl)-4-(4-chlorophenyl)-5-[4-(aminosulfonyl)phenyl]-3(2H)-pyridazinone The title compound from Example 77 was converted to the sulfonamide product according to the method of Example 68 (yield: 540 mg, 70%). mp 154–156° C. $^1$H NMR (300 MHz, CDCl$_3$) δ 4.86 (s, 2H), 4.87 (q, J=9 Hz, 2H), 7.14 (d, J=9 Hz, 2H), 7.29 (d, J=9 Hz, 2H), 7.31 (d, J=9 Hz, 2H), 7.89 (d, J=9 Hz, 2H), 8.00 (s, 1H). MS (DCI/NH$_3$) m/z 444 (M+H)$^+$. Anal. calc. for C$_{18}$H$_{13}$ClF$_3$N$_3$O$_3$S: C, 48.71; H, 2.95; N, 9.46. Found: C, 49.05; H, 3.01; N, 9.15.

EXAMPLE 70

2-(2,2,2-Trifluoroethyl)-4-(2-propoxy)-5-[4-(aminosulfonyl)phenyl]-3(2H)-pyridazinone The methyl sulfide intermediate prepared in Example 83C was oxidized with one equivalent of meta-chloroperoxybenzoic acid to provide the methylsulfoxide which was converted to the sulfonamide final product according to the method of Example 68 (yield: 396 mg, 60%). mp 158–160° C. $^1$H NMR (300 MHz, CDCl$_3$) δ 1.21 (d, J=6 Hz, 6H), 4.83 (q, J=7.5 Hz, 2H), 4.86 (s, 2H), 5.46 (p, J=6 Hz, 1H), 7.72 (d, J=9 Hz, 2H), 7.82 (s, 1H), 8.03 (d, J=9 Hz, 2H). MS (DCI/NH$_3$) m/z 392 (M+H)$^+$. Anal. calc. for C$_{15}$H$_{16}$F$_3$N$_3$O$_4$S: C, 46.03; H, 4.12; N, 10.73. Found: C, 46.08; H, 4.22; N, 10.52.

EXAMPLE 71

2-(2,2,2-Trifluoroethyl)-4-(4-fluorophenoxy)-5-[4-(aminosulfonyl)phenyl]-3(2H)-pyridazinone The methyl sulfide intermediate of Example 76 was oxidized with one equivalent of meta-chloroperoxybenzoic acid to provide the methylsulfoxide which was converted to the sulfonamide final product according to the method of Example 68 (yield: 180 mg, 37%). mp 150–152° C. $^1$H NMR (300 MHz, CDCl$_3$) δ 4.71 (q, J=7.5 Hz, 2H), 4.72 (s, 2H), 6.88 (dd, J=9 Hz, 4.5 Hz, 2H), 7.0 (t, J=9 Hz, 2H), 7.73 (d, J=9 Hz, 2H), 7.98 (s, 1H), 8.05 (d, J=9 Hz, 2H). MS (DCI/NH$_3$) m/z 444 (M+H)$^+$. Anal. calc. for C$_{18}$H$_{13}$F$_4$N$_3$O$_4$S: C, 48.76; H, 2.95; N, 9.47. Found: C, 48.49; H, 2.8; N, 8.95.

EXAMPLE 72

2,4-Bis-(4-fluorophenyl)-5-[3-fluoro-4-(aminosulfonyl)phenyl]-3(2H)-pyridazinone Example 72A 2-Fluorothioanisole A deoxygenated solution of 2-fluorothiophenol (10 g, 78 mmol) in anhydrous DMF (10 mL) was treated with iodomethane (4.9 mL, 78 mmol) and potassium carbonate (10.8 g, 78 mmol). The reaction mixture was stirred at room temperature for 1 hour. A thin layer chromotography (100% hexanes) sample indicated that the reaction had not gone to completion, so an additional equivalent of base and iodomethane were added and the reaction mixture was stirred overnight at room temperature. The reaction was acidified with 10% aqueous citric acid and extracted with hexanes (2×125 mnL). The combined organic extracts were washed with brine, dried over MgSO$_4$, and filtered. The filtrate was concentrated under reduced pressure to provide the desired compound as a pale yellow oil (yield: 6.68 g; 60%).

Example 72B

2-Fluorothioanisole

An alternative method for preparing 2-fluorothioanisole begins with a solution of 1,2-difluorobenzene (0.79 mL, 8 mmol) in anhydrous DMF (50 mL) was treated with sodium thiomethoxide (0.59 g, 8 mmol). The reaction mixture was stirred at room temperature for 6 hours, and partitioned between hexanes and water. The organic layer was washed with brine, dried over MgSO$_4$, and filtered. The filtrate was concentrated under reduced pressure to provide the desired compound (1.1 g, 100%) slightly contaminated with 1,2-bis (methylthio)benzene, a lower Rf material, which was removed by chromatography with 100% hexanes (0.9 g, 80%). $^1$H NMR (300 MHz, CDCl$_3$) δ 2.46 (s, 3H), 6.98–7.19 (m, 3H) 2.26 (dt, J=9 Hz, 3 Hz, 1H).

Example 72C

4-Bromo-2-fluorothioanisole

A solution of 2-fluorothioanisole (1.42 g, 10 mmol) and iron powder (0.03 g, 0.5 mmol) in dichloromethane (20 mL) was chilled to ° C. and treated dropwise with Bromine (0.5 mL, 10 mmol). Upon completion of the Bromine treatment, the reaction was sampled for TLC (100% hexanes). A new, higher Rf material was present but the reaction had not gone to completion so another equivalent of bromine was added along with a catalytic amount of aluminum chloride. The reaction mixture was stirred overnight at room temperature. Aqueous sodium sulfite was added to the reaction mixture and the organic layer was isolated, dried over MgSO$_4$, and filtered. The filtrate was filtered through a pad of silica gel to remove color then concentrated under reduced pressure to provide the product as a clear, colorless oil (yield: 1.3 g; 60%). $^1$H NMR (300 MHz, DMSO-d$_6$) δ 2.48 (s, 3H), 7.31 (t, J=9 Hz, 1H), 7.43 (dd, J=9 Hz, 3 Hz, 1H) 7.54 (dd, J=9 Hz, 3 Hz, 1H).

Example 72D

3-Fluoro-4-(methylthio)benzeneboronic acid

A solution of 4-bromo-2-fluorothioanisole (0.5 g, 22.6 mmol) in dry THF (20 mL) was chilled to −78° C. under a nitrogen atmosphere. The reaction mixture was treated with 1.6 M n-butyllithium in hexanes (1.7 mL, 27.1 mmol), and the mixture was warmed to −40° C. where it was maintained for 0.5 hours. The reaction mixture was then chilled to −78° C. and three equivalents of triisopropyl borate (1.56 mL, 67.8 mmol) were added. The reaction mixture was allowed to warm to room temperature and stirred for 1.5 hours. At this point, 10% aqueous KOH (200 mL, 360 mmol) was added and the mixture was stirred overnight at room temperature. The reaction mixture was then poured into an ice/concentrated HCl mixture with stirring to yield a white precipitate. This solid was dried in a vacuum oven (65° C., 29 in Hg) overnight to provide the title compound (yield: 0.22 g; 52.4%). $^1$H NMR (300 MHz, DMSO-d$_6$) δ 2.48 (s, 3H), 7.31 (t, J=9 Hz, 1H), 7.49 (dd, J=12 Hz, 1.5 Hz, 1H) 7.54 (dd, J=9 Hz, 1.5 Hz, 1H).

Example 72E 2,4-Bis-(4-fluorophenyl)-5-[3-fluoro-4-(aminosulfonyl)phenyl]-3(2H)-pyridazinone 2-Benzyl-4-chloro-5-methoxy-3(2H)-pyridazinone (J. Het. Chem., 1996, 33, 1579–1582) was converted to the 5-hydroxy-analog according to the method of Example 7 and then to the 5-trifluoromethylsulfonyloxy-analog following the method of Example 8. Subsequent coupling to 3-fluoro-4-(methylthio)phenylboronic acid, according to the method of Example 9, provided 2-benzyl-4-chloro-5-[3-fluoro-4-(methylthio)phenyl]-3(2H)-pyridazinone. This intermediate was coupled in the 4-position with 4-fluorophenylboronic acid following the method of Example 6. This product was N-debenzylated according to the method of Example 11 and N-arylated with 4-fluoroiodobenzene according to the method of Example 62. The resulting sulfide was oxidized with one equivalent of meta-chloroperoxybenzoic acid to provide the methylsulfoxide which was converted to the sulfonamide final product according to the method of Example 68 (yield: 500 mg, 75%). mp 222–224° C. $^1$H NMR (300 MHz, CDCl$_3$) δ 5.06 (s, 2H), 7.01 (t, J=9 Hz, 2H), 7.06 (d, J=9 Hz, 2H), 7.10 (d, J=9 Hz, 2H), 7.18 (t, J=9 Hz, 2H), 7.69 (dd, J=9 Hz, 3 Hz, 2H), 7.88 (t, J=9 Hz, 1H), 7.95 (s, 1H). MS (DCI/NH$_3$) m/z 458 (M+H)$^+$. Anal. calc. for C$_{22}$H$_{14}$F$_3$N$_3$O$_3$S: C, 57.76; H, 3.08; N, 9.18. Found: C, 57.5; H, 3.15; N, 8.8.

EXAMPLE 73

2-(2,2,2-Trifluoroethyl)-4-(4-chloro-3-fluorophenyl)-5-[4-(aminosulfonyl)phenyl]-3(2H)-pyridazinone The methyl sulfide intermediate prepared in Example 67 was oxidized with one equivalent of meta-chloroperoxybenzoic acid, according to the method of Example 68 to provide the methyl sulfoxide. The methyl sulfoxide was converted to the sulfonamide product according to the method of Example 68 (yield: 1.5 g, 63%). mp 180–183° C. $^1$H NMR (300 MHz, DMSO-d$_6$) δ 5.09 (q, J=9 Hz, 2H), 7.01 (dd, J=9 Hz, 3 Hz, 1H), 7.15 (dd, J=9 Hz, 3 Hz, 1H), 7.39 (dd, J=9 Hz, 3 Hz, 1H), 7.47 (dd, J=9 Hz, 3 Hz, 1H) 7.55 (t, J=9 Hz, 1H), 7.71 (t, J=9 Hz, 1H), 7.78 (s, 2H), 8.37 (s, 1H). MS (DCI/NH$_3$) m/z 480 (M+H)$^+$. Anal. calc. for C$_{18}$H$_{11}$ClF$_5$N$_3$O$_3$S: C, 45.05; H, 2.31; N, 8.75. Found: C, 46.19; H, 3.02; N, 7.43.

EXAMPLE 74

2-Benzyl-4-(2-propoxy)-5-[4-(methylsulfonyl)phenyl]-3(2H)-pyridazinone

2-Benzyl-4-chloro-5-methoxy-3(2H)-pyridazinone (J. Het. Chem., 1996, 33, 1579–1582) was converted to the 5-hydroxy-analog according to the method of Example 7 and then to the 5-trifluoromethylsulfonyloxy-analog following the method of Example 8. Subsequent coupling to 4-(methylthio)phenylboronic acid according to the method of Example 9 provided 2-benzyl-4-chloro-5-[4-(methylthio)phenyl]-3(2H)-pyridazinone. This 4-chloro-intermediate thus prepared was treated with 2-propanol (20 mL, 261 mmol) and potassium t-butoxide (110 mg, 0.98 mmol) at reflux for 45 minutes furnished 2-benzyl-4-(2-propoxy)-5-[4-(methylthio)pentyl]-3(2H)-pyridazinone This methyl sulfide was oxidized according to the method of Example 10 to provide the title compound (yield: 180 mg, 80%). mp 109–111° C. $^1$H NMR (300 MHz, CDCl$_3$) δ 1.18 (d, J=6 Hz, 6H), 3.12 (s, 3H), 5.36 (s, 2H), 5.49 (h, J=6 Hz, 1H), 7.35 (m, 3H), 7.47 (dd, J=9 Hz, 3 Hz, 2H), 7.74 (d, J=9 Hz, 2H), 7.79 (s, 1H), 8.03 (d, J=9 Hz, 2H). MS (DCI/NH$_3$) m/z 399 (M+H)$^+$. Anal. calc. for C$_{21}$H$_{22}$N$_2$O$_4$S: C, 63.29; H, 5.56; N, 7.03. Found: C, 63.17; H, 5.57; N, 6.95.

EXAMPLE 75

2-Benzyl-4-(4-fluorophenoxy)-5-[4-(methylsulfonyl) phenyl]-3(2H)-pyridazinone

The title compound was prepared according to the method of Example 74 substituting 4-fluorophenol in place of 2-propanol (yield: 180 mg, 99%). mp 188–190° C. $^1$H NMR (300 MHz, CDCl$_3$) δ 3.12 (s, 3H), 5.26 (s, 2H), 6.86 (dd, J=9 Hz, 6 Hz, 2H), 6.99 (t, J=9 Hz, 2H), 7.34 (m, 3H), 7.46 (dd, J=9 Hz, 3 Hz, 2H), 7.72 (d, J=9 Hz, 2H), 7.92 (s, 1H), 8.02 (d, J=9 Hz, 2H). MS (DCI/NH$_3$) m/z 451 (M+H)$^+$. Anal. calc. for C$_{24}$H$_{19}$FN$_2$O$_4$S: C, 63.98; H, 4.25; N, 6.21. Found: C, 63.74; H, 4.2; N, 6.12.

EXAMPLE 76

2-(2,2,2-Trifluoroethyl)-4-(4-fluorophenoxy)-5-[4-(methylsulfonyl)phenyl]-3(2H)-pyridazinone The title compound was prepared according to the method of Example 75 substituting 2-(2,2,2-trifluoroethyl)-4-chloro-5-[4-(methylsulfonyl)phenyl]-3(2H)-pyridazinone in place of 2-benzyl-4-chloro-5-[4-(methylsulfonyl)phenyl]-3(2H)-pyridazinone (yield: 180 mg, 63%). mp 161–164° C. $^1$H NMR (300 MHz, CDCl$_3$) δ 3.09 (s, 3H), 4.81 (q, J=9 Hz, 2H), 6.88 (dd, J=9 Hz, 4.5 Hz, 2H), 7.0 (t, J=9 Hz, 2H), 7.78 (d, J=9 Hz, 2H), 7.79 (s, 1H), 8.06 (d, J=9 Hz, 2H). MS (DCI/NH$_3$) m/z 443 (M+H)$^+$. Anal. calc. for C$_{19}$H$_{14}$F$_4$N$_2$O$_4$S: C, 51.58; H, 3.18; N, 6.33. Found: C, 51.8; H, 3.3; N, 6.22.

EXAMPLE 77

2-(2,2,2-Trifluoroethyl)-4-(4-chlorophenyl)-5-[4-(methylsulfinyl)phenyl]-3(2H)-pyridazinone 2-Benzyl-4-chloro-5-methoxy-3(2H)-pyridazinone (J. Het. Chem., 1996, 33, 1579–1582) was converted to the 5-hydroxy-analog according to the method of Example 7 and then to the 5-trifluoromethylsulfonyloxy-analog according to the method of Example 8. Subsequent coupling to 4-(methylthio)phenylboronic acid, according to the method of Example 9, provided 2-benzyl-4-chloro-5-[4-(methylthio)phenyl]-3(2H)-pyridazinone. This intermediate was coupled with 4-chlorophenylboronic acid according to the method of Example 6. This product was N-debenzylated according to the method of Example 11 and N-alkylated with 2-iodo-1,1,1-trifluoroethane according to the method of Example 20. The resulting sulfide was oxidized to the corresponding sulfoxide with one equivalent of meta-chloroperoxybenzoic acid, according to the method of Example 5 to provide the title compound (yield: 130 mg, 70%). mp 154–155° C. $^1$H NMR (300 MHz, CDCl$_3$) δ 2.74 (s, 3H), 4.88 (q, J=9 Hz, 2H), 7.14 (d, J=9 Hz, 2H), 7.26 (d, J=9 Hz, 2H), 7.31 (d, J=9 Hz, 2H), 7.61 (d, J=9 Hz, 2H), 7.82 (s, 1H). MS (DCI/NH$_3$) m/z 427 (M+H)$^+$. Anal. calc. for C$_{19}$H$_{14}$ClF$_3$N$_2$O$_2$S: C, 53.46; H, 3.3; N, 6.56. Found: C, 53.58; H, 3.34; N, 6.42.

EXAMPLE 78

2-Benzyl-4-chloro-5-[4-(methylsulfonyl)phenyl]-3(2H)-pyridazinone

The title compound was prepared by oxidizing 2-benzyl-4-chloro-5-[4-(methylthio)phenyl]-3(2H)-pyridazinone, (prepared as an intermediate in Example 77) according to the method of Example 10 (yield: 180 mg, 83%). mp 166–167° C. $^1$H NMR (300 MHz, CDCl$_3$) δ 3.12 (s, 3H), 5.41 (s, 2H), 7.37 (m, 3H), 7.53 (dd, J=9 Hz, 3 Hz, 2H), 7.68 (d, J=9 Hz, 2H), 7.74 (s, 1H), 8.08 (d, J=9 Hz, 2H). MS (DCI/NH$_3$) m/z 375 (M+H)$^+$. Anal. calc. for C$_{18}$H$_{15}$ClN$_2$O$_3$S: C, 57.67; H, 4.03; N, 7.47. Found: C, 57.43; H, 4.06; N 7.35.

EXAMPLE 79

2-(2,2,2-Trifluoroethyl)-4-(4-methylphenyl)-5-[4-(methylsulfonyl)phenyl]-3(2H)-pyridazinone 2-Benzyl-4-bromo-5-methoxy-3(2H)-pyridazinone (J. Het. Chem., 1996, 33, 1579–1582) was converted to the 5-hydroxy-analog according to the method of Example 7 and then to the 5-(trifluoromethyl)sulfonyloxy-analog according to the method of Example 8. Subsequent coupling to 4-(methylthio)phenylboronic acid, according to the method of Example 9, provided 2-benzyl-4-bromo-5-[4-(methylthio)phenyl]-3(2H)-pyridazinone. This intermediate was coupled with 4-methylphenylboronic acid according to the method of Example 6. This product was N-debenzylated according to the method of Example 11 and N-alkylated with 2-iodo-1,1,1-trifluoroethane according to the method of Example 20. The resulting sulfide was oxidized to the title compound according to the method of Example 10 (yield: 210 mg, 98%). mp 154–156° C. $^1$H NMR (300 MHz, CDCl$_3$) δ 2.33 (s, 3H), 3.07 (s, 3H), 4.89 (q, J=9 Hz, 2H), 7.08 (s, 4H), 7.37 (d, J=9 Hz, 2H), 7.88 (s, 1H), 7.89 (d, J=9 Hz, 2H). MS (DCI/NH$_3$) m/z 423 (M+H)$^+$. Anal. calc. for C$_{20}$H$_{17}$F$_3$N$_2$O$_3$S: C, 56.86; H, 4.05; N, 6.63. Found: C, 56.59; H, 4.11; N, 6.53.

EXAMPLE 80

2-(2,2,2-Trifluoroethyl)-4-(4-chloro-3-fluorophenyl)-5-[4-(aminosulfonyl)phenyl]-3(2H)-pyridazinone 2-Benzyl-4-chloro-5-methoxy-3(2H)-pyridazinone (J. Het. Chem., 1996, 33, 1579–1582) was converted to the 5-hydroxy-analog according to the method of Example 7 and then to the 5-(trifluoromethyl)sulfonyloxy-analog according to the method of Example 8. Subsequent coupling to 4-(methylthio)phenylboronic acid, according to the method of Example 9, provided 2-benzyl-4-chloro-5-[4-(methylthio)phenyl]-3(2H)-pyridazinone. This intermediate was coupled with 4-chloro-3-fluorophenylboronic acid according to the method of Example 6. This product was N-debenzylated according to the method of Example 11 and N-alkylated with 2-iodo-1,1,1-trifluoroethane according to the method of Example 20. The resulting sulfide was oxidized to the corresponding sulfoxide with one equivalent of meta-chloroperoxybenzoic acid to provide the methylsulfoxide which was converted to the sulfonamide final product according to the method of Example 68 (yield: 500 mg, 75%). mp 214–215° C. $^1$H NMR (300 MHz, CDCl$_3$) δ 4.82 (s, 2H), 4.88 (q, J=9 Hz, 2H), 6.88 (m, 1H), 7.09 (dd, J=9 Hz, 3 Hz, 1H), 7.31 (d, J=9 Hz, 1H), 7.32 (d, J=9 Hz, 2H), 7.90 (s, 1H), 7.92 (d, J=9 Hz, 2H). MS (DCI/NH$_3$) m/z 462 (M+H)$^+$. Anal. calc. for C$_{18}$H$_{12}$F$_4$ClN$_3$O$_3$S: C, 46.81; H, 2.61; N, 9.09. Found: C, 46.79; H, 2.59; N, 8.86.

EXAMPLE 81

2-(2,2,2-Trifluoroethyl)-4-(3,4-dichlorophenyl)-5-[4-(methylsulfonyl)phenyl]-3(2H)-pyridazinone The product described in Example 65 was N-debenzylated according to the method of Example 11. The intermediate was N-alkylated according to the method of Example 20, substituting 2-iodo-1,1,1-trifluoroethane in place of 4-fluorobenzyl bromide to provide the title compound (yield: 165 mg, 55%). mp 197–198° C. $^1$H NMR (300 MHz, CDCl₃) δ 3.09 (s, 3H), 4.88 (q, J=9 Hz, 2H), 6.98 (dd, J=9 Hz, 3 Hz, 1H), 7.37 (d, J=9 Hz, 4H), 7.91 (s, 1H), 7.95 (d, J=9 Hz, 2H). MS (DCI/NH₃) m/z 477 (M+H)⁺. Anal. calc. for $C_{19}H_{13}F_3Cl_2N_2O_3S$: C, 47.81; H, 2.74; N, 5.86. Found: C, 47.94; H, 2.87; N, 5.83.

EXAMPLE 82

2-Benzyl-4-(2-propylamino)-5-[4-(methylsulfonyl)phenyl]-3(2H)-pyridazinone

2-Benzyl-4,5-dibromo-3(2H)-pyridazinone (2 g, 6 mmol) was reacted with 2-aminopropane (2 mL, 23.5 mmol) and potassium t-butoxide (910 mg, 6.6 mmol) in toluene (40 mL) at reflux for 18 hours to provide the 4-(2-propylamino) derivative after column chromatography (silica gel, 92:8 hexanes/ethyl acetate). The intermediate was coupled in the 5-position with 4-(methylthio)phenylboronic acid according to the method of Example 6. The methyl sulfide was oxidized, according to the method of Example 10, to provide the title compound (yield: 120 mg, 48%). mp 146–147° C. ¹H NMR (300 MHz, CDCl₃) δ 0.92 (d, J=6 Hz, 6H), 3.11 (m, 1H), 3.13 (s, 3H), 5.34 (s, 2H), 5.59 (m, 1H), 7.33 (m, 3H), 7.42 (s, 1H), 7.48 (dd, J=9 Hz, 3 Hz, 2H), 7.56 (d, J=9 Hz, 2H), 8.00 (d, J=9 Hz, 2H). MS (DCI/NH₃) m/z 399 (M+H)⁺. Anal. calc. for $C_{21}H_{23}N_3O_3S$: C, 63.45; H, 5.83; N, 10.57. Found: C, 63.31; H, 5.87; N, 10.44.

EXAMPLE 83

2-(2,2,2-Trifluoroethyl)-4-(2-propoxy)-5-[4-(methylsulfonyl)phenyl]-3(2H)-pyridazinone

Example 83A

2-(2,2,2-Trifluoroethyl)-4,5-dibromo-3(2H)-pyridazinone

A solution of mucobromic acid (10 g, 38.8 mmol) and trifluoroethyl hydrazine (70% in water, 4.88 mL, 38.8 mmol) in 100 mL of methanol was prepared and heated at reflux for 3 hours. The reaction mixture was concentrated in vacuo and partitioned between ethyl acetate and water. The ethyl acetate layer was dried over MgSO₄, filtered, passed through a silica gel pad, and concentrated in vacuo. The product was obtained as yellowish solid (yield: 8.8 g, 68%). ¹H NMR (300 MHz, CDCl₃) δ 4.78 (q, J=9 Hz, 2H), 7.87 (s, 1H). MS (DCI/NH₃) m/z 337 (M+H)⁺.

Example 83B

2-(2,2,2-Trifluoroethyl)-4-(2-propoxy)-5-bromo-3(2H)-pyridazinone

A solution of 2-(2,2,2-trifluoroethyl)-4,5-dibromo-3(2H)-pyridazinone (2 g, 6 mmol), isopropyl alcohol (3 mL) and sodium hydride (60% dispersed in oil, 290 mg, 7.2 mmol) in toluene (40 mL) was heated at reflux for 5 hours. The reaction mixture was partitioned between ethyl acetate and water. The ethyl acetate layer was filtered, and concentrated in vacuo. The residue was purified by chromatography (95:5 hexanes/ethyl acetate) to provide the product as a greenish oil (yield: 1.22 g, 65%). ¹H NMR (300 MHz, CDCl₃) δ 1.46 (d, J=7.5 Hz, 6H), 5.48 (h, J=6 Hz, 1H), 7.87 (s, 1H). MS (DCI/NH₃) m/z 316 (M+H)⁺.

Example 83C

2-(2,2,2-Trifluoroethyl)-4-(2-propoxy)-5-[4-(methylthio)phenyl]-3(2H)-pyridazinone A solution of 2-(2,2,2-trifluoroethyl)-4-(2-propoxy)-5-bromo-3(2H)-pyridazinone (1.2 g, 3.8 mmol), 4-(methylthio)phenylboronic acid (704 mg, 4.19 mmol), tetrakis (triphenylphosphine)palladium(0) (220 mg, 5% mmol) and cesium carbonate (2.72 g, 8.3 mmol) in 20 mL of ethylene glycol dimethyl ether was heated to reflux for 5 hours. The mixture was partitioned between ethyl acetate and water. The ethyl acetate layer was washed with water, brine, dried over MgSO₄ and concentrated in vacuo. The residue was purified by chromatography on silica gel (94:6 hexanes/ethyl acetate). The product was obtained as a greenish solid (yield: 1.1 g, 81%). ¹H NMR (300 MHz, CDCl₃) δ 1.19 (d, J=7.5 Hz, 6H), 2.55 (s, 3H), 4.83 (q, J=9 Hz, 2H), 5.28 (h, J=6 Hz, 1H), 7.32 (d, J=9 Hz, 2H), 7.52 (d, J=9 Hz, 2H), 7.85 (s, 1H). MS (DCI) m/z 359 (M+H)⁺.

Example 83D

2-(2,2,2-Trifluoroethyl)-4-(2-propoxy)-5-[4-(methylsulfonyl)phenyl]-3(2H)-pyridazinone The title compound was prepared according to the method of Example 10, substituting 2-(2,2,2-trifluoroethyl)-4-(2-propoxy)-5-[4-(methylthio)phenyl]-3(2H)-pyridazinone in place of 4-(4-fluorophenyl)-5-[4-(methylthio)phenyl]-3(2H)-pyridazinone (yield: 220 mg, 100%). mp 152–153° C. ¹H NMR (300 MHz, CDCl₃) δ 1.2 (d, J=6 Hz, 6H), 3.13 (s, 3H), 4.84 (q, J=9 Hz, 2H), 5.49 (p, J=6 Hz, 1H), 7.78 (d, J=9 Hz, 2H), 7.82 (s, 1H), 8.05 (d, J=9 Hz, 2H). MS (DCI/NH₃) m/z 391 (M+H)⁺. Anal. calc. for $C_{16}H_{17}F_3N_2O_4S$: C, 49.22; H, 4.38; N, 7.17. Found: C, 49.34; H, 4.25; N, 7.01.

EXAMPLE 84

2-(2,2,2-Trifluoroethyl)-4-cyclohexyloxy-5-[4-(methylsulfonyl)phenyl]-3(2H)-pyridazinone The title compound was prepared according to the method of Example 83, substituting cyclohexanol in place of 2-propanol (yield: 250 mg, 52%). mp 129–130° C. ¹H NMR (300 MHz, CDCl₃) δ 1.1–1.6 (m, 8H), 1.84 (m, 2H), 3.12 (s, 3H), 4.83 (q, J=9 Hz, 2H), 5.21 (h, J=4.5 Hz, 1H), 7.77 (s, 1H), 7.80 (d, J=9 Hz, 2H), 8.06 (d, J=9 Hz, 2H). MS (DCI/NH₃) m/z 431 (M+H)⁺. Anal. calc. for $C_{19}H_{21}F_3N_2O_4S$: C, 53.01; H, 4.91; N, 6.50. Found: C, 52.96; H, 4.84; N, 6.45.

EXAMPLE 85

2-(2,2,2-Trifluoroethyl)-4-cyclopentyloxy-5-[4-(methylsulfonyl)phenyl]-3(2H)-pyridazinone The title compound was prepared according to the method of Example 83, substituting cyclopentanol in place of 2-propanol (yield: 250 mg, 52%). mp 148–150° C. ¹H NMR (300 MHz, CDCl₃) δ 1.35–1.55 (m, 4H), 1.68–1.75 (m, 4H), 3.12 (s, 3H), 4.83 (q, J=9 Hz, 2H), 5.89 (h, J=4.5 Hz, 1H), 7.75 (d, J=9 Hz, 2H), 7.83 (s, 1H), 8.04 (d, J=9 Hz, 2H). MS (DCI/NH₃) m/z 417 (M+H)⁺. Anal. calc. for $C_{18}H_{19}F_3N_2O_4S$: C, 51.91; H, 4.59; N, 6.72. Found: C, 52.04; H, 4.50; N, 6.65.

EXAMPLE 86

2-(2,2,2-Trifluoroethyl)-4-(2-propylamino)-5-[4-(methylsulfonyl)phenyl]-3(2H)-pyridazinone

Example 86A 2-(2,2,2-Trifluoroethyl)-4-(2-propylamino)-5-bromo-3(2H)-pyridazinone The title compound was prepared according method of the Example 83B, substituting 2-propylamine in place of 2-propanol (yield: 70%). MS (DCI/NH$_3$) m/z 315 (M+H)$^+$.

Example 86B 2-(2,2,2-Trifluoroethyl)-4-(2-propylamino)-5-[4-(methylthio)phenyl]-3(2H)-pyridazinone The title compound was prepared according method of the Example 83C, substituting 2-(2,2,2-trifluoroethyl)-4-(2-propylamino)-5-bromo-3(2H)-pyridazinone in place of 2-(2,2,2-trifluoroethyl)-4-isopropoxy-5-bromo-3(2H)-pyridazinone (yield: 80%). MS (DCI/NH$_3$) m/z 358 (M+H)$^+$.

Example 86C 2-(2,2,2-Trifluoroethyl)-4-(2-propylamino)-5-[4-(methylsulfonyl)phenyl]-3(2H)-pyridazinone The title compound was prepared according to the method of Example 10, substituting 2-(2,2,2-Trifluoroethyl)-4-(2-propylamino)-5-[4-(methylthio)phenyl]-3(2H)-pyridazinone in place of 4-(4-fluorophenyl)-5-[4-(methylthio)phenyl]-3(2H)-pyridazinone (yield: 180 mg, 83%). mp 173–174° C. $^1$H NMR (300 MHz, CDCl$_3$) δ 0.95 (d, J=6 Hz, 6H), 3.13 (s, 3H), 4.81 (q, J=9 Hz, 2H), 5.97 (s, 1H), 7.45 (s, 1H), 7.59 (d, J=9 Hz, 2H), 8.03 (d, J=9 Hz, 2H). MS (DCI/NH$_3$) m/z 340 (M+H)$^+$. Anal. calc. for C$_{16}$H$_{18}$F$_3$N$_3$O$_4$S: C, 49.35; H, 4.65; N, 10.79. Found: C, 49.29; H, 4.52; N, 10.65.

EXAMPLE 87

2-Benzyl-4-(4-morpholino)-5-[4-(methylsulfonyl)phenyl]-3(2H)-pyridazinone

2-Benzyl-4,5-dichloro-3(2H)-pyridazinone, prepared following the procedure in Example 2, was reacted with morpholine following the procedure of Example 86 to provide the 4-morpholino-derivative. The morpholino intermediate was coupled at the 5-position with 4-(methylthio)phenylboronic acid according to the method of Example 6. The resulting methyl sulfide was oxidized to the title compound according to the method of Example 10 (yield: 150 mg, 69%). mp 158–160° C. $^1$H NMR (300 MHz, CDCl$_3$) δ 3.06 (t, J=4.5 Hz, 3H), 3.12 (s, 3H), 3.69 (t, J=4.5 Hz, 3H), 5.33 (s, 2H), 7.35 (m, 3H), 7.5 (m, 4H), 7.58 (s, 1H), 8.05 (d, J=9 Hz, 2H). MS (DCI/NH$_3$) m/z 426 (M+H)$^+$. Anal. calc. for C$_{22}$H$_{23}$N$_3$O$_4$S: C, 62.10; H, 5.44; N, 9.87. Found: C, 61.74; H, 5.47; N, 9.59.

EXAMPLE 88

2-(2,3,3-Trifluoro-2-propen-1-yl)]-4-(4-fluorophenyl)-5-[4-(methylsulfonyl)phenyl]-3(2H)-pyridazinone

Example 88A

1-Methylsulfonyloxy-2,3,3-trifluoro-2-propene 2,3,3-Trifluoro-2-propen-1-ol was prepared as reported in (J. Org. Chem., (1989) 54, 5640–5642). The mesylate was obtained by reacting 2,3,3-trifluoro-2-propen-1-ol with mesyl chloride in diethyl ether. Standard workup provided the product, which was used without purification.

Example 88B 2-(2,3,3-Trifluoro-2-propen-1-yl)-4-(4-fluorophenyl)-5-[4-(methylthio)phenyl]-3(2H)-pyridazinone 4-(4-Fluorophenyl)-5-[4-(methylthio)phenyl]-3(2H)-pyridazinone is prepared starting with the 2-benzyl-pyridazinone from Example 9 and debenzylating the compound according to the procedure of Example 11.

A mixture of 4-(4-fluorophenyl)-5-[4-(methylthio)phenyl]-3(2H)-pyridazinone (250 mg, 0.8 mmol), Cs$_2$CO$_3$ (650 mg, 2 mmol), and 3-methylsufonyloxy-1,1,2-trifluoropropene (mesylate, 250 mg, 1.19 mmol) in ethyl acetate (30 mL) was stirred at 55° C. for 1.5 hours. The mixture was partitioned between ethyl acetate and water. The organic layer was washed with brine, dried with MgSO$_4$ and filtered. The filtrate was concentrated in vacuo. The residue was purified by column chromatography on silica gel eluted with 15% ethyl acetate/hexanes, to provide the methyl sulfide, 2-(2,3,3-trifluoro-2-propen-1-yl)-4-(4-fluorophenyl)-5-[4-(methylthio)phenyl]-3(2H)-pyridazinone as a greenish oil (yield: 175 mg, 53%).

Example 88C 2-(2,3,3-Trifluoro-2-propen-1-yl)]-4-(4-fluorophenyl)-5-[4-(methylsulfonyl)phenyl]-3(2H)-pyridazinone The methyl sulfide, prepared above, was oxidized to the title compound according to the method of Example 10 (yield: 125 mg, 68%). mp 154–156° C. $^1$H NMR (300 MHz, CDCl$_3$) δ 3.07 (s, 3H), 5.1 (ddd, J=21 Hz, 3 Hz, 1.5 Hz, 2H), 6.98 (t, J=9 Hz, 2H), 7.19 (dd, J=9 Hz, 6 Hz, 2H), 7.35 (d, J=9 Hz, 2H), 7.89 (s, 1H), 7.9 (d, J=9 Hz, 2H). MS (DCI/NH$_3$) m/z 439 (M+H)$^+$. Anal. calc. for C$_{20}$H$_{14}$F$_4$N$_2$O$_3$S: C, 54.79; H, 3.21; N, 6.38. Found: C, 54.52; H, 3.15; N, 6.21.

EXAMPLE 89

2,4-Bis(4-fluorophenyl)-5-[4-(aminosulfonyl)phenyl]-3(2H)-pyridazinone

The title compound was prepared according to the method of Example 68 substituting 2,4-bis(4-fluorophenyl)-5-[4-(methylsulfinyl)phenyl]-3(2H)-pyridazinone in place of 2-(2,2,2-trifluoroethyl)-4-(4-fluorophenyl)-5-[4-(methylsulfinyl)phenyl]-3(2H)-pyridazinone (yield: 118 mg, 43%). mp 213–216° C. $^1$H NMR (300 MHz, DMSO-d$_6$) δ 7.15 (t, 2H), 7.27 (m, 2H), 7.4 (m, 6H), 7.7 (dd, 2H), 7.76 (d, J=9

Hz, 2H), 8.2 (s, 1H). MS (DCI/NH$_3$) m/z 440 (M+H)$^+$, 439.44 (M+NH$_4$)$^+$. Anal. calc. for C$_{21}$H$_{15}$FN$_2$O$_3$S$_2$: C, 60.13; H, 3.44; N, 9.56. Found: C, 59.94; H, 3.37; N, 9.46.

EXAMPLE 90

2-(2,2,2-Trifluoroethyl)-4-cyclopropylmethoxy-5-[4-(methylsulfonyl)phenyl]-3(2H)-pyridazinone

Example 90A 2-(2,2,2-Trifluoroethyl)-4-methoxy-5-bromo-3(2H)-pyridazinone

The title compound was prepared according method of the Example 83B, substituting methanol in place of isopropanol (yield: 78%). $^1$H NMR (300 MHz, CDCl$_3$) δ 4.3 (s, 3H), 4.76 (q, J=9 Hz, 2H), 7.85 (s, 1H). MS (DCI/NH$_3$) m/z 288 (M+H)$^+$.

Example 90B 2-(2,2,2-Trifluoroethyl)-4-methoxy-5-[4-(methylthio)phenyl]-3(2H)-pyridazinone The title compound was prepared according method of the Example 83C, substituting 2-(2,2,2-trifluoroethyl)-4-methoxy-5-bromo-3(2H)-pyridazinone in place of 2-(2,2,2-trifluoroethyl)-4-(2-propoxy)-5-bromo-3(2H)-pyridazinone (yield: 80%). $^1$H NMR (300 MHz, CDCl$_3$) δ 2.54 (s, 3H), 4.11 (s, 3H), 4.82 (q, J=9 Hz, 2H), 7.33 (d, J=9 Hz, 2H), 7.48 (d, J=9 Hz, 2H), 7.84 (s, 1H). MS (DCI/NH$_3$) m/z 331 (M+H)$^+$.

Example 90C 2-(2,2,2-Trifluoroethyl)-4-hydroxy-5-[4-(methylthio)phenyl]-3(2H)-pyridazinone A solution of 2-(2,2,2-Trifluoroethyl)-4-methoxy-5-[4-(methylthio)phenyl]-3(2H)-pyridazinone (2 g, 6.1 mmol) and hydrobromic acid (40% in water, 20 mL) in acetic acid (40 mL) was heated at reflux for 3 hours. The reaction mixture was cooled to room temperature and water (50 mL) was added. The crystals formed were filtered, washed with water and 5% ethyl acetate in hexanes, and dried to constant weight. The product was obtained as a white solid (yield: 1.75 g, 91%). $^1$H NMR (300 MHz, CDCl$_3$) δ 2.54 (s, 3H), 4.82 (q, J=9 Hz, 2H), 7.47 (d, J=9 Hz, 2H), 7.65 (d, J=9 Hz, 2H), 7.73 (br s, 1H), 8.00 (s, 1H). MS (DCI) m/z 317 (M+H)$^+$.

Example 90D 2-(2,2,2-Trifluoroethyl)-4-cyclopropylmethoxy-5-[4-(methylthio)phenyl]-3(2H)-pyridazinone A solution of 2-(2,2,2-trifluoroethyl)-4-hydroxy-5-[4-(methylthio)phenyl]-3(2H)-pyridazinone (150 mg, 0.47 mmol), cyclopropyl methanol (43 mL, 0.52 mmol) and triphenylphosphine (124 mg, 0.47 mmol) in freshly distilled THF was prepared and added dropwise to diethyl azodicarboxylate (75 mL, 0.52 mmol) at 0° C. The mixture was allowed to warm to room temperature, stirred for 5 hours and concentrated in vacuo. The residue was purified by chromatography on silica gel (95:5 hexanes/ethyl acetate) to provide the product as a colorless oil (yield: 140 mg, 81%). $^1$H NMR (300 MHz, CDCl$_3$) δ 0.22 (m, 2H), 0.48 (m, 2H), 1.6 (m, 1H), 2.53 (s, 3H), 4.26 (d, J=7.5 Hz, 2H), 4.72 (q, J=9 Hz, 2H), 7.32 (d, J=9 Hz, 2H), 7.55 (d, J=9 Hz, 2H), 7.87 (s, 1H). MS (DCI/NH$_3$) m/z 371 (M+H)$^+$.

Example 90E 2-(2,2,2-Trifluoroethyl)-4-cyclopropylmethoxy-5-[4-(methylsulfonyl)phenyl]-3(2H)-pyridazinone The title compound was prepared according to the method of example 10, substituting 2-(2,2,2-trifluoroethyl)-4-cyclopropylmethoxy-5-[4-(methylthio)phenyl]-3(2H)-pyridazinone in place of 4-(4-fluorophenyl)-5-[4-(methylthio)phenyl]-3(2H)-pyridazinone (yield: 130 mg, 85%). mp 133–135° C. $^1$H NMR (300 MHz, CDCl$_3$) δ 0.22 (m, 2H), 0.5 (m, 2H), 1.07 (m, 1H), 3.12 (s, 3H), 4.4 (d, J=9 Hz, 2H), 4.83 (q, J=9 Hz, 2H), 7.79 (s, 1H), 7.83 (d, J=9 Hz, 2H), 8.07 (d, J=9 Hz, 2H). MS (DCI/NH$_3$) m/z 403 (M+H)$^+$. Anal. calc. for C$_{17}$H$_{17}$F$_3$N$_2$O$_4$S: C, 50.74; H, 4.25; N, 6.96. Found: C, 50.56; H, 4.09; N, 6.88.

EXAMPLE 91

2-(2,2,2-Trifluoroethyl)-4-(3-propen-1-oxy)-5-[4-(methylsulfonyl)phenyl]-3(2H)-pyridazinone The title compound was prepared according to the method of Example 90, substituting 2-propen-1-ol in place of cyclopropylmethanol (yield: 120 mg, 77%). mp 121–123° C. $^1$H NMR (300 MHz, CDCl$_3$) δ 3.12 (s, 3H), 4.84 (q, J=12 Hz, 2H), 5.07 (d, J=6 Hz, 2H), 5.21 (dd, J=13.5 Hz, 1 Hz, 1H), 5.27 (dd, J=15 Hz, 1 Hz, 1H), 5.85 (m, 1H), 7.25 (d, J=9 Hz, 2H), 7.83 (s, 1H), 8.06 (d, J=9 Hz, 2H). MS (DCI/NH$_3$) m/z 389 (M+H)$^+$. Anal. calc. for C$_{16}$H$_{15}$F$_3$N$_2$O$_4$S: C, 49.48; H, 3.89; N, 7.21. Found: C, 49.24; H, 3.77; N, 7.16.

EXAMPLE 92

2-(2,2,2-Trifluoroethyl)-4-(4-fluoro-α-methylbenzyloxy)-5-[4-(methylsulfonyl)phenyl]-3(2H)-pyridazinone The title compound was prepared according to the method of Example 90, substituting 4-fluoro-alpha-methylbenzyl alcohol in place of cyclopropylmethanol (yield: 155 mg, 76%). mp 133–135° C. $^1$H NMR (300 MHz, CDCl$_3$) δ 1.57 (d, J=6 Hz, 3H), 3.13 (s, 3H), 4.75 (q, J=7.5 Hz, 1H), 4.87 (q, J=7.5 Hz, 1H), 6.34 (q, J=6 Hz, 1H), 6.83 (t, J=9 Hz, 2H), 6.98 (dd, J=9 Hz, 6 Hz, 2H), 7.59 (d, J=9 Hz), 7.70 (s, 1H), 8.03 (d, J=9 Hz, 2H). MS (DCI/NH$_3$) m/z 471 (M+H)$^+$. Anal. calc. for C$_{21}$H$_{18}$F$_4$N$_2$O$_4$S: C, 53.61; H, 3.85; N, 5.95. Found: C, 53.54; H, 3.73; N, 5.86.

EXAMPLE 93

2-[4-(Methylthio)phenyl]-4-(4-fluorophenyl)-5-[4-(methylsulfonyl)phenyl]-3(2H)-pyridazinone A solution of the product from Example 11, 4-(4-Fluorophenyl)-5-[4-(methylsulfonyl)phenyl]-3(2H)-pyridazinone (344 mg, 1.0 mmol), 4-bromothioanisole (812 mg, 4.0 mmol), and copper (70 mg, 1.1 mmol) in 20 mL of pyridine was stirred at reflux under a nitrogen atmosphere for 18 hours. After cooling to room temperature, the reaction mixture was diluted with a mixture of water and ethyl acetate. The two layers were filtered through Celite®, and separated. The organic layer was washed with 10% aqueous citric acid, with brine, dried over MgSO$_4$, and filtered. The filtrate was concentrated in vacuo and the residue purified by column chromatography (silica gel, 93:7 dichloromethane/ethyl acetate) to provide the title compound as a foam (yield: 380 mg, 81.5%). $^1$H NMR (300 MHz, CDCl$_3$) δ 2.55 (s, 3H), 3.05 (s, 3H), 6.98 (t, J=9 Hz, 2H), 7.22 (dd, J=9 Hz, 6 Hz, 2H), 7.38 (dd, J=8 Hz, 2 Hz, 4H), 7.64 (d, J=9 Hz, 2H), 7.91 (d, J=9 Hz, 2H), 7.98 (s, 1H). MS (DCI/NH$_3$) m/z 467 (M+H)$^+$. Anal. calc. for C$_{24}$H$_{19}$FN$_2$O$_3$S$_2$.0.5 H$_2$O: C, 60.63; H, 4.21; N, 5.90. Found: C, 60.72; H, 3.96; N, 5.70.

EXAMPLE 94

2,5-Bis[4-(methylsulfonyl)phenyl]-4-(4-fluorophenyl)-3(2H)-pyridazinone

The title compound was prepared by oxidizing the product of Example 93, according to the method of Example 10 (yield: 156 mg, 78%). $^1$H NMR (300 MHz, CDCl$_3$) δ 3.10 (s, 3H), 3.12 (s, 3H), 7.02 (m, 2H), 7.24 (m, 2H), 7.42 (br d, J=9 Hz, 2H), 7.94 (dd, J=9 Hz, 2 Hz, 2H), 8.02 (dd, J=9 Hz, 2 Hz, 2H), 8.10 (m, 3H). MS (DCI/NH$_3$) m/z 499 (M+H)$^+$, 516 (M+NH$_4$)$^+$. Anal. calc. for C$_{24}$H$_{19}$FN$_2$O$_5$S$_2$.0.5 H$_2$O: C, 56.80; H, 3.94; N, 5.53. Found: C, 56.50; H, 3.88; N, 5.38.

EXAMPLE 95

2-(3-Methyl-2-thienyl)-4-(4-fluorophenyl)-5-[4-(methylsulfonyl)phenyl]-3(2H)-pyridazinone The title compound was prepared according to Example 93, substituting 2-bromo-3-methylthiophene in place of 4-bromothioanisole (yield: 190 mg, 43%). mp 215–217° C. $^1$H NMR (300 MHz, CDCl$_3$) δ 2.21 (s, 3H), 3.08 (s, 3H), 6.90 (d, J=9 Hz, 1H), 6.98 (t, J=9 Hz, 2H), 7.24 (dd, J=9 Hz, 6 Hz, 3H), 7.41 (d, J=9 Hz, 2H), 7.94 (d, J=9 Hz, 2H), 7.98 (s, 1H). MS (DCI/NH$_3$) m/z 441 (M+H)$^+$, 458 (M+NH$_4$)$^+$. Anal. calc. for C$_{22}$H$_{17}$FN$_2$O$_3$S$_2$.0.5 H$_2$O: C, 58.80; H, 4.01; N, 6.24. Found: C, 58.85; H, 3.78; N, 5.99.

EXAMPLE 96

2-(2-Trifluoromethyl-4-nitrophenyl)-4-(4-fluorophenyl)-5-[4-(methylsulfonyl)phenyl]-3(2H)-pyridazinone The title compound was prepared according to Example 93, substituting 2-bromo-5-nitrobenzotrifluoride in place of 4bromothioanisole (yield: 390 mg, 73%). $^1$H NMR (300 MHz, CDCl$_3$) δ 3.08 (s, 3H), 6.98 (t, J=9 Hz, 2H), 7.21 (dd, J=9 Hz, 6 Hz, 2H), 7.43 (d, J=9 Hz, 2H), 7.80 (d, J=9 Hz, 1H), 7.96 (d, J=9 Hz, 2H), 8.02 (s, 1H), 8.61 (dd, J=9 Hz, 3 Hz, 1H), 8.75 (d, J=3 Hz, 1H). MS DCI/NH$_3$) m/z 534 (M+H)$^+$, 551 (M+NH$_4$)$^+$. Anal. calc. for C$_{24}$H$_{15}$F$_4$N$_3$O$_5$S.0.75 H$_2$O: C, 52.70; H, 3.02; N, 7.69. Found: C, 52.42; H, 3.04; N, 6.82.

EXAMPLE 97

2-[3-(Methylthio)phenyl]-4-(4-fluorophenyl)-5-[4-(methylsulfonyl)phenyl]-3(2H)-pyridazinone The title compound was prepared according to Example 93, substituting 3-bromothioanisole in place of 4-bromothioanisole (yield: 355 mg, 76%). mp 196° C. $^1$H NMR (300 MHz, CDCl$_3$) δ 2.55 (s, 3H), 3.08 (s, 3H), 6.99 (t, J=9 Hz, 2H), 7.23 (dd, J=9 Hz, 6 Hz, 2H), 7.28–7.33 (m, 1H), 7.37–7.49 (m, 2H), 7.40 (d, J=9 Hz, 2H), 7.58 (m, 1H), 7.92 (d, J=9 Hz, 2H), 7.99 (m, 1H). MS (DCI/NH$_3$) m/z 467 (M+H)$^+$, 484 (M+NH$_4$)$^+$. Anal. calc. for C$_{24}$H$_{19}$FN$_2$O$_3$S$_2$: C, 61.80; H, 4.08; N, 6.01. Found: C, 61.56; H, 3.93; N, 5.86.

EXAMPLE 98

2-[3-(Methylsulfonyl)phenyl]-4-(4-fluorophenyl)-5-[4-(methylsulfonyl)phenyl]-3(2H)-pyridazinone The title compound was prepared by oxidizing the product of Example 97, according to the method of Example 10 (yield: 98 mg, 65.6%). mp 141–142° C. $^1$H NMR (300 MHz, DMSO-d$_6$) δ 3.25 (s, 3H), 3.35 (s, 3H), 7.18 (t, J=9 Hz, 2H), 7.32 (dd, J=9 Hz, 6 Hz, 2H), 7.52 (d, J=9 Hz, 2H), 7.83 (t, J=9 Hz, 1H), 7.95 (d, J=9 Hz, 2H), 8.05 (m, 1H), 8.25 (t, J=1.5 Hz, 1H), 8.33 (s, 1H). MS (DCI/NH$_3$) m/z 516 (M+NH$_4$)$^+$. Anal. calc. for C$_{24}$H$_{19}$FN$_2$O$_5$S$_2$.H$_2$O: C, 55.81; H, 4.07; N, 5.43. Found: C, 56.24; H, 4.29; N, 5.10.

EXAMPLE 99

2-(4-Fluorophenyl)-4-(4-chlorophenyl)-5-[4-(methylsulfonyl)phenyl]-3(2H)-pyridazinone 4-(4-Chlorophenyl)-5-[4-(methylsulfonyl)phenyl]-3(2H)-pyridazinone is prepared starting with the 2-benzylpyridazinone from Example 53 and debenzylating the compound according to the method of Example 11.

The title compound was prepared according to the method of Example 93, starting with 4-(4-chlorophenyl)-5-[4-(methylsulfonyl)phenyl]-3(2H)-pyridazinone in place of 4-(4-fluorophenyl)-5-[4-(methylsulfonyl)phenyl]-3(2H)-pyridazinone and substituting 1-fluoro-4-iodobenzene in place of 4-bromothioanisole (yield: 245 mg, 54%). mp 195–197° C. $^1$H NMR (300 MHz, CDCl$_3$) δ 3.08 (s, 3H), 7.19 (m, 4H), 7.25 (m, 2H), 7.41 (d, J=9 Hz, 2H), 7.70 (m, 2H), 7.95 (d, J=9 Hz, 2H), 8.01 (s, 1H). MS (DCI/NH$_3$) m/z 455 (M+H)$^+$, 472 (M+NH$_4$)$^+$. Anal. calc. for C$_{23}$H$_{16}$ClFN$_2$O$_3$S: C, 60.78; H, 3.52; N, 6.17. Found: C, 60.81; H, 3.53; N, 5.93.

EXAMPLE 100

2-(5-Chloro-2-thienyl)-4-(4-chlorophenyl)-5-[4-(methylsulfonyl)phenyl]-3(2H)-pyridazinone The title compound was prepared according to Example 93, substituting 4-(4-chlorophenyl)-5-[4-(methylsulfonyl)phenyl]-3(2H)-pyridazinone in place of 4-(4-fluorophenyl)-5-[4-(methylsulfonyl)phenyl]-3(2H)-pyridazinone and substituting 2-bromo-5-chlorothiophene in place of 4-bromothioanisole (yield: 150 mg, 45%). mp 249–251° C. $^1$H NMR (300 MHz, CDCl$_3$) δ 3.05 (s, 3H), 6.92 (d, J=9 Hz, 1H), 7.18 (d, J=9 Hz, 2H), 7.31 (d, J=9 Hz, 2H), 7.39 (d, J=9 Hz, 2H), 7.58 (d, J=6 Hz, 1H), 7.94 (d, J=9 Hz, 2H), 8.04 (s, 1H). MS (DCI/NH$_3$) m/z 477 (M+H)$^+$, 494 (M+NH$_4$)$^+$. Anal. calc. for C$_{21}$H$_{14}$Cl$_2$N$_2$O$_3$S$_2$.H$_2$O: C, 50.9; H, 3.03; N, 5.60. Found: C, 50.5; H, 2.79; N, 5.26.

EXAMPLE 101

2-(3-Trifluoromethylphenyl)-4-(4-chlorophenyl)-5-[4-(methylsulfonyl)phenyl]-3(2H)-pyridazinone The title compound was prepared according to Example 93, starting with 4-(4-chlorophenyl)-5-[4-(methylsulfonyl)phenyl]-3(2H)-pyridazinone in place of 4-(4-fluorophenyl)-5-[4-(methylsulfonyl)phenyl]-3(2H)-pyridazinone and substituting 3-iodobenzotrifluoride in place of 4-bromothioanisole (yield: 210 mg, 59.5%). mp 103–105° C. $^1$H NMR (300 MHz, CDCl$_3$) δ 3.08 (s, 3H), 7.18 (d, J=9 Hz, 2H), 7.28 (d, J=9 Hz, 2H), 7.41 (d, J=9 Hz, 2H), 7.65 (m, 2H), 7.95 (m, 3H), 8.04 (m, 2H). MS (DCI/NH$_3$) m/z 505 (M+H)$^+$, 525 (M+NH$_4$)$^+$. Anal. calc. for C$_{24}$H$_{16}$ClF$_3$N$_2$O$_3$S: C, 57.14; H, 3,17; N, 5.56. Found: C, 56.61; H, 3.28; N, 5.38.

EXAMPLE 102

2-(3-Chloro-4-fluorophenyl)-4-(4-chlorophenyl)-5-[4-(methylsulfonyl)phenyl]-3(2H)-pyridazinone The title compound was prepared according to Example 93, starting with 4-(4-chlorophenyl)-5-[4-(methylsulfonyl)phenyl]-3(2H)-pyridazinone (described in Example 99) in place of 4-(4-fluorophenyl)-5-[4-(methylsulfonyl)phenyl]-3(2H)-pyridazinone and substituting 1-bromo-3-chloro-4-fluorobenzene in place of 4-bromothioanisole (yield: 330 mg, 58.8%). mp 205° C. $^1$H NMR (300 MHz, CDCl$_3$) δ 3.10 (s, 3H), 7.17 (d, J=9 Hz, 2H), 7.23–7.31 (m, 1H), 7.28 (d, J=9 Hz, 2H), 7.41 (d, J=9 Hz, 2H), 7.65 (ddd, J=9 Hz, 3 Hz, 1.5 Hz, 1H), 7.85 (dd, J=9 Hz, 3 Hz, 1H), 7.93 (d, J=9 Hz, 2H), 8.01 (s, 1H). MS (DCI/NH$_3$) m/z 489 (M+H)$^+$, 508 (M+NH$_4$)$^+$. Anal. calc. for C$_{23}$H$_{15}$Cl$_2$N$_2$O$_3$S: C, 56.44; H, 3.17; N, 5.73. Found: C, 56.37; H, 3.19; N, 5.64.

EXAMPLE 103

2-(3-Fluorophenyl)-4-(4-fluorophenyl)-5-[4-(methylsulfonyl)phenyl]-3(2H)-pyridazinone The title compound was prepared according to Example 93, substituting 1-fluoro-3-iodobenzene in place of 4-bromothioanisole (yield: 310 mg, 70.8%). mp 245–247° C. $^1$H NMR (300 MHz, CDCl$_3$) δ 3.08 (s, 3H), 6.98 (t, J=9 Hz, 2H), 7.14 (m, 1H), 7.24 (dd, J=9 Hz, 6 Hz, 2H), 7.40 (m, 2H), 7.52 (m, 3H), 7.92 (d, J=9 Hz, 2H), 8.01 (s, 1H). MS (DCI/NH$_3$) m/z 439 (M+H)$^+$, 456 (M+NH$_4$)$^+$. Anal. calc. for C$_{23}$H$_{16}$F$_2$N$_2$O$_3$S.0.25 H$_2$O: C, 62.34; H, 3.67; N, 6.38. Found: C, 62.33; H, 3.68; N, 6.22.

EXAMPLE 104

2-[2-(Methylthio)phenyl]-4-(4-fluorophenyl)-5-[4-(methylsulfonyl)phenyl]-3(2H)-pyridazinone The title compound was prepared according to Example 93, substituting 2-bromothioanisole in place of 4-bromothioanisole (yield: 280 mg, 60%). mp 206–208° C. $^1$H NMR (300 MHz, CDCl$_3$) δ 2.49 (s, 3H), 3.08 (s, 3H), 6.95 (t, J=9 Hz, 2H), 7.25 (dd, J=9 Hz, 6 Hz, 2H), 7.29–7.51 (m, 4H), 7.43 (d, J=9 Hz, 2H), 7.92 (d, J=9 Hz, 3H), 8.01 (s, 1H), 7.98 (s, 1H). MS (DCI/NH$_3$) m/z 467 (M+H)$^+$, 484 (M+NH$_4$)$^+$. Anal. calc. for C$_{24}$H$_{19}$FN$_2$O$_3$S$_2$.H$_2$O: C, 59.50; H, 4.13; N, 5.79. Found: C, 59.62; H, 4.15; N, 5.52.

EXAMPLE 105

2-(5-Nitro-2-thienyl)-4-(4-fluorophenyl)-5-[4-(methylsulfonyl)phenyl]-3(2H)-pyridazinone The title compound was prepared according to Example 93, substituting 2-bromo-5-nitrothiophene in place of 4-bromothioanisole (yield: 330 mg, 70%). mp 252–253° C. $^1$H NMR (300 MHz, CDCl$_3$) δ 3.06 (s, 3H), 7.05 (t, J=9 Hz, 2H), 7.25 (dd, J=9 Hz, 6 Hz, 2H), 7.40 (d, J=9 Hz, 2H), 7.71 (d, J=6 Hz, 1H), 7.95 (m, 3H), 8.14 (s, 1H). MS (DCI/NH$_3$) m/z 472 (M+H)$^+$, 489 (M+NH$_4$)$^+$. Anal. calc. for C$_{21}$H$_{14}$FN$_3$O$_5$S$_2$.0.5 H$_2$O: C, 52.50; H, 3.02; N, 8.75. Found: C, 52.79; H, 3.18; N, 8.74.

EXAMPLE 106

2-(3,4-Difluorophenyl)-4-(4-chlorophenyl)-5-[4-(methylsulfonyl)phenyl]-3(2H)-pyridazinone The title compound was prepared according to Example 93, starting with 4-(4-chlorophenyl)-5-[4-(methylsulfonyl)phenyl]-3(2H)-pyridazinone in place of 4-(4-fluorophenyl)-5-[4-(methylsulfonyl)phenyl]-3(2H)-pyridazinone and substituting 1-bromo-3,4-difluorobenzene in place of 4-bromothioanisole (yield: 310 mg, 65.7%). mp 187–188° C. $^1$H NMR (300 MHz, CDCl$_3$) δ 3.09 (s, 3H), 7.18 (d, J=9 Hz, 2H), 7.29 (m, 3H), 7.41 (d, J=9 Hz, 2H), 7.52 (m, 1H), 7.65 (m, 1H), 7.92 (d, J=9 Hz, 2H), 8.01 (s, 1H). MS (DCI/NH$_3$) m/z 473 (M+H)$^+$, 490 (M+NH$_4$)$^+$. Anal. calc. for C$_{23}$H$_{15}$ClF$_2$N$_2$O$_3$S.0.5 H$_2$O: C, 57.38; H, 3.33; N, 5.82. Found: C, 57.44; H, 3.38; N, 5.52.

EXAMPLE 107

2-(3-Benzothienyl)-4-(4-fluorophenyl)-5-[4-(methylsulfonyl)phenyl]-3(2H)-pyridazinone The title compound was prepared according to Example 93, substituting 3-bromobenzothiophene in place of 4-bromothioanisole (yield: 185 mg, 41%). mp 265–267° C. $^1$H NMR (300 MHz, CDCl$_3$) δ 3.09 (s, 3H), 7.0 (t, J=9 Hz, 2H), 7.27 (dd, J=9 Hz, 6 Hz, 2H), 7.39–7.47 (m, 2H), 7.44 (d, J=9 Hz, 2H), 7.75–7.82 (m, 1H), 7.87–7.94 (m, 2H), 7.94 (d, J=9 Hz, 2H), 8.05 (s, 1H). MS (DCI/NH$_3$) m/z 477 (M+H)$^+$, 494 (M+NH$_4$)$^+$. Anal. calc. for C$_{25}$H$_{17}$FN$_2$O$_3$S$_2$: C, 63.03; H, 3.57; N, 5.88. Found: C, 62.89; H, 3.55; N, 5.71.

EXAMPLE 108

2-(4-Fluorophenyl)-4-(4-fluorophenoxy)-5-[4-(methylsulfonyl)phenyl]-3(2H)-pyridazinone

Example 108A

4-(4-Fluorophenoxy)-5-[4-(methylsulfonyl)phenyl]-3(2H)-pyridazinone

The title compound was prepared by treating 2-benzyl-4-(4-fluorophenoxy)-5-[4-(methylsulfonyl)phenyl]-3(2H)-pyridazinone (Example 75) with AlBr$_3$ in toluene according to the procedure in Example 11 (yield: 1.8 g, 95%).

Example 108B

2-(4-Fluorophenyl)-4-(4-fluorophenoxy)-5-[4-(methylsulfonyl)phenyl]-3(2H)-pyridazinone

The title compound was prepared according to Example 93, starting with 4-(4-fluorophenoxy)-5-[4-(methylsulfonyl)phenyl]-3(2H)-pyridazinone and substituting 1-fluoro-4-iodobenzene in place of 4-bromothioanisole (yield: 60 mg, 53%). mp 83–85° C. $^1$H NMR (300 MHz, CDCl$_3$) δ 3.10 (s, 3H), 6.89–7.03 (m, 4H), 7.15 (t, J=9 Hz, 2H), 7.65 (dd, J=9 Hz, 6 Hz, 2H), 7.83 (d, J=6 Hz, 2H), 8.07 (d, J=9 Hz, 2H), 8.08 (s, 1H). MS (DCI/NH$_3$) m/z 455 (M+H)$^+$, 472 (M+NH$_4$)$^+$.

EXAMPLE 109

2-(3,4-Difluorophenyl)-4-(4-fluorophenoxy)-5-[4-(methylsulfonyl)phenyl]-3(2H)-pyridazinone

The title compound was prepared according to Example 93, substituting 1-bromo-3,4-difluorobenzene in place of 4-bromothioanisole and 4-(4-fluorophenoxy)-5-[4-(methylsulfonyl)phenyl]-3(2H)-pyridazinone (Example 108A) in place of 4-(4-fluorophenyl)-5-[4-(methylsulfonyl)phenyl]-3(2H)-pyridazinone (yield: 185 mg, 39%). mp 178–180° C. $^1$H NMR (300 MHz, CDCl$_3$) δ 3.11 (s, 3H), 6.89–7.04 (m, 4H), 7.45–7.52 (m, 1H), 7.45–7.52 (m, 1H), 7.61 (dt, J=6 Hz, 3 Hz, 1H), 7.82 (d, J=9 Hz, 2H), 8.07 (d, J=9 Hz, 2H), 8.08 (s, 1H). MS (DCI/NH$_3$) m/z 473 (M+H)$^+$, 490 (M+NH$_4$)$^+$. Anal. calc. for C$_{23}$H$_{15}$F$_3$N$_2$O$_4$S.0.5 H$_2$O: C, 57.38; H, 3.33; N, 5.83. Found: C, 57.17; H, 3.13; N, 5.62.

EXAMPLE 110

2-(3-Bromophenyl)-4-(4-fluorophenoxy)-5-[4-(methylsulfonyl)phenyl]-3(2H)-pyridazinone

The title compound was prepared according to Example 93, substituting 1,3-dibromobenzene in place of 4-bromothioanisole and 4-(4-fluorophenoxy)-5-[4-(methylsulfonyl)phenyl]-3(2H)-pyridazinone (Example 108A) in place of 4-(4-fluorophenyl)-5-[4-(methylsulfonyl)phenyl]-3(2H)-pyridazinone (yield: 260 mg, 50.5%). mp 208–210° C. $^1$H NMR (300 MHz, CDCl$_3$) δ 3.09 (s, 3H), 6.89–7.04 (m, 4H), 7.34 (t, J=9 Hz, 1H), 7.53 (br d, J=9 Hz, 1H), 7.64 (br d, J=9 Hz, 1H), 7.82 (d, J=9 Hz, 2H), 7.87 (t, J=1.5 Hz, 1H), 8.08 (d, J=9 Hz, 2H), 8.09 (s, 1H). MS (DCI/NH$_3$) m/z 517 (M+H)$^+$, 534 (M+NH$_4$)$^+$. Anal. calc. for C$_{23}$H$_{16}$BrFN$_2$O$_4$S: C, 53.7; H, 3.11; N, 5.45. Found: C, 53.46; H, 2.88; N, 5.18.

EXAMPLE 111

2-(3,5-Difluorophenyl)-4-(4-fluorophenoxy)-5-[4-(methylsulfonyl)phenyl]-3(2H)-pyridazinone

The title compound was prepared according to Example 93, substituting 1-bromo-3,4-difluorobenzene in place of 4-bromothioanisole and 4-(4-fluorophenoxy)-5-[4-(methylsulfonyl)phenyl]-3(2H)-pyridazinone (Example 108A) in place of 4-(4-fluorophenyl)-5-[4-(methylsulfonyl)phenyl]-3(2H)-pyridazinone (yield: 175 mg, 37%). mp 209–211° C. $^1$H NMR (300 MHz, CDCl$_3$) δ 3.10 (s, 3H), 6.85 (tt, J=9 Hz, 3 Hz, 1H), 6.90–7.04 (m, 4H), 7.38 (dd, J=9 Hz, 3 Hz, 2H), 7.81 (d, J=9 Hz, 2H), 8.07 (d, J=9 Hz, 2H), 8.10 (s, 1H). MS (DCI/NH$_3$) m/z 473 (M+H)$^+$, 490 (M+NH$_4$)$^+$. Anal. calc. for C$_{23}$H$_{15}$F$_3$N$_2$O$_4$S.H$_2$O: C, 58.47; H, 3.18; N, 5.94. Found: C, 58.31; H, 3.15; N, 5.82.

EXAMPLE 112

2-(3-Chlorophenyl)-4-(4-fluorophenoxy)-5-[4-(methylsulfonyl)phenyl]-3(2H)-pyridazinone

The title compound was prepared according to Example 93, substituting 1-bromo-3-chlorobenzene in place of 4-bromothioanisole and 4-(4-fluorophenoxy)-5-[4-(methylsulfonyl)phenyl]-3(2H)-pyridazinone (Example 108A) in place of 4-(4-fluorophenyl)-5-[4-(methylsulfonyl)phenyl]-3(2H)-pyridazinone (yield: 25 mg, 5.3%). mp 211–213° C. $^1$H NMR (300 MHz, DMSO-d$_6$) δ 3.30 (s, 3H), 7.15 (d, J=9 Hz, 4H), 7.51–7.64 (m, 3H), 7.71–7.75 (m, 1H), 7.91 (d, J=9 Hz, 2H), 8.06 (d, J=9 Hz, 2H), 8.41 (s, 1H). MS (DCI/NH$_3$) m/z 471 (M+H)$^+$, 488 (M+NH$_4$)$^+$. Anal. calc. for C$_{23}$H$_{16}$ClFN$_2$O$_4$S.0.5 H$_2$O: C, 57.62; H, 3.44; N, 5.85. Found: C, 57.62; H, 3.52; N, 5.48.

EXAMPLE 113

2-(4-Nitrobenzyl)-4-(4-fluorophenyl)-5-[4-(methylsulfonyl)phenyl]-3(2H)-pyridazinone

The title compound was prepared according to the method of Example 20, substituting 4-nitrobenzyl bromide in place of 4-fluorobenzyl bromide (yield: 164 mg, 58.9%). mp 183–184° C. $^1$H NMR (300 MHz, CDCl$_3$) δ 3.05 (s, 3H), 5.47 (s, 2H), 6.96 (t, J=9 Hz, 2H), 7.16 (dd, J=9 Hz, 3 Hz, 2H), 7.32 (d, J=9 Hz, 2H), 7.70 (d, J=9 Hz, 2H), 7.87 (s, 1H), 7.88 (d, J=9 Hz, 2H), 8.22 (d, J=9 Hz, 2H). MS (DCI/NH$_3$) m/z 480 (M+H)$^+$, m/z 497 (M+NH$_4$)$^+$. Anal. calc. for C$_{24}$H$_{18}$FN$_3$O$_5$S: C, 60.12; H, 3.78; N, 8.76. Found: C, 59.89; H, 3.83; N, 8.61.

EXAMPLE 114

2-(4-Acetoxybenzyl)-4-(4-fluorophenyl)-5-[4-methylsulfonyl)phenyl]-3(2H)-pyridazinone

The title compound was prepared according to the method of Example 20, substituting 4-(chloromethyl)phenyl acetate in place of 4-fluorobenzyl bromide (yield: 220 mg, 76.9%). mp 172–174° C. $^1$H NMR (300 MHz, CDCl$_3$) δ 2.30 (s, 3H), 3.05 (s, 3H), 5.38 (s, 2H), 6.95 (t, J=9 Hz, 2H), 7.06 (d, J=9 Hz, 2H), 7.16 (dd, J=9 Hz, 5 Hz, 2H), 7.31 (d, J=9 Hz, 2H), 7.60 (d, J=9 Hz, 2H), 7.81 (s, 1H), 7.87 (d, J=9 Hz, 2H). MS (DCI/NH$_3$) m/z 510 (M+NH$_4$)$^+$. Anal. calc. for C$_{26}$H$_{21}$FN$_2$O$_5$S: C, 63.40; H, 4.30; N, 5.69. Found: C, 63.28; H, 4.41; N, 5.39.

EXAMPLE 115

2-(4-Hydroxybenzyl)-4-(4-fluorophenyl)-5-[4-(methylsulfonyl)phenyl]-3(2H)-pyridazinone

A solution of 2-(4-acetoxybenzyl)-4-(4-fluorophenyl)-5-[4-(methylsulfonyl)phenyl]-3(2H)-pyridazinone (0.2 g, 4.06 mmol) (Example 114) in THF (20 mL) was treated with a solution of lithium hydroxide monohydrate (0.05 g, 1.22 mmol) in water (5 mL). Methanol (2 mL) was added to provide a homogeneous solution which was stirred at room temperature overnight. The reaction mixture was then acidified with 10% aqueous citric acid and extracted with ethyl acetate. The ethyl acetate layer was dried over MgSO$_4$ and filtered. The filtrate was concentrated in vacuo to provide a white foam which was purified by column chromatography (silica gel, 65:35 hexanes/ethyl acetate). Product fractions were combined and concentrated in vacuo. The residue was crystallized from ethyl acetate/hexanes (yield: 195 mg, 70%). mp 225–226° C. $^1$H NMR (300 MHz, CDCl$_3$) δ 3.05 (s, 3H), 4.86 (s, 1H), 5.33 (s, 2H), 6.80 (d, J=8.5 Hz, 2H), 6.95 (t, J=9 Hz, 2H), 7.15 (dd, J=9 Hz, 5 Hz, 2H), 7.30 (d, J=8.5 Hz, 2H), 7.46 (d, J=8.5 Hz, 2H), 7.83 (s, 1H), 7.87 (d, J=8.5 Hz, 2H). MS (DCI/NH$_3$) m/z 451 (M+H)$^+$. Anal. calc. for C$_{24}$H$_{19}$FN$_2$O$_4$S: C, 63.99; H, 4.25; N, 6.22. Found: C, 63.73; H, 4.16; N, 6.11.

EXAMPLE 116

2-(3-Nitrobenzyl)-4-(4-fluorophenyl)-5-[4-(methylsulfonyl)phenyl]-3(2H)-pyridazinone The title compound was prepared according to the method of Example 20, substituting 3-nitrobenzyl bromide in place of 4-fluorobenzyl bromide (yield: 195 mg, 70%). mp 156–157° C. $^1$H NMR (300 MHz, CDCl$_3$) δ 3.05 (s, 3H), 5.48 (s, 2H), 6.96 (t, J=9 Hz, 2H), 7.16 (dd, J=9 Hz, 5 Hz, 2H), 7.33 (d, J=8.5 Hz, 2H), 7.54 (t, J=7 Hz, 1H), 7.88 (s, 1H), 7.90 (d, J=8.5 Hz, 2H), 8.19 (br d, J=7 Hz, 1H), 8.37 (t, J=1.7 Hz, 1H). MS (DCI/NH$_3$) m/z 480 (M+H)$^+$, m/z 497 (M+NH$_4$)$^+$. Anal. calc. for C$_{24}$H$_{18}$FN$_3$O$_5$S: C, 60.12; H, 3.78; N, 8.76. Found: C, 59.98; H, 3.73; N, 8.67.

EXAMPLE 117

2-(3,4,4-Trifluoro-3-butenyl)-4-(4-fluorophenyl)-5-[4-(methylsulfonyl)phenyl]-3(2H)-pyridazinone The title compound was prepared according to the method of Example 20, substituting 4-bromo-1,1,2-trifluoro-1-butene in place of 4-fluorobenzyl bromide (yield: 38 mg, 14.5%). mp 131–132° C. $^1$H NMR (300 MHz, CDCl$_3$) δ 62.92 (br d, J=21.7 Hz, 2H), 3.06 (s, 3H), 4.47 (t, J=6.6 Hz, 2H), 6.98 (t, J=9 Hz, 2H), 7.17 (dd, J=9 Hz, 5 Hz, 2H), 7.35 (d, J=8.5 Hz, 2H), 7.85 (s, 1H), 7.89 (d, J=8.5 Hz, 2H). MS (DCI/NH$_3$) m/z 453 (M+H)$^+$, m/z 470 (M+NH$_4$)$^+$. Anal. calc. for C$_{21}$H$_{16}$F$_4$N$_2$O$_3$S: C, 55.75; H, 3.56; N, 6.19. Found: C, 55.63; H, 3.62; N, 6.10.

EXAMPLE 118

2-(2-Hexynyl)-4-(4-fluorophenyl)-5-[4-4-(methylsulfonyl)phenyl]-3(2H)-pyridazinone The title compound was prepared according to the method of Example 20, substituting 1-chloro-2-hexyne in place of 4-fluorobenzyl bromide (yield: 170 mg, 69%). mp 79–80° C. $^1$H NMR (300 MHz, CDCl$_3$) δ 0.99 (t, J=7.5 Hz, 3H), 1.56 (h, J=7.5 Hz, 2H), 2.21 (m, 2H), 3.06 (s, 3H), 5.01 (t, J=3 Hz, 2H), 6.96 (t, J=9 Hz, 2H), 7.18 (dd, J=9 Hz, 6 Hz, 2H), 7.34 (d, J=9 Hz, 2H), 7.88 (s, 1H), 7.89 (d, J=9 Hz, 2H). MS (DCI/NH$_3$) m/z 425 (M+H)$^+$. Anal. calc. for C$_{23}$H$_{21}$FN$_2$O$_3$S: C, 65.07; H, 4.98; N, 6.59. Found: C, 64.87; H, 4.90; N, 6.58.

EXAMPLE 119

2-(3,3-Dichloro-2-propenyl)-4-(4-fluorophenyl)-5-[4-(aminosulfonyl)phenyl]-3(2H)-pyridazinone The title compound was prepared according to the method of Example 20, substituting 1,1,3-trichloropropene in place of 4-fluorobenzyl bromide (yield: 1.15 g, 68%). mp 184–185° C. $^1$H NMR (300 MHz, DMSO-$_6$) δ 4.39 (d, J=7.5 Hz, 2H), 6.43 (t, J=7.5 Hz, 1H), 7.14 (t, J=9 Hz, 2H), 7.23 (dd, J=9 Hz, 6 Hz, 2H), 7.38 (d, J=9 Hz, 2H), 7.43 (s, 2H), 7.73 (d, J=9 Hz, 2H), 8.11 (s, 1H). MS (DCI/NH$_3$) m/z 454 (M+H)$^+$. Anal. calc. for C$_{19}$H$_{14}$Cl$_2$F$_4$N$_3$O$_3$S: C, 50.23; H, 3.1; N, 9.24. Found: C, 50.28; H, 3.29; N, 9.19.

EXAMPLE 120

2-Cyclohexyl-4-(4-fluorophenyl)-5-[4-(methylsulfonyl)phenyl]-3(2H)-pyridazinone

The title compound was prepared according to the method of Example 20 substituting cyclohexyl bromide in place of 4-fluorobenzyl bromide (yield: 163 mg, 76%). mp 169–171° C. $^1$H NMR (DMSO-d$_6$, 300 MHz) δ 1.23 (m, 1H), 1.41 (m, 2H), 1.71 (m, 3H), 1.87 (m, 4H), 3.23 (s, 3H), 4.85 (m, 1H), 7.11 (m, 2H), 7.22 (m, 2H), 7.46 (d, J=9 Hz, 2H), 7.85 (d, J=9 Hz, 2H), 8.11 (s, 1H). MS (DCI/NH$_3$) m/z 427 (M+H)$^+$ and m/z 444 (M+NH$_4$)$^+$. Anal. calc. for C$_{23}$H$_{23}$FN$_2$O$_3$S.0.5 H$_2$O: C, 63.43; H, 5.55; N, 6.43. Found C, 63.25; H, 5.28; N, 6.28.

EXAMPLE 121

2-Cyclopentyl-4-(4-fluorophenyl)-5-[4-(methylsulfonyl)phenyl]-3(2H)-pyridazinone The title compound was prepared according to the method of Example 20, substituting cyclopentyl bromide in place of 4-fluorobenzyl bromide (yield: 165 g, 80%). mp 191–193° C. $^1$H NMR (DMSO-$_6$, 300 MHz) δ 1.67 (m, 2H), 1.85 (m, 4H), 2.05 (m, 2H), 3.23 (s, 3H), 5.36 (m, 1H), 7.12 (t, J=9 Hz, 2H), 7.22 (m, 2H), 7.45 (d, J=9 Hz, 2H), 7.85 (d, J=9 Hz, 2H), 8.13 (s, 1H). MS (DCI/NH$_3$) m/z 413 (M+H)$^+$ and m/z 430 (M+NH$_4$)$^+$. Anal. calc. for C22H$_{21}$FN$_2$O$_3$S.0.5 H$_2$O: C, 62.69; H, 5.26; N, 6.57. Found: C, 62.53; H, 4.93; N, 6.50.

EXAMPLE 122

2-Cyclobutyl-4-(4-fluorophenyl)-5-[4-(methylsulfonyl)phenyl]-3(2H)-pyridazinone

The title compound was prepared according to the method of Example 20, substituting cyclobutyl bromide in place of 4-fluorobenzyl bromide (yield: 270 g, 68%). mp 202–203° C. $^1$H NMR (DMSO-d$_6$, 300 MHz) δ 1.85 (m, 2H), 2.32 (m, 2H), 2.50 (m, 2H), 5.40 (quintet, J=7 Hz, 1H), 7.11 (t, J=9 Hz, 2H), 7.21 (m, 2H), 7.47 (d, J=9 Hz, 2H), 7.86 (d, J=9 Hz, 2H), 8.16 (s, 1H). MS (DCI/NH$_3$) m/z 399 (M+H)$^+$ and m/z 416 (M+NH$_4$)$^+$. Anal. calc. for C$_{21}$H$_{19}$FN$_2$O$_3$S.0.75 H$_2$O: C, 61.22; H, 5.01; N, 6.80. Found: C, 61.19; H, 4.62; N, 6.73.

EXAMPLE 123

2-(3-Methyl-2-butenyl)-4(4-fluorophenyl)-5-[3-fluoro-4-(aminosulfonyl)phenyl]-3(2H)-pyridazinone 2-Benzyl-4-(4-fluorophenyl)-5-[3-fluoro-4-(aminosulfonyl)phenyl]-3(2H)-pyridazinone, prepared according to the method of Example 68, was N-debenzylated according to the method of Example 11. The intermediate was N-alkylated according to the method of Example 20, substituting 1-bromo-3-methyl-2-butene in place of 4-fluorobenzyl bromide, to provide the title compound (yield: 50 mg, 30%). mp 134–136° C. $^1$H NMR (300 MHz, CDCl$_3$) δ 1.79 (s, 3H), 1.86 (s, 3H), 4.78 (s, 2H), 4.85 (d, J=7.5 Hz, 2H), 5.48 (t, J=6 Hz, 1H), 6.96 (t, J=9 Hz, 2H), 7.18 (dd, J=9 Hz, 6 Hz, 2H), 7.28 (d, J=9 Hz, 2H), 7.83 (s, 1H), 7.85 (d, J=9 Hz, 2H). MS (DCI/NH$_3$) m/z 414 (M+H)$^+$. Anal. calc. for C$_{21}$H$_{20}$FN$_3$O$_3$S: C, 61; H, 4.87; N, 10.16. Found: C, 60.98; H, 4.66; N, 9.95.

EXAMPLE 124

2-(2,4-Difluorobenzyl)-4-(4-fluorophenyl -5-4-(aminosulfonyl)phenyl]-3(2H)-pyridazinone 2-Benzyl-4-(4-fluorophenyl)-5-[4-(aminosulfonyl)phenyl]-3(2H)-pyridazinone, prepared according to the method of Example 68, was N-debenzylated according to the method of Example 11. The intermediate was N-alkylated according to the method of Example 20, substituting 2,4-difluorobenzylbromide in place of 4-fluorobenzyl bromide to provide the title compound (yield: 65 mg, 24%). mp 236–238° C. $^1$H NMR (300 MHz, CDCl$_3$) δ 4.78 (s, 2H), 5.43 (s, 2H), 6.88 (m, 2H), 6.97 (t, J=9 Hz, 2H), 7.18 (dd, J=9 Hz, 6 Hz, 2H), 7.38 (d, J=9 Hz, 2H), 7.55 (m, 1H), 7.85 (s, 1H), 7.86 (d, J=9 Hz, 2H). MS (DCI/NH$_3$) m/z 472 (M+H)$^+$. Anal. calc. for C$_{23}$H$_{16}$F$_3$N$_3$O$_3$S: C, 58.59; H, 3.42; N, 8.91. Found: C, 58.44; H, 3.47; N, 8.72.

EXAMPLE 125

2-(Pentafluorobenzyl)-4-(4-fluorophenyl)-5-[4(aminosulfonyl)phenyl]-3(2H)-pyridazinone The title compound was prepared according to the method of Example 124, substituting 2,3,4,5,6-pentafluorobenzyl bromide in place of 1-bromo-3-methyl-2-butene (yield: 105 mg, 35%). mp 201–203° C. $^1$H NMR (300 MHz, CDCl$_3$) δ 4.8 (s, 2H), 5.5 (s, 2H), 6.98 (t, J=9 Hz, 2H), 7.18 (dd, J=9 Hz, 6 Hz, 2H), 7.28 (d, J=9 Hz, 2H), 7.32 (s, 1H), 7.37 (d, J=9 Hz, 2H). MS (DCI/NH$_3$) m/z 526 (M+H)$^+$. Anal. calc. for C$_{23}$H$_{13}$F$_6$N$_3$O$_3$S: C, 52.57; H, 2.49; N, 7.99. Found: C, 52.66; H, 2.68; N, 7.8.

EXAMPLE 126

2-(3-Cyclohexenyl)-4-(4-fluorophenyl)-5-[4-(aminosulfonyl)phenyl]-3(2H)-pyridazinone The title compound was prepared according to the method of Example 124, substituting 3-bromocyclohexene in place of 1-bromo-3-methyl-2-butene (yield: 30 mg, 10%). mp 206–208° C. $^1$H NMR (300 MHz, CDCl$_3$) δ 1.75–1.85 (m, 3H), 2.1–2.3 (m, 3H), 4.8 (s, 2H), 5.75 (m, 2H), 6.1 (m, 1H), 6.97 (t, J=9 Hz, 2H), 7.20 (dd, J=9 Hz, 6 Hz, 2H), 7.28 (d, J=9 Hz, 2H), 7.86 (d, J=9 Hz, 2H), 7.90 (s, 1H). MS (DCI/NH$_3$) m/z 426 (M+H)$^+$. Anal. calc. for C$_{22}$H$_{20}$FN$_3$O$_3$S: C, 62.10; H, 4.73; N, 9.87. Found: C, 61.27; H, 4.75; N, 9.56.

EXAMPLE 127

2-(3,4-Difluorobenzyl)-4-(4-fluorophenyl)-5-[4-(aminosulfonyl)phenyl]-3(2H)-pyridazinone The title compound was prepared according to the method of Example 124, substituting 3,4-difluorobenzyl bromide in place of 1-bromo-3-methyl-2-butene and running the reaction in DMSO instead of DMF to prevent formation of byproducts (yield: 210 mg, 62%). mp 253–255° C. $^1$H NMR (300 MHz, DMSO-d$_6$) δ 5.33 (s, 2H), 7.13 (t, J=9 Hz, 2H), 7.22 (dd, J=9 Hz, 6 Hz, 2H), 7.28 (m, 1H), 7.39 (d, J=9 Hz, 2H), 7.42 (s, 2H), 7.47 (m, 2H), 7.73 (d, J=9 Hz, 2H), 8.12 (s, 1H). MS (DCI/NH$_3$) m/z 472 (M+H)$^+$. Anal. calc. for C$_{23}$H$_{16}$F$_3$N$_3$O$_3$S: C, 58.59; H, 3.42; N, 8.91. Found: C, 58.05; H, 3.55; N, 8.49.

EXAMPLE 128

2-(2,3-Dihydro-1H-inden-2-yl)-4-(4-fluorophenyl)-5-[4-(methylsulfonyl)phenyl]-3(2H)-pyridazinone A solution of 4-(4-fluorophenyl)-5-[4-(methylsulfonyl)phenyl]-3(2H)-pyridazinone (172 mg, 0.5 mmol), prepared in Example 11, 2-indanol (67 mg, 0.5 mmol) and Ph$_3$P (262 mg, 1 mmol) in toluene (20 mL) and ethyl acetate (5 mL) was, prepared and added dropwise a solution of DIAD (0.2 mL, 1 mmol) in toluene (10 mL). The mixture was stirred at room temperature for 6 hours and concentrated in vacuo. The residue was chromatographed (silica gel, 19:1 CH$_2$Cl$_2$-ethyl acetate) to provide 200 mg of product (contaminated with reduced DIAD). A second column chromatography (hexanes-ethyl acetate 1:1) furnished the title product (yield: 170 mg, 74%). mp 97–100° C. $^1$H NMR (DMSO-d$_6$, 300 MHz) δ 3.22 (s, 3H), 3.32 (m, 2H), 3.44 (dd, J=9 Hz and 15 Hz, 2H), 5.83 (m, 1H), 7.25 (m, 4H), 7.34 (m, 4H), 7.46 (d, J=9 Hz, 2H), 7.85 (d, J=9 Hz, 2H), 8.06 (s, 1H). MS (DCI/NH$_3$) m/z 461 (M+H)$^+$ and m/z 478 (M+NH$_4$)$^+$.

EXAMPLE 129

2-(2,3-Dihydro-1H-inden-1-yl)-4-(4-fluorophenyl)-5-[4-(methylsulfonyl)phenyl]-3(2H)-pyridazinone The title compound was prepared according to the method of Example 128 substituting 1-indanol in place of 2-indanol (yield: 110 mg, 48%). mp 128–130° C. $^1$H NMR (DMSO-d$_6$, 300 MHz) δ 2.40 (m, 1H), 2.60 (m, 1H), 3.00 (m, 1H), 3.22 (s+m, 4H), 6.60 (dd, J=9 Hz, 6 Hz, 1H), 7.16 (m, 4H), 7.27 (m, 4H), 7.47 (d, J=9 Hz, 2H), 7.85 (d, J=9 Hz, 2H), 8.02 (s, 1H). MS (DCI/NH$_3$) m/z 461 (M+H)$^+$ and m/z 478 (M+NH$_4$)$^+$.

EXAMPLE 130

2-(4-Tetrahydro-2H-pyran-4-yl)-4-(4-fluorophenyl)-5-[4-(methylsulfonyl)phenyl]-3(2H)-pyridazinone The title compound was prepared according to the method of Example 128 substituting 4-tetrahydropyranol in place of 2-indanol (yield: 140 g, 65%). mp 230–231° C. $^1$H NMR (300 MHz, DMSO-d$_6$) δ 1.75 (m, 2H), 1.93 (m, 2H), 3.14 (s, 3H), 3.46 (m, 2H), 3.93 (m, 2H); 5.02 (m, 1H), 7.05 (t, J=9 Hz, 2H), 7.15 (m, 2H), 7.40 (d, J=9 Hz, 2H), 7.80 (d, J=9 Hz, 2H), 8.08 (s, 1H). MS (APCI–) m/z 428 (M–H)– and m/z 463 (M+Cl)–. Anal. calc. for C$_{22}$H$_{21}$FN$_2$O$_4$S.1.25 H$_2$O: C, 58.59; H, 5.25; N, 6.21. Found: C, 58.31; H, 4.75; N, 6.05.

EXAMPLE 131

2-(2-Methylcyclopentyl)-4-(4-fluorophenyl)-5-[4-(methylsulfonyl)phenyl]-3(2H)-pyridazinone The title compound was prepared according to the method of Example 128 substituting 2-methylcyclopentanol in place of 2-indanol (yield: 230 g, 86%). mp 180–181° C. $^1$H NMR (300 MHz, DMSO-d$_6$) δ 0.75 (d, J=7 Hz, 3H), 1.60 (m, 2H), 1.89 (m, 2H), 2.10 (m, 1H), 2.21 (m, 1H), 2.40 (m, 1H), 3.23 (s, 3H), 5.37 (q, J=7 Hz, 1H), 7.12 (t, J=9 Hz, 2H), 7.21 (m, 2H), 7.47 (d, J=9 Hz, 2H), 7.86 (d, J=9 Hz, 2H), 8.11 (s, 1H). MS (APCI+) m/z 427 (M+H)$^+$ and (APCI−) m/z 461 (M+Cl)$^-$. Anal. calc. for $C_{23}H_{23}FN_2O_3S$: C, 64.77; H, 5.43; N, 6.56. Found: C, 64.71; H, 5.34; N, 6.28.

EXAMPLE 132

2-(2-Adamantyl)-4-(4-fluorophenyl)-5-[4-(methylsulfonyl)phenyl]-3(2H)-pyridazinone The title compound was prepared according to the method of Example 128 substituting 2-adamantanol in place of 2-indanol, (yield: 75 g, 25%). mp 195–197° C. $^1$H NMR (300 MHz, DMSO-$d_6$) δ 1.60 (m, 2H), 1.77 (m, 2H), 1.94 (m, 6H), 2.35 (m, 4H), 3.23 (s, 3H), 4.83 (m, 1H), 7.11 (t, J=9 Hz, 2H), 7.22 (m, 2H), 7.47 (d, J=9 Hz, 2H), 7.87 (d, J=9 Hz, 2H), 8.11 (s, 1H). MS (APCI+) m/z 479 (M+H)$^+$ and (APCI−) m/z 478 (M−H)−, m/z 513 (M+Cl)$^-$. Anal. calc. for $C_{27}H_{27}FN_2O_3S \cdot 0.25\ H_2O$: C, 67.13; H, 5.73; N, 5.79. Found: C, 67.06; H, 5.76; N, 5.06.

EXAMPLE 133

2-(3-Methylcyclopentyl)-4-(4-fluorophenyl)-5-[4-(methylsulfonyl)phenyl]-3(2H)-pyridazinone The title compound was prepared according to the method of Example 128 substituting 3-methylcyclopentanol in place of 2-indanol (yield: 155 g, 73%). mp 169–171° C. $^1$H NMR (300 MHz, DMSO-$d_6$) δ 1.05 (dd, 2:1, 3H), 1.24 (m, 1H), 1.63 (m, 1H), 2.00 (m, 3H), 2.22 (m, 2H), 3.23 (s, 3H), 5.43 (m, 1H), 7.1 (t, J=9 Hz, 2H), 7.21 (m, 2H), 7.46 (d, J=9 Hz, 2H), 7.86 (d, J=9 Hz, 2H), 8.12 (two s, 2:1, 1H). MS (APCI+) m/z 27 (M+H)$^+$ and (APCI−) m/z 426 (M−H)−, m/z 461 (M+Cl)$^-$. Anal. calc. for $C_{27}H_{27}FN_2O_3S \cdot 0.25\ H_2O$: C, 64.09; H, 5.49; N, 6.49. Found: C, 64.27; H, 5.62; N, 6.46.

EXAMPLE 134

2-(1-Methylcyclopentyl)-4-(4-fluorophenyl)-5-[4-(methylsulfonyl)phenyl]-3(2H)-pyridazinone A solution of 4-(4-fluorophenyl)-5-[4-(methylsulfonyl)phenyl]-3(2H)-pyridazinone (206 mg, 0.6 mmol), prepared according to the method of Example 11, 1-methyl-1-cyclopentanol (60 mg, 0.6 mmol), DMAP (18 mg, 0.12 mmol) and Ph$_3$P (262 mg, 1 mmol) in toluene (30 mL) in ethyl acetate (5 mL) was prepared and added dropwise to a solution of DLAD (0.2 mL, 1 mmol) in 10 mL of toluene. The mixture was stirred at room temperature for 6 hours and then concentrated in vacuo. The residue was chromatographed (silica gel, 19:1 CH$_2$Cl$_2$-ethyl acetate) to provide 80 mg of product (contaminated with reduced DLAD). A second column chromatography (hexanes-ethyl acetate 1:1) furnished the title product, (yield: 50 mg, 19%). mp 107–110° C. $^1$H NMR (DMSO-$d_6$, 300 MHz) δ 1.55 (s, 3H), 1.70 (m, 4H), 2.08 (m, 2H), 2.32 (m, 2H), 3.22 (s, 3H), 7.10 (t, J=9 Hz, 2H), 7.20 (m, 2H), 7.45 (d, J=9 Hz, 2H), 7.86 (d, J=9 Hz, 2H), 8.03 (s, 1H). MS (APCI+) m/z 427 (M+H)$^+$ and (APCI−) m/z 426 (M−H)−, m/z 461 (M+Cl)$^-$.

EXAMPLE 135

2-(3,4-Difluorophenyl)-4-(4-fluoro-3-vinylphenyl)-5-[4-(methylsulfonyl)phenyl]-3(2H)-pyridazinone

Example 135A

5-Bromo-2-fluorostyrene

A mixture of methyltriphenylphosphonium bromide (2.14 g, 6 mmol) and potassium t-butoxide (672 mg, 6 mmol) in 50 mL of THF was refluxed for 30 minutes under $N_2$ and then cooled to room temperature. 5-Bromo-2-fluorobenzaldehyde (1.02 g, 5 mmol) was added and the resulting mixture was refluxed for 2 hours (until the TLC showed the disappearance of starting aldehyde). The reaction was concentrated in vacuo and partitioned between water and ethyl acetate. The acetate layer was washed with water and brine. The solution was dried over MgSO$_4$ and concentrated in vacuo. The residue was purified by chromatography (silica gel, 15:1 hexanes-diethyl ether) to provide 900 mg (90%) of 5-bromo-2-fluorostyrene.

Example 135B 2-(3,4-Difluorophenyl)-4-(4-fluoro-3-vinylphenyl)-5-[4-(methylthio)phenyl]-3(2H)-pyridazinone The bromo-styrene compound, Example 135A, in 10 mL of THF was added dropwise to a heated mixture of magnesium turnings (120 mg, 5 mmol) and a few drops of 1,2-dibromoethane in THF (20 mL) at a rate to maintain a gentle reflux. The mixture was refluxed for the next 30 minutes and cooled to room temperature. The Grignard reagent solution was cooled to −78° C. and added, dropwise, to a solution of 2-(3,4-difluorophenyl)-4-methoxy-5-[4-(methylthio)phenyl]-3(2H)-pyridazinone (540 mg, 1.5 mmol) in THF (20 mL). The reaction mixture was allowed to warm to room temperature for 12 hours. Afterwards, a saturated solution of NH$_4$Cl was added and the mixture was extracted with ethyl acetate to provide 320 mg of crude sulfide.

Example 135C 2-(3,4-Difluorophenyl)-4-(4-fluoro-3-vinylphenyl)-5-[4-(methylsulfonyl)phenyl]-3(2H)-pyridazinone The sulfide, Example 135B, was dissolved in CH$_2$Cl$_2$ (20 mL) and at 0° C. was treated with 30% CH$_3$CO$_3$H in CH$_3$CO$_2$H (0.5 mL). After 1.5 hours, 10% NaHCO$_3$ was added and the mixture extracted with CH$_2$Cl$_2$. The extract was concentrated in vacuo and the residue purified by chromatography (silica gel, 1:1 hexanes-ethyl acetate) to provide the title compound (yield: 270 mg, 37%). $^1$H NMR (DMSO-$d_6$, 300 MHz)δ 3.22 (s, 3H), 5.37 (d, J=12 Hz, 1H), 5.65 (d, J=1,8 Hz, 1H), 6.77 (dd, J=12 Hz and 18 Hz, 1H), 7.15 (m, 2H), 7.57 (m, 5H), 7.90 (m, 3H), 8.28 (s, 1H). MS (APCI+) m/z 483 (M+H)$^+$ and (APCI−) m/z 517 (M+Cl)$^-$. Anal. calc. for $C_{25}H_{17}F_3N_2O_3S \cdot 0.5\ H_2O$: C, 61.09; H, 3.69; N, 5.69. Found: C, 61.04; H, 3.71; N, 5.34.

EXAMPLE 136

2-(3,4-Difluorophenyl)-4-(6-methyl-3-heptenyl)-5-[4-(methylsulfonyl)phenyl]-3(2H)-pyridazinone A Grignard, prepared as described in Example 135, substituting 2-(2-bromoethyl)-1,3-dioxane (586 mg, 3 mmol) in place of 5-bromo-2-fluorostyrene, was added to a solution of 2-(3,4-difluorophenyl)-4-methoxy-5-[4-(methylthio)phenyl]-3(2H)-pyridazinone (720 mg, 2 mmol) in THF (30 mL) at −78° C. The mixture was left at room temperature for 14 hours, quenched with a saturated solution of NH$_4$Cl and extracted with ethyl acetate to obtain 900 mg of crude sulfide.

The intermediate sulfide product was dissolved in CH$_2$Cl$_2$ (10 mL) and treated at 0° C. with 33% solution of CH$_3$CO$_3$H in CH$_3$CO$_2$H (0.7 mL) for 1 hour. The mixture was concentrated in vacuo and the residue was partitioned between saturated NaHCO$_3$ and ethyl acetate. The acetate layer was dried over MgSO$_4$ and concentrated in vacuo to provide 950 mg of crude sulfonyl derivative.

The sulfonyl compound, prepared above, was dissolved in acetone (50 mL) and treated with 2 N HCl (10 mL). The resulting mixture was refluxed for 16 hours and concentrated in vacuo. The residue was extracted with ethyl acetate to provide 900 mg of 2-(3,4-difluorophenyl)-4-(2-formylethyl)-5-[4-(methylsulfonyl)phenyl]-3(2H)-pyridazinone (crude aldehyde, contaminated with some unreacted starting dioxane derivative).

A mixture of isoamyltriphenylphosphonium bromide (414 mg, 1 mmol) and potassium t-butoxide (112 mg, 1 mmol) in toluene (25 mL) was refluxed for 30 minutes and then cooled to room temperature. The crude aldehyde was added and the mixture was refluxed for 14 hours. The reaction mixture was then cooled to room temperature and concentrated in vacuo. The residue was dissolved in ethyl acetate and was washed with water, 10% citric acid, brine, dried over MgSO$_4$ and concentrated in vacuo. Purification by column chromatography (silica gel, 1:1 hexanes-ethyl acetate) provided the title compound as an oil (yield: 120 mg, 13%). $^1$H NMR (300 MHz, DMSO-d$_6$) δ 0.74 (d, J=7 Hz, 6H), 1.44 (m, 1H), 1.70 (t, J=7 Hz, 2H), 2.22 (m, 2H), 2.54 (m, 2H); 3.30 (s, 3H), 5.29 (m, 2H), 7.51 (m, 1H), 7.63 (m, 1H), 7.74 (d, J=9 Hz, 2H), 7.82 (m, 1H), 8.02 (s, 1H), 8.10 (d, J=9 Hz, 2H). MS (APCI+) m/z 473 (M+H)$^+$ and (APCI−) m/z 471 (M−H)−, m/z 507 (M+Cl)$^-$. Anal. calc. for C$_{25}$H$_{26}$F$_2$N$_2$O$_3$S: C, 63.54; H, 5.54; N, 5.92. Found: C, 63.74; H, 5.67; N, 5.58.

EXAMPLE 137

2-(3,4-Difluorophenyl)-4-(3-cycloprolpylidengpropyl)-5-[4-(methylsulfonyl)phenyl]-3(2H)-pyridazinone The title compound was prepared according to the method of Example 136 substituting cyclopropyltriphenylphosphonium bromide in place of isoamyltriphenylphosphonium bromide (yield: 55 mg, 12%). mp 128–129° C. $^1$H NMR (300 MHz, DMSO-d$_6$) δ 0.81 (m, 2H), 0.97 (m, 2H), 2.34 (m, 2H), 2.65 (m, 2H), 3.32 (s, 3H), 5.64 (m, 1H), 7.52 (m, 1H), 7.63 (m, 1H), 7.73 (d, J=9 Hz, 2H), 7.81 (m, 1H), 8.02 (s, 1H), 8.10 (d, J=9 Hz, 2H). MS (APCI+) m/z 443 (M+H)$^+$ and (APCI−) m/z 441 (M−H)−, m/z 477 (M+Cl)$^-$. Anal. calc. for C$_{23}$H$_{20}$F$_2$N$_2$O$_3$S.0.5 H$_2$O: C, 61.18; H, 4.68; N, 6.20. Found: C, 61.48; H, 4.60; N, 6.02.

EXAMPLE 138

2-(3,4-Difluorophenyl)-4-(5-methyl-3-hexenyl)-5-[4-(methylsulfonyl)phenyl]-3(2H)-pyridazinone The title compound, an oil, was prepared according to the method of Example 136 substituting isobutyltriphenylphosphonium bromide in place of isoamyltriphenylphosphonium bromide (yield: 170 mg, 74%). $^1$H NMR (300 MHz, DMSO-d$_6$) δ 0.75 (d, J=7 Hz, 6H), 2.22 (m, 3H), 2.54 (m, 2H), 3.32 (s, 3H), 5.12 (m, 2H), 7.52 (m, 1H), 7.60 (m, 1H), 7.72 (d, J=9 Hz, 2H), 7.80 (m, 1H), 8.02 (s, 1H), 8.10 (d, J=9 Hz, 2H). MS (APCI+) m/z 459 (M+H)$^+$ and (APCI−) m/z 457 (M−H)−, m/z 493 (M+Cl)$^-$. Anal. calc. for C$_{24}$H$_{24}$F$_2$N$_2$O$_3$S: C, 62.86; H, 5.27; N, 6.10. Found: C, 62.57; H, 5.32; N, 5.81.

EXAMPLE 139

2-(3,4-Difluorophenyl)-4-(5-methylhexyl)-5-[4-(methylsulfonyl)phenyl]-3(2H)-pyridazinone The title compound, an oil, was prepared according to the method of Example 135B, substituting 5-methylhexylmagnesium bromide for 3-fluoro-4-vinylphenylmagnesium bromide, (yield: 28 mg, 10%). $^1$H NMR (300 MHz, DMSO-d$_6$) δ 0.77 (d, J=7 Hz, 6H), 0.88 (m, 1H), 1.03 (m, 2H), 1.20 (m, 1H), 1.46 (m, 5H), 3.32 (s, 3H), 7.52 (m, 1H), 7.62 (m, 1H), 7.75 (d, J=9 Hz, 2H), 7.82 (m, 1H), 8.02 (s, 1H), 8.11 (d, J=9 Hz, 2H). MS (APCI+) m/z 461 (M+H)$^+$ and (APCI) m/z 459 (M−H)−, m/z 495 (M+Cl)$^-$.

EXAMPLE 140

2-(3-Chloro-1-methyl-2E-propenyl)-4-(4-fluorophenyl)-5-[4-(aminosulfonyl)phenyl]-3(2H)-pyridazinone The title compound was prepared according to the method of Example 124, substituting 1,3-dichloro-1-butene in place of 2,4-difluorobenzyl bromide (yield: 55 mg, 30%). mp 152–154° C. $^1$H NMR (300 MHz, CDCl$_3$) δ 4.71 (dt, J=15 Hz, 7.5 Hz, 2H), 2.28 (d, J=1.5 Hz, 3H), 4.8 (s, 2H), 4.99 (d, J=1 Hz, 1H), 5.02 (d, J=1 Hz, 1H), 5.85 (td, J=4 Hz, 1 Hz, 1H), 6.98 (t, J=9 Hz, 2H), 7.19 (dd, J=9 Hz, 6 Hz, 2H), 7.28 (d, J=9 Hz, 2H), 7.86 (s, 1H), 7.87 (d, J=9 Hz, 2H). MS (DCI/NH$_3$) m/z 434 (M+H)$^+$. Anal. calc. for C$_{20}$H$_{17}$ClFN$_3$O$_3$S: C, 55.36; H, 3.94; N, 9.68. Found: C, 54.99; H, 3.83; N, 9.34.

EXAMPLE 141

2-(2,3,3-Trifluoro-2-propen-1-yl)-4-(4-fluorophenyl)-5-[4-(aminosulfonyl)phenyl]-3(2H)-pyridazinone The title compound was prepared according to the method of Example 124, substituting 1-methylsufonyloxy-2,3,3-trifluoro-2-propene(mesylate), prepared in Example 88, in place of 2,4-difluorobenzyl bromide (yield: 10 mg, 4%). mp 173–175° C. $^1$H NMR (300 MHz, CDCl$_3$) δ 4.39 (s, 2H), 5.09 (ddd, J=26 Hz, J=3 Hz, J=1 Hz, 2H) 6.98 (t, J=9 Hz, 2H), 7.19 (dd, J=9 Hz, J=6 Hz, 2H), 7.29 (d, J=9 Hz, 2H), 7.78 (s, 1H), 7.78 (d, J=9 Hz, 2H). MS (DCI/NH$_3$) m/z 440 (M+H)$^+$, MS (F, high res.) m/z calc. for C$_{19}$H$_{14}$F$_4$N$_3$O$_3$S: 440.0692 (M+H)$^+$. Found: 440.0695 (M+H)$^+$, (0.7 ppm error).

EXAMPLE 142

2-(1,1,2-Trifluoro-2-propenyl)-4-(4-fluorophenyl)-5-[4-(aminosulfonyl)phenyl]-3(2H)-pyridazinone The title compound was isolated from the same reaction mixture (Example 141) that was used to prepare 2-(2,3,3- trifluoro-2-propen-1-yl)-4-(4-fluorophenyl)-5-[4-(aminosulfonyl)phenyl]-3(2H)-pyridazine (The title product is a result of an SN2' attack.) (yield: 50 mg, 20%). mp 230–232° C. $^1$H NMR (300 MHz, CDCl$_3$) δ 4.7 (s, 2H), 5.28 (dd, J=15 Hz, 4.5 Hz, 1H), 5.39 (dd, J=45 Hz, 4.5 Hz, 1H), 6.98 (t, J=9 Hz, 2H), 7.19 (dd, J=9 Hz, 6 Hz, 2H), 7.31 (d, J=9 Hz, 2H), 7.9 (d, J=9 Hz, 2H), 7.92 (s, 1H). MS (DCI/NH$_3$) m/z 440 (M+H)$^+$. Anal. calc. for C$_{19}$H$_{13}$F$_4$N$_3$O$_3$S: C, 51.93; H, 2.98; N, 9.56. Found: C, 51.88; H, 3.01; N, 9.15.

EXAMPLE 143

2-(3,3-Difluoro-2-propenyl)-4-(4-fluorophenyl)-5-[4-(aminosulfonyl)phenyl]-3(2H)-pyridazinone The title compound was prepared according to the method of Example 124, substituting 1,3-dibromo-1,1-difluoropropane in place of 2,4-difluorobenzyl bromide and employing 5 equivalents of potassium carbonate (yield: 220 mg, 65%). mp 191–194° C. $^1$H NMR (300 MHz, DMSO-d$_6$) δ 4.77 (d, J=7.5 Hz, 2H), 4.95 (dtd, J=24 Hz, 7.5 Hz, 1 Hz, 1H), 7.12 (t, J=9 Hz, 2H), 7.23 (dd, J=9 Hz, 6 Hz, 2H), 7.49 (d, J=9 Hz, 2H), 7.50 (s, 2H), 7.74 (d, J=9 Hz, 2H), 8.1 (s, 1H). MS (DCI/NH$_3$) m/z 422 (M+H)$^+$. Anal. calc. for C$_{19}$H$_{14}$F$_3$N$_3$O$_3$S: C, 54.15; H, 3.34; N, 9.97. Found: C, 53.88; H, 3.42; N, 9.76.

EXAMPLE 144

2-(α-Methyl-3-fluorobenzyl)-4-(4-fluorophenyl)-5-[4-(aminosulfonyl)phenyl]-3(2H)-pyridazinone The title compound was prepared according to the method of Example 124, substituting 3-fluoro-α-methylbenzyl chloride in place of 2,4-difluorobenzyl bromide (yield: 220 mg, 65%). mp 192–194° C. $^1$H NMR (300 MHz, DMSO-d$_6$) δ 1.76 (d, 6 Hz, 3H), 6.27 (q, J=7 Hz, 1H), 7.1 (t, J=9 Hz, 2H), 7.22 (dd, J=9 Hz, 6 Hz, 2H), 7.49 (d, J=9 Hz, 2H), 7.51 (s, 2H), 7.72 (d, J=9 Hz, 2H), 8.18 (s, 1H). MS (DCI/NH$_3$) m/z 468 (M+H)$^+$. Anal. calc. for C$_{24}$H$_{19}$F$_2$N$_3$O$_3$S: C, 61.66; H, 4.09; N, 8.98. Found: C, 61.36; H, 3.96; N, 8.86.

EXAMPLE 145

2-(1-Cyclohexenylmethyl)-4-(4-fluorophenyl)-5-[4-(aminosulfonyl)phenyl]-3(2H)-pyridazinone The title compound was prepared according to the method of Example 124, substituting 1-bromomethylcyclohexene in place of 2,4-difluorobenzyl bromide (yield: 70 mg, 28%). mp 192–193° C. $^1$H NMR (300 MHz, DMSO-d$_6$) δ 1.55 (m, 4H), 1.98 (m, 4H), 4.64 (s, 2H), 5.53 (s, 1H), 7.12 (t, J=9 Hz, 2H), 7.22 (dd, J=9 Hz, 6 Hz, 2H), 7.39 (d, J=9 Hz, 2H), 7.39 (s, 2H), 7.72 (d, J=9 Hz, 2H), 8.07 (s, 1H). MS (DCI/NH$_3$) m/z 440 (M+H)$^+$. Anal. calc. for C$_{23}$H$_{22}$FN$_3$O$_3$S: C, 62.85; H, 5.04; N, 9.56. Found: C, 62.47; H, 5.23; N, 9.14.

EXAMPLE 146

2-(α-Methyl-2,3,4-trifluorobenzyl)-4-(4-fluorophenyl)-5-[4-(aminosulfonyl)phenyl]-3(2H)-pyridazinone The title compound was prepared according to the method of Example 124, substituting 2,3,4-trifluoro-α-methylbenzyl chloride in place of 2,4-difluorobenzyl bromide (yield: 70 mg, 50%). mp 192–194° C. $^1$H NMR (300 MHz, CDCl$_3$) δ 1.84 (d, J=6 Hz, 3H), 4.8 (s, 2H), 6.54 (q, J=7 Hz, 1H), 6.96 (t, J=9 Hz, 2H), 6.99 (m, 1H), 7.18 (dd, J=9 Hz, 6 Hz, 2H), 7.2 (m, 1H), 7.38 (d, J=9 Hz, 2H), 7.86 (d, J=9 Hz, 2H), 7.88 (s, 1H). MS (DCI/NH$_3$) m/z 504 (M+H)$^+$. Anal. calc. for C$_{24}$H$_{17}$F$_4$N$_3$O$_3$S: C, 57.25; H, 3.4; N, 8.34. Found: C, 56.84; H, 3.52; N, 7.91.

EXAMPLE 147

2-(α-Methyl-3,5-difluorobenzyl)-4-(4-fluorophenyl)-5-[4-(aminosulfonyl)phenyl]-3(2H)-pyridazinone The title compound was prepared according to the method of Example 124, substituting 3,5-difluoro-α-methylbenzyl chloride in place of 2,4-difluorobenzyl bromide (yield: 80 mg, 45%). mp 139–141° C. $^1$H NMR (300 MHz, CDCl$_3$) δ 1.83 (d, J=6 Hz, 3H), 4.79 (s, 2H), 6.32 (q, J=7 Hz, 1H), 6.84 (m, 1H), 6.97 (t, J=9 Hz, 2H), 7.02 (dd, J=6 Hz, 1.5 Hz, 2H), 7.18 (dd, J=9 Hz, 6 Hz, 2H), 7.28 (d, J=9 Hz, 2H), 7.85 (s, 1H), 7.9 (d, J=9 Hz, 2H). MS (DCI/NH$_3$) m/z 486 (M+H)$^+$. Anal. calc. for C$_{24}$H$_{18}$F$_3$N$_3$O$_3$S: C, 59.37; H, 3.73; N, 8.65. Found: C, 59.00; H, 3.70; N, 8.35.

EXAMPLE 148

2-(α-Methyl-3,4-difluorobenzyl)-4-(4-fluorophenyl)-5-[4-(aminosulfonyl)phenyl]-3(2H)-pyridazinone The title compound was prepared according to the method of Example 124, substituting 3,4-difluoro-α-methylbenzyl chloride in place of 2,4-difluorobenzyl bromide (yield: 200 mg, 58%). mp 214–215° C. $^1$H NMR (300 MHz, CDCl$_3$) δ 1.82 (d, J=6 Hz, 3H), 4.7 (s, 2H), 6.35 (q, J=7 Hz, 1H), 6.96 (t, J=9 Hz, 2H), 7.16 (m, 4H), 7.28 (d, J=9 Hz, 2H), 7.37 (m, 1H), 7.84 (d, J=9 Hz, 2H), 7.90 (s, 1H). MS (DCI/NH$_3$) m/z 486 (M+H)$^+$. Anal. calc. for C$_{24}$H$_{18}$F$_3$N$_3$O$_3$S: C, 59.37; H, 3.73; N, 8.65. Found: C, 59.13; H, 3.73; N, 8.54.

EXAMPLE 149

2-(3-Fluorobenzyl)-4-(4-fluorophenyl)-5-[4-(aminosulfonyl)phenyl]-3(2H)-pyridazinone The title compound was prepared according to the method of Example 124, substituting 3-fluorobenzyl bromide in place of 2,4-difluorobenzyl bromide (yield: 160 mg, 61%). mp 220–222° C. $^1$H NMR (300 MHz, DMSO-d$_6$) δ 5.37 (s, 2H), 7.12 (t, J=9 Hz, 2H), 7.22 (m, 5H), 7.39 (m, 5H), 7.73 (d, J=9 Hz, 2H), 8.11 (s, 1H). MS (DCI/NH$_3$) m/z 454 (M+H)$^+$. Anal. calc. for C$_{23}$H$_{17}$F$_2$N$_3$O$_3$S: C, 60.92; H, 3.77; N, 9.26. Found: C, 61.06; H, 4.22; N, 8.88.

EXAMPLE 150

2-(4-Fluorobenzyl)-4-(4-fluorophenyl)-5-[4-(aminosulfonyl)phenyl]-3(2H)-pyridazinone The title compound was prepared according to the method of Example 124, substituting 4-fluorobenzyl bromide in place of 2,4-difluorobenzyl bromide (yield: 85 mg, 34%). mp 237–239° C. $^1$H NMR (300 MHz, DMSO-d$_6$) δ 5.32 (s, 2H), 7.12 (t, J=9 Hz, 2H), 7.22 (m, 4H), 7.38 (m, 4H), 7.47 (dd, J=9 Hz, 6 Hz, 2H), 7.72 (d, J=9 Hz, 2H), 8.10 (s, 1H). MS (DCI/NH$_3$) m/z 454 (M+H)$^+$. Anal. calc. for C$_{23}$H$_{17}$F$_2$N$_3$O$_3$S: C, 60.92; H, 3.77; N, 9.26. Found: C, 60.61; H, 3.96; N, 8.74.

EXAMPLE 151

2-(2,4,6-Trifluorobenzyl)-4-(4-fluorophenyl)-5-[4-(aminosulfonyl)phenyl]-3(2H)-pyridazinone The title compound was prepared according to the method of Example 124, substituting 2,4,6-trifluorobenzyl bromide in place of 2,4-difluorobenzyl bromide (yield: 255 mg, 73%). mp 201–203° C. $^1$H NMR (300 MHz, DMSO-d$_6$) δ 5.38 (s, 2H), 7.13 (t, J=9 Hz, 2H), 7.23 (m, 4H), 7.38 (d, J=9 Hz, 2H), 7.42 (s, 2H), 7.70 (d, J=9 Hz, 2H), 8.08 (s, 1H). MS (DCI/NH$_3$) m/z 490 (M+H)$^+$. Anal. calc. for C$_{23}$H$_{15}$F$_4$N$_3$O$_3$S: C, 56.44; H, 3.08; N, 8.58. Found: C, 56.31; H, 3.09; N, 8.40.

EXAMPLE 152

2-(2,4,5-Trifluorobenzyl)-4-(4-fluorophenyl)-5-[4-(aminosulfonyl)phenyl]-3(2H)-pyridazinone The title compound was prepared according to the method of Example 124, substituting 2,4,5-trifluorobenzyl bromide in place of 2,4-difluorobenzyl bromide (yield: 180 mg, 49%). mp 236–238° C. $^1$H NMR (300 MHz, DMSO-d$_6$) δ 5.35 (s, 2H), 7.13 (t, J=9 Hz, 2H), 7.23 (dd, J=9 Hz, 6 Hz, 2H), 7.39 (d, J=9 Hz, 2H), 7.41 (s, 2H), 7.6 (m, 2H), 7.72 (d, J=9 Hz, 2H), 8.11 (s, 1H). MS (DCI/NH$_3$) m/z 490 (M+H)$^+$. Anal. calc. for C$_{23}$H$_{15}$F$_4$N$_3$O$_3$S: C, 56.44; H, 3.08; N, 8.58. Found: C, 56.38; H, 3.28; N, 8.41.

EXAMPLE 153

2-(2,3,4-Trifluorobenzyl)-4-(4-fluorophenyl)-5-[4-(aminosulfonyl)phenyl]-3(2H)-pyridazinone The title compound was prepared according to the method of Example 124, substituting 2,3,4-trifluorobenzyl bromide in place of 2,4-difluorobenzyl bromide (yield: 220 mg, 63%). mp 218–220° C. $^1$H NMR (300 MHz, DMSO-d$_6$) δ 5.40 (s, 2H), 7.13 (t, J=9 Hz, 2H), 7.22 (dd, J=9 Hz, 6 Hz, 2H), 7.34 (m, 2H), 7.39 (d, J=9 Hz, 2H), 7.42 (s, 2H), 7.73 (d, J=9 Hz, 2H), 8.12 (s, 1H). MS (DCI/NH$_3$) m/z 490 (M+H)$^+$. Anal. calc. for C$_{23}$H$_{15}$F$_4$N$_3$O$_3$S: C, 56.44; H, 3.08; N, 8.58. Found: C, 56.32; H, 3.24; N, 8.31.

EXAMPLE 154

2-(4,4,4-Trifluoro-3-methyl-2E-butenyl)-4-(4-fluorophenyl)-5-[4-(aminosulfonyl)phenyl]-3(2H)-pyridazinone The title compound was prepared according to the method of Example 124, substituting 1-bromo-3-methyl-4,4,4-trifluoro-2-butene in place of 2,4-difluorobenzyl bromide (yield: 160 mg, 48%). mp 155–157° C. $^1$H NMR (300 MHz, CDCl$_3$) δ 2.00 (s, 3H), 4.8 (s, 2H), 4.96 (d, J=7.5 Hz, 2H), 6.33 (m, 1H), 6.99 (t, J=9 Hz, 2H), 7.19 (dd, J=9 Hz, 6 Hz, 2H), 7.29 (d, J=9 Hz, 2H), 7.95 (s, 1H), 7.97 (d, J=9 Hz, 2H). MS (DCI/NH$_3$) m/z 468 (M+H)$^+$. Anal. calc. for C$_{21}$H$_{17}$F$_4$N$_3$O$_3$S: C, 53.96; H, 3.66; N, 8.98. Found: C, 53.84; H, 3.51; N, 8.77.

EXAMPLE 155

2-(4-Biphenyl)-4-(4-fluorophenyl)-5-[4-(methylsulfonyl)phenyl]-3(2H)-pyridazinone The title compound was prepared according to the method of Example 62 substituting 4-bromobiphenyl in place of 4-iodo-1-fluorobenzene (yield: 0.275 g, 100%). mp 249–251° C. $^1$H NMR (300 MHz, DMSO d$_6$) δ 3.24 (s, 3H), 7.16 (m, 2H), 7.30 (m, 2H), 7.42 (m, 1H), 7.48–7.58 (m, 4H), 7.75 (m, 4H), 7.84 (m, 2H), 7.91 (m, 2H), 8.27 (s, 1H). MS (DCI/NH$_3$) m/z 497 (M+H)$^+$, 514 (M+NH$_4$)$^+$. Anal. calc. for C$_{23}$H$_{21}$FN$_2$O$_3$S: C, 70.15; H, 4.26; N, 5.64. Found: C, 69.81; H, 4.42; N, 5.41.

EXAMPLE 156

2-(4-Bromophenyl)-4-(4-fluorophenyl)-5-[4-(methylsulfonyl)phenyl]-3(2H)-pyridazinone The title compound was prepared according to the method of Example 62 substituting 1,4-dibromobenzene in place of 4-iodo-1-fluorobenzene (yield: 0.337 g, 93%). $^1$H NMR (300 MHz, DMSO d$_6$) δ 3.24 (s, 3H), 7.14 (m, 2H), 7.28 (m, 2H), 7.64 (m, 2H), 7.75 (m, 2H), 7.90 (m, 2H), 8.25 (s, 1H). MS (DCI/NH$_3$) m/z 499 (M+H)$^+$, 518 (M+NH$_4$)$^+$. Anal. calc. for C$_{23}$H$_{16}$BrFN$_2$O$_3$S.0.75 H$_2$O: C, 53.86; H, 3.43; N, 5.46. Found: C, 53.92; H, 3.16; N, 5.34.

EXAMPLE 157

2-(4-Nitrophenyl)-4-(4-fluorophenyl)-5-[4-(methylsulfonyl)phenyl]-3(2H)-pyridazinone The title compound was prepared according to the method of Example 62 substituting 1-iodo-4-nitrobenzene in place of 4-iodo-1-fluorobenzene (yield: 0.45 g, 100%). mp 110–116° C. $^1$H NMR (300 MHz, DMSO d$_6$) δ 3.24 (s, 3H), 7.17 (m, 2H), 7.32 (m, 2H), 7.53 (m, 2H), 7.91 (m, 2H), 8.03 (m, 2H), 8.34 (s, 1H), 8.40 (m, 2H). MS (DCI/NH$_3$) m/z 466 (M+H)$^+$, 483 (M+NH$_4$)$^+$. Anal. calc. for C$_{23}$H$_{16}$FN$_3$O$_5$S: C, 59.35; H, 3.46; N, 9.03. Found: C, 59.02; H, 3.62; N, 8.82.

EXAMPLE 158

2-(4-Phenoxyphenyl)-4-(4-fluorophenyl)-5-[4-(methylsulfonyl)phenyl]-3(2H)-pyridazinone The title compound was prepared according to the method of Example 62 substituting 4-bromodiphenylether in place of 4-iodo-1-fluorobenzene (yield: 0.667 g, 22%). mp 118–125° C. $^1$H NMR (300 MHz, DMSO-d$_6$) δ 3.24 (s, 3H), 7.12 (m, 5H), 7.15–7.33 (m, 4H), 7.46 (m, 2H), 7.52 (m, 2H), 765 (m, 2H), 7.90 (m, 2H), 8.23 (s, 1H). MS (DCI/NH$_3$) m/z 513 (M+H)$^+$. Anal. calc. for C$_{25}$H$_{21}$FN$_2$O$_4$S.0.75 H$_2$O: C, 66.21; H, 4.31; N, 5.32. Found: C, 65.98; H, 4.25; N, 5.27.

EXAMPLE 159

2-(4-t-Butylphenyl)-4-(4-fluorophenyl)-5-[4-(methylsulfonyl)phenyl]-3(2H)-pyridazinone The title compound was prepared according to the method of Example 62 substituting 1-bromo-4-t-butyl-benzene in place of 4-iodo-1-fluorobenzene. No product was observed. The solution was concentrated in vacuo. The resulting solid was dissolved in DMF (5 mL) and CuI (13.3 mg, 0.07 mmol) was added. The solution was allowed to reflux overnight. Upon completion, the mixture was poured into 10% citric acid and extracted with ethyl acetate. The organic layer was washed with water, dried over MgSO$_4$ and concentrated in vacuo. The crude solid was purified using flash chromatography (SiO$_2$), eluting with 5% diethyl ether/CH$_2$Cl$_2$ to provide the desired product (yield: 0.292 g, 84%). mp 132–136° C. $^1$H NMR (300 MHz, DMSO $d_6$) δ 1.34 (s, 9H), 3.24 (s, 3H), 7.14 (m, 2H), 7.29 (m, 2H), 7.54 (m, 6H), 7.90 (m, 2H), 8.23 (s, 1H). MS (DCI/NH$_3$) m/z 477 (M+H)$^+$, 494 (M+NH$_4$)$^+$. Anal. calc. for $C_{27}H_{25}FN_2O_3S$: C, 68.05; H, 5.29; N, 5.88. Found: C, 67.94; H, 5.31; N, 5.67.

EXAMPLE 160

2-(4-Chlorophenyl)-4-(4-fluorophenyl)-5-[4-(methylsulfonyl)phenyl]-3(2H)-pyridazinone The title compound was prepared according to the method of Example 62 substituting 4-bromo-1-chlorobenzene in place of 4-iodo-1-fluorobenzene (yield: 0.254 g, 83.5%). mp 214–216° C. $^1$H NMR (300 MHz, DMSO-$d_6$) δ 3.24 (s, 3H), 7.16 (m, 2H), 7.29 (m, 2H), 7.52 (m, 2H), 7.61 (m, 2H), 7.71 (m, 2H), 7.91 (m, 2H), 8.26 (s, 1H). MS (DCI/NH$_3$) m/z 455 (M+H)$^+$, 472 (M+NH$_4$)$^+$. Anal. calc. for $C_{23}H_{16}ClFN_2O_3S$: C, 60.73; H, 3.55; N, 6.16. Found: C, 60.45, H, 3.41; N, 6.05.

EXAMPLE 161

2-(3-Methylphenyl)-4-(4-fluorophenyl)-5-[4-(methylsulfonyl)phenyl]-3(2H)-pyridazinone The title compound was prepared according to the method of Example 62 substituting 3-bromotoluene in place of 4-iodo-1-fluorobenzene (yield: 0.262 g, 83%). mp 213–216° C. $^1$H NMR (300 MHz, DMSO $d_6$) δ 2.39 (s, 3H), 3.24 (s, 3H), 7.14 (m, 2H), 7.28 (m, 3H), 7.43 (m, 3H), 7.53 (m, 2H), 7.80 (m, 2H), 8.22 (s, 1H). MS (DCI/NH$_3$) m/z 435 (M+H)$^+$, 452 (M+NH$_4$)$^+$. Anal. calc. for $C_{24}H_{19}FN_2O_3S$ : C, 66.35; H, 4.41; N, 6.45. Found: C, 66.00, H, 4.16; N, 6.23.

EXAMPLE 162

2-(3-Vinylphenyl)-4-(4-fluorophenyl)-5-[4-(methylsulfonyl)phenyl]-3(2H)-pyridazinone The title compound was prepared according to the method of Example 62 substituting 3-bromostyrene in place of 4-iodo-1-fluorobenzene (yield: 0.202 g, 62%). mp 182–183° C. $^1$H NMR (300 MHz, DMSO $d_6$) δ 3.25 (s, 3H), 5.35 (d, J=12 Hz, 1H), 5.92 (d, J=15 Hz, 1H), 6.82 (m, 1H), 7.15 (m, 2H), 7.30 (m, 2H), 7.50–7.60 (m, 4H), 7.74 (m, 1H), 7.91 (m, 2H), 8.24 (s, 1H). MS (DCI/NH$_3$) m/z 447 (M+H)$^+$, 464 (M+NH$_4$)$^+$. Anal. calc. for $C_{25}H_{19}FN_2O_3S \cdot 0.50\ H_2O$: C, 65.92; H, 4.42; N, 6.14. Found: C, 65.86; H, 4.40; N, 6.07.

EXAMPLE 163

2-(2-Formylphenyl)-4-(4-fluoropheynyl)-5-[4-(methylsulfonyl)phenyl]-3(2H)-pyridazinone The title was prepared according to the method of Example 62 substituting 2-bromobenzaldehyde in place of 4-iodo-1-fluorobenzene (yield: 0.196 g, 60%). mp 234–236° C. $^1$H NMR (300 MHz, DMSO $d_6$) δ 3.24 (s, 3H), 7.15 (m, 2H), 7.27 (m, 2H), 7.54 (m, 2H), 7.64–7.75 (m, 2H), 7.86–7.95 (m, 3H), 8.01 (m, 1H), 8.29 (s, 1H), 10.02 (s, 1H). MS (DCI/NH$_3$) m/z 449 (M+H)$^+$. Anal. calc. for $C_{24}H_{17}FN_2O_4S \cdot 0.50\ H_2O$: C, 63.01; H, 3.96; N, 6.12. Found: 63.04; H, 3.82; N, 5.88.

EXAMPLE 164

2-(2-Nitrophenyl)-4-(4-fluorophenyl)-5-[4-(methylsulfonyl)phenyl]-3(2H)-pyridazinone The title compound was prepared according to the method of Example 62 substituting 1-bromo-2-nitrobenzene in place of 4-iodo-1-fluorobenzene (yield: 0.307 g, 90.8%). mp 236–239° C. $^1$H NMR (300 MHz, DMSO $d_6$) δ 3.24 (s, 3H), 7.12–7.27 (m, 4H), 7.56 (m, 2H), 7.7–8.01 (m, 5H), 8.18 (m, 1H), 8.35 (s, 1H). MS (DCI/NH$_3$) m/z 466 (M+H)$^+$, 483 (M+NH$_4$)$^+$. Anal. calc. for $C_{23}H_{16}FN_3O_5S \cdot 0.25\ H_2O$: C, 58.78; H, 3.53; N, 8.94. Found: C, 58.63; H, 3.54; N, 8.88.

EXAMPLE 165

2-(3-Chlorophenyl)-4-(4-fluorophenyl)-5-[4-(methylsulfoayl)phenyl]-3(2H)-pyridazinone The title compound was prepared according to the method of Example 62 substituting 1-bromo-3-chlorobenzene in place of 4-iodo-1-fluorobenzene (yield: 0.255 g, 77%). mp 232–235° C. $^1$H NMR (300 MHz, DMSO $d_6$) δ 3.23 (s, 3H), 7.14 (m, 2H), 7.29 (m, 2H), 7.49–7.58 (m, 4H), 7.66 (m, 1H), 7.79 (m, 1H), 7.90 (m, 2H), 8.25 (s, 1H). MS (DCI/NH$_3$) m/z 455 (M+H)$^+$, 472 (M+NH$_4$)$^+$. Anal. calc. for $C_{23}H_{16}ClFN_2O_3S$: C, 60.73; H, 3.55; N, 6.16. Found: C, 60.40; H, 3.43; N, 5.98.

EXAMPLE 166

2-(3-Bromophenyl)-4-(4-fluorophenyl)-5-[4-(methylsulfonyl)phenyl]-3(2H)-pyridazinone The title compound was prepared according to the method of Example 62 substituting 1,3 dibromobenzene in place of 4-iodo-1-fluorobenzene (yield: 0.216 g, 60%). mp 210–212° C. $^1$H NMR (300 MHz, DMSO $d_6$) δ 3.23 (s, 3H), 7.15 (m, 2H), 7.29 (m, 2H), 7.48–7.55 (m, 3H), 7.69 (m, 2H), 7.90 (m, 3H), 8.26 (s, 1H). MS (DCI/NH$_3$) m/z 499 (M+H)$^+$, 519 (M+NH$_4$)$^+$. Anal. calc. for $C_{23}H_{16}BrFN_2O_3S$: C, 55.32; H, 3.23; N, 5.61. Found: C, 55.12; H, 3.12; N, 5.51.

EXAMPLE 167

2-(4-Cyanophenyl)-4-(4-fluorophenyl)-5-[4-(methylsulfopyl)phenyl]-3(2H)-pyridazinone The title compound was prepared according to the method of Example 62 substituting 4-bromobenzonitrile in place of 4-iodo-1-fluorobenzene (yield: 0.349 g, 100%). mp 273–278° C. $^1$H NMR (300 MHz, DMSO $d_6$) δ 3.24 (s, 3H), 7.11–7.21 (m, 2H), 7.25–7.35 (m, 2H), 7.52 (m, 2H), 7.88–7.96 (m, 4H), 8.04 (m, 2H), 8.31 (s, 1H). MS (DCI/NH$_3$) m/z 445 (M+H)$^+$. Anal. calc. for $C_{24}H_{16}FN_3O_3S$: C, 64.71; H, 3.62; N, 9.43. Found: C, 64.50; H, 3.53; N, 9.35.

EXAMPLE 168

2-(5-Methyl-2-thienyl))-4-(4-fluorophenyl)-5-[4-(methylsulfonyl)phenyl]-3(2H)-pyridazinone The title compound was prepared according to the method of Example 62 substituting 2-bromo-5-methylthiophene in place of 4-iodo-1-fluorobenzene (yield: 0.200 g, 62%). mp 219–224° C. $^1$H NMR (300 MHz, DMSO $d_6$) δ 2.45 (s, 3H), 3.23 (s, 3H), 6.80 (m, 1H), 7.17 (m, 2H), 7.29 (m, 2H), 7.52

(m, 3H), 7.89 (m, 2H), 8.33 (s, 1H). MS s (DCI/NH$_3$) m/z 441 (M+H)$^+$, 458 (M+NH$_4$)$^+$. Anal. calc. for C$_{22}$H$_{17}$FN$_2$O$_3$S$_2$: C, 59.99; H, 3.89; N, 6.36. Found: C, 59.90; H, 3.91; N, 6.26.

EXAMPLE 169

2-(3-Biphenyl)-4-(4-fluorophenyl)-5-[4-(methylsulfonyl)phenyl]-3(2H)-pyridazinone The title compound was prepared according to the method of Example 62 substituting 3-bromobiphenyl in place of 4-iodo-1-fluorobenzene (yield: 0.28 g, 78%). mp 126–134° C. $^1$H NMR (300 MHz, DMSO d$_6$) δ 3.24 (s, 3H), 7.15 (m, 2H), 7.31 (m, 2H), 7.37–7.45 (m, 1H), 7.51 (m, 4H), 7.64 (m, 2H), 7.68–7.79 (m, 3H), 7.92 (m, 3H), 8.27 (s, 1H). MS (DCI/NH$_3$) m/z 497 (M+H)$^+$, 514 (M+NH$_4$)$^+$. Anal. calc. for C$_{29}$H$_{21}$FN$_2$O$_3$S: C, 70.15; H, 4.26; N, 5.64. Found: C, 69.91; H, 4.33; N, 5.74.

EXAMPLE 170

2-(3,5-Dimethlphenyl)-4-(4-fluorophenyl)-5-[4-(methylsulfonyl)phenyl]-3(2H)-pyridazinone The title compound was prepared according to the method of Example 62 substituting 5-bromo-m-xylene in place of 4-iodo-1-fluorobenzene (yield: 0.152 g, 46.5%). mp 130–134° C. $^1$H NMR (300 MHz, DMSO d$_6$) δ 2.34 (s, 6H), 3.23 (s, 3H), 7.07–7.12 (m, 2H), 7.15 (m, 1H), 7.21–7.32 (m, 4H), 7.52 (m, 2H), 7.90 (m, 2H), 8.29 (s, 1H). MS (DCI/NH$_3$) m/z 449 (M+H)$^+$, 466 (M+NH$_4$)$^+$. Anal. calc. for C$_{25}$H$_{21}$FN$_2$O$_3$S: C, 66.95; H, 4.72; N, 6.25. Found: C, 66.81; H, 4.57; N, 6.07.

EXAMPLE 171

2-(3,4-Difluorophenyl)-4-(4-fluorobenzyl)-5-[4-(methylsulfonyl)phenyl]-3(2H)-pyridazinone 4-(4-Fluorophenylmethyl)-5-[4-(methylsulfonyl)phenyl]-3(2H)-pyridazinone was prepared according to the method of Example 11, starting with 2-benzyl-4-(4-fluorophenylmethyl)-5-[4-(methylsulfonyl)phenyl]-3(2H)-pyridazinone in place of 2-benzyl-4-(4-fluorophenyl)-5-[4-(methylsulfonyl)phenyl]-3(2H)-pyridazinone (yield: 0.3319 g, 83%).

The title compound was prepared according to the method of Example 62 substituting 4-(4-fluorophenylmethyl)-5-[4-(methylsulfonyl)phenyl]-3(2H)-pyridazinone in place of 4-(4-fluorophenyl)-5-[4-(methylsulfonyl)phenyl]-3(2H)-pyridazinone and substituting 1-bromo-3,4-difluorobenzene in place of 4-iodo-1-fluorobenzene (yield: 0.085 g, 54%). mp 157–159° C. $^1$H NMR (300 MHz, DMSO d$_6$) δ 3.30 (s, 3H), 3.88 (bs, 2H), 7.04 (m, 4H), 7.49–7.66 (m, 2H), 7.70 (m, 2H), 7.81 (m, 1H), 8.12 (s, 1H). MS (DCI/NH$_3$) m/z 471 (M+H)$^+$, 488 (M+NH$_4$)$^+$. Anal. calc. for C$_{24}$H$_{17}$F$_3$N$_2$O$_3$S.0.25 H$_2$O: C, 60.69; H, 3.71; N, 5.84. Found: C, 6.39; H, 3.76; N, 5.81.

EXAMPLE 172

2-(3-Chloro-4-fluorophenyl)-4-(4-fluorobenzyl)-5-[4-(methylsulfonyl)phenyl]-3(2H)-pyridazinone The title compound was prepared according to the method of Example 62 substituting 4-(4-fluorophenylmethyl)-5-[4-(methylsulfonyl)phenyl]-3(2H)-pyridazinone in place of 4-(4-fluorophenyl)-5-[4-(methylsulfonyl)phenyl]-3(2H)-pyridazinone and substituting 4-bromo-2-chloro-1-fluorobenzene in place of 4-iodo-1-fluorobenzene (yield: 0.110 g, 74%). mp 153–156° C. $^1$H NMR (300 MHz, DMSO d$_6$) δ 3.30 (s, 3H), 3.89 (bs, 2H), 7.02–7.07 (m, 4H), 7.59 (m, 1H), 7.65–7.72 (m, 4H), 8.07 (m, 2H), 8.12 (s, 1H). MS (DCI/NH$_3$) m/z 487 (M+H)$^+$, 504 (M+NH$_4$)$^+$. Anal. calc. for C$_{24}$H$_{17}$ClF$_2$N$_2$O$_3$S.0.25 H$_2$O: C, 58.65; H, 3.58; N, 5.64. Found: C, 58.41; H, 3.56; N, 5.36.

EXAMPLE 173

2-(2-Thienyl)-4-(4-fluorophenyl)5-[4-(methylsulfopyl)phenyl]-3(2H)-pyridazinone

The title compound was prepared according to the method of Example 62 substituting 2-bromothiophene in place of 1-bromo-4-fluorobenzene (yield: 98 mg, 40%). mp 215–217° C. $^1$H NMR (300 MHz, DMSO-d$_6$) δ 3.25 (s, 3H), 7.18 (m, J=9 Hz, 3H), 7.29 (m, 2H), 7.42 (d, 2H), 7.75 (d, 1H), 7.93 (d, J=9 Hz), 8.4 (s, 1H). MS (DCI/NH$_3$m/z 427 (M+H)$^+$, 444 (M+NH$_4$)$^+$. Anal. calc. for C$_{21}$H$_{15}$FN$_2$O$_3$S$_2$: C, 59.14; H, 3.54; N, 6.57.

EXAMPLE 174

2-(4-Trifluoromethylphenyl)-4-(4-fluorophenyl)-5-[4-(methylsulfonyl)phenyl]-3(2H)-pyridazinone The title compound was prepared according to the method of Example 62 substituting 1-bromo-4-trifluoromethylbenzene in place of 1-bromo-4-fluorobenzene (yield: 185 mg, 64%). mp 171–173° C. $^1$H NMR (300 MHz, DMSO-d$_6$) δ 3.25 (s, 3H), 7.18 (t, 2H), 7.29 (m, 2H), 7.52 (d, J=9 Hz 2H), 7.91 (d, J=9 Hz, 2H), 7.93 (s, 4H), 8.32 (s, 1H). MS (DCI(NH$_3$) m/z 489 (M+H)$^+$, 506 (M+NH$_4$)$^+$. Anal. calc. for C$_{24}$H$_{16}$F$_4$N$_2$O$_3$S: C, 59.02; H, 3.3; N, 5.74. Found: C, 58.75; H, 3.35; N, 5.69.

EXAMPLE 175

2-[4-(1-Pyrroyl)phenyl]-4-(4-fluorophenyl)-5-[4-(methylsulfonyl)phenyl]-3(2H)-pyridazinone The title compound was prepared according to the method of Example 62 substituting 1-(4-iodophenyl)pyrrole in place of 1-bromo-4-fluorobenzene (yield: 140 mg, 50%). mp 229–231° C. $^1$H NMR (300 MHz, DMSO-d$_6$) δ 3.25 (s, 3H), 6.3 (t, 2H), 7.18 (t, 2H), 7.29 (m, 2H), 7.46 (t, 2H) 7.53 (d, J=9 Hz 2H), 7.75 (s, 4H), 7.91 (d, J=9 Hz, 2H), 8.27 (s, 1H). MS (DCI/NH$_3$) m/z 486 (M+H)$^+$, 504 (M+NH$_4$)$^+$. Anal. calc. for C$_{27}$H$_{20}$FN$_3$O$_3$S.0.5 H$_2$O: C, 66.79; H, 4.15; N, 8.65. Found: C, 65.21; H, 4.29; N, 8.12.

EXAMPLE 176

2-(5-Chloro-2-thienyl)-4-(4-fluorophenyl)-5-[4-(methylsulfonyl)phenyl]-3(2H)-pyridazinone The title compound was prepared according to the method of Example 62 substituting 2-bromo-5-chlorothiophene in place of 1-bromo-4-fluorobenzene (yield: 225 mg, 93%). mp 190–192° C. $^1$H NMR (300 MHz, DMSO-d$_6$) δ 2.38 (s, 3H), δ 3.25 (s, 3H), 7.15 (t, 2H), 7.29 (m, 4H), 7.5 (D, 4H) 7.91 (d, J=9 Hz, 2H), 8.21 (s, 1H). MS (DCI/NH$_3$) m/z 435 (M+H)$^+$, 452 (M+NH$_4$)$^+$. Anal. calc. for C$_{24}$H$_{19}$F N$_2$O$_3$S: C, 66.35; H, 4.41; N, 6.45. Found: C, 66.15; H, 4.37; N, 6.3.

EXAMPLE 177

2-(4-Methylphenyl)-4-(4-fluorophenyl)-5-[4-(methylsulfonyl)phenyl]-3(2H)-pyridazinone The title compound was prepared according to the method of Example 62 substituting 1-bromo-4-methylbenzene in place of 1-bromo-4-fluorobenzene (yield: 79 mg, 31%). mp 190–192° C. $^1$H NMR (300 MHz, DMSO-$d_6$) δ 2.38 (s, 3H), δ 3.25 (s, 3H), 7.15 (t, 2H), 7.29 (m, 4H), 7.5 (D, 4H) 7.91 (d, J=9 Hz, 2H), 8.21 (s, 1H). MS (DCI/NH$_3$) m/z 435 (M+H)$^+$, 452 (M+NH$_4$)$^+$. Anal. calc. for $C_{24}H_{19}FN_2O_3S$: C, 66.35; H, 4.41; N, 6.45. Found: C, 66.15; H, 4.37; N, 6.3.

EXAMPLE 178

2-(4-Fluorophenyl)-4-(2-ethyl-1-hexyloxy)-5-[4-(methylsulfonyl)phenyl]-3(2H)-pyridazinone To a solution of 2-ethyl-1-hexanol (65 mg, 0.5 mmol) in THF (15 mL) at room temperature was added NaH (60% oil suspension) (20 mg, 0.5 mmol) and after 10 minutes 2-(4-fluorophenyl)-4-tosyloxy-5-[4-(methylsulfonyl)phenyl]-3(2H)-pyridazinone (193 mg, 0.5 mmol) was added. The resulting mixture was stirred at room temperature for the next 2 hours. The mixture was quenched with 10% citric acid and extracted with ethyl acetate. The extract was washed with water, brine, dried with MgSO$_4$, and purified by chromatography (silica gel, 2:1 hexanes-ethyl acetate) to provide the desired product (yield: 140 mg, 60%). mp 120–122° C. $^1$H NMR (300 MHz, DMSO-$d_6$) δ 0.75 (m, 6H), 1.1 (m, 6H), 1.20 (quintet, J=7 Hz, 2H), 1.44 (m, 1H), 3.27 (s, 3H), 4.30 (d, J=6 Hz, 2H), 7.37 (t, J=9 Hz, 2H), 7.65 (m, 2H), 7.89 (d, J=9 Hz, 2H), 8.06 (d, J=9 Hz, 2H), 8.18 (s, 1H). MS (APCI+) m/z 473 (M+H)$^+$; (APCI−) m/z 507 (M+Cl)$^−$. Anal. calc. for $C_{25}H_{29}FN_2O_4S \cdot 0.5 H_2O$: C, 62.35; H, 6.27; N, 5.87. Found: C, 62.22; H, 6.14; N, 6.22.

EXAMPLE 179

2-(3-Thienyl)-4-(4-fluorophenyl)-5-[4-(methylsulfonyl)phenyl]-3(2H)-pyridazinone The title compound was prepared according to the method of Example 62 substituting 3-bromothiophene in place of 1-bromo-4-fluorobenzene (yield: 225 mg, 93%). mp 200–202° C. $^1$H NMR (300 MHz, DMSO-$d_6$) δ 3.25 (s, 3H), 7.15 (t, 2H), 7.29 (m, 2H), 7.5 (d, J=9 Hz, 2H), 7.6 (M, 1H) 7.66 (dd, 1H), 7.91 (d, J=9 Hz, 2H), 8.13 (dd, 1H), 8.25 (s, 1H). MS (DCI/NH$_3$) m/z 427 (M+H)$^+$, 444 (M+NH$_4$)$^+$. Anal. calc. for $C_{21}H_{15}FN_2O_3S_2$: C, 55.07; H, 4.07; N, 6.11. Found: C, 54.63; H, 3.47; N, 6.01.

EXAMPLE 180

2-(3,5-Difluorophenyl)-4-(4-fluorophenyl)-5-[4-(methylsulfonyl)phenyl]-3(2H)-pyridazinone The title compound was prepared according to the method of Example 62 substituting 3,5-difluorobromobenzene in place of 1-bromo-4-fluorobenzene (yield: 250 mg, 96%). mp 166–168° C. $^1$H NMR (300 MHz, DMSO-$d_6$) δ 3.25 (s, 3H), δ 7.15 (t, 2H), 7.27 (m, 2H), 7.4 (m, 1H), 7.41 (m, 2H), 7.51 (d, J=9 Hz, 4H), 7.9 (d, J=9 Hz, 2H), 8.3 (s, 1H). MS (DCI/NH$_3$) m/z 457 (M+H)$^+$, 474 (M+NH$_4$)$^+$. Anal. calc. for $C_{23}H_{15}F_3N_2O_3S$: C, 60.13; H, 3.31; N, 6.14. Found: C, 60.49; H, 3.31; N, 6.03.

EXAMPLE 181

2-(2,4-Difluorophenyl)-4-(4-fluorophenyl)-5-[4-(methylsulfonyl)phenyl]-3(2H)-pyridazinone The title compound was prepared according to the method of Example 62 substituting 2,4-difluorobromobenzene in place of 1-bromo-4-fluorobenzene (yield: 40 mg, 15%). mp 245–247° C. $^1$H NMR (300 MHz, DMSO-$d_6$) δ 3.23 (s, 3H), δ 7.15 (t, 2H), 7.3 (t, 2H), 7.54 (m, 2H), 7.57 (m, 2H), 7.75 (m, 1H), 7.9 (d, J=9 Hz, 2H), 8.27 (s, 1H). MS (DCI/NH$_3$) m/z 457 (M+H)$^+$, 474 (M+NH$_4$)$^+$. Anal. calc. for $C_{28}H_{15}F_3N_2O_3S$: C, 60.52; H, 3.31; N, 6.03.

EXAMPLE 182

2-(3,4-Difluorophenyl)-4-(4-fluorophenyl)-5-[4-(methylsulfonyl)phenyl]-3(2H)-pyridazinone The title compound was prepared according to the method of Example 62 substituting 3,4-difluorobromobenzene in place of 1-bromo-4-fluorobenzene (yield: 170 mg, 70%). mp 109–110° C. $^1$H NMR (300 MHz, DMSO-$d_6$) δ 3.23 (s, 3H), δ 7.15 (t, 2H), 7.3 (t, 2H), 7.25 (m, 2H), 7.59 (m, 4H), 7.83 (m, 1H), 7.9 (d, J=9 Hz, 2H), 8.27 (s, 1H). MS (DCIH$_3$) m/z 457 (M+H)$^+$, 474 (M+NH$_4$)$^+$. Anal. calc. for $C_{23}H_{15}F_3N_3O_3S$: C, 60.52; H, 3.31; N, 6.14. Found 60.60; H, 3.48; N, 5.89

EXAMPLE 183

2-(3-Furyl)-4-(4-fluorophenyl)-5-[4-(methylsulfonyl)phenyl]-3(2H)-pyridazinone

The title compound was prepared according to the method of Example 62 substituting 3-bromofuran in place of 1-bromo-4-fluorobenzene (yield: 175 mg, 73%). mp 239–242° C. $^1$H NMR (300 MHz, DMSO-$d_6$) δ 3.25 (s, 3H), 7.09 (d, 1H), 7.15 (t, 2H), 7.29 (m, 2H), 7.5 (d, J=9 Hz 2H), 7.8 (t, 1H) 7.91 (d, J=9 Hz, 2H), 8.3 (s 1H), 8.58 (s, 1H). MS (DCI/NH$_3$) m/z 411 (M+H)$^+$, 428 (M+NH$_4$)$^+$. Anal. calc. for $C_{21}H_{15}FN_2O_4S \cdot 0.5 H_2O$: C, 61.46; H, 3.68; N, 6.83. Found: C, 59.91; H, 3.54; N, 6.54.

EXAMPLE 184

2-(3-Fluoro-4-methoxyphenyl)-4-(4-fluorophenyl)-5-[4-(methylsulfonyl)phenyl]-3(2H)-pyridazinone The title compound was prepared according to the method of Example 62 substituting 3-fluoro-4-methoxybromobenzene in place of 1-bromo-4-fluorobenzene (yield: 230 mg, 85%). mp 97–101° C. $^1$H NMR (300 MHz, DMSO-$d_6$) δ 3.25 (s, 3H), 3.9 (s, 3H), 7.16 (d, 1H), 7.29 (m, 3H), 7.5 (m, 4H), 7.91 (d, J=9 Hz, 2H), 8.23 (s 1H). MS (DCI/NH$_3$) m/z 469 (M+H)$^+$, 491 (M+NH$_4$)$^+$. Anal. calc. for $C_{24}H_{18}F_2N_2O_4S \cdot 0.5 H_2O$: C, 61.53; H, 3.87; N, 5.98. Found: C, 61.18; H, 4.01; N, 5.58.

EXAMPLE 185

2-(2-Fluorophenyl)-4-(4-fluorophenyl-5-[4-(methylsulfonyl)phenyl]-3(2H)-pyridazinone The title compound was prepared according to the method of Example 62 substituting 2-fluorobromobenzene in place of 1-bromo-4-fluorobenzene (yield: 195 mg, 75%). mp 96–103° C. ¹H NMR (300 MHz, DMSO-d₆) δ 3.23 (s, 3H), δ 7.15 (t, 2H), 7.3 (m, 3H), 7.55 (m, 5H), 7.9 (d, J=9 Hz, 2H), 8.27 (s, 1H). MS (ESI) m/z 437 (M–H)⁺). Anal. calc. for $C_{23}H_{16}F_2N_2O_3S$: C, 63.01; H, 3.68; N, 6.39. Found, C, 62.91; H, 4.06; N, 5.99.

EXAMPLE 186

2-[4-(Aminosulfonyl)phenyl]-4-(4-fluorophenyl)-5-[4-(methylsulfonyl)phenyl]-3(2H)-pyridazinone The title compound was prepared according to the method of Example 62 substituting 4-aminosulfonyl-1-bromobenzene in place of 1-bromo-4-fluorobenzene. mp 213–216° C. ¹H NMR (300 MHz, DMSO-d₆) δ 3.25 (s, 3H), 7.15 (t, 2H), 7.29 (m, 2H), 7.53 (s, 2H) 7.55 (s, 1H), 7.7 (dd, 2H) 7.91 (t, 4H), 7.98 (d, 2H), 8.3 (s, 1H). MS (DCI/NH₃) m/z 499 (M+H)⁺, 517 (M+NH₄)⁺. Anal. calc. for $C_{23}H_{18}FN_3O_5S_2 \cdot 0.5\ H_2O$: C, 55.30; H, 3.63; N, 8.41. Found: C, 54.4; H, 3.79; N, 7.78.

EXAMPLE 187

2-(3-Chloro-4-fluorophenyl)-4-(4-fluorophenyl)-5-[4-(methylsulfonyl)phenyl]-3(2H)-pyridazinone The title compound was prepared according to the method of Example 62 substituting 3-chloro-4-fluoro-1-bromobenzene in place of 1-bromo-4-fluorobenzene (yield: 320 mg, 78%). mp 155–157° C. ¹H NMR (300 MHz, DMSO-d₆) δ 3.23 (s, 3H), δ 7.15 (t, 2H), 7.3 (t, 2H), 7.25 (m, 2H), 7.53 (d, J=9 Hz, 2H), 7.59 (t, 1H), 7.73 (m, 1H), 7.9 (d, J=9 Hz, 2H) 7.96 (m, 1H), 8.27 (s, 1H). MS (DCI/NH₃) m/z 473 (M+H)⁺, 490 (M+NH₄)⁺. Anal. calc. for $C_{23}H_{15}ClF_2N_2O_3S$: C, 58.42; H, 3.2; N, 5.92. Found 58.23; H, 2.87; N, 5.70

EXAMPLE 188

2-(3,5-Dichlorophenyl)-4-(4-fluorophenyl)-5-[4-(methylsulfonyl)phenyl]-3(2H)-pyridazinone The title compound was prepared according to the method of Example 62 substituting 3,5-dichlorobenzene in place of 1-bromo-4-fluorobenzene (yield: 360 mg, 78%). mp 289–294° C. ¹H NMR (300 MHz, DMSO-d₆) δ 3.25 (s, 3H), δ 7.15 (t, 2H), 7.27 (m, 2H), 7.51 (d, J=9 Hz, 4H), 7.75 (t, 1H), 7.83 (d, 2H), 7.9 (d, J=9 Hz, 2H), 8.3 (s, 1H). MS (DCI/NH₃) m/z 490 (M+H)⁺, 507 (M+NH₄)⁺. Anal. calc. for $C_{23}H_{15}Cl_2FN_2O_3S \cdot 0.5\ H_2O$: C, 56.45; H, 3.09; N, 5.72. Found: C, 55.36; H, 3.00; N, 5.50.

EXAMPLE 189

2-(4-Fluoro-3-methylphenyl)-4-(4-fluorophenyl)-5-[4-(methylsulfonyl)phenyl]-3(2H)-pyridazinone The title compound was prepared according to the method of Example 62 substituting 1-bromo-4-fluoro-3-methylbenzene in place of 1-bromo-4-fluorobenzene (yield: 275 mg, 71%). mp 168–170° C. ¹H NMR (300 MHz, DMSO-d₆) δ 2.3 (s, 3H), δ 3.25 (s, 3H), 7.15 (t, 2H), 7.3 (m, 3H), 7.56 (m, 4H), 7.9 (d, 2H), 8.23 (s, 2H). MS (DCI/NH₃) m/z 453 (M+H)⁺, 471 (M+NH₄)⁺. Anal. calc. for $C_{24}H_{18}F_2N_2O_3S$: C, 63.71; H, 4.01; N, 6.01. Found: C, 63.53; H, 4.06; N, 5.92.

EXAMPLE 190

2-(4-Chloro-3-fluorophenyl)-4-(4-fluorophenyl)-5-[4-(methylsulfonyl)phenyl]-3(2H)-pyridazinone The title compound was prepared according to the method of Example 62 substituting 4-bromo-1-chloro-2-fluorobenzene in place of 1-bromo-4-fluorobenzene (yield: 220 mg, 80%). mp 102–110° C. ¹H NMR (300 MHz, DMSO-d₆) δ 3.23 (s, 3H), 7.11–7.19 (m, 2H), 7.25–7.32 (m, 2H), 7.51 (d, J=5.6 Hz, 2H), 7.58–7.64 (m, 1H), 7.75–7.87 (m, 2H), 7.91 (d, J=5.6 Hz, 2H), 8.28 (s, 1H). MS (APCI+) m/z 473 (M+H)⁺.

EXAMPLE 191

2-(4Chloro-2-fluorophenyl)-4-(4-fluorophenyl)-5-[4-(methylsulfonyl)phenyl]-3(2H)-pyridazinone The title compound was prepared according to the method of Example 62 substituting 1-bromo-4-chloro-2-fluorobenzene in place of 1-bromo-4-fluorobenzene (yield: 65 mg 24%). mp 250–260° C. ¹H NMR (300 MHz, DMSO-d₆) δ 3.21 (s, 3H), 7.12–7.19 (m, 2H), 7.25–7.32 (m, 2H), 7.49–7.58 (m, 3H), 7.68–7.78 (m, 2H), 7.91 (d, J=8.7 Hz, 2H), 8.29 (s, 1H). MS (APCI+) m/z 473 (M+H)⁺. Anal. calc. for $C_{23}H_{15}ClF_2N_2O_3S$: C, 58.41; H, 3.19; N, 5.92. Found: C, 58.69; H, 3.45; N, 5.78.

EXAMPLE 192

2-(1-Adamantyloxycarbonyl)-4-(4-fluorophenyl)-5-[4-(methylsulfonyl)phenyl]-3(2H)-pyridazinone A solution of 4-(4-fluorophenyl)-5-[4-(methylsulfonyl)phenyl]-3(2H)-pyridazinone, prepared according to the procedure of Example 11 (200 mg, 0.58 mmol) in CH₂Cl₂ (8 ml) was prepared and stirred. 1-Adamantylfluoroformate (172 mg, 0.87 mmol), dimethylaminopyridine (14 mg, 0.011 mmol) and triethylamine (0.12 ml, 0.87 mmol) were added. The reaction mixture was stirred at room temperature overnight. The reaction mixture was diluted with CH₂Cl₂ (50 ml) and washed with 10% citric acid (50 ml), brine (50 ml) and dried over MgSO₄, and concentrated in vacuo. The resulting crude residue was purified using flash chromatography (SiO₂, eluting with 15:1 CH₂Cl₂:diethyl ether) to provide the desired product (yield: 55 mg, 18%). ¹H NMR (300 MHz, DMSO-d₄) δ 1.66 (bs, 6H), 2.25 (bd, 10H), 3.21 (s, 3H), 7.15 (t, 2H), 7.24 (m, 2H), 7.6 (dd, 2H), 7.88 (d, J=9 Hz, 2H), 8.15 (s, 1H). MS (ESI) m/z 521 (M–H)⁺. Anal. calc. for $C_{21}H_{15}F\ N_2O_3S_2$: C 64.35; H, 5.20; N, 5.36.

EXAMPLE 193

2-(2,2,2-Trifluoroethyl)-4-(4-fluorobenzyl)-5-[4-(methylsulfonyl)phenyl]-3 (2H)-pyridazinone

Example 193A 2-(2,2,2-Trifluoroethyl)-4,5-dichloro-3(2H)-pyridazinone 2,2,2-Trifluoroethylhydrazine (70% solution in water, 35.0 g, 0.307 mol) was treated with mucochloric acid (51.88 g, 0.307 mol) in ethanol (300 mL) and refluxed for 5 hours. The solvent was concentrated in vacuo. The crystals obtained were washed with water and air dried (yield: 50 g;

67.5%). $^1$H NMR (300 MHz, CDCl$_3$) δ 4.8 (q, J=9 Hz, 2H), 7.85 (s, 1H). MS (DCl—NH$_3$) m/z 264 (M+NH$_4$)$^+$.

Example 193B

2-(2,2,2-Trifluoroethyl)-4-chloro-5-hydroxy-3(2H)-pyridazinone 2-(2,2,2-Trifluoroethyl)-4,5-dichloro-3(2H)-pyridazinone (15.0 m 60.7 mmol), and potassium carbonate (10 g, 72.4 mmol.) were mixed with water (500 mL) and stirred at reflux for 6 hours. TLC (1:1:2 CH$_2$Cl$_2$/hexanes/ethyl acetate) indicated that all starting material was consumed.) The reaction mixture was cooled to room temperature. The pH of the reaction mixture was adjusted to about 4 with hydrochloric acid (15%). The product was extracted with ethyl acetate (700 mL). The organic phase was washed with brine, dried over anhydrous MgSO$_4$ and filtered. The filtrate was concentrated under reduced pressure. The hydroxy compound was obtained as a light brown solid (yield: 13.1 g, 94%). $^1$H NMR (300 MHz, DMSO-d$_6$) δ 4.92 (q, J=9 Hz, 2H), 7.9 (s, 1H). MS (DCI/NH$_3$) m/z 229 (M+H)$^+$.

Example 193C

2-(2,2,2-Trifluoroethyl)-4-chloro-5-(trifluoromethylsulfonyloxy)-3(2H)-pyridazinone Anhydrous Na$_2$CO$_3$ (9.04 m, 85.32 mmol) was placed in a 500 mL round bottom flask and anhydrous CH$_2$CL$_2$ (200 mL) was added. The reaction mixture was cooled to 0° C. under N$_2$. The halohydroxy pyridazinone prepared in Example 193B was dissolved in CH$_2$CL$_2$ (100 mL) and added slowly to the flask and stirred overnight. The reaction slowly warmed to room temperature. (TLC (2:1 hexanes/ethyl acetate) indicated completion of the reaction.) The reaction was quenched with H$_2$O. The organic phase containing the product was separated, washed with brine and dried over MgSO$_4$. The resulting filtrate was concentrated under reduced pressure. The crude product was isolated as deep red-brown residue. Purification using a silica gel column (30:70 ethyl acetate/pentanes) provided the title compound as a dark, reddish residue (14.3 m, 70%). $^1$H NMR (300 MHz, CDCl$_3$) δ 4.85 (q, J=9 Hz, 2H), 7.9 (s, 1H). MS (DCI/NH$_3$) m/z 378 (M+NH$_4$)$^+$.

Example 193D

2-(2,2,2-Trifluoroethyl)-4-chloro-5-[4(methylthio)phenyl]-3(2H)-pyridazinone A solution of the triflate prepared in Example 193C (1.56 g 4.3 mmol), 4-(methylthio)phenylboronic acid (870 mg, 5.16 mmol), tetrakis(triphenylphosphine)palladium(0) (250 mg, 5% mmol) and triethylamine (1.44 ml, 10.32 mmol) in toluene was heated at reflux for 1 hour. The mixture was partitioned between ethyl acetate and water. The ethyl acetate layer was washed with water, then brine, followed by drying over MgSO$_4$ and filtration. The filtrate was concentrated in vacuo. The residue was purified by column chromatography (silica gel, 92:8 hexanes/ethyl acetate) to provide the coupled intermediate as a pale, greenish-yellow solid (yield: 500 mg, 35%). mp 130–139° C. $^1$H NMR (300 MHz, CDCl$_3$) δ 2.55 (s, 3H), 4.87 (q, J=9 Hz, 2H), 7.37 (d, J=9 Hz, 2H), 7.48 (d, J=9 Hz, 2H), 7.82 (s, 1H). MS (DCI/NH$_3$) m/z 335 (M+H)$^+$.

Example 193E

2-(2,2,2-Trifluoroethyl)-4-chloro-5-[4-(methylsulfonyl)phenyl]-3(2H)-pyridazinone The title compound was prepared according to the method of Example 10, substituting the coupled intermediate prepared in Example 193D in place of 2-benzyl-4-(4-fluorophenyl)-5-[4-(methylthio)phenyl]-3(2H)-pyridazinone (yield: 440 mg, 81%). mp 221–222° C. $^1$H NMR (300 MHz, DMSO-d$_6$) δ 3.33 (s, 3H), 5.10 (q, J=9 Hz, 2H), 7.90 (d, J=9 Hz, 2H), 8.12 (d, J=9 Hz, 2H), 8.20 (s, 1H). MS (DCI/NH$_3$) m/z 367 (M+H)$^+$. X1E AH

Example 193F

2-(2,2,2-Trifluoroethyl)-4-(4-fluorobenzyl)-5-[4-(methylsulfonyl)phenyl]-3(2H)-pyridazinone Magnesium turnings (500 mg) were placed in a dry 250 mL round bottom flask. Anhydrous ether (20 mL) was added under N$_2$ at room temperature then fluorobenzyl bromide (3 mL) was added and stirred. The reaction was heated at 40° C. for 2 hours. All magnesium was consumed resulting in a pale brownish-yellow solution. The 2-(2,2,2-trifluoroethyl)-4-chloro-5-[4-(methylsulfonyl)phenyl]-3(2H)-pyridazinone prepared in Example 193E was dissolved in dry THF (25 mL) and transferred to the Grignard solution. The mixture was heated for 3 hours. TLC (2:1 hexanes/ethyl acetate) indicated that the pyridazinone starting material was consumed.) The reaction was cooled to room temperature then quenched with a saturated NH$_4$Cl solution. The product was extracted with ethyl acetate (250 mL); and the organic layer was washed with saturated NH$_4$Cl, and brine. The ethyl acetate solution was dried over MgSO$_4$ and filtered. The filtrate was concentrated under reduced pressure. The product was isolated as an orange residue. Purification using a silica gel column (20:80 ethyl acetate/pentanes) provided the title compound as a pale yellow powder (yield: 140 mg, 28%). $^1$H NMR (300 MHz, CDCl$_3$) δ 3.13 (s, 3H), 4.85 (m, 2H), 6.93 (m, 4H), 7.49 (d, J=9 Hz, 2H) 7.72 (s, 1H), 8.08 (d, J=9 Hz, 2H). MS (DCI/NH$_3$) m/z 441 (M+H)$^+$. Anal. calc. for C$_{20}$H$_{16}$F$_4$N$_2$O$_3$S.0.5 H$_2$O: C, 53.45; H, 3.81; N, 6.23. Found C, 53.45; H, 3.81; N, 6.23.

EXAMPLE 194

2-(4-Fluorophenyl)-4-(4-fluorophenoxymethyl)-5-[4-(methylsulfonyl)phenyl]-3(2H)-pyridazinone

Example 194A

2-(4-Fluorophenyl)-4,5-dibromo-3(2H)-pyridazinone

Mucobromic acid (5.0 g, 19.4 mmol) dissolved in acetic acid (110 mL) was treated with 4-fluorophenyl hydrazine-.HCl, and the heterogeneous mixture brought to reflux at a bath temperature of 115° C. for 15 hours. During the course of reaction, the mixture became a homogeneous deep red solution, and upon cooling to 23° C., a crystalline precipitate formed. The solution was poured into ice water (1000 mL) and stirred for 20 minutes. The yellow/brown crystals were filtered off, washed with additional cold water, and dried in vacuo to provide 5.8 g (86%) of product. (J. Het. Chem., 1993, 30, 1501; Heterocycles 1985, 23, 2603) $^1$H NMR (300 MHz, DMSO-d$_6$) δ 7.31–7.41 (m, 2H), 7.57–7.64 (m, 2H), 8.29 (s, 1H). MS (DCI+) m/z 347 ($Br_{79}Br_{79}$ M+H)$^+$, m/z 349 ($Br_{79}Br_{81}$ M+H)$^+$, m/z 364 ($Br_{79}Br_{79}$ M+NH$_4$)$^+$, and m/z 366 ($Br_{79}Br_{81}$ M+NH$_4$)$^+$.

Example 194B 2-(4-Fluorophenyl)-4-methoxy-5-bromo-3(2H)-pyridazinone

A 23° C. homogeneous solution of 2-(4-fluorophenyl)-4,5-dibromo-3(2H)-pyridazinone (7.18 g, 20.6 mmol) prepared above in tetrahydrofuran (322 mL) was treated with methanol (0.843 mL, 20.8 mmol) and after 5 minutes with NaH (0.833 g, 20.8 mmol, 60% oil dispersion). The reaction exothermed for several minutes and then was continued for 8 hours at 23° C. (Note: several reactions have run to completion at this point). The reaction did not run to completion, and so the temperature was raised to reflux for 4 hours more. The reaction was still not completed. An additional 0.1 equivalent of NaOMe solution was prepared in a separate flask as above with the quantities: 32 mL of tetrahydrofuran, 0.084 mL of methanol, and 83 mg of 60% NaH oil dispersion. This NaOMe solution was added via syringe to the reaction mixture cooled to 23° C., and then the temperature raised to reflux for 4 hours The reaction was still not complete, and so another 0.1 equivalent NaOMe solution was prepared, added, and the reaction brought to reflux, as above. After this 4 hours, the reaction was completed. The mixture was cooled to 23° C. and diluted to 2000 mL with water. The yellow/white precipitate that formed was filtered off, washed with additional water, and concentrated in vacuo to provide 5.39 g (88%) of product. (J. Het. Chem., 1988, 25, 1757) $^1$H NMR (300 MHz, DMSO-d$_6$) δ 4.13 (s, 3H), 7.30–7.40 (m, 2H), 7.56–7.62 (m, 2H), 8.22 (s, 1H). MS (APCI+) m/z 299 ($^{79}$Br M+H)$^+$ and m/z 301 ($^{81}$Br M+H)$^+$.

Example 194C 2-(4-Fluorophenyl)-4-methoxy-5-[4-(methylthio)phenyl]-3(2H)-pyridazinone The title compound was prepared according to the method of Example 6 starting with 2-(4-fluorophenyl)-4-methoxy-5-bromo-3(2H)-pyridazinone in place of 2-benzyl-4-bromo-5-methoxy-3(2H)-pyridazinone and substituting 4-(methylthio)benzeneboronic acid in place of 4-fluorobenzeneboronic acid (yield: 70 mg, 61%). $^1$H NMR (500 MHz, DMSO-d$_6$) δ 2.54 (s, 3H), 4.02 (s, 3H), 7.35 (dd, J=9.0, 9.0 Hz, 2H), 7.39 (d, J=8.5 Hz, 2H), 7.61 (d, J=8.5 Hz, 2H), 7.65 (dd, J=9.0, 5.0 Hz, 2H), 8.14 (s, 1H). MS (APCI+) m/z 343 (M+H)$^+$.

Example 194D 2-(4-Fluorophenyl)-4-methyl-5-[4-(methylthio)phenyl]-3(2H)-pyridazinone The title compound was prepared according to the method of Example 228 substituting methyl magnesium bromide in place of cyclohexylmagnesium chloride (yield: 0.83 g, 87%). $^1$H NMR (300 MHz, CDCl$_3$) δ 2.25 (s, 3H), 2.55 (s, 3H), 7.17 (dd, J=8.8, 8.8 Hz, 2H), 7.31 (d, J=8.7 Hz, 2H), 7.38 (d, J=8.7 Hz, 2H), 7.61–7.68 (m, 2H), 7.82 (s, 1H). MS (APCI+) m/z 327 (M+H)$^+$.

Example 194E 2-(4-Fluorophenyl)-4-methyl-5-[4-(methylsulfonyl)phenyl]-3(2H)-pyridazinone The title compound was prepared according to the method of Example 10 substituting 2-(4-fluorophenyl)-4-methyl-5-[4-(methylthio)phenyl]-3(2H)-pyridazinone in place of 2-benzyl-4-(4-fluorophenyl)-5-[4-(methylthio)phenyl]-3(2H)-pyridazinone (yield: 473 mg, 86%). $^1$H NMR (300 MHz, CDCl$_3$) δ 2.24 (s, 3H), 3.14 (s, 3H), 7.19 (dd, J=8.8, 8.8 Hz, 2H), 7.61 (d, J=8.4 Hz, 2H), 7.63–7.69 (m, 2H), 7.80 (s, 1H), 8.12 (d, J=8.4 Hz, 2H). MS (APCI+) m/z 359 (M+H)$^+$ and m/z 376 (M+NH$_4$)$^+$.

Example 194F 2-(4-Fluorophenyl)-4-bromomethyl-5-[4-(methylsulfonyl)phenyl]-3(2H)-pyridazinone To a heterogeneous, refluxing solution of 2-(4-fluorophenyl)-4-methyl-5-[4-(methylsulfonyl)phenyl]-3(2H)-pyridazinone (590 mg, 1.65 mmol) and carbon tetrachloride (24 mL) was quickly added N-bromosuccinimide (yield: 308 mg, 1.73 mmol) followed by benzoyl peroxide (12 mg, 0.05 mmol). After 1 hour the reaction had only run to near 50% completion. Additional benzoyl peroxide (12 mg, 0.05 mmol) was added, and the reaction checked after another 1 hour. The reaction was still not complete, and so more benzoyl peroxide (4 mg, 0.017 mmol) was added. After 30 minutes, the reaction was completed. The mixture was cooled to 23° C. and diluted with ethyl acetate. The acetate solution was washed with saturated NaHCO$_3$, water, and brine. The solution was dried over MgSO$_4$, filtered, and concentrated in vacuo. The residue was chromatographed (flash silica gel, ethyl acetate/hexanes gradient 1:1 to 4:1) to provide the product (yield: 530 mg, 74%). $^1$H NMR (300 MHz, CDCl$_3$) δ 3.16 (s, 3H), 4.34 (s, 2H), 7.20 (dd, J=8.8, 8.8 Hz, 2H), 7.67–7.74 (m, 2H), 7.82 (d, J=8.7 Hz, 2H), 7.86 (s, 1H), 8.17 (d, J=8.7 Hz, 2H). MS (APCI+) m/z 437 (M+H)$^+$.

Example 194G 2-(4-Fluorophenyl)-4-(4-fluorophenoxymethyl)-5-[4-(methylsulfonyl)phenyl]-3(2H)-pyridazinone To a homogeneous solution of 2-(4-fluorophenyl)-4-bromomethyl-5-[4-(methylsulfonyl)phenyl]-3(2H)-pyridazinone, Example 194F, (107 mg, 0.246 mmol) and 4-fluorophenol (30.3 mg, 0.270 mmol) dissolved in acetone (4 mL) was added powdered K$_2$CO$_3$ (37.3 mg, 0.270 mmol). The mixture was stirred at 23° C. for 2 hours, filtered through a bed of Celite®, and concentrated in vacuo. The residue was chromatographed (flash silica gel, ethyl acetate/hexanes 3:2) to provide the product (yield: 83 mg, 72%). mp 65–80° C. $^1$H NMR (300 MHz, CDCl$_3$) δ 3.12 (s, 3H), 4.94 (s, 2H), 6.78–6.86 (m, 2H), 6.91–7.00 (m, 2H), 7.15–7.24 (m, 2H), 7.65–7.72 (m, 2H), 7.74 (d, J=8.7 Hz, 2H), 7.93 (s, 1H), 8.08 (d, J=8.7 Hz, 2H). MS (APCI+) m/z 469 (M+H)$^+$. Anal. calc. for C$_{24}$H$_{18}$F$_2$N$_2$O$_4$S: C, 61.53; H, 3.87; N, 5.97. Found: C, 61.22; H, 3.63; N, 5.64.

EXAMPLE 195

2-(4-Fluorophenyl)-4-(3-fluorophenoxymethyl)-5-[4-(methylsulfonyl)phenyl]-3(2H)-pyridazinone The title compound was prepared according to the method of Example 194G substituting 3-fluorophenol in place of 4-fluorophenol (yield: 94 mg, 88%). mp 142–144° C. $^1$H NMR (300 MHz, CDCl$_3$) δ 3.12 (s, 3H), 4.98 (s, 2H), 6.49–6.56 (m, 1H), 6.60–6.73 (m, 2H), 7.15–7.25 (m, 3H), 7.65–7.75 (m, 4H), 7.93 (s, 1H), 8.07 (d, J=8.7 Hz, 2H). MS (APCI+) m/z 469 (M+H)$^+$. Anal. calc. for C$_{24}$H$_{18}$F$_2$N$_2$O$_4$S: C, 61.53; H, 3.87; N, 5.97. Found: C, 61.20; H, 3.92; N, 5.86.

EXAMPLE 196

2-(4-Fluorophenyl)-4-phenoxymethyl-5-[4-(methylsulfonyl)phenyl]-3(2H)-pyridazinone The title compound was prepared according to the method of Example 294G substituting phenol in place of 4-fluorophenol (yield: 67 g, 93%). mp 42–75° C. $^1$H NMR (300 MHz, DMSO-d$_6$) δ 3.28 (s, 3H), 4.92 (s, 2H), 6.83–6.90 (m, 2H), 6.91–6.99 (m, 1H), 7.22–7.30 (m, 2H), 7.35–7.44 (m, 2H), 7.66–7.73 (m, 2H), 7.81–7.88 (m, 2H), 8.02–8.08 (m, 2H), 8.21 (s, 1H). MS (APCI+) m/z 451 (M+H)$^+$.

EXAMPLE 197

2-(4-Fluorophenyl)-4-(t-butylthiomethyl)-5-[4-(methylsulfonyl)phenyl]-3(2H)-pyridazinone A 0° C. solution of the 2-(4-fluorophenyl)-4-bromomethyl-5-[4-(methylsulfonyl)phenyl]-3(2H)-pyridazinone prepared in Example 194F (92.5 mg, 0.212 mmol) in acetone (2.5 mL) was treated with NaI (35 mg, 0.233 mmol), and after 5 minutes, the cooling bath was removed and the reaction warmed to 23° C. After 30 minutes, conversion to the 2-(4-fluorophenyl)-4-iodomethyl-5-[4-(methylsulfonyl)phenyl]-3(2H)-pyridazinone was complete (thin layer chromatography, ethyl acetate/hexanes 4:1). The NaBr and residual NaI were filtered off through a pad of Celite®. Additional acetone (2 mL) was added along with 2-methyl-2-propanethiol (20.5 mg, 0.227 mmol), and the solution cooled to 0° C. before addition of Ag$_2$CO$_3$ (63 mg, 0.227 mmol). After 5 minutes, the cooling bath was removed and the solution warmed to 23° C. for 5 hours. The reaction mixture was filtered through Celite® and concentrated in vacuo. The residue was chromatographed (flash silica gel, ethyl acetate/hexanes gradient 1:1 to 3:2) to provide the product (yield: 57 mg, 60%). mp 50–70° C. $^1$H NMR (300 MHz, CDCl$_3$) δ 1.34 (s, 9H), 3.14 (s, 3H), 3.65 (s, 2H), 7.13–7.21 (m, 2H), 7.63–7.70 (m, 2H), 7.79 (s, 1H), 7.84 (d, J=8.7 Hz, 2H), 8.13 (d, J=8.7 Hz, 2H). MS (APCI+) m/z 447 (M+H)$^+$. Anal. calc. for C$_{22}$H$_{23}$FN$_2$O$_3$S$_2$: C, 59.17; H, 5.19; N, 6.27. Found: C, 59.48; H, 5.36; N, 5.90.

EXAMPLE 198

2-(4-Fluorophenyl)-4-(2-methylpropylthiomethyl)-5-[4-(methylsulfonyl)phenyl]-3(2H)-pyridazinone The title compound was prepared according to the method of Example 197 substituting 2-methyl-1-propanethiol in place of 2-methyl-2-propanethiol (yield: 66 mg, 70%). mp 45–60° C. $^1$H NMR (300 MHz, CDCl$_3$) δ 0.95 (d, J=6.6 Hz, 6H), 1.67–1.82 (m, 1H), 2.62 (d, J=6.6 Hz, 2H), 3.15 (s, 3H), 3.61 (s, 2H), 7.19 (dd, J=8.2, 8.2 Hz, 2H), 7.62–7.71 (m, 2H), 7.75 (d, J=8.4 Hz, 2H), 7.79 (s, 1H), 8.13 (d, J=8.4 Hz, 2H). MS (APCI+) m/z 447 (M+H)$^+$. Anal. calc. for C$_{22}$H$_{23}$FN$_2$O$_3$S$_2$: C, 59.17; H, 5.19; N, 6.27. Found: C, 59.35; H, 5.25; N, 6.05.

EXAMPLE 199

2-(4-Fluorophenyl)-4-(2-propoxy)-5-[4-(methylthio)phenyl]-3(2H)-pyridazinone The title compound was prepared by the following sequence of reactions. Mucobromic acid and 4-fluorophenylhydrazine hydrochloride were reacted to provide 2-(4-fluorophenyl)-4,5-dibromo-3(2H)-pyridazinone following the procedure in Example 194A.

The dibromo intermediate was reacted according to the procedure described in Example 194B, substituting isopropanol in place of methanol, to selectively react at the 4-position and provide 2-(4-fluorophenyl)-4-(2-propoxy)-5-bromo-3(2H)-pyridazinone.

The 5-bromo-compound was coupled to 4-(methylthio)phenylboronic acid according to the method of Example 6 to provide the title compound (yield: 435 mg, 53.9%). mp 135–137° C. $^1$H NMR (300 MHz, CDCl$_3$) δ 1.21 (d, J=6 Hz, 6H), 2.55 (s, 3H), 5.26 (sept, J=6 Hz, 1H), 7.17 (t, J=9 Hz, 2H), 7.34 (d, J=9 Hz, 2H), 7.51 (d, J=9 Hz, 2H), 7.58–7.66 (m, 2H), 7.95 (s, 1H). MS (DCI/NH$_3$) m/z 371 (M+H)$^+$.

EXAMPLE 200

2-(4-Fluorophenyl)-4-(2-propoxy)-5-[4-(methylsulfonyl)phenyl]-3(2H)-pyridazinone The methyl sulfide compound prepared in Example 199 was oxidized according to the method of Example 10 to provide the title compound (yield: 240 mg, 92%). mp 160–162° C. $^1$H NMR (300 MHz, DMSO-d$_6$) δ 1.30 (d, J=6 Hz, 6H), 3.41 (s, 3H), 5.41 (m, 1H), 7.48 (t, J=9 Hz, 2H), 7.77 (dd, J=9 Hz, 6 Hz, 2H), 8.05 (d, J=9 Hz, 2H), 8.19 (d, J=9 Hz, 2H), 8.31 (s, 1H). MS (DCI/NH$_3$) m/z 403 (M+H)$^+$, 420 (M+NH$_4$)$^+$. Anal. calc. for C$_{20}$H$_{19}$FN$_2$O$_4$S: C, 59.70; H, 4.73; N, 6.97. Found: C, 59.40; H, 4.86; N, 6.69.

EXAMPLE 201

2-(3-Chlorophenyl)-4-(2-propoxy)-5-[4-(methylsulfonyl)phenyl]-3(2H)-pyridazinone 2-(3-Chlorophenyl)-4-(2-propoxy)-5-[4-(methylthio)phenyl]-3(2H)-pyridazinone was prepared according to the method of Example 199, substituting 3-chlorophenylhydrazine hydrochloride in place of 4-fluorophenylhydrazine hydrochloride, in the first step. The resulting methyl sulfide was oxidized according to the method of Example 10 to provide the title compound (yield: 260 mg, 80%). mp 134–136° C. $^1$H NMR (300 MHz, CDCl$_3$) δ 1.24 (d, J=6 Hz, 6H), 3.13 (s, 3H), 5.48 (sept, J=6 Hz, 1H), 7.37–7.48 (m, 2H), 7.59 (dt, J=7 Hz, 1.5 Hz, 1H), 7.70 (br s, 1H), 7.84 (d, J=9 Hz, 2H), 7.93 (s, 1H), 8.06 (d, J=9 Hz, 2H). MS (DCI/NH$_3$) m/z 419 (M+H)$^+$, 436 (M+NH$_4$)$^+$. Anal. calc. for C$_{20}$H$_{19}$ClN$_2$O$_4$S: C, 57.42; H, 4.55; N, 6.70. Found: C, 57.08; H, 4.59; N, 6.44.

EXAMPLE 202

2-(3-Fluorophenyl)-4-(2-propoxy)-5-[4-(methylsulfonyl)phenyl]-3(2H)-pyridazinone The methyl sulfide intermediate was prepared according to the method of Example 199, substituting 3-fluorophenylhydrazine hydrochloride in place of 4-fluorophenylhydrazine hydrochloride in the first step. The resulting methyl sulfide compound was oxidized according to the method of Example 10 to provide the title compound (yield: 290 mg, 72%). mp 110–112° C. $^1$H NMR (300 MHz, CDCl$_3$) δ 1.31 (d, J=6 Hz, 6H), 3.11 (s, 3H), 5.47 (sept, J=6 Hz, 1H), 7.09–7.18 (m, 1H), 7.41–7.52 (m, 3H), 7.83 (d, J=9 Hz, 2H), 7.93 (s, 1H), 8.08 (d, J=9 Hz, 2H). MS (DCI/NH$_3$) m/z 403 (M+H)$^+$, 447 (M+NH$_4$)$^+$. Anal. calc. for C$_{20}$H$_{19}$FN$_2$O$_4$S: C, 59.70; H, 4.73; N, 6.97. Found: C, 59.54; H, 4.87; N, 6.70.

EXAMPLE 203

2-(3-Bromophenyl)-4-(2-propoxy)-5-[4-(methylsulfonyl)phenyl]-3(2H)-pyridazinone The methyl sulfide intermediate was prepared according to the method of Example 199, substituting 3-bromophenylhydrazine hydrochloride in place of 4-fluorophenylhydrazine hydrochloride. The resulting methyl sulfide compound was oxidized according to the method of Example 10 to provide the title compound (yield: 75 mg, 77.6%). mp 130–132° C. $^1$H NMR (300 MHz, CDCl$_3$) δ 1.23 (d, J=6 Hz, 6H), 3.15 (s, 3H), 5.48 (sept, J=6 Hz, 1H), 7.38 (t, J=9 Hz, 1H), 7.55 (br d, J=7 Hz, 1H), 7.65 (br d, J=7 Hz, 1H), 7.79–7.87 (m, 1H), 7.83 (d, J=9 Hz, 2H), 8.13 (s, 1H), 8.06 (d, J=9 Hz, 2H). MS (DCI/NH$_3$) m/z 465 (M+H)$^+$, 480 (M+NH$_4$)$^+$. Anal. calc. for C$_{20}$H$_{19}$BrN$_2$O$_4$S: C, 51.84; H, 4.10; N, 6.05. Found: C, 51.95; H, 4.18; N, 5.74.

EXAMPLE 204

2-(2,5-Difluorophenyl)-4-(2-propoxy)-5-[4-(methylsulfonyl)phenyl]-3(2H)-pyridazinone 2-(2,5-Difluorophenyl)-4-(2-propoxy)-5-[4-(methylthio)phenyl]-3(2H)-pyridazinone was prepared according to the method of Example 199, substituting 2,5-difluorophenylhydrazine hydrochloride in place of 4-fluorophenylhydrazine hydrochloride.

The resulting methyl sulfide compound was oxidized according to the method of Example 10 to provide the title compound (yield: 390 mg, 90%). mp 161–164° C. $^1$H NMR (300 MHz, CDCl$_3$) δ 1.23 (d, J=6 Hz, 6H), 3.12 (s, 3H), 5.55 (sept, J=6 Hz, 1H), 7.12–7.29 (m, 3H), 7.82 (d, J=9 Hz, 2H), 7.92 (s, 1H), 8.07 (d, J=9 Hz, 2H). MS (DCI/NH$_3$) m/z 421 (M+H)$^+$, 438 (M+NH$_4$)$^+$. Anal. calc. for C$_{20}$H$_{18}$F$_2$N$_2$O$_4$S·0.5 H$_2$O: C, 55.94; H, 4.31; N, 6.53. Found: C, 55.86; H, 4.19; N, 6.38.

EXAMPLE 205

2-(3-Chloro-4-fluorophenyl)-4-(2-methylpropoxy)-5-[3-fluoro-4-(methylsulfonyl)phenyl]-3(2H)-pyridazinone The title compound was prepared by the following sequence of reactions. Mucobromic acid and 3-chloro-4-fluorophenylhydrazine hydrochloride were reacted to provide 2-(3-chloro-4-fluorophenyl)-4,5-dibromo-3(2H)-pyridazinone according to the method of Example 194A.

The intermediate was selectively reacted at the 4-position with isobutanol and base to provide 2-(4-fluorophenyl)-4-[1-(2-methylpropoxy)]-5-bromo-3(2H)-pyridazinone according to the method of Example 194B The 5-bromo-compound was coupled to 3-fluoro-4-(methylthio)phenylboronic acid prepared in Example 194C according to the method of Example 6 to produce the intermediate methyl sulfide. The sulfide compound was oxidized to the title methyl sulfone according to the method of Example 10 (yield: 810 mg, 83.8%). mp 142–144° C. $^1$H NMR (300 MHz, CDCl$_3$) δ 0.90 (d, J=6 Hz, 6H), 1.95 (sept, J=6 Hz, 1H), 3.30 (s, 3H), 4.37 (d, J=6 Hz, 2H), 7.26 (t, J=9 Hz, 1H), 7.52–7.61 (m, 3H), 7.75 (dd, J=9 Hz, 3 Hz, 1H), 7.89 (s, 1H), 8.10 (t, J=9 Hz, 1H). MS (DCI/NH$_3$) m/z 469 (M+H)$^+$, 486 (M+NH$_4$)$^+$.

EXAMPLE 206

2-(3,4-Difluorophenyl)-4-(4-fluorophenyl)-5-[3-methyl-4-(methylsulfonyl)phenyl]-3(2H)-pyridazinone

Example 206A

2-Methylthioanisole

A solution of 2-bromothioanisole (10.53 g, 52 mmol) in tetrahydrofuran (173 mL) was prepared and cooled to −78° C. n-BuLi (21.8 mL, 54.5 mmol, 2.5 M solution in hexanes) was slowly added along the interior wall of the reaction vessel. The resultant light yellow solution was stirred for 30 minutes before methyl iodide (8.10 g, 57.1 mmol) diluted with tetrahydrofuran (6 mL) was slowly added along the interior wall of the reaction vessel. The mixture was stirred for another 30 minutes at −78° C. The cooling bath was removed, and the mixture stirred for 1 hour. The solution was cooled to 0° C. and a saturated aqueous NH$_4$Cl solution added. The resultant solution was extracted several times with ethyl acetate, and the combined acetate layers washed with brine, dried over MgSO$_4$, filtered, and concentrated in vacuo. The residue was chromatographed (flash silica gel, ethyl acetate/hexanes 1:19) to provide the product (yield: 6.74 g, 94%). $^1$H NMR (300 MHz, CDCl$_3$) δ 2.34 (s, 3H), 2.46 (s, 3H), 7.02–7.09 (m, 1H), 7.12–7.22 (m, 3H).

Example 206B

4-Bromo-2-methylthioanisole

To a 0° C. solution of 2-methylthioanisole (0.50 g, 3.57 mmol) in methylene chloride (40 mL) was added powdered Fe (20 mg, 0.36 mmol) followed by dropwise addition of bromine (0.58 g, 3.54 mmol). After 30 minutes, the starting material had been consumed (thin layer chromatography, hexanes). The excess bromine was quenched by adding a solution of NaHSO$_3$ and stirring for several minutes. The methylene chloride layer was separated, and the aqueous phase extracted with additional methylene chloride. The combined methylene chloride solution was dried over MgSO$_4$, filtered, and concentrated in vacuo. The resultant oil was chromatographed (flash silica gel, ethyl acetate/hexanes 1:49) to provide the product (yield: 0.74 g, 96%). $^1$H NMR (300 MHz, CDCl$_3$) δ 2.30 (s, 3H), 2.45 (s, 3H), 7.00 (d, J=8.4 Hz, 1H), 7.27–7.33 (m, 2H).

Example 206C

3-Methyl-4-(methylthio)benzeneboronic acid

3-Methyl-4-(methylthio)benzeneboronic acid was prepared according to the method of Example 1, substituting 4-bromo-2-(methylthio)anisole in place of 4-bromothioanisole (yield: 5.3 g, 67%). mp 208–210. $^1$H NMR 2.28 (s, 3H), 2.46 (s, 3H), 7.20 (d, J=8.4 Hz, 1H), 7.62 (s, 1H), 7.70 (d, J=8.4 Hz, 1H).

Example 206D

2-(3,4-Difluorophenyl)-4,5-dibromo-3(2H)-pyridazinone

The title compound was prepared according to the method of Example 194A, substituting 3,4-difluorophenyl hydrazine. HCl in place of 4-fluorophenyl hydrazine HCl (yield: 39 g, 78%). $^1$H NMR (300 MHz, DMSO-d$_6$) δ 7.45 (m, 1H), 7.61 (m, 1H), 7.75 (m, 1H), 8.30 (s, 1H). MS (DCI/NH$_3$) m/z 382 (M+NH$_4$)$^+$.

Example 206E

2-(3,4-Difluorophenyl)-4-methoxy-5-bromo-3(2H)-pyridazinone

The title compound was prepared according to the method of Example 194B, substituting 2-(3,4-difluorophenyl)-4,5-dibromo-3(2H)-pyridazinone in place of 2-(4-fluorophenyl)-4,5-dibromo-3(2H)-pyridazinone (yield: 15 mg, 88%). $^1$H NMR (300 MHz, DMSO-d$_6$) δ 4.14 (s, 3H), 7.45 (m, 1H), 7.60 (m, 1H), 7.74 (m, 1H), 8.24 (s, 1H). MS (DCI/NH$_3$) m/z 317 (M+H)$^+$ and m/z 334 (M+NH$_4$)$^+$.

Example 206F

2-(3,4-Difluorophenyl)-4-methoxy-5-[3-methyl-4-(methylthio)phenyl]-3(2H)-pyridazinone The title compound was prepared according to the method of Example 6 starting with 2-(3,4-difluorophenyl)-4-methoxy-5-bromo-3(2H)-pyridazinone in place of 2-benzyl-4-bromo-5-methoxy-3(2H)-pyridazinone and substituting 3-methyl-4-(methylthio)benzeneboronic acid in place of 4-fluorobenzeneboronic acid (yield: 2.0 g, 85%). $^1$H NMR (300 MHz, CDCl$_3$) δ 2.39 (s, 3H), 2.53 (s, 3H), 4.11 (s, 3H), 7.22–7.32 (m, 2H), 7.34 (s, 1H), 7.42–7.50 (m, 2H), 7.55–7.64 (m, 1H), 7.92 (s, 1H). MS (APCI+) m/z 375 (M+H)$^+$.

Example 206G

2-[3,4-Difluorophenyl)-4-(4-fluorophenyl)-5-[3-methyl-4-(methylthio)phenyl]-3(2H)-pyridazinone 2-(3,4-Difluorophenyl)-4-(4-fluorophenyl)-5-[3-methyl-4-(methylthio)phenyl]-3(2H)-pyridazinone, was prepared according to the method of Example 228, starting with 2-(3,4-difluorophenyl)-4-methoxy-5-[3-methyl-4-(methylthio)phenyl]-3(2H)-pyridazinone in place of 2-(4-fluorophenyl)-4-methoxy-5-[4-(methylthio)phenyl]-3(2H)-pyridazinone and substituting 4-fluorophenyl magnesium bromide in place of cyclohexylmagnesium chloride (yield: 330 mg, 56%). $^1$H NMR (300 MHz, CDCl$_3$) δ 2.24 (s, 3H), 2.47 (s, 3H), 6.90–7.03 (m, 6H), 7.22–7.31 (m, 2H), 7.49–7.54 (m, 1H), 7.60–7.68 (m, 1H), 8.02 (s, 1H). MS (APCI+) m/z 439 (M+H)$^+$.

Example 206H

2-(3,4-Difluorophenyl)-4-(4-fluorophenyl)-5-[3-methyl-4-(methylsulfonyl)phenyl]-3(2H)-pyridazinone The title compound was prepared according to the method of Example 10, substituting 2-(3,4-difluorophenyl)-4-(4-fluorophenyl)-5-[3-methyl-4-(methylthio)phenyl]-3(2H)-pyridazinone in place of 2-benzyl-4-(4-fluorophenyl)-5-[4-(methylthio)phenyl]-3(2H)-pyridazinone (yield: 251 mg, 82%) mp 80–100° C. $^1$H NMR (300 MHz, DMSO-d$_6$) δ 2.59 (s, 3H), 3.25 (s, 3H), 7.13–7.34 (m, 5H), 7.45 (s, 1H), 7.52–7.69 (m, 2H), 7.81 (d, J=8.4 Hz, 1H), 7.81–7.90 (m, 1H), 8.27 (s, 1H). MS (APCI+) m/z 471 (M+H)$^+$ and m/z 488 (M+NH$_4$)$^+$. Anal. calc. for C$_{24}$H$_{17}$F$_3$N$_2$O$_3$S: C, 61.27; H, 3.64; N, 5.95. Found: C, 61.53; H, 3.92; N, 5.67.

EXAMPLE 207

2-(3-Chlorophenyl)-4-(4-fluorophenoxymethyl)-5-[4-(methylsulfonyl)phenyl]-3(2H)-pyridazinone

Example 207A

2-(3-Chlorophenyl)-4,5-dibromo-3(2H)-pyridazinone

The title compound was prepared according to the method of Example 194A, substituting 3-chlorophenyl hydrazine-.HCl in place of 4-fluorophenyl hydrazine.HCl (yield: 24.8 g, 88%). $^1$H NMR (300 MHz, DMSO-d$_6$) δ 7.53–7.57 (m, 3H), 7.67–7.70 (m, 1H), 8.29 (s, 1H). MS (DCI/NH$_3$) m/z 365 (M+H)$^+$ and m/z 382 (M+NH$_4$+)$^+$.

Example 207B

2-(3-Chlorophenyl)-4-methoxy-5-bromo-3(2H)-pyridazinone

The title compound was prepared according to the method of Example 194B, substituting 2-(3-chlorophenyl)-4,5-dibromo-3(2H)-pyridazinone in place of 2-(4-fluorophenyl)-4,5-dibromo-3(2H)-pyridazinone (yield: 12.4 g, 95%). $^1$H NMR (300 MHz, DMSO-d$_6$) δ 4.21 (s, 3H), 7.58–7.62 (m, 3H), 7.73–7.76 (m, 1H), 8.28 (s, 1H). MS (DCI/NH$_3$) m/z 317 (M+H)$^+$ and m/z 334 (M+NH$_4$+)$^+$.

Example 207C

2-(3-Chlorophenyl)-4-methoxy-5-[4-(methylthio)phenyl]-3(2H)-pyridazinone

The title compound was prepared according to the method of Example 6 starting with 2-(3-chlorophenyl)-4-methoxy-5-bromo-3(2H)-pyridazinone in place of 2-benzyl-4-bromo-5-methoxy-3(2H)-pyridazinone and substituting 4-(methylthio)benzeneboronic acid in place of 4-fluorobenzeneboronic acid (yield: 3.3 g, 68%). $^1$H NMR (300 MHz, DMSO-d$_6$) δ 2.54 (s, 3H), 4.03 (s, 3H), 7.40 (d, J=9.0 Hz, 2H), 7.50–7.64 (m, 5H), 7.73–7.77 (m, 1H), 8.18 (s, 1H). MS (DCI/NH$_3$) m/z 359 (M+H)$^+$.

Example 207D

2-(3-Chlorophenyl)-4-methyl-5-[3-methyl-4-(methylthio)phenyl]-3(2H)-pyridazinone 2-(3-Chlorophenyl)-4-(4-fluorophenyl)-5-[3-methyl-4-(methylthio)phenyl]-3 (2H)-pyridazinone, was prepared according to the method of Example 228, starting with 2-(3-chlorophenyl)-4-methoxy-5-[3-methyl-4-(methylthio)phenyl]-3(2H)-pyridazinone in place of 2-(4-fluorophenyl)-4-methoxy-5-[4-(methylthio)phenyl]-3(2H)-pyridazinone and substituting 4-fluorophenyl magnesium bromide in place of cyclohexylmagnesium chloride (yield: 180 mg, 94%). $^1$H NMR (300 MHz, CDCl$_3$) δ 2.25 (s, 3H), 2.56 (s, 3H), 7.28–7.45 (m, 6H), 7.58–7.63 (m, 1H), 7.71–7.74 (m, 1H), 7.82 (s, 1H). MS (APCI+) m/z 343 (M+H)$^+$ and m/z 360 (M+NH$_4$)$^+$.

Example 207E 2-(3-Chlorophenyl)-4-methyl-5-[4-(methylsulfonylphenyl]-3(2)-pyridazinone The title compound was prepared according to the method of Example 10, substituting 2-(3-chlorophenyl)-4-methyl-5-[4-(methylthio)phenyl]-3(2H)-pyridazinone for 2-benzyl-4-(4-fluorophenyl)-5-[4-(methylthio)phenyl]-3(2H)-pyridazinone (yield: 125 mg, 67%). mp 164–168. $^1$H NMR (300 MHz, CDCl$_3$) δ 2.23 (s, 3H), 3.13 (s, 3H), 7.37–7.46 (m, 2H), 7.61 (m, 3H), 7.71–7.74 (m, 1H), 7.81 (s, 1H), 8.13 (d, J=8.7 Hz, 2H). MS (APCI+) m/z 343 (M+H)$^+$ and m/z 360 (M+NH$_4$)$^+$.

Example 207F 2-(3-Chlorophenyl)-4-bromomethyl-5-[4-(methylsulfonyl)phenyl]-3(2H)-pyridazinone 2-(3-Chlorophenyl)-4-bromomethyl-5-[4-(methylsulfonyl)phenyl]-3(2H)-pyridazinone was prepared according to the method of Example 194F, substituting 2-(3-chlorophenyl)-4-methyl-5-[4-(methylsulfonyl)phenyl]-3(2H)-pyridazinone in place of 2-(4-fluorophenyl)-4-methyl-5-[4-(methylsulfonyl)phenyl]-3(2H)-pyridazinone (yield: 90 mg, 99%). $^1$H NMR (300 MHz, CDCl$_3$) δ 3.13 (s, 3H), 4.33 (s, 2H), 7.40–7.47 (m, 2H), 7.66 (ddd, J=2.4, 2.4, 7.2 Hz, 1H), 7.76–7.78 (m, 1H), 7.81 (d, J=8.7 Hz, 2H), 7.86 (s, 1H), 8.17 (d, J=8.7 Hz, 2H). MS (APCI+) m/z 453 (M+H)$^+$ and m/z 470 (M+NH$_4$)$^+$.

Example 207G 2-(3-Chlorophenyl)-4-(4-fluorophenoxymethyl)-5-[4-(methylsulfonyl)phenyl]-3(2H)-pyridazinone The title compound was prepared according to the method of Example 194G, substituting 2-(3-chlorophenyl)-4-bromomethyl-5-[4-(methylsulfonyl)phenyl]-3(2H)-pyridazinone in place of 2-(4-fluorophenyl)-4-bromomethyl-5-[4-(methylsulfonyl)phenyl]-3(2H)-pyridazinone (yield: 30 mg, 31%). mp 50–80° C. $^1$H NMR (300 MHz, CDCl$_3$) δ 3.11 (s, 3H), 4.94 (s, 2H), 6.78–6.85 (m, 2H), 6.91–6.99 (m, 2H), 7.39–7.48 (m, 2H), 7.64 (ddd, J=7.5, 1.9, 1.9 Hz, 1H), 7.71–7.77 (m, 3H), 7.93 (s, 1H), 8.08 (d, J=8.7 Hz, 2H). MS (APCI+) m/z 485 (M+H)$^+$.

EXAMPLE 208

2-(3-Chlorophenyl)-4-(benzoyloxymethyl)-5-[4-(methylsulfonyl)phenyl]-3(2H)-pyridazinone The title compound was prepared according to the method of Example 207 substituting benzoic acid in place of 4-fluorophenol (yield: 33 mg, 34%). mp 50–70° C. $^1$H NMR (300 MHz, CDCl$_3$) δ 3.00 (s, 3H), 5.36 (s, 2H), 7.36–7.48 (m, 4H), 7.52–7.59 (m, 1H), 7.61–7.68 (m, 3H), 7.75–7.78 (m, 1H), 7.83–7.88 (m, 2H), 7.89 (s, 1H), 8.02 (d, J=8.7 Hz, 2H). MS (APCI+) m/z 495 (M+H)$^+$.

EXAMPLE 209

2-(2,2,2-Trifluoroethyl)-4-(3-methylbutyl)-5-[4-(methylsulfonyl)phenyl]-3(2H)-pyridazinone The title compound was prepared according to the method of Example 193, substituting 1-bromo-3-methylbutane in place of 4-fluorobenzyl bromide (yield: 80 mg, 19%). $^1$H NMR (300 MHz, CDCl$_3$) δ 0.81 (d, J=7.5 Hz, 6H), 1.3–1.6 (m, 3H), 2.52 (m, 2H), 3.14 (3 H, s) 4.85 (q, J=9 Hz, 2H), 7.55 (d, J=9 Hz, 2H) 7.67 (s, 1H), 8.1 (d, J=9 Hz, 2H). MS (DCI/NH$_3$), m/z 403 (M+H)$^+$. Anal. calc. for C$_{18}$H$_{21}$F$_3$N$_2$O$_3$S.0.25 H$_2$O: C, 53.12; H, 5.32; N, 6.88. Found C, 52.90; H, 5.14; N, 6.43.

EXAMPLE 210

2-(2,2,2-Trifluoroethyl)-4-(4-fluoro-3-methylphenyl)-5-[4-(methylsulfonyl)phenyl]-3(2H)-pyridazinone Example 210A 4-fluoro-3-methylbenzeneboronic acid 5-Bromo-2-fluorotoluene (6 g, 31.7 mmol) was dissolved in dry THF (50 mL) and cooled to −78° C. under N$_2$. n-BuLi (14 mL, 2.5M solution in THF) was added slowly using a dry syringe. Cloudiness appeared. The reaction was stirred for 40 minutes at −78° C. Triisopropyl borate (22 mL, 95 mmol) was slowly added while stirring. The reaction was allowed to warm to room temperature. Stirring continued for an additional 2 hours. A pale yellow, cloudy solution formed. (TLC (1:2 ethyl acetate/hexanes)) indicated disappearance of the starting material. The reaction was quenched by adding 10% aqueous NaOH (200 mL). After stirring for 45 minutes, 10% citric acid solution (300 mL) was added until, pH ~5.0. The product was extracted with ethyl acetate (500 ml). The organic phase was washed with brine and dried over MgSO$_4$, and filtered. The filtrate was concentrated under reduced pressure to provide an off white solid (yield: 4.1 g, 84%).

Example 210B 2-(2,2,2-trifluoroethyl)-4-(4-fluoro-3-methylphenyl)-5-[4-(methylsulfonyl)phenyl]-3(2H)-pyridazinone The boronic acid (231 mg, 1.5 mmol), prepared in example 210A, 2-(2,2,2-trifluoroethyl)-4-chloro-5-[4-(methylsulfonyl)phenyl]-3(2H)-pyridazinone (500 mg, 1.36 mmol), tetrakis-(triphenylphosphine)-palladium(0) (47 mg, 0.041 mmol), and CsF (413 mg, 2.72 mmol) were stirred at reflux in DME (20 mL) under N$_2$ for 5 hours. TLC (1:1 hexanes/ethyl acetate) indicated that all the starting material was consumed. Volatiles were removed in vacuo. The residue was partitioned between water and ethyl acetate. The organic layer was washed with brine, dried over MgSO$_4$, and filtered. The filtrate was concentrated in vacuo. An off white powder was obtained (yield: 275 mg, 46%). mp 88–91° C.; $^1$H NMR (300 MHz, CDCl$_3$, a mixture of rotamers) δ 2.2, 2.25 (2d, J=1.5 Hz, 3H) 3.05, 3.09 (2 s, 3H) 4.78–4.92 (m, 2H) 6.61–6.8 (m, 1H) 6.82–6.98 (m, 1H) 7.35 (d, J=9 Hz, 1H) 7.78 (d, J=9 Hz, 1H) 7.86–8.09 (m, 4H). MS (DCI/NH$_3$), m/z 441 (M+H)$^+$. Anal. calc. for C$_{20}$H$_{16}$F$_4$N$_2$O$_3$S.0.5 H$_2$O: C, 53.45; H, 3.81; N, 6.23. Found C, 53.17; H, 3.65; N, 5.88.

EXAMPLE 211

2-(2,2,2-Trifluoroethyl)-4-(3,5-dichlorophenyl)-5-[4-(methylsulfonyl)phenyl]-3(2H)-pyridazinone 2-(2,2,2-Trifluoroethyl)-4-chloro-5-[4-(methylsulfonyl)phenyl]-3(2H)-pyridazinone (150 mg, 0.409 mmol) (Example 193E) was dissolved in anhydrous DME (8 mL) and heated to reflux with 3,5-dichlorobenzeneboronic acid in presence of CsF (150 mg, 0.98 mmol) and tetrakis(triphenylphosphine)-palladium (17.38 mg, 0.015 mmol) for 6 hours. After cooling to room temperature the reaction mixture was diluted with water and extracted with ethyl acetate (100 mL). The organic layer was washed with brine, dried over $MgSO_4$, and evaporated in vacuo. The compound was purified on a silica gel column, eluting with 30% ethyl acetate in pentanes, to provide the title compound (yield: 110 mg, 58%). $^1$H NMR (300 MHz, $CDCl_3$) δ 3.08 (s, 3H), 4.88 (q, J=9 Hz, 2H), 7.06 (d, J=1.5 Hz, 9 Hz, 2H), 7.31 (t, J=1.5 Hz, 1H), 7.36 (d, J=9 Hz, 2H), 7.94 (s, 1H), 7.96 (d, J=9 Hz, 2H). MS (DCI/$NH_3$) m/z 496 $(M+NH_4)^+$. Anal. calc. for $C_{19}H_{13}Cl_2F_3N_2O_3S$: C, 47.81; H, 2.75; N, 5.87. Found: C, 47.77; H, 2.75; N, 5.65

EXAMPLE 212

2-(2,2,2-Trifluoroethyl)-4-(3-ethoxyphenyl)-5-[4-(methylsulfonyl)phenyl -3(2H)-pyridazinone The title compound was prepared according to the method of Example 211, substituting 3-ethoxyphenylboronic acid for 3,5-dichlorobenzeneboronic acid (yield: 155 mg, 86%). $^1$H NMR (300 MHz, $CDCl_3$) δ 1.42 (t, J=7.5 Hz, 3H), 3.06 (s, 3H), 3.90 (q, J=7.5 Hz, 2H), 4.88 (q, J=9 Hz, 2H), 6.65 (d, J=7.5 Hz, 1H), 6.75 (t, J=1.5 Hz, 1H), 6.85 (dd, J=1.5 Hz, 9 Hz, 1H), 7.15 (t, J=9 Hz, 1H), 7.38 (d, J=9 Hz, 2H), 7.88 (d, J=9 Hz, 2H), 7.90 (s, 1H). MS (DCI3) m/z 470 $(M+NH_4)^+$. Anal. calc. for $C_{21}H_9Cl_2F_3N_2O_4S$: C, 55.75; H, 4.23; N, 6.19. Found: C, 55.62; H, 4.30; N, 5.99

EXAMPLE 213

2-(2,2,2-Trifluoroethyl)-4-(4-trifluoromethylphenyl)-5-[4-(methylsulfonyl)phenyl]-3(2H)-pyridazinone The title compound was prepared according to the method of Example 211, substituting 4-(trifluoromethyl)benzeneboronic acid in place of 3,5-dichlorobenzeneboronic acid (yield: 85 mg, 44%). $^1$H NMR (300 MHz, $CDCl_3$) δ 3.08 (s, 3H), 4.90 (q, J=9 Hz, 2H), 7.35 (t, J=9 Hz, 4H), 7.58 (d, J=9 Hz, 2H), 7.90 (d, J=9 Hz, 3H). MS (DCI/$NH_3$) m/z 494 $(M+NH_4)^+$. Anal. calc. for $C_{20}H_{14}F_6N_2O_3S$: C, 50.42; H, 2.96; N, 5.88. Found: C, 50.20; H, 3.02; N, 5.70

EXAMPLE 214

2-(2,2,2-Trifluoroethyl)-4-(3-nitrophenyl)-5-[4-(methylsulfonyl)phenyl]-3(2H)-pyridazinone The title compound was prepared according to the method of Example 211, substituting 3-nitrobenzeneboronic acid in place of 3,5-dichlorobenzeneboronic acid (yield: 40 mg, 22%). $^1$H NMR (300 MHz, $CDCl_3$) δ 3.05 (s, 3H), 4.92 (q, J=9 Hz, 2H), 7.36 (d, J=9 Hz, 2H), 7.45–7.60 (m, 2H), 7.91 (d, J=9 Hz, 2H), 7.95 (s, 1H), 8.05 (m, 1H), 8.15–8.21 (m, 1H). MS (DCI$D_3$) m/z 471 $(M+NH_4)^+$. Anal. calc. for $C_{19}H_{14}Cl_2F_3N_3O_5S$·0.5 EtOAc: C, 50.70; H, 3.64; N, 8.44. Found: C, 50.61; H, 3.58; N, 8.53

EXAMPLE 215

2-(2,2,2-Trifluoroethyl)-4-(2-methylphenyl)-5-[4-(methylsulfonyl)phenyl]-3(2H)-pyridazinone The title compound was prepared according to the method of Example 211, substituting 2-methylbenzeneboronic acid in place of 3,5-dichlorobenzeneboronic acid (yield: 45 mg, 27%). $^1$H NMR (300 MHz, $CDCl_3$) δ 2.05, 2.12 (2s, 3H), 3.01 (s, 3H), 4.75–5.05 (m, 2H), 6.88 (d, J=9 Hz, 1H), 7.03–7.25 (m, 3H), 7.31 (d, J=9 Hz, 2H), 7.85 (d, J=9 Hz, 2H), 7.95 (s, 1H). MS (DCI/$NH_3$) m/z 440 $(M+NH_4)^+$. Anal. calc. for $C_{20}H_{17}F_3N_2O_3S$: C, 55.10; H, 4.27; N, 6.42. Found: C, 55.17; H, 4.18; N, 6.10

EXAMPLE 216

2-(2,2,2-Trifluoroethyl)-4-(4-vinylphenyl)-5-[4-(methylsulfonyl)phenyl]-3 (2H)-pyridazinone The title compound was prepared according to the method of Example 211, substituting 4-vinylbenzeneboronic acid in place of 3,5-dichlorobenzeneboronic acid (yield: 56 mg, 32%). $^1$H NMR (300 MHz, $CDCl_3$) δ 3.06, 3.08 (2s, 3H), 4.78–4.95 (m, 2H), 5.30 (t, J=6 Hz, 1H), 5.65, 5.75(2d, J=18 Hz, 1H), 6.58–6.92 (m, 1H), 7.1–7.4 (m, 6H), 7.75–8.08 (m, 3H). MS (DCI/$NH_3$) m/z 452 $(M+NH_4)^+$. Anal. calc. for $C_{21}H_{17}F_3N_2O_3S$: C, 58.06; H, 3.94; N, 6.45. Found: C, 57.82; H, 4.01; N, 6.09

EXAMPLE 217

2-(2,2,2-Trifluoroethyl)-4-[3-(trifluoromethyl)phenyl]-5-[4-(methylsulfopyl)phenyl]-3(2H)-pyridazinone The title compound was prepared according to the method of Example 211, substituting 3-trifluoromethylbenzeneboronic acid in place of 3,5-dichlorobenzeneboronic acid (yield: 120 mg, 63%). $^1$H NMR (300 MHz, $CDCl_3$) δ 3.03, 3.08 (2s, 3H), 4.75–4.98 (m, 2H), 7.30–7.60 (m, 6H), 7.75–8.10 (m, 3H). MS (DCI/$NH_3$) m/z 494 $(M+NH_4)^+$. Anal. calc. for $C_{20}H_{14}F_6N_2O_3S$: C, 50.42; H, 2.96; N, 5.88. Found: C, 50.38; H, 2.97; N, 5.74

EXAMPLE 218

2-(2,2,2-Trifluoroethyl)-4-(3-fluoro-4-methoxyphenyl)-5-[4-(methylsulfonyl)phenyl]-3(2H)-pyridazinone The title compound was prepared according to the method of Example 211, substituting 3-fluoro-4-methoxybenzeneboronic acid in place of 3,5-dichlorobenzeneboronic acid (yield: 32 mg, 18%). $^1$H NMR (300 MHz, $CDCl_3$) δ 3.05, 3.09 (2s, 3H), 3.85, 3.87 (2s, 3H), 4.78–4.90 (m, 2H), 6.60–7.10 (m, 3H), 7.30–8.15 (m, 5H). MS (DCI/$NH_3$) m/z 474 $(M+NH_4)^+$. Anal. calc. for $C_{20}H_{16}F_4N_2O_4S$·0.5 $H_2O$: C, 51.61; H, 3.68; N, 6.01. Found: C, 51.52; H, 3.65; N, 5.93

EXAMPLE 219

2-(2,2,2-Trifluoroethyl)-4-(3-fluoro-4-methylphenyl)-5-[4-(methylsulfonyl)phenyl]-3(2H)-pyridazinone The title compound was prepared according to the method of Example 211 substituting 3-fluoro-4-methylbenzeneboronic acid in place of 3,5-dichlorobenzeneboronic acid (yield: 58 mg, 33%). $^1$H NMR (300 MHz, CDCl$_3$) δ 2.21, 2.25 (2d, J=1.5 Hz, 3H), 3.50, 3.55 (2s, 3H), 4.75–4.95 (m, 2H), 6.56–7.15 (m, 3H), 7.30–8.10 (m, 5H). MS (DCI/NH$_3$) m/z 458 (M+NH$_4$)$^+$. Anal. calc. for C$_{20}$H$_{16}$F$_4$N$_2$O$_3$S.0.5 H$_2$O: C, 53.45; H, 3.81; N, 6.23. Found: C, 53.14; H, 3.80; N, 5.97

EXAMPLE 220

2-(2,2,2-Trifluoroethyl)-4-(3,5-difluoro-4-methoxyphenyl)-5-[4-(methylsulfonyl)phenyl]-3(2H)-pyridazinone The title compound was prepared according to the method of Example 211, substituting 3,5-difluoro-4-methoxybenzeneboronic acid in place of 3,5-dichlorobenzeneboronic acid. $^1$H NMR (300 MHz, CDCl$_3$) δ 2.9, 3.1 (2s, 3H), 3.92, 4.01 (2s, 3H), 4.78–4.95 (m, 2H), 6.25–6.80 (m, 1H), 7.30–7.5 (m, 2H), 7.7–8.15 (m, 4H). MS (DCI/NH$_3$) m/z 492 (M+NH$_4$)$^+$. Anal. calc. for C$_{20}$H$_{15}$F$_5$N$_2$O$_4$S: C, 50.64; H, 3.19; N, 5.90. Found: C, 50.542; H, 3.41; N, 5.67

EXAMPLE 221

2-(2,2,2-Trifluoroethyl)4-(1-oxo-1,3-dihydro-2-benzofuran-5-yl)-5-[4-(methylsulfonyl)phenyl]-3(2H)-pyridazinone 6-Bromophthalide (300 mg, 1.40 mmol, Teppema et al Recl. Trav. Chim. Pays-Bays, (1923) 42, 47) and hexamethylditin (326 μL, 1.55 mmol) were dissolved in toluene (5 mL), degassed with a nitrogen stream for 5 minutes, treated with (Ph$_3$P)$_4$Pd (79 mg) and heated at reflux for 1 hour. The reaction was cooled and directly purified by chromatography on a Biotage 40S column (pretreated with hexanes-TEA 400:1 then rinsed with hexanes) eluted with 4:1 hexanes-ethyl acetate. The product fractions were combined and evaporated to provide 6-(trimethyltin)phthalide (yield: 362 mg, 87%).

The tin reagent (180 mg, 0.61 mmol), prepared above, and 2-(2,2,2-trifluoroethyl)-4-chloro-5-[4-(methylsulfonyl)phenyl]-3(2H)-pyridazinone, prepared in Example 193E, (223 mg, 0.61 mmol) were dissolved in dry toluene (10 mL), degassed with an nitrogen stream for 5 minutes, treated with (Ph$_3$P)$_4$Pd (34 mg) and heated at reflux for 1 day. The reaction was cooled and directly purified by chromatography on a Biotage 40S column eluted with 4:1 hexanes-ethyl acetate. The product fractions were combined and evaporated to provide the title compound along with the 4-(1,3-dihydro-1-oxo-6-isobenzofuranyl)-isomer in a 9:1 ratio. Further manipulations to attempt to remove the minor isomer (ie chromatography, recrystallization from ethyl acetate-hexanes) failed (yield: 176 mg, 62%). mp 237–239° C. $^1$H NMR (300 MHz, CDCl$_3$) δ 3.07 (s, 3H), 4.91 (q, J=8 Hz, 2H), 5.30 (s, 2 H, major isomer), 5.33 (s, 2 H, minor isomer), 7.20 (dd, J=1 Hz, 7 Hz, 1H), 7.36 (d, J=8 Hz, 2H), 7.52 (s, 1H), 7.79 (d, J=7 Hz, 1H), 7.92 (d, J=8 Hz, 2H), 7.96 (s, 1H). MS (DCI/NH$_3$) m/z 482 (M+NH$_4$)$^+$. Anal. calc. for C$_{21}$H$_{15}$F$_3$N$_2$O$_5$S: C, 54.31; H, 3.26; N, 6.03. Found: C, 54.15; H, 3.12; N, 5.76.

EXAMPLE 222

2-(2,2,2-Trifluoroethyl)-4-(2-propenyl)-5-[4-(methylsulfonyl)phenyl]-3(2H)-pyridazinone A suspension of 2-(2,2,2-trifluoroethyl)-4-chloro-5-[4-(methylsulfonyl)phenyl]-3(2H)-pyridazinone (200 mg, 0.546 mmol), prepared according to the method of Example 193E, in THF (27 mL) was cooled to −78° C. A solution of isopropenylmagnesium bromide (2.8 mL, 0.5 M in THF, Aldrich) was added. The reaction was warmed to room temperature and stirred for 30 minutes. The reaction was quenched at 0° C. by the addition of saturated ammonium chloride solution and partitioned between ethyl acetate and additional ammonium chloride solution. The organic layer was washed with brine, dried over sodium sulfate, filtered, and concentrated under reduced pressure to provide a reddish brown solid. The crude material was dissolved in methylene chloride and adsorbed onto silica gel (2 g). Solvent was removed under reduced pressure, the adsorbed silica gel layered over an Extract-Clean Cartridge® (Alltech, packing: 5 g silica gel) and the cartridge eluted with a hexanes/acetone step gradient consisting of 40 mL of the following mixtures: hexanes, 8:1 hexanes/acetone, 4:1, 2:1, and 1:1. Fractions containing desired product were combined, concentrated, and further purified using HPLC (Technikrom Kromasil 60-5sil column, 20 mm×25 cm). The column was eluted with a linear gradient consisting of 30% ethyl acetate/hexanes to 100% ethyl acetate at 10 mL/min over 50 minutes. Fractions containing the title product were combined and concentrated under reduced pressure to provide a pale yellow solid (yield: 99.3 mg, 49%). mp 192–195° C. $^1$H NMR (300 MHz, CDCl$_3$) δ 8.03 (d, J=17.4 Hz, 2H), 7.76 (s, 1H), 7.55 (d, 2H, J=17.4 Hz), 5.23 (br s, 1H), 4.84 (m, 3H), 3.11 (s, 3H), 1.98 (s, 3H). MS (DCI/NH$_3$) m/z 373 (M+H)$^+$, m/z 390 (M+NH$_4$)$^+$. Anal. calc. for C$_{16}$H$_{15}$F$_3$N$_2$O$_3$S: C, 51.61; H, 4.06; N, 7.52. Found: C, 51.72; H, 4.24; N, 7.35.

EXAMPLE 223

2-(2,2,2-Trifluoroethyl)-4-(2-buten-2-yl)-5-[4-(methylsulfonyl)phenyl]-3(2H)-pyridazinone The product was prepared according to the method of Example 222 substituting 1-methyl-1-propenylmagnesium bromide in place of isopropenylmagnesium bromide to provide a mixture of geometric isomers (~3:1 ratio) as an off-white solid (yield: 44.8 mg, 21%). mp 175–180° C. $^1$H NMR (300 MHz, CDCl$_3$) δ 8.03 (d, J=18.0 Hz, 1.5H), 8.01 (d, J=18.0 Hz, 0.5H), 7.29 (s, 0.75H), 7.28 (s, 0.25H), 7.56 (d, J=17.4 Hz, 1.5H), 7.51 (d, J=17.4 Hz, 0.5H), 5.55 (m, 0.75H), 5.33 (m, 0.25H), 5.86 (q, J=17.4 Hz, 2H), 3.12 (s, 2.25H), 3.11 (s, 0.75H), 2.88 (m, 2H), 2.85 (m, 1H), 1.27 (m, 3H). MS (DCI/NH$_3$) m/z 387 (M+H)$^+$, m/z 404 (M+NH$_4$)$^+$, m/z 421 (M+2NH$_4$−H)$^+$. Anal. calc. for C$_{17}$H$_{17}$F$_3$N$_2$O$_3$S: C, 52.85; H, 4.43; N, 7.25. Found: C, 53.16; H, 4.68; N, 6.92.

EXAMPLE 224

2-(2,2,2-Trifluoroethyl)-4-(3-fluorobenzyl)-5-[4-(methylsulfonyl)phenyl]-3(2H)-pyridazinone

Example 224A

3-Fluorobenzyl Magnesium Bromide

3-Fluorobenzyl bromide (613 μL, 5 mmol), followed by dibromoethane (10 μL), was added dropwise to an oven-dried flask containing small pieces of magnesium ribbon (134 mg, 5.5 mmol) and diethyl ether (12 mL). Gas evolution was noted followed by gentle reflux of the ether. The reaction was stirred until gas evolution ceased and most of the magnesium had dissolved. The resulting pale yellow solution of 3-fluorobenzylmagnesium bromide was used directly in the next reaction.

Example 224B 2-(2,2,2-Trifluoroethyl)-4-(3-fluorobenzyl)-5-[4-(methylsulfonyl)phenyl]-3(2H)-pyridazinone A suspension of 2-(2,2,2-trifluoroethyl)-4-chloro-5-[4-(methylsulfonyl)phenyl]-3(2H)-pyridazinone (200 mg, 0.546 mmol), prepared according to the method of Example 193E, in THF (10 mL) was cooled to 0° C. A solution of 3-fluorobenzyl magnesium bromide (4.0 mL, ~0.42 M in diethyl ether), prepared above was added. The reaction was stirred at 0° C. for 3 hours, quenched by the addition of saturated ammonium chloride solution, and partitioned, between ethyl acetate and additional ammonium chloride solution. The organic layer was washed with brine, dried over sodium sulfate, filtered, and concentrated under reduced pressure to provide a yellow oil. The crude material was dissolved in methylene chloride and adsorbed onto silica gel (2 g). Solvent was removed under reduced pressure, the silica gel with the product adsorbed was layered over an Extract-Clean Cartridge® (Alltech, packing: 10 g silica gel) and the cartridge eluted with a hexanes/acetone step gradient consisting of 60 mL of each of the following mixtures: hexanes, 8:1 hexanes/acetone, 4:1, 2:1, and 1:1. Fractions containing desired product were combined, concentrated, and further purified using HPLC (Technikrom Kromasil 60-5 sil silica column, 20 mm×25 cm). The column was eluted with a linear gradient consisting of 30% ethyl acetate/hexanes to 100% ethyl acetate at 10 ml/min. for 50 minutes. Fractions containing the title product were combined and concentrated under reduced pressure to provide a pale yellow solid (yield: 130.9 mg, 54%). mp 58–62° C. $^1$H NMR (300 MHz, CDCl$_3$) δ 8.07 (d, J=18.0 Hz, 2H), 7.73 (s, 1H), 7.47 (d, J=17.4 Hz, 2H), 7.18 (m, 1H), 6.88 (m, 1H), 6.76 (br d, J=15.6 Hz, 1H), 6.68 (br d, J=18.6 Hz, 1H), 4.86 (q, J=17.4 Hz, 2H), 3.93 (s, 2H), 3.12 (s, 3H). MS (DCI/NH$_3$) m/z 441 (M+H)$^+$, m/z 458 (M+NH$_4$)$^+$, m/z 475 (M+2NH$_4$–H)$^+$. Anal. calc. for C$_{20}$H$_{16}$F$_4$N$_2$O$_3$S: C, 54.54; H, 3.66; N, 6.36. Found: C, 54.52; H, 3.81; N, 6.17.

EXAMPLE 225

2-(2,2,2-Trifluoroethyl)4-(1-cyclohexenyl)-5-[4-(methylsulfonyl)phenyl]-3(2H)-pyridazinone Example 225A 1-Cyclohexenyltriflate n-Butyllithium (2.5M in hexanes, 2.20 mL, 5.50 mmol) was added to a solution of diisopropylamine (0.77 mL, 5.50 mmol) in THF (20 mL) at −78° C. The resulting pale yellow solution was warmed to 0° C. for 30 minutes then was cooled to −78° C. Cyclohexanone (0.52 mL, 5.0 mmol) was added and the nearly colorless solution was warmed to 0° C. for 1 hour. N-Phenyltrifluoromethanesulfonimide (1.79 g, 5.5 mmol) was added as a solid. The solution was stirred at room temperature for 12 hours. The reaction mixture was then partitioned between diethyl ether and saturated sodium bicarbonate solution. The ether layer was washed with water then brine, dried over sodium sulfate, filtered, and concentrated under reduced pressure. The crude material was purified by flash chromatography (20:1 hexanes/ethyl acetate) to provide the triflate as a pale yellow oil (yield: 0.73 g, 64%).

Example 225B

1-Cyclohexenyltrimethyltin

A solution of 1-cyclohexenyltriflate (412 mg, 1.79 mmol), prepared according to the method of Example 225A, and LiCl (380 mg, 8.95 mmol) in THF (9 mL) was deoxygenated by bubbling a stream of N$_2$ through the solution. Hexamethylditin (339 μL, 1.61 mmol) and tetrakis(triphenylphosphine)palladium(0) (414 mg, 0.36 mmol) were added and the reaction heated at reflux for 12 hours. The reaction was cooled to room temperature and partitioned between diethyl ether and saturated sodium bicarbonate solution. The ether layer was washed with water then brine, dried over sodium sulfate, filtered, and concentrated under reduced pressure. The crude material was dissolved in hexanes (1 mL) and loaded onto an Extract-Clean Cartridge® (Alltech, packing: 10 g silica gel) which had been wetted with 10% triethylamine in hexanes. The cartridge was eluted with hexanes and fractions containing the triflate combined and concentrated under reduced pressure to provide 1-cyclohexenyltrimethyltin as a clear oil (yield: 150 mg, 34%).

Example 225C 2-(2,2,2-Trifluoroethyl)-4-(1-cyclohexenyl)-5-[4-(methylsulfonyl)phenyl]-3(2H)-pyridazinone A solution of 1-cyclohexenyltrimethyltin (150 mg, 0.61 mmol), prepared according to the method of Example 225B, and 2-(2,2,2-trifluoroethyl)-4-chloro-5-[4-(methylsulfonyl)phenyl]-3(2H)-pyridazinone (172 mg, 0.47 mmol), prepared according to the method of Example 193E, in anhydrous N-methylpyrrolidinone (1 mL) was deoxygenated with nitrogen. Dichlorobis(triphenylphosphine) palladium(II) (6.6 mg, 0.009 mmol) and [1,1'-bis(diphenylphosphino) ferrocene] dichloropalladium(II) (7.7 mg, 0.009 mmol) were added and the reaction heated at 80° C. for 16 hours. The reaction mixture was cooled to room temperature and partitioned between diethyl ether and water. The ether was washed with two additional portions water then brine, dried over sodium sulfate, filtered, and concentrated under reduced pressure. The crude material was dissolved in acetone and adsorbed onto silica gel (1 g). Solvent was removed under reduced pressure, the adsorbed silica gel layered over an Extract-Clean Cartridge® (Alltech, packing: 10 g silica gel) and the cartridge eluted with a hexanes/acetone step gradient consisting of the following mixtures: hexanes (60 mL), 8:1 hexanes/acetone (80 mL), 4:1 hexanes/acetone (150 mL). Fractions containing desired product were combined, concentrated, and further purified using HPLC (Technikrom Kromasil 60-5 sil silica column, 20 mm×25 cm). The column was eluted with a linear gradient consisting of 30% ethyl acetate/hexanes to 100% ethyl acetate at 10 mL/min. over 50 minutes. Fractions containing the title product were combined and concentrated under reduced pressure to provide a pale yellow foam (yield: 95.0 mg, 49%). mp 75–81° C. $^1$H NMR (300 MHz, CDCl$_3$) δ 8.02 (d, J=17.4 Hz, 2H), 7.76 (s, 1H), 7.55 (d, J=17.4 Hz, 2H), 5.51 (br s, 1H), 4.83 (br q, J=16.2 Hz, 3H), 3.11 (s, 3H), 2.18 (br, 2H), 1.96 (br, 2H), 1.70–1.50 (m, 4H). MS (DCI/NH$_3$) m/z 413 (M+H)$^+$, m/z 430 (M+NH$_4$)$^+$, m/z 447 (M+2NH$_4$–H)$^+$. Anal. calc. for C$_{19}$H$_{19}$F$_3$N$_2$O$_3$S: C, 55.33; H, 4.64; N. 6.79. Found: C, 55.53; H, 4.71; N, 6.55.

EXAMPLE 226

2-(2,2,2-Trifluoroethyl)-4-(3-methylbutyl)-5-[3-fluoro-4-(aminosulfonyl)phenyl]-3-(2H)-pyridazinone

Example 226A

3-Fluoro-4-(methylthio)benzeneboronic Acid

3-Fluoro-4-(methylthio)benzeneboronic acid was prepared according to the method of Example 1, substituting 4-bromo-2-fluorothioanisole in place of 4-bromothioanisole.

Example 226B

2-Benzyl-4-methoxy-5-bromo-3(2H)-pyridazinone

2-Benzyl-4-methoxy-5-bromo-3(2H)-pyridazinone is prepared according to the method of Example 83B starting with 2-benzyl-4,5-dibromo-3(2H)-pyridazinone, in place of 2-(2,2,2-trifluoroethyl)-4,5-dibromo-3(2H)-pyridazinone and substituting methanol in place of isopropanol.

Example 226C

2-Benzyl-4-methoxy-5-[3-fluoro-4-(methylthio)phenyl]-3(2H)-pyridazinone

3-Fluoro-4-(methylthio)benzeneboronic acid and 2-benzyl-4-methoxy-5-bromo-3(2H)-pyridazinone were coupled according to the method of Example 83C to provide 2-benzyl-4-methoxy-5-[3-fluoro-4-(methylthio)phenyl]-3(2H)-pyridazinone as a yellow solid (yield: 4.98 g, 91%). $^1$H NMR (300 MHz, CDCl3) ? 7.76 (s, 1H), 7.47 (m, 2H), 7.39–7.21 (m, 7H), 5.34 (s, 2H), 4.13 (s, 3H), 2.51 (s, 3H). MS (DCI/NH3) m/z 357 (M+H)$^+$, m/z 374 (M+NH4)$^+$.

Example 226D

3-Methylbutylmagnesium Bromide

An oven-dried flask containing small pieces of magnesium ribbon (134 mg, 5.5 mmol) was charged with diethyl ether (12 mL). 1-Bromo-3-methylbutane (600 µL, 5 mmol) was added dropwise, followed by dibromoethane (10 µL). The reaction required heating at gentle reflux before gas evolution was observed. The reaction was refluxed for 3 hours and cooled to room temperature. The pale gray solution of 3-methylbutylmagnesium bromide was used in the next reaction.

Example 226E

2-Benzyl-4-(3-methylbutyl)-5-[3-fluoro-4-(methylthio)phenyl]-3(2H)-pyridazinone

A solution of 2-benzyl-4-methoxy-5-[3-fluoro-4-(methylthio)phenyl]-3(2H)-pyridazinone (500 mg, 1.40 mmol), prepared according to the method of Example 226C, in THF (20 mL) was cooled to −78° C. 3-Methylbutylmagnesium bromide (5 mL, 1.96 mmol), prepared in Example 226D, was added, dropwise. Upon completion of the addition, the reaction mixture was placed in an ice bath. After 2.5 hours, the reaction was quenched by adding saturated ammonium chloride solution. The crude reaction mixture was partitioned between ethyl acetate and additional ammonium chloride solution. The organic layer was washed with brine, dried over sodium sulfate, filtered, and concentrated under reduced pressure to provide a yellow oil (yield: 550 mg, 99%). $^1$H NMR (300 MHz, CDCl3) δ 7.67 (s, 1H), 7.49 (m, 2H), 7.39–7.25 (m, 4H), 7.02 (m, 2H), 5.35 (s, 2H), 2.57–2.49 (m, 2H), 2.52 (s, 3H), 1.62–1.36 (m, 3H), 0.83 (d, 6H, J=12.0 Hz). MS (DCI/NH3) m/z 397 (M+H)$^+$, m/z 414 (M+NH4)$^+$. MS (DCI/NH$_3$) m/z 397 (M+H)$^+$, m/z 414 (M+NH$_4$)$^+$.

Example 226F 4-(3-Methylbutyl)-5-[3-fluoro-4-(methylthio)phenyl]-3(2H)-pyridazinone 2-Benzyl-4-(3-methylbutyl)-5-[3-fluoro-4-(methylthio)phenyl]-3(2H)-pyridazinone (550 mg, 1.39 mmol), prepared in Example 226E, was debenzylated according to the method of Example 11 to provide 4-(3-methylbutyl)-5-[3-fluoro-4-(methylthio)phenyl]-3(2H)-pyridazinone as a pale yellow solid (yield: 375 mg, 88%). $^1$H NMR (300 MHz, CDCl3) δ 7.65 (s, 1H), 7.34 (dd, 1H, J=16.2, 16.2 Hz), 7.11–6.98 (m, 2H), 2.60–2.50 (m, 2H), 2.54 (s, 3H), 1.65–1.37 (m, 3H), 0.83 (d, 6H, J=12.0 Hz). MS (DCI/NH3) m/z 307 (M+H)$^+$, m/z 324 (M+NH4)$^+$ MS (DCI/NH$_3$) m/z 307 (M+H)$^+$, m/z 324 (M+NH$_4$)$^+$.

Example 226G 2-(2,2,2-Trifluoroethyl)-4-(3-methylbutyl)-5-[3-fluoro-4-(methylthio)phenyl]-3(2H)-pyridazinone 4-(3-Methylbutyl)-5-[3-fluoro-4-(methylthio)phenyl]-3(2H)-pyridazinone (375 mg, 1.23 mmol), prepared in Example 226F, was alkylated according to the method of Example 20 to provide 2-(2,2,2-trifluoroethyl)-4-(3-methylbutyl)-5-[3-fluoro-4-(methylthio)phenyl]-3(2H)-pyridazinone as a clear oil (yield: 331 mg, 69%). $^1$H NMR (300 MHz, CDCl3) δ 7.67 (s, 1H), 7.34 (dd, 1H, J=16.8, 16.8 Hz), 7.11–6.98 (m, 2H), 4.82 (dd, 2H, J=17.4, 17.4 Hz), 2.60–2.51 (m, 2H), 2.53 (s, 3H), 1.61–1.32 (m, 3H), 0.85 (d, 6H, J=12.0 Hz). MS (DCI/NH3) m/z 389 (M+H)$^+$, m/z 406 (M+NH4)$^+$. MS (DCI/NH$_3$) m/z 389 (M+H)$^+$, m/z 406 (M+NH$_4$)$^+$.

Example 226H 2-(2,2,2-Trifluoroethyl)-4-(3-methylbutyl)-5-[3-fluoro-4-(methylsulfinyl)phenyl]-3(2H)-pyridazinone.

2-(2,2,2-Trifluoroethyl)-4-(3-methylbutyl)-5-[3-fluoro-4-(methylthio)phenyl]-3(2H)-pyridazinone 3(2H)-pyridazinone (331 mg, 0.85 mmol), prepared in Example 226G, was oxidized according to the method of Example 5 using only one equivalent of MCA to provide 2-(2,2,2-trifluoroethyl)-4-(3-methylbutyl)-5-[3-fluoro-4-(methylsulfinyl)phenyl]-3(2H)-pyridazinone as an off-white solid (yield: 240 mg, 69%). $^1$H NMR (300 MHz, CDCl$_3$) δ 8.02 (dd, 1H, J=15.0, 15.0 Hz), 7.67 (s, 1H), 7.37 (dd, 1H, J=17.4, 3.0 Hz), 7.11 (dd, 1H, J=18.6, 3.0 Hz), 4.84 (dd, 2H, J=17.4, 17.4 Hz), 2.91 (s, 3H), 2.53 (m, 2H), 1.60–1.35 (m, 3H), 0.57 (d, 6H, J=12.0 Hz). MS (DCI/NH3) m/z 405 (M+H)$^+$, m/z 422 (M+NH4)$^+$. MS (DCI/NH$_3$) m/z 405 (M+H)$^+$, m/z 422 (M+NH$_4$)$^+$.

Example 226I

2-(2,2,2-Trifluoroethyl)-4-(3-methylbutyl)-5-[3-fluoro-4-(aminosulfonyl)phenyl]-3(2H)-pyridazinone 2-(2,2,2-Trifluoroethyl)-4-(3-methylbutyl)-5-[3-fluoro-4-(methylsulfinyl)phenyl]-3(2H)-pyridazinone (240 mg, 0.594 mmol), prepared in Example 226H, was converted to the sulfonamide according to the procedure of Example 68 to provide the title compound as a white solid (yield: 109 mg, 44%). mp 153–156° C. $^1$H NMR (300 MHz, CDCl$_3$) δ 8.07 (dd, J=15.0, 15.0 Hz, 1H), 7.74 (s, 1H), 7.27–7.19 (m, 2H), 5.14 (br s, 2H), 4.83 (q, J=18.0 Hz, 2H), 2.52 (m, 2H), 1.55 (m, 1H), 1.41 (m, 2H), 0.85 (d, J=12.6 Hz, 6H). MS (ESI (−)) m/z 420 (M−H)$^−$. Anal. calc. for C$_{17}$H$_{19}$F$_4$N$_3$O$_3$S: C, 48.45; H, 4.54; N, 9.97. Found: C, 48.24; H, 4.56; N, 9.80.

EXAMPLE 227

2-(2,2,2-Trifluoroethyl)-4-benzyl-5-[4-(methylsulfonyl)phenyl]-3(2H)-pyridazinone The title compound was prepared by adding 1.0 M benzylmagnesium chloride in ether (0.53 mL, 0.53 mmol) to a THF (20 mL) solution of 2-(2,2,2-trifluoroethyl)-4-chloro-5-[4-(methylsulfonyl)phenyl]-3(2H)-pyridazinone (150 mg, 0.41 mmol), prepared according to the method of Example 193E, at 0° C., then allowing the mixture to warm to room temperature over 2 hours. After an aqueous work-up, the crude material was purified by column chromatography (silica gel, 65:35 hexanes/ethyl acetate) and crystallized from ethyl acetate/hexanes to provide white, crystalline product (yield: 74 mg, 43%). mp 112–114° C. $^1$H NMR (300 MHz, CDCl$_3$) δ 3.12 (s, 3H), 3.94 (s, 2H), 4.85 (q, J=12 Hz, 2H), 6.99 (dd, J=7.5 Hz, 3 Hz, 2H), 7.2 (m, 3H), 7.48 (d, J=9 Hz, 2H), 7.72 (s, 1H), 8.06 (d, J=9 Hz, 2H). MS (DCI/NH$_3$) m/z 423 (M+H)+. Anal. calc. for C$_{20}$H$_{17}$F$_3$N$_2$O$_3$S: C, 56.86; H, 4.05; N, 6.63. Found: C, 56.60; H, 4.13; N, 6.57.

EXAMPLE 228

2-(4-Fluorophenyl)-4-cyclohexyl-5-[4-(methylsulfonyl)phenyl]-3(2H)-pyridazinone A solution of 2-(4-fluorophenyl)-4-methoxy-5-[4-(methylthio)phenyl]-3(2H)-pyridazinone, prepared in Example 194C, (200 mg, 0.51 mmol) in THF (8 ml) was cooled to −78° C. and treated with cyclohexylmagnesium chloride, 2 M solution in ether (0.31 ml, 0.7 mmol). The reaction mixture was stirred at −78° C. for 2 hours and then was warmed up to room temperature by removing the cooling bath. Stirred at room temperature for 2 hours water (50 ml) was added to the reaction mixture and extracted with ethyl acetate (50 ml). The organic layer was dried over MgSO$_4$ and concentrated in vacuo. The resulting methyl sulfide compound was purified by flash chromatography (SiO$_2$, eluting with 9:1 hexanes:ethyl acetate) to provide the desired product (yield: 128 mg, 69%). MS (DCI/NH$_3$) m/z 395 (M+H)$^+$, 412 (M+NH$_4$)$^+$.

The methyl sulfide compound, prepared above, (122 mg, 0.3 mmol) in CH$_2$Cl$_2$ (10 ml) at 0° C., was treated with CH$_3$CO$_3$H (0.3 ml, 1 mmol). The reaction was complete in 2 hours. The reaction mixture was diluted with CH$_2$Cl$_2$ and washed with saturated NaHCO$_3$ and brine respectively. The resulting crude residue was purified by flash chromatography (SiO$_2$, eluting with 1:1 hexanes:ethyl acetate) to provide the desired product (yield: 110 mg, 93%). mp 231–233° C. $^1$H NMR (300 MHz, DMSO-d$_6$) δ 1.1 (m, 3H), 1.6 (m, 6H), 2.15 (m, 2H), 7.35 (t, 2H), 7.65 (m, 2H), 7.73 (dd, 2H) 7.93 (s, 1H), 8.1 (d, 2H). MS (DCI/NH$_3$) m/z 427 (M+H)$^+$, 444 (M+NH$_4$)$^+$. Anal. calc. for C$_{23}$H$_{23}$FN$_2$O$_3$S.0.75 H$_2$O: C, 64.77; H, 5.44; N, 6.57. Found: C, 62.86; H, 5.53; N, 5.78.

EXAMPLE 229

2-(4-Fluorophenyl)-4-(4-methylphenyl)-5-[4-(methylsulfonyl)phenyl]-3(2H)-pyridazinone The title compound was prepared according to the method of Example 228, substituting p-tolylmagnesium bromide in place of cyclohexylmagnesium chloride (yield: 90 mg, 39%). mp 242–244° C. $^1$H NMR (300 MHz, DMSO-d$_6$) δ 2.25 (s, 3H), δ 3.25 (s, 3H), 7.1 (t, 4H), 7.35 (t, 2H), 7.5 (d, J=9 Hz, 2H), 7.7 (dd, 2H) 7.9 (d, J=9 Hz, 2H), 8.2 (s, 1H). MS (DCI/NH$_3$) m/z 435 (M+H)$^+$, 452 (M+NH$_4$)$^+$. Anal. calc. for C$_{24}$H$_{19}$FN$_2$O$_3$S.0.5 H$_2$O: C, 66.34; H, 4.41; N, 6.45. Found: C, 64.61; H, 4.57; N, 6.10.

EXAMPLE 230

2-(4-Fluorophenyl)-4-benzyl-5-[4-(methylsulfoflphenyl]-3(2H)-pyridazinone

The title compound was prepared according to the method of Example 228, substituting benzylmagnesium bromide in place of cyclohexylmagnesium chloride (yield: 179 mg, 81%). mp 180–182° C. $^1$H NMR (300 MHz, DMSO-d$_6$) δ 3.3 (s, 3H), 7.0 (d, 2H), 7.2 (m, 3H), 7.35 (t, 2H), 7.65 (m, 2H), 7.72 (d, 2H) 8.05 (m, 3H). MS (DCI/NH$_3$) m/z 435 (M+H)$^+$, 452 (M+NH$_4$)$^+$. Anal. calc. for C$_{24}$H$_{19}$FN$_2$O$_3$S.0.5 H$_2$O: C, 66.34; H, 4.41; N, 6.45. Found: C, 66.48; H, 4.17; N, 6.36.

EXAMPLE 231

2-(4-Fluorophenyl)-4-(phenylethynyl)-5-[4-(methylsulfonyl)phenyl]-3(2H)-pyridazinone The title compound was prepared according to the method of Example 228, substituting phenylacetylene magnesium bromide in place of cyclohexylmagnesium chloride (yield: 150 mg, 55.5%). mp 203–204° C. $^1$H NMR (300 MHz, DMSO-d$_6$) δ 3.3 (s, 3H), 7.4 (m, 8H), 7.7 (m, 2H), 8.16 (m, 4H); 8.35 (s, 1H). MS (DCI/NH$_3$) m/z 435 (M+H)$^+$, 452 (M+NH$_4$)$^+$. Anal. calc. for C$_{25}$H$_{17}$FN$_2$O$_3$S: C, 67.56; H, 3.86; N, 6.30. Found: C, 67.63; H, 3.86; N, 6.30.

EXAMPLE 232

2-(3,4-Difluorophenyl)-4-cyclohexyl-5-[4-(methylsulfonyl)phenyl]-3(2H)-pyridazinone The title compound was prepared according to the method of Example 228, starting with 2-(3,4-difluorophenyl)-4-methoxy-5-[4-(methylthio)phenyl]3(2H)-pyridazinone in place of 2-(4-fluorophenyl)-4-methoxy-5-[4-(methylthio)phenyl]-3(2H)-pyridazinone (yield: 245 mg, 80%). mp 80–83° C. $^1$H NMR (300 MHz, DMSO-d$_6$) δ 1.1 (m, 3H), 1.6 (m, 6H), 2.15 (m, 2H), 7.5 (m, 1H), 7.6 (m, 2H), 7.7 (d, 2H), 7.78 (m, 2H), 7.93 (s, 1H), 8.1 (d, 2H). MS (DCI/NH$_3$) m/z 445 (M+H)$^+$, 462 (M+NH$_4$)+. Anal. calc. for C$_{23}$H$_{22}$F$_2$N$_2$O$_3$S: C, 62.15; H, 4.99; N, 6.30. Found: C, 62.65; H, 5.25; N, 5.97.

EXAMPLE 233

2-(3,4-Difluorophenyl)-4-benzyl-5-[4-(methylsulfonyl)phenyl]-3(2H)-pyridazinone

The title compound was prepared according to the method of Example 228, starting with 2-(3,4-difluorophenyl)-4-methoxy-5-[4-(methylthio)phenyl]-3(2H)-pyridazinone in place of 2-(4-difluorophenyl)-4-methoxy-5-[4-(methylthio)phenyl]-3(2H)-pyridazinone and substituting benzylmagnesium bromide in place of cyclohexylmagnesium chloride (yield 206 mg, 66%). mp 166–168° C. $^1$H NMR (300 MHz, DMSO-$d_6$) δ 3.3 (s, 3H), 3.9 (s, 2H), 7.0 (d, 2H), 7.2 (m, 3H), 7.6 (m, 2H), 7.72 (d, 2H), 7.8 (d, 1H), 8.05 (d, 2H), 8.12 (s, 1H). MS (DCI/NH$_3$) m/z 453 (M+H)$^+$, 470 (M+NH$_4$)$^+$. Anal. calc. for $C_{24}H_{19}F_2N_2O_3S$: C, 63.71; H, 4.01; N, 6.19. Found C, 63.53; H, 4.33; N, 5.76.

EXAMPLE 234

2-(3,4-Difluorophenyl)-4-(4-methylphenyl)-5-[4-(methylsulfonyl)phenyl]-3(2H)-pyridazinone The title compound was prepared according to the method of Example 228, starting with 2-(3,4-difluorophenyl)-4-methoxy-5-[4-(methylthio)phenyl]-3(2H)-pyridazinone in place of 2-(4-difluorophenyl)-4-methoxy-5-[4-(methylthio)phenyl]-3(2H)-pyridazinone and substituting p-tolylmagnesium bromide in place of cyclohexylmagnesium chloride (yield: 140 mg, 56%). mp 190–192° C. $^1$H NMR (300 MHz, DMSO-$d_6$) δ 2.28 (s, 2H), δ 3.25 (s, 3H), 7.1 (s, 4H), 7.5 (m, 4H), 7.89 (m, 3H), 8.05 (d, 2H), 8.23 (s, 1H). MS (DCI/NH$_3$) m/z 453 (M+H)$^+$, 470 (M+NH$_4$)$^+$. Anal. calc. for $C_{24}F_2H_{18}N_2O_3S$: C, 63.71; H, 4.01; N, 6.19. Found: C, 63.69; H, 4.29; N, 5.96.

EXAMPLE 235

2-(3,4-Difluorophenyl)-4-(4-fluoro-3-methylphenyl)-5-[4-(methylsulfonyl)phenyl]-3(2H)-pyridazinone The title compound was prepared according to the method of Example 228, starting with 2-(3,4-difluorophenyl)-4-methoxy-5-[4-(methylthio)phenyl]-3(2H)-pyridazinone in place of 2-(4-fluorophenyl)-4-methoxy-5-[4-(methylthio)phenyl]-3(2H)-pyridazinone and substituting 4-fluoro-3-methylbenzenemagnesium bromide in place of cyclohexylmagnesium chloride (yield: 180 mg, 72.5%). mp 166–168° C. $^1$H NMR (300 MHz, DMSO-$d_6$) δ 2.15 (s, 3H), δ 3.25 (s, 3H), 7.01 (m, 2H), 7.25 (d, 1H), 7.6 (m, 4H), 7.9 (m, 3H), 8.26 (s, 2H). MS (DCI/NH$_3$) m/z 471 (M+H)$^+$, 488 (M+NH$_4$)$^+$. Anal. calc. for $C_{24}F_3H_{17}N_2O_3S$: C, 61.27; H, 3.64; N, 5,95. Found: C, 61.47; H, 3.84; N, 5.67.

EXAMPLE 236

2-(3,4-Difluorophenyl)-5-[4-(methylsulfonyl)phenyl]-4-vinyl-3(2H)-pyridazinone

The title compound was prepared according to the method of Example 228, starting with 2-(3,4-difluorophenyl)-4-methoxy-5-[4-(methylthio)phenyl]-3(2H)-pyridazinone in place of 2-(4-fluorophenyl)-4-methoxy-5-[4-(methylthio)phenyl]-3(2H)-pyridazinone and substituting vinyl magnesium bromide in place of cyclohexylmagnesium chloride (yield: 85 mg, 31.8%). $^1$H NMR (300 MHz, DMSO-$d_6$) δ 2.15 (s, 3H), δ 3.3 (s, 3H), 5.7 (dd, 1H), 6.4 (dd, 1H), 6.7 (dd, 1H) 7.01 (m, 2H), 7.5 (m, 1H), 7.65 (m, 1H), 7.8 (m, 3H), 8.1 (s, 3H). MS (DCI/NH$_3$) m/z 389 (M+H)$^+$, 406 (M+NH$_4$)$^+$.

EXAMPLE 237

2-(3,4-Difluorophenyl)-4-(2-thienyl)-5-[4-(methylsulfonyl)phenyl]-3(2H)-pyridazinone The title compound was prepared according to the method of Example 228, starting with 2-(3,4-difluorophenyl)-4-methoxy-5-[4-(methylthio)phenyl]-3(2H)-pyridazinone in place of 2-(4-fluorophenyl)-4-methoxy-5-[4-(methylthio)phenyl]-3(2H)-pyridazinone and substituting 2-thienylmagnesium bromide in place of cyclohexylmagnesium chloride (yield: 66 mg, 28%). mp 189–191° C. $^1$H NMR (300 MHz, DMSO-$d_6$) δ 3.3 (s, 3H), 6.95 (m, 2H), 7.55 (m, 1H), 7.7 (m, 5H), 7.85 (m, 1H), 8.03 (d, J=9 Hz, 2H), 8.13 (s, 1H). MS (DCI/NH$_3$) m/z 445 (M+H)$^+$, 462 (M+NH$_4$)$^+$. Anal. calc. for $C_{21}H_{14}F_2N_2O_3S_2$: C, 56.75; H, 3.17; N, 6.30. Found: C, 56.92, H, 3.92, N, 5.79.

EXAMPLE 238

2-(3,4-Difluorophenyl)-4-(1-propynyl)-5-[4-(methylsulfonyl)phenyl]-3(2H)-pyridazinone The title compound was prepared according to the method of Example 228, starting with 2-(3,4-difluorophenyl)-4-methoxy-5-[4-(methylthio)phenyl]-3(2H)-pyridazinone in place of 2-(4-fluorophenyl)-4-methoxy-5-[4-(methylthio)phenyl]-3(2H)-pyridazinone and substituting methylacetylenemagnesium bromide in place of cyclohexylmagnesium chloride (yield: 65 mg, 24%). mp 149–150° C. $^1$H NMR (300 MHz, DMSO-$d_6$) δ 2.1 (s, 3H), 3.3 (s, 3H), 7.51 (m, 1H), 7.65 (m, 1H), 7.8 (m, 1H), 8.1 (m, 4H); 8.3 (s, 1H). MS (DCI/NH$_3$) m/z 463M+H)$^+$, 480 (M+NH$_4$)$^+$. Anal. calc. for $C_{20}H_{14}F_2N_2O_3S.0.25$ H2O: C, 59.94; H, 3.52; N, 7.00. Found: C, 59.49; H, 3.63; N, 6.34.

EXAMPLE 239

2-(3,4-Difluorophenyl)-4-t-butyl-5-[4-(methylsulfonyl)phenyl]-3(2H)-pyridazinone The title compound was prepared according to the method of Example 228, starting with 2-(3,4-difluorophenyl)-4-methoxy-5-[4-(methylthio)phenyl]-3(2H)-pyridazinone in place of 2-(4-fluorophenyl)-4-methoxy-5-[4-(methylthio)phenyl]-3(2H)-pyridazinone and substituting t-butylmagnesium bromide in place of cyclohexylmagnesium chloride (yield: 60 mg, 24%). mp 158–161° C. $^1$H NMR (300 MHz, DMSO-$d_6$) δ 1.21, (s, 9H), 3.3 (s, 3H), 7.51 (m, 1H), 7.45 (m, 1H), 7.75 (m, 4H), 8.02 (d, J=9 Hz, 2H). MS (DCI/NH$_3$) m/z 419 (M+H)$^+$, 436 (M+NH$_4$)$^+$. Anal. calc. for $C_{21}H_{20}F_2N_2O_3S$: C, 60.27; H, 4.82; N, 6.69. Found: C, 60.15; H, 5.10; N, 6.39

EXAMPLE 240

2-(2,2,2-Trifluoroethyl)-4-cyclohexyl-5-[4(methylsulfonyl)phenyl]-3(2H)-pyridazinone The title compound was prepared according to the method of Example 228, starting with 2-(2,2,2-trifluoroethyl)-4-chloro-5-[4-(methylthio)phenyl]-3(2H)-pyridazinone, prepared in Example 193D, in place of 2-(4-fluorophenyl)-4-methoxy-5-[4-(methylthio)phenyl]-3(2H)-pyridazinone, (yield: 120 mg, 53%). mp 215–218° C. $^1$H NMR (300 MHz, CDCl$_3$) δ 1.1 (tt, J=9 Hz, J=4.5 Hz, 2H), 1.25 (tt, J=9 Hz, 4.5 Hz, 1H), 1.49 (d, J=12 Hz, 2H), 1.63 (d, J=12 Hz, 1H), 1.75 (dt, J=12 Hz, 3 Hz, 2H), 2.21 (qd, J=9 Hz, 4.5 Hz, 2H), 2.51 (tt, J=12 Hz, 3 Hz, 1H), 3.17 (s, 3H), 4.83 (q, J=12 Hz, 2H), 7.49 (d, J=9 Hz, 2H), 7.6 (s, 1H), 8.09 (d, J=9 Hz, 2H). MS (DCI/NH$_3$) m/z 415 (M+H)$^+$. Anal. calc. for C$_{19}$H$_{21}$F$_3$N$_2$O$_3$S: C, 55.06; H, 5.1; N, 6.75. Found: C, 55.08; H, 5.10; N, 6.70.

EXAMPLE 241

2-(3-Chlorophenyl)-4-(3-fluorobenzyl)-5-[4-(methylsulfonyl)phenyl]-3(2H)-pyridazinone 2-(3-Chlorophenyl)-4-(3-fluorobenzyl)-5-[4-(methylthio)phenyl]-3(2H)-pyridazinone was prepared according to the method of Example 228, starting with 2-(3-chlorophenyl)-4-methoxy-5-[4-(methylthio)phenyl]-3(2H)-pyridazinone, prepared in Example 207C, and substituting 3-fluorobenzylmagnesium chloride in place of cyclohexylmagnesium chloride to provide the methyl sulfide compound.

The methyl sulfide compound was oxidized according to the method of Example 10 to provide the title compound (yield: 180 mg, 55%). mp 142–143° C. $^1$H NMR (300 MHz, CDCl$_3$) δ 3.14 (s, 3H), 3.98 (s, 2H), 6.75 (br d, J=9 Hz, 1H), 6.82 (br d, J=9 Hz, 1H), 6.88 (br t, J=9 Hz, 1H), 7.15–7.23 (m, 1H), 7.37–7.47 (m, 2H), 7.54 (d, J=9 Hz, 2H), 7.63 (dt, J=9 Hz, 2 Hz, 1H), 7.75 (t, J=2 Hz, 1H), 7.82 (s, 1H), 8.10 (d, J=9 Hz, 2H). MS (DCI/NH$_3$) m/z 469 (M+H)$^+$, 486 (M+NH$_4$)$^+$. Anal. calc. for C$_{24}$H$_{18}$ClF$_2$N$_2$O$_3$S.0.5 H$_2$O: C, 60.38; H, 3.88; N, 5.87. Found: C, 60.62; H, 3.89; N, 5.82.

EXAMPLE 242

2-(4-Fluorophenyl)-4-(3-fluorobenzyl)-5-[4-(methylsulfonyl)phenyl]-3(2H)-pyridazinone 2-(4-Fluorophenyl)-4-(3-fluorobenzyl)-5-[4-(methylthio)phenyl]-3(2H)-pyridazinone was prepared according to the method of Example 228, starting with 2-(4-fluorophenyl)-4-methoxy-5-[4-(methylthio)phenyl]-3(2H)-pyridazinone, prepared in Example 194C, and substituting 3-fluorobenzylmagnesium chloride in place of cyclohexylmagnesium chloride to provide the methyl sulfide compound.

The methyl sulfide compound was oxidized according to the method of Example 10, to provide the title compound (yield: 450 mg, 66.8%). mp 176–178° C. $^1$H NMR (300 MHz, CDCl$_3$) δ 3.14 (s, 3H), 3.95 (s, 2H), 6.75 (br d, J=9 Hz, 1H), 6.82 (br d, J=9 Hz, 1H), 6.88 (br t, J=9 Hz, 1H), 7.14–7.23 (m, 3H), 7.54 (d, J=9 Hz, 2H), 7.67 (dd, J=9 Hz, 6 Hz, 2H), 7.81 (s, 1H), 8.10 (d, J=9 Hz, 2H). MS (DCI/NH$_3$) m/z 516 (M+NH$_4$)$^+$. Anal. calc. for C$_{24}$H$_{19}$F$_2$N$_2$O$_5$S.H$_2$O: C, 61.28; H, 4.04; N, 5.96. Found: C, 61.24; H, 4.09; N, 5.77.

EXAMPLE 243

2-(3,4-Difluorophenyl)-4-(3-fluorobenzyl)-5-[4-(methylsulfonyl)phenyl]-3(2H)-pyridazino 2-(3,4-Difluorophenyl)-4-(3-fluorobenzyl)-5-[4-(methylthio)phenyl]-3(2H)-pyridazinone was prepared according to the method of Example 228, starting with 2-(3,4-difluorophenyl)-4-methoxy-5-[4-(methylthio)phenyl]-3(2H)-pyridazinone, and substituting 3-fluorobenzylmagnesium chloride in place of cyclohexylmagnesium chloride to provide the methyl sulfide compound.

The methyl sulfide compound was oxidized according to the method of Example 10 to provide the title compound (yield: 390 mg, 68%). mp 161–163° C. $^1$H NMR (300 MHz, CDCl$_3$) δ 3.14 (s, 3H), 3.95 (s, 2H), 6.74 (br d, J=9 Hz, 1H), 6.82 (br d, J=9 Hz, 1H), 6.89 (br t, J=9 Hz, 1H), 7.15–7.33 (m, 2H), 7.48–7.57 (m, 1H), 7.53 (d, J=9 Hz, 2H), 7.59–7.67 (m, 1H), 7.83 (s, 1H), 8.10 (d, J=9 Hz, 2H). MS (DCI/NH$_3$) m/z 471 (M+H)$^+$, 488 (M+NH$_4$)$^+$. Anal. calc. for C$_{24}$H$_{17}$F$_3$N$_2$O$_3$S.0.5 H$_2$O: C, 60.13; H, 3.65; N, 5.85. Found: C, 60.08; H, 3.81; N, 5.54.

EXAMPLE 244

2-(3-Chlorophenyl)-4-(4-fluoro-3-methylphenyl)-5-[4-(methylsulfonyl)phenyl]-3(2H)-pyridazinone 2-(3-Chlorophenyl)-4-(4-fluoro-3-methylphenyl)-5-[4-(methylthio)phenyl]-3(2H)-pyridazinone was prepared according to the method of Example 228, starting with 2-(3-chlorophenyl)-4-methoxy-5-[4-(methylthio)phenyl]-3(2H)-pyridazinone, prepared in Example 207C, and substituting 4-fluoro-3-methylphenylmagnesium bromide in place of cyclohexylmagnesium chloride to provide the methyl sulfide compound.

The methyl sulfide compound was oxidized according to the method of Example 10 to provide the title compound (yield: 620 mg, 57%). mp 228–230° C. $^1$H NMR (300 MHz, CDCl$_3$) δ 2.20 (s, 3H), 3.06 (s, 3H), 6.83–6.93 (m, 2H), 7.19 (br d, J=9 Hz, 1H), 7.37–7.47 (m, 2H), 7.40 (d, J=9 Hz, 2H), 7.65 (dt, J=7 Hz, 3 Hz, 1H), 7.68 (t, J=3 Hz, 1H), 7.91 (d, J=9 Hz, 2H), 7.98 (s, 1H). MS (DCI/NH$_3$) m/z 469 (M+H)$^+$, 486 (M+NH$_4$)$^+$. Anal. calc. for C$_{24}$H$_{18}$ClFN$_2$O$_3$S: C, 61.54; H, 3.85; N, 5.99. Found: C, 61.39; H, 3.84; N, 5.82.

EXAMPLE 245

2-(4-Fluorophenyl)-4-(4-fluoro-3-methylphenyl)-5-[4-(methylsulfonyl)phenyl]-3(2H)-pyridazinone 2-(4-Fluorophenyl)-4-(4-fluoro-3-methylphenyl)-5-[4-(methylthio)phenyl]-3(2H)-pyridazinone was prepared according to the method of Example 228, starting with 2-(4-fluorophenyl)-4-methoxy-5-[4-(methylthio)phenyl]-3(2H)-pyridazinone, prepared in Example 194C, and substituting 4-fluoro-3-methylphenylmagnesium bromide in place of cyclohexylmagnesium chloride to provide the methyl sulfide compound.

The methyl sulfide compound was oxidized according to the method of Example 10 to provide the title compound (yield: 590 mg, 74.4%). mp 245–247° C. $^1$H NMR (300 MHz, CDCl$_3$) δ 2.01 (s, 3H), 3.07 (s, 3H), 6.87 (m, 2H), 7.21 (m, 3H), 7.41 (d, J=9 Hz, 2H), 7.68 (m, 2H), 7.92 (d, J=9 Hz, 2H), 7.97 (s, 1H). MS (DCI/NH$_3$) m/z 453 (M+H)$^+$, 470 (M+NH$_4$)$^+$. Anal. calc. for C$_{24}$H$_{18}$F$_2$N$_2$O$_3$S.0.5 H$_2$O: C, 62.47; H, 3.90; N, 6.08. Found: C, 62.11; H, 4.11; N, 5.81.

EXAMPLE 246

2-(3-Chloro-4-fluorophenyl)-4-cyclohexyl-5-[4-(methylsulfonyl)phenyl]-3(2H)-pyridazinone

Example 246A 2-(3-Chloro-4-fluorophenyl)-4,5-dibromo-3(2H)-pyridazinone

The title compound is prepared according to the method of Example 194A, substituting 3-chloro-4-fluorophenyl hydrazine.HCl in place of 4-fluorophenyl hydrazine.HCl (yield: 9.1 g, 9%). $^1$H NMR (300 MHz, CDCl$_3$) 7.22 (d, J=9

Hz, 1H), 7.53–7.58 (m, 1H), 7.73 (dd, J=9 Hz, 3 Hz, 1H), 7.94 (s, 1H). MS (DCI/NH$_3$) m/z 383 (M+H)$^+$, 400 (M+NH$_4$)$^+$

Example 246B 2-(3-Chloro-4-fluorophenyl)-4-methoxy-5-bromo-3 (2H)-pyridazinone

The title compound is prepared according to the method of Example 194B, substituting 2-(3-chloro-4-fluorophenyl)-4,5-dibromo-3(2H)-pyridazinone in place of 2-(4-fluorophenyl)-4,5-dibromo-3(2H)-pyridazinone (yield: 5.6 g, 84%). $^1$H NMR (300 MHz, CDCl$_3$) 4.32 (s, 3H), 7.22–7.30 (m, 1H), 7.45–7.55 (m, 1H), 7.64–7.74 (m, 1H), 7.94 (d, J=9 Hz, 1H). MS (DCI/NH$_3$) m/z 335 (M+H)$^+$, 352 (M+NH$_4$)$^+$.

Example 246C 2-(3-Chloro-4-fluorophenyl)-4-methoxy-5-[4-(methylthio)phenyl]-3(2H)-pyridazinone The title compound is prepared according to the method of Example 6 starting with 2-(3-chloro-4-fluorophenyl)-4-methoxy-5-bromo-3(2H)-pyridazinone in place of 2-benzyl-5-methoxy-4-bromo-3(2H)-pyridazinone and substituting 4-(methylthio)benzeneboronic acid in place of 4-fluorobenzeneboronic acid (yield: 3.2 g, 63%). $^1$H NMR (300 MHz, CDCl$_3$) δ 2.53 (s, 3H), 4.13 (s, 3H), 7.25 (t, J=9 Hz, 1H), 7.35 (d, J=9 Hz, 2H), 7.52 (d, J=9 Hz, 2H), 7.55–7.64 (m, 1H), 7.78 (dd, J=9 Hz, 3 Hz, 1H), 7.93 (s, 2H). MS (DCI/NH$_3$) m/z 377 (M+H)$^+$, 394 (M+NH$_4$)$^+$.

Example 246D 2-(3-Chloro-4-fluorophenyl)-4-cyclohexyl-5-[4-(methylthio)phenyl]-3(2H)-pyridazinone The title compound is prepared starting with 2-(3-chloro-4-fluorophenyl)-4-methoxy-5-[4-(methylthio)phenyl]-3 (2H)-pyridazinone in place of 2-(4-fluorophenyl)-4-methoxy-5-[4-(methylthio)phenyl]-3(2H)-pyridazinone by treatment of the methoxy-sulfide compound with cyclohexylmagnesium chloride according to the method of Example 228 to provide the cyclohexyl sulfide compound.

Example 246E 2-(3-Chloro-4-fluorophenyl)-4-cyclohexyl-5-[4-(methylsulfonyl)phenyl]-3(2H)-pyridazinone The methyl sulfide compound was oxidized according to the method of Example 10 to provide the title compound (yield: 150 mg, 53%). mp 180–181° C. $^1$H NMR (300 MHz, CDCl$_3$) δ 1.02–1.36 (m, 2H), 1.49–1.68 (m, 4H), 1.75 (br d, J=12 Hz, 2H), 2.28 (dq, J=12 Hz, 3 Hz, 2H), 2.57 (tt, J=12 Hz, 3 Hz, 1H), 3.17 (s, 3H), 7.25 (t, J=9 Hz, 1H), 7.53 (d, J=9 Hz, 1H), 7.53–7.61 (m, 2H), 7.69 (s, 1H), 7.78 (dd, J=9 Hz, 3 Hz, 1H), 8.12 (d, J=9 Hz, 2H). MS (DCI/NH$_3$) m/z 461 (M+H)$^+$, 478 (M+NH$_4$)$^+$. Anal. calc. for C$_{23}$H$_{22}$ClFN$_2$O$_3$S: C, 60.01; H, 4.78; N, 6.09. Found: C, 59.85; H, 4.97; N, 5.79.

EXAMPLE 247

2-(3-Chloro-4-fluorophenyl)-4-(4-fluoro-3-methylphenyl)-5-[4-(methylsulfonyl)phenyl]-3(2H)-pyridazinone 2-(3-Chloro-4-fluorophenyl)-4-(4-fluoro-3-methylphenyl)-5-[4-(methylthio)phenyl]-3(2H)-pyridazinone was prepared according to the method of Example 228, starting with 2-(3-chloro-4-fluorophenyl)-4-methoxy-5-[4-(methylthio) phenyl]-3(2H)-pyridazinone, prepared in Example 246C, and substituting 4-fluoro-3-methylphenylmagnesium bromide in place of cyclohexylmagnesium chloride to provide the methyl sulfide compound.

The methyl sulfide was oxidized according to the method of Example 10 to provide the title compound (yield: 118 mg, 53.7%). mp 207–208° C. $^1$H NMR (300 MHz, CDCl$_3$) δ 2.21 (br s, 3H), 3.08 (s, 3H), 6.81–6.93 (m, 2H), 7.15–7.30 (m, 2H), 7.41 (d, J=9 Hz, 2H), 7.60–7.68 (m, 1H), 7.85 (dd, J=9 Hz, 3 Hz, 1H), 7.93 (d, J=9 Hz, 2H), 7.99 (s, 1H). MS (DCI/NH$_3$) m/z 487 (M+H)$^+$, 504 (M+NH$_4$)$^+$. Anal. calc. for C$_{24}$H$_{17}$ClF$_2$N$_2$O$_3$S.0.25 H$_2$O: C, 58.75; H, 3.52; N, 5.72. Found: C, 58.74; H, 3.60; N, 5.32.

EXAMPLE 248

2-(3-Chloro-4-fluorophenyl)-4-benzyl-5-[4-(methylsulfonyl)phenyl]-3(2H)-pyridazinone 2-(3-Chloro-4-fluorophenyl)-4-benzyl-5-[4-(methylthio) phenyl]-3(2H)-pyridazinone was prepared according to the method of Example 228, starting with 2-(3-chloro-4-fluorophenyl)-4-methoxy-5-[4-(methylthio)phenyl]-3(2H)-pyridazinone, prepared in Example 246C, and substituting benzylmagnesium chloride in place of cyclohexylmagnesium chloride to provide the methyl sulfide compound.

The methyl sulfide was oxidized according to the method of Example 10 to provide the title compound (yield: 110 mg, 38.4%). mp 164–166° C. $^1$H NMR (300 MHz, CDCl$_3$) δ 3.11 (s, 3H), 3.99 (s, 2H), 7.01–7.06 (m, 2H), 7.17–7.28 (m, 4H), 7.53 (d, J=9 Hz, 2H), 7.59–7.66 (m, 1H), 7.81 (s, 1H), 7.82 (dd, J=6 Hz, 3 Hz, 1H), 8.09 (d, J=9 Hz, 2H). MS (DCI/NH$_3$) m/z 473 (M+H)$^+$, 490 (M+NH$_4$)$^+$. Anal. calc. for C$_{24}$H$_{18}$ClFN$_2$O$_3$S: C, 61.54; H, 3.85; N, 5.99. Found: C, 61.40; H, 3.82; N, 5.54.

EXAMPLE 249

2-(3-Chloro-4-fluorophenyl)-4-(3-fluorobenzyl)-5-[4-(methylsulfonyl)phenyl]-3(2H)-pyridazinone 2-(3-Chloro-4-fluorophenyl)-4-(3-fluorobenzyl)-5-[4-(methylthio)phenyl]-3(2H)-pyridazinone was prepared according to the method of Example 228, starting with 2-(3-chloro-4-fluorophenyl)-4-methoxy-5-[4-(methylthio) phenyl]-3(2H)-pyridazinone, prepared in Example 246C, and substituting 3-fluorobenzylmagnesium chloride in place of cyclohexylmagnesium chloride to provide the methyl sulfide compound.

The methyl sulfide was oxidized according to the method of Example 10 to provide the title compound (yield: 33 mg, 15%). mp 101–103° C. $^1$H NMR (300 MHz, CDCl$_3$) δ 3.15 (s, 3H), 3.95 (s, 2H), 6.73 (br d, J=9 Hz, 1H), 6.81 (br d, J=9 Hz, 1H), 6.88 (br t, J=9 Hz, 1H), 7.15–7.28 (m, 2H), 7.51 (d, J=9 Hz, 2H), 7.53 (ddd, J=9 Hz, 1.5 Hz, 1H), 7.83 (dd, J=6 Hz, 3 Hz, 1H), 7.83 (s, 1H), 8.10 (d, J=9 Hz, 2H). MS (DCI/NH$_3$) m/z 487 (M+H)$^+$, 504 (M+NH$_4$)$^+$. Anal. calc. for C$_{24}$H$_{17}$ClF$_2$N$_2$O$_3$S: C, 58.75; H, 3.52; N, 5.62. Found: C, 58.50; H, 3.65; N, 5.29.

EXAMPLE 250

2-(4-Fluorophenyl)-4-(3-fluoro-4-methylphenyl)-5-[4-(methylsulfonyl)phenyl]-3(2H)-pyridazinone 2-(4Fluorophenyl)-4-(3-fluoro-4-methylphenyl)-5-[4-(methylthio)phenyl]-3(2H)-pyridazinone was prepared according to the method of Example 228, starting with 2-(4-fluorophenyl)-4-methoxy-5-[4-(methylthio)phenyl]-3 (2H)-pyridazinone, prepared in Example 194C, and substituting 3-fluoro-4-methylphenylmagnesium bromide in place of cyclohexylmagnesium chloride to provide the methyl sulfide compound.

The methyl sulfide was oxidized according to the method of Example 10 to provide the title compound (yield: 540 mg, 73%). mp 245–248° C. $^1$H NMR (300 MHz, CDCl$_3$) δ 2.22 (br s, 3H), 3.05 (s, 3H), 6.83 (dd, J=9 Hz, 1.5 Hz, 1H), 6.96 (dd, J=9 Hz, 1.5 Hz, 1H), 7.06 (t, J=9 Hz, 1H), 7.18 (t, J=9 Hz, 2H), 7.41 (d, J=9 Hz, 2H), 7.65–7.72 (m, 2H), 7.91 (d, J=9 Hz, 2H), 7.95 (s, 1H). MS (DCI/NH$_3$) m/z 452 (M+H)$^+$, 470 (M+NH$_4$)$^+$. Anal. calc. for C$_{24}$H$_{18}$F$_2$N$_2$O$_3$S: C, 63.86; H, 3.99; N, 6.21. Found: C, 63.49; H, 4.13; N, 5.98.

EXAMPLE 251

2-(3-Chloro-4-fluorophenyl)-4-(3,5-difluoro-4-methoxyphenyl)-5-[4-(methylsulfonyl)phenyl]-3(2H)-pyridazinone 2-(3-Chloro-4-fluorophenyl)-4-(3,5-difluoro-4-methoxyphenyl)-5-[4-(methylthio)phenyl]-3(2H)-pyridazinone was prepared according to the method of Example 228, starting with 2-(3-chloro-4-fluorophenyl)-4-methoxy-5-[4-(methylthio)phenyl]-3(2H)-pyridazinone, prepared in Example 246C, and substituting 3,5-difluoro-4-methoxyphenylmagnesium bromide in place of cyclohexylmagnesium chloride to provide the methyl sulfide compound.

The methyl sulfide was oxidized according to the method of Example 10 to provide the title compound (yield: 590 mg, 65.7%). mp 195–197° C. $^1$H NMR (300 MHz, CDCl$_3$) δ 3.10 (s, 3H), 4.12 (s, 3H), 6.81 (br d, J=9 Hz, 2H), 7.27 (t, J=9 Hz, 1H), 7.43 (d, J=9 Hz, 2H), 7.60–7.67 (m, 1H), 7.83 (br d, J=9 Hz, 1H), 7.98 (d, J=9 Hz, 2H), 7.98 (s, 1H). MS (DCI/NH$_3$) m/z 487 (M+H)$^+$, 504 (M+NH$_4$)$^+$. Anal. calc. for C$_{24}$H$_{16}$ClF$_3$N$_2$O$_3$S.0.5 H$_2$O: C, 54.44; H, 3.12; N, 5.30. Found: C, 54.50; H, 3.12; N, 5.15.

EXAMPLE 252

2-(3-Chloro-4-fluorophenyl)-4-(3-methylbutyl)-5-[3-fluoro-4-(methylsulfonyl)phenyl]-3(2H)-pyridazinone 2-(3-Chloro-4-fluorophenyl)-4-(3-methylbutyl)-5-[4-(methylthio)phenyl]-3(2H)-pyridazinone was prepared according to the method of Example 228, starting with 2-(3-chloro-4-fluorophenyl)-4-methoxy-5-[4-(methylthio) phenyl]-3(2H)-pyridazinone, prepared in Example 246C, and substituting 1-(3-methylbutyl)magnesium bromide in place of cyclohexylmagnesium chloride to provide the methyl sulfide compound.

The methyl sulfide was oxidized according to the method of Example 10 to provide the title compound (yield: 425 mg, 54.4%). mp 102–104° C. $^1$H NMR (300 MHz, CDCl$_3$) δ 0.85 (d, J=9 Hz, 6H), 1.41–1.62 (m, 1H), 2.50–2.63 (m, 2H), 3.30 (s, 3H), 7.22–7.38 (m, 3H), 7.57–7.64 (m, 1H), 7.72 (br s, 1H), 7.80 (br d, J=6 Hz, 1H), 8.15 (t, J=9 Hz, 1H). MS (DCI/NH$_3$) m/z 467 (M+H)$^+$, 484 (M+NH$_4$)$^+$. Anal. calc. for C$_{22}$H$_{21}$ClF$_2$N$_2$O$_3$S: C, 56.65; H, 4.51; N, 6.01. Found: C, 56.25; H, 4.49; N, 6.06.

EXAMPLE 253

2-(4-Fluorophenyl)-4-(3-fluorobenzyl)-5-[4-(aminosulfonyl)phenyl]-3(2H)-pyridazinone The sulfide from Example 242, 2-(4-fluorophenyl)-4-(3-fluorobenzyl)-5-[4-(methylthio)phenyl]-3(2H)-pyridazinone, was oxidized to the methyl sulfoxide with one equivalent of meta-chloroperoxybenzoic acid according to the procedure in Example 69B to provide the sulfinyl compound.

The sulfoxide was converted to the title sulfonamide according to the method of Example 68 (yield: 120 mg, 31%). mp 199–202° C. $^1$H NMR (300 MHz, DMSO-d$_6$) δ 3.92 (s, 2H), 6.85 (br t, J=9 Hz, 2H), 6.99 (br t, J=9 Hz, 1H), 7.26 (q, J=7 Hz, 1H), 7.35 (t, J=9 Hz, 2H), 7.50 (s, 2H), 7.62–7.71 (m, 4H), 7.95 (d, J=9 Hz, 2H), 8.11 (s, 1H). MS (DCI/NH$_3$) m/z 454 (M+H)$^+$, 471 (M+NH$_4$)$^+$. Anal. calc. for C$_{23}$H$_{17}$F$_2$N$_3$O$_3$S: C, 60.86; H, 3.75; N, 9.27. Found: C, 60.99; H, 3.76; N, 9.02.

EXAMPLE 254

2-(3,4-Difluorophenyl)-4-(phenylethynyl)-5-[4-(methylsulfonyl)phenyl]-3(2H)-pyridazinone The title compound was prepared according to the method of Example 228, starting with 2-(3,4-difluorophenyl)-4-methoxy-5-[4-(methylthio)phenyl]3(2H)-pyridazinone in place of 2-(4-fluorophenyl)-4-methoxy-5-[4-(methylthio)phenyl]-3(2H)-pyridazinone (yield: 245 mg, 80%) and substituting phenylethynylmagnesium bromide in place of cyclohexylmagnesium chloride (yield: 195 mg, 61%). mp 211–213° C. $^1$H NMR (300 MHz, DMSO-d$_6$) δ 7.46 (m, 5H), 7.65 (m, 2H), 8.18 (t, 4H); 8.4 (s, 1H). MS (DCI/NH$_3$) m/z 463M+H)$^+$, 480 (M+NH$_4$)$^+$. Anal. calc. for C$_{25}$H$_{16}$F$_2$N$_2$O$_3$S: C, 64.56; H, 3.49; N, 6.06. Found: C, 64.49; H, 3.68; N, 5.86.

EXAMPLE 255

2-(3,4-Difluorophenyl)-4-(3,4-difluorobenzyl)-5-[4 (methylsulfonyl)phenyl]-3(2H)-pyridazinone 3,4-Difluorobenzyl bromide (0.1 ml, 0.8 mmol) in ether (10 ml) was treated with magnesium turnings (19.4 mg, 0.81 mmol) and the reaction mixture was refluxed for 1 hour. The reaction mixture was cooled and added to a solution of 2-(3,4-difluorophenyl)-4-methoxy-5-[4-(methylthio)phenyl]-3(2H)-pyridazinone (0.25 g, 0.7 mmol) in THF (10 ml) at −78° C. The reaction mixture was stirred at room temperature for 18 hours. Water (50 ml) was added to the reaction mixture and extracted with ethyl acetate (50 ml). The organic layer was dried over MgSO$_4$ and concentrated in vacuo. The resulting crude residue was purified by flash chromatography (SiO$_2$, eluting with 9:1 hexanes:ethyl acetate) to provide 120 mg of desired product and some starting material.

The methylthio compound (120 mg, 0.3 mmol) from above in CH$_2$Cl$_2$ (10 ml) at 0° C., was treated with CH$_3$CO$_3$H (0.3 ml, 1 mmol). The reaction was complete in 2 hours. The reaction mixture was diluted with CH$_2$Cl$_2$ and washed with saturated NaHCO$_3$ and brine respectively. The resulting crude residue was purified by flash chromatography (SiO$_2$, eluting with 1:1 hexanes:ethyl acetate) to provide the desired product (yield: 44 mg, 13%). mp 177–179° C. $^1$H NMR (300 MHz, DMSO-d$_6$) δ 3.3 (s, 3H), 3.9 (s, 2H), 6.85 (m, 1H), 7.15 (m, 1H), 7.25 (m, 2H), 7.6 (m, 7H), 8.15 (m, 3H). MS (DCI/NH$_3$) m/z 489 (M+H)$^+$, 506 (M+NH$_4$)$^+$. Anal. calc. for C$_{24}$H$_{16}$F$_4$N$_2$O$_3$S.0.25 H$_2$O: C, 59.01; H, 3.30; N, 5.74. Found: C, 58.16; H, 3.56; N, 4.51.

EXAMPLE 256

2-(3,4-Difluorophenyl)-4-(3-methylbutyl)-5-[4-(methylsulfonyl)phenyl]-3(2H)-pyridazinone The title compound was prepared according to the method of Example 228, starting with 2-(3,4-difluorophenyl)-4-methoxy-5-[4-(methylthio)phenyl]3(2H)-pyridazinone in place of 2-(4-fluorophenyl)-4-methoxy-5-[4-(methylthio)phenyl]-3(2H)-pyridazinone (yield: 245 mg, 80%) and substituting 1-bromo-3-methylbutane in place of cyclohexylmagnesium chloride (yield: 198 mg, 48%). mp 55–58° C. $^1$H NMR (300 MHz, DMSO-d$_6$) δ 0.75 (d, 6H), 1.4, (m, 3H), 2.48 (m, 2H), 3.3 (s, 3H), 7.51 (m, 1H), 7.65 (m, 1H), 7.75 (d, J=9 Hz, 2H), 7.81 (m, 1H) 8.05 (s, 1H), 8.12 (d, J=9 Hz, 2H). MS (DCI/NH$_3$) m/z 433 (M+H)$^+$, 450 (M+NH$_4$)$_+$. Anal. calc. for C$_{22}$H$_{22}$F$_2$N$_2$O$_3$S.0.25 H$_2$O: C, 61.10; H, 5.13; N, 6.48. Found: C, 61.09; H, 5.23; N, 6.36.

EXAMPLE 257

2-(3-Chloro-4-fluorophenyl)-4-(3-methylbutyl)-5-[4-(methylsulfonyl)phenyl]-3(2H)-pyridazinone The title compound was prepared according to the method of Example 228 starting with 2-(3-chloro-4-fluorophenyl)-4-metoxy-5-[4-(methylthio)phenyl]-3(2H)-pyridazinone from Example 246C in place of 2-(4-fluorophenyl)-4-methoxy-5-[4-(methylthio)phenyl]-3(2H)-pyridazinone and substituting 1-bromo-3-methylbutane in place of cyclohexylmagnesium chloride (yield: 256 mg, 88%). mp 55–58° C. $^1$H NMR (300 MHz, DMSO-d$_6$) δ 0.75 (d, 6H), 1.4, (m, 3H), 2.48 (m, 2H), 3.3 (s, 3H), 7.62 (m, 2H), 7.75 (d, 2H), 7.93 (dd, 1H), 8.05 (s, 1H), 8.12 (d, J=9 Hz, 2H). MS (DCI/NH$_3$) m/z 449 (M+H)$^+$, 466 (M+NH$_4$)$^+$. Anal. calc. for C$_{22}$H$_{22}$FN$_2$O$_3$SCl.0.25 H$_2$O: C, 58.86; H, 4.94; N, 6.24. Found: C, 59.23; H, 5.12; N, 6.00.

EXAMPLE 258

2-(3,4-Difluorophenyl)-4-(3-methylbutyl)-5-[3-fluoro-4-(methylsulfonyl)phenyl]-3(2H)-pyridazinone The title compound was prepared according to the method of Example 228, procedure starting with 2-(3,4-difluorophenyl)-4-methoxy-5-[3-fluoro-4-(methylthio)phenyl]-3(2H)-pyridazinone in place of 2-(4-fluorophenyl)-4-methoxy-5-[3-fluoro-4-(methylthio)phenyl]-3(2H)-pyridazinone and substituting 1-bromo-3-methylbutane in place of cyclohexylmagnesium chloride (yield: 100 mg, 20%). mp 119–121° C. $^1$H NMR (300 MHz, DMSO-d$_6$) δ 0.75 (d, 6H), 1.4, (m, 3H), 2.48 (m, 2H), 3.4 (s, 3H), 7.51 (m, 1H), 7.8 (m, 2H), 7.81 (m, 2H). MS (DCI/NH$_3$) m/z 451 (M+H)$^+$, 468 (M+NH$_4$)$^+$. Anal. calc. for C$_{22}$H$_{21}$F$_3$N$_2$O$_3$S: C, 58.66; H, 4.7; N, 6.22.

EXAMPLE 259

2-[4-Fluoro-3-(methylthio)phenyl]-4-(4-fluorophenyl)-5-[4-(methylsulfonyl)phenyl]-3(2H)-pyridazinone To a stirred solution of 2-(3,4-difluorophenyl)-4-(4-fluorophenyl)-5-[4-(methylsulfonyl)phenyl]-3(2H)-pyridazinone (315 mg, 0.69 mmol), Example 182, in DMF (10 ml) at room temperature was treated with sodium thiomethoxide (51 mg, 0.7 mmol). The reaction mixture was stirred at room temperature for 3.15 hours. The reaction was poured into water (75 ml) and extracted into ethyl acetate. The organic layer was washed two times with brine, dried over MgSO$_4$, and concentrated in vacuo. The resulting crude residue was purified using flash chromatography (SiO$_2$, eluting with (15:1 CH$_2$Cl$_2$:diethyl ether) to provide the desired product (yield: 30 mg, 8%). mp 105–107° C. $^1$H NMR (300 MHz, DMSO-d$_6$) δ 2.55 (s, 3H), 3.23 (s, 3H), δ 7.15 (m, 2H), 7.3 (m, 2H), 7.55 (m, 5H), 7.9 (d, 2H), 8.25 (s, 1H). MS (DCI/NH$_3$) m/z 485 (M+H)$^+$, 502 (M+NH$_4$)$^+$. Anal. calc. for C$_{24}$H$_{18}$F$_2$N$_2$O$_3$S$_2$: C, 59.49; H, 3.74; N, 5.78.

EXAMPLE 260

2-Benzyl-4-(4-fluorophenyl)-5-[4-(trifluoromethylsulfonylphenyl]-3(2H)-pyridazinone

Example 260A

2-Benzyl-4-(4-fluorophenyl)-5-[4-(methylsulfinyl)phenyl]-3(2H)-pyridazinone

The title compound was prepared starting with 2-benzyl-4-(4-fluorophenyl)-5-[4-(methylthio)phenyl]-3(2H)-pyridazinone and oxidizing the sulfide according to the procedure in example 69B

Example 260B

Bis(4-(5-(2-benzyl-4-(4-fluorophenyl)-3(2H)-pyridazinone)phenyl)disulfide

A heterogeneous solution of 2-benzyl-4-(4-fluorophenyl)-5-[4-(methylsulfinyl)phenyl]-3(2H)-pyridazinone (1.0 g, 2.39 mmol) in trifluoroacetic anhydride (10 mL, 70.8 mmol) was rapidly stirred at reflux for 2 hours with a bath temperature of 40–43° C. The reaction solution was cooled to 23° C., concentrated in vacuo, and azeotroped with toluene (2×5–7 mL). The resultant yellow/orange oil was cooled to 0° C., and methanol/triethylamine (1:1, 6 mL) was slowly added, along the interior wall of the reaction vessel with rapid stirring. The bright red-orange solution was stirred for 10 minutes at 0° C., the cooling bath removed, and the reaction mixture stirred an additional 1.5 hours warming to 23° C. The mixture was cooled back to 0° C., and a saturated NH$_4$Cl solution (200 mL) slowly added followed by enough aqueous 1 M HCl to adjust the solution to pH 1–2. The cooling bath was removed and the solution stirred overnight. The mixture was extracted with ethyl acetate. The ethyl acetate solution was washed with water and brine, and concentrated in vacuo. The resultant yellow/brown oil (0.89 g) was a mixture of predominantly the mono-sulfide and desired di-sulfide. Subsequent rapid stirring of a portion of the crude reaction mixture (360 mg) in benzene (100 mL) with I$_2$ (648 mg, 2.55 mmol) at 23° C. for 30 minutes completed the conversion of the mono-sulfide to the di-sulfide. (Chem. Pharm. Bull., 1992, 40, 2842) The mixture was treated with a 0.1 M Na$_2$S$_2$O$_3$ solution to consume the excess I₂. This solution was extracted with ethyl acetate, and the ethyl acetate layers dried over MgSO₄, filtered, and concentrated in vacuo. The residue was dissolved in CH₂Cl₂/hexanes and concentrated in vacuo to provide the of product (yield: 347 mg, 90% for partial conversion). $^1$H NMR (300 MHz, CDCl₃) δ 5.38 (s, 4H), 6.91 (dd, J=8.8, 8.8 Hz, 4H), 7.02 (d, J=8.7 Hz, 4H), 7.11–7.20 (m, 4H), 7.28–7.39 (m, 10H), 7.54 (dd, J=6.9, 1.5 Hz, 4H), 7.83 (s, 2H).

Example 260C

2-Benzyl-4-(4-fluorophenyl)-5-[4-(trifluoromethylthio)phenyl]-3(2H)-pyridazinone A rapidly stirred mixture of bis[4-{5-[2-benzyl-4-(4-fluorophenyl)-3(2H)-pyridazinone]}-phenyl]-disulfide (140 mg, 0.181 mmol), potassium trifluoroacetate (55 mg, 0.361 mmol), and sulfolane (1.5 mL) was immersed in a 180° C. pre-heated oil bath. The oil bath was heated to increase the temperature to 210° C., and the reaction flask was promptly removed from the oil bath after 10 minutes from the point of first immersion. During the course of the reaction, the mixture changed from colorless and heterogeneous to deep, blood red and homogeneous. After cooling to 23° C., the mixture was diluted with ethyl acetate and washed with aqueous 1 M HCl, water, and brine. The ethyl acetate solution was dried over MgSO₄, filtered and concentrated in vacuo. The residue was chromatographed (flash silica gel, ethyl acetate/hexanes 1:4) to provide the product (yield: 17 mg, 41%). (Tetrahedron Lett., 1996, 37, 9057) $^1$H NMR (300 MHz, CDCl₃) δ 5.41 (s, 2H), 6.94 (dd, J=8.2, 8.2 Hz, 2H), 7.11–7.20 (m, 4H), 7.31–7.42 (m, 3H), 7.52–7.61 (m, 4H), 7.86 (s, 1H). MS (APCI+) m/z 457 (M+H)⁺ and m/z 474 (M+NH₄)⁺. silica gel (Biotage 40S) eluted with 2:1 hexanes-ethyl acetate. The product fractions were combined and evaporated to provide the title compound (yield: 137 mg, 76%). mp 145–146° C. $^1$H NMR (300 MHz, DMSO-d₆) δ 0.76 (s, 9H), 3.28 (s, 3H), 4.06 (s, 2H), 5.02 (q, J=9 Hz, 2H), 7.88 (d, J=8 Hz, 2H), 8.04 (d, J=8 Hz, 2H), 8.13 (s, 1H). MS (DCI/NH₃) m/z 419 (M+H)⁺, 436 (M+NH₄)⁺. Anal. calc. for C₁₈H₂₁F₃N₂O₄S: C, 51.67; H, 5.06; N, 6.69. Found: C, 51.47; H, 5.12; N, 6.48.

EXAMPLE 262

2-(2,2,2-Trifluoroethyl)-4-(4-methoxyphenoxy)-5-[4-(methylsulfonyl)phenyl]-3(2H)-pyridazinone The title compound was prepared according to the method of Example 261, substituting 4-methoxyphenol in place of neopentyl alcohol (yield: 130 mg, 54%). mp 194–195° C. $^1$H NMR (300 MHz, DMSO-d₆) δ 2.24 (s, 3H), 3.26 (s, 3H), 5.00 (q, J=9 Hz, 2H), 6.88 (d, J=8 Hz, 2H), 7.09 (d, J=8 Hz, 2H), 7.37 (d, J=8 Hz, 2H), 8.03 (d, J=8 Hz, 2H), 8.33 (s, 1H). MS (ESI–) m/z 439 (M–H)⁻. Anal. calc. for C₁₉H₁₇F₃N₂O₄S: C, 54.79; H, 3.91; N, 6.39. Found: C, 55.04; H, 4.00; N, 6.11.

EXAMPLE 263

2-(2,2,2-Trifluoroethyl)-4-(2-fluoro-5-trifluoromethylphenoxy)-5-[4-(methylsulfonyl)phenyl]-3(2H)-pyridazinone The title compound was prepared according to the method of Example 261, substituting 2-fluoro-5-trifluoromethylphenol in place of neopentyl alcohol (yield: 155 mg, 89%). mp 133–135° C. $^1$H NMR (300 MHz, DMSO-d₆) δ 3.28 (s, 3H), 5.03 (q, J=9 Hz, 2H), 7.10–7.53 (m, 2H), 7.72 (dd, J=1 Hz, 7 Hz 1H), 7.92 (d, J=8 Hz, 2H), 8.07 (d, J=8 Hz, 2H), 8.38 (s, 1H). MS (DCI/NH₃) m/z 528 (M+NH₄)⁺. Anal. calc. for C₂₀H₁₃F₇N₂O₄S: C, 47.66; H, 3.09; N, 5.05. Found: C, 47.68; H, 2.95; N, 5.16.

EXAMPLE 264

2-(2,2,2-Trifluoroethyl)-4-(4-cyanophenoxy)-5-[4-(methylsulfonyl)phenyl]-3(2H)-pyridazinone The title compound was prepared according to the method of Example 261, substituting 4-cyanophenol in place of neopentyl alcohol (yield: 109 mg, 71%). mp 179–181° C. $^1$H NMR (300 MHz, DMSO-d₆) δ 3.26 (s, 3H), 5.02 (q, J=9 Hz, 2H), 7.25 (d, J=9 Hz, 2H), 7.81 (d, J=9 Hz, 2H), 7.86 (d, J=8 Hz, 2H), 8.03 (d, J=8 Hz, 2H), 8.37 (s, 1H). MS (DCI/NH₃) m/z 467 (M+NH₄)⁺. Anal. calc. for C₂₀H₁₄F₃N₃O₄S: C, 53.45; H, 3.14; N, 9.35. Found: C, 53.19; H, 3.01; N, 9.09.

EXAMPLE 265

2-(2,2,2-Trifluoroethyl)-4-(3-pyridyloxy)-5-[4-(methylsulfonyl)phenyl]-3(2H)-pyridazinone The title compound was prepared according to the method of Example 261, substituting 3-hydroxypyridine in place of neopentyl alcohol (yield: 120 mg, 69%). mp 191–193° C. $^1$H NMR (300 MHz, DMSO-d₆) δ 3.26 (s, 3H), 5.01 (q, J=9 Hz, 2H), 7.36 (dd, J=3 Hz, 8 Hz, 1H), 7.55 (ddd, J=1 Hz, 3 Hz, 8 Hz, 1H), 7.88 (d, J=8 Hz, 2H), 8.04 (d, J=8 Hz, 2H), 8.31 (dd, J=1 Hz, 5 Hz, 1H), 8.36 (s, 1H), 8.38 (d, J=3 Hz, 1H). MS (DCI/NH₃) m/z 426 (M+H)₊, 443 (M+NH₄)⁺. Anal. calc. for C₁₈H₁₄F₃N₃O₄S: C, 50.82; H, 3.32; N, 9.88. Found: C, 50.95; H, 3.57; N, 9.71.

EXAMPLE 266

2-(2,2,2-Trifluoroethyl)-4-(4-n-propylphenoxy)-5-[4-(methylsulfonyl)phenyl]-3(2H)-pyridazinone The title compound was prepared according to the method of Example 261, substituting 4-(n-propyl)phenol in place of neopentyl alcohol (yield: 147 mg, 77%). mp 152–153° C. $^1$H NMR (300 MHz, DMSO-d₆) δ 0.87 (t, J=7 Hz, 3H), 1.54 (h, J=7 Hz, 2H), 3.25 (s, 3H), 5.00 (q, J=9 Hz, 2H), 6.88 (d, J=9 Hz, 2H), 7.09 (d, J=9 Hz, 2H), 7.87 (d, J=8 Hz, 2H), 8.02 (d, J=8 Hz, 2H), 8.32 (s, 1H). MS (DCI/NH₃) m/z 484 (M+H)⁺. Anal. calc. for C₂₂H₂₁F₃N₂O₄S: C, 56.33; H, 4.54; N, 6.01. Found: C, 56.23; H, 4.75; N, 5.79.

EXAMPLE 267

2-(2,2,2-Trifluoroethyl)-4-[4-(methylsulfonyl)phenoxy]-5-[4-(methylsulfonyl)phenyl]-3(2H)-pyridazinone The title compound was prepared according to the method of Example 261, substituting 4-(methylsulfonyl)phenol in place of neopentyl alcohol (yield: 115 mg, 56%). mp 212–213° C. $^1$H NMR (300 MHz, DMSO-d₆) δ 3.21 (s, 3H), 3.27 (s, 3H), 5.03 (q, J=9 Hz, 2H), 7.31 (d, J=9 Hz, 2H), 7.83–7.89 (m, 4H), 8.04 (d, J=8 Hz, 2H), 8.40 (s, 1H). MS (DCI/NH₃) m/z 520 (M+NH₄)⁺. Anal. calc. for C₂₀H₁₇F₃N₂O₆S₂: C, 47.81; H, 3.41; N, 5.58. Found: C, 47.92; H, 3.18; N, 5.52.

EXAMPLE 268

2-(2,2,2-Trifluoroethyl)-4-(4-phenylphenoxy)-5-[4-(methylsulfonyl)phenyl]-3(2H)-pyridazinone The title compound was prepared according to the method of Example 261, substituting 4-phenylphenol in place of neopentyl alcohol (yield: 105 mg, 51%). mp 163–165° C. $^1$H NMR (300 MHz, DMSO-d$_6$) δ 3.26 (s, 3H), 5.02 (q, J=9 Hz, 2H), 7.10 (d, J=8 Hz, 2H), 7.33 (br t, J=7 Hz, 1H), 7.44 (t, J=7 Hz, 2H), 7.57–7.63 (m, 4H), 7.92 (d, J=8 Hz, 2H), 8.04 (d, J=8 Hz, 2H), 8.37 (s, 1H). MS (DCI/NH$_3$) m/z 518 (M+NH$_4$)$^+$. Anal. calc. for C$_{25}$H$_{19}$F$_3$N$_2$O$_4$S: C, 60.00; H, 3.83; N, 5.60. Found: C, 60.18; H, 3.66; N, 5.52.

EXAMPLE 269

2-(2,2,2-Trifluoroethyl)-4-[2-(methylthio)ethoxy]-5-[4-(methylsulfonyl)phenyl]-3(2H)-pyridazinone The title compound was prepared according to the method of Example 261, substituting 2-(methylthio)ethanol in place of neopentyl alcohol (yield: 105 mg, 61%). mp 103–105° C. $^1$H NMR (300 MHz, DMSO-d$_6$) δ 2.01 (s, 3H), 2.72 (t, J=7 Hz, 2H), 3.29 (s, 3H), 4.59 (t, J=7 Hz, 2H), 5.03 (q, J=9 Hz, 2H), 7.91 (d, J=8 Hz, 2H), 8.04 (d, J=8 Hz, 2H), 8.15 (s, 1H). MS (DCI/NH$_3$) m/z 423 (M+H)$^+$, 440 (M+NH$_4$)$^+$. Anal. calc. for C$_{16}$H$_{17}$F$_3$N$_2$O$_4$S$_2$: C, 45.49; H, 4.06; N, 6.33. Found: C, 45.83; H, 4.11; N, 6.42.

EXAMPLE 270

2-(2,2,2-Trifluoroethyl)-4-(phenylmethoxy)-5-[4-(methylsulfonyl)phenyl]-3(2H)-pyridazinone The title compound was prepared according to the method of Example 261, substituting benzyl alcohol in place of neopentyl alcohol (yield: 137 mg, 76%). mp 121–123° C. $^1$H NMR (300 MHz, DMSO-d$_6$) δ 3.28 (s, 3H), 5.06 (q, J=9 Hz, 2H), 5.48 (s, 2H), 7.20–7.25 (m, 2H), 7.27–7.81 (m, 3H), 7.76 (d, J=8 Hz, 2H), 7.98 (d, J=8 Hz, 2H), 8.12 (s, 1H). MS (DCI/NH$_3$) m/z 456 (M+H)$^+$. Anal. calc. for C$_{20}$H$_{17}$F$_3$N$_2$O$_4$S: C, 54.79; H, 3.91; N, 6.39. Found: C, 55.10; H, 3.91; N, 6.13.

EXAMPLE 271

2-(2,2,2-Trifluoroethyl)-4-(2-furylmethoxy)-5-[4-(methylsulfonyl)phenyl]-3(2H)-pyridazinone The title compound was prepared according to the method of Example 261, substituting 2-(hydroxymethyl)furan in place of neopentyl alcohol (yield: 101 mg, 58%). mp 113–115° C. $^1$H NMR (300 MHz, DMSO-d$_6$) δ 3.28 (s, 3H), 5.07 (q, J=9 Hz, 2H), 5.52 (s, 2H), 6.41 (dd, J=2 Hz, 3 Hz, 1H), 6.45 (d, J=4 Hz, 1H), 7.62 (d, J=2 Hz, 1H), 7.69 (d, J=8 Hz, 2H), 7.97 (d, J=8 Hz, 2H), 8.13 (s, 1H). MS (DCI/NH$_3$) m/z 446 (M+NH$_4$)$^+$. Anal. calc. for C$_{18}$H$_{15}$F$_3$N$_2$O$_5$S: C, 50.66; H, 3.80; N, 6.21. Found: C, 51.02; H, 3.71; N, 6.23.

EXAMPLE 272

2-(2,2,2-Trifluoroethyl)-4-[2-(3,4-dimethoxyphenyl)ethoxy]-5-[4-(methylsulfonyl)phenyl]-3(2H)-pyridazinone The title compound was prepared according to the method of Example 261, substituting 2-(3,4-dimethoxyphenyl)ethanol in place of neopentyl alcohol (yield: 118 mg, 56%). mp 133–134° C. $^1$H NMR (300 MHz, DMSO-d$_6$) δ 2.82 (t, J=7 Hz, 2H), 3.28 (s, 3H), 3.63 (s, 3H), 3.70 (s, 3H), 4.68 (t, J=7 Hz, 2H), 5.01 (q, J=9 Hz, 2H), 6.61 (dd, J=2 Hz, 8 Hz, 1H), 6.74 (d, J=2 Hz, 1H), 6.77 (d, J=8 Hz, 1H), 7.74 (d, J=8 Hz, 2H), 7.93 (d, J=8 Hz, 2H), 8.11 (s, 1H). MS (DCI/NH$_3$) m/z 530 (M+NH$_4$)$^+$. Anal. calc. for C$_{23}$H$_{23}$F$_3$N$_2$O$_6$S: C, 53.90; H, 4.52; N, 5.47. Found: C, 53.87; H, 4.48; N, 5.45.

EXAMPLE 273

2-(2,2,2-Trifluoroethyl)-4-[2-(4-morpholino)ethoxy)]-5-[4-(methylsulfonyl)phenyl]-3(2H)-pyridazinone The title compound was prepared according to the method of Example 261, substituting 4-(2-hydroxyethyl)morpholine in place of neopentyl alcohol (yield: 111 mg, 59%). mp 147–148° C. $^1$H NMR (300 MHz, DMSO-d$_6$) δ 2.23 (m, 4H), 2.46 (t, J=5 Hz, 2H), 3.28 (s, 3H), 3.40 (m, 4H), 4.60 (t, J=5 Hz, 2H), 5.02 (q, J=8 Hz, 2H), 7.96 (d, J=8 Hz, 2H), 8.03 (d, J=8 Hz, 2H), 8.17 (s, 1H). MS (DCI/NH$_3$) m/z 462 (M+H)$^+$. Anal. calc. for C$_{19}$H$_{22}$F$_3$N$_3$O$_5$S: C, 49.45; H, 4.81; N, 9.11. Found: C, 49.59; H, 4.80; N, 8.88.

EXAMPLE 274

2-(2,2,2-Trifluoroethyl)-4-[2-(1-piperidinyl)ethoxy]-5-[4-(methylsulfonyl)phenyl]-3(2H)-pyridazinone The title compound was prepared according to the method of Example 261, substituting 1-(2-hydroxyethyl)piperidine in place of neopentyl alcohol (yield: 103 mg, 55%). mp 117–118° C. $^1$H NMR (300 MHz, DMSO-d$_6$) δ 1.30 (br s, 6H), 2.20 (br s, 4H), 2.41 (t, J=4 Hz, 2H), 3.28 (s, 3H), 4.60 (t, J=5 Hz, 2H), 5.02 (q, J=9 Hz, 2H), 7.97 (d, J=8 Hz, 2H), 8.03 (d, J=8 Hz, 2H), 8.15 (s, 1H). MS (DCI/NH$_3$) m/z 460 (M+H)+$^+$. Anal. calc. for C$_{20}$H$_{24}$F$_3$N$_3$O$_4$S: C, 52.28; H, 5.26; N, 9.15. Found: C, 52.22; H, 5.08; N, 8.94.

EXAMPLE 275

2-(2,2,2-Trifluoroethyl)-4-[4-(carboxamido)phenoxy)]-5-[4-(methylsulfonyl)phenyl]-3(2H)-pyridazinone The title compound was prepared according to the method of Example 261, substituting 4-hydroxybenzamide in place of neopentyl alcohol (yield: 50 mg, 26%). mp>250° C. $^1$H NMR (300 MHz, DMSO-d$_6$) δ 3.26 (s, 3H), 5.02 (q, J=8 Hz, 2H), 7.08 (d, J=9 Hz, 2H), 7.30 (s, 1H), 7.82 (d, J=9 Hz, 2H), 7.88 (d, J=8 Hz, 2H), 7.92 (s, 1H), 8.03 (d, J=8 Hz, 2H), 8.47 (s, 1H). MS (DCI/NH$_3$) m/z 468 (M+H)$^+$, 485 (M+NH$_4$)$^+$. Anal. calc. for C$_{20}$H$_{16}$F$_3$N$_3$O$_5$S: C, 51.39; H, 3.45; N, 8.99. Found: C, 51.31; H, 3.28; N, 8.77.

EXAMPLE 276

2-(2,2,2-Trifluoroethyl)-4-(1-indanyloxy)-5-[4-(methylsulfonyl)phenyl]-3(2H)-pyridazinone The title compound was prepared according to the method of Example 261, substituting 1-indanol in place of neopentyl alcohol (yield: 84 mg, 44%). mp 113–114° C. $^1$H NMR (300 MHz, DMSO-d$_6$) δ 2.07–2.14 (m, 1H), 2.22–2.35 (m, 1H), 2.73 (dd, J=5 Hz, 7 Hz, 2H), 3.24 (s, 3H), 5.00–5.22 (m, 2H), 6.48 (dd, J=2 Hz, 6 Hz, 1H), 7.12–7.24 (m, 2H), 7.21–7.28 (m, 2H), 7.44 (d, J=8 Hz, 2H), 7.87 (d, J=8 Hz, 2H), 8.09 (s, 1H). MS (DCI/NH$_3$) m/z 482 (M+NH$_4$)$^+$. Anal. calc. for C$_{22}$H$_{19}$F$_3$N$_2$O$_4$S: C, 57.19; H, 4.48; N, 5.80. Found: C, 57.36; H, 4.30; N, 5.78.

EXAMPLE 277

2-(2,2,2-Trifluoroethyl)-4-[4-(acetamido)phenoxy)]-5-[4-(methylsulfonyl)phenyl]-3(2H)-pyridazinone The title compound was prepared according to the method of Example 261, substituting 4-acetamidophenol in place of neopentyl alcohol (yield: 45 mg, 23%). mp 215–216° C. $^1$H NMR (300 MHz, DMSO-d$_6$) δ 2.02 (s, 3H), 3.26 (s, 3H), 5.02 (q, J=8 Hz, 2H), 6.61–6.65 (m, 1H), 7.17–7.20 (m, 2H), 7.34 (br s, 1H), 7.88 (d, J=9 Hz, 2H ), 8.03 (d, J=8 Hz, 2H), 8.36 (s, 1H), 9.97 (s, 1H). MS (DCI/NH$_3$) m/z 499 (M+NH$_4$)$^+$. Anal. calc. for C$_{21}$H$_{18}$F$_3$N$_3$O$_5$S: C, 52.39; H, 3.77; N, 8.73. Found: C, 52.57; H, 4.02; N, 8.37.

EXAMPLE 278

2-(2,2,2-Trifluoroethyl)-4-(2-methylpropoxy)-5-[4-(methylsulfonyl)phenyl]-3(2H)-pyridazinone The title compound was prepared according to the method of Example 261, substituting 2-methylpropanol in place of neopentyl alcohol (yield: 111 mg, 50%). mp 108–110° C. $^1$H NMR (300 MHz, DMSO-d$_6$) δ 0.77 (d, J=6.4 Hz, 6H), 1.52 (sept, J=6.4 Hz, 1H), 3.28 (s, 3H), 4.17 (d, J=6 Hz, 2H), 5.02 (q, J=9 Hz, 2H), 7.88 (d, J=9 Hz, 2H), 8.04 (d, J=9 Hz, 2H), 8.14 (s, 1H). MS (DCI/NH$_3$) m/z 405 (M+H)$^+$, 422 (M+NH$_4$)$^+$. Anal. calc. for C$_{17}$H$_{19}$F$_3$N$_2$O$_4$S: C, 50.49; H, 4.74; N, 6.93. Found: C, 50.69; H, 4.89; N, 6.75.

EXAMPLE 279

2-(2,2,2-Trifluoroethyl)-4-(1-methylcyclopropylmethoxy)-5-[4-(methylsulfonyl)phenyl]-3(2H)-pyridazinone The title compound was prepared according to the method of Example 261, substituting 1-methylcyclopropanemethanol in place of neopentyl alcohol (yield: 360 mg, 75.5%). mp 98–99° C. $^1$H NMR (300 MHz, CDCl$_3$) δ 0.35 (dt, J=40 Hz, 5 Hz, 4H), 0.91 (s, 3H), 3.11 (s, 3H), 4.32 (s, 2H), 4.82 (q, J=8.5 Hz, 2H), 7.80 (d, J=8.5 Hz, 2H), 7.84 (s, 1H), 8.06 (d, J=9 Hz, 2H). MS (DCI/NH$_3$) m/z 417 (M+H)$^+$, m/z 434 (M+NH$_4$)$^+$. Anal. calc. for C$_{18}$H$_{19}$F$_3$N$_2$O$_4$S: C, 51.92; H, 4.60; N, 6.73. Found: C, 51.87; H, 4.72; N, 6.69.

EXAMPLE 280

2-(2,2,2-Trifluoroethyl)-4-(3,3-dimethylbutoxy)-5-[4-(methylsulfonyl)phenyl]-3(2H)-pyridazinone The title compound was prepared according to the method of Example 261, substituting 3,3-dimethyl-1-butanol in place of neopentyl alcohol (yield: 270 mg, 67.4%). mp 83–85°C. $^1$H NMR (300 MHz, CDCl$_3$) δ 0.88 (s, 9H), 1.56 (t, J=8 Hz, 2H), 4.60 (t, J=8 Hz, 2H), 4.83 (q, J=8.5 Hz, 2H), 7.73 (d, J=8.5 Hz, 2H), 7.81 (s, 1H), 8.05 (d, J=8.5 Hz, 2H). MS (DCI/NH$_3$) m/z 433 (M+H)$^+$, m/z 450 (M+NH$_4$)$^+$. Anal. calc. for C$_{19}$H$_{23}$F$_3$N$_2$O$_4$S: C, 52.77; H, 5.36; N, 6.48. Found: C, 52.95; H, 5.29; N, 6.35.

EXAMPLE 281

2-(3,4-Difluorophenyl)-4-(4-chlorophenoxy)-5-[4-(methylsulfonyl)phenyl]-3(2H)-pyridazinone A mixture of 2-benzyl-4-chloro-5-[4-(methylsulfonyl) phenyl]-3(2H)-pyridazinone (187 mg, 0.5 mmol), prepared in Example 78, p-chlorophenol (129 mg, 0.5 mmol) and NaH (60% oil suspension) (40 mg, 1 mmol) in THF (25 mL) was refluxed at 50° C. for 3 hours and then concentrated in vacuo. The residue was partitioned between water and ethyl acetate. The acetate layer was washed with brine, dried over MgSO$_4$ and concentrated in vacuo. The residue was chromatographed (silica gel, 1:1 hexanes-ethyl acetate) to provide 2-benzyl-4-(4-chlorophenoxy)-5-[4-(methylsulfonyl) phenyl]-3(2H)-pyridazinone (yield: 200 mg, 82%).

The above derivative was dissolved in toluene (25 mL) and was treated with AlBr$_3$ (400 mg, 1.5 mmol) for 20 minutes at 80° C. The mixture was cooled to room temperature and poured into ice-10% citric acid-ethyl acetate. The organic layer was separated, dried over MgSO$_4$ and concentrated in vacuo to provide crude desbenzyl derivative. This compound was immediately dissolved in pyridine (50 mL) and was treated with 3,4-difluorobromobenzene (0.17 mL, 1.5 mmol), Cu (20 mg) and K$_2$CO$_3$ (100 Mg, 1.5 mmol) at reflux for 16 hours. After the mixture was concentrated in vacuo, the residue was dissolved in ethyl acetate and was washed with water, 10% citric acid and brine. Purification by column chromatography (silica gel, 1:1 hexanes-ethyl acetate) provided the title compound (yield: 73 mg, 30%). mp 192–194° C. $^1$H NMR (300 MHz, DMSO-d$_6$) δ 3.22 (s, 3H), 7.13 (m, 2H), 7.35 (m, 2H), 7.50 (m, 1H), 7.60 (m, 1H), 7.75 (m, 1H), 7.87 (d, J=9 Hz, 2H), 8.05 (d, J=9 Hz, 2H), 8.41 (s, 1H). MS (APCI+) m/z 488 (M+H)$^+$ and (APCI–) m/z 523 (M+Cl)$^-$.

EXAMPLE 282

2-(3,4-Difluorophenyl)-4-(4-bromophenoxy)-5-[4-(methylsulfonyl)phenyl]-3(2H)-pyridazinone The title compound was prepared according to the method of Example 281, substituting p-bromophenol in place of p-chlorophenol (yield: 54 mg, 20%). mp 196–199° C. $^1$H NMR (300 MHz, DMSO-d$_6$) δ 3.25 (s, 3H), 7.09 (d, J=9 Hz, 2H), 7.47 (d, J=9 Hz, 2H), 7.52 (m, 1H), 7.62 (m, 1H), 7.78 (m, 1H), 7.89 (d, J=9 Hz, 2H), 8.05 (d, J=9 Hz, 2H), 8.41 (s, 1H). MS (APCI+) m/z 533 (M+H)$^+$ and (APCI–) m/z 569 (M+Cl)$^-$.

EXAMPLE 283

2-(2,2,2-Trifluoroethyl)-4-(cyclopentylthio)-5-[4-(methylsulfonyl)phenyl]-3(2H)-pyridazinone To a solution of NaH (26 mg, 1.1 mmol) in acetonitrile (3.0 mL), under nitrogen, was added cyclopentyl mercaptan (120 μL, 1.1 mmol) dropwise via syringe. The resulting solution was flushed with nitrogen for a period of 20 minutes; after which 2-(2,2,2-trifluoroethyl)-4-chloro-5-[4-(methylsulfonyl)phenyl]-3(2H)-pyridazinone, prepared in Example 193E, (200 mg, 0.52 mmol) was added in one portion. The solution was stirred for an additional 20 minutes at which time, all the 4-bromo pyridazinone was consumed. The solution was analyzed by TLC (1:1, ethyl acetate-Hex). Water (5 mL) was carefully added and the reaction partitioned between ethyl acetate (125 mL) and saturated saline (50 mL). The organic layer is washed with saturated saline (50 mL), dried over $MgSO_4$, and concentrated in vacuo. Silica gel chromatography (20% ethyl acetate-80% hexanes) provided a pale yellow solid (yield: 202 mg, 83.1%). mp 149–151° C. $^1$H NMR (300 MHz, $CDCl_3$) δ 1.40–1.34 (m, 2H), 1.62–1.54 (m, 4H), 1.93–1.88 (m, 2H), 3.13 (s, 3H), 4.40–4.35 (m, 1H), 4.85 (q, J=8.2 Hz, 2H), 7.58 (d, J=8.5 Hz, 2H), 7.66 (s, 1H), 8.06 (d, J=8.4 Hz, 2H); MS (DCI/$NH_3$) m/z 432 (M+H)$^+$, (M+$NH_4$)$^+$. Anal. calc. for $C_{18}H_{19}F_3N_2O_3S_2$: C, 49.99; H, 4.43; N, 6.48. Found: C, 50.15; H, 4.39; N, 6.45.

EXAMPLE 284

2-(2,2,2-Trifluoroethyl)-4-(1H-1,2,4-triazole-3-ylthio)-5-[4-(methylsulfonyl)phenyl]-3(2H)-pyridazinone The title compound was prepared according to the method of Example 283, substituting 1H-1,2,4-triazole-3-thiol in place of cyclopentyl mercaptan (yield: 164 mg, 93%). mp 197–200° C. $^1$H NMR (300 MHz, $CDCl_3$) δ 3.14 (s, 3H), 4.84 (q, J=8.1 Hz, 2H), 7.41 (s, 1H), 7.68 (d, J=6.8 Hz, 2H), 7.83 (s, 1H), 8.00 (d, J=7.1 Hz, 2H),8.05 (s, 1H). MS (DCI/$NH_3$) m/z 431 (M+H)$^+$, (M+$NH_4$)$^+$. Anal. calc. for $C_{15}H_{12}F_3N_2O_3S_2$: C, 41.76; H, 2.80; N, 16.23. Found: C, 41.68; H, 2.85; N, 15.99.

EXAMPLE 285

2-(2,2,2-Trifluoroethyl)-4-phenylmethylthio-5-[4-(methylsulfonyl)phenyl]-3(2H)-pyridazinone The title compound was prepared according to the method of Example 283, substituting benzyl mercaptan in place of cyclopentyl mercaptan (yield: 141 mg, 76%). mp 108–111° C. $^1$H NMR (300 MHz, $CDCl_3$) δ 3.01 (s, 3H), 4.38 (s, 2H), 4.87 (q, J=Hz, 2H), 7.10–7.06 (m, 2H), 7.22–7.20 (m, 5H), 7.59 (s, 1H), 7.95 (d, J=8.5 Hz 2H). MS (DCI/$NH_3$) m/z 454 (M+H)$^+$, (M+$NH_4$)$^+$. Anal. calc. for $C_{20}H_{17}F_3N_2O_3S_2$, 0.75 EtOAc: C, 53.06; H, 4.45 ; N, 5.38. Found: C, 53.55; H, 4.16; N, 5.84.

EXAMPLE 286

2-(2,2,2-Trifluoroethyl)-4-(4-fluorophenylthio)-5-[4-(methylsulfonyl)phenyl]-3(2H)-pyridazinone The title compound was prepared according to the method of Example 283, substituting 4-fluorophenylmethyl mercaptan in place of cyclopentyl mercaptan (yield: 184 mg, 73.5%). mp 182–185° C. $^1$H NMR (300 MHz, $CDCl_3$) δ 3.08 (s, 3H), 4.82 (q, J=8.5 Hz, 2H), 6.87–6.81 (m, 2H), 7.19–7.11 (m, 2H), 7.48 (d, J=9.0 Hz, 2H), 7.68 (s, 1H), 7.93 (d, J=8.5 Hz, 2H). MS (DCI/$NH_3$) m/z 458 (M+H)$^+$, (M+$NH_4$)$^+$. Anal. calc. for $C_{19}H_4F_4N_2O_3S_2$: C, 49.78; H, 3.08; N, 6.11. Found: C, 49.89; H, 3.18; N, 5.86

EXAMPLE 287

2-(2,2,2-Trifluoroethyl)-4-(cyclohexylthio)-5-[4-(methylsulfonyl)phenyl]-3(2H)-pyridazinone The title compound was prepared according to the method of Example 283, substituting cyclohexyl mercaptan in place of cyclopentyl mercaptan (yield: 189 mg, 78%). mp 165–167° C. $^1$H NMR (300 MHz, $CDCl_3$) δ 1.28–1.17 (m, 5H), 1.64–1.56 (m, 3H), 1.82–1.79 (m, 2H), 3.13 (s, 3H), 4.08–4.05 (m, 1H), 4.86 (q, J=8.5 Hz, 2H), 7.58 (d, J=8.4 Hz, 2H), 7.67 (s, 1H), 8.06 (d, J=8.5 Hz, 2H). MS (DCI/$H_3$) m/z 446 (M+H)$^+$, (M+$NH_4$)$^+$. Anal. calc. for $C_{19}H_{21}F_3N_2O_3S_2$: C, 51.11; H, 4.74 ; N, 6.27. Found: C, 51.39; H, 4.72 ; N, 5.91.

EXAMPLE 288

2-(2,2,2-Trifluoroethyl)-4-(3-chloro-4-fluorophenylthio)-5-[4-(methylsulfonyl)phenyl]-3(2H)-pyridazinone The title compound was prepared according to the method of Example 283, substituting 3-chloro-4-fluorothiophenol in place of cyclopentyl mercaptan (yield: 190 mg, 65%). mp 142–145° C. $^1$H NMR (300 MHz, $CDCl_3$) δ 3.18 (s, 3H), 4.85 (q, J=8.4 Hz, 2H), 6.96 (ov. t, J=8.5 Hz, 1H), 7.14–7.10 (m, 1H), 7.18 (dd, J=2.1, 6.5 Hz, 1H,), 7.53 (d, J=8.4 Hz, 2H), 7.77 (s, 1H), 7.96 (d, J=8.0 Hz, 2H). MS (CI) m/z 493 (M+1)$^+$, (M+$NH_4$)$^+$. Anal. calc. for $C_{19}H_{13}ClF_4N_2O_3S_2 \cdot 0.25\ C_6H_6 \cdot H_2O$: C, 47.36; H, 2.92; N, 5.41. Found: C, 47.88; H, 2.95; N, 5.24.

EXAMPLE 289

2-(2,2,2-Trifluoroethyl)-4-(2,2,2-trifluoroethylthio)-5-[4-(methylsulfonyl)phenyl]-3(2H)-pyridazinone The title compound was prepared according to the method of Example 283, substituting 2,2,2-trifluoroethyl mercaptan in place of cyclopentyl mercaptan (yield: 175 mg, 66%). mp 155–158° C. $^1$H NMR (300 MHz, $CDCl_3$) δ 3.14 (s, 3H), 3.98 (q, J=9.8 Hz, 2H), 4.86 (q, J=8.1 Hz, 2H), 7.58 (d, J=8.4 Hz, 2H), 7.75 (s, 1H), 8.10 (d, J=8.4 Hz, 2H). MS (DCI/$NH_3$) m/z 446 (M+H)$^+$, (M+$NH_4$)$^+$. Anal. calc. for $C_{15}H_{12}F_6N_2O_3S_2$: C, 40.36; H, 2.71; N, 6.28. Found: C, 40.50; H, 2.72; N, 6.01.

EXAMPLE 290

2-(2,2,2-Trifluoroethyl)-4-(tert-butylthio)-5-[4-(methylsulfonyl)phenyl]-3(2H)-pyridazinone The title compound was prepared according to the method of Example 283, substituting tert-butyl mercaptan in place of cyclopentyl mercaptan (yield: 212 mg, 85%). mp 186–189° C. $^1$H NMR (300 MHz, $CDCl_3$) δ 1.25 (s, 9H), 3.13 (s, 3H), 4.87 (q, J=8.1 Hz, 2H), 7.62 (d, J=8.5 Hz, 2H), 7.67 (s, 1H), 8.05 (d, J=8.1 Hz, 2H). MS (ESI) m/z 420 (M+H)$^+$, (M+Na)$^+$. Anal. calc. for $C_{17}H_{19}F_3N_2O_3S_2$: C, 48.56 ; H, 4.55; N, 6.66. Found: C, 50.15; H, 4.39; N, 6.45.

EXAMPLE 291

2-(2,2,2-Trifluoroethyl)-4-(4-acetamidophenylthio)-5-[4-(methylsulfonyl)phenyl]-3(2H)-pyridazinone The title compound was prepared according to the method of Example 283, substituting 4-acetamidothiophenol in place of cyclopentyl mercaptan (yield: 100 mg, 37%). mp 191–193° C. $^1$H NMR (300 MHz, $CDCl_3$) δ 2.16 (s, 3H), 3.08 (s, 3H), 4.83 (q, J=8.2 Hz, 2H), 7.00 (d, J=8.8 Hz, 2H), 7.19 (d, J=8.8 Hz, 2H), 7.31 (d, J=8.1 Hz, 2H), 7.58 (s, 1H), 7.78 (d, J=8.1 Hz, 2H). MS (CI) m/z 497 (M+H)$^+$, (M+$NH_4$)$^+$. Anal. calc. for $C_{21}H_{18}F_3N_3O_4S_2 \cdot 0.25H_2O$, 0.25 $C_6H_6$: C, 52.83; H, 4.06; N, 7.70. Found: C, 52.97; H, 3.85; N, 7.65.

EXAMPLE 292

2-(2,2,2-Trifluoroethyl)-4-(2-propylthio)-5-[4-(methylsulfonyl)phenyl]-3(2H)-pyridazinone The title compound was prepared according to the method of Example 283, substituting isopropyl mercaptan in place of cyclopentyl mercaptan (yield: 180 mg, 81%). mp 165–167° C. $^1$H NMR (300 MHz, CDCl$_3$) δ 1.17 (d, J=6.8 Hz, 6H), 3.13 (s, 3H), 4.33 (p, J=6.8 Hz, 1H), 4.86 (q, J=8.5 Hz, 2H), 6.59 (d, J=8.5 Hz, 2H), 7.68 (s, 1H), 8.07 (d, J=8.1 Hz, 2H). MS (DCI/NH$_3$) m/z 406 (M+H)$^+$, (M+NH$_4$)$^+$. Anal. calc. for C$_{16}$H$_{17}$F$_3$N$_2$O$_3$S$_2$, 0.75H$_2$O: C, 45.76 ; H, 4.4; N, 6.67. Found: C, 45.91; H, 3.98; N, 6.46.

EXAMPLE 293

2-(2,2,2-Trifluoroethyl)-4-(2-methylprop-1-ylthio)-5-[4-(methylsulfonyl)phenyl]-3(2H)-pyridazinone The title compound was prepared according to the method of Example 283, substituting 2-methyl-1-propyl mercaptan in place of cyclopentyl mercaptan (yield: 100 mg, 83%). mp 135–138° C. $^1$H NMR (300 MHz, CDCl$_3$) δ 0.87 (d, J=6.4 Hz, 6H), 1.67–1.60 (m, 1H), 3.00 (d, J=6.7 Hz, 2H), 3.14 (s, 3H), 4.84 (q, J=8.5 Hz, 2H), 7.61 (d, J=8.4 Hz, 2H), 7.67 (s, 1H), 8.08 (d, J=8.5 Hz, 2H). MS (DCI/NH$_3$) m/z 420 (M+H)$^+$, (M+NH$_4$)$^+$. Anal. calc. for C$_{17}$H$_{19}$F$_3$N$_2$O$_3$S$_2$: C, 48.56 ; H, 4.55; N, 6.66. Found: C, 47.86; H, 4.57; N, 6.51.

EXAMPLE 294

2-(2,2,2-Trifluoroethyl)-4-amino-5-[4-(methylsufonyl)phenyl]-3(2H)-pyridazinone 2-(2,2,2-Trifluoroethyl)-4-chloro-5-[4-(methylsulfonyl)phenyl]-3(2H)-pyridazinone, prepared according to Example 193E, (500 mg, 1.36 mmol) was dissolved in DMF (10 mL) and treated with NaN$_3$ (100 mg, 1.5 mmol). After 2 hours at room temperature, the reaction was diluted with ethyl acetate and washed with water, 4 times, and dried over MgSO$_4$. After filtration of the drying agent and concentration of the filtrate in vacuo, the residue was purified by chromatography on silica gel (Biotage 40S) eluted with 2:1 hexanes-ethyl acetate. The product fractions were combined and evaporated to provide the azido intermediate, 2-(2,2,2-Trifluoroethyl)-4-azido-5-[4-(methylsulfonyl)phenyl]-3(2H)-pyridazinone (yield: 481 mg, 95%).

The 4-azido-compound above (39 mg, 0.105 mmol) was dissolved in THF (3 mL) and MeOH (2 mL) and treated with excess NaH$_4$. After 15 minutes, the reaction was quenched with saturated NH$_4$Cl solution and the product was extracted into ethyl acetate. The organic layer was washed with water, 3 times, and dried over MgSO$_4$. Filtration of the drying agent and evaporation of the solvent provided the title compound (yield: 26 mg, 71%). mp>260° C. $^1$H NMR (300 MHz, DMSO-d$_6$) δ 3.26 (s, 3H), 4.93 (q, J=9 Hz, 2H), 6.71 (s, 2H), 7.72 (s, 1H), 7.76 (d, J=8 Hz, 2H), 8.02 (d, J=8 Hz, 2H). MS (ESI-) m/z 346 (M-H)$^-$. Anal. calc. for C$_{13}$H$_{12}$F$_3$N$_3$O$_3$S: C, 44.96; H, 3.48; N, 12.10. Found: C, 44.59; H, 3.52; N, 11.93.

EXAMPLE 295

2-(2,2,2-Trifluoroethyl)-4-(3-methoxypropylamino)-5-[4-(methylsulfonyl)phenyl]-3(2H)-pyridazinone A solution of 2-(2,2,2-trifluoroethyl)-4-chloro-5-[4-(methylsulfonyl)phenyl]-3(2H)-pyridazinone (200 mg, 0.546 mmol), prepared according to the method of Example 193E, and 3-methoxypropylamine (145 mg, 1.64 mmol) in pyridine (4 mL) was heated at 100° C. for 16 hours. The reaction mixture was cooled to room temperature, mixed with silica gel (2 g), and the solvent removed under reduced pressure. The adsorbed silica gel was layered over an Extract-Clean Cartridge® (Alltech, packing: 10 g silica gel) and the cartridge eluted with a hexanes/acetone step gradient consisting of 60 mL of each of the following mixtures: hexanes, 8:1 hexanes/acetone, 4:1, 2:1, and 1:1. Fractions containing desired product were combined, concentrated, and further purified using HPLC (Technikrom Kromasil 60–5 sil silica column, 20 mm×25 cm). The column was eluted with a linear gradient consisting of 30% ethyl acetate/hexanes to 100% ethyl acetate at 10 mL/min over 50 minutes. Fractions containing product were combined and concentrated under reduced pressure to provide the product as off-white crystals (yield: 215 mg, 95%). mp 110–113° C. $^1$H NMR (300 MHz, CDCl$_3$) δ 8.02 (d, J=18.0 Hz, 2H), 7.55 (d, 2H, J=18.0 Hz), 7.48 (s, 1H), 6.57 (br t, 1H, J=9.0 Hz), 4.81 (q, J=17.4 Hz, 2H), 3.33 (t, J=12.0 Hz, 2H), 3.28 (s, 3H), 3.12 (s, 3H), 2.76 (dt, J=12.0, 12.0 Hz, 2H), 1.65 (tt, J=12.0, 12.0, Hz, 2H). MS (DCI/NH$_3$) m/z 420 (M+H)$^+$, m/z 437 [M+NH$_4$]+. Anal. calc. for C$_{17}$H$_{20}$F$_3$N$_3$O$_4$S: C, 48.68; H, 4.81; N, 10.02. Found: C, 48.74; H, 4.69; N, 9.84.

EXAMPLE 296

2-(2,2,2-Trifluoroethyl)-4-(cyclopentylamino)-5-[4-(methylsulfonyl)phenyl-3(2H)-pyridazinone The product was prepared according to the method of Example 295, substituting cyclopentylamine in place of 3-methoxypropylamine to provide brown crystals (yield: 195 mg, 86%). mp 134–139° C. $^1$H NMR (300 MHz, CDCl$_3$) δ 8.03 (d, J=18.0 Hz, 2 H), 7.56 (d, J=18.0 Hz, 2H), 7.45 (s, 1H), 6.12 (br d, J=16.8 Hz, 1H), 4.79 (q, J=17.4 Hz, 2H), 3.33 (br m, 1H), 3.12 (s, 3H), 1.64–1.23 (br m, 8H). MS (DCI/NH$_3$) m/z 416 (M+H)$^+$, m/z 433 (M+NH$_4$)$^+$. Anal. calc. for C$_{18}$H$_{20}$F$_3$N$_3$O$_3$S: C, 52.04; H, 4.85; N, 10.11. Found: C, 52.40; H, 4.93; N, 10.03.

EXAMPLE 297

2-(2,2,2-Trifluoroethyl)-4-(cyclobutylamino)-5-[4-(methylsulfonyl)phenyl]-3(2H)-pyridazinone The product was prepared according to the method of Example 295, substituting cyclobutylamine in place of 3-methoxypropylamine to provide an off-white solid (yield: 206 mg, 94%). mp 169–172° C. $^1$H NMR (300 MHz, CDCl$_3$) δ 8.03 (d, J=17.4 Hz, 2H), 7.54 (d, J=17.4 Hz, 2H), 7.45 (s, 1H), 6.28 (br d, J=16.2 Hz, 1H), 4.81 (q, J=17.4 Hz, 2H), 3.42 (m, 1H), 3.13 (s, 3H), 1.79 (m, 4H), 1.64 (m, 1H), 1.39 (m, 1H). MS (DCI/NH$_3$) m/z 402 (M+H)$^+$, m/z 419 (M+NH$_4$)$^+$. Anal calc. for C$_{17}$H$_{18}$F$_3$N$_3$O$_3$S.0.25 CH$_3$COCH$_3$; C, 51.25; H, 4.72; N, 10.10; found: C, 51.38; H, 4.68; N, 10.25.

EXAMPLE 298

2-(2,2,2-Trifluoroethyl)-4-(3,4-dimethoxyphenethylamino)-5-[4-(methylsulfonyl)phenyl]-3(2H)-pyridazinone The product was prepared according to the method of Example 295, substituting 3,4-dimethoxyphenethylamine in place of 3-methoxypropylamine to provide an off-white solid (yield: 206 mg, 94%). mp 163–165° C. $^1$H NMR (300

MHz, CDCl$_3$) δ 8.02 (d, J=18.0 Hz, 2H), 7.52 (d, J=18.0 Hz, 2H), 7.45 (s, 1H), 6.75 (d, J=16.2 Hz, 1H), 6.50 (m, 2H), 6.16 (br d, J=11.4 Hz, 1H), 4.79 (q, J=17.4 Hz, 2H), 3.84 (s, 3H), 3.83 (s, 3H), 3.11 (s, 3H), 2.91 (dt, J=12.6, 12.6 Hz, 2H), 2.60 (t, J=13.8 Hz, 2H). MS (DCI/NH$_3$) m/z 529 (M+NH$_4$)$^+$. Anal. calc. for C$_{23}$H$_{24}$F$_3$N$_3$O$_5$S: C, 54.01; H, 4.73; N, 8.21. Found: C, 54.30; H, 4.69; N, 8.16.

EXAMPLE 299

2-(2,2,2-Trifluoroethyl)-4-(cyclohexylamino)-5-[4-(methylsulfonyl)phenyl]-3(2H)-pyridazinone The product was prepared according to the method of Example 295, substituting cyclohexylamine in place of 3-methoxypropylamine to provide an off-white solid (yield: 103 mg, 42%). $^1$H NMR (300 MHz, CDCl$_3$) δ 8.04 (d, J=18.0 Hz, 2H), 7.58 (d, J=18.0 Hz, 2H), 7.44 (s, 1H), 6.06 (br d, J=18.6 Hz, 1H), 4.81 (q, J=18.0 Hz, 2H), 3.11 (s, 3H), 2.70 (m, 1H), 1.66–1.48 (m, 4H), 1.42 (m, 1H), 1.07 (m, 3H), 0.76 (m, 2H). MS (DCI/NH$_3$) m/z 430 (M+H)$^+$, m/z 447 (M+NH$_4$)$^+$. Anal. calc. for C$_{19}$H$_{22}$F$_3$N$_3$O$_3$S: C, 53.14; H, 5.16; N, 9.78. Found: C, 52.86; H, 5.06; N, 9.52.

EXAMPLE 300

2-(2,2,2-Trifluoroethyl)-4-[2-(1-piperidinyl)ethylamino]-5-[4-(methylsulfonyl)phenyl]-3(2H)-pyridazinone The product was prepared according to the method of Example 295, substituting 2-(1-piperdinyl)ethylamine in place of 3-methoxypropylamine to provide an off-white solid (yield: 210 mg, 84%). $^1$H NMR (300 MHz, CDCl$_3$) δ 8.02 (d, J=18.0 Hz, 2H), 7.56 (d, J=18.0 Hz, 2H), 7.49 (s, 1H), 6.91 (br, 1H), 4.82 (q, J=18.0 Hz, 2H), 3.13 (s, 3H), 2.64 (br, 2H), 2.32 (br, 4H), 1.58 (br, 6H), 1.42 (br, 2H). MS (DCI/NH$_3$) m/z 459 (M+H)$^+$. Anal. calc. for C$_{19}$H$_{22}$F$_3$N$_3$O$_3$S: C, 52.39; H, 5.50; N, 12.22. Found: C, 52.64; H, 5.59; N, 12.00.

EXAMPLE 301

2-(2,2,2-Trifluoroethyl)-4-(2-tetrahydrofurfurylamino)-5-[4-(methylsulfonyl)phenyl]-3(2H)-pyridazinone The product was prepared according to the method of Example 295, substituting tetrahydrofurfurylamine in place of 3-methoxypropylamine to provide an off-white solid (yield: 150 mg, 64%). mp 128–129° C. $^1$H NMR (300 MHz, CDCl$_3$) δ 8.03 (d, J=18.0 Hz, 2H), 7.56 (d, J=18.0 Hz, 2H), 7.47 (s, 1H), 6.48 (br t, J=9.0 Hz, 1H), 4.81 (q, J=18.0 Hz, 2H), 3.84 (m, 2H), 3.72 (m, 1H), 3.12 (s, 3H), 2.83 (m, 1H), 2.64 (m, 1H), 1.84 (m, 3H), 1.34 (m, 1H). MS (DCI/NH$_3$) m/z 432 (M+H)$^+$, m/z 449 (M+NH$_4$)$^+$. Anal. calc. for C$_{18}$H$_{20}$F$_3$N$_3$O$_3$S: C, 50.11; H, 4.67; N, 9.74. Found: C, 50.25; H, 4.68; N, 9.68.

EXAMPLE 302

2-(2,2,2-Trifluoroethyl)-4-(cyclopropylmethylamino)-5-[4-(methylsulfonyl)phenyl]-3(2H)-pyridazinone The product was prepared according to the method of Example 295, substituting cyclopropylmethylamine in place of 3-methoxypropylamine to provide an off-white solid (yield: 130 mg, 59%). mp 145–146° C. $^1$H NMR (300 MHz, CDCl$_3$) δ 8.01 (d, J=18.0 Hz, 2H), 7.53 (d, J=18.0 Hz, 2H), 7.48 (s, 1H), 6.20 (br, 1H), 4.82 (q, J=18.0 Hz, 2H), 3.12 (s, 3H), 2.45 (br d, J=13.2 Hz, 2H), 0.88 (m, 1H), 0.51 (m, 2H), 0.10 (m, 2H). MS (DCI/NH$_3$) m/z 402 (M+H)$^+$, m/z 419 (M+NH$_4$)$^+$. Anal. calc. for C$_{17}$H$_{18}$F$_3$N$_3$O$_3$S: C, 50.87; H, 4.52; N, 10.47. Found: C, 51.00; H, 4.52; N, 10.44.

EXAMPLE 303

2-(2,2,2-Trifluoroethyl)-4-(2,3-dihydro-1H-inden-1-ylamino)-5-[4-(methylsulfonyl)phenyl]-3(2H)-pyridazinone The product was prepared according to the method of Example 295, substituting 1-indanylamine in place of 3-methoxypropylamine to provide an off-white solid (yield: 82 mg, 32%). mp 155–158° C. $^1$H NMR (300 MHz, CDCl$_3$) δ 8.04 (d, J=18.0 Hz, 2H), 7.68 (d, J=18.0 Hz, 2H), 7.49 (s, 1H), 7.27–7.14 (m, 4H), 6.30 (br d, J=18.0 Hz, 1H), 4.81 (q, J=18.0 Hz, 2H), 4.57 (m, 1H), 3.09 (s, 3H), 2.89 (m, 1H), 2.60 (m, 1H), 1.85 (m, 1H), 1.68 (m, 1H). MS (ESI (−)) m/z 462 (M−H)$^-$. Anal. calc. for C$_{22}$H$_{20}$F$_3$N$_3$O$_3$S: C, 57.01; H, 4.35; N, 9.07. Found: C, 57.30; H, 4.45; N, 8.86.

EXAMPLE 304

2-(2,2,2-Trifluoroethyl)-4-(1-piperidinyl)-5-[4-(methylsulfonyl)phenyl]-3(2H)-pyridazinone The product was prepared according to the method of Example 295, substituting piperidine in place of 3-methoxypropylamine to provide an off-white solid (yield: 180 mg, 79%). mp 160–161° C. $^1$H NMR (300 MHz, CDCl$_3$) δ 8.04 (d, J=18.0 Hz, 2H), 7.58 (s, 1H), 7.46 (d, J=18.0 Hz, 2H), 4.80 (q, J=18.0 Hz, 2H), 3.13 (s, 3H), 2.96 (m, 4H), 1.65–1.52 (m, 6H). MS (DCI/NH$_3$) m/z 416 (M+H)$^+$. Anal. calc. for C$_{18}$H$_{20}$F$_3$N$_3$O$_3$S.H$_2$O: C, 52.04; H, 4.85; N, 10.11. Found: C, 52.21; H, 5.02; N, 9.75.

EXAMPLE 305

2-(2,2,2-Trifluoroethyl)-4-(3-hydroxypropylamino)-5-[4-(methylsulfonyl)phenyl]-3(2H)-pyridazinone The product was prepared according to the method of Example 295, substituting 3-hydroxypropylamine in place of 3-methoxypropylamine to provide a white solid (yield: 109.6 mg, 50%). mp 152–154° C. $^1$H NMR (300 MHz, CDCl3) δ 8.02 (d, J=18.0 Hz, 2H), 7.56 (d, J=18.0 Hz, 2H), 7.48 (s, 1H), 6.48 (br, 1H), 4.79 (q, J=17.4 Hz, 2H), 3.63 (t, J=12.0 Hz, 2H), 3.12 (s, 3H), 2.81 (dt, J=12.0, 12.0 Hz, 2H), 1.65 (tt, J=12.0, 12.0 Hz, 2H). MS (DCI/NH$_3$) m/z 406 (M+H)$^+$, m/z 423 (M+NH$_4$)$^+$. Anal. calc. for C$_{16}$H$_{18}$F$_3$N$_3$O$_4$S: C, 47.41; H, 4.48; N, 10.37. Found: C, 47.53; H, 4.33; N, 10.27.

EXAMPLE 306

2-(2,2,2-Trifluoroethyl)-4-[3-(1H-imidazol-1-yl)propylamino]-5-[4-(methylsulfonyl)phenyl]-3(2H)-pyridazinone The product was prepared according to the method of Example 295, substituting 1-(3-aminopropyl)imidazole in place of 3-methoxypropylamine. The reaction mixture was concentrated to dryness and the residue purified using RP-HPLC (Rainin Dynamax C-18 column, 60 Å pore size, 21.4 mm i.d.). The column was eluted with a linear gradient consisting of 20% acetonitrile (containing 0.1% TFA)/80% water (containing 0.1% TFA) to 100% acetonitrile (containing 0.1% TFA) at 15 mL/min over 70 minutes. The peak corresponding to the title product was collected and lyophilized to provide a tan hygroscopic foam (yield: 70.2 mg, 28%). $^1$H NMR (300 MHz, DMSO) δ 8.95 (br s, 1H), 7.97 (d, J=16.8 Hz, 2H), 7.66 (d, J=16.2 Hz, 2H), 7.61 (s, 1H), 7.58 (d, J=15.0 Hz, 2H), 6.99 (br t, 1H, J=13.2 Hz), 4.97 (dt, J=18.0, 18.0 Hz, 2H), 3.97 (t, J=13.2 Hz, 2H), 3.28 (s, 3H), 2.69 (m, 2H), 1.81 (tt, J=13.2, 13.2 Hz, 2H). MS (DCI/H$_3$) m/z 456 (M+H)$^+$. Anal. calc. for $C_{19}H_{20}F_3N_5O_3S$.1.4 CF$_3$COOH: C, 42.57; H, 3.51; N, 11.39. Found: C, 42.78; H, 3.58; N, 11.24.

EXAMPLE 307

2-(2,2,2-Trifluoroethyl)-4-(2R-hydroxylpropylamino)-5-[4-(methylsulfonyl)phenyl]-3(2H)-pyridazinone The product was prepared according to the method of Example 295, substituting (R)-(−)-2-propanolamine in place of 3-methoxypropylamine to provide an off-white solid (yield: 109.6 mg, 50%). M.p.=140–142° C. $^1$H NMR (300 MHz, CDCl$_3$) δ 8.04 (d, J=18.0 Hz, 2H), 7.56 (d, J=18.0 Hz, 2H), 7.49 (s, 1H), 6.42 (br, 1H), 4.79 (m, 2H), 3.80 (m, 1H), 3.12 (s, 3H), 2.68 (m, 2H), 1.02 (d, J=12.0 Hz, 3H). MS (DCI/NH$_3$) m/z 406 (M+H)$^+$, m/z 423 (M+NH$_4$)$^+$. Anal. calc. for $C_{16}H_{18}F_3N_3O_4S$: C, 47.41; H, 4.48; N, 10.37. Found: C, 47.56; H, 4.41; N, 10.25.

EXAMPLE 308

2-(2,2,2-Trifluoroethyl)-4-(2-cyanoethylamino)-5-[4-(methylsulfonyl)phenyl]-3(2H)-pyridazinone The product was prepared according to the method of Example 295, substituting 2-cyanoethylamine in place of 3-methoxypropylamine to provide an off-white solid (yield: 27 mg, 12%). mp 172–174° C. $^1$H NMR (300 MHz, CDCl$_3$) δ 8.09 (d, J=18.0 Hz, 2H), 7.63 (d, J=18.0 Hz, 2H), 7.51 (s, 1H), 6.08 (br t, 1H), 4.87 (q, J=18.0 Hz, 2H), 3.17 (dt, J=13.2, 13.2 Hz, 2H), 3.13 (s, 3H), 2.39 (t, J=13.2 Hz, 2H). MS (DCI/NH$_3$) m/z 418 (M+NH$_4$)$^+$. Anal. calc. for $C_{16}H_{15}F_3N_4O_3S$: C, 48.00; H, 3.78; N, 13.99. Found: C, 48.28; H, 3.77; N, 13.80.

EXAMPLE 309

2-(2,2,2-Trifluoroethyl)-4-(4-cyanoanilino)-5-[4-(methylsulfonyl)phenyl]-3(2H)-pyridazinone A suspension of 2-(2,2,2-trifluoroethyl)-4-chloro-5-[4-(methylsulfonyl)phenyl]-3(2H)-pyridazinone (300 mg, 0.820 mmol), prepared according to the method of Example 193E, 4-aminobenzonitrile (290 mg, 2.46 mmol), and silver oxide (760 mg, 3.28 mmol) in pyridine (1.5 mL) was stirred at 80° C. for 24 hours. The reaction was cooled to room temperature, adsorbed onto silica gel (2 g) and solvent removed under reduced pressure. The adsorbed silica gel was layered over an Extract-Clean Cartridge® (Alltech, packing: 10 g silica gel) and the cartridge eluted with a hexanes/acetone step gradient consisting of 60 mL of each of the following mixtures: hexanes, 8:1 hexanes/acetone, 4:1, 2:1, and 1:1. Fractions containing desired product were combined, concentrated, and further purified using HPLC (Technikrom Kromasil 60-5sil column, 20 mm×25 cm). The column was eluted with a linear gradient consisting of 30% ethyl acetate/hexanes to 100% ethyl acetate at 10 mL/min over 50 minutes. Fractions containing product were combined and concentrated under reduced pressure to provide the product as a tan solid (yield: 149.9 mg, 41%). mp>230° C. $^1$H NMR (300 MHz, DMSO) δ 9.49 (s, 1H), 8.00 (s, 1H), 7.69 (d, J=17.4 Hz, 2H), 7.43 (d, J=16.8 Hz, 2H), 7.32 (d, J=18.0 Hz, 2H), 6.78 (d, J=18.0 Hz, 2H), 5.06 (q, J=18.0 Hz, 2H), 3.13 (s, 3H), 2.68 (m, 2H), 1.02 (d, J=12.0 Hz, 3H). MS (DCI/NH$_3$) m/z 466 (M+NH$_4$)$^+$. Anal. calc. for $C_{20}H_{15}F_3N_4O_3S$: C, 53.57; H, 3.37; N, 12.49. Found: C, 53.47; H, 3.49; N, 12.35.

EXAMPLE 310

2-(2,2,2-Trifluoroethyl)-4-[3-methoxy-5-(trifluoromethyl)anilino]-5-[4-(methylsulfonyl)phenyl]-3(2H)-pyridazinone The product was prepared according to the method of Example 309, substituting 3-methoxy-5-(trifluoromethyl)aniline in place of 4-aminobenzonitrile to provide a brown solid (yield: 226.5 mg, 80%). mp 206–208° C. $^1$H NMR (300 MHz, CDCl$_3$) δ 7.90 (s, 1H), 7.77 (s, 1H), 7.71 (d, J=18.0 Hz, 2H), 7.28 (d, J=17.4 Hz, 2H), 6.61 (br s, 1H), 6.46 (br s, 1H), 6.31 (br s, 1H), 4.90 (q, J=17.4 Hz, 2H), 3.72 (s, 3H), 2.94 (s, 3H). MS (DCI/NH$_3$) m/z 539 (M+NH$_4$)$^+$. Anal. calc. for $C_{21}H_{17}F_6N_3O_4S$: C, 48.37; H, 3.29; N, 8.06. Found: C, 48.60; H, 3.33; N, 7.94.

EXAMPLE 311

2-(2,2,2-Trifluoroethyl)-4-anilino-5-[4-(methylsulfonyl)phenyl]-3(2H)-pyridazinone The product was prepared according to the method of Example 309, substituting aniline in place of 4-aminobenzonitrile to provide a tan solid (yield: 90 mg, 53%). mp 154–156° C. $^1$H NMR (300 MHz, CDCl$_3$) δ 7.89 (br s, 1H), 7.72 (s, 1H), 7.62 (d, J=18.0 Hz, 2H), 7.19 (d, J=18.0 Hz, 2H), 7.96–7.82 (m, 3H), 6.61 (d, J=14.4 Hz, 2H), 4.90 (q, J=18.0 Hz, 2H), 2.94 (s, 3H). MS (DCI/NH$_3$) m/z 424 (M+H)$^+$, m/z 441 (M+NH$_4$)$^+$. Anal. calc. for $C_{19}H_{16}F_3N_3O_3S$: C, 53.90; H, 3.81; NY 9.92. Found: C, 53.87; H, 3.73; N, 9.89.

EXAMPLE 312

2-(2,2,2-Trifluoroethyl)-4-(2,5-dimethoxyphenylamino)-5-[4-(methylsulfonyl)phenyl]-3(2H)-pyridazinone The product was prepared according to the method of Example 309, substituting 2,5-dimethoxyaniline in place of 4-aminobenzonitrile to provide a tan solid (yield: 140 mg, 53%). mp 95–96° C. $^1$H NMR (300 MHz, CDCl$_3$) δ 7.78 (br s, 1H), 7.72 (s, 1H), 7.63 (d, J=18.0 Hz, 2H), 7.18 (d, J=18.0 Hz, 2H), 6.54 (d, J=18.0 Hz, 1H), 6.38 (dd, J=6.0, 18.0 Hz, 1H), 4.89 (q, J=18.0 Hz, 2H), 3.73 (s, 3H), 3.47 (s, 3H), 2.96 (s, 3H). MS (DCI/NH$_3$) m/z 484 (M+H)$^+$, m/z 501 (M+NH$_4$)$^+$. Anal. calc. for $C_{21}H_{20}F_3N_3O_5S$: C, 52.17; H, 4.17; N, 8.69. Found: C, 52.47; H, 4.17; N, 8.43.

EXAMPLE 313

2-(2,2,2-Trifluoroethyl)-4-(3-fluoroanilino)-5-[4-(methylsulfonyl)phenyl]-3(2H)-pyridazinone The product was prepared according to the method of Example 309, substituting 3-fluoroaniline in place of 4-aminobenzonitrile to provide a tan solid (yield: 151.3 mg, 42%). mp 156–158° C. $^1$H NMR (300 MHz, DMSO) δ 9.18 (s, 1H), 7.91 (s, 1H), 7.62 (d, J=17.4 Hz, 2H), 7.36 (d, J=17.4 Hz, 2H), 6.88 (dd, J=15.0, 15.0 Hz, 1H), 6.56 (m, 1H), 6.49 (m, 2H), 5.04 (q, J=18.0 Hz, 2H), 3.08 (s, 3H). MS (DCI/NH$_3$) m/z 442 (M+H)$^+$, m/z 459 (M+NH$_4$)$^+$, m/z 476 (M+2NH$_4$−H)$^+$. Anal. calc. for C$_{19}$H$_{15}$F$_4$N$_3$O$_3$S.0.5 CH$_3$COCH$_3$; C, 52.33; H, 3.85; N, 8.93. Found: C, 52.51; H, 3.58; N, 8.81.

EXAMPLE 314

2-(2,2,2-Trifluoroethyl)-4-(2,4-difluoroanilino)-5-[4-(methylsulfonyl)phenyl]-3(2H)-pyridazinone The product was prepared according to the method of Example 309, substituting 2,4-difluoroaniline in place of 4-aminobenzonitrile to provide a tan solid (yield: 63.1 mg, 17%). mp 170–175° C. $^1$H NMR (300 MHz, DMSO) δ 9.00 (s, 1H), 7.80 (s, 1H), 7.57 (d, J=17.4 Hz, 2H), 7.26 (d, J=17.4 Hz, 2H), 7.05 (m, 1H), 6.75 (m, 2H), 5.05 (q, J=18.0 Hz, 2H), 3.09 (s, 3H). MS (DCI/NH$_3$) m/z 460 (M+H)$^+$, m/z 477 (M+NH$_4$)$^+$. Anal. calc. for C$_{19}$H$_{14}$F$_5$N$_3$O$_3$S: C, 49.68; H, 3.07; N, 9.15; found: C, 50.00; H, 2.95; N, 9.10.

EXAMPLE 315

2-(2,2,2-Trifluoroethyl)-4-(2,3,5-trifluoroanilino)-5-[4-(methylsulfonyl)phenyl]-3(2H)-pyridazinone The product was prepared according to the method of Example 309, substituting 2,3,5-trifluoroaniline in place of 4-aminobenzonitrile to provide a pale purple solid (yield: 85.3 mg, 22%). mp 190–194° C. $^1$H NMR (300 MHz, DMSO) δ 9.27 (s, 1H), 7.90 (s, 1H), 7.70 (d, J=17.4 Hz, 2H), 7.39 (d, J=17.4 Hz, 2H), 7.03 (m, 1H), 6.76 (m, 1H), 5.06 (q, J=18.0 Hz, 2H), 3.14 (s, 3H). MS (DCI/NH$_3$) m/z 495 (M+NH$_4$)$^+$. Anal. calc. for C$_{19}$H$_{13}$F$_6$N$_3$O$_3$S: C, 47.80; H, 2.74; N, 8.80. Found: C, 47.51; H, 2.55; N, 8.63.

EXAMPLE 316

2-(2,2,2-Trifluoroethyl)-4-(4-fluoroanilino)-5-[4-(methylsulfonyl)phenyl]-3(2H)-pyridazinone The product was prepared according to the method of Example 309, substituting 4-fluoroaniline in place of 4-aminobenzonitrile to provide a tan solid (yield: 15.8 mg, 4%). mp 158–160° C. $^1$H NMR (300 MHz, CDCl$_3$) δ 7.80 (br s, 1H), 7.69 (s, 1H), 7.65 (d, J=18.0 Hz, 2H), 7.18 (d, J=18.0 Hz, 2H), 6.63 (d, J=3.6 Hz, 2H), 6.61 (s, 2H), 4.89 (q, J=17.4 Hz, 2H), 2.96 (s, 3H). MS (DCI/NH$_3$) m/z 459 (M+NH$_4$)$^+$. Anal. calc. for C$_{19}$H$_{15}$F$_4$N$_3$O$_3$S1.25 H$_2$O: C, 49.19; H, 3.80; N, 9.05. Found: C, 59.57; H, 3.53; N, 8.70.

EXAMPLE 317

2-Benzyl-4-(3-thienyl)-5-[4-(methylsulfonyl)phenyl]-3(2H)-pyridazinone

2-Benzyl-4-chloro-5-[4-(methylsulfonyl)phenyl]-3(2H)-pyridazinone prepared in Example 78 (150 mg, 0.4 mmol), thiophene-3-boronic acid (66.5 mg, 0.52 mmol), CsF (145.8 mg, 0.96 mmol), and tetrakis-(triphenylphosphine)-palladium(0) (13.9 mg, 0.012 mmol) in DME (25 mL) were stirred at reflux for 6 hours TLC (1CH$_2$Cl$_2$:1 hexanes:1.5 ethyl acetate) indicated that all starting materials were consumed. The reaction mixture was cooled to room temperature and concentrated under reduced pressure. The residue was partitioned between water and ethyl acetate. The organic layer was washed with brine, dried over MgSO$_4$, and filtered. The filtrate was concentrated under reduced pressure. The residue was purified using a silica gel column (0.5:2.5:0.5 CH$_2$Cl$_2$/hexanes/ethyl acetate). A yellow powder was obtained (yield: 50 mg, 31%). $^1$H NMR (300 MHz, CDCl$_3$) δ 3.09 (s, 3H), 5.41 (s, 2H), 6.72 (dd, J=1.5 Hz, 9 Hz, 1H), 7.13 (dd, J=3 Hz, 3 Hz, 1H), 7.3–7.45 (m, 5H), 7.5–7.6 (m, 3H), 7.78 (s, 1H), 7.92 (d, 9 Hz, 2H). MS (DCI/NH$_3$) n/z 423 (M+H)$^+$. Anal. calc. for C$_{22}$H$_{18}$N$_2$O$_3$S$_2$.0.5H$_2$O: C, 6.23; H, 4.43; N, 6.49. Found C, 61.29; H, 4.40; N, 6.16.

EXAMPLE 318

2-Benzyl-4-(2-benzofuranyl)-5-[4-(methylsulfonyl)phenyl]-3(2H)-pyridazinone

The title compound was prepared according to the method of Example 317, substituting 2-benzofuranboronic acid for 3-thiopheneboronic acid (yield: 46 mg, 25%). $^1$H NMR (300 MHz, CDCl$_3$) δ 3.13 (s, 3H), 5.5 (s, 2 H,), 6.85–6.92 (m, 1H), 7.15–7.25 (m, 3H), 7.3–7.42 (m, 3H), 7.45–7.7 (m, 5H), 7.79 (s, 1H), 8.0 (d, J=9 Hz, 2H), 8.08 (s, 1H). MS (DCI/NH$_3$), m/z 457 (M+H)$^+$. Anal. calc. for C$_{26}$H$_{20}$N$_2$O$_4$S.H$_2$O: C, 65.80; H, 4.67; N, 5.90. Found C, 65.44; H, 4.42; N, 6.14.

EXAMPLE 319

2-Benzyl-4-(1-oxo-1,3-dihydro-2-benzofuran-5-yl)-5-[4-(methylsulfonyl)phenyl]-3(2H)-pyridazinone The title compound was prepared according to the method of Example 221, substituting 2-benzyl-4-chloro-5-[4-(methylsulfonyl)phenyl]-3(2H)-pyridazinone, prepared in Example 78, in place of 2-(2,2,2-trifluoroethyl)-4-chloro-5-[4-(methylsulfonyl)phenyl]-3(2H)-pyridazinone (yield: 112 mg, 44%). mp>250° C. $^1$H NMR (300 MHz, DMSO-d$_6$) δ 3.20 (s, 3H), 5.34 (s, 2H), 5.36 (s, 2H), 7.30–7.44 (m, 6H), 7.48 (d, J=8 Hz, 2H), 7.57 (s, 1H), 7.73 (d, J=8 Hz, 1H), 7.85 (d, J=8 Hz, 2H), 8.17 (s, 1H). MS (DCI/NH$_3$) m/z 473 (M+H)$^+$, 490 (M+NH$_4$)$^+$. Anal. calc. for C$_{26}$H$_{20}$N$_2$O$_5$S: C, 65.46; H, 4.33; N, 5.87. Found: C, 65.56; H, 4.48; N, 5.75.

EXAMPLE 320

2-Benzyl-4-(5-chloro-2-thienyl)-5-[4-(methylsulfonyl)phenyl]-3(2H)-pyridazinone The title compound was prepared according to the method of Example 317, substituting 5-chloro-2-thiopheneboronic acid in place of 3-thiopheneboronic acid (yield: 21 mg, 17%). $^1$H NMR (300 MHz, CDCl$_3$) δ 3.15 (s, 3H), 5.45 (s, 2H), 6.51 (d, J=4.5 Hz, 1H), 6.7 (d, J=4.5 Hz, 1H), 7.3–7.4 (m, 3H), 7.5=7.6 (m, 4H), 7.6 (s, 1H), 8.05 (d, J=9 Hz, 2H). MS (DCI/NH$_3$), m/z 457 (M+H)$^+$. Anal. calc. for C$_{18}$H$_{15}$ClN$_2$O$_3$S: C, 57.68; H, 4.03; N, 7.47. Found C, 57.61; H, 3.84; N, 7.14.

EXAMPLE 321

2-Benzyl-4-(3-nitrophenyl)-5-[4-(methylsulfonyl)phenyl]-3(2H)-pyridazinone

The title compound was prepared according to the method of Example 317, substituting 3-nitrobenzeneboronic acid in place of 3-thipheneboronic acid (yield: 20 mg, 11%). $^1$H NMR (300 MHz, CDCl$_3$) δ 3.0 (s, 3H), 5.93 (s, 2H), 7.6–7.8 (m, 9H), 7.8 (t, J=4.5 Hz, 3H), 8.04 (s, 1H), 8.15 (m, 1H). MS (DCI/NH$_3$), m/z 462 (M+H)$^+$. Anal. calc. for C$_{24}$H$_{19}$N$_3$O$_5$S. 0.75 H$_2$O: C, 60.68; H, 4.35; N, 8.84. Found C, 60.99; H, 3.97; N, 8.35.

EXAMPLE 322

2-Benzyl-4-(4-vinylphenyl)-5-[4-(methylsulfonyl)phenyl]-3(2H)-pyridazinone

The title compound was prepared according to the method of Example 317, substituting 4-vinylbenzeneboronic acid in place of 3-thipheneboronic acid (yield: 40 mg, 23%). $^1$H NMR (300 MHz, CDCl$_3$) δ 3.05 (s, 3H), 5.28 (d, J=12 Hz, 1H), 5.41 (s, 2H), 5.74 (d, J=18 Hz, 1H) 6.65 (dd, J=12 Hz, 18 Hz, 1H), 7.1–7.6 (m, 11H) 7.83 (d, J=3 Hz, 2H), 7.85 (s, 1H). MS (DCI/NH$_3$), m/z 443 (M+H)$^+$. Anal. calc. for C$_{26}$H$_{22}$N$_2$O$_3$S: C, 70.57; H, 5.01; N, 6.33. Found C, 70.34; H, 4.67; N, 5.97.

EXAMPLE 323

2-Benzyl-4-(4-trifluormethylphenyl)-5-[4-(methylsulfonyl)phenyl]-3(2H)-pyridazinone The title compound was prepared according to the method of Example 317, substituting 4-(trifluoromethyl)benzeneboronic acid in place of 3-thipheneboronic acid (yield: 101 mg, 52%). $^1$H NMR (300 MHz, CDCl$_3$) δ 3.05 (s, 3H), 5.42 (s, 2H), 7.3–7.5 (m, 8H), 7.55–7.6 m, 3H), 7.85 (s, 2H), 7.9 (s, 1H). MS (DCI/NH$_3$) m/z 485 (M+H)$^+$. Anal. calc. for C$_{25}$H$_{19}$F$_3$N$_2$O$_3$S.0.25 H$_2$O: C, 61.40; H, 4.01; N, 5.72. Found C, 61.26; H, 4.01; N, 5.35.

EXAMPLE 324

2-Benzyl-4-(2-methoxyphenyl)-5-[4-(methylsulfonyl)phenyl]-3(2H)-pyridazinone

The title compound was prepared according to the method of Example 317, substituting 2-methoxybenzeneboronic acid in place of 3-thipheneboronic acid (yield: 75 mg, 42%). $^1$H NMR (300 MHz, CDCl$_3$) δ 3.01 (s, 3H), 3.5 (s, 3H), 5.40 (dd, J=12 Hz, 18 Hz, 2H), 6.76 (d, J=9 Hz, 1H), 6.85–6.95 (m, 1H), 7.09 (dd, J=1.5 Hz, 9 Hz, 1H), 7.26–7.41 (m, 6H), 7.55 (dd, J=1.5 Hz, 9 Hz, 2H), 7.82 (d, J=9 Hz, 3H). MS (DCI/NH$_3$) m/z 447 (M+H)$^+$. Anal. calc. for C$_{25}$H$_{22}$N$_2$O$_4$S.0.5 H$_2$O: C, 65.91; H, 5.08; N, 6.14. Found C, 65.86; H, 5.08; N, 5.58.

EXAMPLE 325

2-Benzyl-4-(3,4-dimethylphenyl)-5-[4-(methylsulfonyl)phenyl]-3(2H)-pyridazinone

2-Benzyl-4-chloro-5-[4-(methylsulfonyl)phenyl]-3(2H)-pyridazinone (150 mg, 0.4 mmol) prepared in Example 78 was dissolved in anhydrous DME (10 mL) and heated to reflux with 3,4-dimethylbenzeneboronic acid in presence of CsF (146 mg, 0.96 mmol) and tetrakis(triphenylphosphine)palladium (14 mg, 0.012 mmol) for 6 hours. After cooling to room temperature the reaction mixture was diluted with water and extracted with ethyl acetate (100 mL). The organic layer was washed with brine, dried over MgSO$_4$, and evaporated in vacuo. The compound was purified on a silica gel column, eluting with 30% ethyl acetate in pentanes, providing the desired compound (yield: 100 mg, 56%). $^1$H NMR (300 MHz, CDCl$_3$) δ 2.15, 2.20 (2s, 3H), 2.25, 2.30 (2s, 3H), 3.05, 3.08 (2s, 3H), 5.35, 5.40 (2s, 2H), 6.60–7.1 (m, 3H), 7.30–7.40 (m, 4H), 7.42–7.60 (m, 2H), 7.70–8.02 (m, 4H). MS (DCI/NH$_3$) m/z 445 (M+H)$^+$. Anal. calc. for C$_{26}$H$_{24}$N$_2$O$_3$S.H$_2$O: C, 67.51; H, 5.66; N, 6.05. Found: C, 67.45; H, 5.56; N, 5.85.

EXAMPLE 326

2-Benzyl-4-(3-fluoro-4-methoxyphenyl)-5-[4-(methylsulfonyl)phenyl]-3(2H)-pyridazinone The title compound was prepared according to the method of Example 325, substituting 3-fluoro-4-methoxybenzeneboronic acid in place of 3,4-dimethylbenzeneboronic acid (yield: 35 mg, 19%). $^1$H NMR (300 MHz, CDCl$_3$) δ 3.05 (s, 3H), 3.85 (s, 3H), 5.3, 5.4 (2s, 2H), 6.75–7.03 (m, 3H), 7.3–7.40 (m, 5H), 7.4–7.55 (dd, J=1.5 Hz; 7.5 Hz, 2H), 7.8–7.95 (m, 3H). MS (DCI/NH$_3$) m/z 465 (M+H)$^+$. Anal. calc. for C$_{25}$H$_{21}$N$_2$O$_4$S.0.25 H$_2$O: C, 64.02; H, 4.62; N, 5.97. Found: C, 63.93; H, 4.54; N, 5.43

EXAMPLE 327

2-Benzyl-4-(2-methoxypyrid-3-yl)-5-[4-(methylsulfonyl)phenyl]-3(2H)-pyridazinone The title compound was prepared according to the method of Example 325, substituting 2-methoxy-3-pyridylboronic acid in place of 3,4-dimethylbenzeneboronic acid (yield: 35 mg, 19%). $^1$H NMR (300 MHz, CDCl$_3$) δ 3.05 (s, 3H), 3.58 (s, 3H), 5.4 (dd, J=15 Hz, 18 Hz; 2H), 6.88 (m, 1H), 7.28–7.40 (m, 1H), 7.5–7.6 (dd, J=1.5 Hz; 7.5 Hz, 3H), 7.82 (s, 1H), 7.85 (d, J=18 Hz, 2H), 8.15 (br s, 1H). MS (DCI/NH$_3$) m/z 448 (M+H)$^+$. Anal. calc. for C$_{24}$H$_{21}$N$_3$O$_4$S: C, 64.42; H, 4.73; N, 9.39. Found: C, 64.17; H, 5.11; N, 9.04

EXAMPLE 328

2-Benzyl-4-(3-ethoxyphenyl)-5-[4-(methylsulfonyl)phenyl]-3(2H)-pyridazinone

The title compound was prepared according to the method of Example 325, substituting 3-ethoxybenzeneboronic acid in place of 3,4-dimethylbenzeneboronic acid (yield: 115 mg, 67%). $^1$H NMR (300 MHz, CDCl$_3$) δ 1.31 (t, J=7.5 Hz, 3H), 3.05 (s, 3H), 3.89 (q, J=7.5 Hz, 2H), 5.14 (s, 2H), 6.65 (d, J=9 Hz, 1H), 6.72 (t, J=1.5 Hz, 1H), 6.8 (dd, J=1.5 Hz, 9 Hz, 1H), 7.15 (t, J=9 Hz, 1H), 7.3–7.4 (m, 5H), 7.5–7.6 (m, 2H), 7.85 (d, J=9 Hz, 3H). MS (DCI/NH$_3$) m/z 461 (M+H)$^+$. Anal. calc. for C$_{26}$H$_{24}$N$_2$O$_4$S.0.5H$_2$O: C, 66.50; H, 5.36; N, 5.96. Found: C, 66.39; H, 5.02; N, 5.77

EXAMPLE 329

2-Benzyl-4-(4-fluorobenzyl)-5-[4-(methylsulfonyl)phenyl]-(2H)-pyridazinone

Example 329A

2-Benzyl-4,5-dibromo-3(2H)-pyridazinone

The title compound was prepared according to the method of Example 194A, substituting benzyl hydrazine hydrochloride in place of 4-fluorophenyl hydrazine hydrochloride (yield: 7.86 g, 60%). $^1$H NMR (300 MHz, DMSO d$_6$) δ 5.27 (s, 2H), 7.26–7.41 (m, 5H), 8.19 (s, 1H). MS (DCI/NH$_3$) m/z 345 (M+H)$^+$, 362 (M+H)$^+$.

Example 329B

2-Benzyl-5-bromo-4-methoxy-3(2H)-pyridazinone

The title compound was prepared according to the method described in Example 194B, substituting 2-benzyl-4,5-dibromo-3(2H)-pyridazinone for 2-(4-fluorophenyl)-4,5-dibromo-3(2H)-pyridazinone (yield: 2.877 g; 85%). $^1$H NMR (300 MHz, DMSO-d$_6$) δ 4.14 (s, 3H), 5.23 (s, 2H), 7.26–7.38 (m, 5H), 8.11 (s, 1H). MS (DCl-NH$_3$) m/z 295 (M+H)$^+$, 312 (M+NH$_4$)$^+$.

Example 329C

2-Benzyl-4-methoxy-5-[4-(methylthio)phenyl]-3(2H)-pyridazinone

The title compound was prepared according to the method described in Example 6, substituting 2-benzyl-4-methoxy-5-bromo-3(2H)-pyridazinone for 2-benzyl-4-methoxy-5-bromo-3(2H)-pyridazinone (yield: 3.705 g). $^1$H NMR (300 MHz, DMSO-d$_6$) δ 2.52 (s, 3H), 3.99 (s, 3H), 5.28 (s, 2H), 7.26–7.41 (m, 7H), 7.55 (m, 2H), 8.02 (s, 1H). MS (DCl-NH$_3$) m/z 339 (M+H)$^+$, 356 (M+NH$_4$)$^+$.

Example 329D

2-Benzyl-4-(4-fluorobenzyl-5-[4-(methylthio)phenyl]-3(2H)-pyridazinone

The title compound was prepared according to the method of Example 228, substituting 4-fluorobenzyl magnesium chloride in place of cyclohexylmagnesium chloride and 2-benzyl-4-methoxy-5-[4-(methylthio)phenyl]-3(2H)-pyridazinone was substituted in place of 2-(4-fluorophenyl)-4-methoxy-5-[4-(methylthio)phenyl]-3(2H)-pyridazinone.

Example 329E

2-Benzyl-4-(4-fluorobenzyl)-5-[4-(methylsulfonyl)phenyl]-(2H)-pyridazinone

The sulfide compound, Example 329D, was oxidized to the methyl sulfonyl compound according to the method of Example 10. mp 186–189° C. $^1$H NMR (300 MHz, DMSO d$_6$) δ 3.27 (s, 3H), 3.83 (s, 2H), 5.31 (s, 2H), 6.94–7.05 (m, 4H), 7.27–7.40 (m, 5H), 7.67 (m, 2H), 7.94 (s, 1H), 8.03 (m, 2H). MS (DCI/NH$_3$) m/z 449 (M+H)$^+$, 466 (M+NH$_4$)$^+$. Anal. calc. for C$_{25}$H$_{21}$FN$_2$O$_3$S: C, 66.95; H, 4.72; N, 6.25. Found: C, 66.68; H, 4.75; N, 6.14.

EXAMPLE 330

2-(tert-Butyl)-4-(3-methylbutoxy)-5-[4-(methylsulfonyl)phenyl]-3(2H)pyridazinone

Example 330A 2-(tert-Butyl)-4,5-dichloro-3(2H)-pyridazinone

A solution of mucochloric acid (33.8 g, 200 mmol) and tert.-butylhydrazine hydrochloride (24.9 g, 200 mmol) in methanol (400 mL) was stirred at reflux overnight. Methanol was removed in vacuo and the residue was partitioned between ether and water. The organic layer was dried over MgSO$_4$ and filtered. The filtrate was concentrated in vacuo and the residue was purified by column chromatography (silica gel, 100% hexanes). Product-containing fractions were combined and the title compound was crystallized from ether/hexanes (yield: 10.0 g, 22.6%). mp 63–64° C. $^1$H NMR (300 MHz, CDCl$_3$) δ 1.65 (s, 9H), 7.73 (s, 1H). MS (DCI/NH$_3$) m/z 221 (M+H)$^+$, 238 (M+NH$_4$)$^+$.

Example 330B 2-(tert-Butyl)-4-(3-methylbutoxy)-5-chloro-3(2H)-pyridazinone

A stirred, room temperature solution of 3-methyl-1-butanol (0.5 mL, 4.52 mmol) in tetrahydrofuran (10 mL) was treated with a 60% oil suspension of sodium hydride (0.24 g, 5.88 mmol). After 5 minutes, hydrogen gas evolution had subsided, so the dichloro-intermediate from Example 330A (1.0 g, 4.52 mmol) was added and the reaction mixture was stirred at room temperature for 20 hours. The reaction was quenched with 10% aqueous citric acid and extracted with ethyl acetate. The organic layer was washed with brine, dried over MgSO$_4$, and filtered. The filtrate was concentrated in vacuo, and the residue was purified by column chromatography (silica gel, 100% hexanes). The title compound was obtained as a pale yellow oil (yield: 0.7 g, 56.7%). $^1$H NMR (300 MHz, CDCl$_3$) δ 0.95 (d, J=6 Hz, 6H), 1.63 (s, 9H), 1.64 (q, J=6 Hz, 2H), 1.85 (nonet, J=6 Hz, 1H), 4.49 (t, J=6 Hz, 2H), 7.64 (s, 1H). MS (DCI/NH$_3$) m/z 273 (M+H)$^+$, 290 (M+NH$_4$)$^+$.

Example 330C 2-(tert-Butyl)-4-(3-methylbutoxy)-5-[4-(methylthio)phenyl]-3(2H)-pyridazinone A solution of the intermediate from Example 330B (700 mg, 2.57 mmol), 4-(methylthio)benzeneboronic acid (560 mg, 3.34 mmol), cesium carbonate (2.17 g, 6.67 mmol), and tetrakis(triphenylphosphine)palladium(0) (210 mg, 0.18 mmol) in dimethoxyethane (40 mL) was heated at reflux for 5 hours. The heat source was then removed and the reaction mixture was stirred at room temperature for 64 hours. The reaction mixture was filtered and the filtrate was concentrated in vacuo to provide a brown oil. This oil was purified by column chromatography twice (silica gel, 97:3 hexanes/ethyl acetate, then 96:4 hexanes/ethyl acetate) to provide a semi-solid product (yield: 270 mg, 29.2%). $^1$H NMR (300 MHz, CDCl$_3$) δ 0.81 (d, J=6 Hz, 6H), 1.49 (q, J=6 Hz, 2H), 1.63 (nonet, J=6 Hz, 1H), 1.69 (s, 9H), 2.52 (s, 3H), 7.32 (d, J=9 Hz, 2H), 7.50 (d, J=9 Hz, 2H), 7.73 (s, 1H). MS (DCI) m/z 361 (M+H)$^+$.

Example 330D 2-(tert-Butyl)-4-(3-methylbutoxy)-5-[4-(methylsulfonyl)phenyl]-3(2H)-pyridazinone The title compound was prepared according to the method of Example 10, substituting 2-(tert.-butyl)4-(3-methylbutoxy)-5-[4-(methylthio)phenyl]-3(2H)-pyridazinone for 4-(4-fluorophenyl)-5-[4-(methylthio)phenyl]-3(2H)-pyridazinone (yield: 188 mg, 63.9%). mp 138–139° C. $^1$H NMR (300 MHz, CDCl$_3$) δ 0.81 (d, J=6 Hz, 2H), 1.48 (q, J=6 Hz, 2H), 1.48–1.68 (m, 1H), 1.69 (s, 9H), 3.10 (s, 3H), 4.38 (t, J=6 Hz, 2H), 7.71 (s, 1H), 7.74 (d, J=9 Hz, 2H), 8.03 (d, J=9 Hz, 2H). MS (DCI/NH$_3$) m/z 393 (M+H)$^+$. Anal. calc. for C$_{20}$H$_{28}$N$_2$O$_4$S: C, 61.20; H, 7.19; N, 7.14. Found: C, 61.13; H, 7.23; N, 6.89.

EXAMPLE 331

2-(3-Chlorophenyl)-4-methoxy-5-[4-(methylsulfonyl)phenyl]-3(2H)-pyridazinone

The title compound was prepared according to the method of Example 10, substituting 2-(3-chlorophenyl)-4-methoxy-5-[4-(methylthio)phenyl]-3(2H)-pyridazinone (Example 207C) in place of 2-benzyl-4-(4-fluorophenyl)-5-[4-(methylthio)phenyl]-3(2H)-pyridazinone (yield: 3.31 g, 96%). mp 112–114° C. $^1$H NMR (300 MHz, DMSO d$_6$) δ 3.31 (m, 3H), 4.10 (m, 3H), 7.52–7.65 (m, 3H), 7.75 (m, 1H), 7.90 (m, 2H), 8.07 (m, 2H), 8.21 (s, 1H). MS (DCI/NH$_3$) m/z 391 (M+H)$^+$, 408 (M+NH$_4$)$^+$. Anal. calc. for: C$_{18}$H$_{15}$ClN$_2$O$_4$S.0.25 H$_2$O: C, 54.68; H, 3.95; N, 7.08. Found: C, 54.59; H, 3.65; N, 6.98.

EXAMPLE 332

2-(3-Chlorophenyl)-4-hydroxy-5-[4-(methylsulfonyl)phenyl]-3(2H)-pyridazinone

A suspension of 2-(3-chlorophenyl)-4-(methoxy)-5-[4-(methylsulfonyl)phenyl]-3(2H)-pyridazinone (6.26 g, 16 mmol) in 5% NaOH (54 mL) dioxane (39.4 mL) was heated at reflux and stirred for 1.5 hours. As the reaction proceeds, the solution becomes orange and homogeneous. The mixture was cooled and poured into 1N HCl, with constant stirring. The resulting white solid was filtered and rinsed with H$_2$O and left to dry overnight. The mostly dry product was taken up in CH$_2$Cl$_2$ and azeotroped with toluene to remove any remaining H$_2$O, to provide the desired product as a white solid (yield: 6.79 g, >100%). $^1$H NMR (300 MHz, DMSO d$_6$) δ 2.27 (s, 3H), 7.51–7.62 (m, 2H), 7.68 (m, 1H), 7.79 (m, 1H), 8.03 (m, 4H), 8.24 (s, 1H). MS (DCI/NH$_3$) m/z 377 (M+H)$^+$, 396 (M+NH$_4$)$^+$.

EXAMPLE 333

2-(3-Chlorophenyl)-4-tosyloxy-5-[4-(methylsulfonyl)phenyl]-3(2H)-pyridazinone

To a 0° C. solution of 2-(3-chlorophenyl)-4-hydroxy-5-[4-(methylsulfonyl)phenyl]-3(2H)-pyridazinone, prepared in Example 332, (6.79 g, 16 mmol) in pyridine (160 mL) was added p-toluenesulfonyl chloride (3.06 g, 16 mmol). The solution was left to warm slowly to room temperature with stirring under nitrogen. After 2.5 hours, the mixture was poured into H$_2$O with constant stirring. The resulting off-white solid was filtered, rinsed with H$_2$O and dried to provide the desired product (yield: 6.26 g, 79%). mp 198–200° C. $^1$H NMR (300 MHz, DMSO d$_6$) δ 2.35 (s, 3H), 3.28 (s, 3H), 7.20 (m, 2H), 7.52–7.64 (M, 5H), 7.70 (m, 3H), 7.89 (m, 2H), 8.32 (s, 1H). MS APCI+531 (M+H)$^+$, 548 (M+H$_2$O)$^+$, APCI–493 (M+35)$^-$. Anal. calc. for C$_{24}$H$_{19}$ClN$_2$O$_6$S$_2$: C, 54.29; H, 3.61; N, 5.28. Found: C, 54.55; H, 3.46; N, 5.57.

EXAMPLE 334

2-(3-Chlorophenyl)-4-chloro-5-[4-(methylsulfonyl)phenyl]-3(2H)-pyridazinone

A solution of 2-(3-chlorophenyl)-4-hydroxy-5-[4-(methylsulfonyl)phenyl]-3(2H)-pyridazinone, prepared in Example 332, in POCl$_3$ was heated to reflux for 3 hours while stirring under nitrogen. The mixture was cooled to room temperature and poured into ice with constant swirling. The resulting white solid was extracted with ethyl acetate. The combined organics were washed with H$_2$O, dried over MgSO$_4$, and concentrated to a solid. The crude product was purified using flash chromatography (SiO$_2$, eluting with 1:1 ethyl acetate/hexanes) to provide the desired product (yield: 0.151 g, 29%). mp 203–204° C. $^1$H NMR (300 MHz, DMSO d$_6$) δ 3.29–3.36 (3H, obstructed by H$_2$O), 7.60 (m, 3H), 7.76 (m, 1H), 7.92 (m, 2H), 8.14 (m, 2H), 8.25 (s, 1H). MS (DCI/NH$_3$) m/z 395 (M+H)$^+$, 412 (M+NH$_4$)$^+$. Anal. calc. for C$_{17}$H$_{12}$Cl$_2$N$_2$O$_3$S: C, 51.66; H, 3.06; N, 7.09. Found: C, 51.67; H, 3.03; N, 6.93.

EXAMPLE 335

2-(3-Chlorophenyl)-4-(2-methylpropoxy)-5-[4-(methylsulfonyl)phenyl]-3(2H)-pyridazinone To a stirred suspension of 2-(3-chlorophenyl)-4-tosyloxy-5-[4-(methylsulfonyl)phenyl]-3(2H)-pyridazinone, prepared in Example 333, (0.175 g, 0.33 mmol) in THF (3.3 mL) was added isobutanol (0.03 mL, 0.33 mmol), and NaH (0.0132 g, 0.33 mmol). The resulting solution was stirred under nitrogen for 1 hour. The reaction was poured into H$_2$O and extracted with ethyl acetate. The combined organics were dried over MgSO$_4$ and concentrated in vacuo. The crude solid was purified using flash chromatography (SiO$_2$, 2:1 hexanes:ethyl acetate) to provide the desired product (yield: 0.1088 g 76%). mp 166–169° C. $^1$H NMR (300 MHz, DMSO d$_6$) δ 0.78 (d, J=6 Hz, 6H), 1.84 (m, 1H), 3.29 (s, 3H), 4.20 (d, J=6 Hz, 2H), 7.51–7.63 (m, 3H), 7.76 (m, 1H), 7.92 (m, 2H), 8.07 (m, 2H), 8.21 (s, 1H). MS (DCI/NH$_3$) m/z 433 (M+H)$^+$, 450 (M+NH$_4$)$^+$. Anal. calc. for C$_{21}$H$_{21}$ClN$_2$O$_4$S: C, 57.07; H, 5.01; N, 6.33. Found: C, 57.06; H, 4.78; N, 6.13.

EXAMPLE 336

2-(3-Chlorophenyl)-4-(t-butoxy)-5-[4-(methylsulfonyl)phenyl]-3(2H)-pyridazinone

The title compound was prepared according to the method of Example 335, substituting t-butanol in place of isobutanol (yield: 0.093 g, 66%). mp 232–235° C. $^1$H NMR (300 MHz, DMSO d$_6$) δ 1.18 (s, 9H), 3.30 (s, 3H), 7.52–7.64 (m, 3H), 7.74 (m, 1H), 7.92 (m, 2H), 8.08 (m, 2H), 8.20 (s, 1H). MS (DCI/NH$_3$) m/z 433 (M+H)$^+$, 450 (M+NH$_4$)$^+$. Anal. calc. for C$_{21}$H$_{21}$ClN$_2$O$_4$S: C, 58.26; H, 4.89; N, 6.47. Found: C, 58.21; H, 4.88; N, 6.28.

EXAMPLE 337

2-(3-Chlorophenyl)-4-(cyclohexyloxy)-5-[4-(methylsulfonyl)phenyl]-3(2H)-pyridazinone The title compound was prepared according to the method of Example 335, substituting cyclohexanol in place of isobutanol (yield: 0.139 g, 92%). semi-solid; $^1$H NMR (300 MHz, CDCl$_3$) δ 1.09–1.50 (m, 6H), 1.57 (m, 2H), 1.88 (m, 2H), 3.13 (s, 3H). 5.19 (m, 1H), 7.38–7.48 (m, 2H), 7.59 (m, 1H), 7.70 (m, 1H), 7.83 (m, 2H), 7.92 (s, 3H), 8.07 (m, 2H). MS APCI+459 (M+H)$^+$, 476 (M+H$_2$O)$^+$, APCI–458 (M)–, 493 (M+35)$^-$. Anal. calc. for C$_{23}$H$_{23}$ClN$_2$O$_4$S.0.25 H$_2$O: C, 59.60; H, 5.11; N, 6.04. Found: C, 59.48; H, 4.86; N, 5.88.

EXAMPLE 338

2-(3-Chlorophenyl)-4-(2,2-dimethylpropoxy)-5-[4-(methylsulfonyl)phenyl]-3(2H)-pyridazinone The title compound was prepared according to the method of Example 335, substituting neopentyl alcohol in place of isobutanol (yield: 0.109 g, 74%). mp 151–153° C. $^1$H NMR (300 MHz, DMSO d$_6$) δ 0.78 (s, 9H), 3.29 (s, 3H), 4.10 (s, 2H), 7.52–7.64 (m, 3H), 7.76 (m, 1H), 7.92 (m, 2H), 8.07 (m, 2H), 8.20 (s, 1H). MS (DCI/NH$_3$) m/z 447 (M+H)$^+$, 464 (M+NH$_4$)$^+$. Anal. calc. for C$_{22}$H$_{23}$ClN$_2$O$_4$S: C, 59.12; H, 5.19; N, 6.27. Found C, 59.40; H, 5.31; N, 5.99.

EXAMPLE 339

2-(3-Chlorophenyl)-4-(3-methylbutoxy)-5-[4-(methylsulfonyl)phenyl]-3(2H)-pyridazinone The title compound was prepared according to the method of Example 335, substituting 3-methyl-1-butanol in place of isobutanol (yield: 0.229 g, 80.5%). mp 134–135° C. $^1$H NMR (300 MHz, DMSO d$_6$) δ 0.79 (d, J=6 Hz, 6H), 1.42–1.64 (m, 3H), 3.30 (s, 3H), 4.43 (t, J=6 Hz, 2H), 7.52–7.65 (m, 3H), 7.76 (m, 1H), 7.90 (m, 2H), 8.07 (m, 2H), 8.21 (s, 1H). MS (DCI/NH$_3$) m/Z 447 (M+H)$^+$, 464 (M+NH$_4$)$^+$. Anal. calc. for C$_{22}$H$_{23}$ClN$_2$O$_4$S: c, 59.12; H, 5.19; N, 6.27. Found: C, 58.91; H, 5.12; N, 6.01.

EXAMPLE 340

2-(3-Chlorophenyl)-4-(3-octyn-1-yloxy)-5-[4-(methylsulfonyl)phenyl]-3(2H)-pyridazinone The title compound was prepared according to the method of Example 335, substituting 3-octyn-1-ol in place of isobutanol (yield: 0.128 g, 77%). Oil. $^1$H NMR (300 MHz, CDCl$_3$) δ 0.88 (m, 3H), 1.25–1.44 (m, 4H), 2.05 (m, 2H), 2.52 (m, 2H), 4.68 (t, J=6 Hz, 2H), 7.43 (m, 2H), 7.59 (m, 1H), 7.70 (m, 1H), 7.86 (m, 2H), 7.92 (s, 1H). MS (DCI/NH$_3$) m/z 485 (M+H)$^+$. Anal. calc. for C$_{25}$H$_{25}$ClN$_2$O$_4$S: C, 61.94; H, 5.20; N, 5.78. Found: C, 61.82; H, 4.99; N, 5.57.

EXAMPLE 341

2-(3-Chlorophenyl)-4-[2-(dimethylamino)ethoxy]-5-[4-(methylsulfonyl)phenyl]-3(2H)-pyridazinone The title compound was prepared according to the method of Example 335, substituting N,N-(dimethyl)ethanolamine in place of isobutanol (yield: 0.111 g, 75%). mp 110–113° C. $^1$H NMR (300 MHz, DMSO d$_6$) δ 2.29 (bs, 6H), 2.68 (bs, 2H), 4.68 (t, J=5 Hz, 2H), 7.38–7.48 (m, 2H), 7.57 (m, 1H), 7.68 (m, 1H), 7.89 (m, 2H), 8.07 (m, 2H). MS (DCI/NH$_3$) m/z 448 (M+H)$^+$. Anal. calc. for C$_{21}$H$_{22}$ClN$_3$O$_4$S.0.50 H$_2$O: C, 55.19; H, 5.07; N, 9.19. Found: C, 55.24; H, 4.97; N, 9.07.

EXAMPLE 342

2-(3-Chlorophenyl)-4-[2-methyl-1-(1-methylethyl)propoxy]-5-[4-(methylsulfonyl)phenyl]-3(2H)-pyridazinone The title compound was prepared according to the method of Example 335, substituting 2,4-dimethyl-3-pentanol in place of isobutanol (yield: 0.075 g, 48%). Semi-solid; $^1$H NMR (300 MHz, DMSO d$_6$) δ 0.79 (m, 12H), 1.78–1.92 (m, J=6 Hz, 2H), 3.29 (s, 3H), 5.40 (t, J=6 Hz, 1H), 7.57 (m, 3H), 7.72 (m, 1H), 7.91 (m, 2H), 8.07 (m, 2H), 8.17 (m, 1H). MS (DCl/NH$_3$) m/z 475 (M+H)$^+$, 492 (M+NH$_4$)$^+$. Anal. calc. for C$_{24}$H$_{27}$ClN$_2$O$_4$S (0.75 H$_2$O): C, 59.00; H, 5.88; N, 5.78. Found: C, 58.83; H, 5.74; N, 5.52.

EXAMPLE 343

2-(3-Chlorophenyl)-4-(phenoxy)-5-[4(methylsulfonyl)phenyl]-3(2H)-pyridazinone

The title compound was prepared according to the method of Example 335, substituting phenol in place of isobutanol (yield: 0.053 g, 35%). mp 205–207° C. $^1$H NMR (300 MHz, DMSO d$_6$) δ 3.28 (s, 3H), 7.08 (m, 3H), 7.31 (m 2H), 7.50–7.64 (m, 3H), 7.73 (m, 1H), 7.90 (m, 2H), 8.05 (m, 2H), 8.40 (s, 1H). MS (DCI/NH$_3$) m/z 453 (M+H)$^+$, 470 (M+NH$_4$)$^+$. Anal. calc. for C$_{23}$H$_{17}$ClN$_2$O$_4$S: C, 60.99; H, 3.78; N, 6.19. Found: C, 60.79; H, 3.65; N, 5.87.

EXAMPLE 344

2-(3-Chlorophenyl)-4-[3-(dimethylamino)phenoxy]-5-[4-(methylsulfonylphenyl]-3(2H)-pyridazinone The title compound was prepared according to the method of Example 335, substituting 3-(dimethylamino)phenol in place of isobutanol (yield: 0.057 g, 60%). mp 191–193; $^1$H NMR (300 MHz, DMSO d$_6$) δ 2.85 (s, 6H), 3.27 (s, 3H), 6.36 (m, 3H), 7.05 (m, 1H), 7.51–7.63 (m, 3H), 7.72 (m, 1H), 7.90 (m, 2H), 8.05 (m, 2H), 8.39 (s, 1H). MS APCI+ 495 (M+H)$^+$, APCI–, 495 (M)–, 590 (M+35)$^-$. Anal. calc. for C$_{25}$H$_{22}$ClN$_3$O$_4$S: C, 60.54; H, 4.47; N, 8.47. Found: C, 60.04; H, 4.49; N, 8.26.

EXAMPLE 345

2-(3-Chlorophenyl)-4-(4-methoxyphenoxy)-5-[4-methylsulfonyl)phenyl]-3(2H)-pyridazinone The title compound was prepared according to the method of Example 335, substituting 4-methoxyphenol in place of isobutanol (yield: 0.080 g, 69%). mp 182–184° C. $^1$H NMR (300 MHz, DMSO d$_6$) δ 3.27 (s, 3H), 3.70 (s, 3H), 6.84 (m, 2H), 7.00 (m, 2H), 7.56 (m, 3H), 7.72 (m, 1H), 7.90 (m, 2H), 8.04 (m, 2H), 8.38 (s, 1H). MS (DCI/NH$_3$) m/z 483 (M+H)$^+$, 500 (M+NH$_4$)$^+$. Anal. calc. for C$_{24}$H$_{19}$ClN$_2$O$_5$S: C, 59.64; H, 3.97; N, 5.80. Found: C, 59.86; H, 3.94; N, 5.62.

EXAMPLE 346

2-(3,4-Difluorophenyl)-4-(2-methylpropoxy)-5-[4-(methylsulfonyl)phenyl]-3(2H)-pyridazinone The title compound was prepared according to the method of Example 335, substituting 2-(3,4-difluorophenyl)-4-tosyloxy-5-[4-(methylsulfonyl)phenyl]-3(2H)-pyridazinone in place of 2-(3-chlorophenyl)-4-tosyloxy-5-[4-(methylsulfonyl)phenyl]-3(2H)-pyridazinone (yield: 150 mg, 61%). mp 116–117° C. $^1$H NMR (300 MHz, DMSO-$d_6$) δ 0.78 (d, 6H), 1.84, (m, 1H), 3.3 (s, 3H), 4.2 (d, 2H), 7.54 (m, 1H), 7.6 (m, 1H), 7.82 (m, 1H), 7.91 (d, 2H), 8.07 (d, 2H), 8.21 (s, 1H). MS (DCI/NH$_3$) m/z 435 (M+H)$^+$, 452 (M+NH$_4$)$^+$. Anal. calc. for $C_{21}F_2H_{20}N_2O_4S$: C, 58.06; H, 4.64; N, 6.45.

EXAMPLE 347

2-(3,4-Difluorophenyl)-4-(3-methyl-1-butoxy)-5-[4-(methylsulfonyl)phenyl]-3(2H)-pyridazinone The title compound was prepared according to the method of Example 346 substituting 3-methyl-1-butanol in place of isobutanol (yield: 63 mg, 23%). mp 121–123° C. $^1$H NMR (300 MHz, DMSO-$d_6$) δ0.78 (d, 6H), 1.48, (m, 3H), 3.3 (s, 3H), 4.43 (t, 2H), 7.54 (m, 1H), 7.6 (m, 1H), 7.82 (m, 1H), 7.91 (d, J=9 Hz, 2H), 8.07 (d, J=9 Hz, 2H), 8.2 (s, 1H). MS (DCI/NH$_3$) m/z 449 (M+H)$^+$, 466 (M+NH$_4$)$^+$. Anal. calc. for $C_{22}H_{22}F_2N_2O_4S$: C, 58.92; H, 4.94; N, 6.25. Found, C, 59.22; H, 4.97; N, 6.07.

EXAMPLE 348

2-(3,4-Difluorophenyl)-4-(4-fluorophenoxy)-5–3-fluoro-4-(methylsulfonyl)phenyl]-3(2H)-pyridazinone The title compound was prepared according to the method of Example 346, starting with 2-(3,4-difluorophenyl)-4-tosyloxy-5-[3-fluoro-4-(methylsulfonyl)phenyl]-3(2H)-pyridazinone in place of 2-(3,4-difluorophenyl)-4-tosyloxy-5-[4-(methylsulfonyl)phenyl]-3(2H)-pyridazinone and substituting 4-fluorophenol in place of isobutanol mp 168–170° C. $^1$H NMR (300 MHz, DMSO-$d_6$) δ 3.39 (s, 3H), 7.15 (d, 4H), 7.51 (m, 1H), 7.6 (m, 1H) 7.75 (m, 3H), 7.97 (t, 1H); 8.4 (s, 1H). MS (DCI/NH$_3$) m/z 491 (M+H)$^+$, 508 (M+NH$_4$)$^+$. Anal. calc. for $C_{23}H_4F_4N_2O_4S$: C, 56.33; H, 2.88; N, 5.71. Found, C, 56.07; H, 2.94; N, 5.33.

EXAMPLE 349

2-(3,4-Difluorophenyl)-4-(2,2-dimethylpropoxy)-5-[4-(methylsulfonyl)phenyl]-3(2H)-pyridazinone The title compound was prepared according to the method of Example 346 substituting neopentyl alcohol in place of isobutanol (yield: 1.18 g, 94%). mp 126–128° C. $^1$H NMR (300 MHz, DMSO-$d_6$) δ 0.78 (s, 9H), 3.3 (s, 3H), 4.1 (s, 2H), 7.51 (m, 1H), 7.6 (m, 1H), 7.82 (m, 1H), 7.91 (d, J=9 Hz, 2H), 8.07 (d, J=9 Hz, 2H), 8.21 (s, 1H). MS (DCI/NH$_3$) m/z 449 (M+H)$^+$, 466 (M+NH$_4$)$^+$. Anal. calc. for $C_{22}H_{22}F_2N_2O_4S$: C, 58.92; H, 4.94; N, 6.25. Found: C, 59.03; H, 5.03; N, 6.18.

EXAMPLE 350

2-(3,4-Difluorophenyl)-4-[2-(isopropoxy)ethoxy]-5-[4-(methylsulfonyl)phenyl]-3(2H)-pyridazinone The title compound was prepared according to the method of Example 346 substituting 2-(isopropoxy)ethanol in place of isobutanol (yield: 432 mg, 72%). mp 105–107° C. $^1$H NMR (300 MHz, DMSO-$d_6$) δ 0.95 (d, 6H), 3.3 (s, 3H), 3.43 (m, 1H), 3.54 (m, 2H), 4.63 (m, 2H), 7.54 (m, 1H), 7.6 (m, 1H), 7.8 (m, 1H), 8.01 (m, 4H), 8.2 (s, 1H). MS (DCI/NH$_3$) m/z 465 (M+H)$^+$, 482 (M+NH$_4$)$^+$. Anal. calc. for $C_{22}H_{22}F_2N_2O_5S$: C, 56.89; H, 4.77; N, 6.03. Found, C, 57.03; H, 4.65; N, 5.83.

EXAMPLE 351

2-(3,4-Difluorophenyl)-4-(3-methylpentyloxy)-5-[4-(methylsulfonyl)phenyl]-3(2H)-pyridazinone The title compound was prepared according to the method of Example 346 substituting 3-methylpentyl-1-ol in place of isobutanol (yield: 400 mg, 80%). mp 100–102° C. $^1$H NMR (300 MHz, DMSO-$d_6$) δ 0.75 (m, 6H), 1.05 (m, 1H), 1.28 (m, 3H) 1.6 (m, 1H), 3.3 (s, 3H), 4.45 (m, 2H), 7.5 (m, 1H), 7.6 (m, 1H), 7.8 (m, 1H), 7.9 (d, J=9 Hz, 2H) 8.05 (d, J=9 Hz, 2H), 8.2 (s, 1H). MS (DCI/NH$_3$) m/z 463 (M+H)$^+$, 480 (M+NH$_4$)$^+$. Anal. calc. for $C_{23}H_{24}F_2N_2O_4S$: C, 59.73; H, 5.23; N, 6.06. Found, C, 59.78; H, 5.31; N, 6.00.

EXAMPLE 352

2-(3,4-Difluorophenyl)-4-(4-methyl-3-penten-1-yloxy)-5-[4-(methylsulfonyl)phenyl]-5-3(2H)-pyridazinone The title compound was prepared according to the method of Example 346 substituting 4-methyl-3-pentene-1-ol in place of isobutanol (yield: 405 mg, 67.8%). mp 88–90° C. $^1$H NMR (300 MHz, DMSO-$d_6$) δ 1.5 (d, 6H), 2.27 (m, 2H) 3.3 (s, 3H), 4.43 (t, 2H), 4.95 (m, 1H), 7.5 (m, 1H), 7.6 (m, 1H), 7.8 (m, 1H), 7.9 (d, 2H), 8.06 (d, 2H), 8.2 (s, 1H). MS (DCI/NH$_3$) m/z 461 (M+H)$^+$, 478 (M+NH$_4$)$^+$. Anal. calc. for $C_{23}H_{22}F_2N_2O_4S$: C, 59.99; H, 4.82; N, 6.08. Found, C, 59.88; H, 4.76; N, 5.84.

EXAMPLE 353

2-(3,4-Difluorophenyl)-4-[3-(methoxy)butoxy]-5-[4-(methylsulfonyl)phenyl]-3(2H)-pyridazinone The title compound was prepared according to the method of Example 346 substituting 3-methoxybutyl-1-ol in place of isobutanol (yield: 350 mg, 68%). mp 99–101° C. $^1$H NMR (300 MHz, DMSO-$d_6$) δ 0.97 (d, 3H), 1.7 (m, 2H), 3.05 (s, 3H), 3.2 (m, 1H) 3.3 (s, 3H), 4.45 (m, 2H), 7.54 (m, 1H), 7.6 (m, 1H), 7.8 (m, 1H), 7.9 (d, J=9 Hz, 2H) 8.01 (d, J=9 Hz, 2H), 8.2 (s, 1H). MS (DCI/NH$_3$) m/z 465 (M+H)$^+$, 482 (M+NH$_4$)$^+$. Anal. calc. for $C_{22}H_{22}F_2N_2O_5S$: C, 56.89; H, 4.77; N, 6.03. Found, C, 56.60; H, 4.83; N, 5.96.

EXAMPLE 354

2-(3-Chlorophenyl)-4-(N-methylbenzylamino)-5-[4-(methylsulfonyl)phenyl]-3(2H)-pyridazinone To a rapidly stirred 0° C. mixture of N-methylbenzylamine (67.5 mg, 0.56 mmol) and tetrahydrofuran (3.7 mL) was slowly added dropwise an n-BuLi solution (0.235 mL, 0.59 mmol, 2.5 M in hexanes). The reaction mixture was stirred for 10 minutes at 0° C. and 1 hour at 23° C. The solution was cooled to −78° C., and a tetrahydrofuran (10–15 mL) solution of the 2-(3-chlorophenyl)-4-methoxy-5-[4-(methylthio)phenyl]-3(2H)-pyridazinone (200 mg, 0.56 mmol) slowly added along the interior wall of the reaction vessel. This reaction mixture was stirred overnight, slowly warming to 23° C. as the cooling bath evaporated. The reaction was quenched with water and diluted with a large excess of ethyl acetate. The layers were separated, and the ethyl acetate layer washed with additional water and brine and dried over $MgSO_4$, filtered, and concentrated in vacuo. The residue was chromatographed (flash silica gel, ethyl acetate/hexanes 1:9) to provide 2-(3-chlorophenyl)-4-(N-methyl benzylamino)-5-[4-(methylthio)phenyl]-3(2H)-pyridazinone (yield: 145 mg, 58%).

The title compound was prepared according to the method of Example 10, substituting 2-(3-chlorophenyl)-4-(N-methylbenzylamino)-5-[4-(methylthio)phenyl]-3(2H)-pyridazinone in place of 2-benzyl-4-(4-fluorophenyl)-5-[4-(methylthio)phenyl]-3(2H)-pyridazinone (yield: 143 mg, 95%). mp 60–85° C. $^1H$ NMR (300 MHz, $CDCl_3$) δ 2.46 (s, 3H), 3.09 (s, 3H), 4.63 (s, 2H), 7.19 (d, J=8.7 Hz, 2H), 7.24–7.29 (m, 2H), 7.32–7.48 (m, 5H), 7.60 (ddd, J=7.2, 1.8, 1.8 Hz, 1H), 7.67 (s, 1H), 7.70 (dd, J=1.8, 1.8 Hz, 1H), 7.91 (d, J=8.7 Hz, 2H). MS (APCI+) m/z 480 (M+H)$^+$.

EXAMPLE 355

2-(4-Fluorophenyl)-4-(1-piperidinyl)-5-[4-(methylsulfonyl)phenyl]-3(2H)-pyridazinone To a slightly heterogeneous solution of piperidine (99.7 mg, 1.17 mmol) and toluene (8 mL) cooled to −78° C. was slowly added dropwise an n-BuLi solution (0.235 mL, 0.59 mmol, 2.5 M in hexanes). After stirring at −78° C. for 10 minutes, the cooling bath was removed and the mixture stirred an additional 1 hour at 23° C. The 2-(4-fluorophenyl)-4-methoxy-5-[4-(methylthio)phenyl]-3(2H)-pyridazinone (400 mg, 1.17 mmol) was dissolved in portions in toluene (3×6–7 mL aliquots) with a heat gun and cooled to 0° C. prior to transfer via syringe to the lithium amide solution (cooled to −78° C.). The addition was made slowly along the interior wall of the reaction vessel. This reaction mixture was stirred overnight, slowly warming to 23° C. as the cooling bath evaporated. The reaction was quenched with water and diluted with a large excess of ethyl acetate. The layers were separated, and the ethyl acetate layer washed with additional water and brine and dried over $MgSO_4$, filtered, and concentrated in vacuo. The residue was chromatographed (flash silica gel, ethyl acetate/hexanes 1:2) to provide 440 mg (95%) of 2-(4-fluorophenyl)-5-[4-(methylthio)phenyl]-4-piperidino-3(2H)-pyridazinone.

The title compound was prepared according to the method of Example 10, substituting 2-(4-fluorophenyl)-5-[4-(methylthio)phenyl]-4-piperidino-3(2H)-pyridazinone in place of 2-benzyl-4-(4-fluorophenyl)-5-[4-(methylthio)phenyl]-3 (2H)-pyridazinone (yield: 165 mg, 98%). mp 80–100° C. $^1H$ NMR (300 MHz, $CDCl_3$) δ 1.59 (br s, 6H), 2.59 (br s, 4H), 3.14 (s, 3H), 7.17 (dd, J=8.7, 8.7 Hz, 2H), 7.51 (d, J=8.7 Hz, 2H), 7.55–7.62 (m, 2H), 7.68 (s, 1H), 8.06 (d, J=8.7 Hz, 2H). MS (APCI+) m/z 428 (M+H)$^+$. Powdered out in $CH_2Cl_2$/$C_6H_{14}$. Anal. calc. for $C_{22}H_{22}FN_3O_3S$.$0.25C_6H_{14}$: C, 62.85; H, 5.72; N, 9.35. Found: C, 62.46; H, 5.77; N, 9.13.

EXAMPLE 356

2-(4-Fluorophenyl)-4-(1-pyrrolidinyl)-5-[4-(methylsulfonyl)phenyl]-3(2H)-pyridazinone The title compound was prepared according to the method of Example 355, substituting pyrrolidine for piperidine (yield: 107 mg, 82%). mp 192–195° C. $^1H$ NMR (300 MHz, $CDCl_3$) δ 1.71–1.80 (m, 4H), 3.13 (s, 3H), 3.40–3.49 (m, 4H), 7.16 (dd, J=8.7, 8.7 Hz, 2H), 7.47–7.60 (m, 5H), 7.99 (d, J=8.7 Hz, 2H). MS (APCI+) m/z 414 (M+H)$^+$. Anal. calc. for $C_{21}H_{20}FN_3O_3S$: C, 61.00; H, 4.87; N, 10.16. Found: C, 60.95; H, 4.94; N, 10.07.

EXAMPLE 357

2-(3-Chlorophenyl)-4-(4-methylphenylthio)-5-[4-(methylsulfonyl)phenyl]-3(2H)-pyridazinone To a stirred suspension of 2-(3-chlorophenyl)-4-tosyloxy-5-[4-(methylsulfonyl)phenyl]-3(2H)-pyridazinone, prepared in Example 333, (0.0802 g, 0.15 mmol) in EtOH (1.5 mL) was added thiocresol (0.019 g, 0.15 mmol) and $K_2CO_3$ (0.0203 g, 0.15 mmol). The suspension was heated to 50° C. with stirring for 2.5 hours. The mixture was poured into $H_2O$ with constant stirring. The resulting precipitate was filtered, rinsed with $H_2O$ and dried to provide the desired product (yield: 0.060 g, 83%). mp 178–178° C. $^1H$ NMR (300 MHz, DMSO $d_6$) δ 2.19 (s, 3H), 3.23 (s, 3H), 6.95 (m, 2H), 7.08 (m, 2H), 7.52–7.66 (m, 3H), 7.72 (m, 1H), 7.88 (m, 2H), 8.08 (s, 1H). MS (DCI/$NH_3$) m/z 483 (M+H)$^+$, 500 (M+$NH_4$)$^+$. Anal. calc. for: $C_{24}H_{19}ClN_2O_3S_2$.$0.75 H_2O$: C, 58.05; H, 4.16; N, 5.64. Found: C, 57.99; H, 3.69; N, 5.76.

EXAMPLE 358

2-(3-Chlorophenyl)-4-(2-pyridylthio)-5-[4-(methylsulfonyl)phenyl]-3(2H)-pyridazinone The title compound was prepared according to the method of Example 357, substituting 2-mercaptopyridine in place of thiocresol (yield: 0.061 g, 39%). mp 110–114° C. $^1H$ NMR (300 MHz, DMSO $d_6$) δ 3.28 (s, 3H), 7.16 (m, 1H), 7.37 (m, 1H), 7.51–7.71 (m, 5H), 7.81 (m, 2H), 8.03 (m, 2H), 8.27 (s, 1H), 8.34 (m, 1H). MS (DCI/$NH_3$) m/z 470 (M+H)$^+$. Anal. calc. for $C_{22}H_{16}ClN_3O_3S_2$.$0.50 H_2O$: C, 55.16; H, 3.57; N, 8.77. Found: C, 54.88; H, 3.19; N, 8.59.

EXAMPLE 359

2-(3-Chlorophenyl)-4-(phenylmethylthio)-5-[4-(methylsulfonyl)phenyl]-3(2H)-pyridazinone To a stirred suspension of 2-(3-chlorophenyl)-4-tosyloxy-5-[4-(methylsulfonyl)phenyl]-3(2H)-pyridazinone, prepared in Example 333, (0.175 g, 0.33 mmol) in THF (3.3 mL) was added benzyl mercaptan (0.04 mL, 0.33 mmol) and TEA (0.046 mL, 0.33 mmol). The resulting solution was stirred at room temperature under nitrogen for 1 hour. The mixture was poured into $H_2O$ and extracted with ethyl acetate. The combined organics were dried over $MgSO_4$ and concentrated in vacuo. The resulting crude product was purified using flash chromatography ($SiO_2$, 2:1 hexanes:ethyl acetate) to provide the desired product (yield: 0.136 g 85%).

mp 142–145° C. ¹H NMR (300 MHz, DMSO d₆) δ 3.31 (s, 3H), 4.36 (s, 2H), 7.17 (m, 2H), 7.21–7.33 (m, 3H), 7.51 (m, 2H), 7.57–7.64 (m, 3H), 7.74 (m, 1H), 8.01 (m, 2H). MS (DCI/NH₃) m/z 483 (M+H)⁺, 500 (M+NH₄)⁺. Anal. calc. for $C_{24}H_{19}ClN_2O_3S_2$: C, 59.68; H, 3.96; N, 5.80. Found: C, 59.40; H, 4.11; N, 5.71.

EXAMPLE 360

2-(3-Chlorophenyl)-4-(2-furylmethylthio)-5-[4-(methylsulfonyl)phenyl]-3(2H)-pyridazinone The title compound was prepared according to the method of Example 359, substituting furfuryl mercaptan in place of benzyl mercaptan (yield: 0.162 g, 100%). mp 140–149° C. ¹H NMR (300 MHz, DMSO d₆) δ 3.31 (s, 3H), 4.46 (s, 2H), 6.20 (m, 1H), 6.37 (m, 1H), 7.50–7.67 (m, 6H), 7.77 (m, 1H), 8.03 (m, 2H), 8.08 (s, 1H). MS (DCI/NH₃) m/z 473 (M+H)⁺, 490 (M+NH₄)⁺. Anal. calc. for $C_{22}H_{17}ClN_2O_4S_2$: C, 55.87; H, 3.62; N, 5.92. Found: C, 55.84; H, 3.61; N, 5.82.

EXAMPLE 361

2-(3-Chlorophenyl)-4-]2-(methylpropyl)thio]-5-[4-(methylsulfonyl)phenyl]-3(2H)-pyridazinone The title compound was prepared according to the method of Example 359, substituting 2-methyl-1-propanethiol in place of benzyl mercaptan (yield: 0.134 g, 91%). Oil. ¹H NMR (300 MHz, DMSO d₆) δ 0.61 (d, J=6 Hz, 6H), 1.54–1.69 (m, 1H), 2.91 (d, J=6 Hz, 2H), 3.33 (s, 3H), 7.52–7.64 (m, 3H), 7.74 (m, 1H), 7.79 (m, 2H), 8.04 (m, 3H). MS (DCI/NH₃) m/z 449 (M+H)⁺, 466 (M+NH₄)⁺. Anal. calc. for $C_{21}H_{21}ClN_2O_3S_2$ (0.50 H₂O): C, 55.07; H, 4.84; N, 6.11. Found: C, 54.70; H, 4.64; N, 5.85.

EXAMPLE 362

2-(3-Chlorophenyl)-4-(cyclopentyl)-5-[4-(methylsulfonyl)phenyl]-3(2H)-pyridazinone To a −78° C. solution of 2-(3-chlorophenyl)-4-tosyloxy-5-[4-(methylsulfonyl)phenyl]-3(2H)-pyridazinone, prepared in Example 333, (0.175 g, 0.33 mmol) in THF (3.3 mL) was added cyclopentyl magnesium chloride (0.17 mL, 1.0 M in diethyl ether). The resulting solution was stirred under nitrogen less than 1 hour with warming to room temperature. The reaction was poured into water and extracted with ethyl acetate. The combined organics were dried over MgSO₄ and concentrated in vacuo. The resulting crude product was purified using flash chromatography (SiO₂, 2:1 ethyl acetate: hexanes) to provide the desired product (yield: 0.1328 g, 94%). mp 155–157° C. ¹H NMR (300 MHz, DMSO d₆) δ 1.50 (m, 2H), 1.66 (m, 2H), 1.79 (m, 2H), 2.09 (m, 2H), 2.90 (m, J=8 Hz, 1H), 3.26–3.37 (3H, obstructed by H₂O), 7.49–7.63 (m, 3H), 7.71 (m, 3H), 7.97 (s, 1H), 8.10 (m, 2H). MS (DCI/NH₃) m/z 429 (M+H)⁺, 446 (M+NH₄)⁺. Anal. calc. for $C_{22}H_{21}ClN_2O_3S$: C, 61.60; H, 4.93; N, 6.53. Found: C, 61.48; H, 4.81; N, 6.22.

EXAMPLE 363

2-(3-Chlorophenyl)-4-(2-methylpropyl)-5-[4-(methylsulfonyl)phenyl]-3(2H)-pyridazinone The title compound, an oil, was prepared according to the method of Example 362, substituting isobutyl magnesium chloride in place of cyclopentylmagnesium chloride, (yield: 0.132 g, 96%). ¹H NMR (300 MHz, CDCl₃) δ 0.77 (d, J=6 Hz, 6H), 2.08 (m, 1H), 2.54 (d, J=7 Hz, 2H), 7.36–7.46 (m, 2H), 7.56 (m, 2H), 7.62 (m, 1H), 7.73 (m, 2H), 8.11 (m, 2H). MS (DCI/NH₃) m/z 417 (M+H)⁺, 434 (M+NH₄)⁺. Anal. calc. for $C_2H_{21}ClN_2O_3S\cdot 0.50$ H₂O: C, 59.21; H, 5.20; N, 6.57. Found: C, 59.27; H, 5.40; N, 6.12.

EXAMPLE 364

2-(3-Chlorophenyl)-4-(cyclopentylmethyl)-5-[4-(methylsulfonyl)phenyl-3(2H)-pyridazinone The title compound, an oil, was prepared according to the method of Example 362, substituting cyclopentylmethyl magnesium bromide in place of cyclopentyl magnesium chloride (yield: 0.0579 g, 38%). ¹H NMR (300 MHz, DMSO d₆) δ 0.66 (m, 2H), 1.03 (m, 3H), 1.50 (m, 6H), 1.61 (m, 1H), 2.46 (m, 1H), 3.27–3.42 (3H, obstructed by H₂O), 7.50–7.66 (m, 3H), 7.75 (m, 3H), 7.99 (s, 1H), 8.10 (m, 2H). MS (DCI/NH₃) m/z 457 (M+H)⁺, 474 (M+NH₄)⁺. Anal. calc. for $C_{24}H_{25}ClN_2O_3S$: C, 63.08; H, 5.51; N, 6.13. Found: C, 63.08; H, 5.47; N, 6.04.

EXAMPLE 365

2-(3-Chlorophenyl)-4-(2-cyclopentylethyl)-5-[4-(methylsulfonyl)phenyl]-3(2H)-pyridazinone The title compound was prepared according to the method of Example 362, substituting cyclopentylethyl magnesium bromide in place of cyclopentyl magnesium chloride (yield: 0.165 g, 94%). ¹H NMR (300 MHz, DMSO d₆) δ 0.76 (m, 3H), 0.99–1.21 (m, 5H), 1.31–1.62 (m, 8H), 2.42–2.56 (1H, obstructed by DMSO), 3.25–3.34 (2H, obstructed by H₂O), 7.48–7.65 (m, 3H), 7.48–7.65 (m, 3H), 7.76 (m, 3H), 8.01 (s, 1H), 8.10 (m, 2H). MS (DCI/NH₃) m/z 471 (M+H)⁺, 488 (M+NH₄)⁺. Anal. calc. for $C_{25}H_{27}ClN_2O_3S$: C, 63.75; H, 5.78; N, 5.95. Found: C, 63.48; H, 5.70; N, 5.67.

EXAMPLE 366

2-(3-Chlorophenyl)-4-(3-methylbutyl)-5-[4-(methylsulfonyl)phenyl]-3(2H)-pyridazinone The title compound was prepared according to the method of Example 362, substituting 3-methylbutyl magnesium bromide in place of cyclopentylmagnesium chloride (yield: 0.0221 g, 16%). mp 60–65° C. ¹H NMR (300 MHz, DMSO d₆) δ 0.75 (d, J=7 Hz, 6H), 1.32–1.52 (m, 3H), 3.31 (s, 3H), 7.50–7.65 (m, 3H), 7.77 (m, 3H), 8.03 (s, 1H), 8.11 (m, 2H). MS (DCI/NH₃) m/z 431 (M+H)⁺, 448 (M+NH₄)⁺. Anal. calc. for $C_{22}H_{23}ClN_2O_3S\cdot 0.25$ H₂O: C, 60.68; H, 5.43; H, 6.43. Found C, 60.29; H, 5.60; N, 6.17.

EXAMPLE 367

2-(3-Chlorophenyl)-4-benzyl-5-[4-(methylsulfonyl)phenyl]-3(2H)-pyridazinone

The title compound was prepared according to the method of Example 362, substituting benzyl magnesium chloride in place of cyclopentylmagnesium chloride. mp 174–177° C. (yield: 25.9 g, 57%). ¹H NMR (300 MHz, DMSO d₆) δ 3.30 (s, 3H), 3.91 (bs, 2H), 7.02 (m, 2H), 7.12–7.25 (m, 3H), 7.51–7.64 (m, 3H), 7.72 (m, 3H), 8.07 (m, 2H), 8.12 (s, 1H). MS (DCI/NH₃) m/z 451 (M+H)⁺, 468 (M+NH₄)⁺. Anal.

calc. for $C_{24}H_{19}ClN_2O_3S$: C, 63.92; H, 4.25; N, 6.21. Found: C, 63.69; H, 4.28; N, 6.02.

EXAMPLE 368

2-(3-Chlorophenyl)-4-cyclohexyl-5-[(methylsulfonyl)phenyl]-3(2H)-pyridazinone The title compound was prepared according to the method of Example 362 substituting cyclohexylmagnesium chloride in place of cyclopentylmagnesium chloride (yield: 0.099 g, 68%). mp 85–90° C. $^1$H NMR (300 MHz, CDCl$_3$) δ 1.01–1.30 (m, 3H), 1.48–1.69 (m, 3H), 1.75 (m, 2H), 2.28 (m, 2H), 2.57 (m, 1H), 3.16 (s, 3H), 7.35–7.46 (m, 2H), 7.50–7.62 (m, 3H), 7.68 (m, 2H), 8.11 (m, 2H). MS (DCI/NH$_3$) m/z 443 (M+H)$^+$, 460 (M+NH$_4$)$^+$. Anal. calc. for $C_{23}H_{23}ClN_2O_3S$ (1.25 H$_2$O): C, 59.34; H, 5.52; N, 6.01. Found: C, 59.02; H, 5.24; N, 5.65.

EXAMPLE 369

2-(3-Chlorophenyl)-4-(4-fluorobenzyl)-5-[4-(methylsulfonyl)phenyl]-3(2H)-pyridazinone The title compound was prepared according to the method of Example 228 using the product from Example 207C and substituting 4-fluorobenzyl magnesium chloride in place of cyclohexyl magnesium chloride (yield: 0.1895 g, 41%). mp 183–185° C. $^1$H NMR (300 MHz, DMSO d$_6$) δ 3.25–3.36 (3H, obstructed by H$_2$O), 3.89 (bs, 2H), 6.97–7.09 (m, 4H), 7.50–7.64 (m, 3H), 7.71 (m, 3H), 8.06 (m, 2H), 8.11 (s, 1H). MS (DCI/NH$_3$) m/z 469 (M+H)$^+$, 486 (M+NH$_4$)$^+$. Anal. calc. for $C_{24}H_{18}ClFN_2O_3S$: C, 61.47; H, 3.87; N, 5.97. Found: C, 61.23; H, 3.84; N, 5.77.

EXAMPLE 370

2-(3-Chlorophenyl)-4-(4-methylphenyl)-5-[4-(methylsulfonyl)phenyl]-3(2H)-pyridazinone The title compound was prepared according to the method of Example 362 substituting p-tolylmagnesium bromide in place of cyclopentylmagnesium chloride (yield: 65 mg, 40.9%). mp 222–224° C. $^1$H NMR (300 MHz, DMSO-d$_6$) δ 2.28 (s, 3H), 3.25 (s, 3H), 7.12 (t, 4H), 7.6 (m, 5H), 7.79 (t, 1H) 7.9 (d, J=9 Hz, 2H), 8.22 (s, 1H). MS (DC/NH$_3$) m/z 451 (M+H)$^+$, 468 (M+NH$_4$)$^+$. Anal. calc. for $C_{24}H_{19}ClN_2O_3S\cdot0.25$ H$_2$O: C, 63.92; H, 4.25; N, 6.21. Found: C, 62.99; H, 4.28; N, 5.85.

EXAMPLE 371

2-(3,4-Difluorophenyl)-4-(3-fluoro-4-methylphenyl)-5-[4-(methylsulfonyl)phenyl]-3(2H)-pyridazinone 2-(3,4-Difluorophenyl)-4-(3-fluoro-4-methylphenyl)-5-[4-(methylsulfonyl)phenyl]-3(2H)-pyridazinone was prepared according to the method of Example 362, starting with 2-(3,4-difluorophenyl)-4-tosyloxy-5-[4-(methylsulfonyl)phenyl]-3(2H)-pyridazinone and substituting 3-fluoro-4-methylphenylmagnesium bromide in place of cyclopentylmagnesium chloride to provide the methyl sulfide compound.

The methyl sulfide was oxidized according to the method of Example 10 to provide the title compound (yield: 265 mg, 85.4%). mp 204–206° C. $^1$H NMR (300 MHz, CDCl$_3$) δ 2.25 (br s, 3H), 3.08 (s, 3H), 6.83 (dd, J=9 Hz, 1.5 Hz, 1H), 6.96 (dd, J=9 Hz, 1.5 Hz, 1H), 7.08 (t, J=9 Hz, 1H), 7.23–7.33 (m, 1H), 7.41 (d, J=9 Hz, 2H), 7.49–7.56 (m, 1H), 7.61–7.69 (m, 1H), 7.93 (d, J=9 Hz, 2H), 7.99 (s, 1H). MS (DCI/NH$_3$) m/z 471 (M+H)$^+$, 488 (M+NH$_4$)$^+$. Anal. calc. for $C_{24}H_{17}F_3N_2O_3S$: C, 61.28; H, 3.62; N, 5.96. Found: C, 61.07; H, 3.95; N, 5.56.

EXAMPLE 372

2-(3-Chlorophenyl)-4-(phenethyl)-5-[4-(methylsulfonyl)phenyl]-3(2H)-pyridazinone The title compound was prepared according to the method of Example 228, starting with 2-(3-chlorophenyl)-4-methoxy-5-[4-(methylthio)phenyl]-3(2H)-pyridazinone in place of 2-(4-fluorophenyl)-4-methoxy-5-[4-(methylthio)phenyl]-3(2H)-pyridazinone and substituting phenethyl magnesium chloride in place of cyclohexylmagnesium chloride then oxidizing by the method of Example 10 (yield: 0.100 g, 39%). mp 142–145° C. $^1$H NMR (300 MHz, DMSO d$_6$) δ 2.80 (m, 4H), 3.30 (s, 3H), 7.01 (m, 2H), 7.21 (m, 3H), 7.51–7.60 (m, 4H), 7.63 (m, 1H), 7.78 (m, 1H), 8.03 (m, 3H). MS (DCI/NH$_3$) m/z 465 (M+H)$^+$, 482 (M+NH$_4$)$^+$. Anal. calc. for $C_{25}H_{21}ClN_2O_3S$: C, 64.58; H, 4.55; N, 6.02. Found: C, 64.24; H, 4.50; N, 5.90.

EXAMPLE 373

2-(3-Chlorophenyl)-4-(2-methylpropoxy)-5-[3-fluoro-4-(methylsulfonyl)phenyl]-3(2H)-pyridazinone

Example 373A

2-(3-Chlorophenyl)-4-(2-methylpropoxy)-5-bromo-3(2H)-pyridazinone

The title compound was prepared according to the method of Example 194B, starting with 2-(3-chlorophenyl)-4,5-dibromo-3(2H)-pyridazinone (Example 207A) in place of 2-(4-fluorophenyl)-4,5-dibromo-3(2H)-pyridazinone and substituting 2-methyl-1-propanol in place of methanol.

Example 373B

2-(3-Chlorophenyl)-4-(2-methylpropoxy)-5-[3-fluoro-4-(methylthio)phenyl]-3(2H)-pyridazinone The title compound was prepared according to the method of Example 6, starting with 2-(3-chlorophenyl)-4-(2-methylpropoxy)-5-bromo-3(2H)-pyridazinone in place of 2-benzyl-4-bromo-5-methoxy-3(2H)-pyridazinone and substituting 3-fluoro-4-(methylthio)benzeneboronic acid (Example 72D) in place of 4-fluorobenzeneboronic acid.

Example 373C

2-(3-Chlorophenyl)-4-(2-methylpropoxy)-5-[3-fluoro-4-(methylsulfonyl)phenyl]-3(2H)-pyridazinone Example 373B was oxidized according to the method of Example 10 to provide the title compound (yield: 0.73 g, 100%). mp 180–183° C. $^1$H NMR (300 MHz, DMSO d$_6$) δ 0.82 (d, J=6 Hz, 2H), 3.30–3.39 (3H, obstructed by H$_2$O) 4.25 (d, J=6 Hz, 2H), 7.57 (m, 3H), 7.75 (m, 1H), 7.85 (m, 1H), 8.00 (m, 1H), 8.23 (s, 1H). MS (DCI/NH$_3$) m/z 451 (M+H)$^+$, 468 (M+NH$_4$)$^+$. Anal. calc. for C$_{21}$H$_{20}$ClFN$_2$O$_4$S: C, 55.94; H, 4.47; N, 6.21. Found: C, 55.73; H, 4.58; N, 6.01.

EXAMPLE 374

2-(3-Chlorophenyl)-4-(benzyloxy)-5-[4-(methylsulfonyl)phenyl]-3(2H)-pyridazinone To a stirred solution of 2-(3-chlorophenyl)-4-hydroxy-5-[4-(methylsulfonyl)phenyl]-3(2H)-pyridazinone (Example 332) (0.100 g, 0.28 mmol) in DMF (2.8 mL) was added benzyl chloride (0.32 mL, 0.28 mmol). The resulting solution was stirred with heating to 60° C. overnight. The solvent was removed in vacuo and the resulting residue partitioned between ethyl acetate and 10% citric acid. After extracting with ethyl acetate, the combined organics were dried over MgSO$_4$ and concentrated in vacuo. The crude product was purified using flash chromatography (SiO$_2$, 1:1 ethyl acetate: hexanes) to provide the desired product (yield: 0.096 g, 76%). mp 110–113° C. $^1$H NMR (300 MHz, DMSO d$_6$) δ 3.39 (s, 3H), 5.48 (s, 2H), 7.29 (m, 4H), 7.59–7.71 (m, 3H), 7.76 (m, 3H), 8.00 (m, 2H), 8.21 (s, 1H). MS (DCI/NH$_3$) m/z 467 (M+H)$^+$, 484 (M+NH$_4$)$^+$. Anal. calc. for C$_{24}$H$_{19}$ClN$_2$O$_4$S: C, 61.73; H, 4.10; N, 6.00. Found: C, 62.00; H, 4.18; N, 5.93.

EXAMPLE 375

2-(4-Fluorophenyl)-4-(3-methylbutoxy)-5-[4-(methylsulfonyl)phenyl]-3(2H)-pyridazinone 2-(4-Fluorophenyl)-4-methoxy-5-bromo-3(2H)-pyridazinone (Example 194B) was converted into 2-(4-fluorophenyl)-4-methoxy-5-[4-(methylthio)phenyl]-3(2H)-pyridazinone according to the method of Example 194C followed by the oxidation method in Example 10. The methoxy compound was converted to the 2-(4-fluorophenyl)-4-hydroxy-5-[4-(methylsulfonyl)phenyl]-3(2H)-pyridazinone, by treatment with NaOH according to the procedure of Example 332. The hydroxy compound was treated with p-toluenesulfonyl chloride according to the procedure of Example 333, to furnish 2-(4-fluorophenyl)-5-[4-(methylsulfonyl)phenyl]-4-tosyloxy-3(2H)-pyridazinone.

The title compound was prepared according to the method of Example 335, starting with 2-(4-fluorophenyl)-5-[4-(methylsulfonyl)phenyl]-4-tosyloxy-3(2H)-pyridazinone in place of 2-(3-chlorophenyl)-5-[4-(methylsulfonyl)phenyl]-4-tosyloxy-3(2H)-pyridazinone substituting 3-methyl-1-butanol in place of isobutanol (yield: 0.3932 g, 94%). mp 117–120° C. $^1$H NMR (300 MHz, DMSO d$_6$) δ 0.79 (d, J=6 Hz, 6H), 1.41–1.59 (m, 3H), 3.30 (s, 3H), 4.42 (d, J=5 Hz, 2H), 7.36 (m, 2H), 7.65 (m, 2H), 7.90 (m, 2H), 8.06 (m, 2H), 8.18 (s, 1H). MS (DCI/NH$_3$) m/z 431 (M+H)$^+$, 448 (M+NH$_4$)$^+$. Anal. calc. for C$_{22}$H$_{23}$FN$_2$O$_4$S: C, 61.38; H, 5.39; N, 6.51. Found: C, 61.42; H, 5.30; N, 6.40.

EXAMPLE 376

2-(4-Fluorophenyl)-4-(2-methylpropoxy)-5-[4-(methylsulfonyl)phenyl]-3(2H)-pyridazinone The title compound was prepared according to the method of Example 335, substituting 2-(4-fluorophenyl)-5-[4-(methylsulfonyl)phenyl]-4-tosyloxy-3(2H)-pyridazinone (prepared as an intermediate in Example 375) in place of 2-(3-chlorophenyl)-5-[4-(methylsulfonyl)phenyl]-4-tosyloxy-3(2H)-pyridazinone (yield: 0.486 g, 100%). mp 121–128° C. $^1$H NMR (300 MHz, DMSO d$_6$) δ 0.78 (d, J=7 Hz, 6H), 1.84 (m, 1H), 3.30 (s, 3H), 4.20 (d, J=6 Hz, 2H), 7.37 (m, 2H), 7.66 (m, 2H), 7.92 (m, 2H), 8.07 (m, 2H), 8.19 (s, 1H). MS (DCI/NH$_3$) m/z 417 (M+H)$^+$, 434 (M+NH$_4$)$^+$. Anal. calc. for C$_{21}$H$_{21}$FN$_2$O$_4$S.0.50 H$_2$O: C, 59.28; H, 5.21; N, 6.58. Found: C, 59.49; H, 4.97; N, 6.34.

EXAMPLE 377

2-(4-Fluorophenyl)-4-(4-fluorobenzyl)-5-[4-(methylsulfonyl)phenyl]-3(2H)-pyridazinone The title compound was prepared according to the method of Example 62, starting with 4-(4-fluorophenylmethyl)-5-[4-(methylsulfonyl)phenyl]-3(2H)-pyridazinone and reacting with 1-iodo-4-fluorobenzene (yield: 0.0881 g, 78%). mp 175–177° C. $^1$H NMR (300 MHz, DMSO d$_6$) δ 3.27–3.36 (3H, obstructed by H$_2$O), 3.88 (bs, 2H), 6.98–7.09 (m, 4H), 7.34 (m, 2H), 7.65 (m, 2H), 7.71 (m, 2H), 8.06 (m, 3H). MS (DCI/NH$_3$) m/z 453 (M+H)$^+$, 470 (M+NH$_4$)$^+$. Anal. calc. for C$_{24}$H$_{18}$F$_2$N$_2$O$_3$S: C, 63.71; H, 4.01; N, 6.19. Found: C, 63.61; H, 4.26; N, 6.03.

EXAMPLE 378

2-(4-Fluorophenyl)-4-(3-methylbutyl)-5-[4-(methylsulfonyl)phenyl]-3(2H)-pyridazinone The title compound was prepared according to the method of Example 228, substituting 3-methylbutyl magnesium bromide in place of cyclohexylmagnesium chloride (yield: 0.325 g, 69%). mp 151–154° C. $^1$H NMR (300 MHz, DMSO d$_6$) δ 0.75 (d, J=7 Hz, 6H), 1.32–1.51 (m, 3H), 3.31 (s, 3H), 7.37 (m, 2H), 7.66 (m, 2H), 7.77 (m, 2H), 8.00 (s, 1H), 8.10 (m, 2H). MS (DCI/NH$_3$) m/z 415 (M+H)$^+$, 432 (M+NH$_4$)$^+$. Anal. calc. for C$_{22}$H$_{23}$FN$_2$O$_3$S.0.50 H$_2$O: C, 62.39; H, 5.71; N, 6.61. Found: C, 62.04; H, 5.78; N, 6.46.

EXAMPLE 379

2-(Tetrahydro-2H-pyrano-2-yl)-4-(4-fluorophenyl)-5-[4-(methylsulfonyl)phenyl]-3(2H)-pyridazinone To the solution of 4-(4-fluorophenyl)-5-[4-(methylsulfonyl)phenyl]-3(2H)-pyridazinone prepared according to Example 11 (172 mg, 0.5 mmol) and p-toluenesulfonic acid hydrate (19 mg, 0.1 mmol) in dioxane (10 mL) was added 2,3-dihydropyran (2 mL). The mixture was stirred at room temperature for 6 hours. The mixture was then poured into a solution of saturated NaHCO$_3$ and extracted with ethyl acetate. The ethyl acetate was concentrated in vacuo and the residue was chromatographed (silica gel, 1:1 hexanes-ethyl acetate) to provide the title compound (yield: 25 mg, 11%). $^1$H NMR (DMSO-d$_6$, 300 MHz) δ 1.54 (m, 2H), 1.74 (m, 2H), 2.00 (m, 1H), 2.17 (m, 1H), 3.23 (s, 3H), 3.62 (m, 1H), 4.00 (m, 1H), 5.98 (m, 1H), 7.13 (7, J=9 Hz, 2H), 7.23 (m, 2H), 7.47 (d, J=9 Hz, 2H), 7.86 (d, J=9 Hz, 2H), 8.12 (s, 1H). MS (DCI/NH$_3$) m/z 429 (M+H)$^+$.

EXAMPLE 380

2-(3-(4-Fluorophenyl)phenyl)-4-(4-fluorophenyl)-5-[4-(methylsulfonyl)phenyl]-3(2H)-pyridazinone The title compound was prepared according to the method of Example 4, starting with 2-(3-bromophenyl)-4-(4-fluorophenyl)-5-[4-(methylsulfonyl)phenyl]-3(2H)-pyridazinone (Example 166) in place of 2-benzyl-4-bromo-5-[4-(methylthio)phenyl]-3(2H)-pyridazinone and substituting cesium fluoride for sodium carbonate (yield: 0.62g, 62%). mp 222–225° C. $^1$H NMR (300 MHz, DMSO d$_6$) δ 3.24 (s, 3H), 7.16 (m, 2H), 7.36 (m, 3H), 7.53 (m, 2H), 7.64 (m, 2H), 7.73–7.81 (m, 3H), 7.93 (m, 3H), 8.27 (s, 1H). MS (DCI/NH$_3$) m/z 515 (M+H)$^+$, 532 (M+NH$_4$)$^+$. Anal. calc. for C$_{29}$H$_{20}$F$_2$N$_2$O$_3$S.0.25 H$_2$O: C, 67.10; H, 3.98; N, 5.35. Found: C, 66.93; H, 3.99; N, 5.17.

EXAMPLE 381

2-(2,2,2-Trifluoroethyl)-4-(2,2-dimethylpropoxy)-5-[3-fluoro-4-(aminosulfonyl)phenyl]-3(2H)-pyridazinone 2-(2,2,2-Trifluoroethyl)-4-(2,2-dimethylpropoxy)-5-[3-fluoro-4-(methylthio)phenyl]-3(2H)-pyridazinone was prepared according to the method of Example 261, substituting 2-(2,2,2-trifluoroethyl)-4-chloro-5-[3-fluoro-4-(methylthio)phenyl]-3(2H)-pyridazinone in place of 2-(2,2,2-trifluoroethyl)-4chloro-5-[4-(methylsulfonyl)phenyl]-3(2H)-pyridazinone.

The methyl sulfide was oxidized with one equivalent of meta-chloroperoxybenzoic acid to give the methyl sulfoxide. The sulfoxide was converted to the title compound according to the method of Example 68 (yield: 196 mg, 28%). mp 144–145° C. $^1$H NMR (300 MHz, CDCl$_3$) δ 0.86 (s, 9H), 4.23 (s, 2H), 4.82 (q, J=8 Hz, 2H), 5.10 (s, 2H), 7.46 (s, 1H), 7.48 (br s, 1H), 7.79 (s, 1H), 8.03 (t, J=8 Hz, 1H). MS (DCI/NH$_3$) m/z 438 (M+H)$^+$. Anal. calc. for C$_{17}$H$_{19}$F$_4$N$_3$O$_4$S: C, 46.68; H, 4.38; N, 9.61. Found: C, 46.76; H, 4.30; N, 9.52.

EXAMPLE 382

2-(2,2,2-Trifluoroethyl)-4-(2-methylpropoxy)-5-[3-fluoro-4-(aminosulfonyl)phenyl]-3(2H)-pyridazinone The title compound was prepared according to the method of Example 68 substituting 2-(2,2,2-trifluoroethyl)-4-(2-methylpropoxy)-5-[4-(methylsulfinyl)phenyl]-3(2H)-pyridazinone in place of 2-(2,2,2-trifluoroethyl)-4-(4-fluorophenyl)-5-[4-(methylsulfinyl)phenyl]-3(2H)-pyridazinone (yield: 260 mg, 26%). mp 163–164° C. $^1$H NMR (300 MHz, CDCl$_3$) δ 0.86 (d, J=6.6 Hz, 6H), 1.91 (septet, J=6.6 Hz, 1H), 4.34 (d, J=6.6 Hz, 2H), 5.11 (br s, 2H), 7.43–7.52 (m, 2H), 7.80 (s, 1H), 8.02 (t, J=8 Hz, 1H). MS (DCI/NH$_3$) m/z 424 (M+H)$^+$, m/z 441 (M+NH$_4$)$^+$. Anal. calc. for C$_{16}$H$_{17}$F$_4$N$_3$O$_4$S: C, 45.39; H, 4.05; N, 9.92. Found: C, 59.89; H, 3.83; N, 8.61.

EXAMPLE 383

2-Benzyl-4(4-fluorobenzyl)-5-[4-(aminosulfonyl)phenyl]-3(2H)-pyridazinone

The title compound was prepared according to the method of Example 384, substituting 2-benzyl-4-(4-fluorophenylmethyl)-5-[4-(methylsulfonyl)phenyl]-3(2H)-pyridazinone in place of 2-(3,4-difluorophenyl)-4-(4-fluorophenyl)-5-[4-(methylsulfonyl)phenyl]-3(2H)-pyridazinone (yield: 0.5723 g 34%). mp 120–123° C. $^1$H NMR (300 MHz, DMSO d$_6$) δ 3.83 (bs, 2H), 5.30 (bs, 2H), 6.95–7.06 (m, 4H), 7.28–7.40 (m, 5H), 7.48 (m, 2H), 7.60 (m, 2H), 7.91 (m, 2H), 7.95 (s, 1H). MS (DCI/NH$_3$) m/z 450 (M+H)$^+$, 467 (M+NH$_4$)$^+$. Anal. calc. for C$_{24}$H$_{20}$FN$_3$O$_3$S: C, 64.13; H, 4.48; N, 9.35. Found: C, 63.76; H, 4.71; N, 9.02.

EXAMPLE 384

2-Benzyl-4-(4-fluorophenyl)-5-[4-(aminosulfonyl)phenyl]-3(2H)-pyridazinone

To a solution of 2-benzyl-4-(4-fluorophenyl)-5-[4-(methylsulfonyl)phenyl]-3(2H)-pyridazinone (130 mg, 0.3 mmol) and di-t-butylazodicarboxylate (DBAD) (69 mg, 0.3 mmol) in THF (30 mL) at −78° C. was added dropwise a 1 N solution of lithium 1,1,1,3,3,3-hexamethyldisilazide (0.9 mL, 0.9 mmol) in THF After addition, the reaction was stirred an additional 45 minutes at −78° C. (or until the TLC indicated a disappearance of starting material). The reaction was quenched with a saturated solution of NH$_4$Cl and extracted with ethyl acetate. The acetate extract was dried over MgSO$_4$ and concentrated in vacuo to obtain 220 mg of crude adduct.

The above adduct was dissolved in THF (30 ML) and was treated at room temperature with 1 N NaOH (3 mL) for 5 hours. Sodium acetate (NaOAc.3 H$_2$O, 1.38 g, 10 mmol) was added followed by addition of hydroxylamine-O-sulfonic acid (1.13 g, 10 mmol) and H$_2$O (30 mL). The resulting mixture was stirred at room temperature for 18 hours and then extracted with ethyl acetate. The extract was washed with water, brine, dried over MgSO$_4$ and concentrated in vacuo. The residue was purified by chromatography (silica gel, 1:1 hexanes-ethyl acetate) to provide the desired product (yield: 70 mg, 54%). mp 185–189° C. $^1$H NMR (DMSO-d$_6$, 300 MHz) δ 5.33 (s, 2H), 7.11. (m, 2H), 7.22 (m, 2H), 7.40 (m, 7H), 7.83 (d, J=9 Hz, 2H), 8.10 (s, 1H). MS (DCI/NH$_3$) m/z 436 (M+H)$^+$. Anal. calc. for C$_{23}$H$_{18}$FN$_3$O$_3$S.0.75 H$_2$O: C, 61.65; H, 4.26; N, 9.04. Found: C, 61.67; H, 4.61; N, 8.66.

EXAMPLE 385

2-(4-Fluorophenyl)4-(4-fluorophenoxy)-5-[4-(aminosulfonyl)phenyl]-3(2H) pyridazinone The product from Example 108 was converted to the title sulfonamide according to the method of Example 384, (yield: 65 mg, 28.8%). mp 227–229° C. $^1$H NMR (300 MHz, DMSO-d$_6$) δ 7.08–7.17 (m, 4H), 7.36 (t, J=3 Hz, 2H), 7.47 (br s, 2H), 7.61–7.69 (m, 2H), 7.83 (d, J=9 Hz, 2H), 7.93 (d, J=9 Hz, 2H), 8.40 (s, 1H). MS (DCI/NH$_3$) m/z 469 (M+H)$^+$, 486 (M+NH$_4$)$^+$. Anal. calc. for C$_{24}$H$_{15}$F$_2$N$_3$O$_4$S: C, 58.02; H, 3.30; N, 9.24. Found: C, 57.84; H, 3.34; N, 9.01.

EXAMPLE 386

2-(3,4-Difluorophenyl)-4-(3-fluoro-4-methylphenyl)-5-[4-(aminosulfonyl)phenyl]-3(2H)-pyridazinone The product from Example 371 was converted to the title sulfonamide according to the method of Example 384 (yield: 45 mg, 28%). mp 198–200° C. $^1$H NMR (300 MHz, DMSO-d$_6$) δ 6.87 (dd, J=9 Hz, 3 Hz, 1H), 7.13 (dt, J=9 Hz, 3 Hz, 1H), 7.19 (t, J=7 Hz, 1H), 7.46 (d, J=9 Hz, 2H), 7.47 (br s, 2H), 7.52–7.69 (m, 2H), 7.79 (d, J=9 Hz, 2H), 7.82–7.89 (m, 1H), 8.25 (s, 1H). MS (DCI/NH$_3$) m/z 472 (M+H)$^+$, 489 (M+NH$_4$)$^+$.

EXAMPLE 387

2-(4-Fluorophenyl)-4-(3-fluoro-4-methylphenyl)-5-[4-(aminosulfonyl)phenyl]-3(2H)-pyridazinone The product from Example 250 was converted to the title sulfonamide according to the method of Example 384 (yield: 185 mg, 46%). mp 187–188° C. $^1$H NMR (300 MHz, DMSO-$d_6$) δ 2.22 (br s, 3H), 6.87 (dd, J=9 Hz, 3 Hz, 1H), 7.16 (q, J=9 Hz, 2H), 7.38 (t, J=9 Hz, 2H), 7.46 (br s, 2H), 7.47 (d, J=9 Hz, 2H), 7.67–7.73 (m, 2H), 7.77 (d, J=9 Hz, 2H), 8.22 (s, 1H). MS (DCI/NH$_3$) m/z 454 (M+H)$^+$, 471 (M+NH$_4$)$^+$. Anal. calc. for $C_{23}H_{17}F_2N_3O_3S.0.25\ H_2O$: C, 60.36; H, 3.87; N, 9.19. Found: C, 60.30; H, 4.26; N, 8.83.

EXAMPLE 388

2-(3,4-Difluorophenyl)-4-(4-fluorophenoxy)-5-[4-(aminosulfonyl)phenyl]-3(2H)-pyridazinone The product from Example 109 was converted to the title sulfonamide according to the method of Example 384 (yield: 110 mg, 45.7%). mp 224–226° C. $^1$H NMR (300 MHz, CDCl$_3$) δ 4.86 (br s, 2H), 6.89–7.03 (m, 4H), 7.19–7.30 (m, 1H), 7.45–7.52 (m, 1H), 7.56–7.66 (m, 1H), 7.79 (d, J=9 Hz, 2H), 8.04 (d, J=9 Hz, 1H), 8.08 (s, 1H). MS (DCI/NH$_3$) m/z 474 (M+H)$^+$, 491 (M+NH$_4$)$^+$. Anal. calc. for $C_{22}H_{14}F_3N_3O_4S.0.25\ H_2O$: C, 55.32; H, 2.93; N, 8.80. Found: C, 55.26; H, 3.11; N, 8.58.

EXAMPLE 389

2-(3-Chloro-4-fluorophenyl)-4-(4-fluoro-3-methylphenyl)-5-[4-(aminosulfonyl)phenyl]-3(2H)-pyridazinone The product from Example 247 was converted to the title sulfonamide according to the method of Example 384 (yield: 230 mg, 38%). mp 243–245° C. $^1$H NMR (300 MHz, DMSO-$d_6$) δ 2.17 (br s, 3H), 6.94–7.09 (m, 2H), 7.25 (dd, J=9 Hz, 3 Hz, 1H), 7.41–7.48 (m, 4H), 7.60 (t, J=9 Hz, 1H), 7.68–7.75 (m, 1H), 7.77 (d, J=9 Hz, 2H), 7.95 (dd, J=6 Hz, 3 Hz, 1H), 8.25 (s, 1H). MS (DCI/NH$_3$) m/z 469 (M+H)$^+$, 486 (M+NH$_4$)$^+$. Anal. calc. for $C_{23}H_{16}ClF_2N_3O_3S$: C, 56.67; H, 3.29; N, 8.63. Found: C, 56.81; H, 3.35; N, 8.95.

EXAMPLE 390

2-(4-Fluorophenyl)-4-(4-fluoro-3-methylphenyl)-5-[4-(aminosulfonyl)phenyl]-3(2H)-pyridazinone The methyl sulfone product of Example 245 was converted to the title sulfonamide according to the method of Example 384 (yield: 78 mg, 28.3%). mp 202–204° C. $^1$H NMR (300 MHz, CDCl$_3$) δ 2.22 (s, 3H), 4.86 (s, 2H), 6.83–6.91 (m, 2H), 7.14–7.25 (m, 3H), 7.36 (d, J=9 Hz, 2H), 7.65–7.72 (m, 2H), 7.91 (d, J=9 Hz, 2H), 8.0 (s, 1H). MS (DCI/NH$_3$) m/z 454 (M+H)$^+$, 471 (M+NH$_4$)$^+$. Anal. calc. for $C_{23}H_{17}F_2N_3O_3S.0.25\ H_2O$: C, 60.36; H, 3.77; N, 9.19. Found: C, 60.24; H, 3.93; N, 9.25.

EXAMPLE 391

2-(3-Chlorophenyl)-4-(4-fluoro-3-methylphenyl)-5-[4-(aminosulfonyl)phenyl]-3(2h)-pyridazinone The methyl sulfone product of Example 244 was converted to the title sulfonamide according to the method of Example 384 (yield: 125 mg, 39%). mp 187–188° C. $^1$H NMR (300 MHz, CDCl$_3$) δ 2.21 (s, 3H), 4.71 (s, 2H), 6.85–6.92 (m, 2H), 7.21 (d, J=9 Hz, 1H), 7.32–7.47 (m, 2H), 7.37 (d, J=9 Hz, 2H), 7.64 (dt, J=7 Hz, 3 Hz, 1H), 7.77 (br s, 1H), 7.91 (d, J=9 Hz, 2H). MS (DCI/NH$_3$) m/z 470 (M+H)$^+$, 487 (M+NH$_4$)$^+$. Anal. calc. for $C_{23}H_{17}ClFN_3O_3S.0.25\ H_2O$: C, 58.32; H, 3.65; N, 8.88. Found: C, 58.27; H, 3.91; N, 8.62.

EXAMPLE 392

2-(3-Chlorophenyl)-4-(3-methylbutyl)-5-[4-(aminosulfonyl)phenyl]-3(2H)-pyridazinone The title compound was prepared according to the method of Example 384, substituting 2-(3-chlorophenyl)-4-(3-methylbutyl)-5-[4-(methylsulfonyl)phenyl]-3(2H)-pyridazinone (Example 366) in place of 2-benzyl-4-(4-fluorophenyl)-5-[4-(methylsulfonyl)phenyl]-3(2H)-pyridazinone (yield: 0.0756 g, 16%). mp 167–170° C. $^1$H NMR (300 MHz, DMSO $d_6$) δ 0.78 (d, J=6 Hz, 6H), 1.47 (5H, obstructed by hexanes), 7.51–7.65 (m, 4H), 7.68 (m, 2H), 7.75 (m, 1H), 7.98 (m, 2H), 8.03 (s, 1H), 8.60 (bs, 1H). MS (DCI/NH$_3$) m/z 432 (M+H)$^+$, 449 (M+NH$_4$)$^+$. Anal. calc. for $C_{21}H_{22}ClN_3O_3S$ (0.25 H$_2$O): C, 57.79; H, 5.19; N, 9.62. Found: C, 57.78; H, 5.02; N, 9.40.

EXAMPLE 393

2-(3-Chlorophenyl)-4-(phenethyl)-5-[4-(aminosulfonyl)phenyl]-3(2H)-pyridazinone

The title compound was prepared according to the method of Example 384, substituting 2-(3-chlorophenyl)-4-(phenethyl)-5-[4-(methylsulfonyl)phenyl]-3(2H)-pyridazinone (Example 372) in place of 2-benzyl-4-(4-fluorophenyl)-5-[4-(methylsulfonyl)phenyl]-3(2H)-pyridazinone (yield: 0.075 g, 17%). semi-solid; $^1$H NMR (300 MHz, DMSO $d_6$) δ 2.80 (m, 4H), 3.29–3.42 (3H, obstructed by H$_2$O), 6.96 (m, 2H), 7.14–7.28 (m, 3H), 7.46–7.68 (m, 7H), 7.78 (m, 1H), 7.92 (m, 2H), 8.01 (s, 1H). MS (DCI/NH$_3$) m/z 466 (M+H)$^+$, 483 (M+NH$_4$)$^+$. Anal. calc. for $C_{24}H_{20}ClN_2O_3S.0.25\ H_2O$: C, 61.27; H, 4.39; N, 8.93. Found: 61.18; H, 4.68; N, 8.58.

EXAMPLE 394

2-(3-Chlorophenyl)-4-(3-methylbutoxy)-5-[4-(aminosulfonyl)phenyl]-3(2H)-pyridazinone The title compound was prepared according to the method of Example 384, substituting 2-(3-chlorophenyl)-4-(3-methylbutoxy)-5-[4-(methylsulfonyl)phenyl]-3(2H)-pyridazinone (Example 339) in place of 2-benzyl-4-(4-fluorophenyl)-5-[4-(methylsulfonyl)phenyl]-3(2H)-pyridazinone (yield: 0.575 g, 18%). mp 137–139° C. $^1$H NMR (300 MHz, DMSO $d_6$) δ 0.81 (d, J=7 Hz, 6H), 1.49 (m, 2H), 1.57 (m, 1H), 4.42 (t, J=7 Hz, 2H), 7.44–7.65 (m, 5H), 7.76 (m, 1H), 7.84 (m, 2H), 7.94 (m, 2H), 8.20 (s, 1H). MS (DCI/NH$_3$) m/z 448 (M+H)$^+$, 465 (M+NH$_4$)$^+$. Anal. calc. for $C_{21}H_{22}ClN_3O_4S$: C, 56.31; H, 4.95; N, 9.38. Found C, 56.02; H, 4.82; N, 9.31.

EXAMPLE 395

2-(3-Chlorophenyl)-4-(2-methylpropoxy)-5-[4-(aminosulfonyl)phenyl]-3(2H)-pyridazinone The title compound was prepared according to the method of Example 384, substituting 2-(3-chlorophenyl)-4-(2-methylpropoxy)-5-[4-(methylsulfonyl)phenyl]-3(2H)-pyridazinone (Example 335) in place of 2-benzyl-4-(4-fluorophenyl)-5-[4-(methylsulfonyl)phenyl]-3(2H)-pyridazinone (yield: 0.0458 g, 25%). mp 80–85° C. $^1$H NMR (300 MHz, DMSO d$_6$) δ 0.80 (d, J=6 Hz, 6H), 1.74–1.92 (m, 3H), 4.20 (d, J=6 Hz, 2H), 7.49–7.64 (m, 5H), 7.76 (m, 1H), 7.85 (m, 2H), 7.95 (m, 2H), 8.21 (m, 1H). MS (DCI/NH$_3$) m/z 434 (M+H)$^+$, 451 (M+NH$_4$)$^+$. Anal. calc. for C$_{20}$H$_{20}$ClN$_3$O$_4$S: C, 55.36; H, 4.65; N, 9.68. Found: C, 55.12; H, 4.58; N, 9.42.

EXAMPLE 396

2-(4-Fluorophenyl)-4-(3-methylbutyl)-5-[4-(aminosulfonyl)phenyl]-3(2H)-pyridazinone The title compound was prepared according to the method of Example 384, substituting 2-(4-fluorophenyl)-4-(3-methylbutyl)-5-[4-(methylsulfonyl)phenyl]-3(2H)-pyridazinone (Example 378) in place of 2-benzyl-4-(4-fluorophenyl)-5-[4-(methylsulfonyl)phenyl]-3(2H)-pyridazinone (0.090 g 21%). mp 180–183° C. $^1$H NMR (300 MHz, DMSO d$_6$) δ 0.78 (d, J=6 Hz, 6H), 1.49 (m, 5H), 7.36 (m, 2H), 7.53 (m, 2H), 7.62–7.73 (m, 4H), 7.98 (m, 3H). MS (DCI/NH$_3$) m/z 416 (M+H)$^+$, 433 (M+NH$_4$)$^+$. Anal. calc. for C$_{21}$H$_{22}$FN$_3$O$_3$S: C, 60.71; H, 5.34; N, 10.11. Found: C, 60.37, H, 5.36, N, 9.84.

EXAMPLE 397

2-(4-Fluorophenyl)-4-(2-methylpropoxy)-5-[4-(aminosulfonyl)phenyl]-3(2H)-pyridazinone The title compound was prepared according to the method of Example 384, substituting 2-(4-fluorophenyl)-4-(2-methylpropoxy)-5-[4-(methylsulfonyl)phenyl]-3(2H)-pyridazinone (Example 376) in place of 2-benzyl-4-(4-fluorophenyl)-5-[4-(methylsulfonyl)phenyl]-3(2H)-pyridazinone (yield: 0.024 g, 6%). mp 132–136° C. $^1$H NMR (300 MHz, DMSO d$_6$) δ 0.79 (d, J=6 Hz, 6H), 1.83 (m, 1H), 4.19 (d, J=6 Hz, 2H), 7.36 (m, 2H), 7.50 (m, 2H), 7.66 (m, 2H), 7.84 (m, 2H), 7.95 (m, 2H), 8.18 (s, 1H). MS (DCI/NH$_3$) m/z 418 (M+H)$^+$, 435 (M+NH)$^+$. Anal. calc. for C$_{20}$H$_{20}$FN$_3$O$_4$S: C, 57.54; H, 4.83; N, 10.07. Found C, 57.26; H, 5.00; N, 9.78.

EXAMPLE 398

2-(4-Fluorophenyl)-4-(3-methylbutoxy)-5-[4-(aminosulfonyl)phenyl]-3(2H)-pyridazinone The title compound was prepared according to the method of Example 384, substituting 2-(4-fluorophenyl)-4-(3-methylbutoxy)-5-[4-(methylsulfonyl)phenyl]-3(2H)-pyridazinone (Example 375) in place of 2-benzyl-4-(4-fluorophenyl)-5-[4-(methylsulfonyl)phenyl]-3(2H)-pyridazinone (yield: 0.051 g, 18%). Yellow oil. $^1$H NMR (300 MHz, DMSO d$_6$) δ 0.80 (d, J=5 Hz, 6H), 1.47 (m, 3H), 4.42 (t, J=6 Hz, 2H), 7.37 (m, 2H), 7.50 (m, 1H), 7.65 (m, 2H), 7.83 (m, 2H), 7.93 (m, 2H), 8.18 (s, 1H), 8.60 (bs, 1H). MS (DCI/NH$_3$) m/z 432 (M+H)$^+$, 449 (M+NH$_4$)$^+$. Anal. calc. for C$_{21}$H$_{22}$FN$_3$O$_4$S: C, 58.46; H, 5.14; N, 9.74. Found: C, 58.16; H, 5.21; N, 9.57.

EXAMPLE 399

2-(t-Butyl)-4-(3-methyl-1-butoxy)-5-[4-(aminosulfonyl)phenyl]-3(2H)-pyridazinone 2-(t-Butyl)-4-(3-methyl-1-butoxy)-5-[4-(methylthio)phenyl]-3(2H)-pyridazinone prepared in Example 330C was oxidized with one equivalent of meta-chloroperoxybenzoic acid to the corresponding methyl sulfoxide. The sulfoxide was converted to the title sulfonamide by the method of Example 68 (yield: 1.25 g, 54%). mp 153–155° C. $^1$H NMR (300 MHz, CDCl$_3$) δ 0.82 (d, J=6 Hz, 2H), 1.48 (q, J=6 Hz, 2H), 1.49–1.69 (m, 1H), 1.70 (s, 9H), 4.37 (t, J=6 Hz, 2H), 4.32 (s, 2H), 7.70 (d, J=9 Hz, 2H), 7.72 (s, 1H), 8.01 (d, J=9 Hz, 2H). MS (DCI/NH$_3$) m/z 394 (M+H)$^+$. Anal. calc. for C$_{19}$H$_{27}$N$_3$O$_4$S: C, 57.99; H, 6.91; N, 10.67. Found: C, 58.11; H, 6.71; N, 10.58.

EXAMPLE 400

2-(3,4-Difluorophenyl)-4-(4-fluorophenyl)-5-[4-(aminosulfonyl)phenyl]-3(2H)-pyridazinone The title compound was prepared according to Example 384 substituting 2-(3,4-difluorophenyl)-4-(4-fluorophenyl)-5-[4-(methylsulfonyl)phenyl]-3(2H)-pyridazinone (Example 182) in place of 2-benzyl-4-(4-fluorophenyl)-5-[4-(methylsulfonyl)phenyl]-3(2H)-pyridazinone (yield: 950 mg, 54%). mp 177–181° C. $^1$H NMR (300 MHz, DMSO-d$_6$) δ 7.15 (t, 2H), 7.29 (m, 2H), 7.43 (s, 1H), 7.45 (bs, 2H), 7.59 (m, 2H), 7.76 (d, J=9 Hz, 2H), 7.85 (m, 1H), 8.27 (s, 1H). MS (DCI/NH$_3$) m/z 458 (M+H)$^+$, 475 (M+NH$_4$)$^+$. Anal. calc. for C$_{22}$H$_{14}$F$_3$N$_3$O$_3$S: C, 57.77; H, 3.08; N, 9.19. Found, C, 57.22; H, 3.28; N, 8.99.

EXAMPLE 401

2-(3-Chloro-4-fluorophenyl)4-(4-fluorophenyl)-5-[4-(aminosulfonyl)phenyl]-3(2H-pyridazinone The title compound was prepared according to the method of Example 384, substituting 2-(3-chloro-4-fluorophenyl)-4-(4-fluorophenyl)-5-[4-(methylsulfonyl)phenyl]-3(2H)-pyridazinone in place of 2-benzyl-4-(4-fluorophenyl)-5-[4-(methylsulfonyl)phenyl]-3(2H)-pyridazinone (yield: 380 mg, 47%). mp 208–210° C. $^1$H NMR (300 MHz, DMSO-d$_6$) δ 7.15 (t, 2H), 7.27 (m, 2H), 7.43 (s, 1H), 7.45 (bs, 2H) 7.51 (d, J=9 Hz, 4H), 7.6 (t, 1H), 7.7 (m, 1H), 7.75 (d, J=9 Hz, 2H), 7.94 (dd, 1H), 8.25 (s, 1H). MS (DCI/NH$_3$) m/z 474 (M+H)$^+$, 491 (M+NH$_4$)$^+$. Anal. calc. for C$_{22}$H$_{14}$F$_2$Cl$_2$N$_3$O$_3$S.0.5 H$_2$O: C, 55.76; H, 2.98; N, 8.87. Found: C, 56.05; H, 3.42; N, 8.65.

EXAMPLE 402

2-(3,4-Difluorophenyl)-4-(4-fluoro-3-methylphenyl)-5-[4-(aminosulfonyl)phenyl]-3(2H-pyridazinone The title compound was prepared according to the method of procedure Example 384, substituting 2-(3,4-difluorophenyl)-4-(4-fluoro-3-methylphenyl)-5-[4-(methylsulfonyl)phenyl]-3(2H)-pyridazinone in place of 2-benzyl-4-(4-fluorophenyl)-5-[4-(methylsulfonyl)phenyl]-3(2H)-pyridazinone (yield: 105 mg, 27%). mp 243–245° C. $^1$H NMR (300 MHz, DMSO-d$_6$) δ 2.2 (s, 3H), 7.01 (m, 2H), 7.25 (m, 1H), 7.45 (s, 1H), 7.45 (s, 1H), 7.47 (bs, 2H), 7.6

(m, 2H), 7.77 (d, J=9 Hz, 2H), 7.85 (m, 1H), 8.26 (s, 2H). MS (DCI/NH$_3$) m/z 472 (M+H)$^+$, 489 (M+NH$_4$)$^+$. Anal. calc. for C$_{24}$H$_{17}$F$_3$N$_2$O$_3$S.0.5 H$_2$O: C, 58.59; H, 3.42; N, 8.91. Found: C, 57; H, 4.23; N, 8.89.

EXAMPLE 403

2-(3,4-Difluorophenyl)-4-(2-methylpropoxy)-5-[4-(aminosulfonyl)phenyl]-3(2H)-pyridazinone The title compound was prepared according to the method of Example 384, substituting 2-(3,4-difluorophenyl)-4-(2-methylpropoxy)-5-[4-(methylsulfonyl)phenyl]-3(2H)-pyridazinone in place of 2-benzyl-4-(4-fluorophenyl)-5-[4-(methylsulfonyl)phenyl]-3(2H)-pyridazinone (yield: 35 mg, 42%). mp 169–171° C. $^1$H NMR (300 MHz, DMSO-d$_6$) δ 0.78 (d, 6H), 1.84, (m, 1H), 4.2 (d, 2H), 7.54 (m, 3H), 7.6 (m, 1H), 7.82 (m, 3H), 7.91 (d, 2H), 8.21 (s, 1H). MS (DCI/NH$_3$) m/z 436 (M+H)$^+$, 453 (M+NH$_4$)$^+$. Anal. calc for C$_{20}$H$_{19}$F$_2$N$_3$O$_4$S.0.25 H$_2$O: C, 55.17; H, 4.40; N, 9.65. Found: C, 54.19; H, 4.25; N, 9.35

EXAMPLE 404

2-(3,4-Difluorophenyl)-4-(3-methylbutyl)-5-[4-(aminosulfonyl)phenyl]-3(2H)-pyridazinone The title compound was prepared according to the method of Example 384, substituting 2-(3,4-difluorophenyl)-4-(3-methylbutyl)-5-[4-(methylsulfonyl)phenyl]-3(2H)-pyridazinone in place of 2-benzyl-4-(4-fluorophenyl)-5-[4-(methylsulfonyl)phenyl]-3(2H)-pyridazinone (yield: 58 mg, 52%). mp 171–173° C. $^1$H NMR (300 MHz, DMSO-d$_6$) δ 0.75 (d, 6H), 1.4, (m, 3H), 2.48 (m, 2H), 3.3 (s, 3H), 7.51 (m, 1H), 7.65 (m, 1H), 7.75 (d, J=9 Hz, 2H), 7.81 (m, 1H) 8.05 (s, 1H), 8.12 (d, J=9 Hz, 2H). MS (DCI/NH$_3$) m/z 434 (M+H)$^+$, 451 (M+NH$_4$)$^+$. Anal. calc. for C$_{21}$H$_{21}$F$_2$N$_3$O$_3$S.0.25 H$_2$O: C, 58.19; H, 4.88; N, 9.69. Found: C, 57.69; H, 5.01; N, 9.18.

EXAMPLE 405

2-(3-Chloro-4-fluorophenyl)-4-(3-methylbutyl)-5-[4-(aminosulfonyl)phenyl]-3(2H)-pyridazinone The title compound was prepared according to the method of Example 384, substituting 2-(3-chloro-4-fluorophenyl)-4-(3-methylbutyl)-5-[4-(methylsulfonyl)phenyl]-3(2H)-pyridazinone in place of 2-benzyl-4-(4-fluorophenyl)-5-[4-(methylsulfonyl)phenyl]-3(2H)-pyridazinone (yield: 102 mg, 61.8%). mp 154–156° C. $^1$H NMR (300 MHz, DMSO-d$_6$) δ 0.75 (d, 6H), 1.4, (m, 3H), 2.48 (m, 2H), 7.54 (s, 2H), 7.6 (m, 1H), 7.69 (m, 2H), 7.93 (dd, 1H), 8.05 (m, 2H). MS (DCI/NH$_3$) m/z 450 (M+H)$^+$, 468 (M+NH$_4$)$^+$. Anal. calc. for C$_{22}$H$_{22}$FN$_2$O$_3$SCI.0.25 H$_2$O: C, 58.86; H, 4.94; N, 6.24. Found: C, 59.23; H, 5.12; N, 6.00.

EXAMPLE 406

2-(3 Difluorophenyl)-4-(2,2-dimethylpropoxy)-5-[4-(aminosulfonyl)phenyl]-3(2H)-pyridazinone The title compound was prepared according to the method of Example 384 substituting 2-(3,4-difluorophenyl)-4-(2,2-dimethylpropoxy)-5-[4-(methylsulfonyl)phenyl]-3(2H)-pyridazinone in place of 2-benzyl-4-(4-fluorophenyl)-5-[4-(methylsulfonyl)phenyl]-3(2H)-pyridazinone (yield: 310 mg, 38%). mp 173–175° C. $^1$H NMR (300 MHz, DMSO-d$_6$) δ 0.8 (s, 9H), 3.3 (s, 3H), 4.1 (s, 2H), 7.51 (m, 3H), 7.6 (m, 1H), 7.85 (m, 3H), 7.95 (d, J=9 Hz, 2H), 8.21 (s, 1H). MS (DCI/NH$_3$) m/z 450 (M+H)$^+$, 467 (M+NH$_4$)$^+$. Anal. calc. for C$_{21}$H$_{21}$F$_2$N$_3$O$_4$S: C, 56.12; H, 4.71; N, 9.35. Found, C, 55.83; H, 4.73; N, 9.08.

EXAMPLE 407

2-(3,4-Difluorophenyl)-4-(4-fluorophenoxy)-5–3-fluoro-4-(aminosulfonyl)phenyl]-3(2H)-pyridazinone The title compound was prepared according to the method of Example 384 substituting 2-(3,4-difluorophenyl)-4-(4-fluorophenoxy)-5-[3-fluoro-4-(methylsulfonyl)phenyl]-3 (2H)-pyridazinone in place of 2-benzyl-4-(4-fluorophenyl)-5-[4-(methylsulfonyl)phenyl]-3(2H)-pyridazinone (yield: 125 mg, 31%). mp 224–226° C. $^1$H NMR (300 MHz, DMSO-d$_6$) δ 7.15 (d, 4H), 7.51 (m, 1H), 7.6 (m, 2H) 7.75 (m, 4H), 7.9 (t, 1H); 8.4 (s, 1H). MS (DCI/NH$_3$) m/z 492 (M+H)$^+$, 509 (M+NH4)$^+$. Anal. calc. for C$_{22}$H$_{13}$F$_4$N$_3$O$_4$S: C, 53.77; H, 2.67; N, 8.55. Found,; C, 53.33; H, 2.84; N, 8.22

EXAMPLE 408

2-(3,3-Difluoro-2-propenyl)]-4-(4-fluorophenyl)-5-[3-fluoro-4-(aminosulfonyl)phenyl]-3(2H)-pyridazinone The intermediate, 2-benzyl-4-(4-fluorophenyl)-5-[3-fluoro-4-(methylthio)phenyl]-3(2H)-pyridazinone prepared according to the method of Example 72, was oxidized with one equivalent of meta-chloroperoxybenzoic acid to provide the methyl sulfoxide which was converted to the sulfonamide according to the method of Example 68. The sulfonamide material was N-debenzylated according to the method of Example 11 and N-alkylated according to the method of Example 20, substituting 1,3-dibromo-1,1-difluoropropane in place of 4-fluorobenzyl bromide and employing 4 equivalents of potassium carbonate to provide the title compound (yield: 120 mg, 27%). mp 180–183° C. $^1$H NMR (300 MHz, CDCl$_3$) δ 4.71 (dt, J=15 Hz, 7.5 Hz, 2H), 4.75 (d, J=7.5 Hz, 2H), 5.06 (s, 2H), 7.02 (m, 2H), 7.19 (dd, J=9 Hz, 6 Hz, 2H), 7.81 (s, 1H), 7.87 (t, J=7.5 Hz, 2H). MS (DCI/NH$_3$) m/z 440 (M+H)$^+$. Anal. calc. for C$_{19}$H$_{13}$F$_4$N$_3$O$_3$S: C, 51.93; H, 2.98; N, 9.56. Found: C, 51.71; H, 3.15; N, 9.28.

EXAMPLE 409

2-(3,4-Difluorophenyl)-4-[2-(2-propoxyethoxy]-5-[4-(aminosulfonylphenyl]-3(2H)-pyridazinone The title compound was prepared according to the method of Example 384, substituting 2-(3,4-difluorophenyl)-4-[2-(2-propoxy)ethoxy]-5-[4-(methylsulfonyl)phenyl]-3(2H)-pyridazinone in place of 2-benzyl-4-(4-fluorophenyl)-5-[4-(methylsulfonyl)phenyl]-3(2H)-pyridazinone (yield: 110 mg, 34%). mp 54–56° C. $^1$H NMR (300 MHz, DMSO-d$_6$) δ 1.0 (d, 6H), 3.43 (m, 1H), 3.54 (m, 2H), 4.63 (m, 2H), 7.5 (m, 3H), 7.6 (m, 1H), 7.8 (m, 1H), 7.95 (m, 4H), 8.2 (s, 1H). MS (DCI/NH$_3$) m/z 466 (M+H)$^+$, 483 (M+NH$_4$)$^+$. Anal. calc. for C$_{21}$H$_{21}$F$_2$N$_3$O$_5$S: C, 54.19; H, 4.55; N, 9.03. Found, C, 54.29; H, 4.67; N, 8.95.

EXAMPLE 410

2-(3,4-Difluorophenyl)-4-(4-methyl-3-pentenyloxy)-5-[4-(aminosulfonyl)phenyl]-3(2H)-pyridazinone The title compound was prepared according to the method of Example 384 substituting 2-(3,4-difluorophenyl)-4-(4-methyl-3-pentenyloxy)-5-[4-(methylsulfonyl)phenyl]-3(2H)-pyridazinone in place of 2-benzyl-4-(4-fluorophenyl)-5-[4-(methylsulfonyl)phenyl]-3(2H)-pyridazinone. mp 70–73° C. $^1$H NMR (300 MHz, DMSO-d$_6$) δ 1.5 (d, 6H), 2.27 (m, 2H) 4.43 (t, 2H), 4.5 (m, 1H), 7.5 (m, 2H), 7.6 (m, 1H), 7.8 (m, 2H), 7.92 (d, J=2 H, 2H), 8.2 (s, 1H). MS (DCI/NH$_3$) m/z 462 (M+H)$^+$, 479 (M+NH$_4$)$^+$. Anal. calc. for C$_{22}$H$_{21}$F$_2$N$_3$O$_4$S: C, 57.26; H, 4.59; N, 9.11. Found, : C, 56.96; H, 4.70; N, 9.01.

EXAMPLE 411

2-(3-Chlorophenyl)-4-(3-fluorophenoxy)-5-[4-(methylsulfonyl)phenyl]-3(2H)-pyridazinone The title compound was prepared according to the method of Example 335, substituting 3-fluorophenol in place of isobutanol (yield: 0.034 g, 22%). mp 178–180° C. $^1$H NMR (300 MHz, DMSO d$_6$) δ 3.27 (s, 3H), 6.88–7.00 (m, 2H), 7.10 (m, 1H), 7.36 (m, 1H), 7.59 (m, 3H), 7.74 (m, 1H), 7.90 (m, 2H), 8.06 (m, 2H), 8.43 (s, 1H). MS (DCI/NH$_3$) m/z 488 (M+H)$^+$. Anal. calc. for C$_{23}$H$_{16}$ClFN$_2$O$_4$S.0.25 H$_2$O: C, 58.10; H, 3.49; N, 5.89. Found C, 58.04; H, 3.59; N, 5.80.

EXAMPLE 412

2-(3-Chlorophenyl)-4-(2-methylpropoxy)-5-[3-fluoro-4-(aminosulfonyl)phenyl]-3(2H)-pyridazinone The title compound was prepared according to the method of Example 384, substituting 2-(3-chlorophenyl)-4-(2-methylpropoxy)-5-[3-fluoro-4-(methylsulfonyl)phenyl]-3(2H)-pyridazinone in place of 2-benzyl-4-(4-fluorophenyl)-5-[4-(methylsulfonyl)phenyl]-3(2H)-pyridazinone (yield: 0.019 g, 10%). mp 157–159° C. $^1$H NMR (300 MHz, DMSO d$_6$) δ 0.81 (d, J=6 Hz, 6H), 1.86 (m, 1H), 4.24 (d, J=6 Hz, 2H), 7.75 (m, 3H), 7.66 (m, 1H), 7.73 (m, 2H), 7.83 (m, 2H), 7.91 (m, 1H), 8.23 (s, 1H). Anal. calc. for C$_{21}$H$_{19}$ClFN$_3$O$_4$S: C, 53.16; H, 4.24; N, 9.30. Found: C, 53.02; H, 4.43; N, 9.10.

EXAMPLE 413

2-(3-Chlorophenyl)-4-(4-methylpentyloxy)-5-[4-(methylsulfonyl)phenyl]-3(2H)-pyridazinone The title compound was prepared according to the method of Example 335, substituting 4-methyl-1-pentanol in place of isobutanol (yield: 0.137 g, 90%). mp 139–140° C. $^1$H NMR (300 MHz, DMSO d$_6$) δ 0.74 (d, J=6 Hz, 6H), 1.03 (m, 2H), 1.39 (m, 1H), 1.54 (m, 2H), 3.29 (s, 3H), 4.40 (t, J=5 Hz, 2H), 7.51–7.60 (m, 3H), 7.75 (m, 1H), 7.90 (m, 2H), 8.07 (m, 2H), 8.20 (s, 1H). MS (DCI/NH$_3$) m/z 461 (M+H)$^+$, 478 (M+NH$_4$)$^+$. Anal. calc. for C$_{23}$H$_{25}$ClN$_2$O$_4$S: C, 59.95; H, 5.97; N, 6.08. Found: C, 59.62; H, 5.63; N, 5.86.

EXAMPLE 414

2-(4-Fluorophenyl)-4-(4-methylpentyloxy)-5-[4-(methylsulfonyl)phenyl]-3(2H)-pyridazinone The title compound was prepared according to the method of Example 335, starting with 2-(4-fluorophenyl)-4-tosyloxy-5-[4-(methylsulfonyl)phenyl]-3(2H)-pyridazinone in place of 2-(3-chlorophenyl)-4-tosyloxy-5-[4-(methylsulfonyl)phenyl]-3(2H)-pyridazinone and substituting 4-methyl-1-pentanol in place of isobutanol (yield: 0.128 g, 85%). mp 123–125° C. $^1$H NMR (300 MHz, DMSO d$_6$) δ 0.74 (d, J=6 Hz, 6H), 1.03 (m, 2H), 1.39 (m, 1H), 1.54 (m, 2H), 3.28 (s, 3H), 4.39 (t, J=6 Hz, 2H), 7.37 (m, 2H), 7.66 (m, 2H), 7.91 (m, 2H), 8.07 (m, 2H), 8.18 (s, 1H). MS (DCI/NH$_3$) m/z 445 (M+H)$^+$. Anal. calc. for C$_{23}$H$_{25}$FN$_2$O$_4$S: C, 62.14; H, 5.67; N, 6.30. Found: C, 62.28; H, 5.59; N, 6.25.

EXAMPLE 415

2-(4-Fluorophenyl)-4-hydroxy-5-[4-(methylsulfonyl)phenyl]-3(2H)-pyridazinone

The title compound was prepared according to the method of Example 332, substituting 2-(4-fluorophenyl)-4-methoxy-5-[4-(methylsulfonyl)phenyl]-3(2H)-pyridazinone for 2-(3-chlorophenyl)-4-methoxy-5-[4-(methylsulfonyl)phenyl]-3(2H)-pyridazinone (yield: 2.022 g, 97%). $^1$H NMR (300 MHz, DMSO d$_6$) δ 3.28 (s, 3H), 7.38 (m, 2H), 7.70 (m, 2H), 8.03 (m, 4H), 8.22 (s, 1H). MS (APCI–+Q1MS) 361 (M+H)$^+$, (–Q1MS) 359 (M–H)$^-$.

EXAMPLE 416

2-(4-Fluorophenyl)-4-cyclopropylmethoxy-5-[4-(methylsulfonyl)phenyl]-3(2H)-pyridazinone The title compound was prepared according to the method of Example 335, substituting 2-(4-fluorophenyl)-4-tosyloxy-5-[4-(methylsulfonyl)phenyl]-3(2H)-pyridazinone in place of 2-(3-chlorophenyl)-4-tosyloxy-5-[4-(methylsulfonyl)phenyl]-3(2H)-pyridazinone and substituting cyclopropylmethanol in place of isobutanol (yield: 0.117 g, 83%). mp 166–167° C. $^1$H NMR (300 MHz, DMSO d$_6$) δ 0.22 (m, 2H), 0.46 (m, 2H), 1.10 (m, 1H), 3.31 (s, 3H), 4.30 (d, J=7 Hz, 2H), 7.36 (m, 2H), 7.66 (m, 2H), 7.96 (m, 2H), 8.07 (m, 2H), 8.20 (s, 1H). MS (DCI/NH$_3$) m/z 415 (M+H)$^+$, 432 (M+NH$_4$)$^+$. Anal. calc. for C$_{23}$H$_{25}$ClN$_2$O$_4$S: C, 60.86; H, 4.62; N, 6.76. Found: C, 60.76; H, 4.72; N, 6.61.

EXAMPLE 417

2-(4-Fluorophenyl)-4-(2-cyclopropyl-1-ethoxy)-5-[4-(methylsulfonyl)phenyl]-3(2H)-pyridazinone The title compound was prepared according to the method of Example 335, substituting 2-(4-fluorophenyl)-4-tosyloxy-5-[4-(methylsulfonyl)phenyl]-3(2H)-pyridazinone in place of 2-(3-chlorophenyl)-4-tosyloxy-5-[4-(methylsulfonyl)phenyl]-3(2H)-pyridazinone and substituting 2-cyclopropane ethanol in place of isobutanol (yield: 0.1472 g, 100%). mp 111–117° C. $^1$H NMR (300 MHz, DMSO d$_6$) δ –0.01 (m, 2H), 0.31 (m, 2H), 0.60 (m, 1H), 1.49 (q, J=6 Hz, 2H), 3.29 (s, 3H), 4.48 (t, J=6 Hz, 2H), 7.37 (m, 2H), 7.65 (m, 2H), 7.91 (m, 2H), 8.06 (m, 2H), 8.17 (s, 1H). MS (DCI/NH$_3$) m/z 429 (M+H)$^+$, 446 (M+NH$_4$)$^+$. Anal. calc. for C$_{22}$H$_{21}$FN$_2$O$_4$S: C, 61.67; H, 4.94; N, 6.54. Found: C, 61.59; H, 5.02; N, 6.45.

EXAMPLE 418

2-(3-Chlorophenyl)-4-cyclopropanemethoxy-5-[4-(methylsulfonyl)phenyl]-3(2H)-pyridazinone The title compound was prepared according to the method of Example 335, substituting cyclopropane methanol in place of isobutanol (yield: 0.0917 g, 64%). mp 158–161° C. $^1$H NMR (300 MHz, DMSO d$_6$) δ 0.22 (m, 2H), 0.46 (m, 2H), 1.13 (m, 1H), 3.31 (s, 3H), 4.31 (d, J=7 Hz, 2H), 7.57 (m, 3H), 7.75 (m, 1H), 7.96 (m, 2H), 8.08 (m, 2H), 8.23 (s, 1H). MS (DCI/NH$_3$) m/z 431 (M+H)$^+$, 448 (M+NH$_4$)$^+$. Anal. calc. for C$_{21}$H$_{19}$ClN$_2$O$_4$S.0.25 H$_2$O: C, 57.92; H, 4.51; N, 6.43. Found: C, 57.86; H, 4.35; N, 6.27.

EXAMPLE 419

2-(3-Chlorophenyl)-4-(2-cyclopropane-1-ethoxy)-5-[4-(methylsulfonyl)phenyl]-3(2H)-pyridazinone The title compound was prepared according to the method of Example 335, substituting 2-cyclopropane ethanol in place of isobutanol (yield: 0.114 g, 78%). mp 124–128° C. $^1$H NMR (300 MHz, DMSO d$_{16}$) δ 0.00 (m, 2H), 0.32 (m, 2H), 0.61 (m, 1H), 1.49 (q, J=6 Hz, 2H), 3.30 (s, 3H), 4.50 (t, J=6 Hz, 2H), 7.58 (m, 3H), 7.76 (m, 1H), 7.91 (m, 2H), 8.07 (m, 2H), 8.21 (s, 1H). MS (DCI/NH$_3$) m/z 445 (M+H)$^+$, 462 (M+NH$_4$)$^+$. Anal. calc. for C$_{22}$H$_{21}$ClN$_2$O$_4$S: C, 59.39; H, 4.76; N, 6.30. Found: C, 58.92; H, 4.94; N, 6.15.

EXAMPLE 420

2-(4-Fluorophenyl)-4-(4-methylpentyl)-5-[4-(methylsulfonyl)phenyl]-3(2H)-pyridazinone The title compound was prepared according to the method of Example 362, substituting 2-(4-fluorophenyl)-4-tosyloxy-5-[4-(methylsulfonyl)phenyl]-3(2H)-pyridazinone in place of 2-(3-chlorophenyl)-4-tosyloxy-5-[4-(methylsulfonyl)phenyl]-3(2H)-pyridazinone and substituting 4-methylpentane-1-magnesium bromide for cyclopentyl magnesium chloride (yield: 0.165 g, 99%). mp 112–115° C. $^1$H NMR (300 MHz, DMSO d$_6$) δ 0.75 (d, J=7 Hz, 6H), 1.07 (q, J=7 Hz, 2H), 1.32–1.53 (m, 3H), 2.45 (t, 2H), 3.31 (s, 3H), 7.37 (m, 2H), 7.66 (m, 2H), 7.76 (m, 2H), 8.00 (s, 1H), 8.10 (m, 2H). MS (DCI/NH$_3$) m/z 429 (M+H)$^+$, 446 (M+NH$_4$)$^+$. Anal. calc. for C$_{23}$H$_{25}$FN$_2$O$_3$S: C, 64.47; H, 5.88; N, 6.54. Found: C, 64.44; H, 5.90; N, 6.49.

EXAMPLE 421

2-(3-Chlorophenyl)-4-(4-methylpentyl)-5-[4-(methylsulfonyl)phenyl]-3(2H)-pyridazinone The title compound was prepared according to the method of Example 362, substituting 4-methylpentane-1-magnesium bromide in place of cyclopentyl magnesium chloride (yield: 165 mg, 98%). oil. $^1$H NMR (300 MHz, DMSO d$_6$) δ 0.76 (d, J=6 Hz, 6H), 1.07 (m, 2H), 1.33–1.55 (m, 3H), 2.45 (m, 2H), 3.32 (s, 3H), 7.51–7.65 (m, 4H), 7.76 (m, 2H), 8.03 (s, 1H), 8.11 (m, 2H). MS (DCI/NH$_3$) m/z 445 (M+H)$^+$, 462 (M+NH$_4$)$^+$. Anal. calc. for C$_{23}$H$_{25}$ClN$_2$O$_3$S: C, 62.06; H, 5.66; N, 6.30. Found: C, 61.86; H, 5.64; N, 6.18.

EXAMPLE 422

2-(4-Fluorophenyl)-4-(3-methyl-2-butenoxy)-5-[4-(methylsulfonylphenyl]-3(2H)-pyridazinone The title compound was prepared according to the method of Example 335, substituting 2-(4-fluorophenyl)-4-tosyloxy-5-[4-(methylsulfonyl)phenyl]-3(2H)-pyridazinone in place of 2-(3-chlorophenyl)-4-tosyloxy-5-[4-(methylsulfonyl)phenyl]-3(2H)-pyridazinone and substituting 3-methyl-2-buten-1-ol in place of isobutanol (yield: 0.1284 g, 88%). mp 128–132° C. $^1$H NMR (300 MHz, DMSO d$_6$) δ 1.58 (s, 3H), 1.67 (s, 3H), 3.30 (s, 3H), 4.95 (d, J=7 Hz, 2H), 5.31 (m, 1H), 7.38 (m, 2H), 7.65 (m, 2H), 7.89 (m, 2H), 8.06 (m, 2H), 8.18 (s, 1H). MS (DCI/NH$_3$) m/z 429 (M+H)$^+$, 446 (M+NH$_4$)$^+$. Anal. calc. for C$_{22}$H$_{21}$FN$_2$O$_4$S: C, 61.67; H, 4.94; N, 6.54. Found: C, 61.41; H, 4.95; N, 6.47.

EXAMPLE 423

2-(3-Chlorophenyl)-4-(3-methyl-2-butenoxy)-5-[4-(methylsulfonyl)phenyl]-3(2H)-pyridazinone The title compound was prepared according to the method of Example 335, substituting 3-methyl-2-buten-1-ol in place of isobutanol (yield: 0.119 g, 81%). mp 113–115° C. $^1$H NMR (300 MHz, DMSO d$_6$) δ 1.58 (s, 3H), 1.67 (s, 3H), 3.31 (s, 3H), 4.96 (m, 2H), 5.32 (m, 1H), 7.58 (m, 3H), 7.75 (m, 1H), 7.89 (m, 2H), 8.07 (m, 2H), 8.21 (s, 1H). MS (APCI+Q1MS) 445 (M+H)$^+$, (APCI−Q1MS) 479 (M+35)$^-$. Anal. calc. for C$_{22}$H$_{21}$ClN$_2$O$_4$S: C, 59.39; H, 4.76; N, 6.30. Found: C, 59.14; H, 4.66; N, 6.16.

EXAMPLE 424

2-(4-Fluorophenyl)-4-(4methyl-3-pentenyloxy)-5-[4-(methylsulfonyl)phenyl]-3(2H)-pyridazinone The title compound was prepared according to the method of Example 335, substituting 2-(4-fluorophenyl)-4-tosyloxy-5-[4-(methylsulfonyl)phenyl]-3(2H)-pyridazinone in place of 2-(3-chlorophenyl)-4-tosyloxy-5-[4-(methylsulfonyl)phenyl]-3(2H)-pyridazinone and substituting 4-methyl-3-penten-1-ol in place of isobutanol (yield: 0.1165 g, 77%). mp 111–114° C. $^1$H NMR (300 MHz, DMSO d$_6$) δ 1.46 (s, 3H), 1.56 (s, 3H), 2.26 (m, 2H), 3.30 (s, 1H), 4.43 (t, J=7 Hz, 2H), 4.96 (m, 1H), 7.37 (m, 2H), 7.65 (m, 2H), 7.91 (m, 2H), 8.06 (m, 2H), 8.18 (s, 1H). MS (DCI/NH$_3$) m/z 443 (M+H)$^+$, 460 (M+NH$_4$)$^+$. Anal. calc. for C$_{23}$H$_{23}$FN$_2$O$_4$S: C, 62.43; H, 5.24; N, 6.33. Found: C, 62.32; H, 5.30; N, 6.25.

EXAMPLE 425

2-(4-Fluorophenyl)-4-(3-methyl-3-butenoxy)-5-[4-(methylsulfonyl)phenyl]-3(2H)-pyridazinone The title compound was prepared according to the method of Example 335, substituting 2-(4-fluorophenyl)-4-tosyloxy-5-[4-(methylsulfonyl)phenyl]-3(2H)-pyridazinone in place of 2-(3-chlorophenyl)-4-tosyloxy-5-[4-(methylsulfonyl)phenyl]-3(2H)-pyridazinone and substituting 3-methyl-3-butene-1-ol in place of isobutanol (yield: 0.1327 g, 91%). mp 109–111° C. $^1$H NMR (300 MHz, DMSO d$_6$) δ 1.61 (s, 3H), 2.32 (t, J=7 Hz, 2H), 3.30 (s, 3H), 4.56 (t, J=7 Hz, 2H), 4.63 (bs, 1H), 4.68 (bs, 1H), 7.37 (m, 2H), 7.66 (m, 2H), 7.90 (m, 2H), 8.05 (m, 2H), 8.19 (s, 1H). MS (DCI/NH$_3$) m/z 429 (M+H)$^+$, 446 (M+NH$_4$)$^+$. Anal. calc. for C$_{22}$H$_{21}$FN$_2$O$_4$S: C, 61.67; H, 4.94; N, 6.54. Found: C, 61.50; H, 5.00; N, 6.45.

EXAMPLE 426

2-(3-Chlorophenyl)-4-(4-methyl-3-pentenyloxy)-5-[4-(methylsulfonyl)phenyl]-3(2H)-pyridazinone The title compound was prepared according to the method of Example 335, substituting 4-methyl-3-pentene-1-ol in place of isobutanol (yield: 0.1149 g, 76%). mp 110–111° C. $^1$H NMR (300 MHz, DMSO d$_6$) δ 1.47 (s, 3H), 1.55 (s, 3H), 2.27 (m, 2H), 3.30 (s, 3H), 4.44 (t, J=6 Hz, 2H), 4.96 (m, 1H), 7.52–7.64 (m, 3H), 7.75 (m, 1H), 7.91 (M, 2H), 8.06 (m, 2H), 8.21 (s, 1H). MS (DCI/NH$_3$) m/z 459 (M+H)$^+$, 476 (M+NH$_4$)$^+$. Anal. calc. for C$_{23}$H$_{23}$ClN$_2$O$_4$S: C, 60.19; H, 5.05; N, 6.10. Found: C, 60.06; H, 4.90; N, 5.96.

EXAMPLE 427

2-(3-Chlorophenyl)-4-(3-methyl-3-butenoxy)-5-[4-(methylsulfonyl)phenyl]-3(2H)-pyridazinone The title compound was prepared according to the method of Example 335, substituting 3-methyl-3-butene-1-ol in place of isobutanol (yield: 0.1159 g, 79%). mp 110–112° C. $^1$H NMR (300 MHz, DMSO d$_6$) δ 1.62 (s, 3H), 2.32 (t, J=7 Hz, 2H), 3.30 (s, 3H), 4.57 (t, J=6 Hz, 2H), 4.63 (bs, 1H), 4.68 (bs, 1H), 7.51–7.64 (m, 3H), 7.76 (m, 1H), 7.90 (m, 2H), 8.05 (m, 2H), 8.21 (s, 1H). MS (DCI/NH$_3$) m/z 445 (M+H)$^+$, 462 (M+NH$_4$)$^+$. Anal. calc. for C$_{22}$H$_{21}$ClN$_2$O$_4$S: C, 59.39; H, 4.76; N., 6.30. Found: C, 59.27; H, 4.68; N, 6.18.

EXAMPLE 428

2-(4-Fluorophenyl)-4-(1,5-hexadienyl-3-oxy)-5-[4-(methylsulfonyl)phenyl]-3(2H)-pyridazinone The title compound was prepared according to the method of Example 178, substituting 1,5-hexadien-3-ol in place of 2-ethyl-1-hexanol (yield: 150 mg, 85%). mp 104–105° C. $^1$H NMR (300 MHz, DMSO-d$_6$) δ 2.42 (m, 2H), 3.30 (s, 3H), 5.00 (m, 2H), 5.17 (m, 2H), 5.64 (m, 2H), 7.36 (t, J=9 Hz, 2H), 7.64 (m, 2H), 7.92 (d, J=9 Hz, 2H), 8.06 (d, J=9 Hz, 2H), 8.19 (s, 1H). MS (APCI+) m/z 441 (M+H)$^+$; (APCI−) m/z 475 (M+Cl)$^-$. Anal. calc. for C$_{23}$H$_{21}$FN$_2$O$_4$S: C, 62.71; H. 4.80; N, 6.35. Found: C, 62.96; H, 4.93; N, 5.85.

EXAMPLE 429

2-(4-Fluorophenyl)-4-(5-methyl-2-hexyloxy)-5-[4-(methylsulfonyl)phenyl]-3(2H)-pyridazinone The title compound was prepared according to the method of Example 178, substituting 5-methyl-2-hexanol in place of 2-ethyl-1-hexanol (yield: 150 mg, 82%). mp 102–103° C. $^1$H NMR (300 MHz, DMSO-d$_6$) δ 0.73 (d, J=7 Hz, 6H), 1.04 (m, 2H), 1.14 (d, J=7 Hz, 3H), 1.40 (m, 3H), 3.29 (s, 3H), 5.12 (m, 1H), 7.36 (t, J=9 Hz, 2H), 7.66 (m, 2H), 7.92 (d, J=9 Hz, 2H), 8.07 (d, J=9 Hz, 2H), 8.19 (s, 1H). MS (APCI+) m/z 459 (M+H)$^+$; (APCI−) m/z 493 (M+Cl)$^-$. Anal. calc. for C$_{24}$H$_{27}$FN$_2$O$_4$S: C, 62.86; H, 5.93; N, 6.10. Found: C, 62.83; H, 5.99; N, 6.07.

EXAMPLE 430

2-(4-Fluorophenyl)-4-(2-ethyl-1-butoxy)-5-[4-(methylsulfonyl)phenyl]-3(2H)-pyridazinone The title compound was prepared according to the method of Example 178, substituting 2-ethyl-1-butanol in place of 2-ethyl-1-hexanol (yield: 140 mg, 80%). mp 107–108° C. $^1$H NMR (300 MHz, DMSO-d$_6$) δ 0.73 (t, J=7 Hz, 6H), 1.20 (quintet, J=7 Hz, 4H), 1.40 (m, 1H), 3.29 (s, 3H), 4.29 (d, J=7 Hz, 2H), 7.37 (t, J=9 Hz, 2H), 7.66 (m, 2H), 7.90 (d, J=9 Hz, 2H), 8.07 (d, J=9 Hz, 2H), 8.19 (s, 1H). MS (APCI+) m/z 445 (M+H)$^+$; (APCI−) m/z 479 (M+Cl)$^-$. Anal. calc. for C$_{23}$H$_{25}$FN$_2$O$_4$S: C, 62.14; H, 5.66; N, 6.30. Found: C, 62.05; H, 5.86; N, 6.30.

EXAMPLE 432

2-(4-Fluorophenyl)-4-(2-thioisopropyl-1-ethoxy)-5-[4-(methylsulfonyl)phenyl]-3(2H)-pyridazinone The title compound was prepared according to the method of Example 178, substituting 2-(isopropylthio)ethanol in place of 2-ethyl-1-hexanol (yield: 138 mg, 74%). mp 137–139° C. $^1$H NMR (300 MHz, DMSO-d$_6$) δ 1.13 (d, J=7 Hz, 6H), 2.77 (t, J=7 Hz, 2H), 2.88 (quintet, J=7 Hz, 1H), 3.29 (s, 3H), 4.58 (t, J=7 Hz, 2H), 7.37 (t, J=9 Hz, 2H), 7.66 (m, 2H), 7.92 (d, J=9 Hz, 2H), 8.06 (d, J=9 Hz, 2H), 8.18 (s, 1H). MS (APCI+) m/z 463 (M+H)$^+$. Anal. calc. for C$_{22}$H$_{23}$FN$_2$O$_4$S$_2$: C, 57.12; H, 5.01; N, 6.05. Found: C, 56.82; H, 4.91; N, 5.99.

EXAMPLE 433

2-(4-Fluorophenyl)-4-(3-methylthio-1-hexyloxy)-5-[4-(methylsulfonyl)phenyl]-3(2H)-pyridazinone The title compound was prepared according to the method of Example 178, substituting 3-(methylthio)-1-hexanol in place of 2-ethyl-1-hexanol (yield: 155 mg, 79%). mp 90–92° C. $^1$H NMR (300 MHz, DMSO-d$_6$) δ 0.78 (t, J=7 Hz, 3H), 1.30 (m, 4H), 1.76 (m, 2H), 2.82 (s, 3H), 2.38 (m, 1H), 3.29 (s, 3H), 4.55 (m, 2H), 7.37 (t, J=9 Hz, 2H), 7.66 (m, 2H), 7.92 (d, J=9 Hz, 2H), 8.06 (d, J=9 Hz, 2H), 8.18 (s, 1H). MS (APCI+) m/z 491 (M+H)$^+$; (APCI+) m/z 525 (M+Cl)$^-$. Anal. calc. for C$_{24}$H$_{27}$FN$_2$O$_4$S$_2$: C, 58.75; H, 5.54; N, 5.70. Found: C, 58.66; H, 5.54; N, 5.66.

EXAMPLE 434

2-(4-Fluorophenyl)-4-(2-methyl-4-pentenyl-1-oxy)-5-[4-(methylsulfonyl)phenyl]-3(2H)-pyridazinone The title compound was prepared according to the method of Example 178, substituting 2-methyl-4-penten-1-ol in place of 2-ethyl-1-hexanol (yield: 135 mg, 76%). mp 106–107° C. $^1$H NMR (300 MHz, DMSO-d$_6$) δ 0.76 (d, J=7 Hz, 3H), 1.78 (m, 2H), 2.00 (m, 1H), 3.29 (s, 3H), 4.25 (m, 2H), 4.90 (m, 2H), 5.67 (m, 1H), 7.37 (t, J=9 Hz, 2H), 7.66 (m, 2H), 7.92 (d, J=9 Hz, 2H), 8.06 (d, J=9 Hz, 2H), 8.18 (s, 1H). MS (APCI+) m/z 443 (M+H)$^+$; (APCI−) m/z 477 (M+Cl)$^-$. Anal. calc. for C$_{23}$H$_{23}$FN$_2$O$_4$S: C, 62.42; H, 5.23; N, 6.33. Found: C, 62.13; H, 5.12; N, 6.22.

EXAMPLE 435

2-(3,4-Difluorophenyl)-4-(3-trifluoromethyl-1-butoxy)-5-[4-(methylsulfonyl)phenyl]-3(2H)-pyridazinone To a solution of 2-(3,4-difluorophenyl)-4-hydroxy-5-[4-(methylsulfonyl)phenyl]-3(2H)-pyridazinone (189mg, 0.5 mmol), Ph$_3$P (262 mg, 1 mmol) and 3-trifluoromethyl-1-butanol (66 mg, 0.5 mmol) in THF (25 mL) was added dropwise a solution of DIAD (0.2 mL, 1 mmol) in THF (5 mL) and the resulting mixture was stirred at room temperature for 8 hours. The mixture was concentrated in vacuo and the residue was chromatographed (silica gel, 1:1 hexanes-ethyl acetate) to provide the desired product, (yield: 180 mg 71%). mp 126–128° C. $^1$H NMR (300 MHz, DMSO-$d_6$) δ 0.96 (d, J=7 Hz, 3H), 1.55 (m, 1H), 1.97 (m, 1H), 2.30 (m, 1H), 3.29 (s, 3H), 4.46 (m, 2H), 7.52 (m, 1H), 7.62 (m, 1H), 7.81 (m, 1H), 7.90 (d, J=9 Hz, 2H), 8.08 (d, J=9 Hz, 2H), 8.22 (s, 1H). MS (APCI+) m/z 503 (M+H)$^+$; (APCI–) m/z 537 (M+Cl)$^-$. Anal. calc. for $C_{22}H_{19}F_5N_2O_4S$: C, 52.59; H, 3.81; N, 5.57. Found: C, 52.70; H, 3.73; N, 5.63.

EXAMPLE 436

2-(3,4-Difluorophenyl)-4-ethoxy-5-[4-(methylsulfonylphenyl]-3(2H)-pyridazinone

The title compound was prepared according to the method of Example 178, starting with 2-(3,4-difluorophenyl)-4-tosyloxy-5-[4-(methylsulfonyl)phenyl]-3(2H)-pyridazinone in place of 2-(4-fluorophenyl)-4-tosyloxy-5-[4-(methylsulfonyl)phenyl]-3(2H)-pyridazinone and substituting ethanol in place of 2-ethyl-1-hexanol (yield: 25 mg, 12%). mp 121–123° C. $^1$H NMR (300 MHz, DMSO-$d_6$) δ 1.23 (t, J=7 Hz, 3H), 3.30 (s, 3H), 4.51 (q, J=7 Hz, 2H), 7.52 (m, 1H), 7.62 (m, 1H), 7.81 (m, 1H), 7.90 (d, J=9 Hz, 2H), 8.08 (d, J=9 Hz, 2H), 8.22 (s, 1H). MS (APCI+) m/z 407 (M+H)$^+$; (APCI–) m/z 441 (M+Cl)$^-$. Anal. calc. for $C_{19}H_{16}F_2N_2O_4S.0.25 H_2O$: C, 55.53; H, 4.04; N, 6.81. Found: C, 55.58; H, 4.21; N, 6.61.

EXAMPLE 437

2-(3,4-Difluorophenyl)-4-(4-methyl-1-pentyloxy)-5-[4-(methylsulfonyl)phenyl]-3(2H)-pyridazinone The title compound was prepared according to the method of Example 178, starting with 2-(3,4-difluorophenyl)-4-tosyloxy-5-[4-(methylsulfonyl)phenyl]-3(2H)-pyridazinone in place of 2-(4-fluorophenyl)-4-tosyloxy-5-[4-(methylsulfonyl)phenyl]-3(2H)-pyridazinone and substituting 4-methyl-1-pentanol in place of 2-ethyl-1-hexanol (yield: 120 mg, 52%). mp 98–99° C. $^1$H NMR (300 MHz, DMSO-$d_6$) δ 0.73 (d, J=7 Hz, 6H), 1.02 (m, 2H), 1.29 (m, 1H), 1.54 (m, 2H), 3.30 (s, 3H), 4.40 (t, J=7 Hz, 2H), 7.52 (m, 1H), 7.62 (m, 1H), 7.81 (m, 1H), 7.90 (d, J=9 Hz, 2H), 8.08 (d, J=9 Hz, 2H), 8.22 (s, 1H). MS (APCI+) m/z 463 (M+H)$^+$; (APCI–) m/z 497 (M+Cl)$^-$. Anal. calc. for $C_{23}H_{24}F_2N_2O_4S$: C, 59.72; H, 5.23; N, 6.05. Found: C, 59.57; H, 5.28; N, 6.01.

EXAMPLE 438

2-(3,4-Difluorophenyl)-4-(4-methyl-2-pentyloxy)-5-[4-(methylsulfonyl)phenyl]-3(2H)-pyridazinone The title compound was prepared according to the method of Example 178, starting with 2-(3,4-difluorophenyl)-4-tosyloxy-5-[4-(methylsulfonyl)phenyl]-3(2H)-pyridazinone in place of 2-(4-fluorophenyl)-4-tosyloxy-5-[4-(methylsulfonyl)phenyl]-3(2H)-pyridazinone and substituting 4-methyl-2-pentanol for 2-ethyl-1-hexanol (yield: 115 mg, 50%). mp 132–133° C. $^1$H NMR (300 MHz, DMSO-$d_6$) δ 0.80 (d, J=7 Hz, 3H), 0.87 (d, J=7 Hz, 3H), 1.10 (d, J=7 Hz, 3H), 1.26 (m, 1H), 1.50 (m, 1H), 1.63 (m, 1H), 3.30 (s, 3H), 5.31 (m, 1H), 7.52 (m, 1H), 7.62 (m, 1H), 7.81 (m, 1H), 7.90 (d, J=9 Hz, 2H), 8.08 (d, J=9 Hz, 2H), 8.22 (s, 1H). MS (APCI+) m/z 463 (M+H)$^+$; (APCI–) m/z 497 (M+Cl)$^-$. Anal. calc. for $C_{23}H_{24}F_2N_2O_4S$: C, 59.72; H, 5.23; N, 6.05. Found: C, 59.44; H, 5.26; N, 5.99.

EXAMPLE 439

2-(3,4-Difluorophenyl)-4-(2-cyclopentyl-1-ethoxy)-5-[4-(methylsulfonyl)phenyl]-3(2H)-pyridazinone The title compound was prepared according to the method of Example 178, starting with 2-(3,4-difluorophenyl)-4-tosyloxy-5-[4-(methylsulfonyl)phenyl]-3(2H)-pyridazinone in place of 2-(4-fluorophenyl)-4-tosyloxy-5-[4-(methylsulfonyl)phenyl]-3(2H)-pyridazinone and substituting 2-cyclopentyl-1-ethanol in place of 2-ethyl-1-hexanol (yield: 115 mg, 60%). mp 100–101° C. $^1$H NMR (300 MHz, DMSO-$d_6$) δ 1.00 (m, 2H), 1.38 (m, 2H), 1.57 (m, 7H), 3.30 (s, 3H), 4.42 (t, J=7 Hz, 2H), 7.52 (m, 1H), 7.62 (m, 1H), 7.81 (m, 1H), 7.90 (d, J=9 Hz, 2H), 8.08 (d, J=9 Hz, 2H), 8.22 (s, 1H). MS (APCI+) m/z 475 (M+H)$^+$; (APCI–) m/z 509 (M+Cl)$^-$. Anal. calc. for $C_{24}H_{24}F_2N_2O_4S.0.25 H_2O$: C, 60.17; H, 5.15; N, 5.84. Found: C, 60.12; H, 5.14; N, 5.76.

EXAMPLE 440

2-(3,4-Difluorophenyl)-4-(2-cyclopent-2-enyl-1-ethoxy)-5-[4-(methylsulfonyl)phenyl]-3(2H)-pyridazinone The title compound was prepared according to the method of Example 178, starting with 2-(3,4-difluorophenyl)-4-tosyloxy-5-[4-(methylsulfonyl)phenyl]-3(2H)-pyridazinone in place of 2-(4-fluorophenyl)-4-tosyloxy-5-[4-(methylsulfonyl)phenyl]-3(2H)-pyridazinone and substituting 2-cyclopent-2-enyl-1-ethanol in place of 2-ethyl-1-hexanol (yield: 95 mg, 48%). mp 126–127° C. $^1$H NMR (300 MHz, DMSO-$d_6$) δ 1.30 (m, 1H), 1.57 (sextet, J=7 Hz, 1H), 1.69 (sextet, J=7 Hz, 1H), 1.87 (m, 2H), 2.57 (m, 1H), 3.30 (s, 3H), 4.45 (m, 2H), 5.60 (m, 1H), 5.68 (m, 1H), 7.52 (m, 1H), 7.62 (m, 1H), 7.81 (m, 1H), 7.90 (d, J=9 Hz, 2H), 8.08 (d, J=9 Hz, 2H), 8.22 (s, 1H). MS (APCI+) m/z 473 (M+H)$^+$; (APCI–) m/z 507 (M+Cl)$^-$. Anal. calc. for $C_{24}H_{22}F_2N_2O_4S$: C, 61.00; H, 4.69; N, 5.92. Found: C, 60.76; H, 4.65; N, 5.80.

EXAMPLE 441

2-(2-Hydroxy-2-phenylethyl)-4-(4-fluorophenyl)-5-[4-(methylsulfonyl)phenyl]-3(2H)-pyridazinone A mixture of the product from Example 46, 2-phenacyl-4-(4-fluorophenyl)-5-[4-(methylsulfonyl)phenyl]-3(2H)-pyridazinone (700 mg, 1.5 mmol), and sodium borohydride (69 mg, 1.8 mmol) in ethanol (200 mL), was stirred at 40° C. for 2 hours. The reaction mixture was then concentrated in vacuo and the residue was partitioned between ethyl acetate and 2 N aqueous hydrochloric acid. The organic layer was washed with brine, dried over $MgSO_4$, and filtered. The filtrate was concentrated in vacuo to provide a pale yellow solid which was crystallized from ethyl acetate/hexanes to provide the title compound as white crystals (yield: 540 mg, 78%). mp 205–207° C. $^1$H NMR (300 MHz, $CDCl_3$) δ 3.07 (s, 3H), 3.75 (br s, 1H), 4.63–4.47 (m, 2H), 5.33 (dd, J=9 Hz, 3 Hz, 1H), 7.00 (t, J=9 Hz, 2H), 7.20 (dd, J=9 Hz, 3 Hz, 2H), 7.30–7.45 (m, 5H), 7.52 (d, J=9 Hz, 2H), 7.91 (s, 1H), 7.91 (d, J=9 Hz, 2H). MS (DCI/$NH_3$) m/z 465 (M+H)$^+$. Anal. calc. for $C_{25}H_{21}FN_2O_4S$: C, 64.64; H, 4.55; N, 6.03. Found: C, 64.34; H, 4.66; N, 5.93.

EXAMPLE 442

2-(2-Methoxy-2-phenylethyl)-4-(4-fluorophenyl)-5-[4-(methylsulfonyl)phenyl]-3(2H)-pyridazinone A mixture of the product from Example 441, 2-(2-hydroxy-2-phenylethyl)-4-(4-fluorophenyl)-5-[4-(methylsulfonyl)phenyl]-3(2H)-pyridazinone (210 mg, 0.45 mmol), iodomethane (56 µL, 0.90 mmol), and an 80% oil dispersion of sodium hydride (18 mg, 0.59 mmol) in anhydrous DMF (16 mL) was stirred at room temperature for 18 hours. The reaction mixture was partitioned between ethyl acetate and 2 N aqueous hydrochloric acid. The organic layer was washed with brine, dried over $MgSO_4$, and filtered. The filtrate was concentrated in vacuo to provide a yellow oil which was purified by column chromatography (silica gel, 70:30 hexanes/ethyl acetate). Fractions containing product were combined and concentrated in vacuo, and the residue was triturated with hexanes to provide the title compound (yield: 75 mg, 34.7%). mp 135–137° C. $^1$H NMR (300 MHz, $CDCl_3$) δ 3.07 (s, 3H), 3.26 (s, 3H), 4.33–4.52 (m, 2H), 4.91 (dd, J=9 Hz, 3 Hz, 1H), 6.99 (t, J=9 Hz, 2H), 7.20 (dd, J=9 Hz, 3 Hz, 2H), 7.31–7.50 (m, 7H), 7.87 (s, 1H), 7.89 (d, J=9 Hz, 2H). MS (DCI/$NH_3$) m/z 479 (M+H)$^+$. Anal. calc. for $C_{26}H_{23}FN_2O_4S$: C, 65.25; H, 4.84; N, 5.85. Found: C, 64.98; H, 4.83; N, 5.81.

EXAMPLE 443

2-(2-Methoxyimino-2-phenylethyl)-4-(4-fluorophenyl)-5-[4-(methylsulfonyl)phenyl]-3(2H)-pyridazinone A mixture of the product from Example 46, 2-phenacyl-4-(4-fluorophenyl)-5-[4-(methylsulfonyl)phenyl]-3(2H)-pyridazinone (220 mg, 0.476 mmol), methoxylamine hydrochloride (318 mg, 3.8 mmol), and sodium acetate (518 mg, 3.8 mmol) in methanol (100 mL) was stirred at reflux for 48 hours. The reaction mixture was concentrated in vacuo, and the residue was partitioned between ethyl acetate and saturated aqueous ammonium chloride. The organic layer was washed with brine then dried over $MgSO_4$, and filtered. The filtrate was concentrated in vacuo to provide a brown oil which was purified by column chromatography (silica gel, 70:30 hexanes/ethyl acetate). Fractions containing product were combined and concentrated in vacuo. The residue was crystallized from methanol/water to provide the title compound as a mixture of E and Z oximes (yield: 82 mg, 35%). mp 95–99° C. $^1$H NMR (300 MHz, $CDCl_3$) δ 3.03 (s, 3H), 4.07 (s, 3H), 5.57 (s, 2H), 6.94 (t, J=9 Hz, 2H), 7.07 (dd, J=9 Hz, 3 Hz, 2H), 7.24 (d, J=9 Hz, 2H), 7.31–7.37 (m, 3H), 7.60–7.67 (m, 2H), 7.74 (s, 1H), 7.83 (d, J=9 Hz, 2H). MS (DCI/$NH_3$) m/z 492 (M+H)$^+$. Anal. calc. for $C_{26}H_{22}FN_3O_4S$: C, 63.53; H, 4.51; N, 8.54. Found: C, 63.40; H, 4.51; N, 8.31.

EXAMPLE 444

2-(3,4-Difluorophenyl)-4-(4-methylpentyl)-5-[4-(methylsulfonyl)phenyl]-3(2H)-pyridazinone The title compound was prepared according to the method of Example 255, substituting 1-bromo-4-methylpentane in place of 3,4-difluorobenzyl bromide (yield: 145 mg, 58%). m; 111–113° C. $^1$H NMR (300 MHz, DMSO-$d_6$) δ 0.75 (d, 6H), 1.09 (m, 2H), 1.4 (m, 3H), 2.48 (m, 2H), 3.4 (s, 3H), 7.61 (m, 2H), 7.75 (d, 2H), 7.81 (m, 1H), 8.02 (s, 1H), 8.1 (d, 2H). MS (DCI/$NH_3$) m/z 447 (M+H)$^+$, 464 (M+$NH_4$)$^+$. Anal. calc. for $C_{23}H_{24}F_2N_2O_3S$: C, 61.87; H, 5.42; N, 6.27. Found: C, 61.76; H, 5.55; N, 6.11.

EXAMPLE 445

2-(3,4-Difluorophenyl)-4-(3-methyl-1-butoxy)-5-[4-(aminosulfonyl)phenyl]-3(2H)-pyridazinone The title compound was prepared as described in Example 384, substituting 2-(3,4-difluorophenyl)-4-(3-methyl-1-butoxy)-5-[4-(methylsulfonyl)phenyl]-3(2H)-pyridazinone (Example 347) in place of 2-benzyl-4-(4-fluorophenyl)-5-[4-(methylsulfonyl)phenyl]-3(2H)-pyridazinone (yield: 248 mg, 42%). mp 149–151° C. $^1$H NMR (300 MHz, DMSO-$d_6$) δ 0.8 (d, J=6 Hz, 6H), 1.48 (m, 2H), 1.54 (m, 1H), 4.4 (t, 2H), 7.51 (m, 3H), 7.6 (m, 1H), 7.85 (m, 3H), 7.95 (d, J=9 Hz, 2H), 8.21 (s, 1H). MS (DCI/$NH_3$) m/z 450 (M+H)$^+$, 467 (M+$NH_4$)$^+$. Anal. calc. for $C_{21}H_{21}F_2N_3O_4S$: C, 56.12; H, 4.71; N, 9.35. Found, C, 56.12; H, 4.67; N, 9.15.

EXAMPLE 446

2-(2,2,2-Trifluoroethyl)-4-(2,2-dimethylpropoxy)-5-[4-f aminosulfonyl)phenyl]-3(2H)-pyridazinone The intermediate, 2-(2,2,2-trifluoroethyl)-4-hydroxy-5-[4-(methylthio)phenyl]-3(2H)-pyridazinone prepared in Example 90C was reacted with 2,2-dimethylpropanol to provide 2-(2,2,2-trifluoroethyl)-4-(2,2-dimethylpropoxy)-5-[4-(methylthio)phenyl]-3(2H)-pyridazinone according to the method of Example 90D.

The product was oxidized with one equivalent of meta-chloroperoxybenzoic acid to provide the methyl sulfoxide. The sulfoxide was converted to the title compound according to the method of Example 68, substituting 2-(2,2,2-trifluoroethyl)-4-(2,2-dimethylpropoxy)-5-[4-(methylsulfinyl)phenyl]-3(2H)-pyridazinone for 2-(2,2,2-trifluoroethyl)-4-(4-fluorophenyl)-5-[4-(methylsulfinyl)phenyl]-3(2H)-pyridazinone (yield: 125 mg, 53%). mp 123–124° C. $^1$H NMR (300 MHz, $CDCl_3$) δ 0.82 (s, 9H), 4.18 (s, 2H), 4.82 (q, J=9 Hz, 2H), 4.84 (s, 2H), 7.70 (d, J=9 Hz, 2H), 7.81 (s, 1H), 8.04 (d, J=9 Hz, 2H). MS (DCI $NH_3$) m/z 420 (M+H)$^+$. Anal. calc. for $C_{17}H_{20}F_3N_3O_4S$: C, 48.68; H, 4.80; N, 10.01. Found: C, 48.76; H, 4.77; N, 9.94.

EXAMPLE 447

2-(2,2,2-Trifluoroethyl)-4-(3-methylbutoxy)-5-[4-(methylsulfonyl)phenyl]-3(2H)-pyridazinone The title compound was prepared according to the method of Example 83, substituting 3-methyl-1-butanol in place of isopropanol (yield: 65 mg, 85%). mp 111–113° C. $^1$H NMR (300 MHz, $CDCl_3$) δ 0.84 (d, J=6 Hz, 6H), 1.51 (m, 2H), 1.63 (m, 1H), 3.11 (s, 3H), 4.54 (t, J=6 Hz, 2H), 4.83 (q, J=9 Hz, 2H), 7.73 (d, J=9 Hz, 2H), 7.82 (s, 1H), 8.05 (d, J=9 Hz, 2H); MS (DCI/$NH_3$) m/z 419 (M+H)$^+$. Anal. calc. for $C_{18}H_{21}F_3N_2O_4S$: C, 51.66; H, 5.05; N, 6.69. Found: C, 51.91; H, 5.06; N, 6.56.

EXAMPLE 448

2-(2,2,2-Trifluoroethyl)-4-(3-methylbutoxy)-5-[4-(aminosulfonyl)phenyl]-3(2H)-pyridazinone The intermediate, 2-(2,2,2-trifluoroethyl)-4-hydroxy-5-[4-(methylthio)phenyl]-3(2H)-pyridazinone prepared in Example 90C was reacted with 3-methyl-1-butanol to provide 2-(2,2,2-trifluoroethyl)-4-(3-methylbutoxy)-5-[4-(methylthio)phenyl]-3(2H)-pyridazinone according to the method of Example 90D.

The product was oxidized with one equivalent of meta-chloroperoxybenzoic acid to provide the methyl sulfoxide. The sulfoxide was converted to the title compound according to the method of Example 68, substituting 2-(2,2,2-trifluoroethyl)-4-(3-methylbutoxy)-5-[4-(methylsulfinyl)phenyl]-3(2H)-pyridazinone for 2-(2,2,2-trifluoroethyl)-4-(4-fluorophenyl)-5-[4-(methylsulfinyl)phenyl]-3(2H)-pyridazinone (yield: 65 mg, 50%). mp 123–124° C. $^1$H NMR (300 MHz, CDCl$_3$) δ 0.84 (d, J=6 Hz, 6H), 1.52 (q, J=6 Hz, 2H), 1.60 (h, J=7.5 Hz, 1H), 4.52 (t, J=6 Hz, 2H), 4.83 (q, J=9 Hz, 2H), 4.90 (s, 2H), 7.69 (d, J=9 Hz, 2H), 7.82 (s, 1H), 8.04 (d, J=9 Hz, 2H). MS (DCI/NH$_3$) m/z 420 (M+H)$^+$. Anal. calc. for C$_{17}$H$_{20}$F$_3$N$_3$O$_4$S: C, 48.68; H, 4.80; N, 10.01. Found: C, 48.86; H, 4.83; N, 9.92.

EXAMPLE 449

2-(2,2,2-Trifluoroethyl)-4-(2-methylpropoxy)-5-[4-(aminosulfonyl)phenyl]-3(2H)-pyridazinone The intermediate, 2-(2,2,2-trifluoroethyl)-4-hydroxy-5-[4-(methylthio)phenyl]-3(2H)-pyridazinone prepared in Example 90C was reacted with 2-methyl-1-propanol to provide 2-(2,2,2-trifluoroethyl)-4-(2-methylpropoxy)-5-[4-(methylthio)phenyl]-3(2H)-pyridazinone according to the method of Example 90D.

The product was oxidized with one equivalent of meta-chloroperoxybenzoic acid to provide the methyl sulfoxide. The sulfoxide was converted to the title compound according to the method of Example 68, substituting 2-(2,2,2-trifluoroethyl)-4-(2-methylpropoxy)-5-[4-(methylsulfinyl)phenyl]-3(2H)-pyridazinone for 2-(2,2,2-trifluoroethyl)-4-(4-fluorophenyl)-5-[4-(methylsulfinyl)phenyl]-3(2H)-pyridazinone (yield: 120 mg, 40%). mp 170–172° C. $^1$H NMR (300 MHz, CDCl$_3$) δ 0.83 (d, J=6 Hz, 6H), 1.9 (m, 1H), 4.3 (m, 2H), 4.82 (s, 2H), 4.88 (m, 2H), 7.70 (d, J=9 Hz, 2H), 7.79 (s, 1H), 8.03 (d, J=9 Hz, 2H); MS (DCI/NH$_3$) m/z 406 (M+H)$^+$. Anal. calc. for C$_{16}$H$_{18}$F$_3$N$_3$O$_4$S: C, 47.4; H, 4.47; N, 10.36. Found: C, 47.48; H, 4.36; N, 10.25.

EXAMPLE 450

2-(2,3,3-Trifluoropropenyl)-4-(4-fluorophenyl)-5-[4-(aminosulfonyl)phenyl]-3(2H)-pyridazinone The product of Example 4,2-benzyl-4-(4-fluorophenyl)-5-[4-(methylthio)phenyl]-3(2H)-pyridazinone, was N-debenzylated by the method of Example 11 to provide 4-(4-fluorophenyl)-5-[4-(methylthio)phenyl]-3(2H)-pyridazinone. The intermediate was mixed with one equivalent of 1-methylsufonyloxy-2,3,3-trifluoro-2-propene, (Example 88A) in ethyl acetate, followed by one equivalent of cesium carbonate. The reaction mixture was heated to 50° C. for 5 hours. Aqueous work-up, followed by chromatography provided 2-(2,3,3-trifluoropropenyl)-4-(4-fluorophenyl)-5-[4-(methylthio)phenyl]-3(2H)-pyridazinone (650 mg, 63%). The product was oxidized with one equivalent of meta-chloroperoxybenzoic acid to provide the methyl sulfoxide which was converted to the title compound according to the method of Example 68, substituting 2-(2,3,3-trifluoropropenyl)-4-(4-fluorophenyl)-5-[4-(methylsulfinyl)phenyl]-3(2H)-pyridazinone for 2-(2,2,2-trifluoroethyl)-4-(4-fluorophenyl)-5-[4-(methylsulfinyl)phenyl]-3(2H)-pyridazinone (yield: 65 mg, 35%). mp 190–193° C. $^1$H NMR (300 MHz, CDCl$_3$) δ 5.07 (s, 2H), 5.10 (dt, J=21 Hz, J=3 Hz, 2H), 7.05 (m, 4H), 7.19 (dd, J=9 Hz, J=6 Hz, 2H), 7.84 (s, 1H), 7.87 (t, J=7.5 Hz, 1H). MS (ESI–NH$_3$) m/z 456 (M–H)$^+$. Anal. calc. for C$_{19}$H$_{12}$F$_5$N$_3$O$_3$S: C, 49.89; H, 2.64; N, 9.18. Found: C, 49.89; H, 2.73; N, 9.03.

EXAMPLE 451

2-(4-Fluorophenyl)-4-(3-hydroxy-3-methyl-1-butoxy)-5-[4-(methylsulfonyl)phenyl]-3(2H)-pyridazinone The title compound was prepared according to the method of Example 178, substituting 3-methyl-1,3-butanediol in place of 2-ethyl-1-hexanol (yield: 110 mg, 61%). mp 133–134° C.; $^1$H NMR (300 MHz, DMSO-d$_6$) δ 1.04 (s, 6H), 1.72 (t, J=7 Hz, 2H) 3.29 (s, 3H), 4.32 (s, 1H), 4.53 (t, J=7 Hz, 2H), 7.37 (t, J=9 Hz, 2H), 7.66 (m, 2H), 7.90 (d, J=9 Hz, 2H), 8.07 (d, J=9 Hz, 2H), 8.19 (s, 1H); MS (APCI+) m/z 447 (M+H)$^+$; (APCI–) m/z 481 (M+Cl)$^-$; Anal. calc. for C$_{22}$H$_{23}$FN$_2$O$_5$S.0.25 H$_2$O: C, 58.59; H, 5.25; N, 6.21. Found: C, 58.42; H, 5.00; N, 6.02.

EXAMPLE 452

2-(3,4-Difluorophenyl)-4-(2-hydroxy-2-methyl-1-propoxy)-5-[4-(methylsulfonyl)phenyl]-3(2H)-pyridazinone The title compound was prepared according to the method of Example 178, substituting 2-(3,4-difluorophenyl)-4-tosyloxy-5-[4-(methylsulfonyl)phenyl]-3(2H)-pyridazinone in place of 2-(4-fluorophenyl)-4-tosyloxy-5-[4-(methylsulfonyl)phenyl]-3(2H)-pyridazinone and substituting 2-methyl-1,2-propanediol in place of 2-ethyl-1-hexanol (yield: 55 mg, 31%). $^1$H NMR (300 MHz, DMSO-d$_6$) δ 0.97 (s, 6H), 3.30 (s, 3H), 4.20 (s, 2H), 4.54 (s, 1H), 7.52 (m, 1H), 7.62 (m, 1H), 7.81 (m, 1H), 7.98 (d, J=9 Hz, 2H), 8.05 (d, J=9 Hz, 2H), 8.21 (s, 1H); MS (APCI+) m/z 451 (M+H)$^+$; (APCI–) m/z 485 (M+Cl)$^-$; Anal. calc. for C$_{21}$H$_{20}$F$_2$N$_2$O$_5$S: C, 55.99; H, 4.47; N, 6.21. Found: C, 56.00; H, 4.48; N, 5.87.

EXAMPLE 453

2-(3,4-Difluorophenyl)-4-methoxy-5-[4-(methylsulfonyl)phenyl]-3(2H)-pyridazinone The title compound was isolated from the reaction mixture in Example 233, as a product of oxidation of unreacted starting material (yield: 22 mg, 8%). mp 113–115° C. $^1$H NMR (300 MHz, DMSO-d$_6$) δ 3.3 (s, 3H), 4.1 (s, 3H), 7.53 (m, 1H), 7.63 (m, 1H), 7.8 (m, 1H), 8.15 (d, 2H), 8.2 (s, 2H). MS (DCI/NH$_3$) m/z 393 (M+H)$^+$, 410 (M+NH$_4$)$^+$. Anal. calc. for C$_{18}$H$_{14}$F$_2$N$_2$O$_4$S: C, 55.10; H, 3.60; N, 7.14.

EXAMPLE 454

2-(2,3,4,5,6-Pentafluorobenzyl)-4-(4-fluorophenyl)-5-[4-(dimethylamino)methylaminosulfonylphenyl]-3(2H)-pyridazinone The title compound was isolated from the reaction mixture in Example 125, as a product resulting from a reaction with the solvent, N,N-dimethylformamide (yield: 53 mg, 16%). mp 194–196° C. $^1$H NMR (300 MHz, CDCl$_3$) δ 3.05 (s, 3H), 3.17 (s, 3H), 5.49 (s, 2H), 6.97 (t, J=9 Hz, 2H), 7.18 (dd, J=9 Hz, 6 Hz, 2H), 7.20 (d, J=9 Hz, 2H), 7.81 (s, 1H), 7.82 (d, J=9 Hz, 2H), 8.14 (s, 1H). MS (DCI/NH$_3$) m/z 581 (M+H)$^+$. Anal. calc. for C$_{26}$H$_{18}$F$_6$N$_4$O$_3$S: C, 53.79; H, 3.12; N, 9.65. Found: C, 53.50; H, 3.24; N, 9.56.

EXAMPLE 455

2-(2,4-Difluorobenzyl)-4-(4-fluorophenyl)-5-[4-(dimethylamino)methylaminosulfonylphenyl]-3(2H)-pyridazinone The title compound was isolated from the reaction mixture in Example 124, as a product resulting from a reaction with the solvent, N,N-dimethylformamide (yield: 55 mg, 18%). mp 193–195° C. $^1$H NMR (300 MHz, CDCl$_3$) δ 3.03 (s, 3H), 3.16 (s, 3H), 5.43 (s, 2H), 6.88 (m, 2H), 6.95 (t, J=9 Hz, 2H), 7.18 (dd, J=9 Hz, 6 Hz, 2H), 7.20 (d, J=9 Hz, 2H), 7.52 (m, 1H), 7.81 (d, J=9 Hz, 2H), 7.84 (s, 1H), 8.13 (s, 1H). MS (DCI/NH$_3$) m/z 527 (M+H)$^+$. Anal. calc. for C$_{26}$H$_{21}$F$_3$N$_4$O$_3$S: C, 59.30; H, 4.02; N, 10.64. Found: C, 59.08; H, 3.97; N, 10.48.

EXAMPLE 456

(4-Fluorophenyl)-5-[4-(methylselenonyl)phenyl]-3(2H)-pyridazinone

Example 456A

4-Bromoselenoanisole

Freshly crushed magnesium turnings (6.1 g, 0.25 mol) were suspended with vigorous stirring in a solution of diethyl ether (360 mL) and 1,4-dibromobenzene (10 g, 0.04 mol). The solution was brought to reflux for 30 minutes, without initiation. Several crystals of iodine were added which initiated the reaction to a self-sustained reflux. The reflux was maintained as the remainder of the 1,4-dibromobenzene (49 g, 0.21 mol) was slowly added. The reaction was refluxed for an additional 2 hours after addition of the 1,4-dibromobenzene was completed. When nearly all of the magnesium turnings had been consumed, the yellow/gray heterogeneous solution was cooled to 23° C., and selenium (19 g, 0.24 mol) was added in small portions via spatula so as to maintain a gentle reflux. The selenium that became stuck to the sides of the flask was washed in with additional diethyl ether. After addition, the solution was stirred for 20 minutes at 23° C. and then was cooled to 0° C. A diethyl ether (20 mL) solution of methyl iodide (35.5 g, 0.25 mol) was slowly added dropwise to the reaction mixture. Upon completion of addition, the cooling bath was removed, and the solution stirred for 3 hours at 23° C. The reaction solution was slowly poured into ice water/1 M HCl, and then the biphasic solution filtered through a glass wool plug. The ethereal layer was separated and the aqueous phase extracted twice more with diethyl ether. The combined ethereal extracts were dried over MgSO$_4$, filtered, and concentrated in vacuo to provide a semi-viscous orange oil. On standing overnight at −20° C., large yellow needles formed. The residual oil was drawn off via pipette to provide 17 g (27%) of crystalline product. (J. Org. Chem., 1983, 48, 4169) $^1$H NMR (300 MHz, CDCl$_3$) δ 2.46 (s, 3H), 7.12 (d, J=8.7 Hz, 2H), 7.39 (d, J=8.7 Hz, 2H). MS (APCI+) m/z 248 (Se$_{76}$ M+H)$^+$, m/z 250 (Se$_{78}$ M+H)$^+$, m/z 252 (Se$_{80}$ M+H)$^+$, and m/z 254 (Se$_{82}$ M+H)$^+$.

Example 456B 2,4-Bis(4-fluorophenyl)-5-[4-(methylseleno)phenyl]-3(2H)-pyridazinone The title compound was prepared according to the method of Example 228, substituting 2-(4-fluorophenyl)-4-methoxy-5-[4-(methylseleno)phenyl]-3(2H)-pyridazinone (prepared according to the method of Example 194C, substituting 4-(methylseleno)benzeneboronic acid from Example 1 in place of 4-(methylthio)benzeneboronic acid) in place of 2-(4-fluorophenyl)-4-methoxy-5-[4-(methylthio)phenyl]-3(2H)-pyridazinone and substituting 4-fluorophenyl magnesium bromide in place of cyclohexylmagnesium chloride (yield: 44 mg, 69%). $^1$H NMR (300 MHz, CDCl$_3$) δ 2.37 (s, 3H), 6.98 (dd, J=8.8, 8.8 Hz, 2H), 7.05 (d, J=8.7 Hz, 2H), 7.17 (dd, J=8.7, 8.7 Hz, 2H), 7.23–7.31 (m, 2H), 7.32 (d, J=8.7 Hz, 2H), 7.65–7.72 (m, 2H), 8.00 (s, 1H). MS (APCI+) m/z 455 (M+H)+.

Example 456C 2,4-Bis(4-fluorophenyl)-5-[4-(methylselenonyl)phenyl]-3(2H)-pyridazinone A stirred solution of the 2,4-bis(4-fluorophenyl)-4-(4-fluorophenyl)-5-[4-(methylseleno)phenyl]-3(2H)-pyridazinone (40 mg, 88.1 mmol) in methylene chloride (2 mL) was treated with 3-chloroperoxybenzoic acid (100 mg, 342 mmol, 57–86%) at 23° C. After 2 hours, the reaction appeared to be only slightly more than 50% completed. Additional 3-chloroperoxybenzoic acid (80 mg, 274 mmol, 57–86%) was added. The reaction ran to completion over the next 16 hours of stirring at 23° C. The solution was diluted with ethyl acetate and carefully shaken with a NaHSO$_3$ solution (two times) for several minutes to consume the excess 3-chloroperoxybenzoic acid. The ethyl acetate solution was subsequently washed with a saturated Na$_2$CO$_3$ solution (two times), water, and brine and dried over MgSO$_4$, filtered, and concentrated in vacuo. The residue was chromatographed (flash silica gel, acetone/methylene chloride/hexanes 2:2:1) to provide the product (yield; 40 mg, 93%). (J. Chem. Soc., Chem. Commun., 1985, 569). mp 110–150° C. $^1$H NMR (300 MHz, CDCl$_3$) δ 3.32 (s, 3H), 6.91 (dd, J=8.7, 8.7 Hz, 2H), 7.14–7.27 (m, 4H), 7.48 (d, J=8.4 Hz, 2H), 7.65–7.73 (m, 2H), 7.97 (s, 1H), 8.00 (d, J=8.4 Hz, 2H). MS (APCI+) m/z 487 (M+H)$^+$ and m/z 504 (N+NH$_4$)$^+$. Anal. calc. for C$_{23}$H$_{16}$F$_2$N$_2$O$_3$Se.0.5 H$_2$O: C, 55.88; H, 3.46; N, 5.66. Found: C, 55.60; H, 3.61; N, 5.29.

EXAMPLE 457

2-(3,4-Difluorophenyl)-4-(3-fluorophenyl)-5-[4-(methylsulfonyl)phenyl]-3(2H)-pyridazinone The title compound was prepared as described in Example 62, starting with 4-(3,4-difluorophenyl)-5-[4-(methylsulfonyl)phenyl]-3(2H)-pyridazinone in place of 4-(4-fluorophenyl)-5-[4-(methylsulfonyl)phenyl]-3(2H)-pyridazinone and substituting 3,4-difluorobromobenzene in place of 1-bromo-4-fluorobenzene (yield: 185 mg, 46.5%). mp 182–185° C. $^1$H NMR (300 MHz, DMSO-d$_6$) δ 3.23 (s, 3 H), 6.98 (d, J=9 Hz, 1H), 7.18 (m, 2H), 7.32 (m, 1H), 7.52 (d, J=9 Hz, 2 H), 7.6 (m, 2H), 7.85 (m, 1 H), 7.9 (d, J=9 Hz, 2H), 8.3 (s, 1 H). MS (DCI/NH$_3$) m/z 457 (M+H)$^+$, 474 (M+NH$_4$)$^+$.

EXAMPLE 458

2-(4-Fluorophenyl)-4-(3-fluorophenyl)-5-[4-(methylsulfonyl)phenyl]-3(2H)-pyridazinone The title compound was prepared as described in Example 62, substituting 4-(3-fluorophenyl)-5-[4-(methylsulfonyl)phenyl]-3(2H)-pyridazinone in place of 4-(4-fluorophenyl)-5-[4-(methylsulfonyl)phenyl]-3(2H)-pyridazinone (yield: 135 mg, 34%). mp 199–201° C. $^1$H NMR (300 MHz, DMSO-d$_6$) δ 3.24 (s, 3H), 6.98 (d, J=9 Hz, 1H), 7.18 (m, 2H), 7.32 (m, 1H), 7.39 (t, 1H), 7.54 (d, J=9 Hz, 2 H), 7.71 (m, 2H), 7.91 (d, J=9 Hz, 2 H), 8.27 (s, 1 H). MS (DCI/NH$_3$) m/z 439 (M+H)$^+$, 456 (M+NH$_4$)$^+$.

EXAMPLE 459

2-(3,4-Difluorophenyl)-4-(2-hydroxy-2-methyl-1-propoxy)-5-[4-(aminosulfonyl)phenyl]-3(2H)-pyridazinone To a solution of 2-(3,4-difluorophenyl)-4-(2-hydroxy-2-methyl- -propoxy)-5-[4-(methylsulfonyl)phenyl]-3(2H)-pyridazinone (139 mg, 0.309 mmol) and di-t-butylazodicarboxylate (71.2 mg, 0.309 mmol) in THF (25 mL) at −78° C. was added dropwise a 1M solution of NaHMDS (0.93 mL, 0.928 mmol) in THF. After addition the reaction was stirred another 45 min at −78° C. (or until TLC indicated a disappearance of starting material) and then was treated with 1N NaOH (20 mL). The reaction mixture was stirred at room temperature for the next 18 h. Sodium acetate trihydrate (758 mg, 5.57 mmol) was added followed by addition of hydroxylamine-O-sulphonic acid (630 mg, 5.57 mmol) and H$_2$O (50 mL). The resulting mixture was stirred at ambient temperature for the next 18 hours and then extracted with EtOAc. The extract was washed with water, brine, dried over MgSO$_4$ and concentrated in vacuo. The residue was purified by chromatography (silica gel, 1:1 hexanes-EtOAc) to provide the title compound (yield: 25 mg; 18%). mp 65–69° C; $^1$H NMR (300 MHz, DMSO-d$_6$) δ 1.0 (s, 6H), 4.2 (s, 2H), 4.56 (s, 1H), 7.51 (m, 3H), 7.6 (m, 1H), 7.85 (m, 1H), 7.95 (s, 4H), 8.21 (s, 1H); MS (DCI/NH$_3$) m/z 451 (M+H)$^+$, 467 (M+NH$_4$)$^+$.

EXAMPLE 460

2-(3,4-Difluorophenyl)-4-(2-oxo-1-propoxy)-5-[4-(methylsulfonyl)phenyl]-3(2H)-pyridazinone A solution of 2-(3,4-difluorophenyl)-4-hydroxy-5-[4-(methylsulfonyl)phenyl]-3(2H)-pyridazinone (378 mg, 1 mmol), Ph$_3$P (524 mg, 2 mmol) and acetol (74 mg, 1 mmol) in THF (25 mL) at room temperature was treated dropwise with a solution of DIAD (0.4 mL, 2 mmol) in THF (5 mL). The mixture was stirred at room temperature for 6 hours and concentrated in vacuo. The residue was chromatographed (silica gel, 1:1 hexanes-ethyl acetate) to provide the desired product (yield: 205 mg, 48%). mp 169–170° C; $^1$H NMR (300 MHz, DMSO-d$_6$) δ 2.08 (s, 3H), 3.30 (s, 3H), 5.30 (s, 2H), 7.48 (m, 1H), 7.62 (q, J=10 Hz, 1H), 7.75 (m, 1H), 7.94 (d, J=9 Hz, 2H), 8.05 (d, J=9 Hz, 2H), 8.21 (s, 1H); MS (APCI+) m/z 435 (M+H)$^+$, (APCI−) m/z 469 (M+Cl)−; Anal. calc. for C$_{20}$H$_{16}$F$_2$N$_2$O$_5$S.0.75H$_2$O: C, 53.62; H, 3.93; N, 6.25. Found: C, 53.26; H, 3.61; N, 6.08.

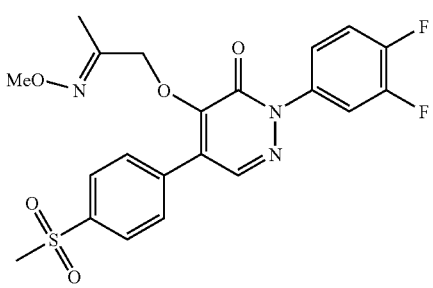

EXAMPLE 461

2-(3,4-Difluorophenyl)-4-[2-(methoxyimino)-1-propoxy]-5-[4-(methylsulfonyl)phenyl]-3(2H)-pyridazinone A mixture of 2-(3,4-difluorophenyl)-4-(2-oxo-1-propoxy)-5-[4-(methylsulfonyl)phenyl]-3(2H)-pyridazinone from Example 460 (150 mg, 0.3 mmol) in H$_2$O (10 mL) and dioxane (20 mL) was treated with methoxyamine hydrochloride (84 mg, 1 mmol) and sodium acetate trihydrate (138 mg, 1 mmol). The mixture was stirred at room temperature for 6 hours. The reaction mixture was extracted with ethyl acetate and purified by column chromatography (silica gel, 1:1 hexanes-ethyl acetate) to provide the title compound (yield: 20 mg, 15%). mp 143–145° C.; $^1$H NMR (300 MHz, DMSO-d$_6$) δ 1.63 (s, 3H), 3.30 (s, 3H), 3.74 (s, 3H), 4.93 (s, 2H), 7.54 (m, 1H), 7.65 (q, J=10 Hz, 1H), 7.82 (m, 1H), 7.92 (d, J=9 Hz, 2H), 8.07 (d, J=9 Hz, 2H), 8.24 (s, 1H); MS (APCI+) m/z 464 (M+H)$^+$; (APCI−) m/z 498 (M+Cl)$^−$. Anal. calc. for C$_{21}$H$_{19}$F$_2$N$_3$OS: C, 54.42; H, 4.13; N, 9.06. Found: C, 54.33; H, 3.93; N, 8.92.

EXAMPLE 462

(S)-2-(3,4-Difluorophenyl)-4-(3-hydroxy-2-methyl-1-propoxy)-5-[4-(methylsulfonyl)phenyl]-3(2H)-pyridazinone Example 462A (R)-3-t-Butoxy-2-methyl-1-propanol A solution of (S)-(+)-methyl 3-hydroxy-2-methylpropionate (1.18 g, 10 mmol) in t-butyl acetate (30 mL) was treated with 70% HClO$_4$ (0.1 mL) and the reaction mixture was left at room temperature in a tightly closed flask for 24 hours. The mixture was then poured into a saturated solution of NaHCO$_3$ and extracted with ethyl ether. The ether was removed in vacuo and the residue was dissolved in THF (50 mL). To the resulting solution was added NaBH4 (925 mg, 25 mmol) and at 55° C. dropwise methanol (10 mL). The reaction was continued at 55° C. for 1 hours, then it was cooled to ambient temperature, acidified with 10% citric acid to pH 5 and extracted with ethyl acetate. The acetate extract was washed with water, brine, dried with MgSO$_4$ and concentrated in vacuo. The residue was chromatographed (silica gel, 2:1 hexane-ethyl acetate) to provide (R)-3-t-butoxy-2-methyl-1-propanol (yield: 1 g, 68%). $^1$H NMR (300 MHz, CDCl$_3$) δ 0.85 (d, J=7 Hz, 3H), 1.20 (s, 9H), 2.03 (m, 1H), 3.30 (t, J=12 Hz, 1H), 3.53 (dd, J=4.5 Hz, 12 Hz, 1H), 3.70 (m, 2 H); MS (DCI/NH$_3$) m/z 164 (M+NH$_4$)$^+$.

Example 462B (S)-2-(3,4-Difluorophenyl)-4-(3-t-butoxy-2-methyl-1-propoxy)-5-(4-methylsulfonyl)phenyl]-3(2H)-pyridazinone To a solution 2-(3,4-difluorophenyl)-4-hydroxy-5-[4-(methylsulfonyl)phenyl-3(2H)-pyridazinone (378 mg, 1 mmol), Ph$_3$P (524 mg, 2 mmol) and Example 462A (146 mg, 1 mmol) in THF (25 mL) at room temperature was added dropwise a solution of DIALD (0.4 mL, 2 mmol) in THF (5 mL). The mixture was then stirred at room temperature for 6 hours and concentrated in vacuo. The residue was passed through a silica gel pad (hexane-ethyl acetate as an eluent)

to provide 550 mg of roughly purified (S)-2-(3,4-difluorophenyl)-4-(3-t-butoxy-2-methyl-1-propoxy)-5-[4-(methylsulfonyl)phenyl]-3(2H)-pyridazinone, still contaminated with reduced DIAD. MS (APCI+) m/z 507 (M+H)⁺; (APCI−) m/z 541 (M+Cl)⁻.

Example 462C (S)-2-(3,4-Difluorophenyl)-4-(3-hydroxy-2-methyl-1-propoxy)-5-[4-(methylsulfonyl)phenyl]-3(2H)-pyridazinone A mixture of Example 462B (100 mg, ~2 mmol) in TFA (5 mL) was left at ambient temperature for 24 hours. The mixture was then concentrated in vacuo, the residue was neutralized with saturated solution of NaHCO₃ and extracted with ethyl acetate. Purification on a column (silica gel, 1:2 hexanes-EtOAc) gave a foamy product (yield: 51 mg, 56%). ¹H NMR (300 MHz, DMSO-d₆) δ 0.75 (d, J=7 Hz, 3H), 1.81 (sextet (J=7 Hz, 1H), 3.21 (d, J=6 Hz, 2H), 3.30 (s, 3H), 4.29 (dd, J=6 Hz, 12 Hz, 1H), 4.40 (dd, J=6 Hz, 12 Hz, 1H), 4.48 (br s, 1H), 7.52 (m, 1H), 7.61 (m, 1H), 7.80 (m, 1H), 7.91 (d, J=9 Hz, 2H), 8.07 (d, J=9 Hz, 2H), 8.20 (s, 1H); MS (APCI+) m/z 451 (M+H)⁺; (APCI−) m/z 485 (M+Cl)−; Anal. calc. for C₂₁H₂₀F₂N₂O₅S: C, 55.99; H, 4.47; N, 6.21. Found: C, 55.65; H, 4.65; N, 5.92.

EXAMPLE 463

(R)-2-(3,4-Difluorophenyl)-4-(3-hydroxy-2-methyl-1-propoxy)-5-[4-(methylsulfonyl)phenyl]-3(2H)-pyridazinone The title compound was prepared by the method described in Example 462, substituting (R)-(−)-methyl 3-hydroxy-2-methylpropionate in place of (S)-(+)-methyl 3-hydroxy-2-methylpropionate (yield: 65 mg, 61%). ¹H NMR (300 MHz, DMSO-d₆) δ 0.75 (d, J=7 Hz, 3H), 1.81 (sextet, J=7 Hz, 1H), 3.21 (t, J=6 Hz, 2H), 3.30 (s, 3H), 4.29 (dd, J=6 Hz and 12 Hz, 1H), 4.40 (dd, J=6 Hz, 12 Hz, 1H), 4.49 (t, J=6 Hz, 1H), 7.52 (m, 1H), 7.61 (m, 1H), 7.80 (m, 1H), 7.91 (d, J=9 Hz, 2H), 8.07 (d, J=9 Hz, 2H), 8.20 (s, 1H); MS (APCI+) m/z 451 (M+H)⁺; (APCI−), m/z 485 (M+Cl)−. Anal. calc. for C₂₁H₂₀F₂N₂O₅S: C, 55.99; H, 4.47; N, 6.21. Found: C, 55.62; H, 4.52; N, 6.06.

EXAMPLE 464

(S)-2-(3,4-Difluorophenyl)-4-(3-hydroxy-2-methyl-1-propoxy)-5-[4-(aminosulfonyl)phenyl]-3(2H)-pyridazinone To a solution of (S)-2-(3,4-difluorophenyl)-4-(3-t-butoxy-2-methyl-1-propoxy)-5-[4-(methylsulfonyl)phenyl]-3(2H)-pyridazinone (Example 462B, 450 mg, ~0.9 mmol) and DBAD (207 mg, 0.9 mmol) in THF (25 mL) at −78° C. was added dropwise a 1M solution of LiHMDS (3 mL, 3 mmol) and the resulting mixture was stirred at −78° C. for 2 hours. The mixture was warmed to room temperature and 1N NaOH (5 mL, 5 mmol) was added. After 12 hours at ambient temperature, sodium acetate trihydrate (2.76 g, 20 mmol) and water (10 mL) followed by hydroxylamine-O-sulfonic acid (2 g, 15 mmol) were added and the mixture was stirred at room temperature for 5 hours. The product was extracted with ethyl acetate and purified by chromatography (silica gel, 1:2 hexanes-EtOAc) to afford crude intermediate (yield: 160 mg, 35%). MS (APCI+) m/z 508 (M+H)⁺; (APCI−) m/z 542 (M+Cl)−.

TFA (5 mL) was added to the above intermediate and the resulting solution was left at room temperature for 24 hours. The TFA was removed in vacuo, then the residue was neutralized with saturated NaHCO₃ and extracted with ethyl acetate. The organic layer was dried over MgSO₄ then filtered. The filtrate was concentrated in vacuo and the residue was purified by column chromatography (silica gel, 1:2 hexane-ethyl acetate) to provide the title compound (yield: 50 mg, 33%). ¹H NMR (300 MHz, DMSO-d₆) δ 0.76 (d, J=7 Hz, 3H), 1.81 (sextet, J=7 Hz, 1H), 3.22 (t, J=6 Hz, 2H), 4.28 (dd, J=6 Hz, 12 Hz, 1H), 4.40 (dd, J=6 Hz, 12 Hz, 1H), 4.50 (t, J=6 Hz, 1H), 7.51 (m, 3H), 7.61 (m, 1H), 7.80 (m, 1H), 7.84 (d, J=9 Hz, 2H), 7.95 (d, J=9 Hz, 2H), 8.20 (s, 1H); MS (APCI+) m/z 452 (M+H)⁺; (APCI−) m/z 486 (M+Cl)−.

EXAMPLE 465

(R)-2-(3,4-Difluorophenyl)-4-(3-hydroxy-2-methyl-1-propoxy)-5-[4-(aminosulfonyl)phenyl]-3(2H)-pyridazinone The desired material was prepared according to the procedure of Example 464 substituting (R)-2-(3,4-difluorophenyl)-4-(3-t-butoxy-2-methyl-1-propoxy)-5-[4-(methylsulfonyl)phenyl]-3(2H)-pyridazinone in place of (S)-2-(3,4-difluorophenyl)-4-(3-t-butoxy-2-methyl-1-propoxy)-5-[4-(methylsulfonyl)phenyl]-3(2H)-pyridazinone (yield: 30 mg, 20%). ¹H NMR (300 MHz, DMSO-d₆) δ 0.76 (d, J=7 Hz, 3H), 1.81 (sextet, J=7 Hz, 1H), 3.22 (t, J=6 Hz, 2H), 4.28 (dd, J=6 Hz, 12 Hz, 1H), 4.40 (dd, J=6 Hz and 12 Hz, 1H), 4.50 (t, J=6 Hz, 1H), 7.51 (m, 3H), 7.61 (m, 1H), 7.80 (m, 1H), 7.84 (d, J=9 Hz, 2H), 7.95 (d, J=9 Hz, 2H), 8.20 (s, 1H); MS (APCI+) m/z 452 (M+H)⁺; (APCI−) m/z 486 (M+Cl)−. Anal. calc. for C₂₀H₁₉F₂N₃O₅S: C, 53.21; H, 4.24; N, 9.30. Found: C, 53.45; H, 5.53; N, 9.50.

EXAMPLE 466

2-(4-Fluorophenyl)-4-(4-hydroxy-3-methyl-1-butoxy)-5-[4-(methylsulfonyl)phenyl]-3(2H)-pyridazinone The title compound was prepared according to the method of Example 178, substituting 2-methyl-1,4-butandiol in place of 2-ethyl-1-hexanol and separating the regioisomeric products by multiple preparative thin layer chromatography runs, eluting with 4:1 ethyl acetate/hexanes (yield: 65 mg, 19%). ¹H NMR (300 MHz, CDCl₃) δ 0.87 (d, J=8.1 Hz, 3H), 1.48–1.87 (m, 4H), 3.13 (s, 3H), 3.41 (dd, J=6.3, 13.5 Hz, 1H), 3.46 (dd, J=6.3, 13.5 Hz, 1H), 4.48–4.63 (m, 2H), 7.15–7.24 (m, 2H), 7.58–7.66 (m, 2H), 7.79 (d, J=10.5 Hz, 2H), 7.91 (s, 1H), 8.07 (d, J=10.5 Hz, 2H); MS (APCI+) m/z 447 (M+H)⁺.

EXAMPLE 467

2-(3,4-Difluorophenyl)-4-(3-oxo-1-butoxy)-5-[4-(methylsulfonyl)phenyl]-3(2H)-pyridazinone The title compound was prepared according to the method of Example 460 substituting 4-hydroxy-2-butanone in place of acetol. (yield: 95.0 mg, 21%). mp 134–135° C.; ¹H NMR (300 MHz, CDCl₃) δ 2.06 (s, 3H), 2.81 (t, J=9 Hz, 2H), 3.13 (s, 3H), 4.75 (t, J=9 Hz, 2H), 7.30 (m, 1H), 7.45 (m, 1H), 7.58 (m, 1H), 7.73 (d, J=9 Hz, 2H), 7.89 (s, 1H), 8.05 (d, J=9 Hz, 2H); MS (DCI/NH₃) m/z 449 (M+H)⁺, 466 (M+NH₄)⁺. Anal. calc. for C₂₁H₁₈F₂N₂O₅S: C, 56.25; H, 4.02; N, 6.25. Found: C, 55.97; H, 4.17; N, 6.11.

EXAMPLE 468

2-(4-Fluorophenyl)-4-(3-oxo-1-butoxy)-5-[4-(methylsulfonyl)phenyl]-3(2H)-pyridazinone The title compound was prepared according to the method of Example 460 starting with 2-(4-fluorophenyl)-4-hydroxy-5-[4-(methylsulfonyl)phenyl]-3(2H)-pyridazinone in place of 2-(3,4-difluorophenyl)-4-hydroxy-5-[4-(methylsulfonyl)phenyl]-3(2H)-pyridazinone and substituting 4-hydroxy-2-butanone in place of acetol. (yield: 85.0 mg, 20%). mp 133–136° C.; $^1$H NMR (300 MHz, CDCl$_3$) δ 2.04 (s, 3H), 2.80 (t, J=9 Hz, 2H), 3.13 (s, 3H), 4.76 (t, J=9 Hz, 2H), 7.20 (t, J=9 Hz, 2H), 7.55 (m, 2H), 7.75 (d, J=9 Hz, 2H), 7.91 (s, 1H), 8.05 (d, J=9 Hz, 2H). MS (DCI/NH$_3$) m/z 431 (M+H)$^+$, 448 (M+NH$_4$)$^+$. Anal. calc. for C$_{21}$H$_{19}$FN$_2$O$_5$S: C, 58.60; H, 4.42; N, 6.52. Found: C, 58.87; H, 4.55; N, 6.51.

EXAMPLE 469

2-(4-Fluorophenyl)-4-(4-hydroxy-2-methyl-1-butoxy)-5-[4-(methylsulfonyl)phenyl]-3(2H)-pyridazinone The title compound was prepared according to the method of Example 178, substituting 2-methyl-1,4-butandiol in place of 2-ethyl-1-hexanol and separating the regioisomeric products by multiple preparative thin layer chromatography runs, eluting with 4:1 ethyl acetate/hexanes (yield: 43 mg, 12%). $^1$H NMR (300 MHz, CDCl$_3$) δ 0.87 (d, J=8.1 Hz, 3H), 1.33–1.46 (m, 1H), 1.50–1.67 (m, 2H), 1.93–2.04 (m, 1H), 3.13 (s, 3H), 3.54–3.72 (m, 2H), 4.29 (dd, J=6.0, 9.3 Hz, 1H), 4.43 (dd, J=6.0, 9.3 Hz, 1H), 7.15–7.24 (m,2H), 7.58–7.66 (m, 2H), 7.79 (d, J=10.5 Hz, 2H), 7.91 (s, 1H), 8.07 (d, J=10.5 Hz, 2H); MS (APCI+) m/z 447 (M+H)$^+$.

EXAMPLE 470

2-(4-Fluorophenyl)-4-(3-hydroxy-3-methyl-1-butoxy)-5-[4-(aminosulfonyl)phenyl]-3(2H)-pyridazinone The title compound was prepared according to the method of Example 459, substituting 2-(4-fluorophenyl)-4-(3-hydroxy-3-methyl-1-butoxy)-5-[4-(methyl-sulfonyl)phenyl]-3(2H)-pyridazinone in place of 2-(3,4-difluorophenyl)-4-(2-hydroxy-2-methyl-1-propoxy)-5-[4-(methylsulfonyl)phenyl]-3(2H)-pyridazinone (yield: 600 mg, 60%). mp 163–164° C.; $^1$H NMR (300 MHz, DMSO-d$_6$) δ 1.05 (s, 6H), 1.73 (t, J=6 Hz, 2H), 4.30 (s, 1H), 4.52 (t, J=6 Hz, 2H), 7.37 (t, J=9 Hz, 1H), 7.47 (s, 2H), 7.65 (dd, J=9 Hz, J=3 Hz, 2H), 8.83 (d, J=9 Hz, 2H), 8.95 (d, J=9 Hz, 2H), 8.18 (s, 1H); MS (DCI/NH$_3$) m/z 448 (M+H)$^+$. Anal. calcd. for C$_{21}$H$_{22}$FN$_3$O$_5$S: C, 56.36; H, 4.95; N, 9.39. Found: C, 55.96; H, 4.89; N, 9.09.

EXAMPLE 471

2-(3,4-Difluorophenyl)-4-(3-hydroxy-3-methyl-1-butoxy)-5-[4-(methylsulfonyl)phenyl]-3(2H)-pyridazinone

Example 471A 3,4-Difluorophenylhydrazine

A stirred mixture of 3,4-difluoroaniline (12.9 g, 0.1 mol) in concentrated hydrochloric acid (60 mL) was chilled to −10° C. with an ice/methanol bath. A solution of sodium nitrite (6.9 g, 0.1 mol) in water (30 mL) was added at a rate which maintained the temperature of the reaction mixture below 10° C. After stirring for 2 hours, the reaction mixture was cooled to 0° C. and a solution of tin(II) chloride (56.88 g, 0.3 mol) in concentrated hydrochloric acid (50 mL) was added dropwise with vigorous stirring. Additional concentrated hydrochloric acid (150 mL) was added to the reaction mixture and stirring was continued for 2 hours. The reaction mixture was filtered to collect the precipitated hydrochloride salt of the title compound. This precipitate was dissolved in water (75 mL) and the resulting solution was basified with 50% aqueous sodium hydroxide and extracted with ethyl acetate. The organic extracts were dried (Na$_2$SO$_4$) and filtered. The filtrate was concentrated in vacuo to provide the title intermediate as a brown oil (8.11 g, 57.4%).

Example 471B 2-(3,4-Difluorophenyl)-4,5-dibromo-3(2H)-pyridazinone

The title intermediate was prepared by the method of Example 194A, substituting 3,4-difluorophenylhydrazine (Example 471A) for 4-fluorophenylhydrazine hydrochloride.

Example 471C 2-(3,4-Difluorophenyl)-4-(3-hydroxy-3-methyl-1-butoxy)-5-bromo-3(2H)-pyridazinone The dibromo-intermediate from Example 471B was reacted according to the procedure described in Example 194B, substituting 3-methyl-1,3-butanediol in place of methanol, to selectively react at the 4-position and provide the title intermediate.

Example 471D 2-(3,4-Difluorophenyl)-4-(3-hydroxy-3-methyl-1-butoxy)-5-[4-(methylthio)phenyl]-3(2H)-pyridazinone The product from Example 471C (12.79 g, 32.86 mmol) was coupled to 4-(methyl-thio)phenylboronic acid (6.07 g, 36.15 mmol) with K$_2$CO$_3$ (10 g, 72.3 mmol) and PdCl$_2$(PPh$_3$)$_2$ (1.15 g, 1.64 mmol) in ethanol (200 mL) at 60–65° C. for 40–70 minutes to provide the title intermediate (yield: 9.16 g, 64.5%).

Example 471E 2-(3,4-Difluorophenyl)-4-(3-hydroxy-3-methyl-1-butoxy)-5-[4-(methylsulfonyl)phenyl]-3(2H)-pyridazinone The sulfide from Example 471D was oxidized to the title compound by the method of Example 10 (yield: 7.46 g, 76%). m.p. 131–133° C.; $^1$H NMR (300 MHz, DMSO-d$_6$) δ 1.04 (s, 6H), 1.73 (t, J=6 Hz, 2H), 3.29 (s, 3H), 4.43 (s, 1H), 4.54 (t, J=6 Hz, 2H), 7.52 (m, 1H), 7.62 (ddd, J=9 Hz, J=9 Hz, J=1.5 Hz, 1H), 7.82 (ddd, J=9 Hz, J=9 Hz, J=3 Hz, 1H), 7.91 (d, J=9 Hz, 1H), 8.08 (d, J=9 Hz, 2H), 8.20 (s, 1H); MS (DCI–NH$_3$) m/e 465 (M+H)$^+$. Anal. calcd. for C$_{22}$H$_{22}$F$_2$N$_2$O$_5$S: C, 56.88; H, 4.77; N, 6.03 Found: C, 56.92; H, 4.88; N, 5.94.

EXAMPLE 472

2-(3,4-Difluorophenyl)-4-(3-hydroxy-3-methyl-1-butoxy)-5-[4-(aminosulfonyl)phenyl]-3(2H)-pyridazinone The title compound was prepared according to the method of Example 459, substituting 2-(3,4-difluorophenyl)-4-(3-hydroxy-3-methyl-1-butoxy)-5-[4-(methylsulfonyl)phenyl]-3(2H)-pyridazinone in place of 2-(3,4-difluorophenyl)-4-(2-hydroxy-2-methyl-1-propoxy)-5-[4-(methylsulfonyl) phenyl]-3(2H)-pyridazinone (yield: 300 mg, 50%). mp 181–181° C.; $^1$H NMR (300 MHz, DMSO-$d_6$) δ 1.04 (s, 6H), 1.72 (t, J=6 Hz, 2H), 4.43 (s, 1H), 4.53 (t, J=6 Hz, 2H), 7.49 (s, 2H), 7.53 (m, 1H), 7.63 (ddd, J=9 Hz, J=9 Hz, J=1.5 Hz, 1H), 7.79 (ddd, J=9 Hz, J=9 Hz, J=3 Hz, 1H), 7.83 (d, J=9 Hz, 1H), 7.95 (d, J=9 Hz, 2H), 8.19 (s, 1H); MS (DCI/NH$_3$) m/z 466 (M+H)$^+$. Anal. calcd. for $C_{21}H_{21F2}N_2O_5S$: C, 54.12; H, 4.66; N, 8.81. Found: C, 54.19; H, 4.55; N, 9.03.

EXAMPLE 473

2-(3-Chloro-4-fluorophenyl)-4-(3-hydroxy-3-methyl-1-butoxy)-5-[4-(methylsulfonyl)phenyl]-3(2H)-pyridazinone The title compound was prepared according to the sequence of reactions described in Example 471, substituting 3-chloro-4-fluorophenylhydrazine in place of 3,4-difluorophenylhydrazine (yield: 200 mg, 89%). mp 108–110° C.; $^1$H NMR (300 MHz, CDCl$_3$) δ 1.24 (s, 6H), 1.89 (t, 2H, J=6 Hz), 2.34 (s, 1H), 3.12 (s, 3H), 4.57 (t, J=6 Hz, 2H), 7.25 (t, J=9 Hz, 1H), 7.60 (m, 1H), 7.78 (d, J=6 Hz, 1H), 7.79 (d, J=9 Hz, 2H), 7.92 (s, 1H), 8.08 (d, J=9 Hz, 2H); MS (DCI/NH$_3$) m/z 481 (M+H)$^+$; Anal. calcd. for $C_{22}H_{22}FClN_2O_5S$: C, 54.94; H, 4.61; N, 5.82. Found: C, 54.87; H, 4.65; N, 5.72.

EXAMPLE 474

2-(3-Chloro-4-fluorophenyl)-4-(3-hydroxy-3-methyl-1-butoxy)-5-[4-(aminosulfonyl)phenyl]-3(2H)-pyridazinone The title compound was prepared according to the method of Example 459, substituting 2-(3-chloro-4-fluorophenyl)-4-(3-hydroxy-3-methyl-1-butoxy)-5-[4-(methylsulfonyl) phenyl]-3(2H)-pyridazinone (Example 473) in place of 2-(3,4-difluorophenyl)-4-(2-hydroxy-2-methyl-1-propoxy)-5-[4-(methylsulfonyl)phenyl]-3(2H)-pyridazinone (yield: 160 mg, 45%). mp 59–62° C.; $^1$H NMR (300 MHz, DMSO-$d_6$) δ 1.05 (s, 6H), 1.73 (t, 2H, J=6 Hz), 4.32 (s, 1H), 4.54 (t, J=6 Hz, 2H), 7.50 (s, 2H), 7.60 (t, J=9 Hz, 1H), 7.66 (m, 1H), 7.73 (d, J=9 Hz, 2H), 7.74 (d, J=9 Hz, 2H), 7.75 (m, 1H), 8.22 (s, 1H); MS (DCI/NH$_3$) m/z 482 (M+H)$^+$. Anal. calcd. for $C_{21}H_{21}FClN_3O_5S$: C, 52.33; H, 4.39; N, 8.71. Found: C, 52.30; H, 5.03; N. 8.10.

EXAMPLE 475

2-(3-Chlorophenyl)-4-(3-hydroxy-3-methyl-1-butoxy)-5-[4-(methylsulfonyl)phenyl]-3(2H)-pyridazinone The title compound was prepared according to the sequence of reactions described in Example 471, substituting 3-chlorophenylhydrazine in place of 3,4-difluorophenylhydrazine (yield: 200 mg, 89%). $^1$H NMR (300 MHz, CDCl$_3$) δ 8.04 (d, J=8.5 Hz, 2H), 7.91 (s, 1H), 7.77 (d, J=8.5 Hz, 2H), 7.67 (m, 1H), 7.57 (m, 1H), 7.40 (t, =8.8 Hz, 1H), 7.36 (m, 1H), 4.54 (t, J=6.3 Hz, 2H), 3.10 (s, 3H), 2.56 (s, 1H), 1.86 (t, J=6.3 Hz, 2H), 1.20 (s, 6H), MS (DCI/NH$_3$) m/z 462(M+H)$^+$.

EXAMPLE 476

2-(3-Chlorophenyl)-4-(3-hydroxy-3-methyl-1-butoxy)-5-[4-(aminosulfonyl)phenyl]-3(2H)-pyridazinone The title compound was prepared according to the method of Example 459, substituting 2-(3-chlorophenyl)-4-(3-hydroxy-3-methyl-1-butoxy)-5-[4-(methylsulfonyl)phenyl]-3 (2H)-pyridazinone (Example 475) in place of 2-(3,4-difluorophenyl)-4-(2-hydroxy-2-methyl-1-propoxy)-5-[4-(methylsulfonyl)phenyl]-3 (2H)-pyridazinone. $^1$H NMR (300 MHz, CDCl$_3$) δ 8.03 (d, J=8.7 Hz, 2H), 7.91 (s, 1H), 7.70 (d, J=8.7 Hz, 2H), 7.68 (m, 1H), 7.57 (m, 1H), 7.41 (m, 1H), 7.38 (m, 1H), 5.65 (s, 2H), 4.51 (t, J=6.6 Hz, 2H), 2.70 (br s, 1H), 1.87 (t, J=6.6 Hz, 2H), 1.20 (s, 6H); MS (DCI/NH$_3$) m/z 463 (M+H)$^+$.

EXAMPLE 477

2-(4-Fluorophenyl)-4-(2-hydroxy-2-methyl-1-propoxy)-5-[4-(methylsulfonyl)phenyl]-3(2H)-pyridazinone The title compound was prepared according to the sequence of reactions described in Example 471, substituting 4-fluorophenylhydrazine in place of 3,4-difluorophenylhydrazine and substituting 2-methyl-1,2-propanediol (prepared by the LAH reduction of methyl 2-hydroxyisobutyrate) in place of 3-methyl-1,3-butanediol. mp 152–154° C., $^1$H NMR (300 MHz, CDCl$_3$) δ 8.10 (d, 2H, J=18 Hz), 7.95 (s, 1H), 7.83 (d, 2H, J=18 Hz), 7.63 (d, 1H, J=18 Hz), 7.61 (d, 1H, J=18 Hz), 4.18 (s, 2H), 3.13 (s, 3H), 1.19 (s, 6H), MS (DCI/NH$_3$) m/z 433 (M+H)$^+$, 450 (M+NH$_4$)$^+$, Analysis for $C_{21}H_{21}FN_2O_5S$, Calcd: C, 58.32; H, 4.89; N, 6.48. Found: C, 58.42; H, 5.05; N, 6.43.

EXAMPLE 478

2-(4-Fluorophenyl)-4-(2-hydroxy-2-methyl-1-propoxy)-5-[4-(aminosulfonyl)phenyl]-3(2H)-pyridazinone The title compound was prepared according to the method of Example 459, substituting 2-(4-fluorophenyl)-4-(2-hydroxy-2-methyl-1-propoxy)-5-[4-(methyl-sulfonyl)phenyl]-3(2H)-pyridazinone (Example 477) in place of 2-(3,4-difluoro-phenyl)-4-(2-hydroxy-2-methyl-1-propoxy)-5-[4-(methylsulfonyl)phenyl]-3(2H)-pyridazinone. mp 155–158° C; $^1$H NMR (300 MHz, DMSO-$d_6$) δ 8.17 (s, 1H), 7.92 (s, 4H), 7.67 (d, 1H, J=18 Hz), 7.64 (d, 1H, J=18 Hz), 7.49 (s, 2H), 7.38 (d, 1H, J=18 Hz), 7.35 (d, 1H, J=18 Hz), 4.54 (s, 1H), 4.19 (s, 2H), 1.00 (s, 6H), MS (ESI+): m/z 434 (M+H)$^+$, 456 (M+Na)$^+$, 889 (2M+Na)$^+$; Analysis for $C_{20}H_{20}FN_3O_5S$, Calcd: C, 55.42; H, 4.65; N, 9.69. Found: C, 55.64; H, 4.85; N, 9.53.

EXAMPLE 479

2-(3-Chloro-4-fluorophenyl)-4-(2-hydroxy-2-methyl-1-propoxy)-5-[4-(methylsulfonyl)phenyl]-3(2H)-pyridazinone The title compound was prepared according to the sequence of reactions described in Example 471, substituting 3-chloro-4-fluorophenylhydrazine in place of 3,4-difluorophenylhydrazine and substituting 2-methyl-1,2-propanediol (prepared by the LAH reduction of methyl 2-hydroxyisobutyrate) in place of 3-methyl-1,3-butanediol. mp 122–124° C., $^1$H NMR (300 MHz, CDCl$_3$) δ 0.98 (s, 6H), 3.29 (s, 3H), 4.21 (s, 2H), 4.56 (s, 1H), 7.61 (dd, 1H, J=7,17 Hz), 7.67 (ddd, 1H, J=2,4,7 Hz), 7.93 (dd, 1H, J=2,7 Hz), 7.98 (d, 2H, J=8 Hz), 8.06 (d, 2H, J=8 Hz), 8.22 (s, 1H); MS (DCI/NH$_3$) m/z 465(M−H)$^-$; Anal. Calcd for C$_{21}$H$_{20}$ClFN$_2$O$_5$S: C 54.02, H 4.32, N 6.00. Found: C 54.06, H 4.57, N 5.95.

EXAMPLE 480

2-(3-Chloro-4-fluorophenyl)-4-(2-hydroxy-2-methyl-1-propoxy)-5-[4-(aminosulfonyl)phenyl]-3(2H)-pyridazinone The title compound was prepared according to the method of Example 459, substituting 2-(3-chloro-4-fluorophenyl)-4-(2-hydroxy-2-methyl-1-propoxy)-5-[4-(methylsulfonyl)phenyl]-3(2H)-pyridazinone (Example 479) in place of 2-(3,4-difluorophenyl)-4-(2-hydroxy-2-methyl-1-propoxy)-5-[4-(methylsulfonyl)phenyl]-3(2H)-pyridazinone. mp 176–178° C., $^1$H NMR (300 MHz, CDCl$_3$) δ 1.00 (s, 6H), 4.19 (s, 2H), 4.54 (s, 1H), 7.49 (s, 2H), 7.62 (t, 1H, J=9 Hz), 7.66 (ddd, 1H, J=2,5,9 Hz), 7.92 (s, 4.5H), 7.94 (d, 0.5H, J=2 Hz), 8.20 (s, 1H); MS (DCI/NH$_3$) m/z 468 (M+H)$^+$; 1 Cl, 490 (M+Na)$^+$; 1 Cl; Anal. Calcd for C$_{20}$H$_{19}$ClFN$_3$O$_5$S: C 51.34, H 4.09, N 8.98. Found: C 51.33, H 4.23, N 8.76.

EXAMPLE 481

2-(3-Chlorophenyl)-4-(2-hydroxy-2-methyl-1-propoxy)-5-[4-(methylsulfonyl)phenyl]-3(2H)-pyridazinone The title compound was prepared according to the sequence of reactions described in Example 471, substituting 3-chlorophenylhydrazine in place of 3,4-difluorophenylhydrazine and substituting 2-methyl-1,2-propanediol (prepared by the LAH reduction of methyl 2-hydroxyisobutyrate) in place of 3-methyl-1,3-butanediol. $^1$H NMR (300 MHz, CDCl$_3$) δ 8.15 (m, 2H), 7.98 (s, 1H), 7.85 (m, 2H), 7.76 (m, 1H), 7.62 (m, 1H), 7.43 (m, 2H), 4.22 (s, 2H), 3.15 (s, 3H), 1.21 (s, 6H); MS (DCI/NH$_3$) m/z 449 (M+H)$^+$; Anal. Calcd for C$_{21}$H$_{21}$ClN$_2$O$_5$S: C 56.18, H 4.72, N 6.24. Found: C 56.08, H 4.67, N 6.23.

EXAMPLE 482

2-(3-Chlorophenyl)-4-(2-hydroxy-2-methyl-1-propoxy)-5-[4-(aminosulfonyl)phenyl]-3(2H)-pyridazinone The title compound was prepared according to the method of Example 459, substituting 2-(3-chlorophenyl)-4-(2-hydroxy-2-methyl-1-propoxy)-5-[4-(methylsulfonyl)phenyl]-3(2H)-pyridazinone (Example 481) in place of 2-(3,4-difluorophenyl)-4-(2-hydroxy-2-methyl-1-propoxy)-5-[4-(methylsulfonyl)phenyl]-3(2H)-pyridazinone. $^1$H NMR (400 MHz, DMSO-d$_6$) δ 8.19 (s, 1H), 7.93 (m, 4H), 7.75 (m, 1H), 7.61–7.48 (m, 5H), 4.53 (s, 2H), 4.20 (s, 3H), 1.00 (s, 6H); MS (ESI−) m/z 448 (M−H)$^-$; Anal. Calcd for C$_{20}$H$_{20}$ClN$_3$O$_5$S: C 53.39, H 4.48, N 9.34. Found: C 53.11, H 4.82, N 9.24.

EXAMPLE 483

2-(2,2,2-Trifluoroethyl)-4-(2-hydroxy-2-methyl-1-propoxy)-5-[4-(methylsulfonyl)phenyl]-3(2H)-pyridazinone The title compound was prepared according to the sequence of reactions described in Example 471, substituting 2,2,2-trifluoroethylhydrazine in place of 3,4-difluorophenylhydrazine and substituting 2-methyl-1,2-propanediol (prepared by the LAH reduction of methyl 2-hydroxyisobutyrate) in place of 3-methyl-1,3-butanediol. $^1$H NMR (300 MHz, CDCl$_3$) δ 1.18 (s, 6H), 2.62 (br s, 1H), 3.15 (s, 3H), 4.20 (s, 2H), 4.85 (q, J=9 Hz, 2H), 7.78 (d, J=9 Hz, 2H), 7.85 (s, 1H), 8.08 (d, J=9 Hz, 2H); MS (DCI/NH$_3$) m/z 421 (M+1)$^+$; Analysis calculated for C$_{17}$H$_{19}$F$_3$N$_2$O$_5$S: C, 48.57; H, 4.56; N, 6.66. Found: C, 48.72; H, 4.78; N, 6.56.

EXAMPLE 484

2-(2,2,2-Trifluoroethyl)-4-(2-hydroxy-2-methyl-1-propoxy)-5-[4-(aminosulfonyl)phenyl]-3(2H)-pyridazinone The title compound was prepared by the following sequence of reactions. Mucobromic acid and 2,2,2-trifluoroethylhydrazine hydrochloride were reacted to provide 2-(2,2,2-trifluoroethyl)-4,5-dibromo-3(2H)-pyridazinone following the procedure in Example 194A. The dibromo-intermediate was reacted according to the procedure described in Example 194B, substituting 2-methyl-1,2-propanediol in place of methanol, to selectively react at the 4-position and provide 2-(2,2,2-trifluoroethyl)-4-(2-hydroxy-2-methyl-1-propoxy)-5-bromo-3(2H)-pyridazinone. This 5-bromo-compound was coupled to 4-[2-(tetrahydropyranyl)thio]phenylboronic acid (prepared from THP-protected 4-bromothiophenol and triisopropyl borate) with K$_2$CO$_3$ and PdCl$_2$(PPh$_3$)$_2$ in ethanol at 60–65° C. for 40–70 minutes to provide 2-(2,2,2-trifluoroethyl)-4-(2-hydroxy-2-methyl-1-propoxy)-5-[4-[2-(tetrahydropyranyl)thio]phenyl]-3(2H)-pyridazinone. This intermediate THP-sulfide was then converted to the title compound by treatment with N-chloro-succinimide (3.5 equivalents) at 0° C. in THF/H$_2$O for 15 minutes to an hour followed by addition of excess ammonium hydroxide at 0° C. and stirring at ambient temperature for 3 hours. Aqueous work-up and column chromatographic purification (80:20 pentane/ethyl acetate) provided the title compound. $^1$H NMR (300 MHz, CDCl$_3$) δ 1.18 (s, 6H), 2.65 (br s, 1H), 4.15 (s, 2H), 4.85 (q, J=9 Hz, 2H), 4.9 (s, 2H), 7.75 (d, J=9 Hz, 1H), 8.05 (d, J=9 Hz, 2H); MS (DCI/NH$_3$) m/z 422 (M+H)$^+$; Analysis calculated for C$_{16}$H$_{18}$F$_3$N$_3$O$_5$S: C, 45.60; H, 4.30; N, 9.97. Found: C, 45.86; H, 4.63; N, 9.81.

EXAMPLE 485

2-(2,2,2-Trifluoroethyl)-4-(3-hydroxy-2,2-dimethyl-1-propoxy)-5-[4-(methylsulfonyl)phenyl]-3(2H)-pyridazinone The title compound may be prepared according to the method of Example 483, substituting neopentyl glycol in place of 2-methyl-1,2-propanediol.

EXAMPLE 486

2-(2,2,2-Trifluoroethyl)-4-(3-hydroxy-2,2-dimethyl-1-propoxy)-5-[4-(aminosulfonyl)phenyl]-3(2H)-pyridazinone The title compound may be prepared according to the method of Example 484, substituting neopentyl glycol in place of 2-methyl-1,2-propanediol.

EXAMPLE 487

2-(4-Fluorophenyl)-4-(4-hydroxy-3-methyl-1-butoxy)-5-[4-(aminosulfonyl)phenyl]-3(2H)-pyridazinone The title compound may be prepared according to the method of Example 459, substituting 2-(4-fluorophenyl)-4-(4-hydroxy-3-methyl-1-butoxy)-5-[4-(methylsulfonyl)phenyl]-3(2H)-pyridazinone (Example 466) for 2-(3,4-difluorophenyl)-4-(2-hydroxy-2-methyl-1-propoxy)-5-[4-(methylsulfonyl)phenyl]-3(2H)-pyridazinone.

EXAMPLE 488

2-(3,4-Difluorophenyl)-4-(4-hydroxy-3-methyl-1-butoxy)-5-[4-(methylsulfonyl)phenyl]-3(2H)-pyridazinone The title compound may be prepared according to the sequence of reactions described in Example 471, substituting 2-methyl-1,4-butanediol for 3-methyl-1,3-butanediol, then separating the regioisomeric products by multiple preparative thin layer chromatography runs.

EXAMPLE 489

2-(3-Chloro-4-fluorophenyl)-4-(4-hydroxy-3-methyl-1-butoxy)-5-[4-(methylsulfonyl)phenyl]-3(2H)-pyridazinone The title compound may be prepared according to the sequence of reactions described in Example 471, substituting 3-chloro-4-fluorophenylhydrazine for 3,4-difluorophenylhydrazine and substituting 2-methyl-1,4-butanediol for 3-methyl-1,3-butanediol, then separating the regioisomeric products by multiple preparative thin layer chromatography runs.

EXAMPLE 490

2-(3-Chlorophenyl)-4-(4-hydroxy-3-methyl-1-butoxy)-5-[4-(methylsulfonyl)phenyl]-3(2H)-pyridazinone The title compound may be prepared according to the sequence of reactions described in Example 471, substituting 3-chlorophenylhydrazine for 3,4-difluorophenylhydrazine and substituting 2-methyl-1,4-butanediol for 3-methyl-1,3-butanediol, then separating the regioisomeric products by multiple preparative thin layer chromatography runs.

EXAMPLE 491

2-(3,4-Difluorophenyl)-4-(4-hydroxy-3-methyl-1-butoxy)-5-[4-(aminosulfonyl)phenyl]-3(2H)-pyridazinone The title compound may be prepared according to the method of Example 459, substituting 2-(3,4-difluorophenyl)-4-(4-hydroxy-3-methyl-1-butoxy)-5-[4-(methylsulfonyl)phenyl]-3(2H)-pyridazinone (Example 488) for 2-(3,4-difluorophenyl)-4-(2-hydroxy-2-methyl-1-propoxy)-5-[4-(methylsulfonyl)phenyl]-3(2H)-pyridazinone.

EXAMPLE 492

2-(3-Chloro-4-fluorophenyl)-4-(4-hydroxy-3-methyl-1-butoxy)-5-[4-(aminosulfonyl)phenyl]-3(2H)-pyridazinone The title compound may be prepared according to the method of Example 459, substituting 2-(3-chloro-4-fluorophenyl)-4-(4-hydroxy-3-methyl-1-butoxy)-5-[4-(methylsulfonyl)phenyl]-3(2H)-pyridazinone (Example 489) for 2-(3,4-difluorophenyl)-4-(2-hydroxy-2-methyl-1-propoxy)-5-[4-(methylsulfonyl)phenyl]-3(2H)-pyridazinone.

EXAMPLE 493

2-(3-Chlorophenyl)-4-(4-hydroxy-3-methyl-1-butoxy)-5-[4-(aminosulfonyl)phenyl]-3(2H)-pyridazinone The title compound may be prepared according to the method of Example 459, substituting 2-(3-chlorophenyl)-4-(4-hydroxy-3-methyl-1-butoxy)-5-[4-(methylsulfonyl)phenyl]-3(2H)-pyridazinone (Example 490) for 2-(3,4-difluorophenyl)-4-(2-hydroxy-2-methyl-1-propoxy)-5-[4-(methylsulfonyl)phenyl]-3(2H)-pyridazinone.

EXAMPLE 494

(S)-2-(4-Fluorophenyl)-4-(3-hydroxy-2-methyl-1-propoxy)-5-[4-(aminosulfonyl)phenyl]-3(2H)-pyridazinone The title compound may be prepared according to the method of Example 464, substituting (S)-2-(4-fluorophenyl)-4-(3-t-butoxy-2-methyl-1-propoxy)-5-[4-(methylsulfonyl)phenyl]-3(2H)-pyridazinone for (S)-2-(3,4-difluorophenyl)-4-(3-t-butoxy-2-methyl-1-propoxy)-5-[4-(methylsulfonyl)phenyl]-3(2H)-pyridazinone.

EXAMPLE 495

(R)-2-(4-Fluorophenyl)-4-(3-hydroxy-2-methyl-1-propoxy)-5-[4-(aminosulfonyl)phenyl]-3(2H)-pyridazinone The title compound may be prepared according to the method of Example 465, substituting (R)-2-(4-fluorophenyl)-4-(3-t-butoxy-2-methyl-1-propoxy)-5-[4-(methylsulfonyl)phenyl]-3(2H)-pyridazinone for (R)-2-(3,4-difluorophenyl)-4-(3-t-butoxy-2-methyl-1-propoxy)-5-[4-(methylsulfonyl)phenyl]-3(2H)-pyridazinone.

EXAMPLE 496

(S)-2-(3-Chloro-4-fluorophenyl)-4-(3-hydroxy-2-methyl-1-propoxy)-5-[4-(methylsulfonyl)phenyl]-3(2H)-pyridazinone The title compound may be prepared according to the method of Example 462, substituting 2-(3-chloro-4-fluorophenyl)-4-hydroxy-5-[4-(methylsulfonyl)phenyl]-3(2H)-pyridazinone in place of 2-(3,4-difluorophenyl)-4-hydroxy-5-[4-(methylsulfonyl)phenyl-3(2H)-pyridazinone.

EXAMPLE 497

(S)-2-(3-Chloro-4-fluorophenyl)-4-(3-hydroxy-2-methyl-1-propoxy)-5-[4-(aminosulfonyl)phenyl]-3(2H)-pyridazinone The title compound can be prepared according to the method of Example 464, substituting (S)-2-(3-chloro-4-fluorophenyl)-4-(3-t-butoxy-2-methyl-1-propoxy)-5-[4-(methylsulfonyl)phenyl]-3(2H)-pyridazinone in place of (S)-2-(3,4-difluorophenyl)-4-(3-t-butoxy-2-methyl-1-propoxy)-5-[4-(methylsulfonyl)phenyl]-3(2H)-pyridazinone.

EXAMPLE 498

(R)-2-(3-Chloro-4-fluorophenyl)-4-(3-hydroxy-2-methyl-1-propoxy)-5-[4-(methylsulfonyl)phenyl]-3(2H)-pyridazinone The title compound may be prepared according to the method of Example 463, substituting 2-(3-chloro-4-fluorophenyl)-4-hydroxy-5-[4-(methylsulfonyl)phenyl]-3(2H)-pyridazinone in place of 2-(3,4-difluorophenyl)-4-hydroxy-5-[4-(methylsulfonyl)phenyl-3(2H)-pyridazinone.

EXAMPLE 499

(R-2-(3-Chloro-4-fluorophenyl)-4-(3-hydroxy-2-methyl-1-propoxy)-5-[4-(aminosulfonyl)phenyl]-3(2H)-pyridazinone The title compound may be prepared according to the method of Example 464, substituting (R)-2-(3-chloro-4-fluorophenyl)-4-(3-t-butoxy-2-methyl-1-propoxy)-5-[4-(methylsulfonyl)phenyl]-3(2H)-pyridazinone in place of (S)-2-(3,4-difluorophenyl)-4-(3-t-butoxy-2-methyl-1-propoxy)-5-[4-(methylsulfonyl)phenyl]-3(2H)-pyridazinone.

EXAMPLE 500

(S)-2-(3-Chlorophenyl)-4-(3-hydroxy-2-methyl-1-propoxy)-5-[4-(methylsulfonyl)phenyl]-3(2H)-pyridazinone The title compound may be prepared according to the method of Example 462, substituting 2-(3-chlorophenyl)-4-hydroxy-5-[4-(methylsulfonyl)phenyl]-3(2H)-pyridazinone in place of 2-(3,4-difluorophenyl)-4-hydroxy-5-[4-(methylsulfonyl)phenyl-3(2H)-pyridazinone.

EXAMPLE 501

(S)-2-(3-Chlorophenyl)-4-(3-hydroxy-2-methyl-1-propoxy)-5-[4-(aminosulfonyl)phenyl]-3(2H)-pyridazinone The title compound may be prepared according to the method of Example 464, substituting (S)-2-(3-chlorophenyl)-4-(3-t-butoxy-2-methyl-1-propoxy)-5-[4-(methylsulfonyl)phenyl]-3(2H)-pyridazinone in place of (S)-2-(3,4-difluorophenyl)-4-(3-t-butoxy-2-methyl-1-propoxy)-5-[4-(methylsulfonyl)phenyl]-3(2H)-pyridazinone.

EXAMPLE 502

(R)-2-(3-Chlorophenyl)-4-(3-hydroxy-2-methyl-1-propoxy)-5-[4-(methylsulfonyl)phenyl]-3(2H)-pyridazinone The title compound can be prepared according to the method of Example 463, substituting 2-(3-chlorophenyl)-4-hydroxy-5-[4-(methylsulfonyl)phenyl]-3(2H)-pyridazinone in place of 2-(3,4-difluorophenyl)-4-hydroxy-5-[4-(methylsulfonyl)phenyl]-3(2H)-pyridazinone.

EXAMPLE 503

(R)-2-(3-Chlorophenyl)-4-(3-hydroxy-2-methyl-1-propoxy)-5-[4-(aminosulfonyl)phenyl]-3(2H)-pyndazinone The title compound can be prepared according to the method of Example 464, substituting (R)-2-(3-chlorophenyl)-4-(3-t-butoxy-2-methyl-1-propoxy)-5-[4-(methylsulfonyl)phenyl]-3(2H)-pyridazinone in place of (S)-2-(3,4-difluorophenyl)-4-(3-t-butoxy-2-methyl-1-propoxy)-5-[4-(methylsulfonyl)phenyl]-3(2H)-pyridazinone.

EXAMPLE 504

(S)-2-(2,2,2-Trifluoroethyl)-4-(3-hydroxy-2-methyl-1-propoxy)-5-[4-(methylsulfonyl)phenyl]-3(2H)-pyridazinone The title compound may be prepared according to the method of Example 462, substituting 2-(2,2,2-trifluoroethyl)-4-hydroxy-5-[4-(methylsulfonyl)phenyl]-3(2H)-pyridazinone in place of 2-(3,4-difluorophenyl)-4-hydroxy-5-[4-(methylsulfonyl)phenyl-3(2H)-pyridazinone.

EXAMPLE 505

(S)-2-(2,2,2-Trifluoroethyl)-4-(3-hydroxy-2-methyl-1-propoxy)-5-[4-(aminosulfonyl)phenyl]-3(2H)-peridazinone The title compound may be prepared according to the method of Example 484, substituting (R)-3-t-butoxy-2-methyl-1-propanol (Example 462A) in place of 2-methyl-1,2-propanediol. After Suzuki coupling with 4-[2-(tetrahydropyranyl)thio]phenylboronic acid, the resulting intermediate is treated with NCS and NH$_4$OH as in Example 484. This sulfonamide product is then treated with TFA (as in Example 462C) to cleave the t-butyl ether and provide the title compound.

EXAMPLE 506

(R)-2-(2,2,2-Trifluoroethyl)-4-(3-hydroxy-2-methyl-1-propoxy)-5-[4-(methylsulfonyl)phenyl]-3(2H)-pyridazinone The title compound may be prepared according to the method of Example 463, substituting 2-(2,2,2-trifluoroethyl)-4-hydroxy-5-[4-(methylsulfonyl)phenyl]-3(2H)-pyridazinone in place of 2-(3,4-difluorophenyl)-4-hydroxy-5-[4-(methylsulfonyl)phenyl-3(2H)-pyridazinone.

EXAMPLE 507

(R)-2-(2,2,2-Trifluoroethyl)-4-(3-hydroxy-2-methyl-1-propoxy)-5-[4-(aminosulfonyl)phenyl]-3(2H)-pyridazinone The title compound may be prepared according to the method of Example 505, substituting (S)-3-t-butoxy-2-methyl-1-propanol in place of (R)-3-t-butoxy-2-methyl-1-propanol.

EXAMPLE 508

2-(4-Fluorophenyl)-4-(3-hydroxy-2,2-dimethyl-1-propoxy)-5-[4-(methylsulfonyl)phenyl]-3(2H)-pyridazinone The title compound may be prepared according to the sequence of reactions described in Example 471, substituting 4-fluorophenylhydrazine in place of 3,4-difluorophenylhydrazine and substituting neopentyl glycol in place of 3-methyl-1,3-butanediol.

EXAMPLE 509

2-(4-Fluorophenyl)-4-(3-hydroxy-2,2-dimethyl-1-propoxy)-5-[4-(aminosulfonyl)phenyl]-3(2H)-pyridazinone The title compound may be prepared according to the method of Example 459, substituting 2-(4-fluorophenyl)-4-(3-hydroxy-2,2-dimethyl-1-propoxy)-5-[4-(methylsulfonyl)phenyl]-3(2H)-pyridazinone for 2-(3,4-difluorophenyl)-4-(2-hydroxy-2-methyl-1-propoxy)-5-[4-(methylsulfonyl)phenyl]-3(2H)-pyridazinone.

EXAMPLE 510

2-(3,4-Difluorophenyl)-4-(3-hydroxy-2,2-dimethyl-1-propoxy)-5-[4-(methylsulfonyl)phenyl]-3(2H)-pyridazinone The title compound was prepared according to the sequence of reactions described in Example 471, substituting neopentyl glycol in place of 3-methyl-1,3-butanediol (yield: 300 mg, 71%). mp 161–162° C.; $^1$H NMR (300 MHz, DMSO-$d_6$) δ 0.72 (s, 6H), 3.05 (d, J=6 Hz, 2H), 3.30 (s, 3H), 4.19 (s, 2H), 4.54 (t, J=6 Hz, 1H), 7.52 (m, 1H), 7.62 (dd, J=9 Hz, J=9 Hz, 1H), 7.82 (ddd, J=9 Hz, J=9 Hz, J=3 Hz, 1H), 7.92 (d, J=9 Hz, 1H), 8.08 (d, J=9 Hz, 2H), 8.21 (s, 1H); MS (DCI/NH$_3$) m/z 465 (M+H)$^+$; Anal. calcd. for $C_{22}H_{22}F_2N_2O_5S$: C, 56.88; H, 4.77; N, 6.03. Found: C, 56.84; H, 4.83; N, 5.99.

EXAMPLE 511

2-(3,4-Difluorophenyl)-4-(3-hydroxy-2,2-dimethyl-1-propoxy)-5-[4-(aminosulfonyl)-phenyl]-3(2H)-pyridazinone The title compound may be prepared according to the method of Example 459, substituting 2-(3,4-difluorophenyl)-4-(3-hydroxy-2,2-dimethyl-1-propoxy)-5-[4-(methylsulfonyl)phenyl]-3(2H)-pyridazinone for 2-(3,4-difluorophenyl)-4-(2-hydroxy-2-methyl-1-propoxy)-5-[4-(methylsulfonyl)phenyl]-3(2H)-pyridazinone.

EXAMPLE 512

2-(3-Chloro4-fluorophenyl)-4-(3-hydroxy-2,2-dimethyl-1-propoxy)-5-[4-(methylsulfonyl)phenyl]-3(2H)-pyridazinone The title compound may be prepared according to the sequence of reactions described in Example 471, substituting 3-chloro-4-fluorophenylhydrazine in place of 3,4-difluorophenylhydrazine and substituting neopentyl glycol in place of 3-methyl-1,3-butanediol.

EXAMPLE 513

2-(3-Chloro-4-fluorophenyl)-4-(3-hydroxy-2,2-dimethyl-1-propoxy)-5-[4-(amino-sulfonyl)phenyl]-3(2H)-pyridazinone The title compound may be prepared according to the method of Example 459, substituting 2-(3-chloro-4-fluorophenyl)-4-(3-hydroxy-2,2-dimethyl-1-propoxy)-5-[4-(methylsulfonyl)phenyl]-3(2H)-pyridazinone for 2-(3,4-difluorophenyl)-4-(2-hydroxy-2-methyl-1-propoxy)-5-[4-(methylsulfonyl)phenyl]-3(2H)-pyridazinone.

EXAMPLE 514

2-(3-Chlorophenyl)-4(3-hydroxy-2,2-dimethyl-1-propoxy)-5-[4-(methylsulfonyl)phenyl]-3(2H)-pyridazinone The title compound may be prepared according to the sequence of reactions described in Example 471, substituting 3-chlorophenylhydrazine in place of 3,4-difluorophenylhydrazine and substituting neopentyl glycol in place of 3-methyl-1,3-butanediol.

EXAMPLE 515

2-(3-Chlorophenyl)-4-(3-hydroxy-2,2-dimethyl-1-propoxy)-5-[4-(aminosulfonyl)phenyl]-3(2H)-pyridazinone The title compound may be prepared according to the method of Example 459, substituting 2-(3-chlorophenyl)-4-(3-hydroxy-2,2-dimethyl-1-propoxy)-5-[4-(methyl-sulfonyl)phenyl]-3(2H)-pyridazinone for 2-(3,4-difluorophenyl)-4-(2-hydroxy-2-methyl-1-propoxy)-5-[4-(methylsulfonyl)phenyl]-3(2H)-pyridazinone.

EXAMPLE 516

N-[[4-[2-(3,4-Difluorophenyl)-4-(2-methyl-1-propoxy)-2H-pyridazin-3-on-5-yl]phenyl]sulfonyl]acetamide A mixture of 2-(3,4-difluorophenyl)-4-(2-methyl-1-propoxy)-5-[4-(aminosulfonyl)phenyl]-3(2H)-pyridazinone (Example 403, 1 equivalent), acetic anhydride (3 equivalents), 4-(dimethylamino)pyridine (0.3 equivalents), and triethylamine (1.2 equivalents) is stirred at room temperature for 16 hours. The reaction mixture is partitioned between ethyl acetate and water. The organic layer is washed with brine then dried over MgSO$_4$ and filtered. The filtrate is concentrated in vacuo to give the title compound.

EXAMPLE 517

N-[[4-[2-(3,4-Difluorophenyl)-4-(2-methyl-1-propoxy)-2H-pyridazin-3-on-5-yl]phenyl]-sulfonyl] acetamide, sodium salt To a suspension of N-[[4-[2-(3,4-Difluorophenyl)-4-(2-methyl-1-propoxy)-2H-pyridazin-3-on-5-yl]phenyl]sulfonyl]acetamide (Example 516, 1 equivalent) in absolute ethanol is added a solution of sodium hydroxide (1 equivalent) in absolute ethanol. The mixture is stirred at room temperature for 10 minutes and concentrated in vacuo. The residue is dried at high vacuum to provide the title compound.

EXAMPLE 518

N-[[4-[2-(4-Fluorophenyl)-4-(3-hydroxy-3-methyl-1-butoxy)-2H-pyridazin-3-on-5-yl]phenyl]sulfonyl] acetamide A mixture of 2-(4-fluorophenyl)-4-(3-hydroxy-3-methyl-1-butoxy)-5-[4-(aminosulfonyl)phenyl]-3(2H)-pyridazinone (Example 470, 1 equivalent), acetic anhydride (3 equivalents), 4-(dimethylamino)pyridine (0.3 equivalents), and triethylamine (1.2 equivalents) is stirred at room temperature for 16 hours. The reaction mixture is partitioned between ethyl acetate and water. The organic layer is washed with brine then dried over MgSO$_4$ and filtered. The filtrate is concentrated in vacuo to give the title compound.

EXAMPLE 519

N-[[4-[2-(4-Fluorophenyl)-4-(3-hydroxy-3-methyl-1-butoxy)-2H-pyridazin-3-on-5-yl]phenyl]sulfonyl] acetamide, sodium salt To a suspension of N-[[4-[2-(4-Fluorophenyl)-4-(3-hydroxy-3-methyl-1-butoxy)-2H-pyridazin-3-on-5-yl]phenyl] sulfonyl]acetamide (Example 518, 1 equivalent) in absolute ethanol is added a solution of sodium hydroxide (1 equivalent) in absolute ethanol. The mixture is stirred at room temperature for 10 minutes and concentrated in vacuo. The residue is dried at high vacuum to provide the title compound.

EXAMPLE 520

N-[[4-[2-(3,4-Difluorophenyl)-4-(2-hydroxy-2-methyl-1-propoxy)-2H-pyridazin-3-on-5-yl]phenyl] sulfonyl]acetamide A mixture of 2-(3,4-difluorophenyl)-4-(2-hydroxy-2-methyl-1-propoxy)-5-[4-(aminosulfonyl)phenyl]-3(2H)-pyridazinone (Example 459, 1 equivalent), acetic anhydride (3 equivalents), 4-(dimethylamino)pyridine (0.3 equivalents), and triethylamine (1.2 equivalents) is stirred at room temperature for 16 hours. The reaction mixture is partitioned between ethyl acetate and water. The organic layer is washed with brine then dried over MgSO$_4$ and filtered. The filtrate is concentrated in vacuo to give the title compound.

EXAMPLE 521

N-[[4-[2-(3,4-Difluorophenyl)-4-(2-hydroxy-2-methyl-1-propoxy)-2H-pyridazin-3-on-5yl]phenyl]sulfonyl]acetamide, sodium salt To a suspension of N-[[4-[2-(3,4-difluorophenyl)-4-(2-hydroxy-2-methyl-1-propoxy)-2H-pyridazin-3-on-5-yl]phenyl]sulfonyl]acetamide (EXAMPLE 520, 1 equivalent) in absolute ethanol is added a solution of sodium hydroxide (1 equivalent) in absolute ethanol. The mixture is stirred at room temperature for 10 minutes and concentrated in vacuo. The residue is dried at high vacuum to provide the title compound.

EXAMPLE 522

N-[[4-[2-(3-Chloro-4-fluorophenyl)-4-(2-hydroxy-2-methyl-1-propoxy)-2H-pyridazin-3-on-5-yl]phenyl] sulfonyl]acetamide A mixture of 2-(3-chloro-4-fluorophenyl)-4-(2-hydroxy-2-methyl-1-propoxy)-5-[4-(aminosulfonyl)phenyl]-3(2H)-pyridazinone (Example 480, 1 equivalent), acetic anhydride (3 equivalents), 4-(dimethylamino)pyridine (0.3 equivalents), and triethylamine (1.2 equivalents) is stirred at room temperature for 16 hours. The reaction mixture is partitioned between ethyl acetate and water. The organic layer is washed with brine then dried over MgSO$_4$ and filtered. The filtrate is concentrated in vacuo to give the title compound.

EXAMPLE 523

N-[[4-[2-(3-Chloro-4-fluorophenyl)-4-(2-hydroxy-2-methyl-1-propoxy)-2H-pyridazin-3-on-5-yl]phenyl] sulfonyl]acetamide, sodium salt To a suspension of N-[[4-[2-(3-chloro-4-fluorophenyl)-4-(2-hydroxy-2-methyl-1-propoxy)-2H-pyridazin-3-on-5-yl] phenyl]sulfonyl]acetamide (Example 522, 1 equivalent) in absolute ethanol is added a solution of sodium hydroxide (1 equivalent) in absolute ethanol. The mixture is stirred at room temperature for 10 minutes and concentrated in vacuo. The residue is dried at high vacuum to provide the title compound.

EXAMPLE 524

N-[[4-[2-(3-Chlorophenyl)-4-(2-hydroxy-2-methyl-1-propoxy)-2H-pyridazin-3-on-5-yl]phenyl]sulfonyl] acetamide A mixture of 2-(3-chlorophenyl)-4-(2-hydroxy-2-methyl-1-propoxy)-5-[4-(amino-sulfonyl)phenyl]-3(2H)-pyridazinone (Example 482, 1 equivalent), acetic anhydride (3 equivalents), 4-(dimethylamino)pyridine (0.3 equivalents), and triethylamine (1.2 equivalents) is stirred at room temperature for 16 hours. The reaction mixture is partitioned between ethyl acetate and water. The organic layer is washed

EXAMPLE 525

N-[[4-[2-(3-Chlorophenyl)-4-(2-hydroxy-2-methyl-1-propoxy)-2H-pyridazin-3-on-5-yl]phenyl]sulfonyl]acetamide, sodium salt To a suspension of N-[[4-[2-(3-chlorophenyl)-4-(2-hydroxy-2-methyl-1-propoxy)-2H-pyridazin-3-on-5-yl]phenyl]sulfonyl]acetamide (Example 525, 1 equivalent) in absolute ethanol is added a solution of sodium hydroxide (1 equivalent) in absolute ethanol. The mixture is stirred at room temperature for 10 minutes and concentrated in vacuo. The residue is dried at high vacuum to provide the title compound.

EXAMPLE 526

N-[[4-[2-(2,2,2-Trifluoroethyl)-4-(2-hydroxy-2-methyl-1-propoxy)-2H-pyridazin-3-on-5-yl]phenyl]sulfonyl]acetamide A mixture of 2-(2,2,2-trifluoroethyl)-4-(2-hydroxy-2-methyl-1-propoxy)-5-[4-(aminosulfonyl)phenyl]-3(2H)-pyridazinone (Example 484, 1 equivalent), acetic anhydride (3 equivalents), 4-(dimethylamino)pyridine (0.3 equivalents), and triethylamine (1.2 equivalents) is stirred at room temperature for 16 hours. The reaction mixture is partitioned between ethyl acetate and water. The organic layer is washed with brine then dried over MgSO$_4$ and filtered. The filtrate is concentrated in vacuo to give the title compound.

EXAMPLE 527

N-[[4-[2-(2,2,2-Trifluoroethyl)-4-(2-hydroxy-2-methyl-1-propoxy)-2H-pyridazin-3-on-5-yl]phenyl]sulfonyl]acetamide, sodium salt To a suspension of N-[[4-[2-(2,2,2-trifluoroethyl)-4-(2-hydroxy-2-methyl-1-propoxy)-2H-pyridazin-3-on-5-yl]phenyl]sulfonyl]acetamide (Example 526, 1 equivalent) in absolute ethanol is added a solution of sodium hydroxide (1 equivalent) in absolute ethanol. The mixture is stirred at room temperature for 10 minutes and concentrated in vacuo. The residue is dried at high vacuum to provide the title compound.

EXAMPLE 528

N-[[4-[2-(2,2,2-Trifluoroethyl)-4-(3-hydroxy-2,2-dimethyl-1-propoxy)-2H-pyridazin-3-on-5-yl]phenyl]sulfonyl]acetamide A mixture of 2-(2,2,2-trifluoroethyl)-4-(3-hydroxy-2,2-dimethyl-1-propoxy)-5-[4-(aminosulfonyl)phenyl]-3(2H)-pyridazinone (Example 486, 1 equivalent), acetic anhydride (3 equivalents), 4-(dimethylamino)pyridine (0.3 equivalents), and triethylamine (1.2 equivalents) is stirred at room temperature for 16 hours. The reaction mixture is partitioned between ethyl acetate and water. The organic layer is washed with brine then dried over MgSO$_4$ and filtered. The filtrate is concentrated in vacuo to give the title compound.

EXAMPLE 529

N-[[4-[2-(2,2,2-Trifluoroethyl)-4-(3-hydroxy-2,2-dimethyl-1-propoxy)-2H-pyridazin-3-on-5-yl]phenyl]sulfonyl]acetamide, sodium salt To a suspension of N-[[4-[2-(2,2,2-trifluoroethyl)-4-(3-hydroxy-2,2-dimethyl-1-propoxy)-2H-pyridazin-3-on-5-yl]phenyl]sulfonyl]acetamide (Example 528, 1 equivalent) in absolute ethanol is added a solution of sodium hydroxide (1 equivalent) in absolute ethanol. The mixture is stirred at room temperature for 10 minutes and concentrated in vacuo. The residue is dried at high vacuum to provide the title compound.

EXAMPLE 530

2-(2,2,2-Trifluoroethyl)-4-(3-hydroxy-3-methyl-1-butoxy)-5-[4-(methylsulfonyl)phenyl]-3(2H)-pyridazinone The title compound was prepared according to the sequence of reactions described in Example 471, substituting 2,2,2-trifluoroethylhydrazine in place of 3,4-difluorophenylhydrazine. $^1$H NMR (300 MHz, CDCl$_3$) δ 1.25 (s, 6H), 1.88 (t, 2H, J=9 Hz), 2.35 (br s, 1H), 3.15 (s, 3H), 4.55 (t, 2H, J=7.5 Hz), 4.85 (q, 2H, J=9 Hz), 7.75 (d, 2H J=9 Hz), 7.65 (s, 1H), 8.05 (d, 2H J=9 Hz); MS (DCI/NH$_3$) m/z 435 (M+H)$^+$; Analysis calculated for C$_{18}$H$_{21}$F$_3$N$_2$O$_5$S: C, 49.77; H, 4.87; N, 6.45. Found: C, 49.71; H, 4.90; N, 6.45.

EXAMPLE 531

2-(2,2,2-Trifluoroethyl)-4-(3-hydroxy-3-methyl-1-butoxy)-5-[4-(aminosulfonyl)phenyl]-3(2H)-pyridazinone The title compound was prepared according to the method of Example 484, substituting 3-methyl-1,3-butanediol in place of 2-methyl-1,2-propanediol. $^1$H NMR (300 MHz, CDCl$_3$) δ 1.85 (t, 2H, J=6 Hz), 2.78 (s, 6H), 4.55 (t, 2H, J=6 Hz), 4.85 (q, 2H, J=9 Hz), 5.3 (s, 2H), 7.68 (d, 2H J=9 Hz), 7.85 (s, 1H), 8.05 (d, 2H J=9 Hz), 8.45 (br s, 1H); MS (DCI/NH$_3$) m/z 436 (M+H)$^+$; Analysis calculated for C$_{17}$H$_{20}$F$_3$N$_3$O$_5$S: C, 46.89; H, 4.62; N, 9.65. Found: C, 47.18; H, 4.93; N, 9.86.

EXAMPLE 532

2-(3,4-Dichlorophenyl)-4-(3-hydroxy-3-methyl-1-butoxy)-5-[4-(methylsulfonyl)phenyl]-3(2H)-pyridazinone The title compound was prepared according to the sequence of reactions described in Example 471, substituting 3,4-dichlorophenylhydrazine in place of 3,4-difluorophenylhydrazine. mp 118–120° C.; $^1$H NMR (300 MHz, CDCl$_3$) δ 1.25 (s, 6H), 1.92 (t, J=6 Hz, 2H), 3.13 (s, 3H), 4.07 (t, J=6 Hz, 2H), 7.58 (d, J=9 Hz, 1H), 7.59 (dd, J=9 Hz, J=2 Hz, 1H), 7.80 (d, J=9 Hz, 2H), 7.87 (d, J=2 Hz, 1H), 7.84 (s, 1H), 8.19 (d, J=9 Hz, 2H); MS (DCI/NH$_3$) m/z 497 (M+H)$^+$. Anal. calcd. for C$_{22}$H$_{22}$Cl$_2$N$_2$O$_5$S: C, 53.12; H, 4.45; N, 5.63. Found: C, 52.80; H, 4.53; N, 5.35.

EXAMPLE 533

2-[(3-Trifluoromethyl)phenyl]-4-(2-hydroxy-2-methyl-1-propoxy)-5-[4-(methylsulfonyl)phenyl]-3(2H)-pyridazinone The title compound was prepared according to the sequence of reactions described in Example 471, substituting 3-(trifluoromethyl)phenylhydrazine in place of 3,4-difluorophenylhydrazine and substituting 2-methyl-1,2-propanediol (prepared by the LAH reduction of methyl 2-hydroxyisobutyrate) in place of 3-methyl-1,3-butanediol (yield: 200 mg, 75%). mp 143–144° C; $^1$H NMR (300 MHz, CDCl$_3$) δ 1.20 (s, 6H), 3.13 (s, 3H), 4.11 (s, 2H), 7.64 (m, 2H), 7.84 (d, J=9 Hz, 2H), 7.90 (d, J=9 Hz, 1H), 7.97 (d, J=9 Hz, 1H), 7.98 (s, 1H), 8.13 (d, J=9 Hz, 2H); MS (DCI/NH$_3$) m/z 483 (M+H)$^+$; Anal. calcd. for C$_{22}$H$_{21}$F$_3$N$_2$O$_5$S.0.5C$_4$H$_{10}$O$_2$: C, 54.75; H, 4.79; N, 5.32. found: C, 55.15; H, 4.77; N, 5.09.

EXAMPLE 534

2-(3,4-Dichlorophenyl)-4-(2-hydroxy-2-methyl-1-propoxy)-5-[4-(methylsulfonyl)phenyl]-3(2H)-pyridazinone The title compound was prepared according to the sequence of reactions described in Example 471, substituting 3,4-dichlorophenylhydrazine in place of 3,4-difluorophenylhydrazine and substituting 2-methyl-1,2-propanediol (prepared by the LAH reduction of methyl 2-hydroxyisobutyrate) in place of 3-methyl-1,3-butanediol (yield: 1.7 g, 75%). mp 108–110° C.; $^1$H NMR (300 MHz, DMSO-d$_6$) δ 0.96 (s, 6H), 3.38 (s, 3H), 4.20 (s, 2H), 4.52 (s, 1H), 7.68 (dd, J=9 Hz, J=3 Hz, 1H), 7.83 (d, J=9 Hz, 1H), 7.78 (d, J=9 Hz, 2H), 7.79 (d, J=3 Hz, 1H), 8.04 (d, J=9 Hz, 2H), 8.22 (s, 1H); MS (DCI/NH$_3$) m/z 483 (M+H)$^+$; Anal. calcd. for C$_{21}$H$_{20}$Cl$_2$N$_2$O$_5$S: C, 52.18; H, 4.17; N, 5.79. Found: C, 52.41; H, 4.22; N, 5.53.

EXAMPLE 535

(R,S)-2-(4-Fluorophenyl)-4-(3-hydroxy-1-butoxy)-5-[4-(methylsulfonyl)phenyl]-3(2H)-pyridazinone The title compound was prepared by reacting the product from Example 468, 2-(4-fluorophenyl)-4-(3-oxo-1-butoxy)-5-[4-(methylsulfonyl)phenyl]-3(2H)-pyridazinone (20 mg, 0.05 mmol) in methanol (5 mL) at 0° C. with sodium borohydridre (4 mg, 0.1 mmol). The reaction mixture was allowed to warm to room temperature, then volatile components were removed under reduced pressure. The residue was treated with water and 10% aqueous citric acid solution was added to bring the pH to 7. The resulting precipitate was collected by filtration and dried to provide the title compound as an off-white solid (11 mg, 50.9%). mp 63–66° C.; $^1$H NMR (300 MHz, CDCl$_3$) δ 1.21 (d, J=6 Hz, 3H), 1.60–1.73 (m, 1H), 1.84–1.96 (m, 1H), 3.14(s, 3H), 4.01–4.14 (m, 1H), 4.20–4.28 (m, 1H), 4.64 (dt, J=3 Hz, J=9 Hz, 1H), 7.20 (t, J=9 Hz, 2H), 7.43–7.55 (m, 2H), 7.81 (d, J=9 Hz, 2H), 7.96 (s, 1H), 8.10 (d, J=9 Hz, 2H); MS (DCI/NH$_3$) m/z 433 (M+H)$^+$.

EXAMPLE 536

2-(3,4-Difluorophenyl)-4-(1-butoxy)-5-[4-(methylsulfonyl)phenyl]-3(2H)-pyridazinone

Example 536A 2-(3,4-Difluorophenyl)-4-(1-butoxy)-5-chloro-3(2H)-pyridazinone To a stirred, room temperature solution of n-butanol (0.81 g, 10.93 mmol, 1.1 equiv.) in THF (20 mL) was slowly added 1.0 M sodium bis(trimethylsilyl)amide in THF (12 mL, 12 mmol, 1.2 equiv.). The reaction mixture was stirred for 0.5 hours, then it was transferred to a solution of 2-(3,4-difluorophenyl)-4,5-dichloro-3(2H)-pyridazinone (2.88 g, 10.4 mmol, 1.0 equiv.) in THF (80 mL). The resulting reaction mixture was stirred for 0.5 hours at room temperature to provide the title compound (2.5 g, 79.4%).

Example 536B 2-(3,4-Difluorophenyl)-4-(1-butoxy)-5-[4-(methylthio)phenyl]-3(2H)-pyridazinone A slurry of palladium(II) acetate (9.0 mg, 0.04 mmol), triphenylphosphine (21.0 mg, 0.08 mmol) and isopropanol (1 mL) was stirred at room temperature for 10 minutes. To this mixture was added 2-(3,4-Difluorophenyl)-4-(1-butoxy)-5-chloro-3(2H)-pyridazinone (Example 536A, 0.63 g, 2 mmol), 4-(methylthio)benzeneboronic acid (0.403 mg, 2.4 mmol) and isopropanol (4 mL). A solution of K$_3$PO$_4$ (0.66 g, 3 mmol) in water (1 mL) was also added and the resulting reaction mixture was deoxygenated by bubbling nitrogen through it for 2 minutes. The reaction mixture was then stirred under a nitrogen atmosphere for 15 hours at 70° C. The reaction mixture was then cooled to room temperature and water (15 mL) was added to provide a precipitate. The precipitate was collected by filtration and rinsed with water then hexane to give after drying the title compound (0.77 g, 95%).

Example 536C 2-(3,4-Difluorophenyl)-4(1-butoxy)-5-[4-(methylsulfonyl)phenyl]-3(2H)-pyridazinone To a solution of 2-(3,4-difluorophenyl)-4-(1-butoxy)-5-[4-(methylthio)phenyl]-3(2H)-pyridazinone (Example 536B, 0.6 g, 1.5 mmol) in acetone (10 mL) at −20° C. was slowly added over 5 minutes a 32% solution of peracetic acid in acetic acid (3.75 mmol). The reaction mixture was allowed to warm to room temperature at which point water (30 mL) was added. Stirring was continued for 0.5 hours, then the precipitate was collected by filtration and washed with water to provide the title compound (0.61 g, 94%). mp 129–132° C.; $^1$H NMR (300 MHz, CDCl$_3$) δ 0.88 (t, J=6 Hz, 3H), 1.20–1.36 (m, 2H), 1.54–1.68 (m, 2H), 3.14 (s, 3H), 4.52 (t, J=6 Hz, 2H), 7.25–7.34 (m, 1H), 7.44–7.50 (m, 1H), 7.55–7.62 (m, 2H), 7.77–7.82 (m, 2H), 7.92 (s, 1H), 8.05–8.10 (m, 2H); MS (DCI/NH$_3$) m/z 435 (M+H)$^+$; Anal. calcd. for C$_{21}$H$_{20}$F$_2$N$_2$O$_4$S: C, 58.06; H, 4.64; N, 6.44. Found: C, 57.82; H, 4.53; N, 6.31.

EXAMPLE 537

2-(3-Chloro-4-fluorophenyl)-4-(2-methyl-1-propoxy)-5-[4-(methylsulfonyl)phenyl]-3(2H)-pyridazinone The title compound was prepared according to the method of Example 536 substituting 2-methyl-1-propanol in place of n-butanol and substituting 2-(3-chloro-4-fluorophenyl)-4,5-dibromo-3(2H)-pyridazinone for 2-(3,4difluorophenyl)-4,5-dichloro-3(2H)-pyridazinone in Example 536A. The resulting intermediate was subjected to the conditions in Example 536B, substituting the catalyst $PdCl_2(PPh_3)_2$ in place of the palladium(II) acetate-triphenylphosphine slurry. The resulting intermediate was then oxidized by the method of Example 536C to provide the title compound (0.58 g, 92%). mp 116–120° C.; $^1$H NMR (300 MHz, $CDCl_3$) δ 0.86 (d, J=6 Hz, 6H), 1.85–1.94 (m, 1H), 3.14 (s, 3H), 4.32 (d, J=6 Hz, 2H), 7.24–7.30 (m, 1H), 7.56–7.62 (m, 1H), 7.77–7.83 (m, 3H), 7.86 (m, 1H), 7.92 (s, 1H), 8.05–8.10 (m, 2H); MS (DCI/$NH_3$) m/z 451 (M+H)$^+$; Anal. calcd. for $C_{21}H_{20}ClFN_2O_4S$: C, 55.94; H, 4.47; N, 6.21. Found: C, 55.81; H, 4.38; N, 6.18.

EXAMPLE 538

2-(3-Chloro-4-fluorophenyl)-4-(3-methyl-1-butoxy)-5-[4-(methylsulfonyl)phenyl]-3(2H)-pyridazinone The title compound was prepared according to the method of Example 536 substituting 3-methyl-1-butanol in place of n-butanol to provide the title compound (0.62 g, 92%). mp 148–152° C.; $^1$H NMR (300 MHz, $CDCl_3$) δ 0.86 (d, J=6 Hz, 6H), 1.50–1.70 (m, 3H), 3.14 (s, 3H), 4.54 (t, J=6 Hz, 2H), 7.24–7.30 (m, 1H), 7.56–7.62 (m, 7.83 (m, 3H), 7.86 (m, 1H), 7.92 (s, 1H), 8.05–8.10 (m, 2H); MS (DCI/$NH_3$) m/z 465 (M+H)$^+$; Anal. calcd. for $C_{22}H_{22}ClFN_2O_4S$: C, 56.83; H, 4.77; N, 6.02. Found: C, 56.70; H, 4.77; N, 6.11.

EXAMPLE 539

2-(3,4-Dichlorophenyl)-4-(2-methyl-1-propoxy)-5-[4-(methylsulfonyl)phenyl]-3(2H)-pyridazinone The title compound was prepared according to the method of Example 536 substituting 2-methyl-1-propanol in place of n-butanol and substituting 2-(3,4-dichlorophenyl)-4,5-dibromo-3(2H)-pyridazinone for 2-(3,4-difluorophenyl)-4,5-dichloro-3(2H)-pyridazinone to provide the title compound (0.63 g, 98%). mp 127–129° C.; 1H NMR (300 MHz, $CDCl_3$) δ 0.86 (d, J=6 Hz, 6H), 1.82–1.94 (m, 1H), 3.14 (s, 3H), 4.30 (d, J=6 Hz, 2H), 7.56–7.62 (m, 2H), 7.77–7.82 (m, 2H), 7.86 (m, 1H), 7.92 (s, 1H), 8.06–8.10 (m, 2H); MS (DCI/$NH_3$) m/z 467 (M+H)$^+$; Anal. calcd. for $C_{21}H_{20}Cl_2N_2O_4S$: C, 53.97; H, 4.31; N, 5.99. Found: C, 53.82; H, 4.29; N, 5.89.

EXAMPLE 540

2-(3,4-Dichlorophenyl)-4-(3-methyl-1-butoxy)-5-[4-(methylsulfonyl)phenyl]-3(2H)-pyridazinone The title compound was prepared according to the method of Example 536 substituting 3-methyl-1-butanol in place of n-butanol to provide the title compound (0.63 g, 98%). mp 130–134° C.; $^1$H NMR (300 MHz, $CDCl_3$) δ 0.86 (d, J=6 Hz, 6H), 1.50–1.68 (m, 3H), 3.14 (s, 3H), 4.51 (t, J=6 Hz, 2H), 7.56–7.62 (m, 2H), 7.77–7.82 (m, 2H), 7.86 (m, 1H), 7.92 (s, 1H), 8.06–8.10 (m, 2H); MS (DCI/$NH_3$) m/z 481 (M+H)$^+$; Anal. calcd. for $C_{22}H_{22}Cl_2N_2O_4S$: C, 54.89; H, 4.61; N, 5.82. Found: C, 54.72; H, 4.56; N, 5.73.

EXAMPLE 541

2-(3,4-Difluorophenyl)-4-(4-hydroxy-1-butoxy)-5-[4-(methylsulfonyl)phenyl]-3(2H)-pyridazinone The title compound was prepared according to the method of Example 536 substituting 1,4-butanediol in place of n-butanol and substituting 2-(3,4-difluorophenyl)-4,5-dibromo-3(2H)-pyridazinone for 2-(3,4-difluorophenyl)-4,5-dichloro-3(2H)-pyridazinone to provide the title compound (0.61 g, 95%). mp 110–113° C.; $^1$H NMR (300 MHz, $CDCl_3$) δ 1.52–1.60 (m, 2H), 1.72–1.82 (m, 2H), 3.15 (s, 3H), 3.62 (t, J=6 Hz, 2H), 4.52 (t, J=6 Hz, 2H), 7.25–7.34 (m, 1H), 7.44–7.50 (m, 1H), 7.55–7.62 (m, 1H), 7.77–7.82 (m, 2H), 7.92 (s, 1H), 8.05–8.10 (m, 2H); MS (DCI/$NH_3$) m/z 468 (M+H)$^+$; Anal. calcd. for $C_{21}H_{20}F_2N_2O_5S$: C, 55.99; H, 4.48; N, 6.22. Found: C, 55.79; H, 4.41; N, 5.96.

EXAMPLE 542

2-[3-(Trifluoromethyl)phenyl]-4-(2-methyl-1-propoxy)-5-[4-(methylsulfonyl)phenyl]-3(2H)-pyridazinone The title compound was prepared according to the method of Example 536 substituting 2-methylpropanol for n-butanol and substituting 2-[3-(trifluoromethyl)phenyl]-4,5-dibromo-3(2H)-pyridazinone in place of 2-(3,4-difluorophenyl)-4,5-dichloro-3(2H)-pyridazinone to provide the title compound (0.58 g, 90%). mp 125–127° C.; $^1$H NMR (300 MHz, $CDCl_3$) δ 0.84 (d, J=6 Hz, 6H), 1.86–1.98 (m, 1H), 3.14 (s, 3H), 4.30 (d, J=6 Hz, 2H), 7.60–7.70 (m, 2H), 7.79–7.84 (m, 2H), 7.94 (s, 1H), 7.88–7.98 (m, 2H), 8.06–8.12 (m, 2H); MS (DCI/$NH_3$) m/z 484 (M+H)$^+$; Anal. calcd. for $C_{22}H_{21}F_3N_2O_4S$: C, 56.65; H, 4.54; N, 6.00. Found: C, 56.49; H, 4.56; N, 5.81.

EXAMPLE 543

2-[3-(Trifluoromethyl)phenyl]-4-(3-methyl-1-butoxy)-5-[4-(methylsulfonyl)phenyl]-3(2H)-pyridazinone The title compound was prepared according to the method of Example 536 substituting 3-methyl-1-butanol in place of n-butanol and substituting 2-[3-(trifluoromethyl)phenyl]-4,5-dibromo-3(2H)-pyridazinone in place of 2-(3,4-difluorophenyl)-4,5-dichloro-3(2H)-pyridazinone to provide the title compound (0.53 g, 74%). mp 82–85° C.; $^1$H NMR (300 MHz, $CDCl_3$) δ 0.95 (d, J=6 Hz, 6H), 1.52–1.64 (m, 3H), 3.14 (s, 3H), 4.52 (d, J=6 Hz, 2H), 7.60–7.70 (m, 2H), 7.79–7.84 (m, 2H), 7.94 (s, 1H), 7.88–7.98 (m, 2H), 8.06–8.12 (m, 2H); MS (DCI/$NH_3$) m/z 498 (M+H)$^+$; Anal. calcd. for $C_{23}H_{23}F_3N_2O_4S$: C, 57.49; H, 4.82; N, 5.83. Found: C, 57.47; H, 4.94; N, 5.60.

EXAMPLE 544

2-[3-(Trifluoromethyl)phenyl]-4(3-hydroxy-3-methyl-1-butoxy)-5-[4-(methylsulfonyl)phenyl]-3(2H)-pyridazinone The title compound was prepared according to the method of Example 536 substituting 3-methyl-1,3-butanediol in place of n-butanol and substituting 2-[3-(trifluoromethyl)phenyl]-4,5-dibromo-3(2H)-pyridazinone in place of 2-(3, 4-difluorophenyl)-4,5-dichloro-3(2H)-pyridazinone to provide the title compound (1.2 g, 75%). mp 90–93° C.; $^1$H NMR (300 MHz, CDCl$_3$) δ 1.14 (s, 6H), 1.90 (t, J=6 Hz, 2H), 3.14 (s, 3H), 4.58 (t, J=6 Hz, 2H), 7.60–7.70 (m, 2H), 7.79–7.84 (m, 2H), 7.94 (s, 1H), 7.88–7.98 (m, 2H), 8.06–8.12 (m, 2H); MS (DCI/NH$_3$) m/z 514 (M+H)$^+$; Anal. calcd. for C$_{23}$H$_{23}$F$_3$N$_2$O$_5$S: C, 55.64; H, 4.67; N, 5.64. Found: C, 56.01; H, 4.83; N, 5.06.

EXAMPLE 545

(R)-2-(3,4-Difluorophenyl)-4-(3-hydroxy-1-butoxy)-5-[4-(methylsulfonyl)phenyl]-3(2H)-pyridazinone Example 545A Ethyl (R)-3-(tert-butyldimethylsiloxy)butanoate To a stirred, room temperature solution of ethyl (R)-3-hydroxybutanoate (5.00 g, 37.8 mmol) and tert-butyldimethylsilyl chloride (6.85 g, 45.5 mmol) in DMF (90 mL) was added imidazole (3.87 g, 56.9 mmol). This reaction mixture was stirred at room temperature for 18 hours. The reaction mixture was partitioned between hexane (300 mL) and water (100 mL). The organic layer was washed with water (2×100 mL) then dried (MgSO$_4$) and filtered. The filtrate was concentrated under reduced pressure to give the title compound.

Example 545B (R)-3-(tert-Butyldimethylsiloxy)-1-butanol

The crude product from Example 545A (~37 mmol) was dissolved in dichloromethane (100 mL). To this stirred solution, chilled to −78° C., was added dropwise a 1M solution of diisobutylaluminum hydride in dichloromethane (185 mL, 185 mmol). The reaction mixture was stirred at −78° C. for two hours, then it was allowed to warm to −30° C. and stirred an additional 0.5 hours. Methanol was then added carefully at −20° C. to quench any remaining hydride. The reaction mixture was then diluted with methyl tert-butylether (200 mL) and washed with aqueous sodium tartrate solution (4×100 mL) and brine (2×100 mL). The organic layer was dried (MgSO$_4$) and filtered. The filtrate was concentrated under reduced pressure to give the crude title compound (6.3 g, 83%).

Example 545C (R)-2-(3,4-Difluorophenyl)-4-[3-(tert-butyldimethylsiloxy)-1-butoxy]-5-bromo-3(2H)-pyridazinone To a stirred, 0° C. solution of the product from Example 545B (3.4 g, 10 mmol) in THF (20 mL) was added 1M sodium bis(trimethylsilyl)amide in THF (12 mL, 12 mmol). The reaction mixture was stirred at room temperature for 0.5 hours, then it was transferred to a stirred, −30° C. solution of 2-(3,4-difluorophenyl)-4,5-dibromo-3(2H)-pyridazinone (3.66 g, 10 mmol) in THF (100 mL). The reaction mixture was stirred at −30° C. for 1 hour, then overnight while warming to room temperature. The reaction was quenched with saturated aqueous ammonium chloride solution (100 mL) and extracted with ethyl acetate (2×100 mL). The organic layer was washed with brine (2×20 mL), then dried (MgSO$_4$), and filtered. The filtrate was concentrated under reduced pressure and the residue was purified by column chromatography (silica gel, 90:10 hexane/ethyl acetate) to provide the title intermediate (2.5 g, 51%).

Example 545D (R)-2-(3,4-Difluorophenyl)-4-[3-(tert-butyldimethylsiloxy)-1-butoxy]-5-[4-(methylthio)phenyl]-3(2H)-pyridazinone Under a nitrogen atmosphere, a mixture of the product from Example 545C (0.98 g, 2 mmol), 4-(methylthio)benzeneboronic acid (0.4 g, 2.4 mmol), K$_3$PO$_4$ (1.2 g, 6 mmol), PdCl$_2$(PPh$_3$)$_2$ (28 mg, 0.04 mmol), isopropanol (9 mL), and water (1 mL) was stirred at 70° C. for 4 hours. The reaction mixture was then cooled to room temperature, water (30 mL) was added and stirring was continued for 2 hours. The crude black precipitate was collected by filtration then washed with water (10 mL) and hexane (10 mL). This title intermediate was used without further purification in the following oxidation/deprotection step.

Example 545E (R)-2-(3,4-Difluorophenyl)-4-(3-hydroxy-1-butoxy)-5-[4-(methylsulfonyl)phenyl]-3(2H)-pyridazinone A stirred solution of the product from step Example 545D(~2 mmol) in acetone (10 mL) was chilled to 0° C. To this was added 32% peracetic acid in acetic acid solution (1.42 mL, 6 mmol). The reaction mixture was stirred for 1 hour while warming to room temperature. At this point the oxidation was complete, but some of the product's hydroxy group was still silylated so 1M tetrabutylammonium fluoride in THF (4 mL, 4 mmol) was added and stirring was continued for 0.5 hours. The reaction mixture was then treated with 5% aqueous sodium thiosulfate solution (30 mL) for 2 hours. The precipitated product was collected by filtration, washed with water (10 mL) and hexane (10 mL). The solid was stirred in isopropanol (5 mL) for 6 hours then collected by filtration and dried to provide the title compound (0.78 g, 87%). mp 126–129° C.; $^1$H NMR (300 MHz, CDCl$_3$) δ 1.22 (d, J=6 Hz, 3H), 1.62–1.74 (m, 1H), 1.84–1.94 (m, 1H), 3.16 (s, 3H), 3.30 (s br, 1H), 4.00–4.10 (m, 1H), 4.20–4.30 (m, 1H), 4.63 (td, J=9.6 Hz, J=4 Hz, 1H), 7.25–7.34 (m, 1H), 7.46–7.52 (m, 1H), 7.56–7.64 (m, 1H), 7.78–7.84 (m, 2H), 7.97 (s, 1H), 8.06–8.12 (m, 2H); MS (DCI/NH$_3$) m/z 468 (M+NH$_4$)$^+$.

EXAMPLE 546

(S)-2-(3,4-Difluorophenyl)-4-(3-hydroxy-1-butoxy)-5-[4-(methylsulfonyl)phenyl]-3(2H)-pyridazinone The title compound was prepared according to the method of Example 545 substituting ethyl (S)-3-hydroxybutanoate in place of ethyl (R)-3-hydroxybutanoate (0.72 g, 80%). mp 128–130° C.; $^1$H NMR (300 MHz, CDCl$_3$) δ 1.22 (d, J=6 Hz, 3H), 1.62–1.74 (m, 1H), 1.84–1.94 (m, 1H), 3.16 (s, 3H), 3.30 (s br, 1H), 4.00–4.10 (m, 1H), 4.20–4.30 (m, 1H), 4.63 (td, J=9.6 Hz, J=4 Hz, 1H), 7.25–7.34 (m, 1H), 7.46–7.52 (m, 1H), 7.56–7.64 (m, 1H), 7.78–7.84 (m, 2H), 7.97 (s, 1H), 8.06–8.12 (m, 2H); MS (DCI/NH$_3$) m/z 468 (M+NH$_4$)$^+$.

EXAMPLE 547

(S)-2-(3,4-Difluorophenyl)-4-(2-hydroxy-3-methyl-1-butoxy)-5-[4-(methylsulfonyl)phenyl]-3(2H)-pyridazinone

Example 547A

Methyl (S)-2-hydroxy-3-methylbutanoate

The title compound (CAS Registry #[17392-84-6]) is prepared by literature procedures (e.g. Journal of Organic Chemistry, (1994) 59(7), 1933–1936).

Example 547B

Methyl (S)-2-(tert-butyldimethylsiloxy)-3-methylbutanoate

The title compound is prepared by the method of Example 545A, substituting methyl (S)-2-hydroxy-3-methylbutanoate (Example 547A) in place of ethyl (R)-3-hydroxybutanoate.

Example 547C (S)-2-(tert-Butyldimethylsiloxy)-3-methyl-1-butanol

The title compound is prepared by the method of Example 545B, substituting methyl (S)-2-(tert-butoxydimethylsiloxy)-3-methylbutanoate (Example 547B) in place of ethyl (R)-3-(tert-butyldimethylsiloxy)butanoate (Example 545A).

Example 547D (S)-2-(3,4-Difluorophenyl)-4-[2-(tert-butyldimethylsiloxy)-3-methyl-1-butoxy]-5-bromo-3(2H)-pyridazinone The title compound is prepared by the method of Example 545C, substituting (S)-2-tert-butyldimethylsiloxy-3-methyl-1-butanol (Example 547C) in place of (R)-3-(tert-butyldimethylsiloxy)-1-butanol (Example 545B).

Example 547E 2-(tert-butyldimethylsiloxy)-3-methyl-1-butoxy]-5-[4-(methylthio)phenyl]-3(2H)-pyridazinone The title intermediate is prepared by the method of Example 545D, substituting (S)-2-(3,4-difluorophenyl)-4-[2-(tert-butyldimethylsiloxy)-3-methyl-1-butoxy]-5-bromo-3(2H)-pyridazinone (Example 547D) in place of (R)-2-(3,4-difluorophenyl)-4-[3-(tert-butyldimethylsiloxy)-1-butoxy]-5-bromo-3(2H)-pyridazinone (Example 545C).

Example 547F (S)-2-(3,4-Difluorophenyl)-4-(2-hydroxy-3-methyl-1-butoxy)-5-[4-(methylsulfonyl)phenyl]-3(2H)-pyridazinone The title compound is prepared by the method of Example 545E, substituting (S)-2-(3,4-difluorophenyl)-4-[2-(tert-butyldimethylsiloxy)-3-methyl-1-butoxy]-5-[4-(methylthio)phenyl]-3(2H)-pyridazinone (Example 547E) in place of (R)-2-(3,4-difluorophenyl)-4-[3-(tert-butyldimethylsiloxy)-1-butoxy]-5-[4-(methylthio)phenyl]-3(2H)-pyridazinone (Example 545D).

EXAMPLES 548–558

The following compounds may be prepared according to the sequence of reactions described in Example 547, substituting the appropriate 2-(X-phenyl)-4,5-dibromo-3(2H)-pyridazinone in place of 2-(3,4-difluorophenyl)-4,5-dibromo-3(2H)-pyridazinone.

| Example Number | X |
| --- | --- |
| 548 | 4-F |
| 549 | 4-Cl |
| 550 | 3-F |
| 551 | 3-Cl |
| 552 | 3-Br |
| 553 | 3-$CF_3$ |
| 554 | 3-Cl-4-F |
| 555 | 4-Cl-3-F |
| 556 | 3,4-di-Cl |
| 557 | 4-F-3-$CF_3$ |
| 558 | 3-Br-4-F |

EXAMPLE 559

(R)-2-(3,4-Difluorophenyl)-4-(2-hydroxy-3-methyl-1-butoxy)-5-[4-(methylsulfonyl)phenyl]-3(2H)-pyridazinone The title compound may be prepared according to the sequence of reactions described in Example 547, substituting methyl (R)-2-hydroxy-3-methyl-butanoate [17392-84-6] prepared as described in (Tetrahedron, 1995, 51(38), 10513–10522) in place of methyl (S)-2-hydroxy-3-methylbutanoate.

EXAMPLES 560–570

The following compounds can be prepared according to the sequence of reactions described in Example 559, substituting the appropriate 2-(X-phenyl)-4,5-dibromo-3(2H)-pyridazinone in place of 2-(3,4-difluorophenyl)-4,5-dibromo-3(2H)-pyridazinone.

| Example Number | X |
| --- | --- |
| 560 | 4-F |
| 561 | 4-Cl |
| 562 | 3-F |
| 563 | 3-Cl |
| 564 | 3-Br |
| 565 | 3-$CF_3$ |
| 566 | 3-Cl-4-F |
| 567 | 4-Cl-3-F |
| 568 | 3,4-di-Cl |
| 569 | 4-F-3-$CF_3$ |
| 570 | 3-Br-4-F |

EXAMPLE 571

2-(3,4-Difluorophenyl)-4-[(S)-2,3-dihydroxy-3-methyl-1-butoxy]-5-[4-(methylsulfonyl)phenyl]-3(2H)-pyridazinone The title compound may be prepared according to the sequence of reactions described in Example 547, substituting methyl (R)-2,3-dihydroxy-3-methylbutanoate [37504-90-8] (Australian Journal of Chemistry, (1986) 39(11), 1907–1909) in place of methyl (S)-2-hydroxy-3-methylbutanoate.

EXAMPLES 572–582

The following compounds may be prepared according to the sequence of reactions described in Example 571, substituting the appropriate 2-(X-phenyl)-4,5-dibromo-3(2H)-pyridazinone in place of 2-(3,4-difluorophenyl)-4,5-dibromo-3(2H)-pyridazinone.

| Example Number | X |
|---|---|
| 572 | 4-F |
| 573 | 4-Cl |
| 574 | 3-F |
| 575 | 3-Cl |
| 576 | 3-Br |
| 577 | 3-CF$_3$ |
| 578 | 3-Cl-4-F |
| 579 | 4-Cl-3-F |
| 580 | 3,4-di-Cl |
| 581 | 4-F-3-CF$_3$ |
| 582 | 3-Br-4-F |

EXAMPLE 583

2-(3,4-Difluorophenyl)-4-[(R)-2,3-dihydroxy-3-methyl-1-butoxy]-5-[4-(methylsulfonyl)phenyl]-3(2H)-pyridazinone The title compound may be prepared according to the sequence of reactions described in Example 547, substituting methyl (S)-2,3-dihydroxy-3-methylbutanoate [75347-92-1] (Journal of Organic Chemistry, 1980, 45(25), 5218–5220) in place of methyl (S)-2-hydroxy-3-methylbutanoate.

EXAMPLES 584–594

The following compounds may be prepared according to the sequence of reactions described in Example 571, substituting the appropriate 2-(X-phenyl)-4,5-dibromo-3(2H)-pyridazinone in place of 2-(3,4-difluorophenyl)-4,5-dibromo-3(2H)-pyridazinone.

| Example Number | X |
|---|---|
| 584 | 4-F |
| 585 | 4-Cl |
| 586 | 3-F |
| 587 | 3-Cl |
| 588 | 3-Br |
| 589 | 3-CF$_3$ |
| 590 | 3-Cl-4-F |
| 591 | 4-Cl-3-F |
| 592 | 3,4-di-Cl |
| 593 | 4-F-3-CF$_3$ |
| 594 | 3-Br-4-F |

EXAMPLE 595

2-(3,4-Difluorophenyl)-4-(4-hydroxy-4-methyl-1-pentyloxy)-5-[4-(methylsulfonyl)phenyl]-3(2H)-pyridazinone The title compound may be prepared according to the sequence of reactions described in Example 471, substituting 4-methyl-1,4-pentanediol [1462-10-8] (Journal of Organic Chemistry, (1972) 37, 3310–3322) in place of methyl 3-methyl-1,3-butanediol.

EXAMPLE 596–606

The following compounds may be prepared according to the sequence of reactions described in Example 471, substituting 4-methyl-1,4-pentanediol [1462-10-8] (Journal of Organic Chemistry, (1972) 37, 3310–3322) in place of methyl 3-methyl-1,3-butanediol and substituting the appropriate 2-(X-phenyl)-4,5-dibromo-3(2H)-pyridazinone in place of 2-(3,4-difluorophenyl)-4,5-dibromo-3(2H)-pyridazinone.

| Example Number | X |
|---|---|
| 596 | 4-F |
| 597 | 4-Cl |
| 598 | 3-F |
| 599 | 3-Cl |
| 600 | 3-Br |
| 601 | 3-CF$_3$ |
| 602 | 3-Cl-4-F |
| 603 | 4-Cl-3-F |
| 604 | 3,4-di-Cl |
| 605 | 4-F-3-CF$_3$ |
| 606 | 3-Br-4-F |

EXAMPLE 607

2-(3,4-Difluorophenyl)-4-[3-(2-aminoacetyloxy)-3-methyl-1-butoxy]-5-[4-(methylsulfonyl)phenyl]-3(2H)-pyridazinone The title compound may be prepared by a carbodiimide-mediated coupling (method described in Angew. Chem., Int. Ed. Engl., (1979) 18(9), 686) of 2-(3,4-difluorophenyl)-4-(3-hydroxy-3-methyl-1-butoxy)-5-[4-(methylsulfonyl)phenyl]-3(2H)-pyridazinone (Example 471) with an N-protected-glycine (such as N-Fmoc-glycine); followed by an amino group deprotection step (such as treatment at room temperature with tetrabutylammonium fluoride in DMF).

EXAMPLES 608–618

The following compounds may be prepared by the method of Example 607, substituting the appropriate 2-(X-phenyl)-4-(3-hydroxy-3-methyl-1-butoxy)-5-[4-(methylsulfonyl)phenyl]-3(2H)-pyridazinone in place of 2-(3,4-difluorophenyl)-4-(3-hydroxy-3-methyl-1-butoxy)-5-[4-(methylsulfonyl)phenyl]-3(2H)-pyridazinone (Example 471).

| Example Number | X |
|---|---|
| 608 | 4-F |
| 609 | 4-Cl |
| 610 | 3-F |
| 611 | 3-Cl |
| 612 | 3-Br |
| 613 | 3-CF$_3$ |
| 614 | 3-Cl-4-F |
| 615 | 4-Cl-3-F |
| 616 | 3,4-di-Cl |
| 617 | 4-F-3-CF$_3$ |
| 618 | 3-Br-4-F |

EXAMPLE 619

2-(3,4-Difluorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone The title compound may be prepared in a manner similar to that described in J. Chem. Soc., Chem Commun., (1993) 410–412, reacting 2-(3,4-difluorophenyl)-4-(3-hydroxy-3-methyl-1-butoxy)-5-[4-(methylsulfonyl)phenyl]-3(2H)-pyridazinone (Example 471) with an appropriately protected L-tartaric acid diester (such as below), followed by deprotection.

Example 619A dibenzyl (2R,3R)-2,3-bis {[tert-butyl(diphenyl)silyl]oxy}butanedioate The alcohol groups of (+)-dibenzyl-L-tartrate can be protected as the tert-butyldiphenylsilyl ethers by standard methods as described in (Greene, T W, Wuts, P G M; Protective Groups in Organic Synthesis; 3$^{rd}$ Edition; 1999; John Wiley & Sons, Inc.; NY, N.Y.; 141–144) to provide the title intermediate.

Example 619B (2R,3R)-2,3-bis{[tert-butyl(diphenyl)silyl]oxy}butanedioic acid The dibenzyl ester of Example 619A can be cleaved by standard hydrogenolysis procedures as described in (Greene, T W, Wuts, P G M; Protective Groups in Organic Synthesis; 3$^{rd}$ Edition; 1999; John Wiley & Sons, Inc.; NY, N.Y.; 415–419) to provide the title intermediate.

Example 619C (3R,4R)-3,4-bis{[tert-butyl(diphenyl)silyl]oxy}dihydro-2,5-furandione Example 619B may be reacted by standard methods as described in (Journal of Organic Chemistry, (1987) 52(3), 455–457) with trifluoroacetic anhydride to provide the title intermediate.

Example 619D (2R,3R)-2,3-bis{[tert-butyl(diphenyl)silyl]oxy}-4-methoxy-4-oxobutanoic acid Example 619C may be reacted with anhydrous methanol by standard methods as described in (Organic Syntheses, Collective Volume III, (1955) 169–171) to provide the title intermediate.

Example 619E 1-isopropenyl 4-methyl (2R,3R)-2,3-bis{[tert-butyl(diphenyl)silyl]oxy}butanedioate Example 619D may be reacted with isopropenyl acetate in the presence of catalytic boron trifluoride etherate and mercury(II) acetate as described in (J. Chem. Soc., Chem Commun., (1993) 410–412) to provide the title intermediate.

Example 619F 2-(3,4-Difluorophenyl)-4-{3-[((2R,3R)-2,3-bis{[tert-butyl(diphenyl)silyl]oxy}-4-methoxy-4-oxobutanoyl)oxy]-3-methylbutoxy}-5-[4-(methylsulfonyl)phenyl]-3(2H)-pyridazinone Example 619E may be coupled to 2-(3,4difluorophenyl)-4-(3-hydroxy-3-methyl-1-butoxy)-5-[4-(methylsulfonyl)phenyl]-3(2H)-pyridazinone (Example 471) in the presence of catalytic 4-toluene sulfonic acid by the method described in (J. Chem. Soc., Chem Commun., (1993) 410–412) to provide the title intermediate.

Example 619G 2-(3,4-Difluorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenol]-3(2H)-pyridazinone Example 619F can be treated with aqueous sodium hydroxide in methanol as described in (J. Chem. Soc., Chem Commun., (1993) 410–412) to provide the title compound.

EXAMPLE 620–630

The following compound may be prepared by the method of Example 619F, substituting the appropriate 2-(X-phenyl)-4-(3-hydroxy-3-methyl-1-butoxy)-5-[4-(methylsulfonyl)phenyl]-3(2H)-pyridazinone in place of 2-(3,4-difluorophenyl)-4-(3-hydroxy-3-methyl-1-butoxy)-5-[4-(methylsulfonyl)phenyl]-3(2H)-pyridazinone (Example 471), followed by treatment with aqueous sodium hydroxide in methanol as in Example 619G.

| Example Number | X |
|---|---|
| 620 | 4-F |
| 621 | 4-Cl |
| 622 | 3-F |
| 623 | 3-Cl |
| 624 | 3-Br |
| 625 | 3-CF$_3$ |
| 626 | 3-Cl-4-F |
| 627 | 4-Cl-3-F |
| 628 | 3,4-di-Cl |
| 629 | 4-F-3-CF$_3$ |
| 630 | 3-Br-4-F |

EXAMPLE 631

3-({2-(3,4-difluorophenyl)-5-[4-(methylsulfonyl)phenyl]-3-oxo-2,3-dihydro-4-pyridazinyl}oxy)-1,1-dimethylpropyl dihydrogen phosphate The title compound may be prepared as described in (Kosolapoff, G M and Maier, L, Organic Phosphorus Compounds, (1973) Volume 6, John Wiley & Sons, NY, N.Y.); such as reacting 2-(3,4-difluorophenyl)-4-(3-hydroxy-3-methyl-1-butoxy)-5-[4-(methylsulfonyl)phenyl]-3(2H)-pyridazinone (Example 471) with 2-cyanoethylphosphate (Fieser, L F and Fieser, M, Reagents for Organic Synthesis, 1967, Volume 1, 172–173, John Wiley & Sons, NY, N.Y.) in the presence of DCC and pyridine. Mild alkaline. hydrolysis of the cyanoethyl ester selectively provides the title compound.

EXAMPLE 632–642

The following compounds may be prepared by the method of Example 631, substituting the appropriate 2-(X-phenyl)-4-(3-hydroxy-3-methyl-1-butoxy)-5-[4-(methylsulfonyl)phenyl]-3(2H)-pyridazinone in place of 2-(3,4-difluorophenyl)-4-(3-hydroxy-3-methyl-1-butoxy)-5-[4-(methylsulfonyl)phenyl]-3(2H)-pyridazinone (Example 471).

| Example Number | X |
|---|---|
| 632 | 4-F |
| 633 | 4-Cl |
| 634 | 3-F |
| 635 | 3-Cl |
| 636 | 3-Br |
| 637 | 3-$CF_3$ |
| 638 | 3-Cl-4-F |
| 639 | 4-Cl-3-F |
| 640 | 3,4-di-Cl |
| 641 | 4-F-3-$CF_3$ |
| 642 | 3-Br-4-F |

EXAMPLE 643

2-(tert-Butyl)-4-(3-hydroxy-3-methyl-1-butoxy)-5-[4-(methylsulfonyl)phenyl]-3(2H)-pyridazinone The title compound may be prepared according to the sequence of reactions described in Example 471, substituting 2-tert-butyl-4,5-dichloro-3(2H)-pyridazinone (Example 330A) in place of 2-(3,4-difluorophenyl)-4,5-dibromo-3(2H)-pyridazinone.

EXAMPLE 644

2-(tert-Butyl)-4-[3-(2-aminoacetyloxy)-3-methyl-1-butoxy]-5-[4-(methylsulfonyl)phenyl]-3(2H)-pyridazinone The title compound may be prepared by the method of Example 607, substituting 2-(tert-butyl)-4-(3-hydroxy-3-methyl-1-butoxy)-5-[4-(methylsulfonyl)phenyl]-3(2H)-pyridazinone (Example 643) in place of 2-(3,4-difluorophenyl)-4-(3-hydroxy-3-methyl-1-butoxy)-5-[4-(methylsulfonyl)phenyl]-3(2H)-pyridazinone (Example 471).

EXAMPLE 645

2-(tert-Butyl)-4-[3-{[(2R,3R)-3-carboxy-2,3-dihydroxypropanoyl]oxy}-3-methylbutoxy]-3-methyl-1-butoxy]-5-[4-(methylsulfonyl)-phenyl]-3(2H)-pyridazinone The title compound may be prepared by the method of Example 619, substituting 2-(tert-butyl)-4-(3-hydroxy-3-methyl-1-butoxy)-5-[4-(methylsulfonyl)-phenyl]-3(2H)-pyridazinone (Example 643) in place of 2-(3,4-difluorophenyl)-4-(3-hydroxy-3-methyl-1-butoxy)-5-[4-(methylsulfonyl)-phenyl]-3(2H)-pyridazinone (Example 471).

EXAMPLE 646

3-({2-(tert-Butyl)-5-[4-(methylsulfonyl)phenyl]-3-oxo-2,3-dihydro-4-pyridazinyl}oxy)-1,1-dimethyl-propyl dihydrogen phosphate The title compound may be prepared by the method of Example 631, substituting 2-(tert-butyl)-4-(3-hydroxy-3-methyl-1-butoxy)-5-[4-(methylsulfonyl)-phenyl]-3(2H)-pyridazinone (Example 643) in place of 2-(3,4-difluorophenyl)-4-(3-hydroxy-3-methyl-1-butoxy)-5-[4-(methylsulfonyl)-phenyl]-3(2H)-pyridazinone (Example 471).

Prostaglandin Inhibition Determination

Compound Preparation and Administration

For oral administration, test compounds were suspended on the day of use in 100% polyethyleneglycol (PEG 400) with a motorized homogenizer equipped with a Teflon-coated pestle (TRI-R Instrument, Jamaica, N.Y.).

To compare the mean responses of the treatment groups, analysis of variance was applied. Percent inhibition values were determined by comparing the individual treatment mean values to the mean of the control group. Linear regression was used to estimate $IC_{50}$'s/$ED_{50}$'s in appropriate assays.

EIA Determination of Prostaglandins

EIA reagents for prostaglandin determination were purchased from Perseptive Diagnostics, (Cambridge, Mass.). Prostaglandin $E_2$ ($PGE_2$) levels in lavage fluids were determined after the samples were dried under nitrogen and reconstituted with assay buffer. $PGE_2$ levels in enzyme assays or cell culture media were measured against standards prepared in the same milieu. The immunoassays were conducted as recommended by the manufacturer. The EIA was conducted in 96 well microtiter plates (Nunc Roskilde, Denmark) and optical density was measured using a microplate reader (Vmax, Molecular Devices Corp., Menlo Park, Calif.).

Recombinant Human PGHS-1 and PGHS-2 Enzyme Assays

Inhibition of prostaglandin biosynthesis in vitro was evaluated using recombinant human Cox-1 (r-hu Cox1) and Cox-2 (r-hu Cox-2) enzyme assays. Representative compounds dissolved in DMSO (3.3% v/v) were preincubated with microsomes from recombinant human PGHS-1 or PGHS-2 expressed in the baculovirus/Sf9 cell system (Gierse, J. K., Hauser, S. D., Creely, D. P., Koboldt, C., Rangwala, S., H., Isakson, P. C., and Seibert, K. *Expression and selective inhibition of the constituitive and inducible forms of cyclooxygenase*, Biochem J. 1995, 305: 479.), together with the cofactors phenol (2 mM) and hematin (1 μM) for 60 minutes prior to the addition of 10 μM arachidonic acid. The reaction was allowed to run for 2.5 minutes at room temperature prior to quenching with HCl and neutralization with NaOH. $PGE_2$ production in the presence and absence of the drug was determined by EIA analysis. The EIA was conducted in 96 well microtiter plates (Nunc Roskilde, Denmark) and optical density was measured using a microplate reader (Vmax, Molecular Devices Corp., Menlo Park, Calif.). EIA reagents for prostaglandin determination were purchased from Perseptive Diagnostics (Cambridge, Mass.). $PGE_2$ levels were measured against standards prepared in the same milieu. The immunoassays were conducted as recommended by the manufacturer.

The data illustrating the inhibition of prostaglandin biosynthesis in vitro by compounds of this invention is shown in Table 1. The compounds are designated by the Example Number. Column 2 shows Cox-1 percent inhibition at the particular micromolar dose level and Column 3 shows Cox-2 percent inhibition at the particular nanomolar dose level. Values for Cox-1 and Cox-2 inhibition that are parenthetical indicate $IC_{50}$ values.

TABLE 1

| Example Number | RHUCX1 % Inh. at Dose (μM) | RHUCX2 % Inh. at Dose (μM) |
|---|---|---|
| 10 | 2 @ 100 | (0.014) |
| 12 | 0 @ 100 | 97 @ 10 |
|  |  | 77 @ 1 |
|  |  | 9 @ 0.1 |
| 20 | 10 @ 100 | 86 @ 0.1 |
|  |  | 9 @ 0.01 |
| 21 | 19 @ 100 | (0.92) |
| 22 | 25 @ 100 | 91 @ 0.03 |
|  |  | 35 @ 0.01 |
| 23 | 0 @ 100 | 68 @ 0.1 |
|  |  | 27 @ 0.01 |
| 24 | 60 @ 100 | 99 @ 1 |
|  | 0 @ 10 | 61 @ 0.1 |
|  |  | 45 @ 0.01 |
| 25 | 1 @ 100 | 93 @ 1 |
|  |  | 66 @ 0.1 |
| 26 | 10 @ 100 | 91 @ 1 |
|  |  | 44 @ 0.1 |
|  |  | 44 @ 0.01 |
| 32 | 20 @ 100 | 96 @ 1 |
|  |  | 83 @ 0.1 |
| 34 | 16 @ 100 | (0.92) |
| 35 | 34 @ 100 | (0.017) |
| 36 | 21 @ 10 | (0.57) |
| 39 | 0 @ 100 | (0.44) |
| 40 | 76 @ 10 | 97 @ 1 |
|  | 69 @ 1 | 89 @ 0.1 |
| 41 | 13 @ 100 | 49 @ 1 |
|  |  | 17 @ 0.1 |
| 42 | 0 @ 100 | 99 @ 1 |
|  |  | 92 @ 0.1 |
| 43 | 8 @ 100 | 100 @ 1 |
|  |  | 96 @ 0.1 |
| 45 | 5 @ 100 | 85 @ 1 |
|  |  | 63 @ 0.1 |
| 48 | 0 @ 100 | 73 @ 1 |
|  |  | 2 @ 0.1 |
| 50 | 23 @ 100 | 99 @ 1 |
|  |  | 59 @ 0.1 |
| 52 | 32 @ 10 | 99 @ 1 |
|  |  | 83 @ 0.1 |
| 53 | 10 @ 100 | 99 @ 1 |
|  |  | 77 @ 0.1 |
| 54 | 0 @ 100 | 95 @ 1 |
|  |  | 58 @ 0.1 |
| 58 | 0 @ 100 | (0.95) |
| 60 | 7 @ 100 | 100 @ 1,000 |
| 62 | 6 @ 100 | (0.624) |
| 64 | 68 @ 1 | 34 @ 1 |
|  |  | 36 @ 0.1 |
| 65 | 13 @ 100 | 98 @ 1 |
|  |  | 65 @ 0.1 |
| 68 | 32 @ 100 | (0.297) |
| 69 | 2 @ 100 | 88 @ 1 |
|  |  | 29 @ 0.1 |
|  |  | 30 @ 0.01 |
| 72 | 0 @ 100 | 65 @ 1 |
|  |  | 18 @ 0.1 |
| 73 | 9 @ 100 | (1.34) |
| 74 | 11 @ 100 | 86 @ 1 |
|  |  | 75 @ 0.1 |
| 77 | 35 @ 100 | 82 @ 10 |
|  |  | 39 @ 1 |

TABLE 1-continued

| Example Number | RHUCX1 % Inh. at Dose (μM) | RHUCX2 % Inh. at Dose (μM) |
|---|---|---|
| 80 | 41 @ 10 | (0.064) |
|  | 37 @ 1 |  |
| 81 | 6 @ 100 | 97 @ 1 |
|  |  | 44 @ 0.1 |
| 84 | 49 @ 10 | 87 @ 0.3 |
|  | 9 @ 1 |  |
| 88 | 0 @ 100 | 97 @ 1,000 |
|  |  | 35 @ 0.1 |
| 89 | 62 @ 30 | (0.35) |
|  | 40 @ 10 |  |
| 97 | 35 @ 100 | (0.332) |
| 100 | 62 @ 10 | 100 @ 10 |
|  | 65 @ 1 | 61 @ 0.1 |
| 105 | 85 @ 1 | 98 @ 1 |
|  |  | 52 @ 0.1 |
| 106 | 19 @ 200 | (0.135) |
| 107 | 88 @ 10 | 86 @ 1 |
|  | 50 @ 1 | 36 @ 0.1 |
| 108 | 0 @ 100 | (0.279) |
| 109 | 6 @ 100 | (0.147) |
| 110 | 5 @ 100 | 93 @ 1 |
|  |  | 50 @ 0.1 |
| 111 | 13 @ 100 | (0.052) |
| 112 | 5 @ 100 | (0.136) |
| 118 | 31 @ 100 | 72 @ 0.1 |
|  |  | 17 @ 0.01 |
| 119 | (0.178) | (0.027) |
| 120 | 15 @ 100 | 97 @ 1 |
|  |  | 45 @ 0.1 |
| 121 | 0 @ 100 | (0.005) |
| 122 | 1 @ 100 | (0.285) |
| 124 | 26 @ 100 | (0.044) |
| 127 | 50 @ 10 | 74 @ 1 |
|  | 30 @ 1 | 51 @ 0.1 |
| 128 | 14 @ 100 | (0.477) |
| 132 | 93 @ 1 | 88 @ 1 |
|  |  | 43 @ 0.1 |
| 133 | 23 @ 100 | (0.358) |
| 134 | 54 @ 100 | (0.053) |
|  | 35 @ 10 |  |
| 140 | (3.06) | (0.022) |
| 141 | 55 @ 100 | 99 @ 1 |
|  | 62 @ 10 | 95 @ 0.1 |
| 142 | 80 @ 10 | 96 @ 1 |
|  | 53 @ 1 | 45 @ 0.1 |
|  |  | 32 @ 0.01 |
| 143 | 62 @ 100 | (0.076) |
|  | 43 @ 10 |  |
| 144 | (0.058) | 88 @ 1 |
|  |  | 78 @ 0.1 |
|  |  | 65 @ 0.01 |
| 145 | (0.238) | 86 @ 0.1 |
|  |  | 56 @ 0.01 |
| 146 | 82 @ 10 | 100 @ 1 |
|  | 53 @ 1 | 73 @ 0.1 |
| 147 | (0.067) | 100 @ 1 |
|  |  | 64 @ 0.1 |
|  |  | 0 @ 0.03 |
| 149 | 45 @ 10 | (0.003) |
|  | 40 @ 1 |  |
| 150 | 56 @ 100 | 100 @ 0.1 |
|  | 39 @ 10 |  |
| 153 | 54 @ 100 | (0.062) |
|  | 35 @ 10 |  |
| 154 | (0.126) | (0.018) |
| 165 | 0 @ 100 | (1.08) |
| 166 | 3 @ 100 | (0.199) |
| 168 | 0 @ 100 | 85 @ 1 |
|  |  | 93 @ 0.1 |
| 171 | 0 @ 100 | 82 @ 10 |
|  |  | 74 @ 1 |
|  |  | 61 @ 0.1 |
| 178 | 6 @ 100 | 92 @ 1,000 |
|  |  | 34 @ 10 |
| 180 | 8 @ 100 | 78 @ 1 |
|  |  | 48 @ 0.1 |

TABLE 1-continued

| Example Number | RHUCX1 % Inh. at Dose (μM) | RHUCX2 % Inh. at Dose (μM) |
|---|---|---|
| 182 | (5.01) | (0.07) |
| 183 | 25 @ 100 | 97 @ 1 |
| | | 51 @ 0.1 |
| 187 | 2 @ 100 | (0.094) |
| 188 | 18 @ 100 | (0.526) |
| 190 | (1.88) | (0.134) |
| 194 | 35 @ 100 | 90 @ 10 |
| | | 73 @ 1 |
| | | 72 @ 0.1 |
| 198 | 10 @ 100 | 68 @ 1 |
| | | 23 @ 0.1 |
| 207 | | 97 @ 1 |
| | | 81 @ 0.1 |
| 209 | 0 @ 100 | 79 @ 1 |
| | | 55 @ 0.1 |
| | | 40 @ 0.01 |
| 213 | 0 @ 100 | (0.812) |
| 219 | 20 @ 100 | 90 @ 1 |
| | | 75 @ 0.1 |
| 220 | 51 @ 100 | 96 @ 1 |
| | 38 @ 1 | 90 @ 0.1 |
| 226 | 0 @ 100 | (1.09) |
| 228 | 7 @ 100 | (0.209) |
| 230 | 4 @ 100 | (0.215) |
| 231 | 7 @ 100 | 90 @ 1 |
| | | 68 @ 0.1 |
| 232 | 23 @ 100 | (0.024) |
| 234 | 0 @ 100 | (0.328) |
| 235 | 22 @ 100 | (0.21) |
| 237 | 54 @ 10 | 89 @ 0.1 |
| | 44 @ 1 | |
| 240 | 14 @ 100 | (0.297) |
| 241 | 0 @ 100 | (0.028) |
| 245 | 9 @ 100 | (1.38) |
| 246 | 0 @ 100 | (0.054) |
| 247 | 72 @ 10 | 99 @ 10 |
| | 55 @ 1 | 71 @ 1 |
| | | 51 @ 0.1 |
| 248 | 13 @ 100 | (0.08) |
| 249 | 6 @ 100 | 98 @ 1 |
| | | 68 @ 0.1 |
| | | 43 @ 0.01 |
| 252 | 0 @ 100 | 87 @ 1 |
| | | 26 @ 0.01 |
| 253 | 77 @ 100 | (0.272) |
| | 29 @ 10 | |
| 254 | 7 @ 100 | 84 @ 1 |
| | | 48 @ 0.1 |
| 256 | 0 @ 100 | (0.134) |
| 257 | 0 @ 100 | (0.04) |
| 260 | 8 @ 100 | 2 @ 10 |
| 261 | 0 @ 200 | (0.161) |
| 262 | 15 @ 100 | (0.432) |
| 263 | 1 @ 100 | 85 @ 10 |
| | | 76 @ 1 |
| | | 53 @ 0.1 |
| 265 | 8 @ 100 | 53 @ 10 |
| | | 48 @ 1 |
| | | 33 @ 0.1 |
| 272 | 0 @ 100 | 70 @ 1 |
| | | 55 @ 0.1 |
| 273 | 16 @ 100 | 54 @ 10 |
| | | 42 @ 1 |
| 278 | 36 @ 100 | 96 @ 1 |
| | | 91 @ 0.1 |
| 279 | 0 @ 100 | 60 @ 1 |
| | | 31 @ 0.1 |
| 281 | 7 @ 100 | 71 @ 1 |
| | | 52 @ 0.1 |
| | | 47 @ 0.01 |
| 283 | 0 @ 100 | 90 @ 10 |
| | | 71 @ 1 |
| | | 54 @ 0.1 |
| 287 | 0 @ 100 | 93 @ 10 |
| | | 79 @ 1 |
| | | 25 @ 0.1 |
| 314 | 7 @ 100 | 51 @ 10 |
| | | 4 @ 1 |
| 318 | 23 @ 100 | 97 @ 1 |
| | | 77 @ 0.1 |
| 321 | 4 @ 100 | (0.192) |
| 322 | 39 @ 100 | (0.058) |
| | | 54 @ 10 |
| 323 | 1 @ 100 | (0.365) |
| 325 | | (0.199) |
| 330 | 15 @ 100 | 85 @ 1 |
| | | 72 @ 0.03 |
| | | 5 @ 0.01 |
| 335 | 5 @ 100 | (0.001) |
| 338 | 0 @ 100 | 100 @ 1 |
| | | 83 @ 0.1 |
| 339 | 2 @ 100 | (0.088) |
| 344 | 16 @ 100 | (0.897) |
| 345 | 0 @ 100 | (0.242) |
| 346 | 14 @ 100 | 94 @ 1 |
| | | 76 @ 0.1 |
| | | 48 @ 0.01 |
| 347 | 11 @ 100 | (0.075) |
| 349 | 0 @ 100 | (0.086) |
| 351 | 3 @ 100 | 91 @ 1 |
| | | 63 @ 0.1 |
| | | 42 @ 0.01 |
| 352 | 0 @ 100 | (0.154) |
| 353 | 6 @ 100 | (0.826) |
| 354 | 0 @ 100 | 45 @ 10 |
| | | 45 @ 1 |
| | | 36 @ 0.1 |
| 355 | 0 @ 100 | 79 @ 10 |
| | | 66 @ 1 |
| | | 46 @ 0.1 |
| 358 | 30 @ 100 | (2.45) |
| 361 | 3 @ 100 | (0.011) |
| 362 | 1 @ 100 | 84 @ 10 |
| | | 49 @ 1 |
| 364 | 0 @ 100 | 86 @ 1 |
| | | 0 @ 0.1 |
| 366 | 0 @ 100 | (0.03) |
| 367 | 0 @ 100 | (0.077) |
| 368 | 13 @ 100 | 96 @ 1 |
| | | 65 @ 0.1 |
| 369 | 0 @ 100 | 70 @ 1 |
| | | 48 @ 0.1 |
| 370 | 8 @ 100 | (0.048) |
| 371 | 8 @ 100 | (0.166) |
| 372 | 0 @ 100 | 94 @ 10 |
| | | 88 @ 1 |
| | | 59 @ 0.1 |
| 374 | 2 @ 100 | (0.02) |
| 375 | 46 @ 100 | (0.18) |
| | 31 @ 10 | |
| 376 | 12 @ 100 | (0.027) |
| 381 | 0 @ 100 | (0.188) |
| 384 | 82 @ 100 | 99 @ 1 |
| | 49 @ 10 | 78 @ 0.1 |
| 386 | 58 @ 100 | 83 @ 1 |
| | | 63 @ 0.1 |
| | 47 @ 1 | 58 @ 0.01 |
| 387 | 57 @ 10 | 76 @ 1 |
| | 60 @ 1 | 65 @ 0.1 |
| | | 56 @ 0.01 |
| 388 | 74 @ 10 | (0.049) |
| | 36 @ 1 | |
| 390 | 88 @ 10 | 99 @ 10 |
| | 45 @ 1 | 72 @ 1 |
| | | 60 @ 0.1 |
| 392 | 56 @ 100 | 82 @ 0.1 |
| | 35 @ 10 | 65 @ 0.01 |
| 393 | 15 @ 100 | 85 @ 1 |
| | | 58 @ 0.1 |
| 394 | 86 @ 100 | 94 @ 1 |
| | 38 @ 10 | 64 @ 0.1 |
| | | 20 @ 0.01 |

TABLE 1-continued

| Example Number | RHUCX1 % Inh. at Dose (μM) | RHUCX2 % Inh. at Dose (μM) |
|---|---|---|
| 395 | 91 @ 100 | 93 @ 1 |
|  | 35 @ 10 | 77 @ 0.1 |
|  |  | 34 @ 0.01 |
| 396 | 22 @ 100 | (0.059) |
| 397 | 25 @ 100 | 93 @ 1 |
|  |  | 58 @ 0.1 |
|  |  | 39 @ 0.01 |
| 398 | 26 @ 100 | (0.202) |
| 400 | 27 @ 100 | (0.142) |
| 401 | (0.753) | 96 @ 1 |
|  |  | 62 @ 0.1 |
|  |  | 48 @ 0.01 |
| 402 | 89 @ 1 | (0.221) |
| 403 | (150.76) | 92 @ 1 |
|  |  | 64 @ 0.1 |
|  |  | 36 @ 0.01 |
| 404 | 77 @ 100 | 92 @ 0.1 |
|  | 47 @ 10 | 57 @ 0.01 |
| 405 | 90 @ 100 | (0.198) |
|  | 61 @ 10 |  |
| 406 | 23 @ 100 | 100 @ 1 |
|  |  | 64 @ 0.1 |
|  |  | 18 @ 0.01 |
| 407 | 32 @ 100 | (0.17) |
| 408 | 0 @ 100 | (0.279) |
| 410 | 48 @ 100 | 67 @ 0.035 |
|  | 1 @ 10 | 47 @ 0.017 |
| 411 | 96 @ 10 | (0.009) |
|  | 81 @ 1 |  |
| 412 | 31 @ 100 | (0.002) |
| 413 | 0 @ 100 | (0.11) |
| 414 | 0 @ 100 | 87 @ 1 |
|  |  | 76 @ 0.1 |
| 418 | 33 @ 100 | 85 @ 1 |
|  |  | 52 @ 0.1 |
|  |  | 53 @ 0.025 |
| 419 | 12 @ 100 | (0.1) |
| 420 | 29 @ 100 | (0.323) |
| 421 | (0.269) | 92 @ 1 |
|  |  | 81 @ 0.1 |
|  |  | 38 @ 0.01 |
| 422 | 53 @ 100 | 52 @ 1 |
|  | 82 @ 10 | 37 @ 0.1 |
|  | 76 @ 1 |  |
| 423 | 0 @ 100 | 87 @ 1 |
|  |  | 68 @ 0.1 |
|  |  | 36 @ 0.01 |
| 424 | 7 @ 100 | 75 @ 1 |
|  |  | 58 @ 0.1 |
|  |  | 33 @ 0.01 |
| 425 | 12 @ 100 | 69 @ 0.1 |
|  |  | 31 @ 0.01 |
| 426 | 1 @ 100 | (0.057) |
| 434 | 0 @ 100 | (0.081) |
| 437 | 16 @ 100 | (0.124) |
| 438 | 0 @ 100 | (0.127) |
| 440 | 20 @ 100 | 84 @ 1 |
|  |  | 59 @ 0.1 |
|  |  | 22 @ 0.01 |
| 442 | 55 @ 100 | 90 @ 0.1 |
|  |  | 56 @ 0.01 |
| 443 | 35 @ 100 | 86 @ 0.1 |
|  |  | 74 @ 0.01 |
| 444 | 0 @ 100 | 83 @ 1 |
|  |  | 62 @ 0.1 |
|  |  | 14 @ 10 |
| 445 | (56.62) | (0.069) |
| 446 | 0 @ 200 | (0.373) |
| 447 | 0 @ 100 | 90 @ 1 |
|  |  | 57 @ 0.1 |
|  |  | 35 @ 0.01 |
| 449 | 5 @ 200 | (0.129) |
| 450 | 29 @ 100 | 87 @ 1 |
|  |  | 40 @ 0.1 |
|  |  | 22 @ 0.01 |
| 451 | 10 @ 100 | (0.470) |
| 452 | 14 @ 100 | 15 @ 1 |
| 467 | 4 @ 100 | (1.96) |
| 475 | 0 @ 100 | (0.71) |
| 471 | (3.68) | (0.49) |
| 478 | 33 @ 100 | (0.81) |
| 528 | (3.4) | (0.72) |

IL-1β Induced PGE$_2$ Production in WISH Cells

Human amnionic WISH cells were grown to 80% confluence in 48 well plates. Following removal of the growth medium and two washings with Gey's Balanced Salt Solutn, 5 ng IL-1β/ml (UBI, Lake Placid, N.Y.) was added to the cells with or without test compound in DMSO (0.01% v/v) in Neuman-Tytell Serumless Medium (GIBCO, Grand Island, N.Y.). Following an 18 hour incubation to allow for the maximal induction of PGHS-2, the conditioned medium was removed and assayed for PGE$_2$ content by EIA analysis as described above.

Monocyte U937 (ATCC, Rockville, Md.) cells were grown in a similar fashion to the WISH cells. After incubation, the conditioned medium was removed and assayed for Cox-1 content by EIA analysis as described above.

The data illustrating the inhibition of prostaglandin biosynthesis in vitro by compounds of this invention is shown in Table 2. U937 values indicate Cox-1 percent inhibition at the particular micromolar dose level while partenthetical values indicate IC$_{50}$ values. WISH cell values indicate percent inhibition at the particular micromolar dose level while parenthetical values indicate IC$_{50}$ values.

Human Whole Platelet Cyclooxygenase-1 Assay (HWCX)

Blood from normal healthy volunteers is collected into tubes containing ACD (acid citrate dextrose) as the anticoagulant. This blood is centrifuged at 175×g to prepare platelet rich plasma. The platelet rich plasma is then centrifuged at 100×g to pellet the white blood cells, leaving the platelets in the supernatant. The supernatant is layered on a cushion of 0.7 mL of 10% bovine serum albumin in Tyrodes solution (Gibco; Grand Island, N.Y.) and then centrifuged at 1000×g. The resulting supernatant from this centrifugation is then removed and 11 mL of Tyrodes solution is added to the remaining pellet of platelets. The platelets are then aliquoted at 120 μl into a 96 well plate. Experimental compounds are added and allowed to pre-incubate for 10 minutes. At the end of this pre-incubation period, the calcium ionophore A23187 is added to a final concentration of 8.8 μM and the incubation is continued for ten minutes. The reaction is stopped by adding cold 6 mM EDTA, the incubation mixture is centrifiged at 220×g, and the supernatants are then analyzed for thromboxane using a commercial kit from Cayman Chemical (Ann Arbor, Mich.).

TABLE 2

| Example Numbers | U937 % Inhib. at Dose (μM) | HWPX % Inhib. at Dose (μM) | Wish % Inhib. at Dose (μM) |
|---|---|---|---|
| 10 |  | (4.1) | (0.014) |
| 20 | 33 @ 1 |  | (0.001) |

TABLE 2-continued

| Example Numbers | U937 % Inhib. at Dose (μM) | HWPX % Inhib. at Dose (μM) | Wish % Inhib. at Dose (μM) |
|---|---|---|---|
| 24 | (0.19) | | (0.007) |
| 43 | | 86 @ 10 | (0.008) |
| | | 9 @ 1 | |
| 53 | | 78 @ 10 | 90 @ 0.1 |
| | | 8 @ 1 | 44 @ 0.01 |
| 65 | | | (0.02) |
| 69 | | (1.14) | (0.02) |
| 72 | | (25) | (0.072) |
| 75 | | 84 @ 10 | (0.001) |
| | | 0 @ 3 | |
| 77 | | (8.8) | (0.126) |
| 85 | | | (0.47) |
| 86 | | | 52 @ 1 |
| | | | 47 @ 0.01 |
| 89 | (3.8) | (2.1) | (0.05) |
| 100 | | (0.13) | (0.02) |
| 102 | | | (0.05) |
| 105 | | 62 @ 1 | (0.018) |
| 106 | | (17.5) | (0.03) |
| 108 | | (8) | (0.097) |
| 109 | | (2.693) | (0.018) |
| 119 | | (0.076) | (0.001) |
| 120 | | 74 @ 3 | (0.025) |
| | | 58 @ 1 | |
| 121 | | | (0.041) |
| 123 | | 90 @ 1 | (0.001) |
| | | 29 @ .1 | |
| 126 | | | (0.05) |
| 129 | | | (0.04) |
| 132 | | | 100 @ 0.1 |
| | | | 36 @ 0.01 |
| 140 | | (0.773) | (0.01) |
| 141 | | 56 @ 0.3 | (0.004) |
| 142 | | (7.53) | (0.088) |
| 143 | | | (0.007) |
| 145 | | 72 @ 1 | (0.009) |
| | | 30 @ .3 | |
| 146 | | 84 @ 10 | (0.044) |
| | | 46 @ 3 | |
| 147 | | 84 @ 0.3 | (0.029) |
| 148 | | 51 @ 0.3 | (0.042) |
| 149 | | 89 @ 10 | (0.03) |
| | | 34 @ 3 | |
| 152 | | | (0.029) |
| 153 | | (2.95) | (0.046) |
| 154 | | 81 @ .3 | 100 @ 0.1 |
| | | 48 @ .1 | 69 @ 0.01 |
| 160 | | (7.2) | (0.03) |
| 162 | | | (0.034) |
| 165 | | (1.9) | (0.030) |
| 166 | | (9.4) | (0.02) |
| 168 | | 47 @ 1 | (0.009) |
| 171 | | | 90 @ 1 |
| | | | 56 @ 0.1 |
| 187 | | (12.6) | (0.015) |
| 189 | | 31 @ 100 | (0.041) |
| 190 | | (9.96) | (0.03) |
| 191 | | | (0.06) |
| 194 | | (28.09) | (0.069) |
| 198 | | | (0.184) |
| 203 | | | 77 @ 1 |
| | | | 23 @ 0.1 |
| 207 | | | (0.068) |
| 228 | | (19.6) | (0.086) |
| 241 | | | (0.0474) |
| 243 | | | (0.03) |
| 244 | | (3.67) | (0.019) |
| 245 | | | (0.046) |
| 246 | | | (0.02) |
| 247 | | (7.76) | (0.02) |
| 248 | | 82 @ 30 | (0.005) |
| | | 17 @ 10 | |
| 252 | | | (0.044) |
| 256 | | (4.7) | (0.028) |
| 261 | | (34) | (0.099) |
| 271 | | | 52 @ 1 |
| | | | 15 @ 0.1 |
| 278 | | | (0.07) |
| 279 | | | (0.391) |
| 287 | | | (0.16) |
| 317 | | | (0.027) |
| 320 | | 29 @ 3 | 78 @ .1 |
| | | | 15 @ .01 |
| 321 | | | 50 @ 0.01 |
| 322 | | | (0.026) |
| 323 | | | 57 @ 0.01 |
| 324 | | | (0.047) |
| 325 | | (2.3) | (0.04) |
| 326 | | | (0.05) |
| 330 | | (16.7) | (0.005) |
| 335 | | | (0.023) |
| 338 | | (14.93) | (0.004) |
| 339 | | (0.393) | (0.026) |
| 343 | | (0.191) | (0.016) |
| 344 | | | (0.1) |
| 345 | | | (0.03) |
| 349 | | 34 @ 100 | (0.041) |
| 352 | | (5.5) | (6.048) |
| 358 | | | 69 @ 1 |
| | | | 0 @ 0.1 |
| 366 | | (1.615) | (0.002) |
| 367 | | 50 @ 1 | (0.018) |
| | | 8 @ .3 | |
| 368 | | (13.7) | 64 @ 0.03 |
| | | | 33 @ 0.01 |
| 370 | | (8.4) | (0.02) |
| 375 | | (2.04) | (0.089) |
| 381 | | 31 @ 30 | (0.075) |
| | | 91 @ 100 | |
| 385 | | (2.18) | (0.023) |
| 388 | | 0 @ .3 | (0.032) |
| 392 | | (1.95) | (0.02) |
| 394 | | | (0.019) |
| 396 | | (12.7) | (0.02) |
| 397 | | (13.8) | (0.04) |
| 399 | | | 82 @ 0.1 |
| | | | 39 @ 0.03 |
| 400 | | (0.3) | (0.026) |
| 401 | | (0.32) | (0.017) |
| 403 | | (0.902) | (0.018) |
| 404 | | (0.337) | 96 @ 0.1 |
| | | | 58 @ 0.01 |
| 406 | | (1.61) | (0.026) |
| 408 | | | (0.029) |
| 410 | | | (0.053) |
| 414 | | | 54 @ 1 |
| | | | 46 @ 0.1 |
| 418 | | (14.25) | (0.25) |
| 430 | | 34 @ 10 | (0.054) |
| | | 89 @ 100 | |
| 442 | | | (0.42) |
| 445 | | 100 @ 100 | (0.025) |
| | | 22 @ 10 | |
| 446 | | (24.4) | (0.02) |
| 449 | | (40) | (0.089) |
| 450 | | | (0.05) |
| 451 | | (22.4) | (0.15) |
| 452 | | | 56 @ 1 |
| | | | 1 @ 0.1 |
| 475 | | 50 @ 100 | (0.44) |
| 467 | | | (0.135) |
| 471 | | (0.32) | (0.04) |
| 478 | | (0.5) | (0.108) |
| 528 | | (3.5) | (0.054) |

Carrageenan Induced Paw Edema (CPE) in Rats

Hindpaw edema was induced in male rats as described by Winter et al., Proc. Soc. Exp. Biol. Med., 1962, 111, 544. Briefly, male Sprague-Dawley rats weighing between 170 and 190 g were administered test compounds orally 1 hour prior to the subplantar injection of 0.1 ml of 1% sodium cargeenan (lambda carrageenan, Sigma Chemical Co., St Louis, Mo.) into the right hindpaw. Right paw volumes (ml) were measured immediately following injection of carrageenan for baseline volume measurements using a Buxco plethysmograph (Buxco Electronics, Inc., Troy, N.Y.). Three hours after the injection of carrageenan, right paws were remeasured and paw edema calculated for each rat by subtracting the zero time reading from the 3 hour reading. Data are reported as mean percent inhibition +/−SEM. Statistical significance of results was analyzed by Dunnetts multiple comparison test where p<0.05 was considered statistically significant.

RAT Carrageenan Pleural Inflammation (CIP) Model

Pleural inflammation was induced in male adrenalectomized Sprague-Dawley rats following the meth of Vinegar et al., Fed. Proc. 1976, 35, 2447–2456. Animals were orally dosed with experimental compounds, 30 minutes prior to the intrapleural injection of 2% lambda carrageenan (Sigma Chemical Co., St. Louis Mo.). Four hours later the animals were euthanized and the pleural cavities lavaged with ice cold saline. The lavage fluid was then added to two volumes of ice cold methanol (final methanol concentration 66%) to lyse cells and precipitate protein. Eicosanoids were determined by EIA as described above.

The data illustrating the inhibition of prostaglandin biosynthesis in vivo by the compounds of this invention is shown in Table 3. Values reported are percent inhibition at 10 milligrams per kilogram body weight.

Carrageenan induced air pouch prostaglandin biosynthesis model (CAP) Air pouches are formed in the backs of male Sprague Dawley rats by injecting 20 mL of sterile air on day 0. Three days later the pouch was reinflated with an additional 10 mL of sterile air. On day 7, 1 mL of saline containing 0.2% lambda carrageenan (Sigma Chemical Co.) is injected into the pouch to induce the inflammatory reaction that is characterized by the release of prostaglandins. Test compounds are dosed at 0.1 to 10 mg/kg 30 minutes prior to carrageenan. Four hours after the carrageenan injection the pouch is ravaged and levels of prostaglandins are determined by enzyme immuno-assay using commercially available kits. Percent inhibitions are calculated by comparing the response in animals which have received vehicle to those which received compound. Values for Cox-2 inhibition that are parenthetical indicate $ED_{50}$ values.

The data illustrating the inhibition of prostaglandin biosynthesis in vivo by the compounds of this invention is shown in Table 3. Values reported are percent inhibition at 10 milligrams per kilogram body weight for CIP and CPE tests and at 3 milligrams per kilogram body weight for CAP testing.

TABLE 3

| Example Numbers | CIP % Inhib. @ 10 mpk | CPE % Inhib. @ 10 mpk | CAP % Inhib. @ 3 mpk |
|---|---|---|---|
| 10 | 44 | | |
| 12 | 42 | 25 | |
| 34 | 36 | 31 | |
| 54 | 31 | 30 | |
| 58 | 42 | 14 | 67 |
| 62 | 57 | 21 | |
| 66 | 59 | 7 | 0 |
| 67 | 40 @ 3 mpk | | |
| 68 | 64 | 40.3 | |
| 69 | 61 | 45.5 $ED_{30} = 5.4$ | 87 |
| 72 | | | |
| 73 | | 46 | 29 |
| 74 | 46.5 | 18 | 34 |
| 77 | 51 | 21 | |
| 80 | 60 | 28.5 | 91 |
| 89 | 68.3 $ED_{50} = 3.4$ | 45.5 | 94 |
| 106 | | | 47 |
| 109 | | 13 | 71 |
| 112 | | 21 | 42.5 |
| 119 | 82 | 27 | 76 |
| 120 | 5 | 11 | |
| 121 | 19 | 8 | |
| 123 | | | 23 |
| 143 | | | 59 |
| 153 | | | 51 |
| 160 | 56 | 35 | |
| 166 | 40 | | 59 |
| 168 | 0 | 6 | |
| 180 | 34.5 | | |
| 182 | 59 | 27 | 98 |
| 185 | 59 | 20 | 53 |
| 187 | 51 | 28 | 30 |
| 190 | 60 | 28 | 71 |
| 205 | | | 54 |
| 226 | | 21 | 40.5 |
| 243 | | | 7 |
| 245 | | | 47 |
| 246 | | | 48 |
| 248 | | | 49 |
| 256 | | | 47 |
| 257 | | | 60 |
| 261 | | 28 | 79 |
| 330 | | | 4.5 |
| 335 | | | 45 |
| 339 | | 43 | 90.5 $ED_{50} = 0.58$ |
| 346 | | | 49.5 |
| 347 | | 27 | 66.5 |
| 349 | | | 63 |
| 351/64 | | | 0 |
| 352 | | | 89 $ED_{50} = 5.0$ |
| 353/63 | | | 0 |
| 361 | | | 65 |
| 366 | | | 63 $ED_{50} = 1.5$ |
| 367 | | | 48 |
| 375 | | 47 | 77.5 $ED_{50} = 0.57$ |
| 376 | | 17 | 77.5 |
| 378 | | | 59 |
| 384/33 | 51 | 15 | 51 |
| 385 | | | 65 |
| 388 | | 28 | 80 |
| 390 | | | 60 |
| 391 | | | 61 |
| 392 | | | 60 |
| 394 | | | 70 |
| 395 | | | 71 |
| 396 | | 23 | 85 |
| 397 | | | 70 |
| 400 | 65 | 41 | 82.5 |
| 403 | | 43 | 68.5 $ED_{50} = 0.35$ |
| 405 | | | 53 |
| 406 | | 23 | 66.5 |
| 407 | | | 61 |
| 419 | | | 48 |
| 427 | | | 78 |

TABLE 3-continued

| Example Numbers | CIP % Inhib. @ 10 mpk | CPE % Inhib. @ 10 mpk | CAP % Inhib. @ 3 mpk |
|---|---|---|---|
| 445 | | 15 | 73 |
| 446 | | 44 | 92 |
| 449 | | 23 | $ED_{50} = 0.5$ 76 |
| 450 | | | $ED_{50} = 1.8$ 86 |
| 451 | | $ED_{30} = 0.82$ | 80.5 $ED_{50} = 0.7$ |
| 452 | | | 71 |
| 459 | | | 45 |
| 464 | | | 70 |
| 475 | | 33 | $ED_{50} = 1.4$ |
| 467 | | $ED_{30} = 17$ | $ED_{50} = 0.4$ |
| 471 | | 41 | $ED_{50} = 0.9$ |
| 478 | | 26 | 75 |
| 528 | | 40 | $ED_{50} = 1.4$ |

Human Whole Blood Assays

Cyclooxygenase-1

Heparin anticoagulatd blood was incubated with drugs dissolved in DMSO. The samples are incubated at 37 degrees Celsius for 4.5 hours after which calcium ionophore at a final concentration of 30 μM was added and the mixture allowed to incubate for 30 minutes. The reaction was stopped with the addition of EGTA and cold methanol (50% final concentration). After 18 hours at −70 degrees Celsius, the plates were centrifuged and supernatants analyzed for $TXB_2$.

Cyclooxygenase-2

Heparin anticoagulated blood was incubated with drugs dissolved in DMSO. The samples are incubated at 37 degrees Celsius for 15 minutes. E. coli lipopolysaccaride (LPS) 5 μg/ml was then added and the samples incubated for 5 hours. The reaction was stopped with the addition of EGTA and cold methanol (50% final concentration). After 18 hours at −70 degrees Celsius, the plates were centrifuged and supernatants analyzed for $TXB_2$.

Example 451—Human whole blood Cox-1 $IC_{50}$=29.12 micromolar

Example 451—Human whole blood Cox-2 $IC_{50}$=0.47 micromolar

Example 471—Human whole blood Cox-1=55.5% at 30 micromolar

Example 471—Human whole blood Cox-2=85% at 0.03 micromolar

The 4-hydroxyalkoxy-3(2H)-pyridazinone Cox-2 inhibition and in vivo activity has been found to be suprisingly good. In addition, when compared to the 4-alkoxy-3(2H)-pyridazinones, the hydroxyalkoxy compounds typically possess a superior oral pharmacokinetic profile, such as better plasma half-life, plasma concentration maxima, and area under the curve. For example, Example 375 shows a 14 day plasma micromolar concentration (based on 10 mg/kg dosage) of 0.0 while Example 451 shows a 3.43 micromolar level. In addition, the half life of Rat IV (3 mg/kg) for Example 375 was 2.9 while Example 451 showed 5.2. The AUC value (micromolar/hour) for Example 375 was 1.8 while Example 451 was 69.

It is anticipated that the 4-hydroxyalkoxy compounds are preferred to parent alkoxy compounds with regard to once-a-day dosing to achieve predictable exposure levels across a wide range of doses while producing an antiinflammatory effect.

Pharmaceutical Compositions

The present invention also provides pharmaceutical compositions which comprise compounds of the present invention formulated together with one or more non-toxic pharmaceutically acceptable carriers. The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the procedures and judgements well known to one skilled in the art. The pharmaceutical compositions of this invention can be administered to humans and other animals orally, rectally, parenterally, intracistemally, intravaginally, intraperitoneally, topically (as by powders, ointments, or drops), bucally, or as an oral or nasal spray.

The compounds of the present invention may be potentially useful in the treatment of several illness or disease states such as inflammatory diseases, dysmennorhea, asthma, premature labor, adhesions and in particular pelvic adhesions, osteoporosis, and ankylosing spondolitis. Current Drugs Ltd, ID Patent Fast Alert, AG16, May 9, 1997.

The compounds of the present invention may also be potentially useful in the treatment of cancers, and in particular, colon cancer. Proc. Natl. Acad. Sci., 94, pp. 3336–3340, 1997.

The compounds of the present invention may be useful by providing a pharmaceutical composition for inhibiting prostaglandin biosynthesis comprising a therapeutically effective amount of a compound of formula I or a pharmaceutically acceptable salt, ester, or prodrug thereof, and a pharmaceutically acceptable carrier.

In addition, the compounds of the present invention may be useful by providing a method for inhibiting prostaglandin biosynthesis comprising administering to a mammal in need of such treatment a therapeutically effective amount of a compound of formula I or a pharmaceutically acceptable salt, ester, or prodrug thereof.

In addition, the compounds of the present invention may be useful by providing a method for treating pain, fever, inflamation, rheumatoid arthritis, osteoarthritis, adhesions, and cancer comprising administering to a mammal in need of such teratmnent a therapeutically effective amount of a compound of formula I.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (such as, for example, cottonseed, groundnut, corn, germ, olive, castor, sesame oils, and the like), glycerol, tetrahydrofurfuryl alcohol, poly-ethyl-ene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, such as, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, such as, for example, a solution in 1,3-butanediol. Among the acceptable vehicles and solvents that may be employed are water, Ringer's solution, isotonic sodium chloride solution, and the like. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectable preparations.

The injectable formulations can be sterilized by any method known in the art, such as, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and thus melt in the rectum or vaginal cavity and release the active compound.

Solid dosage forms for oral administration include capsules, tablets, pills, powders, and granules. In such solid dosage forms, the active compound is usually mixed with at least one inert, pharmaceutically acceptable excipient or carrier such as, for example, sodium citrate or dicalcium phosphate and/or a) fillers or extenders such as, for example, starches, lactose, sucrose, glucose, mannitol, and silicic acid, b) binders such as, for example, carboxymethylcellulose, alginates, gelatin, polyvinylpyrrolidinone, sucrose, and acacia, c) humectants such as, for example, glycerol, d) disintegrating agents such as, for example, agar-agar, calcium carbonate, potato or tapioca starch, alginic acid, certain silicates, and sodium carbonate, e) solution retarding agents such as, for example, paraffin, f) absorption accelerators such as, for example, quaternary ammonium compounds, g) wetting agents such as, for example, cetyl alcohol and glycerol monostearate, h) absorbents such as, for example, kaolin and bentonite clay, and) lubricants such as, for example, talc, calcium stearate, magnesium stearate, solid polyethylene glycols, sodium lauryl sulfate, and mixtures thereof In the case of capsules, tablets and pills, the dosage form may also comprise buffering agents.

Solid compositions of a similar type may also be employed as fillers in soft and hard-filled gelatin capsules using such excipients such as, for example, lactose or milk sugar as well as high molecular weight polyethylene glycols and the like.

Solid compositions of a similar type may also be employed as fillers in soft and hard-filled gelatin capsules using excipients such as, for example, lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulation art. In such solid dosage forms the active compound may be admixed with at least one inert diluent such as, for example, sucrose, lactose or starch. Such dosage forms may also comprise, as is normal practice, additional substances other than inert diluents, e.g., tableting lubricants and other tableting aids such as, for example, magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as, for example, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as, for example, lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in a suitable medium. Absorption enhancers can also be used to increase the flux of the compound across the skin. The rate can be controlled by either providing a rate controlling membrane or by dispersing the compound in a polymer matrix or gel.

According to the methods of treatment of the present invention, a patient, such as a human or mammal, is treated by administering to the patient a therapeutically effective amount of a compound of the invention, in such amounts and for such time as is necessary to achieve the desired result. By a "therapeutically effective amount" of a compound of the invention is meant a sufficient amount of the compound to provide the relief desired, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.001 to about 1000 mg/kg body weight daily or more preferably from about 0.1 to about 100 mg/kg body weight for oral administration or 0.01 to about 10 mg/kg for parenteral administration daily. Single dose compositions may contain such amounts or submultiples thereof to make up the daily dose.

The amount of active ingredient that may be combined with the carrier materials to produce a single dosage form will vary depending upon the host treated and the particular mode of administration.

The reagents required for the synthesis of the compounds of the invention are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA); Alfa Aesar (Ward Hill, Mass. 01835–9953); Eastman Chemical Company (Rochester, N.Y. 14652–3512); Lancaster Synthesis Inc. (Windham, N.H. 03087–9977); Spectrum Chemical Manufacturing Corp. (Janssen Chemical) (New Brunswick, N.J. 08901); Pfaltz and Bauer (Waterbury, Conn. 06708). Compounds which are not commercially available can be prepared by employing known methods from the chemical literature.

What is claimed is:
1. A compound of formula I:

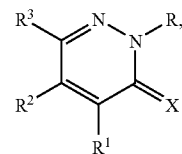

or pharmaceutically acceptable salt or ester thereof, wherein
X is O;
R is alkyl or phenyl optionally substituted with 1, 2, 3, 4, or 5 substituents each independently selected from the group consisting of halogen, alkyl, and haloalkyl;
$R^1$ is selected from the group consisting of carboxyalkylcarbonyloxyalkoxy, aminoalkylcarbonyloxyalkoxy, and phosphonatoalkoxy;
$R^3$ is hydrogen;
$R^2$ is selected from the group consisting of

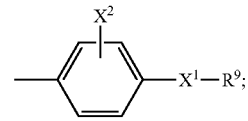

$X^1$ is $S(O)_2$;
$X^2$ is selected from the group consisting of hydrogen, alkyl and halogen; and
$R^9$ is selected from the group consisting of alkyl and amino.

2. A compound of claim 1 wherein R is selected from the group consisting of tert-butyl, difluorophenyl, fluorophenyl, chlorophenyl, bromophenyl, trifluoromethylphenyl, chlorofluorophenyl, dichlorophenyl, 3-trifluoromethyl-4-fluorophenyl, and bromofluorophenyl.

3. A compound according to claim 1 selected from the group consisting of
2-(tert-butyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;
3-({2-(3,4-difluorophenyl)-5-[4-(methylsulfonyl)phenyl]-3-oxo-2,3-dihydro-4-pyridazinyl}oxy)-1,1-dimethylpropyl dihydrogen phosphate;
3-({2-(4-fluorophenyl)-5-[4-(methylsulfonyl)phenyl]-3-oxo-2,3-dihydro-4-pyridazinyl}oxy)-1,1-dimethylpropyl dihydrogen phosphate;
3-({2-(4-chlorophenyl)-5-[4-(methylsulfonyl)phenyl]-3-oxo-2,3-dihydro-4-pyridazinyl}oxy)-1,1-dimethylpropyl dihydrogen phosphate;
3-({2-(3-fluorophenyl)-5-[4-(methylsulfonyl)phenyl]-3-oxo-2,3-dihydro-4-pyridazinyl}oxy)-1,1-dimethylpropyl dihydrogen phosphate;
3-({2-(3-chlorophenyl)-5-[4-(methylsulfonyl)phenyl]-3-oxo-2,3-dihydro-4-pyridazinyl}oxy)-1,1-dimethylpropyl dihydrogen phosphate;
3-({2-(3-bromophenyl)-5-[4-(methylsulfonyl)phenyl]-3-oxo-2,3-dihydro-4-pyridazinyl}oxy)-1,1-dimethylpropyl dihydrogen phosphate;
3-({2-(3-trifluoromethylphenyl)-5-[4-(methylsulfonyl)phenyl]-3-oxo-2,3-dihydro-4-pyridazinyl}oxy)-1,1-dimethylpropyl dihydrogen phosphate;

3-({2-(3-chloro-4-fluorophenyl)-5-[4-(methylsulfonyl) phenyl]-3-oxo-2,3-dihydro-4pyridazinyl}oxy)-1,1-dimethylpropyl dihydrogen phosphate;

3-({2-(3-fluoro-4-chlorophenyl)-5-[4-(methylsulfonyl) phenyl]-3-oxo-2,3-dihydro-4pyridazinyl}oxy)-1,1-dimethylpropyl dihydrogen phosphate;

3-({2-(3,4-dichlorophenyl)-5-[4-(methylsulfonyl)phenyl]-3-oxo-2,3-dihydro-4-pyridazinyl}oxy)-1,1-dimethylpropyl dihydrogen phosphate;

3-({2-(3-trifluoromethyl-4-fluorophenyl)-5-[4-(methylsulfonyl)phenyl]-3-oxo-2,3-dihydro-4-pyridazinyl}oxy)-1,1-dimethylpropyl dihydrogen phosphate;

3-({2-(3-bromo-4-fluorophenyl)-5-[4-(methylsulfonyl) phenyl]-3-oxo-2,3-dihydro-4-pyridazinyl}oxy)-1,1-dimethylpropyl dihydrogen phosphate;

3-({2-(tert-butyl)-5-[4-(methylsulfonyl)phenyl]-3-oxo-2,3-dihydro-4-pyridazinyl}oxy)-1,1-dimethylpropyl dihydrogen phosphate;

2-(3,4-difluorophenyl)-4-[3-{[(2R,3R)-3-carboxy-2,3-dihydroxypropanoyl]oxy}-3-methylbutoxy]-3-methyl-1-butoxy]-5-4-(methylsulfonyl)phenyl]-3(2H)-pyridazinone;

2-(4-fluorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(4-chlorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-fluorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-chlorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-bromophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-trifluoromethylphenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-chloro-4-fluorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-fluoro-4-chlorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3,4-dicholorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-trifluoromethyl-4-fluorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(3-bromo-4-fluorophenyl)-4-[3-{[(2R,3R)-3-carboxy-2,3-dihydroxypropanoyl]oxy}-3-methylbutoxy]-3-methyl-1-butoxy]-5-[4-(methylsulfonyl)phenyl]-3(2H)-pyridazinone;

2-(tert-butyl)-4-[3-(2-aminoacetyloxy)-3-methyl-1-butoxy]-5-[4-(methylsulfonyl)phenyl]-3(2H)-pyridazinone;

2-(3,4-difluorophenyl)-4-[3-(2-aminoacetyloxy)-3-methyl-1-butoxy]-5-[4-(methylsulfonyl)phenyl]-3(2H)-pyridazinone;

2-(4-fluorophenyl)-4-[3-(2-aminoacetyloxy)-3-methyl-1-butoxy]-5-[4-(methylsulfonyl)phenyl]-3(2H)-pyridazinone;

2-(4-chlorophenyl)-4-[3-(2-aminoacetyloxy)-3-methyl-1-butoxy]-5-[4-(methylsulfonyl)phenyl]-3(2H)-pyridazinone;

2-(3-fluorophenyl)-4-[3-(2-aminoacetyloxy)-3-methyl-1-butoxy]-5-[4-(methylsulfonyl)phenyl]-3(2H)-pyridazinone;

2-(3-chlorophenyl)-4-[3-(2-aminoacetyloxy)-3-methyl-1-butoxy]-5-[4-(methylsulfonyl)phenyl]-3(2H)-pyridazinone;

2-(3-bromophenyl)-4-[3-(2-aminoacetyloxy)-3-methyl-1-butoxy]-5-[4(methylsulfonyl)phenyl]-3(2H)-pyridazinone;

2-(3-trifluoromethylphenyl)-4-[3-(2-aminoacetyloxy)-3-methyl-1-butoxy]-5-[4-(methylsulfonyl)phenyl]-3 (2H)-pyridazinone;

2-(3-chloro-4-fluorophenyl)-4-[3-(2-aminoacetyloxy)-3-methyl-1-butoxy]-5-[4-(methylsulfonyl)phenyl]-3 (2H)-pyridazinone;

2-(3-fluoro-4-chlorophenyl)-4-[3-(2-aminoacetyloxy)-3-methyl-1-butoxy]-5-[4-(methylsulfonyl)phenyl]-3 (2H)-pyridazinone;

2-(3,4-dichlorophenyl)-4-[3-(2-aminoacetyloxy)-3-methyl-1-butoxy]-5-[4-(methylsulfonyl)phenyl]-3(2H)-pyridazinone;

2-(4-fluoro-3-trifluoromethylphenyl)-4-[3-(2-aminoacetyloxy)-3-methyl-1-butoxy]-5-[4-(methylsulfonyl)phenyl]-3(2H)-pyridazinone; and 2-(3-bromo-4-fluorophenyl)-4-[3-(2-aminoacetyloxy)-3-methyl-1-butoxy]-5-[4-(methylsulfonyl)phenyl]-3 (2H)-pyridazinone.

4. A pharmaceutical composition comprising a compound of claim 1 and a pharmaceutically acceptable carrier.

5. A method for treating pain, fever, inflammation, rheumatoid arthritis and osteoarthritis comprising administering a compound of claim 1.

6. A compound of formula II:

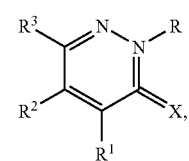

or a pharmaceutically acceptable salt or ester thereof, wherein

X is 0;

R is selected from the group consisting of pyridyl, benzothienyl, and thienyl;

$R^1$ is selected from the group of consisting of 2-hydroxy-2-propoxy and 3-hydroxy-3-methylbutoxy, 3-hydroxy-2-methyl-1-propoxy; and 3-hydroxy-1-butoxy;

$R^3$ is independently selected from the group consisting of alkoxyalkyl, alkyl, aminocarbonylalkyl, phenyl, benzyl, cyano, haloalkyl, and halogen;

$R^2$ is selected from the group consisting of

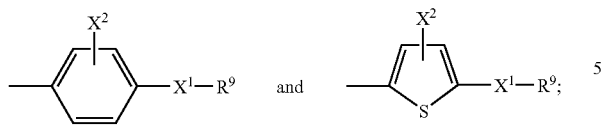

$X^1$ is $S(O)_2$;

$X^2$ is selected from the group consisting of hydrogen, alkyl and halogen; and $R^9$ is selected from the group consisting of alkyl and amino.

7. A compound according to claim 6 wherein $R^9$ is methyl or amino; and R is pyridyl.

8. A pharmaceutical composition comprising a therapeutically effective amount of the compound of claim 6 and a pharmaceutically acceptable carrier.

9. A method for treating pain, fever, inflammation, rheumatoid arthritis, and osteoarthritis comprising administering to a therapeutically effective amount of a compound of claim 6.

10. A method for treating pain, fever, inflammation, rheumatoid arthritis, and osteoarthritis comprising administering to a therapeutically effective amount of a compound of formula III

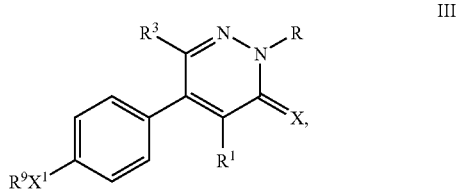

or a pharmaceutically acceptable salt or ester thereof, wherein

R is selected from the group consisting of a) alkyl, b) aryl, wherein the aryl is optionally substituted phenyl wherein said substituents are selected from alkyl, halogen, and haloalkyl, c) arylalkyl wherein the aryl of arylalkyl is optionally substituted phenyl wherein said substituents are selected from alkyl, halogen, and haloalkyl, d) haloalkyl, and e) haloalkenyl;

$R^1$ is hydroxyalkoxy; and $R^9$ is selected from the group consisting of alkyl and amino.

* * * * *

UNITED STATES PATENT AND TRADEMARK OFFICE
CERTIFICATE OF CORRECTION

| | | |
|---|---|---|
| PATENT NO. | : 7,115,591 B2 | Page 1 of 1 |
| APPLICATION NO. | : 10/464928 | |
| DATED | : October 3, 2006 | |
| INVENTOR(S) | : Lawrence A. Black et al. | |

It is certified that error appears in the above-identified patent and that said Letters Patent is hereby corrected as shown below:

Column 8, line 46, "inflamation, rheumatoid arthritis, osteoartbritis" to read as --inflammation, rheumatoid arthritis, osteoarthritis--

Column 27, line 1, "Examples of particular esters includes" to read as --Examples of particular esters include--

Column 52, line 32, "The methyl thioether compound which can be treated" to read as --The methyl thioether compound can be treated--

Column 244, line 54, "inhibition of the constituitive" to read as --inhibition of the constitutive--

Column 253, line 3, "sodium cargeenan" to read as --sodium carrageenan--

Column 255, line 26, "Heparin anticoagulatd" to read as --Heparin anticoagulated--

Column 256, line 40, "intracistemally," to read as --intracisternally,--

Column 256, line 42, "bucally," to read as --buccally,--

Column 256, line 46, "dysmennorhea," to read as --dysmenorrhea,--

Column 256, line 48, "ankylosing spondolitis" to read as --ankylosing spondylitis--

Column 257, line 1, "inflamation" to read as --inflammation--

Column 257, line 3, "teratmnent" to read as --treatment--

Signed and Sealed this

Twentieth Day of July, 2010

David J. Kappos
*Director of the United States Patent and Trademark Office*